US009956293B2

(12) United States Patent
Chimmanamada et al.

(10) Patent No.: US 9,956,293 B2
(45) Date of Patent: May 1, 2018

(54) TARGETED THERAPEUTICS

(71) Applicant: Madrigal Pharmaceuticals, Inc., West Conshohocken, PA (US)

(72) Inventors: Dinesh U. Chimmanamada, Arlington, MA (US); Weiwen Ying, Lexington, MA (US)

(73) Assignee: MADRIGAL PHARMACEUTICALS, INC., West Conshohocken, PA (US)

( * ) Notice: Subject to any disclaimer, the term of this patent is extended or adjusted under 35 U.S.C. 154(b) by 0 days. days.

(21) Appl. No.: 15/266,411

(22) Filed: Sep. 15, 2016

(65) Prior Publication Data

US 2017/0056511 A1 Mar. 2, 2017

Related U.S. Application Data

(63) Continuation of application No. PCT/US2015/021184, filed on Mar. 18, 2015.

(60) Provisional application No. 61/954,823, filed on Mar. 18, 2014.

(51) Int. Cl.
| | | |
|---|---|---|
| A61K 47/48 | (2006.01) | |
| A61K 31/4192 | (2006.01) | |
| A61K 31/167 | (2006.01) | |
| A61K 31/337 | (2006.01) | |
| A61K 31/357 | (2006.01) | |
| A61K 31/4184 | (2006.01) | |
| A61K 31/4196 | (2006.01) | |
| A61K 31/454 | (2006.01) | |
| A61K 31/4545 | (2006.01) | |
| A61K 31/4745 | (2006.01) | |
| A61K 31/513 | (2006.01) | |
| A61K 31/519 | (2006.01) | |
| A61K 31/58 | (2006.01) | |
| A61K 31/704 | (2006.01) | |

(52) U.S. Cl.
CPC ...... *A61K 47/48061* (2013.01); *A61K 31/167* (2013.01); *A61K 31/337* (2013.01); *A61K 31/357* (2013.01); *A61K 31/4184* (2013.01); *A61K 31/4196* (2013.01); *A61K 31/454* (2013.01); *A61K 31/4545* (2013.01); *A61K 31/4745* (2013.01); *A61K 31/513* (2013.01); *A61K 31/519* (2013.01); *A61K 31/58* (2013.01); *A61K 31/704* (2013.01); *A61K 47/481* (2013.01)

(58) Field of Classification Search
CPC ........... A61K 47/48061; A61K 31/167; A61K 31/337; A61K 31/357; A61K 31/4184; A61K 31/4196; A61K 31/454; A61K 31/4545; A61K 31/4745; A61K 31/513; A61K 31/519; A61K 31/58; A61K 31/704; A61K 47/481

USPC ...................................................... 548/267.2
See application file for complete search history.

(56) References Cited

U.S. PATENT DOCUMENTS

| | | | |
|---|---|---|---|
| 6,214,345 | B1 | 4/2001 | Firestone et al. |
| 6,372,712 | B1 | 4/2002 | Briesewitz et al. |
| 7,344,699 | B2 | 3/2008 | Lappin et al. |
| 7,671,010 | B2 | 3/2010 | Arap et al. |
| 7,769,423 | B2 | 8/2010 | Viglianti et al. |
| 7,834,181 | B2 | 11/2010 | Chiosis et al. |
| 2007/0134154 | A1 | 6/2007 | Chang et al. |
| 2007/0297980 | A1 | 12/2007 | Xie et al. |
| 2009/0226431 | A1 | 9/2009 | Habib |
| 2009/0298857 | A1 | 12/2009 | Chiosis et al. |
| 2011/0064751 | A1 | 3/2011 | Mossner et al. |
| 2011/0217241 | A1 | 9/2011 | Yu et al. |
| 2011/0245221 | A1 | 10/2011 | Giannini et al. |
| 2012/0003160 | A1 | 1/2012 | Wolf et al. |
| 2013/0116252 | A1 | 5/2013 | Nakamura et al. |
| 2015/0104407 | A1 | 4/2015 | Yurkovetskiy et al. |
| 2015/0105539 | A1 | 4/2015 | Miao et al. |
| 2015/0105540 | A1 | 4/2015 | Miao et al. |
| 2015/0250896 | A1 | 9/2015 | Zhao |

FOREIGN PATENT DOCUMENTS

| | | |
|---|---|---|
| EP | 2133094 A1 | 12/2009 |
| JP | 2005-520795 | 7/2005 |
| JP | 2012-502921 | 2/2012 |
| WO | 2000/61578 A1 | 10/2000 |
| WO | 2002/036171 A1 | 5/2002 |
| WO | 2003/050295 A2 | 6/2003 |
| WO | 2004/054624 A1 | 7/2004 |

(Continued)

OTHER PUBLICATIONS

Jaracz, S. et al., "Recent advances in tumor-targeting anticancer drug conjugates" (2005) Bioorganic & Medicinal Chemistry 13:5043-5054.
Anonymous, "Synta Announces Publication of First Patent Application Covering it Hsp90-inhibitor Drug Conjugate (HDC) Platform", Oct. 31, 2013 Internet: http://www.evaluategroup.com/Universal/View.aspx?type=Story&id=466037.
Taddei et al., Synthesis and Evaluation of New Hsp90 Inhibitors Based on a 1,4,5-Trisubstituted 1,2,3-Triazole Scaffold (Mar. 3, 2014) J. Med. Chem. 57:2258-2274.

(Continued)

*Primary Examiner* — Kristin Vajda
(74) *Attorney, Agent, or Firm* — DT Ward, PC; Donna T. Ward; Heng Zhu

(57) ABSTRACT

The present invention provides pharmacological compounds including an effector moiety conjugated to a binding moiety that directs the effector moiety to a biological target of interest. Likewise, the present invention provides compositions, kits, and methods (e.g., therapeutic, diagnostic, and imaging) including the compounds. The compounds can be described as a protein interacting binding moiety-drug conjugate (SDC-TRAP) compounds, which include a protein interacting binding moiety and an effector moiety. For example, in certain embodiments directed to treating cancer, the SDC-TRAP can include an Hsp90 inhibitor conjugated to a cytotoxic agent as the effector moiety.

16 Claims, 15 Drawing Sheets

(56) References Cited

FOREIGN PATENT DOCUMENTS

| | | |
|---|---|---|
| WO | 2006/087077 A2 | 8/2006 |
| WO | 2007/053792 A1 | 5/2007 |
| WO | 2007/077209 A1 | 7/2007 |
| WO | 2008/044029 A1 | 4/2008 |
| WO | 2009/036092 A2 | 3/2009 |
| WO | 2010/028389 A1 | 3/2010 |
| WO | 2010/033733 A1 | 3/2010 |
| WO | 2011/116181 A1 | 9/2011 |
| WO | 2011/133879 A2 | 10/2011 |
| WO | 2012/052843 A1 | 4/2012 |
| WO | 2012/096919 A1 | 7/2012 |
| WO | 2013/158644 A2 | 10/2013 |
| WO | 2015/038649 A1 | 3/2015 |
| WO | 2015/066053 A2 | 5/2015 |
| WO | 2015/095829 A1 | 6/2015 |
| WO | 2015/134464 A2 | 9/2015 |

OTHER PUBLICATIONS

International Search Report and Written Opinion dated Aug. 10, 2015 in Application No. PCT/US2015/021184, entitled: Targeted Therapeutics.

Arap, W. et al., "Cancer Treatment by Targeted Drug Delivery to Tumor Vasculature in a Mouse Model" (1998) Science 279:377-380.

Bader, R.A., "The Development of Targeted Drug Delivery Systems for Rheumatoid Arthritis Treatment" (2012) Book edited by Andrew B. Lemmey, ISBN 978-953-307-850-2, http://www.intechopen.com/books/rheumatoid-arthritis-treatment.

Baker, J.R., Jr., "Dendrimer-based nanoparticles for cancer therapy" (2009) Hematology pp. 708-719.

Borgman, S., "Biodistribution of HPMA Copolymer-Aminohexylgeldanamycin-RGDfK Conjugates for Prostate Cancer Drug Delivery" (2009) Molecular Pharmaceuticals 6(6):1836-1847.

Borman, S. "Multivalency: Strength in Numbers" (2000) C&EN pp. 48-53.

Then, C. Y.-C., "Bioinformatics, chemoinformatics, and pharmainformatics analysis of HER2/HSP90 dual-targeted inhibitors" (2010) J. Taiwan Chem. Eng. 41:143-149.

Dharap, S.S. et al., "Tumor-specific targeting of an anticancer drug delivery system by LHRH peptide" (2005) PNAS 102(36):12962-12967.

Du, Y. et al., "High-Throughput Screening Fluorescence Polarization Assay for Tumor Specific Hsp90" (2007) J. Biomolecular Screening 12(7):915-924.

Ducry, L. and B. Stump, "Antibody-Drug Conjugates: Linking Cytotoxic Payloads to Monoclonal Antibodies" (2010) Bioconjugate Chem. 21(1):5-13.

Gerber, D.E., "Targeted Therapies: A New Generation of Cancer Treatments" (2008) American Family Physician 77(3):311-319.

Graham, B. et al., "The heat shock protein 90 inhibitor, AT13387, displays a long duration of action in vitro and in vivo in non-small cell lung cancer" (2012) Cancer Science 103(3):522-527.

Hatakeyama, S. et al., "Targeted drug delivery to tumor vasculature by a carbohydrate mimetic peptide" (2011) PNAS 108(49):19587-19592.

Inoue, T. et al., "An inducible translocation strategy to rapidly activate and inhibit small GTPase signaling pathways" (2005) Nature Methods 2(2):415-418.

Janáky, T. et al., "Analogues of luteinizing hormone-releasing hormone containing cytotoxic groups" (1992) Proc. Natl. Acad. Sci. 89:972-976.

Jhaveri, K. et al., "Ganetespib:research and clinical development" (2015) Onco Targets and Therapy 8:1849-1858.

Kim, Y.-S. et al., "Effects of Targeting Moiety, Linker, Bifunctional Chelator, and Molecular Charge on Biological Properties of 64Cu-Labeled Triphenylphosphonium Cations" (2008) J. Med. Chem. 51:2971-2984.

Koga, F. et al., "Inhibition of Cancer Invasion and Metastasis by Targeting the Molecular Chaperone Heat-shock Protein 90" (2009) Anticancer Research 29:797-808.

Kuduk, S.D., et al., "Synthesis and Evaluation of Geldanamycin-Testosterone Hybrids" (2000) Bioorg. Med. Chem. Letters 10:1303-1306.

Leamon, C.P. and J.A. Reddy, "Folate-targeted chemotherapy" (2004) Advanced Drug Delivery Reviews 56:1127-1141.

Mandler, R. e tal., "Synthesis and Evaluation of Antiproliferative Activity of a Geldanamycin-HerceptinTM Immunoconjugate" (2000) Bioorg. & Med. Chem. Letters 10:1025-1028.

Nagy, A. et al., "Selective coupling of methotrexate to peptide hormone carriers through a γ-carboxamide linkage of its glutamic acid moiety: Benzotriazol-1-yloxytris(dimethylamino)phosphonium hexafluorophosphate activation in salt coupling" (1993) Proc. Natl. Acad. Sci. 90(13):6373-6376.

Norez, C. et al., "Chemical conjugation of F508-CFTR corrector deoxyspergualin to transporter human serum albumin enhances its ability to rescue Cl-channel functions" (2008) Am. J. Physiol. Lung Cell Mol. Physiol 295:L336-L347.

Park, D. et al., "Noninvasive Imaging of Cell Death Using an Hsp90 Ligand" (2011) J. Am. Chem. Soc. 133(9):2832-2835.

Rigaudy, P. et al., "Attempts to Target Antitumor Drugs toward Opioid Receptor-rich Mouse Tumor Cells with Enkephalin-Ellipticinium Conjugates" (1989) Cancer Research 49(7):1836-1842.

Scarano, W. et al., "Folate Conjugation to Polymeric Micelles via Boronic Acid Ester to Deliver Platinum Drugs to Ovarian Cancer Cell Lines" (2013) Biomacromolecules 14:962-975.

Sidera, K. and E. Patsavoudi, "Extracellular HSP92" (2008) Cell Cycle 7(10):1564-1568.

Sinha, R., "Nanotechnology in cancer therapeutics: bioconjugated nanoparticles for drug delivery" (2006) Mol. Cancer Ther. 5(8):1909-1917.

Sprancmanis, L.A., et al., "Determination of the anticancer drug, 15-deoxyspergualin, in plasma ultrafiltrate by liquid chromatography and precolumn derivatization with naphthalene-2,3-dicarboxaldehyde/cyanide*" (1990) J. Pharma. & Biomed. Analysis 8(2):165-175.

Stangl, S. et al., "In vivo imaging of CT26 mouse tumours by using cmHsp70.1 monoclonal antibody" (2011) 15(4):874-887.

Tse, A.N. et al., "90-kDa Heat Shock Protein Inhibition Abrogates the Topoisomerase I Poison-Induced G2/M Checkpoint in p53-Null Tumor cells by depleting Chk1 and Wee1" (2009) Molecular pharmacology 75(1):124-133.

Wang, Y. et al., "STA-9090, a small-molecule Hsp90 inhibitor for the potential treatment of cancer" (2010) Current Opinion in Investigational Drugs 11(12):1466-1476.

Webb, S. "Back on target" (2013) Nature Biotechnology 31(3):191-193.

Wick, M.C. et al., "In vivo imaging of the effect of LPS on arterial endothelial cells:molecular imaging of heat shock protein 60 expression" (2008) Cell Stress and Chaperones 13:275-285.

Extended European Search Report dated Sep. 25, 2017, in co-pending European application No. 15765206.6, entitled: Targeted Therapeutics.

FIG. 9
SDC-TRAP-0063 Tissue Distribution Study in Female SCID Mice
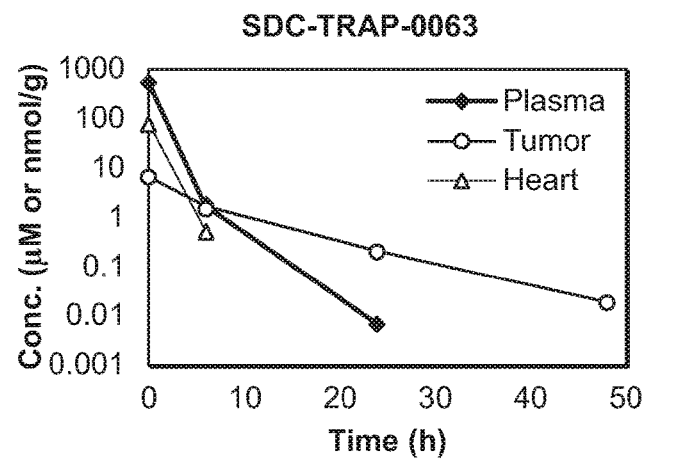
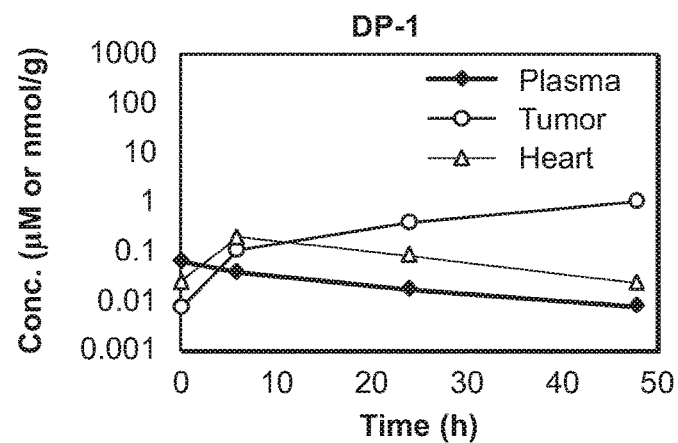
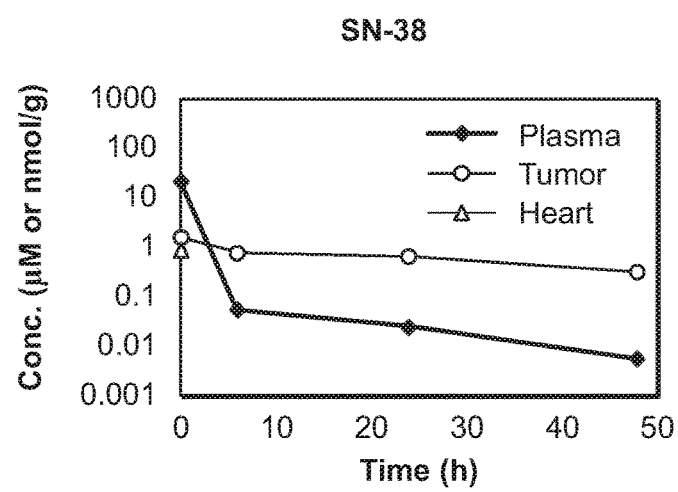

FIG. 10
SDC-TRAP-0063 Tissue Distribution Study in Male SD Mice
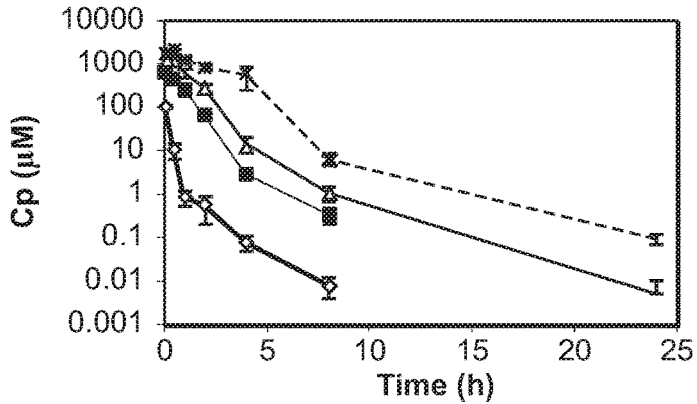
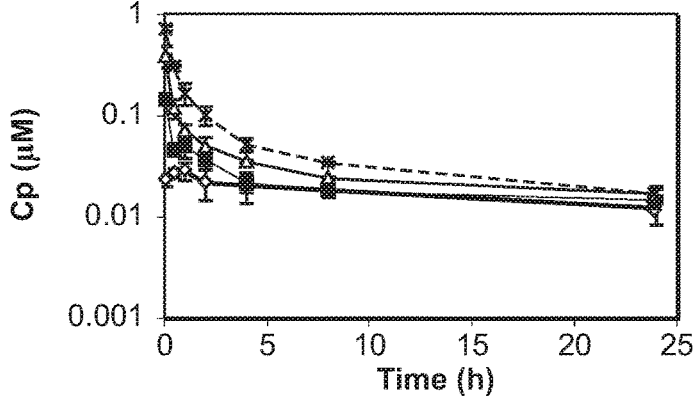
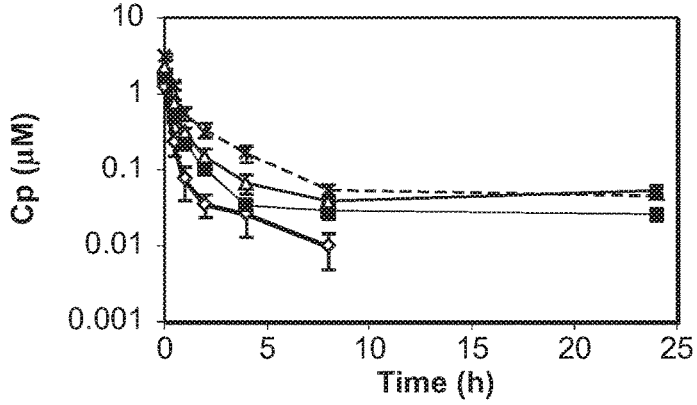

FIG. 12 SDC-TRAP Stability in Mouse Plasma

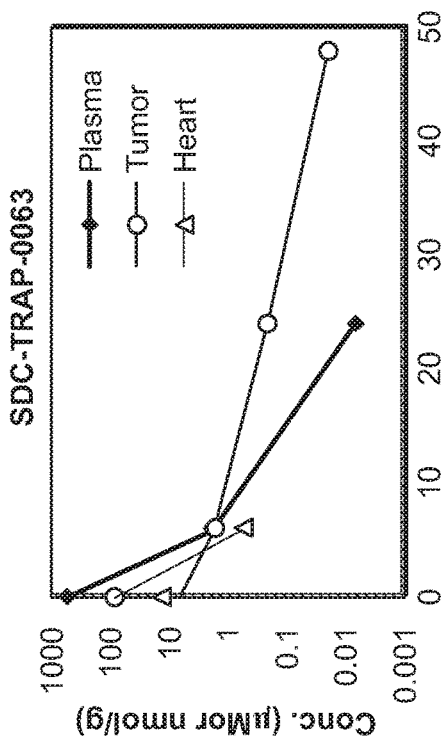
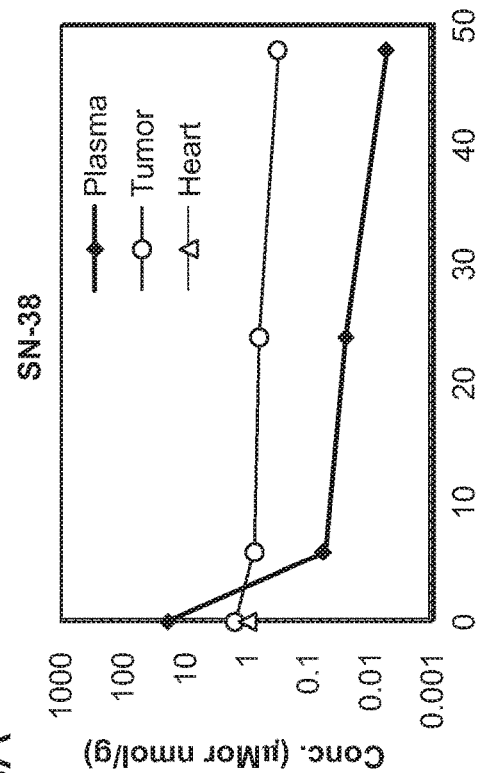
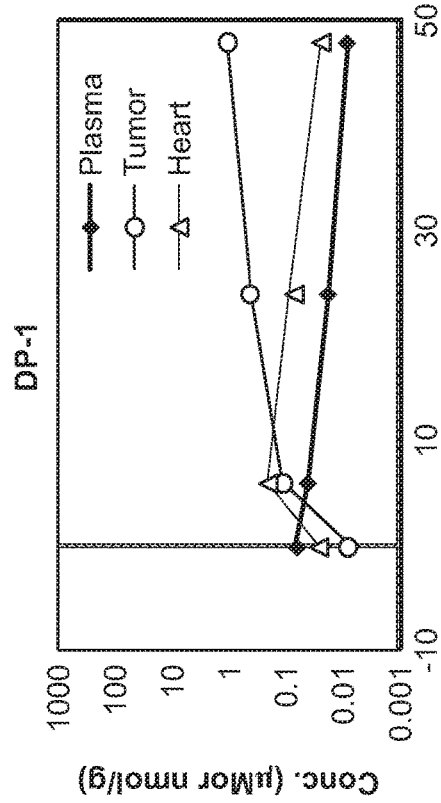

FIG. 16

| | Drug | Dose (nM) 3000 | 1000 | 333.3 | 111.1 | 37.0 | 12.3 | Dose (nM) 3000 | 1000 | 333.3 | 111.1 | 37.0 | 12.3 | Drug |
|---|---|---|---|---|---|---|---|---|---|---|---|---|---|---|
| Plate #1(contiuous), #2(pulse) | ganetespib | | | | | | | | | | | | | SDC-TRAP-0018 |
| | SDC-TRAP-0003 | | | | | | | | | | | | | SDC-TRAP-0019 |
| | SDC-TRAP-0004 | | | | | | | | | | | | | SDC-TRAP-0020 |
| | SDC-TRAP-0005 | | | | | | | | | | | | | SDC-TRAP-0021 |
| | SDC-TRAP-0006 | | | | | | | | | | | | | SDC-TRAP-0022 |
| | SDC-TRAP-0010 | | | | | | | | | | | | | SDC-TRAP-0023 |
| | SDC-TRAP-0015 | | | | | | | | | | | | | SDC-TRAP-0024 |
| | SDC-TRAP-0017 | | | | | | | | | | | | | DMSO |

| | Drug | Dose (nM) 3000 | 1000 | 333.3 | 111.1 | 37.0 | 12.3 | Dose (nM) 3000 | 1000 | 333.3 | 111.1 | 37.0 | 12.3 | Drug |
|---|---|---|---|---|---|---|---|---|---|---|---|---|---|---|
| Plate #3(contiuous), #4(pulse) | ganetespib | | | | | | | | | | | | | SDC-TRAP-0036 |
| | SDC-TRAP-0027 | | | | | | | | | | | | | SDC-TRAP-0224 |
| | SDC-TRAP-0028 | | | | | | | | | | | | | SDC-TRAP-0225 |
| | SDC-TRAP-0029 | | | | | | | | | | | | | SDC-TRAP-0226 |
| | SDC-TRAP-0030 | | | | | | | | | | | | | SDC-TRAP-0227 |
| | SDC-TRAP-0032 | | | | | | | | | | | | | SDC-TRAP-0228 |
| | SDC-TRAP-0034 | | | | | | | | | | | | | SDC-TRAP-0223 |
| | SDC-TRAP-0035 | | | | | | | | | | | | | DMSO |

TARGETED THERAPEUTICS

RELATED APPLICATIONS

This application is a continuation of International Application No. PCT/US2015/021184, filed on Mar. 18, 2015, which claims the benefit of priority to U.S. Provisional Patent Application No. 61/954,823, filed on Mar. 18, 2014, the entire contents of which are hereby incorporated herein by reference.

FIELD OF THE INVENTION

The present invention relates to pharmacological compounds including an effector moiety conjugated to a binding moiety that directs the effector moiety to a biological target of interest. The compounds have broad pharmacological applications, including therapeutics, diagnostics, and imaging. For example, the compounds can specifically direct therapeutic effector moieties to target cells or tissue of interest, for targeted chemotherapeutic treatment of conditions such as cancer.

BACKGROUND OF THE INVENTION

Although tremendous advances have been made in chemotherapy, currently available therapeutics and therapies remain unsatisfactory and the prognosis for the majority of patients diagnosed with chemotherapeutically treated diseases (e.g., cancer) remains poor. Often, the applicability and/or effectiveness of chemotherapy, as well as other therapies and diagnostics employing potentially toxic moieties, is limited by undesired side effects.

Many disease and disorders are characterized by the presence of high levels of certain proteins in specific types of cells. In some cases, the presence of these high levels of protein is caused by overexpression. Historically, some of these proteins have been useful targets for therapeutic molecules or used as biomarkers for the detection of disease. One class of overexpressed intracellular protein that has been recognized as a useful therapeutic target is known as the heat shock proteins.

Heat shock proteins (HSPs) are a class of proteins that are up-regulated in response to elevated temperature and other environmental stresses, such as ultraviolet light, nutrient deprivation, and oxygen deprivation. HSPs have many known functions, including acting as chaperones to other cellular proteins (called client proteins) to facilitate their proper folding and repair, and to aid in the refolding of misfolded client proteins. There are several known families of HSPs, each having its own set of client proteins. Hsp90 is one of the most abundant HSP families, accounting for about 1-2% of proteins in a cell that is not under stress and increasing to about 4-6% in a cell under stress.

Inhibition of Hsp90 results in degradation of its client proteins via the ubiquitin proteasome pathway. Unlike other chaperone proteins, the client proteins of Hsp90 are mostly protein kinases or transcription factors involved in signal transduction, and a number of its client proteins have been shown to be involved in the progression of cancer. Hsp90 has been shown by mutational analysis to be necessary for the survival of normal eukaryotic cells. However, Hsp90 is overexpressed in many tumor types, indicating that it may play a significant role in the survival of cancer cells and that cancer cells may be more sensitive to inhibition of Hsp90 than normal cells. For example, cancer cells typically have a large number of mutated and overexpressed oncoproteins that are dependent on Hsp90 for folding. In addition, because the environment of a tumor is typically hostile due to hypoxia, nutrient deprivation, acidosis, etc., tumor cells may be especially dependent on Hsp90 for survival. Moreover, inhibition of Hsp90 causes simultaneous inhibition of a number of oncoproteins, as well as hormone receptors and transcription factors, making it an attractive target for an anti-cancer agent. In view of the above, Hsp90 has been an attractive target of drug development, including such Hsp90 inhibitor (Hsp90i) compounds as ganetespib, AUY-922, and IPI-504. At the same time, the advancement of certain of these compounds which showed early promise, e.g., geldanamycin, has been slowed by those compounds' toxicity profile. Hsp90i compounds developed to date are believed to show great promise as cancer drugs, but other ways the ubiquity of Hsp90 in cancer cells might be leveraged have heretofore remained unexplored until now. Accordingly, the need exists for therapeutic molecules that selectively target proteins, such as Hsp90, that are overexpressed in cells associated with particular diseases or disorders.

SUMMARY OF THE INVENTION

The present invention provides pharmacological molecules ("SDC-TRAPs") including an effector moiety conjugated to a binding moiety, which directs the effector moiety into a target cell of interest in a manner that traps the molecule in the target cell. In a specific embodiment, the effector moiety is conjugated via a cleavable bond or linker to the binding moiety, such that the cleavable bond or linker is preferentially cleaved after the SDC-TRAP enters the target cell. The inventors of the instant application have discovered that the SDC-TRAP molecules of the invention can be used to selectively deliver an effector moiety to a specific type of cell in order to increase the intracellular level of the effector moiety in the target cell as compared to other cells. The inventors have demonstrated that certain SDC-TRAP molecules of the invention enter target cells by passive diffusion and are selectively retained in the target cells. Specifically, the inventors have shown that certain SDC-TRAP molecules of the invention are selectively retained only in cells that overexpress or otherwise have a high intracellular level of the protein to which the binding moiety binds. There are numerous advantages to these SDC-TRAP molecules and to methods of using these molecules that are described herein.

Specifically, the invention provides SDC-TRAP molecules that are targeted to cells of interest and trapped intracellularly for a sufficient period of time such that the effector moiety has the desired biological effect. In one embodiment, these SDC-TRAPs allow for the targeting of an effector moiety to a particular type of cell based on the overexpression of an intracellular protein that is characteristic of a particular disease or disorder. Accordingly, the present invention provides compositions, kits, and methods (e.g., therapeutic, diagnostic, and imaging) including the compounds.

In a specific embodiment, the application exemplifies the use of Hsp90 interacting moieties, e.g., inhibitors, as the binding moiety in the SDC-TRAPs. However, the invention is intended to include other binding moieties, including those that are contemplated, listed and exemplified herein. Accordingly, in certain embodiments directed to treating cancer or inflammation, the SDC-TRAP includes an Hsp90 inhibitor moiety conjugated to an effector moiety. In certain embodiments, the effector moiety is a cytotoxic effector moiety.

In another embodiment, the SDC-TRAP includes an effector moiety that is effective while still linked to the binding moiety. In such embodiment, cleavage of the bond or linker in the target cell is not a necessary feature of the invention. In other cases, such as cytotoxic effector moieties, the effector moiety should only be effective after the linker or bond is cleaved and the effector moiety is released from the SDC-TRAP molecule inside the target cell. In either case, SDC-TRAPs that do not enter into the target cell should be rapidly cleared (e.g., from the plasma or other non-target cells or tissues).

In another embodiment, the binding moiety of the SDC-TRAP binds a protein within the target cell, which may itself produce a desired biological effect (e.g., such as inhibiting Hsp90 within the target cell). In one embodiment, the binding moiety can contribute to the overall efficacy of the SDC-TRAP by not only binding an intracellular protein present in the target cell but by also conveying a particular desired biological effect. For example, if the binding moiety is an Hsp90 inhibitor and the target cell is a cancer cell, than the overall activity of the SDC-TRAP may not only result from the effector moiety, but also from the biological activity of the Hsp90 inhibitor.

Alternatively, interaction of the binding moiety with its protein target may not impart a biological effect, but rather only serve to attract and retain the SDC-TRAP within the target cell. In this embodiment, the binding moiety may reversibly bind to the intracellular target protein and create an intracellular equilibrium between free and bound SDC-TRAP molecules. This equilibrium may allow for cleavage of the SDC-TRAP and more effective delivery of the effector moiety, e.g., release of the effector moiety from the binding moiety by, for example, enzymatic cleavage, hydrolysis or degradation. In some cases, the effector moiety may be inactive until such release occurs.

In various aspects and embodiments, the present invention provides numerous advantages. For example, the SDC-TRAP can provide for targeted therapy, maximizing efficacy and/or minimizing undesired side effects. The SDC-TRAP can provide for targeted use of an effector moiety that would otherwise be unsuitable for administration alone due to toxicity and/or undesired systemic effects. The SDC-TRAP can facilitate targeting such effector moieties to intracellular targets—that is, due to its size and chemical properties, the SDC-TRAP can passively diffuse (or in some cases be actively transported) into a cell having an intracellular target of interest. Alternatively, the SDC-TRAP can deliver in a selective manner a cytotoxic molecule to destroy a target cell, such as a cancer or inflammatory cell.

Additional advantages are discussed in detail below.

These and other advantages of the present invention are of particular interest, for example, in chemotherapy where despite tremendous recent advances, currently available therapeutics and therapies remains unsatisfactory and the prognosis for the majority of patients diagnosed with diseases such as cancer remains poor. However, while many of the illustrative embodiments and examples are presented in the context of cancer, a person of ordinary skill in the art would understand that the present invention has applications across therapeutic, diagnostic, and imaging applications that require, or would benefit from, targeting of an effector moiety.

In various aspects, the invention provides an SDC-TRAP comprising a binding moiety and an effector moiety.

In various aspects, the invention provides an SDC-TRAP comprising a binding moiety and an effector moiety, wherein the SDC-TRAP is able to enter a cell by active transport.

In various aspects, the invention provides an SDC-TRAP comprising a binding moiety and an effector moiety, wherein the SDC-TRAP has a molecular weight of less than about 1600 Daltons.

In various aspects, the invention provides an SDC-TRAP comprising a binding moiety and an effector moiety, wherein the binding moiety has a molecular weight of less than about 800 Daltons.

In various aspects, the invention provides an SDC-TRAP comprising a binding moiety and an effector moiety, wherein the effector moiety has a molecular weight of less than 800 Daltons.

In various aspects, the invention provides an SDC-TRAP comprising a binding moiety and an effector moiety, wherein the binding moiety and the effector moiety are approximately equal in size.

In various aspects, the invention provides an SDC-TRAP comprising an Hsp90 binding moiety and an effector moiety, wherein the Hsp90 binding moiety interacts with the N-terminal domain of Hsp90.

In various aspects, the invention provides an SDC-TRAP comprising an Hsp90 binding moiety and an effector moiety, wherein the Hsp90 binding moiety interacts with the C-terminal domain of Hsp90.

In various aspects, the invention provides an SDC-TRAP comprising an Hsp90 binding moiety and an effector moiety, wherein the Hsp90 binding moiety interacts with the middle domain of Hsp90.

In various aspects, the invention provides an SDC-TRAP comprising a binding moiety and an effector moiety, wherein the binding moiety interacts with a predetermined domain of a multidomain target protein molecule.

In various aspects, the invention provides an SDC-TRAP comprising a binding moiety (e.g., an Hsp90 binding moiety) and an effector moiety, wherein the binding moiety (e.g., Hsp90 binding moiety) has a $K_d$ of 100 nM or higher (e.g., for a predetermined target molecule, for example, Hsp90).

In various aspects, the invention provides an SDC-TRAP comprising a binding moiety (e.g., Hsp90 binding moiety) and an effector moiety, wherein when administered to a subject, the SDC-TRAP is present at a ratio of 2:1 in target (e.g., tumor) cells compared to plasma. In another embodiment, the invention provides an SDC-TRAP comprising a binding moiety (e.g., Hsp90 binding moiety) and an effector moiety, wherein when administered to a subject the SDC-TRAP present at a ratio of 2:1 in target (e.g., tumor) cells compared to normal cells.

In various aspects, the invention provides an SDC-TRAP comprising a binding moiety (e.g., Hsp90 binding moiety) and an effector moiety, wherein the SDC-TRAP is present in target (e.g., cancer) cells for at least 24 hours.

In various aspects, the invention provides an SDC-TRAP comprising a binding moiety (e.g., Hsp90 binding moiety) and an effector moiety, wherein the effector moiety is released for a period of at least 6 hours (e.g., within a target cell and/or tissue).

In various aspects, the invention provides an SDC-TRAP comprising a binding moiety (e.g., Hsp90 binding moiety) and an effector moiety, wherein the effector moiety is selectively released inside a target (e.g., cancer) cell.

In various aspects, the invention provides an SDC-TRAP comprising a binding moiety (e.g., Hsp90 binding moiety) and an effector moiety, wherein the SDC-TRAP allows for the use of an effector moiety that is toxic or otherwise unfit for administration to a subject.

In various aspects, the invention provides an SDC-TRAP comprising a binding moiety (e.g., Hsp90 binding moiety) and an effector moiety, wherein the Hsp90 is an inhibitor (e.g., Hsp90 inhibitor) that is ineffective as a therapeutic agent when administered alone.

In various aspects, the invention provides an SDC-TRAP comprising an Hsp90 binding moiety and an effector moiety.

In various aspects, the invention provides pharmaceutical compositions comprising a therapeutically effective amount of at least one SDC-TRAP, and at least one pharmaceutical excipient.

In various aspects, the invention provides methods for treating a subject in need thereof comprising administering a therapeutically effective amount of at least one SDC-TRAP to the subject, thereby treating the subject.

In various aspects, the invention provides methods for imaging, diagnosing, and/or selecting a subject comprising administering an effective amount of at least one SDC-TRAP to the subject, thereby imaging, diagnosing, and/or selecting the subject.

In various aspects, the invention provides kits for treating a subject in need thereof comprising at least one SDC-TRAP and instruction for administering a therapeutically effective amount of the at least one SDC-TRAP to the subject, thereby treating the subject.

In various aspects, the invention provides kits for imaging, diagnosing, and/or selecting a subject comprising at least one SDC-TRAP and instruction for administering an effective amount of at least one SDC-TRAP to the subject, thereby imaging, diagnosing, and/or selecting the subject.

In various embodiments, the invention can include any one or more of the aspects disclosed herein having any one or more of the features disclosed herein.

In various embodiments, the binding moiety interacts with a protein that is overexpressed in cancerous cells compared to normal cells.

In various embodiments, the protein is a chaperonin protein. The chaperonin can be, for example, Hsp90.

In various embodiments, the chaperonin is an Hsp90 binding moiety.

In various embodiments, the binding moiety is an Hsp90 ligand or a prodrug thereof. The Hsp90 ligand can be, for example, an Hsp90 inhibitor.

An Hsp90 inhibitor can be selected from the group consisting of ganetespib, geldanamycin (tanespimycin), macbecins, tripterins, tanespimycins, KF-55823, radicicols, KF-58333, KF-58332, 17-DMAG, IPI-504, BIIB-021, BIIB-028, PU-H64, PU-H71, PU-DZ8, PU-HZ151, SNX-2112, SNX-2321, SNX-5422, SNX-7081, SNX-8891, SNX-0723, SAR-567530, ABI-287, ABI-328, AT-13387, NSC-113497, PF-3823863, PF-4470296, EC-102, EC-154, ARQ-250-RP, BC-274, VER-50589, KW-2478, BHI-001, AUY-922, EMD-614684, EMD-683671, XL-888, VER-51047, KOS-2484, KOS-2539, CUDC-305, MPC-3100, CH-5164840, PU-DZ13, PU-HZ151, PU-DZ13, VER-82576, VER-82160, VER-82576, VER-82160, NXD-30001, NVP-HSP990, SST-0201CL1, SST-0115AA1, SST-0221AA1, SST-0223AA1, novobiocin, herbinmycin A, radicicol, CCT018059, PU-H71, and celastrol.

In various embodiments, the binding moiety can be an Hsp90-targeting moiety, for example a triazole/resorcinol-based compound that binds Hsp90, or a resorcinol amide-based compound that binds Hsp90, e.g., ganetespib, AUY-922, or AT-13387.

In various embodiments, the binding moiety comprises compounds of the general formula I

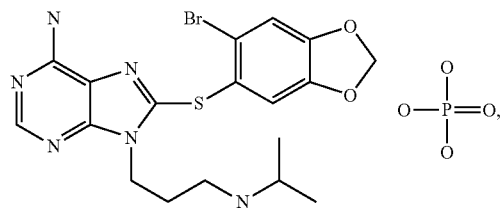

wherein
$R^1$ may be alkyl, aryl, halide, carboxamide or sulfonamide; $R^2$ may be alkyl, cycloalkyl, aryl or heteroaryl, wherein when $R^2$ is a six-membered aryl or heteroaryl, $R^2$ is substituted at the 3- and 4-positions relative to the connection point on the triazole ring, through which a linker L is attached; and $R^3$ may be SH, OH, —CONHR⁴, aryl or heteroaryl, wherein when $R^3$ is a six-membered aryl or heteroaryl, $R^3$ is substituted at the 3 or 4 position.

In various embodiments, the binding moiety comprises compounds of the general formula II:

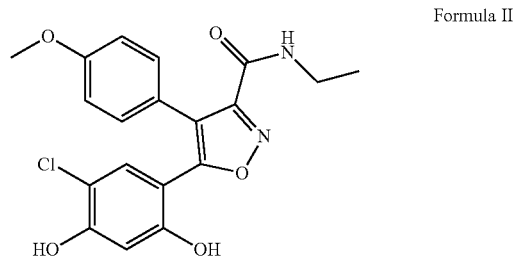

Formula II wherein
$R^1$ may be alkyl, aryl, halo, carboxamido, sulfonamido; and $R^2$ may be optionally substituted alkyl, cycloalkyl, aryl or heteroaryl. Examples of such compounds include 5-(2,4-dihydroxy-5-isopropylphenyl)-N-(2-morpholinoethyl)-4-(4-(morpholinomethyl)phenyl)-4H-1,2,4-triazole-3-carboxamide and 5-(2,4-dihydroxy-5-isopropylphenyl)-4-(4-(4-methylpiperazin-1-yl)phenyl)-N-(2,2,2-trifluoroethyl)-4H-1,2,4-triazole-3-carboxamide.

In various embodiments, the binding moiety comprises compounds of the general formula III:

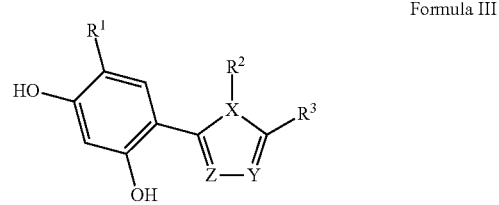

Formula III wherein
X, Y, and Z may independently be CH, N, O or S (with appropriate substitutions and satisfying the valency of the corresponding atoms and aromaticity of the ring); $R^1$ may be alkyl, aryl, halide, carboxamido or sulfonamido; $R^2$ may be substituted alkyl, cycloalkyl, aryl or heteroaryl, where a linker L is connected directly or to the extended substitutions on these rings; $R^3$ may be SH, OH, NR⁴R⁵ AND —CONHR⁶, to which an effector moiety may be connected; $R^4$ and $R^5$ may independently be H, alkyl, aryl, or heteroaryl;

and R⁶ may be alkyl, aryl, or heteroaryl, having a minimum of one functional group to which an effector moiety may be connected.

In various embodiments, the binding moiety comprises compounds of the general formula IV Formula IV

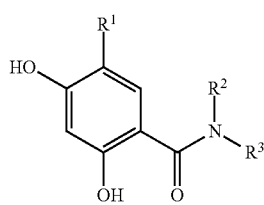

wherein
R¹ may be alkyl, aryl, halo, carboxamido or sulfonamido; R² and R³ are independently $C_1$-$C_5$ hydrocarbyl groups optionally substituted with one or more of hydroxy, halogen, $C_1$-$C_2$ alkoxy, amino, mono- and di-$C_1$-$C_2$ alkylamino; 5- to 12-membered aryl or heteroaryl groups; or, R² and R³, taken together with the nitrogen atom to which they are attached, form a 4- to 8-membered monocyclic heterocyclic group, of which up to 5 ring members are selected from O, N and S. Examples of such compounds include AT-13387:

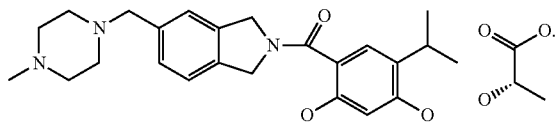

In various embodiments, the binding moiety comprises compounds of the following general formula V Formula V

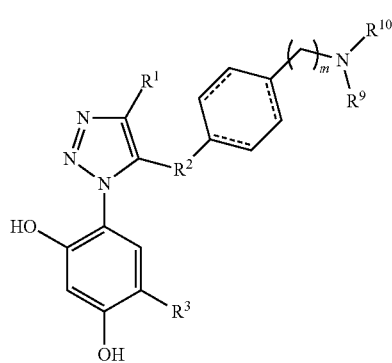

wherein:
R¹ is H, or CONR⁴R⁵;
R⁵ is H, ($C_1$-$C_6$)-alkyl, or ($C_3$-$C_{10}$)-cycloalkyl, each being optionally substituted once or more with OH, OMe, Cl, or F;
R⁴ is H, ($C_1$-$C_4$)-alkyl, or CH(R¹¹)COR¹²; or
R⁴ and R⁵, taken together with the nitrogen atom to which they are attached, form a three- to seven-membered heterocycle optionally containing a further heteroatom selected from the group consisting of N, O and S; and wherein the heterocycle is optionally substituted once or more by OH, OMe, ($C_1$-$C_4$)-alkyl, optionally substituted phenyl, or benzyl;
R¹¹ is a side chain of a natural α-amino acid;

R¹² is OH, amino, alkylamino or dialkylamino;
R² is a bond, —NH(CO)—, —N(R⁷)— or —N(R⁷)CH₂—;
R⁷ is H, ($C_1$-$C_4$)-alkyl or CO₂R⁸;
R⁸ is ($C_1$-$C_4$)-alkyl or benzyl;
the endocyclic symbols ===== are, for each single compound, all double bonds or all single bonds;
m is an integer comprised between 0 and 3;
R⁹ and R¹⁰ are, independently from each other, ($C_1$-$C_4$)-alkyl optionally substituted with OH, cycloalkyl, heterocycloalkyl, OMe, amino, ($C_1$-$C_6$)-alkylamino or ($C_1$-$C_{10}$)-dialkylamino; heterocycloalkyl optionally substituted once or more by alkyl, amino, ($C_1$-$C_6$)-alkylamino or ($C_1$-$C_6$)-dialkylamino; cycloalkyl; or
R⁹ and R¹⁰, taken together with the nitrogen atom to which they are attached, form a heterocycle ring chosen from the group consisting of piperidyl, pyrrolidinyl, piperazinyl and morpholinyl, each of them being optionally substituted once or more by F, Cl, Br, OH, OMe, amino, ($C_1$-$C_6$)-alkylamino, ($C_1$-$C_6$)-dialkylamino, ($C_1$-$C_4$)-alkyl, hydroxyalkyl, optionally substituted phenyl, or benzyl; or an imidazole unsaturated heterocycle;
R³ is Cl, Et or i-Pr;
their tautomers, their geometrical isomers, their optically active forms such as enantiomers, diastereomers and their racemate forms, as well as their pharmaceutically acceptable salts thereof.

3,4-isopropyl-6-[5-(4-(morpholin-4-ylmethyl-phenyl)-[1,2,3]-triazol-1-yl)benzene-1,3-diol;

4-{5-[4-(3-hydroxy-piperidin-1-ylmethyl)-phenyl]-[1,2,3]triazol-1-yl}-6-isopropyl-benzene-1,3-diol;

4-{5-[4-(4-benzyl-piperazin-1-ylmethyl)-phenyl]-[1,2,3]triazol-1-yl}-6-isopropyl-benzene-1,3-diol;

4-isopropyl-6-{5-[4-(4-phenyl-piperazin-1-ylmethyl)-phenyl]-[1,2,3]triazol-1-yl}-benzene-1,3-diol;

1-(2,4-dihydroxy-5-isopropyl-phenyl)-5-(4-morpholin-4-ylmethyl-phenyl)-1H-[1,2,3]triazole-4-carboxylic ethyl amide;

(R,S)-1-(2,4-dihydroxy-5-isopropyl-phenyl)-5-[4-(3-hydroxy-piperidin-1-ylmethyl)-phenyl]-1H-[1,2,3]triazole-4-carboxylic acid ethylamide;

1-(2,4-dihydroxy-5-isopropyl-phenyl)-5-(4-{[ethyl-(2-hydroxy-ethyl)-amino]-methyl})-phenyl)-1H-[1,2,3]triazole-4-carboxylic acid ethylamide;

1-(2,4-dihydroxy-5-isopropyl-phenyl)-5-{4-[2-(2-hydroxyethyl)-piperidin-1-ylmethyl]-phenyl}-1H-[1,2,3]triazole-4-carboxylic acid ethylamide;

1-(2,4-dihydroxy-5-isopropyl-phenyl)-5-(4-piperidin-1-ylmethyl-phenyl)-1H-[1,2,3]triazole-4-carboxylic acid ethylamide;

5-(4-diethylaminomethyl-phenyl)-1-(2,4-dihydroxy-5-isopropyl-phenyl)-1H-[1,2,3]triazole-4-carboxylic acid ethylamide;

1-(2,4-dihydroxy-5-isopropyl-phenyl)-5-[4-(4-methyl-piperazin-1-ylmethyl)-phenyl]-1H-[1,2,3]triazole-4-carboxylic acid ethylamide;

1-(2,4-dihydroxy-5-isopropylphenyl)-5-(4-piperazin-1-ylmethyl-phenyl)-1H-[1,2,3]triazole-4-carboxylic acid ethylamide;

1-(2,4-dihydroxy-5-isopropyl-phenyl)-5-[4-(4-dimethylamino-piperidin-1-ylmethyl)-phenyl]-1H-[1,2,3]triazole-4-carboxylic acid ethylamide;

1-(2,4-dihydroxy-5-isopropyl-phenyl)-5-{4-[(2-morpholin-4-yl-ethylamino)-methyl]-phenyl}-1H-[1,2,3]triazole-4-carboxylic acid ethylamide;

5-{4-[(cyclohexylmethyl-amino)methyl]-phenyl}-1-(2,4-dihydroxy-5-isopropyl-phenyl)-1H-1,2,3]triazole-4-carboxylic acid ethylamide;

5-(4-cyclohexylaminomethyl-phenyl)-1-(2,4-dihydroxy-5-isopropyl-phenyl)-1H-[1,2,3]triazole-4-carboxylic acid ethylamide;
5-{4-[(2-diethylaminoethylamino)-methyl]-phenyl}-1-(2,4-dihydroxy-5-isopropyl-phenyl)-1H-[1,2,3]triazole-4-carboxylic acid ethylamide;
5-{4-[(3-diethylamino-propylamino)-methyl]-phenyl}-1-(2,4-dihydroxy-5-isopropyl-phenyl)-1H-[1,2,3]triazole-4-carboxylic acid ethylamide;
1-(2,4-dihydroxy-5-isopropyl-phenyl)-5-{4-[(1-methyl-piperidin-4-ylamino)-methyl]-phenyl}-1H-[1,2,3]triazole-4-carboxylic acid ethylamide;
1-(2,4-dihydroxy-5-isopropyl-phenyl)-5-[4-((S)-3-dimethylamino-pyrrolidin-1-ylmethyl)-5 phenyl]-1H-[1,2,3]triazole-4-carboxylic acid ethylamide;
1-(2,4-dihydroxy-5-isopropyl-phenyl)-51H-[1,2,3]triazole-4-carboxylic acid ethylamide;
1-(2,4-dihydroxy-5-isopropyl-phenyl)-5-(4-imidazol-1-ylmethylphenyl)-1H-[1,2,3]triazole-4-carboxylic acid ethylamide;
4-isopropyl-6-[5-(4-morpholin-4-yl-phenylamino)-[1,2,3]triazol-1-yl]-benzene-1,3-diol;
(4-morpholin-4-yl-benzylamino)-[1,2,3]triazol-1-yl]-benzene-1,3-diol;
4-isopropyl-6-[5-1-(2,4-dihydroxy-5-isopropyl-phenyl)-5-(4-morpholin-4-yl-phenylamino)-1H-[1,2,3]triazole-4-carboxylic acid ethylamide;
1-(2,4-dihydroxy-5-isopropyl-phenyl)-5-(4-morpholin-4-yl-benzylamino)-1H-[1,2,3]triazole-4-carboxylic acid ethylamide;
1-(2,4-dihydroxy-5-isopropyl-phenyl)-5-(4-morpholin-4-ylmethyl-phenyl)-1H-[1,2,3]triazole-4-carboxylic acid hexylamide;
1-(2,4-dihydroxy-5-isopropyl-phenyl)-5-(4-morpholin-4-ylmethyl-phenyl)-1H-[1,2,3]triazole-4-carboxylic acid cyclopentylamide;
1-(2,4-dihydroxy-5-isopropyl-phenyl)-5-(4-morpholin-4-ylmethyl-phenyl)-1H-[1,2,3]triazole-4-carboxylic acid cyclohexylamide;
[1-(2,4-dihydroxy-5-isopropylphenyl)-5-(4-morpholin-4-ylmethyl-phenyl)-1H-[1,2,3]triazol-4-yl]-morpholin-4-yl-methanone;
(S)-2-{[1-(2,4-dihydroxy-5-isopropyl-phenyl)-5-(4-morpholin-4-ylmethylphenyl)-1H-[1,2,3]triazole-4-carbonyl]-amino}-3-methyl-butyric acid;
4-isopropyl-6-[5-(4-pyrrolidin-1-ylmethyl-phenyl)-[1,2,3]triazol-1-yl]-benzene-1,3-diol;
4-isopropyl-6-[5-(4-isoxazolidin-2-ylmethyl-phenyl)-[1,2,3]triazol-1-yl]-benzene-1,3-diol;
1-(2,4-dihydroxy-5-isopropyl-phenyl)-5-(4-isoxazolidin-2-ylmethyl-phenyl)-1H-[1,2,3]triazole-4-carboxylic acid ethylamide;
1-(2,4-dihydroxy-5-isopropyl-phenyl)-5-[4-(4-phenyl-piperazin-1-ylmethyl)-phenyl]-1H-[1,2,3]triazole-4-carboxylic acid ethylamide;
4-{5-(4-{[ethyl-(2-hydroxy-ethyl)-amino]-methyl}-phenyl)-[1,2,3]triazol-1-yl]-6-isopropyl-benzene-1,3-diol;
4-(5-{4-[2-(2-Hydroxy-ethyl)-piperidin-1-ylmethyl]-phenyl}-[1,2,3]triazol-1-yl)-6-isopropyl-benzene-1,3-diol;
4-isopropyl-6-[5-(4-piperidin-1-ylmethyl-phenyl)-[1,2,3]triazol-1-yl]-benzene-1,3-diol;
4-[5-(4-diethylaminomethyl-phenyl)-[1,2,3]triazol-1-yl]-6-isopropyl-benzene-1,3-diol;
N-[3-(2,4-dihydroxy-5-isopropyl-phenyl)-3H-[1,2,3]triazol-4-yl]-4-morpholin-4-yl-benzamide;
1-(2,4-dihydroxy-5-isopropyl-phenyl)-5-(4-morpholin-4-yl-benzoylamino)-1H-[1,2,3]triazole-4-carboxylic acid ethylamide;
N-[3-(2,4-dihydroxy-5-isopropyl-phenyl)-3H-[1,2,3]triazol-4-yl]-4-piperidin-1-yl-benzamide;
1-(2,4-dihydroxy-5-isopropyl-phenyl)-5-(4-piperidin-1-yl-benzoylamino)-1H-[1,2,3]triazole-4-carboxylic acid ethylamide;
N-[3-(2,4-dihydroxy-5-isopropyl-phenyl)-3H-[1,2,3]triazol-4-yl]-4-(3-hydroxy-piperidin-1-yl)-benzamide;
1-(2,4-dihydroxy-5-isopropyl-phenyl)-5-[4-(3-hydroxy-piperidin-1-yl)-benzoylamino]-1H-[1,2,3]triazole-4-carboxylic acid ethylamide;
N-[3-(2,4-dihydroxy-5-isopropyl-phenyl)-3H-[1,2,3]triazol-4-yl]-4-morpholin-4-ylmethyl-benzamide;
1-(2,4-dihydroxy-5-isopropyl-phenyl)-5-(4-morpholin-4-ylmethyl-benzoylamino)-1H-[1,2,3]triazole-4-carboxylic acid ethylamide;
4-morpholin-4-ylmethyl-cyclohexanecarboxylic acid [3-(2,4-dihydroxy-5-isopropyl-phenyl)-3H-[1,2,3]triazol-4-yl]-amide;
1-(2,4-dihydroxy-5-isopropyl-phenyl)-5-[(4-morpholin-4-ylmethyl-cyclohexanecarbonyl)-amino]-1H-[1,2,3]triazole-4-carboxylic acid ethylamide;
4-isopropyl-6-{5-[4-(4-methyl-piperazin-1-ylmethyl)-phenyl]-[1,2,3]triazol-1-yl}-benzene-1,3-diol;
4-isopropyl-6-[5-(4-morpholin-4-ylmethyl-phenyl)-[1,2,3]triazol-1-yl]-benzene-1,3-diol;
1-(2,4-dihydroxy-5-isopropyl-phenyl)-5-(4-morpholin-4-ylmethyl-phenyl)-1H-[1,2,3]triazole-4-carboxylic acid ethylamide;
5-[4-(4-benzyl-piperazin-1-ylmethyl)-phenyl]-1-(2,4-dihydroxy-5-isopropyl-phenyl)-1H-[1,2,3]triazole-4-carboxylic acid ethylamide;
N-[3-(2,4-dihydroxy-5-isopropyl-phenyl)-3H-[1,2,3]triazol-4-yl]-4-pyrrolidin-1-yl-benzamide;
1-(2,4-dihydroxy-5-isopropyl-phenyl)-5-(4-pyrrolidin-1-yl-benzoylamino)-1H-[1,2,3]triazole-4-carboxylic acid ethylamide; or
1-(2,4-dihydroxy-5-isopropylphenyl)-5-(4-morpholin-4-ylmethyl-phenyl)-1H-[1,2,3]triazole-4-carboxylic acid (2-chloro-ethyl)-amide.

In other certain embodiments, the binding moiety comprises compounds of the following general formula VI

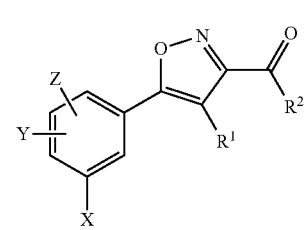

Formula VI wherein:
X is halogen, alkyl, alkenyl, haloalkyl, aryl, heteroaryl, benzyl, amino, alkylamino, or aminocarbonyl;
Y and Z, the same or different, are halogen, nitro, haloalkyl, $R^3$, $OR^3$, amino, alkylamino, or aminocarbonyl;
$R^3$ is hydrogen or alkyl;
$R^1$ is $NHC(=D)ER^4$ or $NR^5R^6$;
D is O or S;
E is O, $NR^7$ or is absent;
$R^7$ is hydrogen or alkyl;

R⁴ is alkyl optionally substituted once with alkoxy or amino; alkenyl, aryl optionally substituted once or more with alkoxy, halo or heterocycloalkylalkyl; cycloalkyl optionally substituted once or more with alkyl, haloalkyl, alkoxy, amino or aminoalkyl; norbornyl, adamantyl, heteroaryl optionally substituted once or more with alkyl, alkylaminocarbonyl; heterocycloalkyl optionally substituted once or more with alkyl; or heterocycloalkylalkyl optionally substituted once or more with alkyl;

R⁵ and R⁶ independently are hydrogen, alkyl, cycloalkyl, heterocycloalkyl optionally substituted once or more with alkyl; alkenyl, benzyl, aryl, arylalkyl optionally substituted with alkoxy; heteroaryl, heteroarylalkyl optionally substituted once or more with alkyl, hydroxyalkyl, alkoxy, alkoxycarbonyl; or R⁵ and R⁶, taken together with the nitrogen atom to which they are attached, form an optionally substituted five to seven-membered heterocycle ring, which optional substitution being halogen, hydroxyl, alkoxyl, alkyl, aryl, arylalkyl, alkylcarbonyl or aminocarbonyl;

R² is NR⁸R⁹;

R⁸ and R⁹ are the same or different, and are chosen from H, alkyl optionally substituted with halogen, haloalkyl, aryl, cycloalkyl, heterocycloalkyl and heteroaryl; or R⁸ and R⁹, taken together with the nitrogen atom to which they are attached, form a heterocycle that may contain one or two further heteroatoms selected from O, S or N and which can optionally be substituted once or twice with alkyl or halogen; and their tautomers, their geometrical isomers, their optically active forms such as enantiomers, diastereomers and their racemate forms, as well as their pharmaceutically acceptable salts thereof;

5,4-acetylamino-5-(5-chloro-2,4-dihydroxy-phenyl)-isoxazole-3-carboxylic acid ethylamide;

5-(5-chloro-2,4-dihydroxy-phenyl)-4-(4-methoxy-benzoylamino)-isoxazole-3-carboxylic acid ethylamide;

5-(5-chloro-2,4-dihydroxy-phenyl)-4-(3,4-dimethoxy-benzoylamino)-isoxazole-3-carboxylic acid ethylamide;

5-(5-chloro-2,4-dihydroxy-phenyl)-4-(3,4,5-trimethoxy-benzoylamino)-isoxazole-3-carboxylic acid ethylamide;

5-(5-chloro-2,4-dihydroxy-phenyl)-4-(2,2-dimethyl-propionylamino)-isoxazole-3-carboxylic acid ethylamide;

4-[(adamantane-1-carbonyl)-amino]-5-(5-chloro-2,4-dihydroxy-phenyl)-isoxazole-3-carboxylic acid ethylamide;

4-acryloylamino-5-(5-chloro-2,4-dihydroxy-phenyl)-isoxazole-3-carboxylic acid ethylamide;

5-(5-chloro-2,4-dihydroxy-phenyl)-4-[(3-methyl-thiophene-2-carbonyl)-amino]-isoxazole-3-carboxylic acid ethylamide;

5-(5-chloro-2,4-dihydroxy-phenyl)-4-(3-morpholin-4-yl-propionylamino)-isoxazole-3-carboxylic acid ethylamide;

4-(4-bromo-benzoylamino)-5-(5-chloro-2,4-dihydroxy-phenyl)-isoxazole-3-carboxylic acid ethylamide;

5-(2,4-dihydroxy-5-isopropyl-phenyl)-4-(4-methoxy-benzoylamino)-isoxazole-3-carboxylic acid ethylamide;

4-acetylamino-5-(2,4-dihydroxy-5-isopropyl-phenyl)-isoxazole-3-carboxylic acid ethylamide;

5-(2,4-dihydroxy-5-isopropyl-phenyl)-4-(2,2-dimethyl-propionylamino)-isoxazole-3-carboxylic acid ethylamide;

5-(2,4-dihydroxy-5-isopropyl-phenyl)-4-[(3-methyl-thiophene-2-carbonyl)-amino]-isoxazole-3-carboxylic acid ethylamide;

5-(2,4-dihydroxy-5-isopropyl-phenyl)-4-(3-morpholin-4-yl-propionylamino)-isoxazole-3-carboxylic acid ethylamide;

4-(3-(4-methylpiperazin-1-yl)propanamido)-N-ethyl-5-(2,4-dihydroxy-5-isopropylphenyl)-isoxazole-3-carboxamide;

1H-indole-6-carboxylic acid [5-(2,4-dihydroxy-5-isopropyl-phenyl)-3-ethyl carbamoyl-isoxazol-4-yl]-amide;

5-(2,4-dihydroxy-5-isopropyl-phenyl)-4-(4-morpholin-4-yl-methyl-benzoyl amino)-isoxazole-3-carboxylic acid ethylamide hydrochloride;

4-(cyclohexanecarbonyl-amino)-5-(2,4-dihydroxy-5-isopropyl-phenyl)-isoxazole-3-carboxylic acid ethylamide;

5-(2,4-dihydroxy-5-isopropyl-phenyl)-4-[(trans-4-pentyl-cyclohexanecarbonyl)-amino]-isoxazole-3-carboxylic acid ethylamide;

5-(2,4-dihydroxy-5-isopropyl-phenyl)-4-[(4-trifluoromethyl-cyclohexane carbonyl)-amino]-isoxazole-3-carboxylic acid ethylamide;

N⁵-(3-(ethylcarbamoyl)-5-(2,4-dihydroxy-5-isopropylphenyl)-isoxazol-4-yl)-N³-ethylisoxazole-3,5-dicarboxamide;

5-(2,4-dihydroxy-5-isopropyl-phenyl)-4-[(4-methoxy-cyclohexanecarbonyl)-amino]-isoxazole-3-carboxylic acid ethylamide;

4-[(4-tert-butyl-cyclohexanecarbonyl)-amino]-5-(2,4-dihydroxy-5-isopropyl-1-phenyl)-isoxazole-3-carboxylic acid ethylamide;

4-[(4-amino-cyclohexanecarbonyl)-amino]-5-(2,4-dihydroxy-5-isopropyl-phenyl)-isoxazole-3-carboxylic acid ethylamide;

4-[(4-aminomethyl-cyclohexanecarbonyl)-amino]-5-(2,4-dihydroxy-5-isopropyl-phenyl)-isoxazole-3-carboxylic acid ethylamide;

4-(4-methoxybenzylamino)-5-(5-chloro-2,4-dihydroxyphenyl)-N-ethylisoxazole-3-carboxamide;

4-((3-methylthiophen-2-yl)methyl amino)-5-(5-chloro-2,4-dihydroxyphenyl)-N-ethylisoxazole-3-carboxamide;

5-(5-chloro-2,4-dihydroxyphenyl)-4-(cyclohexylamino)-N-ethylisoxazole-3-carboxamide;

4-(1-methylpiperidin-4-ylamino)-5-(5-chloro-2,4-dihydroxyphenyl)-N-ethylisoxazole-3-carboxamide;

Methyl-5-((3-(ethylcarbamoyl)-5-(5-chloro-2,4-dihydroxyphenyl)isoxazol-4-ylamino-)methyl)isoxazole-3-carboxylate;

4-((3-(hydroxymethyl)isoxazol-5-yl)methylamino)-5-(5-chloro-2,4-dihydroxy-phenyl)-N-ethylisoxazole-3-carboxamide;

4-(4-methoxybenzamido)-5-(5-chloro-2,4-dihydroxyphenyl)-N-(2,2,2-trifluoroethyl)-isoxazole-3-carboxamide;

4-(4-methoxybenzamido)-5-(5-chloro-2,4-dihydroxyphenyl)-isoxazol-3-yl-(3,3-difluoroazetidinyl)-methanone;

5-(5-chloro-2,4-dihydroxy-phenyl)-4-(4-methoxy-benzoylamino)-isoxazol-3-yl-(4-methylpiperazin-1-yl)-methanone;

5-(2,4-dihydroxy-5-isopropyl-phenyl)-4-(3,4-dimethoxy-benzoylamino)-isoxazole-3-carboxylic acid ethylamide;

5-(2,4-dihydroxy-5-isopropyl-phenyl)-4-(3,4,5-trimethoxy-benzoylamino)-isoxazole-3-carboxylic acid ethylamide;

4-[(adamantane-1-carbonyl)-amino]-5-(2,4-dihydroxy-5-isopropyl-phenyl)-isoxazole-3-carboxylic acid ethylamide;

4-acryloylamino-5-(2,4-dihydroxy-5-isopropyl-phenyl)-isoxazole-3-carboxylic acid ethylamide;

4-(4-bromo-benzoylamino)-5-(2,4-dihydroxy-5-isopropyl-phenyl)-isoxazole-3-carboxylic acid ethylamide;

5-(2,4-dihydroxy-5-isopropyl-phenyl)-4-(4-methoxy-benzenesulfonylamino)-isoxazole-3-carboxylic acid ethylamide;

4-amino-5-(2,4-dihydroxy-5-isopropyl-phenyl)-isoxazole-3-carboxylic acid ethylamide;

5-(2,4-dihydroxy-5-isopropyl-phenyl)-4-(toluene-4-sulfonylamino)]-isoxazole-3-carboxylic acid ethylamide; or 5-(2,4-dihydroxy-5-isopropyl-phenyl)-4-[bis-(toluene-4-sulfonylamino)]-isoxazole-3-carboxylic acid ethylamide.

In other various embodiments, the binding moiety comprises:

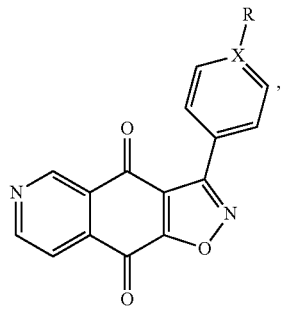

wherein X=C, R is F, OCH$_3$, or

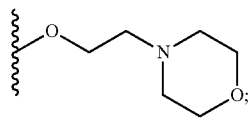 [SMILES: *OCCN1CCOCC1]

or, X=N, and R is absent.

In other various embodiments, the binding moiety comprises:

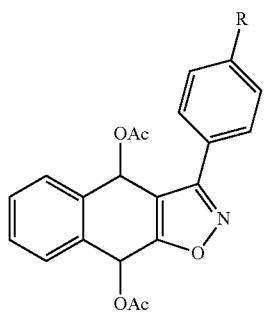

wherein R is —OCH$_3$ or F.

In other various embodiments, the binding moiety comprises:

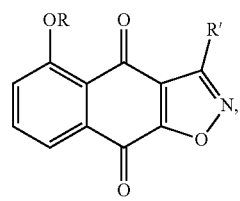

wherein R is H, CH$_3$, or Ac; and R' is 4-pyridyl, or 4-fluorophenyl.

In other various embodiments, the binding moiety comprises:

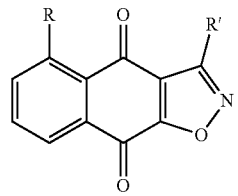

wherein:
R is H, OH, OCH$_3$, or OAc; and
R' is

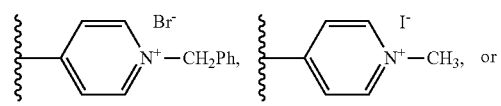

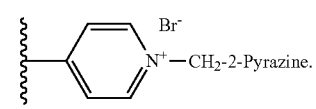

In other various embodiments, the binding moiety comprises:

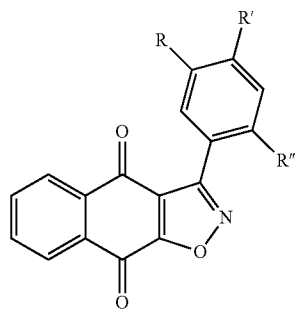

wherein:
R is H, or Cl;
R' is H, F, OH, OCH$_3$, or

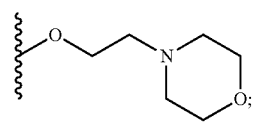 [SMILES: *OCCN1CCOCC1]

and
R" is H, OH, or OCH$_3$.

In other various embodiments, the binding moiety comprises:

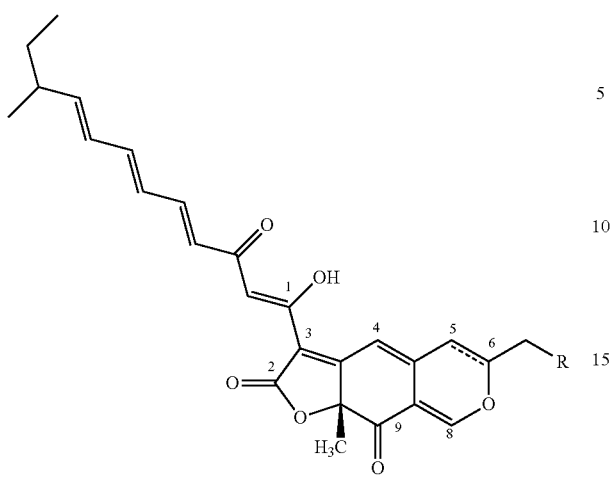

wherein:

R is H, and $C_5$-$C_6$ is a single bond or a double bond; or

R is OH, and $C_5$-$C_6$ is a single bond.

In other various embodiments, the binding moiety comprises:

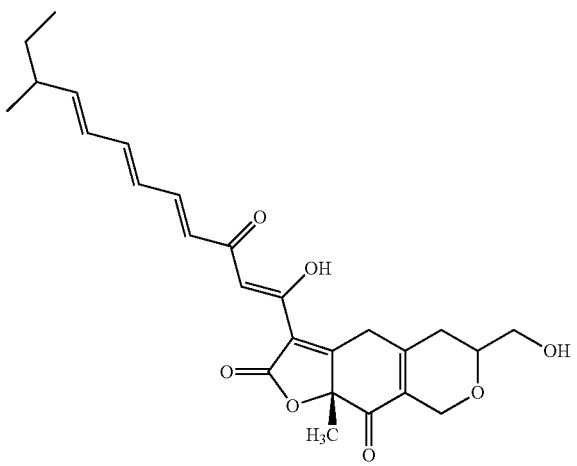 [SMILES: CCC(C)/C=C/C=C/C=C/C(=O)/C=C(\O)C1=C2CC3=C(COC(CO)C3)C(=O)[C@]2(C)OC1=O]

In other various embodiments, the binding moiety comprises:

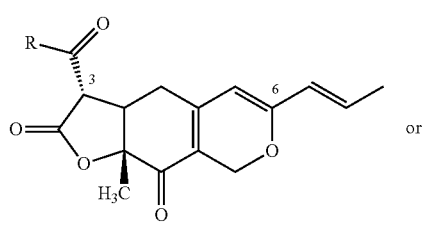

or

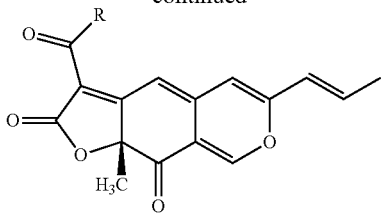

wherein R is —$C_7H_{15}$, or —$C_5H_{11}$.

In other various embodiments, the binding moiety comprises:

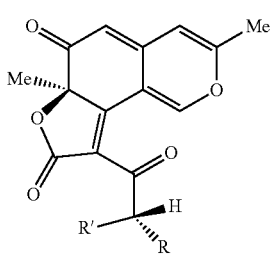

wherein R is —$C_6H_{13}$, —$C_8H_{17}$, or —$C_{10}H_{21}$, and R' is H or $CH_3$.

As used herein, the term "alkyl" means a saturated straight chain or branched non-cyclic hydrocarbon having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. The term "($C_1$-$C_6$)alkyl" means a saturated straight chain or branched non-cyclic hydrocarbon having from 1 to 6 carbon atoms. Representative ($C_1$-$C_6$)alkyl groups are those shown above having from 1 to 6 carbon atoms. Alkyl groups included in compounds of this invention may be optionally substituted with one or more substituents.

As used herein, the term "alkenyl" means a saturated straight chain or branched non-cyclic hydrocarbon having from 2 to 10 carbon atoms and having at least one carbon-carbon double bond. Representative straight chain and branched ($C_2$-$C_{10}$)alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. Alkenyl groups may be optionally substituted with one or more substituents.

As used herein, the term "alkynyl" means a saturated straight chain or branched non-cyclic hydrocarbon having from 2 to 10 carbon atoms and having at least one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like. Alkynyl groups may be optionally substituted with one or more substituents.

As used herein, the term "cycloalkyl" means a saturated, mono- or polycyclic alkyl radical having from 3 to 20 carbon atoms. Representative cycloalkyls include cyclopropyl, 1-methylcyclopropyl, cyclobutyl, cyclopentyl, cyclohexyl, cycloheptyl, cyclooctyl, cyclononyl, -cyclodecyl, octahydro-pentalenyl, and the like. Cycloalkyl groups may be optionally substituted with one or more substituents.

As used herein, the term "cycloalkenyl" means a mono- or poly-cyclic non-aromatic alkyl radical having at least one carbon-carbon double bond in the cyclic system and from 3 to 20 carbon atoms. Representative cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl, 1,2,3,4,5,8-hexahydronaphthalenyl and the like. Cycloalkenyl groups may be optionally substituted with one or more substituents.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

As used herein, an "alkoxy" is an alkyl group which is attached to another moiety via an oxygen linker.

As used herein, an "haloalkoxy" is an haloalkyl group which is attached to another moiety via an oxygen linker.

As used herein, the term an "aromatic ring" or "aryl" means a hydrocarbon monocyclic or polycyclic radical in which at least one ring is aromatic. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Aryl groups may be optionally substituted with one or more substituents. In one embodiment, the aryl group is a monocyclic ring, wherein the ring comprises 6 carbon atoms, referred to herein as "$(C_6)$aryl."

As used herein, the term "aralkyl" means an aryl group that is attached to another group by a $(C_1$-$C_6)$alkylene group. Representative aralkyl groups include benzyl, 2-phenylethyl, naphth-3-yl-methyl and the like. Aralkyl groups may be optionally substituted with one or more substituents.

As used herein, the term "alkylene" refers to an alkyl group that has two points of attachment. The term "$(C_1$-$C_6)$ alkylene" refers to an alkylene group that has from one to six carbon atoms. Straight chain $(C_1$-$C_6)$alkylene groups are preferred. Non-limiting examples of alkylene groups include methylene (—$CH_2$—), ethylene (—$CH_2CH_2$—), n-propylene (—$CH_2CH_2CH_2$—), isopropylene (—$CH_2CH(CH_3)$—), and the like. Alkylene groups may be optionally substituted with one or more substituents.

As used herein, the term "heterocyclyl" means a monocyclic (typically having 3- to 10-members) or a polycyclic (typically having 7- to 20-members) heterocyclic ring system which is either a saturated ring or a unsaturated non-aromatic ring. A 3- to 10-membered heterocycle can contain up to 5 heteroatoms; and a 7- to 20-membered heterocycle can contain up to 7 heteroatoms. Typically, a heterocycle has at least on carbon atom ring member. Each heteroatom is independently selected from nitrogen, which can be oxidized (e.g., N(O)) or quaternized; oxygen; and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, the heterocyclyl may be optionally substituted with one or more substituents. Only stable isomers of such substituted heterocyclic groups are contemplated in this definition.

As used herein, the term "heteroaromatic", "heteroaryl" or like terms means a monocyclic or polycyclic heteroaromatic ring comprising carbon atom ring members and one or more heteroatom ring members. Each heteroatom is independently selected from nitrogen, which can be oxidized (e.g., N(O)) or quaternized; oxygen; and sulfur, including sulfoxide and sulfone. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4] pyrimidinyl, imidazo[1,2-a]pyridyl, and benzothienyl. In one embodiment, the heteroaromatic ring is selected from 5-8 membered monocyclic heteroaryl rings. The point of attachment of a heteroaromatic or heteroaryl ring to another group may be at either a carbon atom or a heteroatom of the heteroaromatic or heteroaryl rings. Heteroaryl groups may be optionally substituted with one or more substituents.

As used herein, the term "$(C_5)$heteroaryl" means an aromatic heterocyclic ring of 5 members, wherein at least one carbon atom of the ring is replaced with a heteroatom such as, for example, oxygen, sulfur or nitrogen. Representative $(C_5)$heteroaryls include furanyl, thienyl, pyrrolyl, oxazolyl, imidazolyl, thiazolyl, isoxazolyl, pyrazolyl, isothiazolyl, pyrazinyl, triazolyl, thiadiazolyl, and the like.

As used herein, the term "$(C_6)$heteroaryl" means an aromatic heterocyclic ring of 6 members, wherein at least one carbon atom of the ring is replaced with a heteroatom such as, for example, oxygen, nitrogen or sulfur. Representative $(C_6)$heteroaryls include pyridyl, pyridazinyl, pyrazinyl, triazinyl, tetrazinyl and the like.

As used herein, the term "heteroaralkyl" means a heteroaryl group that is attached to another group by a $(C_1$-$C_6)$ alkylene. Representative heteroaralkyls include 2-(pyridin-4-yl)-propyl, 2-(thien-3-yl)-ethyl, imidazol-4-yl-methyl and the like. Heteroaralkyl groups may be optionally substituted with one or more substituents.

As used herein, the term "halogen" or "halo" means —F, —Cl, —Br or —I.

Suitable substituents for an alkyl, alkylene, alkenyl, alkynyl, cycloalkyl, cycloalkenyl, heterocyclyl, aryl, aralkyl, heteroaryl, and heteroaralkyl groups include any substituent which will form a stable compound of the invention. Examples of substituents for an alkyl, alkylene, alkenyl, alkynyl, cycloalkyl, cycloalkenyl, heterocyclyl, aryl, aralkyl, heteroaryl, and heteroarylalkyl include an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, or a haloalkyl.

In addition, alkyl, cycloalkyl, alkylene, a heterocyclyl, and any saturated portion of a alkenyl, cycloalkenyl, alkynyl, aralkyl, and heteroaralkyl groups, may also be substituted with =O, or =S.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

As used herein, the term "lower" refers to a group having up to four atoms. For example, a "lower alkyl" refers to an alkyl radical having from 1 to 4 carbon atoms, "lower alkoxy" refers to "—O—($C_1$-$C_4$)alkyl and a "lower alkenyl" or "lower alkynyl" refers to an alkenyl or alkynyl radical having from 2 to 4 carbon atoms, respectively.

Unless indicated otherwise, the compounds of the invention containing reactive functional groups (such as (without limitation) carboxy, hydroxy, thiol, and amino moieties) also include protected derivatives thereof. "Protected derivatives" are those compounds in which a reactive site or sites are blocked with one or more protecting groups. Examples of suitable protecting groups for hydroxyl groups include benzyl, methoxymethyl, allyl, trimethylsilyl, tert-butyldimethylsilyl, acetate, and the like. Examples of suitable amine protecting groups include benzyloxycarbonyl, tert-butoxycarbonyl, tert-butyl, benzyl and fluorenylmethyloxy-carbonyl (Fmoc). Examples of suitable thiol protecting groups include benzyl, tert-butyl, acetyl, methoxymethyl and the like. Other suitable protecting groups are well known to those of ordinary skill in the art and include those found in T. W. Greene, Protecting Groups in Organic Synthesis, John Wiley & Sons, Inc. 1981.

Exemplary Hsp90 inhibitors include those disclosed in U.S. Pat. Nos. 8,362,055 and 7,825,148. Examples of such compounds include AUY-922:

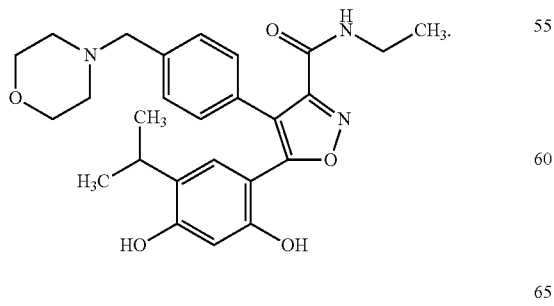

In various embodiments, the binding moiety includes an Hsp90 ligand or a prodrug thereof. In further related embodiments, the Hsp90 ligand is an Hsp90-targeting moiety, for example one or more geldanamycins, e.g., IPI-493

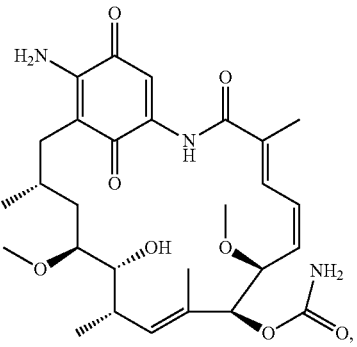 [SMILES: CO[C@H]1/C=C\C=C(/C)C(=O)NC2=CC(=O)C(N)=C(C[C@@H](C)C[C@H](OC)[C@H](O)[C@@H](C)/C=C(\C)[C@@H]1OC(N)=O)C2=O]

macbecins, tripterins, tanespimycins, e.g., 17-AAG

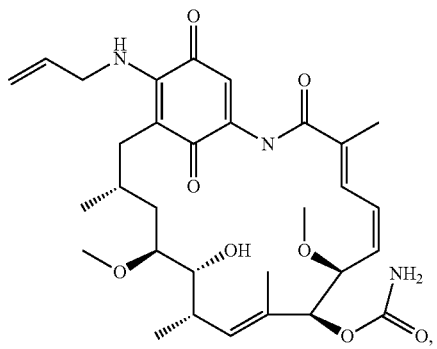 [SMILES: C=CCNC1=C2C[C@@H](C)C[C@H](OC)[C@H](O)[C@@H](C)/C=C(\C)[C@H](OC(N)=O)[C@@H](OC)/C=C\C=C(/C)C(=O)NC(=CC1=O)C2=O]

KF-55823

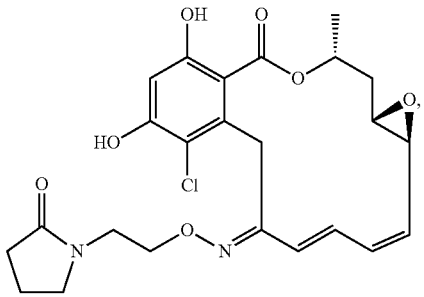 [SMILES: C[C@@H]1C[C@@H]2O[C@H]2\C=C/C=C/C(=N/OCCN2CCCC2=O)Cc2c(Cl)c(O)cc(O)c2C(=O)O1]

radicicols, KF-58333

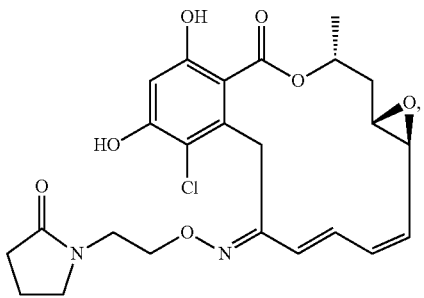 [SMILES: C[C@@H]1C[C@@H]2O[C@H]2\C=C/C=C/C(=N/OCCN2CCCC2=O)Cc2c(Cl)c(O)cc(O)c2C(=O)O1]

KF-58332
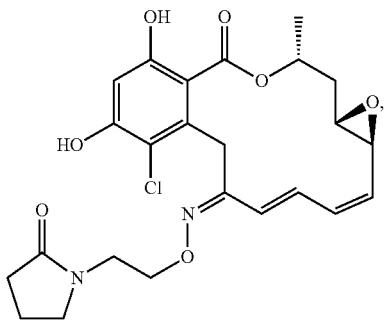 [SMILES: C[C@@H]1C[C@@H]2O[C@H]2\C=C/C=C/C(=N\OCCN2CCCC2=O)Cc2c(Cl)c(O)cc(O)c2C(=O)O1]
BIIB-028, PU-H64
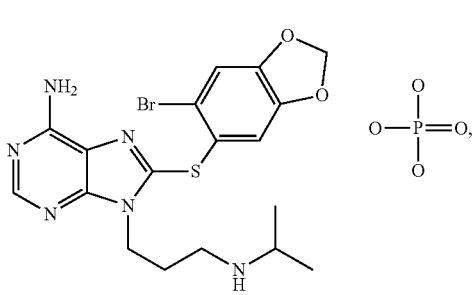
17-DMAG
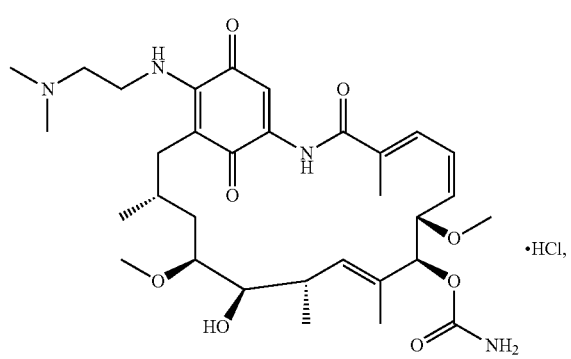
PU-H71
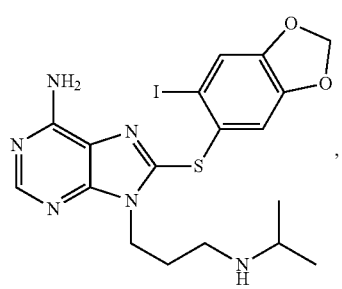
IPI-504
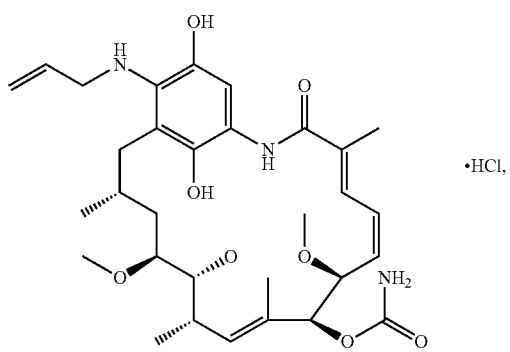 [SMILES: C=CCNc1c(O)cc2c(O)c1C[C@@H](C)C[C@H](OC)[C@H](O)[C@@H](C)/C=C(\C)[C@H](OC(N)=O)[C@@H](OC)/C=C\C=C(/C)C(=O)N2 ; "·HCl,"]
PU-DZ8
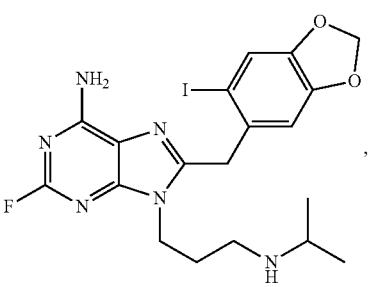
BIIB-021
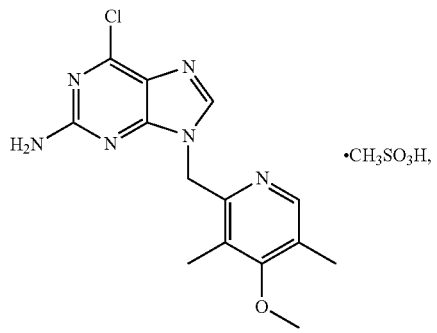 [SMILES: COc1c(C)cnc(Cn2cnc3c(Cl)nc(N)nc32)c1C ; "·CH3SO3H,"]
PU-HZ151
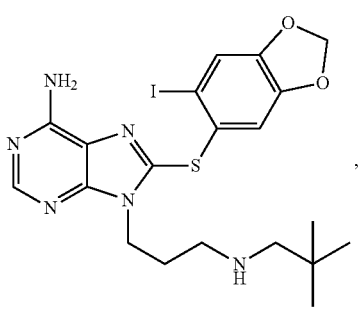 [SMILES: CC(C)(C)CNCCCn1c(Sc2cc3c(cc2I)OCO3)nc2c(N)ncnc21]

SNX-2112
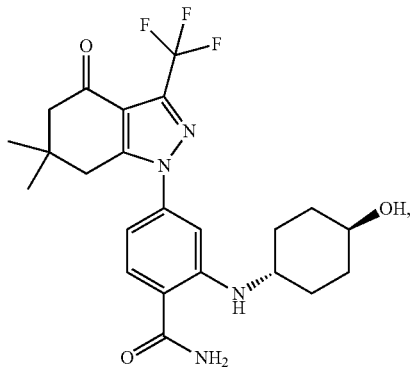 [SMILES: CC1(C)CC(=O)c2c(C(F)(F)F)nn(-c3ccc(C(N)=O)c(N[C@H]4CC[C@H](O)CC4)c3)c2C1]
SNX-8891, SNX-0723
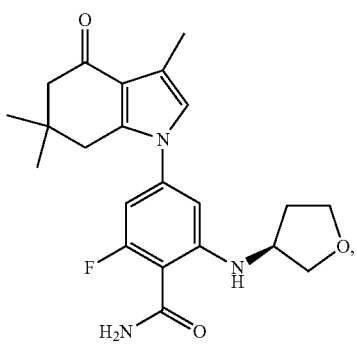
SNX-2321
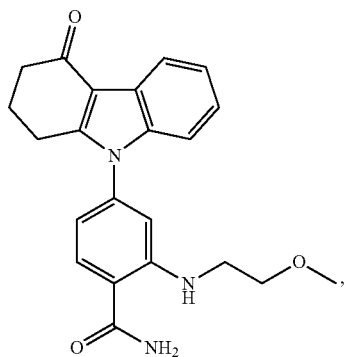 [SMILES: COCCNc1cc(-n2c3c(c4ccccc42)C(=O)CCC3)ccc1C(N)=O]
SAR-567530, ABI-287, ABI-328, AT-13387
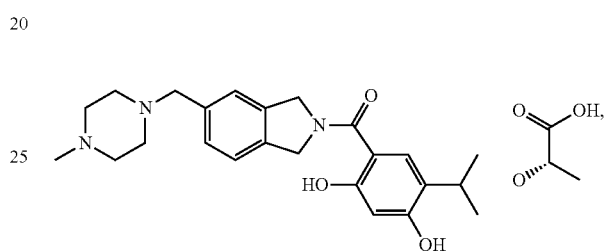
NSC-113497
SNX-5422
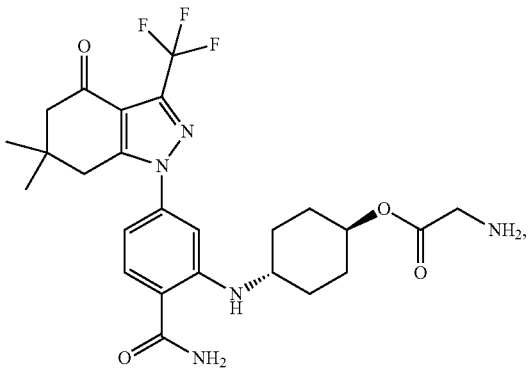 [SMILES: CC1(C)CC(=O)c2c(C(F)(F)F)nn(-c3ccc(C(N)=O)c(N[C@H]4CC[C@H](OC(=O)CN)CC4)c3)c2C1]
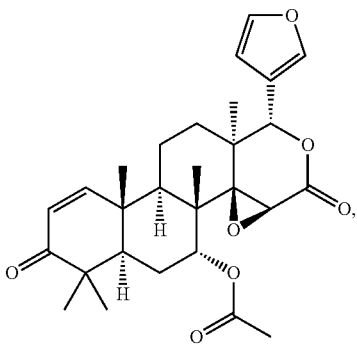
SNX-7081
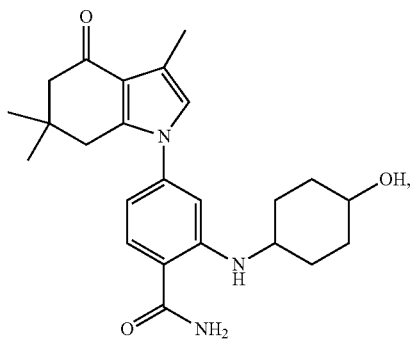 [SMILES: Cc1cn(-c2ccc(C(N)=O)c(NC3CCC(O)CC3)c2)c2c1C(=O)CC(C)(C)C2]
PF-3823863
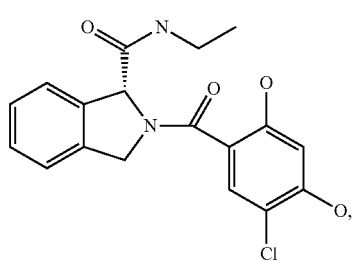

PF-4470296
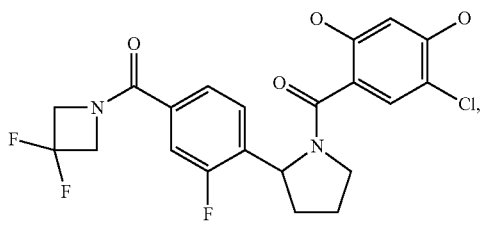 [SMILES: O=C(c1ccc(C2CCCN2C(=O)c2cc(Cl)c(O)cc2O)c(F)c1)N1CC(F)(F)C1]
EC-102, EC-154, ARQ-250-RP, BC-274
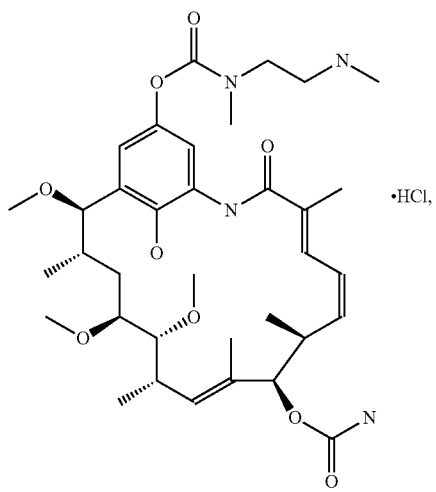
VER-50589
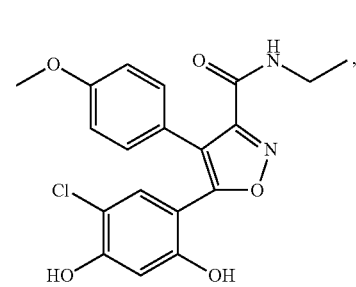 [SMILES: CCNC(=O)c1noc(-c2cc(Cl)c(O)cc2O)c1-c1ccc(OC)cc1]
KW-2478
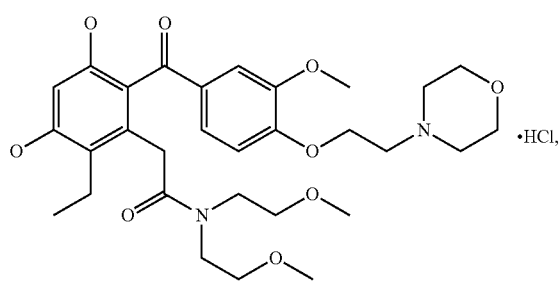
BHI-001, AUY-922
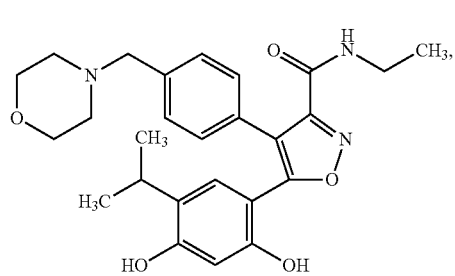 [SMILES: CCNC(=O)c1noc(-c2cc(C(C)C)c(O)cc2O)c1-c1ccc(CN2CCOCC2)cc1]
EMD-614684
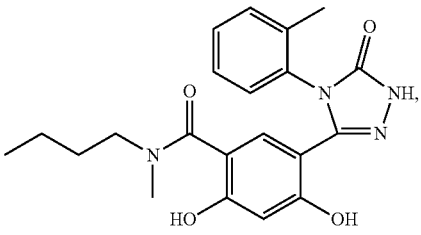 [SMILES: CCCCN(C)C(=O)c1cc(-c2n[nH]c(=O)n2-c2ccccc2C)c(O)cc1O]
EMD-683671, XL-888, VER-51047
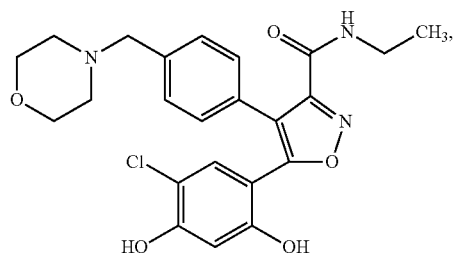 [SMILES: CCNC(=O)c1noc(-c2cc(Cl)c(O)cc2O)c1-c1ccc(CN2CCOCC2)cc1]
KOS-2484, KOS-2539, CUDC-305
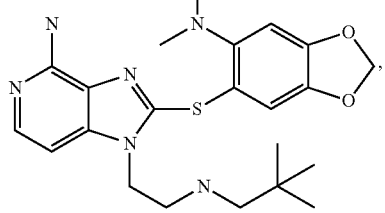

MPC-3100
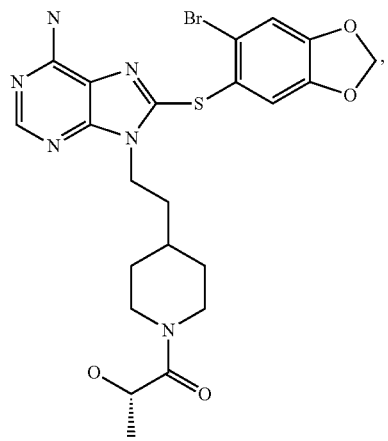 [SMILES: C[C@H](O)C(=O)N1CCC(CCn2c(Sc3cc4c(cc3Br)OCO4)nc3c(N)ncnc32)CC1]
CH-5164840
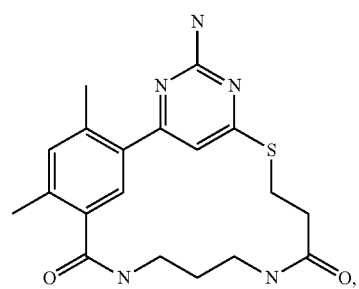
PU-DZ13
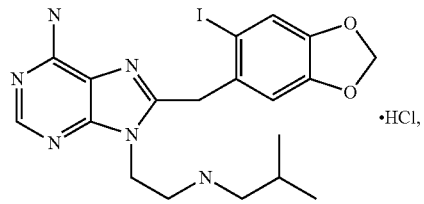
PU-HZ151
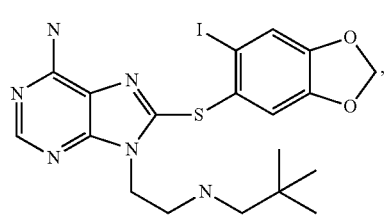 [SMILES: CC(C)(C)CNCCn1c(Sc2cc3c(cc2I)OCO3)nc2c(N)ncnc21]
PU-DZ13
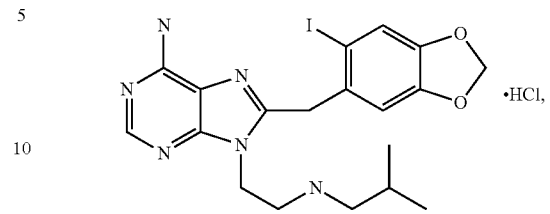
VER-82576
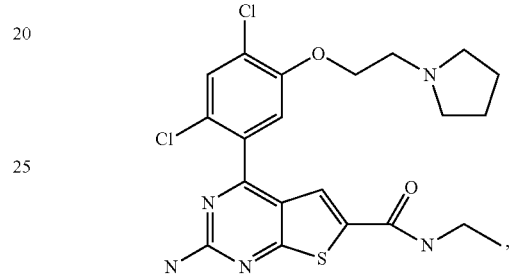
VER-82160
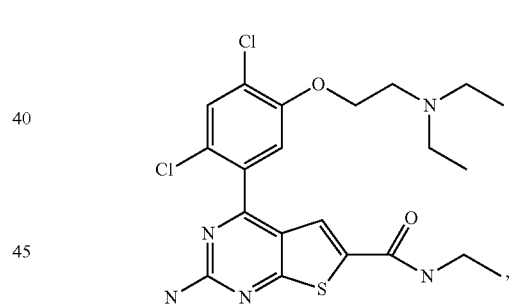
VER-82576
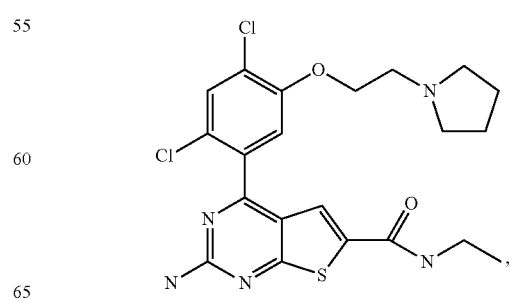

VER-82160

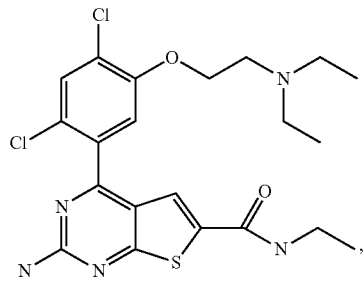 [SMILES: CCNC(=O)c1cc2c(-c3cc(OCCN(CC)CC)c(Cl)cc3Cl)nc(N)nc2s1]

NXD-30001

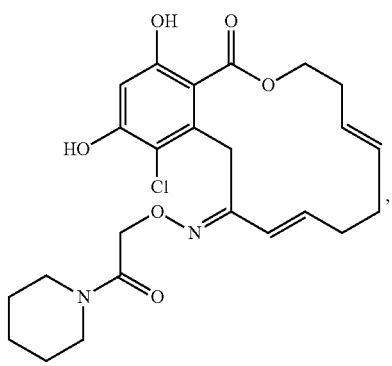 [SMILES: O=C1OCC/C=C/CC/C=C/C(=N/OCC(=O)N2CCCCC2)Cc2c(Cl)c(O)cc(O)c21]

NVP-HSP990

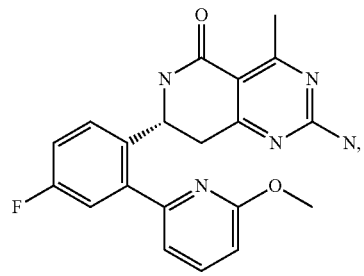

SST-0201CL1

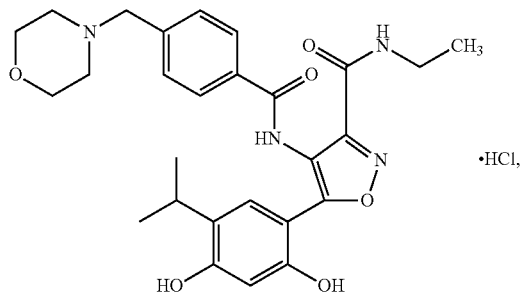 [SMILES: CCNC(=O)c1noc(-c2cc(C(C)C)c(O)cc2O)c1NC(=O)c1ccc(CN2CCOCC2)cc1]

SST-0115AA1

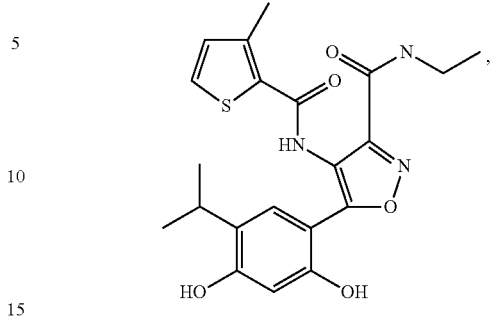

SST-0221AA1

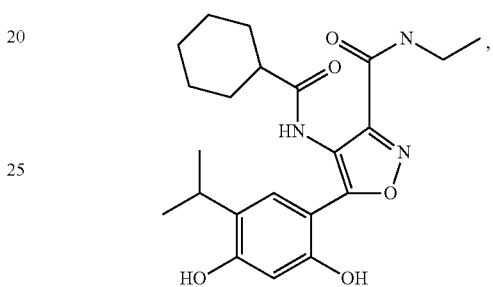

SST-0223AA1

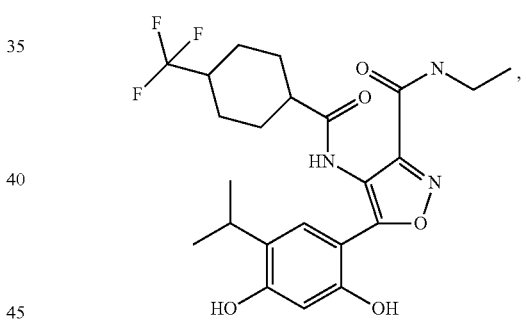

novobiocin (a C-terminal Hsp90i.)

In various embodiments, the effector moiety is a therapeutic moiety. The therapeutic moiety can be, for example, a cytotoxic moiety. A cytotoxic moiety can be SN-38, bendamustine, a VDA, doxorubicin, pemetrexed, vorinostat, lenalidomide, irinotecan, ganetespib, docetaxel, 17-AAG, 5-FU, abiraterone, crizotinib, KW-2189, BUMB2, DC1, CC-1065, adozelesin, or (a) fragment(s) thereof.

In various embodiments, the effector moiety may include pan-CDK Inhibitors, such as flavopiridol; EGFR/EGFR2 inhibitors, such as lapatinib; VEGFR inhibitors, such as axitinib; mBRAF inhibitors, such as vemurafenib; BCR-ABL/Kit inhibitors, such as imatinib; multi-target kinase inhibitors, such as staurosporine; epigenetic regulators, such as panobinostat; proteasome inhibitors, such as carfilzomib; and IDO inhibitors, such as INCB024360 and methyl tryptophan.

In various embodiments, the effector moiety is an antifolate or fragments thereof (e.g., temozolamide, mitozolamide, nitrogen mustards, estramustine, or chloromethine).

In various embodiments, the effector moiety includes one or more: peptidyl-prolyl isomerase ligands, e.g., FK506

(tacrolimus); rapamycin, cyclosporin A; steroid hormone receptor ligands, e.g., naturally occurring steroid hormones, such as estrogen, progestin, testosterone, as well as synthetic derivatives and mimetics thereof; small molecules that bind to cytoskeletal proteins, e.g., antimitotic agents, such as taxanes, colchicine, colcemid, nocadozole, vinblastine, and vincristine, actin binding agents, such as cytochalasin, latrunculin, phalloidin; lenalidomide, pomalidomide, camptothecins including SN-38

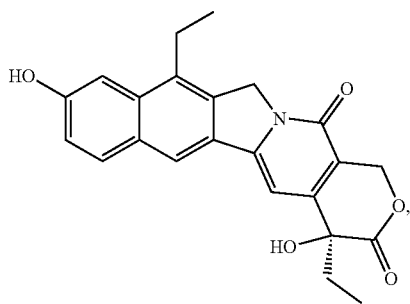 [SMILES: CCc1c2c(cc3ccc(O)cc13)-c1cc3c(c(=O)n1C2)COC(=O)[C@]3(O)CC]

topotecan, combretastatins, capecitabine, gemcitabine, vinca alkaloids, platinum-containing compounds, metformin, HDAC inhibitors (e.g., suberoylanilidehydroxamic acid (SAHA)), thymidylate synthase inhibitors such as methotrexate, pemetrexed, and raltitrexed; nitrogen mustards such as bendamustine and melphalan; 5-fluorouracil (5-FU) and its derivatives; and agents used in ADC drugs, such as vedotin and DM1.

In various embodiments, the effector moiety is derived from one or more: central nervous system depressants, e.g., general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres) and antiemetics (anticholinergics, antihistamines, antidopaminergics); central nervous system stimulants, e.g., analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics; psychopharmacological/psychotropics, e.g., anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives), antidepressants (tricyclic compounds, MAO inhibitors).

In various embodiments, the effector moiety is derived from one or more: respiratory tract drugs, e.g., central antitussives (opium alkaloids and their derivatives); immunosuppressive agents; pharmacodynamic agents, such as peripheral nervous system drugs, e.g., local anesthetics (ester derivatives, amide derivatives); drugs acting at synaptic or neuroeffector junctional sites, e.g., cholinergic agents, cholinergic blocking agents, neuromuscular blocking agents, adrenergic agents, antiadrenergic agents; smooth muscle active drugs, e.g., spasmolytics (anticholinergics, musculotropic spasmolytics), vasodilators, smooth muscle stimulants; histamines and antihistamines, e.g., histamine and derivative thereof (betazole), antihistamines ($H_1$-antagonists, $H_2$-antagonists), histamine metabolism drugs; cardiovascular drugs, e.g., cardiotonics (plant extracts, butenolides, pentadienolids, alkaloids from erythrophleum species, ionophores-adrenoceptor stimulants), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemostyptics; chemotherapeutic agents, such as antiinfective agents, e.g., ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, and cytostatics, i.e., antineoplastic agents or cytotoxic drugs, such as alkylating agents, e.g., mechlorethamine hydrochloride (nitrogen mustard, mustargen, HN2), cyclophosphamide (Cytovan, Endoxana), ifosfamide (IFEX), chlorambucil (Leukeran), Melphalan (phenylalanine mustard, L-sarcolysin, Alkeran, L-PAM), busulfan (Myleran), Thiotepa (triethylenethiophosphoramide), carmustine (BiCNU, BCNU), lomustine (CeeNU, CCNU), streptozocin (Zanosar); plant alkaloids, e.g., vincristine (Oncovin), vinblastine (Velban, Velbe), paclitaxel (Taxol); antimetabolites, e.g., methotrexate (MTX), mercaptopurine (Purinethol, 6-MP), thioguanine (6-TG), fluorouracil (5-FU), cytarabine (Cytosar-U, Ara-C), azacitidine (Mylosar, 5-AZA); antibiotics, e.g., dactinomycin (Actinomycin D, Cosmegen), doxorubicin (Adriamycin), daunorubicin (duanomycin, Cerubidine), idarubicin (Idamycin), bleomycin (Blenoxane), picamycin (Mithramycin, Mithracin), mitomycin (Mutamycin), and other anticellular proliferative agents, e.g., hydroxyurea (Hydrea), procarbazine (Mutalane), dacarbazine (DTIC-Dome), cisplatin (Platinol) carboplatin (Paraplatin), asparaginase (Elspar), etoposide (VePesid, VP-16-213), amsarcrine (AMSA, m-AMSA), mitotane (Lysodren), or mitoxantrone (Novatrone).

In various embodiments, the effector moiety is derived from one or more: anti-inflammatory agents; antibiotics, such as: aminoglycosides, e.g., amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g., azidamfenicol, chloramphenicol, florfenicol, and theimaphenicol; ansamycins, e.g., rifamide, rifampin, rifamycin, rifapentine, rifaximin; β-lactams, e.g., carbacephems, carbapenems, cephalosporins, cehpamycins, monobactams, oxaphems, penicillins; lincosamides, e.g., clinamycin, lincomycin; macrolides, e.g., clarithromycin, dirthromycin, erythromycin; polypeptides, e.g., amphomycin, bacitracin, capreomycin; tetracyclines, e.g., apicycline, chlortetracycline, clomocycline; synthetic antibacterial agents, such as 2,4-diaminopyrimidines, nitrofurans, quinolones and analogs thereof, sulfonamides, or sulfones.

In various embodiments, the effector moiety is derived from one or more: antifungal agents, such as: polyenes, e.g., amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g., butenafine, naftifine, terbinafine; imidazoles, e.g., bifonazole, butoconazole, chlordantoin, chlormidazole, thiocarbamates, e.g., tolciclate, triazoles, e.g., fluconazole, itraconazole, or terconazole.

In various embodiments, the effector moiety is derived from one or more: anthelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, or diethylcarbamazine.

In various embodiments, the effector moiety is derived from one or more: antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, or dibasic sodium arsenate.

In various embodiments, the effector moiety is derived from one or more: antiprotozoan agents, such as: acranil, tinidazole, ipronidazole, ethylstibamine, pentamidine, acetarsone, aminitrozole, anisomycin, nifuratel, tinidazole, benzidazole, or suramin.

In various embodiments, the effector moiety includes one or more of: docetaxel, paclitaxel, BEZ235, temsirolimus, PLX4032, cisplatin, AZD8055, crizotinib, topotecan and irinotecan.

In various embodiments, the effector moiety includes a topotecan or irinotecan.

In various embodiments, the cytotoxic moiety is not suitable for administration alone. The cytotoxic moiety can be unsuitable for administration alone due to toxicity. The cytotoxic moiety can be unsuitable for administration alone due to undesired targeting or a lack of targeting.

In various embodiments, the binding moiety and the effector moiety are covalently attached. The binding moiety and the effector moiety can be covalently attached, for example by a linker. The linker can comprise a cleavable linker. The cleavable linker can comprise an enzymatically cleavable linker. The linker can be selected from the group consisting of disulfide, carbamate, amide, ester, and ether linkers.

In various embodiments, the SDC-TRAP has a molecular weight of less than about 1600 Dalton. For example, the SDC-TRAP molecular weight can be less than about 1600, 1550, 1500, 1450, 1400, 1350, 1300, 1250, 1200, 1150, 1100, 1050, 1000, 950, 900, 850, 800, 750, 700, 650, 600, 550, 500, 450, 400, 350, 300, 250, or 200 Dalton.

In various embodiments, the binding moiety has a molecular weight of less than about 800 Dalton. For example, the binding moiety molecular weight can be less than about 800, 750, 700, 650, 600, 550, 500, 450, 400, 350, 300, 250, 200, 150, or 100 Dalton.

In various embodiments, the effector moiety has a molecular weight of less than about 800 Dalton. For example, the effector moiety molecular weight can be less than about 800, 750, 700, 650, 600, 550, 500, 450, 400, 350, 300, 250, 200, 150, or 100 Dalton.

In various embodiments, the binding moiety and the effector moiety are approximately equal in size. For example, the binding moiety and the effector moiety can have less than about a 25, 50, 75, 100, 125, 150, 175, 200, 225, 250, 275, 300, 325, 350, 375, or 400 Dalton difference in molecular weight.

In various embodiments, the binding moiety has a high affinity for a molecular target. For example, the binding moiety has a high affinity for a molecular target that is a $K_d$ of 50, 100, 150, 200, 250, 300, 350, 400 nM or higher.

In various embodiments, when administered to a subject, the SDC-TRAP is present at a ratio of about 2:1, 5:1, 10:1, 25:1, 50:1, 75:1, 100:1, 150:1, 200:1, 250:1, 300:1, 400:1, 500:1, 600:1, 700:1, 800:1, 900:1, 1000:1, or greater. The ratio can be, for example, at 1, 2, 3, 4, 5, 6, 7, 8, 12, 24, 48, 72, or more hours from administration.

In various embodiments, the SDC-TRAP is present in target cells and/or tissue for at least 24 hours. The SDC-TRAP can be present in cancer cells for longer, for example, for at least 48, 72, 96, or 120 hours.

In various embodiments, the effector moiety is released for a period of at least 6 hours. The effector moiety can be released for a longer period, for example, for at least 12, 24, 48, 72, 96, or 120 hours.

In various embodiments, the effector moiety is selectively released inside a target cell and/or tissue.

In various embodiments, the present invention provides SDC-TRAP molecules comprising a binding moiety is an inhibitor of a target protein but that is ineffective as a therapeutic agent when administered alone. In these, and in other embodiments, the SDC-TRAP may facilitate an additive or synergistic effect between the binding moiety and effector moiety.

In various embodiments, the binding moiety-drug conjugate (SDC-TRAP) is an SDC-TRAP selected from the group consisting of: SDC-TRAP-0008, SDC-TRAP-0015, SDC-TRAP-0016, SDC-TRAP-0017, SDC-TRAP-0018, SDC-TRAP-0019, SDC-TRAP-0020, SDC-TRAP-0021, SDC-TRAP-0022, SDC-TRAP-0010, SDC-TRAP-0023, SDC-TRAP-0027, SDC-TRAP-0028, SDC-TRAP-0029, SDC-TRAP-0031, SDC-TRAP-0024, SDC-TRAP-0025, SDC-TRAP-0033, SDC-TRAP-0037, SDC-TRAP-0038, SDC-TRAP-0039, SDC-TRAP-0040, SDC-TRAP-0041, SDC-TRAP-0042, SDC-TRAP-0043, SDC-TRAP-0044, SDC-TRAP-0045, SDC-TRAP-0046, SDC-TRAP-0047, SDC-TRAP-0048, SDC-TRAP-0049, SDC-TRAP-0050, SDC-TRAP-0051, SDC-TRAP-0063, SDC-TRAP-0178, SDC-TRAP-0069, SDC-TRAP-0211, SDC-TRAP-0098, SDC-TRAP-0198, SDC-TRAP-0199, SDC-TRAP-0219, SDC-TRAP-0200, SDC-TRAP-0068, SDC-TRAP-0093, SDC-TRAP-0117, SDC-TRAP-0201, SDC-TRAP-0204, SDC-TRAP-0171, SDC-TRAP-0196, SDC-TRAP-0003, SDC-TRAP-0004, SDC-TRAP-0005, SDC-TRAP-0006, SDC-TRAP-0030, SDC-TRAP-0032, SDC-TRAP-0034, SDC-TRAP-0035, SDC-TRAP-0036, SDC-TRAP-0224, SDC-TRAP-0225, SDC-TRAP-0226, SDC-TRAP-0227, SDC-TRAP-0228, SDC-TRAP-0223, SDC-TRAP-0002, SDC-TRAP-0056, SDC-TRAP-0052, SDC-TRAP-0064, SDC-TRAP-0172, SDC-TRAP-0180, SDC-TRAP-0184, SDC-TRAP-0185, SDC-TRAP-0186, SDC-TRAP-0118, SDC-TRAP-0009, SDC-TRAP-0013, SDC-TRAP-0137, SDC-TRAP-0150, SDC-TRAP-0151, SDC-TRAP-0153, SDC-TRAP-0134, SDC-TRAP-0139, SDC-TRAP-0138, SDC-TRAP-0142, SDC-TRAP-0105, SDC-TRAP-0108, SDC-TRAP-0126, SDC-TRAP-0132, SDC-TRAP-0127, SDC-TRAP-0133, SDC-TRAP-0135, SDC-TRAP-0140, SDC-TRAP-0136, SDC-TRAP-0231, SDC-TRAP-0147, SDC-TRAP-0165, SDC-TRAP-0163, SDC-TRAP-0164, SDC-TRAP-0166, SDC-TRAP-0188, SDC-TRAP-0189, SDC-TRAP-0190, SDC-TRAP-0191, SDC-TRAP-0192, SDC- TRAP-0193, SDC-TRAP-0122, SDC-TRAP-0123, SDC-TRAP-0124, SDC-TRAP-0125, SDC-TRAP-0155, SDC-TRAP-0156, SDC-TRAP-0157, SDC-TRAP-0160, SDC-TRAP-0167, SDC-TRAP-0168, SDC-TRAP-0170, SDC-TRAP-0171, SDC-TRAP-0182, SDC-TRAP-0187, SDC-TRAP-0109, SDC-TRAP-0110, SDC-TRAP-0114, SDC-TRAP-0115, SDC-TRAP-0116, SDC-TRAP-0119, SDC-TRAP-0120, SDC-TRAP-0121, SDC-TRAP-0128, SDC-TRAP-0129, SDC-TRAP-0131, SDC-TRAP-0149, SDC-TRAP-0152, SDC-TRAP-0168, SDC-TRAP-0173, SDC-TRAP-0174, SDC-TRAP-0175, SDC-TRAP-0176, SDC-TRAP-0177, SDC-TRAP-0178, SDC-TRAP-0194, SDC-TRAP-0195, SDC-TRAP-0078, SDC-TRAP-0082, SDC-TRAP-0093, SDC-TRAP-0102, SDC-TRAP-0103, SDC-TRAP-0130, SDC-TRAP-0011, SDC-TRAP-0012, SDC-TRAP-0014, SDC-TRAP-0065, SDC-TRAP-0066, SDC-TRAP-0084, SDC-TRAP-0086, SDC-TRAP-0088, SDC-TRAP-0087, SDC-TRAP-0089, SDC-TRAP-0090, SDC-TRAP-0091, SDC-TRAP-0092, SDC-TRAP-0104, SDC-TRAP-0106, SDC-TRAP-0107, SDC-TRAP-0145, SDC-TRAP-0207, SDC-TRAP-0206, SDC-TRAP-0205, SDC-TRAP-0208, SDC-TRAP-0209, SDC-TRAP-0210, SDC-TRAP-0213, SDC-TRAP-0214, SDC-TRAP-0215, SDC-TRAP-0216, SDC-TRAP-0217, SDC-TRAP-0218, SDC-TRAP-0067, SDC-TRAP-0070, SDC-TRAP-0077, SDC-TRAP-0079, SDC-TRAP-0081, SDC-TRAP-0083, SDC-TRAP-0094, SDC-TRAP-0095, SDC-TRAP-0101, SDC-TRAP-0220, SDC-TRAP-0026, SDC-TRAP-0055, SDC-TRAP-0057, SDC-TRAP-0058, SDC-TRAP-0060, SDC-TRAP-0061, SDC-TRAP-0071, SDC-TRAP-0072, SDC-TRAP-0073, SDC-TRAP-0074, SDC-TRAP-0075, SDC-TRAP-0076, SDC-TRAP-0097, SDC-TRAP-0100, SDC-TRAP-0111, SDC-TRAP-0112, SDC-TRAP-0113, SDC-TRAP-0154, SDC-TRAP-0169, SDC-TRAP-0181, SDC-TRAP-0202, SDC-TRAP-0203, SDC-TRAP-0221, SDC-TRAP-0222, SDC-TRAP-0148, SDC-TRAP-0159, SDC-TRAP-0099, SDC-TRAP-0158, SDC-TRAP-0085, SDC-TRAP-0232, SDC-TRAP-0233 and SDC-TRAP-0234.

In other embodiments the present invention features methods for treating a subject having a disease or disorder comprising administering a therapeutically effective amount of at least one SDC-TRAP to the subject, thereby treating the disease or disorder, wherein the SDC-TRAP comprises an SDC-TRAP of any one of the aspects or embodiments described herein.

In one embodiment, the disease or disorder is selected from the group consisting of neoplastic diseases, autoimmune diseases, inflammatory diseases, central nervous system diseases, neurodegenerative diseases, cardiovascular diseases, hormonal abnormality diseases and infectious diseases. In another embodiment, the disease or disorder is selected from the group consisting of chronic bronchitis, asthma, cancer and actinic keratosis.

In still other embodiments, the invention features a method for treating a subject having a cancer comprising administering a therapeutically effective amount of at least one SDC-TRAP to the subject, thereby treating the cancer, wherein the SDC-TRAP comprises the SDC-TRAP of any one of the aspects or embodiments described herein.

In certain embodiments, the cancer is skin cancer.

The present invention is described in further detail by the figures and examples below, which are used only for illustration purposes and are not limiting.

BRIEF DESCRIPTION OF THE DRAWINGS

FIG. 9 shows the results of SDC-TRAP-0063 tissue distribution studies in female SCID mice. FIG. 9 shows that following SDC-TRAP intravenous injection, binding moiety and effector moiety accumulate and persist in tumor, but rapidly diminish in plasma and heart in three mouse strains.

FIG. 10 shows the results of SDC-TRAP-0063 tissue distribution studies in Male SD mice. FIG. 10 shows that following SDC-TRAP intravenous injection, binding moiety and effector moiety accumulate and persist in tumor, but rapidly diminish in plasma and heart in three mouse strains.

FIG. 11 shows that following SDC-TRAP intravenous injection, binding moiety and effector moiety accumulate and persist in tumor, but rapidly diminish in plasma and heart in three mouse strains.

FIG. 15A is a graph that depicts the tissue distribution of SDC-TRAP-0063 in plasma, tumor and heart.

FIG. 15B is a graph that depicts the tissue distribution of DP-1 in plasma, tumor and heart.

FIG. 15C is a graph that depicts the tissue distribution of SN-38 in plasma, tumor and heart.

FIG. 16 is a graph showing 96-well plates used in Example 9, where each cell represents a well in the plate.

Figure 1:
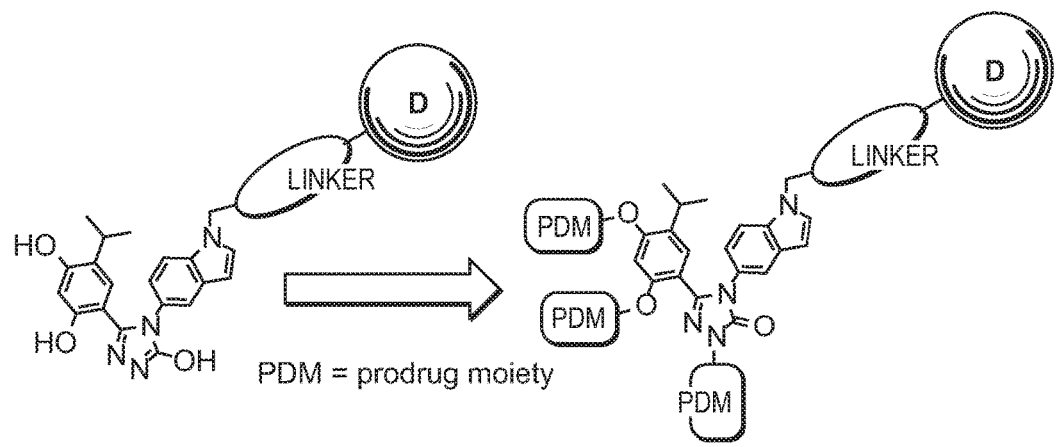
FIG. 1 shows how an illustrative Hsp90-targeting moiety may be suitably modified at one or more positions to enhance the physical, pharmacokinetic, or pharmacodynamic properties of the conjugate.

Other features and advantages of the instant invention will be apparent from the following detailed description and claims.

DETAILED DESCRIPTION OF THE INVENTION

The present invention provides molecules including an effector moiety conjugated to a binding moiety that directs the effector moiety to a biological target of interest. The molecules of the invention allow for selective targeting of an effector moiety by trapping the molecules of the invention in a desired cell, e.g., a cancer cell. The molecules can be described as Small Molecule Drug Congugates that are TRAPped intracellularly (SDC-TRAP), due to their selective binding to high concentration intracellular proteins. In order for the molecules of the invention to be trapped within the cells of interest, the binding moieties that are part of the SDC-TRAP molecules interact with proteins that are overexpressed in targeted cells. In exemplary embodiments, the proteins that are overexpressed are characteristic of a particular disease or disorder. Accordingly, the present invention provides compositions, kits, and methods (e.g., therapeutic, diagnostic, and imaging) that include the molecules of the invention.

In one embodiment of the invention, SDC-TRAPs allow for the delivery of a effector molecule that would otherwise be unsuitable for administration alone due to toxicity and/or undesired systemic effects. Using the targeted delivery molecules described herein (SDC-TRAPs) allows for effector moieties that are too toxic to administer by current methods to be dosed at lower levels thereby allowing the toxic effector to be targeted to specific diseased cells at sub-toxic levels.

In various exemplary aspects and embodiments, the present invention provides compounds for treating cancer. For example, an SDC-TRAP can comprise an Hsp90 binding moiety (i.e., targeting Hsp90, which is overexpressed in cancer cells compared to normal cells) and an effector moiety (e.g., the Hsp90 binding moiety can be an Hsp90 inhibitor that is conjugated to a cytotoxic agent). As indicated above, the invention is exemplified herein in terms of Hsp90-targeted binding moieties and cytotoxic agents. Other binding moieties that are contemplated, mentioned or described herein are intended to be included within the scope of the invention.

In various aspects and embodiments, the present invention provides an SDC-TRAP comprising a binding moiety and an effector moiety, wherein the SDC-TRAP molecule is able to enter a cell by passive transport. The ability of an SDC-TRAP to enter a cell by passive transport can be a result of one or more unique chemical properties of the SDC-TRAP (e.g., size, weight, charge, polarity, hydrophobicity, etc.) and can facilitate the delivery and/or action of the SDC-TRAP. The ability of an SDC-TRAP to enter a cell by passive transport is a functional property, which along with its physico-chemical properties, differentiates SDC-TRAPs from other targeted molecules such as antibody-drug conjugates.

In various aspects and embodiments, the present invention provides an SDC-TRAP comprising a binding moiety and an effector moiety, wherein SDC-TRAP molecule is able to enter a cell by active transport. The ability of an SDC-TRAP to enter a cell by active transport can be a result of one or more unique chemical properties of the SDC-TRAP and can facilitate the delivery and/or action of the SDC-TRAP. Example of SDC-TRAP active transport can include, for example, endocytosis, phagocytosis, pinocytosis, and exocytosis.

In various aspects and embodiments, the present invention provides an SDC-TRAP having a molecular weight of less than about 1600 Dalton (e.g., less than about 1600, 1550, 1500, 1450, 1400, 1350, 1300, 1250, 1200, 1150, 1100, 1050, 1000, 950, 900, 850, 800, 750, 700, 650, 600, 550, 500, 450, 400, 350, 300, 250, 200, etc.). Similarly, in various aspects and embodiments, the present invention provides a binding moiety having a molecular weight of less than about 800 Dalton (e.g., less than about 800, 750, 700, 650, 600, 550, 500, 450, 400, 350, 300, 250, 200, 150, 100, etc.) and/or an effector moiety having a molecular weight of less than about 800 Dalton (e.g., less than about 800, 750, 700, 650, 600, 550, 500, 450, 400, 350, 300, 250, 200, 150, 100, etc.). The overall molecular weight of an SDC-TRAP, and the individual weights of a binding moiety, effector moiety, and any linking moiety, can affect transport of the SDC-TRAP. In various examples, it has been observed that lower molecular weights can facilitate delivery and/or activity of an SDC-TRAP.

In various aspects and embodiments, the present invention provides an SDC-TRAP comprising an Hsp90 binding moiety and an effector moiety, wherein the Hsp90 binding moiety and the effector moiety are approximately equal in size (e.g., the Hsp90 binding moiety and the effector moiety have less than about a 25, 50, 75, 100, 125, 150, 175, 200, 225, 250, 275, 300, 325, 350, 375, 400, etc. Dalton difference in molecular weight.) In various examples, it has been observed that lower differences in molecular weight can facilitate delivery and/or activity of an SDC-TRAP.

In various aspects and embodiments, the present invention provides an SDC-TRAP comprising a target protein-interacting binding moiety. A target protein-interacting binding moiety can selectively interact with any one or more domains of a target protein. For example, where a target protein is Hsp90, the binding moiety can be an Hsp90 binding moiety that interacts with the N-terminal domain of Hsp90, the C-terminal domain of Hsp90, and/or the middle domain of Hsp90. Selective interaction with any one or more domains of a target protein can advantageously increase specificity and/or increase the concentration of molecular targets within a target tissue and/or cell.

In various aspects and embodiments, the present invention provides an SDC-TRAP comprising a binding moiety having a high affinity for a molecular target (e.g., a $K_d$ of 50, 100, 150, 200, 250, 300, 350, 400 nM or higher). For example, where a binding moiety is an Hsp90 binding moiety, the Hsp90 binding moiety can have a $K_d$ of 50, 100, 150, 200, 250, 300, 350, 400 nM or higher. A binding moiety having a high affinity for a molecular target can advantageously improve targeting and/or increase the resonance time of the SDC-TRAP in a target cell and/or tissue.

In various aspects and embodiments, the present invention provides an SDC-TRAP comprising a binding moiety (e.g., Hsp90 binding moiety) and an effector moiety, wherein when administered to a subject the SDC-TRAP is present at a ratio of about 2:1 in tumor cells compared to plasma. The ratio can be higher, for example, about 5:1, 10:1, 25:1, 50:1, 75:1, 100:1, 150:1, 200:1, 250:1, 300:1, 400:1, 500:1, 600:1, 700:1, 800:1, 900:1, 1000:1, or greater. In various aspects and embodiments, the ratio is at 1, 2, 3, 4, 5, 6, 7, 8, 12, 24, 48, 72, or more hours from administration. The effectiveness of targeting can be reflected in the ratio of SDC-TRAP in a target cell and/or tissue compared to plasma.

In various aspects and embodiments, the present invention provides an SDC-TRAP comprising a binding moiety (e.g., Hsp90 binding moiety) and an effector moiety, wherein the SDC-TRAP is present in target (e.g., cancer) cells for at least 24 hours. The SDC-TRAP can be present in cancer cells for longer, for example, for at least 48, 72, 96, or 120 hours. It can be advantageous for an SDC-TRAP to be present in target cells for longer periods of time to increase the therapeutic effect of a given dose of SDC-TRAP and/or increase an interval between administrations of SDC-TRAP.

In various aspects and embodiments, the present invention provides an SDC-TRAP comprising a binding moiety (e.g., Hsp90 binding moiety) and an effector moiety, wherein the effector moiety is released for a period of at least 6 hours. The effector moiety can be released for a longer period, for example, for at least 12, 24, 48, 72, 96, or 120 hours. Selective release can be used to control, delay, and/or extend the period of release of an effector moiety and, therefore, increase the therapeutic effect of a given dose of SDC-TRAP, decrease the undesired side effects of a given dose of SDC-TRAP, and/or increase an interval between administrations of SDC-TRAP.

In various aspects and embodiments, the present invention provides an SDC-TRAP comprising an Hsp90 binding moiety and an effector moiety, wherein the effector moiety is selectively released inside a target (e.g., cancer) cell. Selective release can be achieved, for example, by a cleavable linker (e.g., an enzymatically cleavable linker). Selective release can be used to decrease undesired toxicity and/or unwanted side effects. For example, an SDC-TRAP can be designed where an effector moiety such is inactive (or relatively inactive) in a conjugated form, but active (or more active) after it is selectively released inside a target (e.g., cancer) cell.

In various aspects and embodiments, the present invention provides an SDC-TRAP comprising a binding moiety (e.g., Hsp90 binding moiety) and an effector moiety, wherein the SDC-TRAP allows for the use of an effector moiety that is otherwise toxic or unfit for administration to a subject. The effector moiety can be unfit for administration to a subject because of undesired toxicity. In such cases, a strategy such as selective release may be used to address the undesired toxicity. The effector moiety can be unfit for administration to a subject because of undesired targeting or a lack of targeting. Targeting can address such problems, for example, by minimizing systemic toxicity while maximizing local toxicity at a target (e.g., a tumor).

In various aspects and embodiments, the present invention provides an SDC-TRAP comprising a binding moiety (e.g., Hsp90 binding moiety) and an effector moiety, wherein the binding moiety is an inhibitor (e.g., Hsp90 inhibitor) that is ineffective as a therapeutic agent when administered alone. In such cases, the SDC-TRAP may facilitate an additive or synergistic effect between the binding moiety and effector moiety, thereby advantageously improving the efficacy and/or reducing the side effects of a therapy.

In order that the present invention may be more readily understood, certain terms are first defined. In addition, it should be noted that whenever a value or range of values of a parameter are recited, it is intended that values and ranges intermediate to the recited values are also intended to be part of this invention. Unless defined otherwise, all technical and scientific terms used herein have the same meaning as commonly understood to one of ordinary skill in the art to which this invention belongs. It is also to be understood that the terminology employed is for the purpose of describing particular embodiments, and is not intended to be limiting.

Definitions

The articles "a," "an," and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to."

The term "or" is used herein to mean, and is used interchangeably with, the term "and/or," unless context clearly indicates otherwise.

The term "such as" is used herein to mean, and is used interchangeably, with the phrase "such as but not limited to."

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the term "subject" refers to human and non-human animals, including veterinary subjects. The term "non-human animal" includes all vertebrates, e.g., mammals and non-mammals, such as non-human primates, mice, rabbits, sheep, dog, cat, horse, cow, chickens, amphibians, and reptiles. In a preferred embodiment, the subject is a human and may be referred to as a patient.

As used herein, the terms "treat," "treating" or "treatment" refer, preferably, to an action to obtain a beneficial or desired clinical result including, but not limited to, alleviation or amelioration of one or more signs or symptoms of a disease or condition, diminishing the extent of disease, stability (i.e., not worsening) state of disease, amelioration or palliation of the disease state, diminishing rate of or time to progression, and remission (whether partial or total), whether detectable or undetectable. "Treatment" can also mean prolonging survival as compared to expected survival in the absence of treatment. Treatment does not need to be curative.

A "therapeutically effective amount" is that amount sufficient to treat a disease in a subject. A therapeutically effective amount can be administered in one or more administrations.

By "diagnosing" and the like, as used herein, refers to a clinical or other assessment of the condition of a subject based on observation, testing, or circumstances for identifying a subject having a disease, disorder, or condition based on the presence of at least one indicator, such as a sign or symptom of the disease, disorder, or condition. Typically, diagnosing using the method of the invention includes the observation of the subject for multiple indicators of the disease, disorder, or condition in conjunction with the methods provided herein. Diagnostic methods provide an indicator that a disease is or is not present. A single diagnostic test typically does not provide a definitive conclusion regarding the disease state of the subject being tested.

The terms "administer," "administering" or "administration" include any method of delivery of a pharmaceutical composition or agent into a subject's system or to a particular region in or on a subject. In certain embodiments of the invention, an agent is administered intravenously, intramuscularly, subcutaneously, intradermally, intranasally, orally, transcutaneously, or mucosally. In a preferred embodiment, an agent is administered intravenously. Administering an agent can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, intratumoral delivery, etc.

As used herein, the term "survival" refers to the continuation of life of a subject which has been treated for a disease or condition, e.g., cancer. The time of survival can be defined from an arbitrary point such as time of entry into a clinical trial, time from completion or failure or an earlier treatment regimen, time from diagnosis, etc.

As used herein, the term "recur" refers to the re-growth of tumor or cancerous cells in a subject in whom primary treatment for the tumor has been administered. The tumor may recur in the original site or in another part of the body. In one embodiment, a tumor that recurs is of the same type as the original tumor for which the subject was treated. For example, if a subject had an ovarian cancer tumor, was treated and subsequently developed another ovarian cancer tumor, the tumor has recurred. In addition, a cancer can recur in or metastasize to a different organ or tissue than the one where it originally occurred.

As used herein, the terms "identify" or "select" refer to a choice in preference to another. In other words, to identify a subject or select a subject is to perform the active step of picking out that particular subject from a group and confirming the identity of the subject by name or other distinguishing feature.

As used herein, the term "benefit" refers to something that is advantageous or good, or an advantage. Similarly, the term "benefiting," as used herein, refers to something that improves or advantages. For example, a subject will benefit from treatment if they exhibit a decrease in at least one sign or symptom of a disease or condition (e.g., tumor shrinkage, decrease in tumor burden, inhibition or decrease of metastasis, improving quality of life ("QOL"), if there is a delay of time to progression ("TTP"), if there is an increase of overall survival ("OS"), etc.), or if there is a slowing or stopping of disease progression (e.g., halting tumor growth or metastasis, or slowing the rate of tumor growth or metastasis). A benefit can also include an improvement in quality of life, or an increase in survival time or progression free survival.

The terms "cancer" or "tumor" are well known in the art and refer to the presence, e.g., in a subject, of cells possessing characteristics typical of cancer-causing cells, such as uncontrolled proliferation, immortality, metastatic potential, rapid growth and proliferation rate, decreased cell death/apoptosis, and certain characteristic morphological features. Cancer cells are often in the form of a solid tumor. However, cancer also includes non-solid tumors, e.g., blood tumors, e.g., leukemia, wherein the cancer cells are derived from bone marrow. As used herein, the term "cancer" includes pre-malignant as well as malignant cancers. Cancers include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, Burkitt's lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin, and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer, and Wilms' tumor. Other cancers include primary cancer, metastatic cancer, oropharyngeal cancer, hypopharyngeal cancer, liver cancer, gall bladder cancer, bile duct cancer, small intestine cancer, urinary tract cancer, kidney cancer, urothelium cancer, female genital tract cancer, uterine cancer, gestational trophoblastic disease, male genital tract cancer, seminal vesicle cancer, testicular cancer, germ cell tumors, endocrine gland tumors, thyroid cancer, adrenal cancer, pituitary gland cancer, hemangioma, sarcoma arising from bone and soft tissues, Kaposi's sarcoma, nerve cancer, ocular cancer, meningial cancer, glioblastomas, neuromas, neuroblastomas, Schwannomas, solid tumors arising from hematopoietic malignancies such as leukemias, metastatic melanoma, recurrent or persistent ovarian epithelial cancer, fallopian tube cancer, primary peritoneal cancer, gastrointestinal stromal tumors, colorectal cancer, gastric cancer, melanoma, glioblastoma multiforme, non-squamous non-small-cell lung cancer, malignant glioma, epithelial ovarian cancer, primary peritoneal serous cancer, metastatic liver cancer, neuroendocrine carcinoma, refractory malignancy, triple negative breast cancer, HER2-amplified breast cancer, nasopharageal cancer, oral cancer, biliary tract, hepatocellular carcinoma, squamous cell carcinomas of the head and neck (SCCHN), non-medullary thyroid carcinoma, recurrent glioblastoma multiforme, neurofibromatosis type 1, CNS cancer, liposarcoma, leiomyosarcoma, salivary gland cancer, mucosal melanoma, acral/lentiginous melanoma, paraganglioma, pheochromocytoma, advanced metastatic cancer, solid tumor, triple negative breast cancer, colorectal cancer, sarcoma, melanoma, renal carcinoma, endometrial cancer, thyroid cancer, rhabdomysarcoma, multiple myeloma, ovarian cancer, glioblastoma, gastrointestinal stromal tumor, mantle cell lymphoma, and refractory malignancy.

"Solid tumor," as used herein, is understood as any pathogenic tumor that can be palpated or detected using imaging methods as an abnormal growth having three dimensions. A solid tumor is differentiated from a blood tumor such as leukemia. However, cells of a blood tumor are derived from bone marrow; therefore, the tissue producing the cancer cells is a solid tissue that can be hypoxic.

"Tumor tissue" is understood as cells, extracellular matrix, and other naturally occurring components associated with the solid tumor.

As used herein, the term "isolated" refers to a preparation that is substantially free (e.g., 50%, 60%, 70%, 80%, 90% or more, by weight) from other proteins, nucleic acids, or compounds associated with the tissue from which the preparation is obtained.

The term "sample" as used herein refers to a collection of similar fluids, cells, or tissues isolated from a subject. The term "sample" includes any body fluid (e.g., urine, serum, blood fluids, lymph, gynecological fluids, cystic fluid, ascetic fluid, ocular fluids, and fluids collected by bronchial lavage and/or peritoneal rinsing), ascites, tissue samples (e.g., tumor samples) or a cell from a subject. Other subject samples include tear drops, serum, cerebrospinal fluid, feces, sputum, and cell extracts. In one embodiment, the sample is removed from the subject. In a particular embodiment, the sample is urine or serum. In another embodiment, the sample does not include ascites or is not an ascites sample. In another embodiment, the sample does not include peritoneal fluid or is not peritoneal fluid. In one embodiment, the sample comprises cells. In another embodiment, the sample does not comprise cells. Samples are typically removed from the subject prior to analysis. However, tumor samples can be analyzed in the subject, for example, using imaging or other detection methods.

The term "control sample," as used herein, refers to any clinically relevant comparative sample, including, for example, a sample from a healthy subject not afflicted with cancer, a sample from a subject having a less severe or slower progressing cancer than the subject to be assessed, a sample from a subject having some other type of cancer or disease, a sample from a subject prior to treatment, a sample of non-diseased tissue (e.g., non-tumor tissue), a sample from the same origin and close to the tumor site, and the like. A control sample can be a purified sample, protein, and/or nucleic acid provided with a kit. Such control samples can be diluted, for example, in a dilution series to allow for quantitative measurement of analytes in test samples. A control sample may include a sample derived from one or more subjects. A control sample may also be a sample made at an earlier time point from the subject to be assessed. For example, the control sample could be a sample taken from the subject to be assessed before the onset of the cancer, at an earlier stage of disease, or before the administration of treatment or of a portion of treatment. The control sample may also be a sample from an animal model, or from a tissue or cell lines derived from the animal model, of the cancer. The level in a control sample that consists of a group of measurements may be determined, e.g., based on any appropriate statistical measure, such as, for example, measures of central tendency including average, median, or modal values.

As used herein, the term "obtaining" is understood herein as manufacturing, purchasing, or otherwise coming into possession of.

As used herein, the term "identical" or "identity" is used herein in relation to amino acid or nucleic acid sequences refers to any gene or protein sequence that bears at least 30% identity, more preferably 40%, 50%, 60%, 70%, 75%, 80%, 81%, 82%, 83%, 84%, 85%, 86%, 87%, 88%, 89%, 90%, 91%, 92%, 93%, 94%, and most preferably 95%, 96%, 97%, 98%, 99% or more identity to a known gene or protein sequence over the length of the comparison sequence. Protein or nucleic acid sequences with high levels of identity throughout the sequence can be said to be homologous. A "homologous" protein can also have at least one biological activity of the comparison protein. In general, for proteins, the length of comparison sequences will be at least 10 amino acids, preferably 10, 20, 30, 40, 50, 60, 70, 80, 90, 100, 150, 175, 200, 250, or at least 300 amino acids or more. For nucleic acids, the length of comparison sequences will generally be at least 25, 50, 100, 125, 150, 200, 250, 300, 350, 400, 450, 500, 550, 600, 650, 700, 800, or at least 850 nucleotides or more.

As used herein, "detecting," "detection" and the like are understood that an assay performed for identification of a specific analyte in a sample. The amount of analyte or activity detected in the sample can be none or below the level of detection of the assay or method.

The terms "modulate" or "modulation" refer to upregulation (i.e., activation or stimulation), downregulation (i.e., inhibition or suppression) of a level, or the two in combination or apart. A "modulator" is a compound or molecule that modulates, and may be, e.g., an agonist, antagonist, activator, stimulator, suppressor, or inhibitor.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, or protein, or both.

The terms "level of expression of a gene" or "gene expression level" refer to the level of mRNA, as well as pre-mRNA nascent transcript(s), transcript processing intermediates, mature mRNA(s) and degradation products, or the level of protein, encoded by the gene in the cell.

As used herein, "level of activity" is understood as the amount of protein activity, typically enzymatic activity, as determined by a quantitative, semi-quantitative, or qualitative assay. Activity is typically determined by monitoring the amount of product produced in an assay using a substrate that produces a readily detectable product, e.g., colored product, fluorescent product, or radioactive product.

As used herein, "changed as compared to a control" sample or subject is understood as having a level of the analyte or diagnostic or therapeutic indicator (e.g., marker) to be detected at a level that is statistically different than a sample from a normal, untreated, or control sample control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g., β-galactosidase or luciferase). Depending on the method used for detection the amount and measurement of the change can vary. Changed as compared to a control reference sample can also include a change in one or more signs or symptoms associated with or diagnostic of disease, e.g., cancer. Determination of statistical significance is within the ability of those skilled in the art, e.g., the number of standard deviations from the mean that constitute a positive result.

"Elevated" or "lower" refers to a patient's value of a marker relative to the upper limit of normal ("ULN") or the lower limit of normal ("LLN") which are based on historical normal control samples. As the level of the marker present in the subject will be a result of the disease, and not a result of treatment, typically a control sample obtained from the patient prior to onset of the disease will not likely be available. Because different labs may have different absolute results, values are presented relative to that lab's upper limit of normal value (ULN).

The "normal" level of expression of a marker is the level of expression of the marker in cells of a subject or patient not afflicted with cancer. In one embodiment, a "normal" level of expression refers to the level of expression of the marker under normoxic conditions.

An "over-expression" or "high level of expression" of a marker refers to an expression level in a test sample that is greater than the standard error of the assay employed to assess expression, and is preferably at least 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 4, 5, 6, 7, 8, 9, or 10 times the expression level of the marker in a control sample (e.g., sample from a healthy subject not having the marker associated disease, i.e., cancer). In one embodiment, expression of a marker is compared to an average expression level of the marker in several control samples.

A "low level of expression" or "under-expression" of a marker refers to an expression level in a test sample that is less than at least 0.9, 0.8, 0.7, 0.6, 0.5, 0.4, 0.3, 0.2, or 0.1 times the expression level of the marker in a control sample (e.g., sample from a healthy subject not having the marker associated disease, i.e., cancer). In one embodiment, expression of a marker is compared to an average expression level of the marker in several control samples.

As used herein, "binding" is understood as having at least a $10^2$ or more, $10^3$ or more, preferably $10^4$ or more, preferably $10^5$ or more, preferably $10^6$ or more preference for binding to a specific binding partner as compared to a non-specific binding partner (e.g., binding an antigen to a sample known to contain the cognate antibody).

"Determining" as used herein is understood as performing an assay or using a diagnostic method to ascertain the state of someone or something, e.g., the presence, absence, level, or degree of a certain condition, biomarker, disease state, or physiological condition.

"Prescribing" as used herein is understood as indicating a specific agent or agents for administration to a subject.

As used herein, the terms "respond" or "response" are understood as having a positive response to treatment with a therapeutic agent, wherein a positive response is understood as having a decrease in at least one sign or symptom of a disease or condition (e.g., tumor shrinkage, decrease in tumor burden, inhibition or decrease of metastasis, improving quality of life ("QOL"), delay of time to progression ("TTP"), increase of overall survival ("OS"), etc.), or slowing or stopping of disease progression (e.g., halting tumor growth or metastasis, or slowing the rate of tumor growth or metastasis). A response can also include an improvement in quality of life, or an increase in survival time or progression free survival.

The terms "administer," "administering" or "administration" can include any method of delivery of a pharmaceutical composition or agent into a subject's system or to a particular region in or on a subject. In certain embodiments of the invention, an Hsp90 inhibitor is administered intravenously, intramuscularly, subcutaneously, intradermally, intranasally, orally, transcutaneously, or mucosally. In a preferred embodiment, an agent is administered intravenously. Administering can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, intratumoral delivery, etc.

As used herein, the term "high concentration" refers to the concentration of SDC-TRAP that accumulates in target cells of the invention due to the selective binding of the binding moiety of the SDC-TRAP to the target protein. In one embodiment, the concentration is higher than in similar cells that do not overexpress the target protein, e.g., lung cancer cells as compared to non-cancerous lung cells. In another embodiment, the concentration is higher in target cells compared to cells that do not express, or overexpress, the target protein. In exemplary embodiments, the high concentration is 1.5, 2, 3, 4, 5, 10, 15, 20, 50, 100, 1000 times or more than cells that are not targeted by the SDC-TRAP molecules of the invention.

The term "moiety" refers generally to a portion of a molecule, which may be a functional group, a set of functional groups, and/or a specific group of atoms within a molecule, that is responsible for a characteristic chemical, biological, and/or medicinal property of the molecule.

The term "binding moiety" refers to low molecular weight (e.g., less than about 800, 700, 600, 500, 400, 300, 200, or 100 etc. Dalton) organic compounds, which may serve as a therapeutic or a regulator of a biological process. Binding moieties include molecules that can bind to a biopolymer such as protein, nucleic acid, or polysaccharide and acts as an effector, altering the activity or function of the biopolymer. Binding moieties can have a variety of biological functions, serving as cell signaling molecules, as tools in molecular biology, as drugs in medicine, as pesticides in farming, and in many other roles. These compounds can be natural (such as secondary metabolites) or artificial (such as antiviral drugs); they may have a beneficial effect against a disease (such as drugs) or may be detrimental (such as teratogens and carcinogens). Biopolymers such as nucleic acids, proteins, and polysaccharides (such as starch or cellulose) are not binding moieties, although their constituent monomers—ribo- or deoxyribo-nucleotides, amino acids, and monosaccharides, respectively—are often considered to be. Small oligomers are also usually considered binding moieties, such as dinucleotides, peptides such as the antioxidant glutathione, and disaccharides such as sucrose.

As used herein, a "protein interacting binding moiety" or "binding moiety" refers to a binding moiety, or portion thereof, that interacts with a predetermined target. The interaction is achieved through some degree of specificity and/or affinity for the target. Both specificity and affinity is generally desirable, although in certain cases higher specificity may compensate for lower affinity and higher affinity may compensate for lower specificity. Affinity and specificity requirements will vary depending upon various factors including, but not limited to, absolute concentration of the target, relative concentration of the target (e.g., in cancer vs. normal cells), potency and toxicity, route of administration, and/or diffusion or transport into a target cell. The target can be a molecule of interest and/or localized in an area of interest. For example, the target can be a therapeutic target and/or localized in an area targeted for a therapy (e.g., a protein that is overexpressed in cancerous cells, as compared to normal cells). In one particular example, a target can be a chaperonin protein such as Hsp90 and the binding moiety can be an Hsp90 binding moiety (e.g., therapeutic, cytotoxic, or imaging moiety). Preferentially, the binding moiety will enhance, be compatible with, or not substantially reduce, passive transport of a conjugate including the binding moiety into a cell, e.g., a cell comprising a target protein.

The term "effector moiety" refers to a molecule, or portion thereof, that has an effect on a target and/or proximally to the target. In various preferred embodiments, the effector moiety is a binding moiety, or portion thereof. An effect can include, but is not limited to, a therapeutic effect, an imaging effect, and/or a cytotoxic effect. At a molecular or cellular level, an effect can include, but is not limited to, promotion or inhibition of the target's activity, labeling of the target, and/or cell death. Preferentially, the effector moiety will enhance, be compatible with, or not substantially reduce, passive transport of a conjugate including the effector moiety into a cell comprising a target. Different effector moieties can be used together and therapeutics in accordance with the present invention may include more than one effector moiety (e.g., two or more different (or same) effector moieties in a single therapeutic in accordance with the present invention, two or more different therapeutics in accordance with the present invention including different effector moieties).

In some embodiments, the effector moiety is selected from the group consisting of peptidyl-prolyl isomerase ligands; rapamycin, cyclosporin A; steroid hormone receptor ligands, antimitotic agents, actin binding agents, camptothecins, topotecan, combretastatins, capecitabine, gemcitabine, vinca alkaloids, platinum-containing compounds, metformin, HDAC inhibitors, thymidylate synthase inhibitors; nitrogen mustards; 5-fluorouracil (5-FU) and its derivatives, or a combination thereof.

In some embodiments, the effector moiety is selected from the group consisting of FK506; rapamycin, cyclosporin A, estrogen, progestin, testosterone, taxanes, colchicine, colcemid, nocadozole, vinblastine, vincristine, cytochalasin, latrunculin, phalloidin, lenalidomide, pomalidomide, SN-38, topotecan, combretastatins, capecitabine, gemcitabine, vinca alkaloids, metformin, suberoylanilidehydroxamic acid (SAHA), methotrexate, pemetrexed, raltitrexed, bendamustine, melphalan; 5-fluorouracil (5-FU), vedotin and DM1, or a combination thereof.

The term "small molecule drug conjugate that is trapped intracellularly" or "binding moiety drug conjugate that is trapped intracellularly" or "SDC-TRAP" refers to a binding moiety and effector moiety joined to one another, or acting as if joined to one another. A binding moiety and effector moiety can be joined through essentially any chemical or physical force, either directly (e.g., binding moiety and effector moiety viewed as two moieties on the same molecule, or a single moiety having both functions) or through an intermediate (e.g., linker). For example, a binding moiety and effector moiety can be joined by one or more covalent bonds, ionic bonds, hydrogen bonds, the hydrophobic effect, dipole-dipole forces, ion-dipole forces, dipole-induced dipole forces, instantaneous dipole-induced dipole forces, and/or combinations thereof. Preferentially, the SDC-TRAP will be capable of passive and/or active transport into a cell comprising a target. Moreover, SDC-TRAP molecules of the invention may comprise multiple effector molecules conjugated to the binding moiety.

The term "linker" or "linking moiety," as used herein in the context of binding moiety, effector moieties, and/or SDC-TRAPs refers to a chemical moiety that joins two other moieties (e.g., a binding moiety and an effector moiety). A linker can covalently join a binding moiety and an effector moiety. A linker can include a cleavable linker, for example an enzymatically cleavable linker. A linker can include a disulfide, carbamate, amide, ester, and/or ether linkers.

As used herein, a "ligand" is a substance (e.g., a binding moiety) that can form a complex with a biomolecule. The ligand and/or formation of the ligand-biomolecule complex can have a biological or chemical effect, such as a therapeutic effect, cytotoxic effect, and/or imaging effect.

As used herein, a "prodrug" is a pharmacological substance that is administered in an inactive or less than fully active form and that is subsequently converted to an active pharmacological agent (i.e., the drug) through a metabolic processes. Prodrugs can be used to improve how the intended drug is absorbed, distributed, metabolized, and/or excreted. A prodrug may also be used to improve how selectively the intended drug interacts with cells or processes that are not its intended target (e.g., to reduce adverse or unintended effects of the intended drug, for example a chemotherapy drug).

The phrase "Hsp90 ligand or a prodrug thereof" refers generally to molecules that bind to and in some cases effect Hsp90, and inactive forms (i.e., prodrugs) thereof. An Hsp90 ligand can be an "Hsp90 inhibitor," which is understood as a therapeutic agent that reduces the activity of Hsp90 either by directly interacting with Hsp90 or by, for example, preventing the formation of the Hsp90/CDC37 complex such that the expression and proper folding of at least one client protein of Hsp90 is inhibited. "Hsp90" includes each member of the family of heat shock proteins having a mass of about 90-kilodaltons. For example, in humans the highly conserved Hsp90 family includes cytosolic Hsp90$^\alpha$ and Hsp90$^\beta$ isoforms, as well as GRP94, which is found in the endoplasmic reticulum, and HSP75/TRAP1, which is found in the mitochondrial matrix. As used herein, Hsp90 inhibitors include, but are not limited to ganetespib, geldanamycin (tanespimycin), e.g., IPI-493, macbecins, tripterins, tanespimycins, e.g., 17-AAG (alvespimycin), KF-55823, radicicols, KF-58333, KF-58332, 17-DMAG, IPI-504, BIIB-021, BIIB-028, PU-H64, PU-H71, PU-DZ8, PU-HZ151, SNX-2112, SNX-2321, SNX-5422, SNX-7081, SNX-8891, SNX-0723, SAR-567530, ABI-287, ABI-328, AT-13387, NSC-113497, PF-3823863, PF-4470296, EC-102, EC-154, ARQ-250-RP, BC-274, VER-50589, KW-2478, BHI-001, AUY-922, EMD-614684, EMD-683671, XL-888, VER-51047, KOS-2484, KOS-2539, CUDC-305, MPC-3100, CH-5164840, PU-DZ13, PU-HZ151, PU-DZ13, VER-82576, VER-82160, VER-82576, VER-82160, NXD-30001, NVP-HSP990, SST-0201CL1, SST-0115AA1, SST-0221AA1, SST-0223AA1, novobiocin (a C-terminal Hsp90i, herbinmycin A, radicicol, CCT018059, PU-H71, or celastrol.

The term "therapeutic moiety" refers to molecule, compound, or fragment thereof that is used for the treatment of a disease or for improving the well-being of an organism or that otherwise exhibit healing power (e.g., pharmaceuticals, drugs, and the like). A therapeutic moiety can be a chemical, or fragment thereof, of natural or synthetic origin used for its specific action against disease, for example cancer. Therapeutic agents used for treating cancer may be called chemotherapeutic agents. As described herein, a therapeutic moiety is preferentially a small molecule. Exemplary small molecule therapeutics include those that are less than 800 Daltons, 700 Daltons, 600 Daltons, 500 Daltons, 400 Daltons, or 300 Daltons.

The term "cytotoxic moiety" refers to molecule, compound, or fragment thereof that has a toxic or poisonous effect on cells, or that kills cells. Chemotherapy and radiotherapy are forms of cytotoxic therapy. Treating cells with a cytotoxic moiety can produce a variety of results—cells may undergo necrosis, stop actively growing and dividing, or activate a genetic program of controlled cell death (i.e., apoptosis). Examples of cytotoxic moieties include, but are not limited to, SN-38, bendamustine, VDA, doxorubicin, pemetrexed, vorinostat, lenalidomide, irinotecan, ganetespib, docetaxel, 17-AAG, 5-FU, abiraterone, crizotinib, KW-2189, BUMB2, DC1, CC-1065, adozelesin, or fragment(s) thereof.

The term "imaging moiety" refers to a molecule, compound, or fragment thereof that facilitates a technique and/or process used to create images or take measurements of a cell, tissue, and/or organism (or parts or functions thereof) for clinical and/or research purposes. An imaging moiety can produce, for example, a signal through emission and/or interaction with electromagnetic, nuclear, and/or mechanical (e.g., acoustic as in ultrasound) energy. An imaging moiety can be used, for example, in various radiology, nuclear medicine, endoscopy, thermography, photography, spectroscopy, and microscopy methods.

"Pharmaceutical conjugate" refers to a non-naturally occurring molecule that includes a binding moiety (e.g., an Hsp90-targeting moiety) associated with an effector moiety, where these two components may also be covalently bonded to each other either directly or through a linking group.

The term "drug" refers to any active agent that affects any biological process. Active agents that are considered drugs for purposes of this application are agents that exhibit a pharmacological activity. Examples of drugs include active agents that are used in the prevention, diagnosis, alleviation, treatment or cure of a disease condition.

By "pharmacologic activity" is meant an activity that modulates or alters a biological process so as to result in a phenotypic change, e.g., cell death, cell proliferation etc.

By "pharmacokinetic property" is meant a parameter that describes the disposition of an active agent in an organism or host.

By "half-life" is meant the time for one-half of an administered drug to be eliminated through biological processes, e.g., metabolism, excretion, etc.

The term "efficacy" refers to the effectiveness of a particular active agent for its intended purpose, i.e., the ability of a given active agent to cause its desired pharmacologic effect.

Binding Moiety-Effector Moiety Drug Conjugates that are Trapped Intracellularly (SDC-TRAPs)

The present invention provides SDC-TRAPs, as well as SDC-TRAP compositions, kits, and methods of use thereof. SDC-TRAPs include a binding moiety (e.g., a binding moiety such as a ligand) conjugated to an effector moiety (e.g., a pharmacological agent such as a drug or imaging agent). These two moieties can be joined by a linker, e.g., a covalently-bonded linking group. SDC-TRAPs are useful in a variety of therapeutic, imaging, diagnostic, and/or research applications. In one illustrative example of cancer therapy, an SDC-TRAP can be a pharmaceutical conjugate of an Hsp90-binding moiety such as an Hsp90 ligand or inhibitor associated with an effector moiety such as a therapeutic or cytotoxic agent.

In various embodiments, an SDC-TRAP can be further characterized in that the binding moiety (e.g., targeting moiety) and effector moiety are different, such that the pharmaceutical conjugate may be viewed as a heterodimeric compound produced by the joining of two different moieties. In terms of function, SDC-TRAP molecules have a targeting functionality and effector functionality (e.g., therapeutic, imaging, diagnostic). These functions are provided by corresponding chemical moieties that can be different (or, in some cases, the same). SDC-TRAPs can include any one or more binding moieties conjugated to any one or more effector moieties. In some embodiments, a composition or method can include a combination of two or more binding moeities and/or two or more effector moieties (e.g., a combination therapy and/or multi target therapy) embodied in one or more different types of SDC-TRAPs.

In various embodiments, an SDC-TRAP is further characterized by its ability to passively diffuse and/or be actively transported into a target cell of interest. The diffusion and/or transport properties of the SDC-TRAP can be derived, at least in part, from ionic, polar, and/or hydrophobic properties of the SDC-TRAP. In preferred embodiments, the SDC-TRAP enter cells primarily by passive diffusion. The diffusion and/or transport properties of the SDC-TRAP can be derived, at least in part, from the molecular weight of the SDC-TRAP, the binding moiety, the effector moiety, and/or the similarity in weight between the binding moiety and the effector moiety. SDC-TRAPs are desirably small, such as in comparison to antibody-drug conjugates ("ADCs"). For example, the molecular weight of an SDC-TRAP can be less than about 1600, 1500, 1400, 1300, 1200, 1100, 1000, 900, 800, 700, 600, 500, or 400 Daltons. A binding moiety and an effector moiety can each be less than about 1000, 900, 800, 700, 600, 500, 400, 300, or 200 Daltons. A binding moiety and an effector moiety can be approximately equal in size (e.g., differ in weight by less than 400, 350, 300, 250, 200, 150, 100, or 50 Daltons).

Delivery of an effector molecule by an SDC-TRAP can result in greater potency compared to administering an untargeted drug comprising the same effector moiety, for example, because the SDC-TRAP can be localized at a desired target for an extended period of time through the association of a binding moiety and its target. Such localization can cause an effector moiety to be active and/or released in a target cell and/or tissue over an extended period of time. This resonance time can be selected through deliberate design of a linker moiety. In contrast, administration of the drug by itself in vivo can be more apt to have a shorter resonance time in a given target cell and/or tissue—if it traverses into the cell at all—due to the lack of an "anchor" within the cell.

SDC-TRAPs, in part because they comprise a targeting moiety and are relatively small in size, can be efficiently taken up or internalized by a target cell. Conversely, uptake or internalization is relatively inefficient for ADCs, which must deal with limited antigen expression and relatively inefficient internalization mechanisms for the antibody portion of the molecule. Hsp90 provides a good illustrative example of a difference between SDC-TRAPs and conventional ADCs. By way of comparison, the localization rate of radiolabeled monoclonal antibodies at a tumor in patients is low, on the order of 0.003-0.08% of the injected dose/g tumor. In contrast, a much higher accumulation rate (15-20% injected dose/g tumor) has been measured for SDC-TRAPs in mouse tumor xenografts.

SDC-TRAP pharmaceutical conjugates in accordance with the present invention can represent a significant advance over the state of the art in targeted drugs. SDC-TRAPs have broad application in many therapeutic, imaging, and diagnostic application. As discussed above, SDC-TRAPs are advantageously small in comparison to ADCs, enabling better penetration of solid tumors and more rapid clearance from normal tissues (e.g., reduced toxicity). The design of SDC-TRAPs (e.g., a structure-property relationship) can be established using methods and rationales within the grasp of those of ordinary skill in the art, and companion imaging diagnostics for targeted therapies may also easily be provided, in view of the simpler chemistry involved.

SDC-TRAPs of the invention are characterized by selective targeting of SDC-TRAPs to target cells in which a target protein is overexpressed. This leads to high intracellular concentrations of SDC-TRAP molecules in target cells as compared to non-targeted cells. Likewise, SDC-TRAPs of the invention are characterized by low concentrations of SDC-TRAP in non-targeted cells.

One illustrative embodiment involves a conjugate of an Hsp90 binding moiety linked to a chelator (i.e., the effector moiety, for metals such as In or Gd, which conjugate may function as an imaging agent for the cells/tissues targeted by the conjugate). Another, illustrative embodiment involves a conjugate of an Hsp90 binding moiety linked to a chemotherapeutic (i.e., the effector moiety, for example, SN-38). Alternatively, an illustrative SDC-TRAP is contemplated wherein an Hsp90 targeting moiety bearing radiolabeled halogen (e.g., such as an iodine isotope) can serve to image the cells/tissues targeted by the conjugate, and the effector moiety can be drug to treat the targeted cells/tissues. The progression of treatment may therefore be determined by imaging the tissues being treated and reviewing the images for the presence or absence of the labeled conjugate. Such embodiments are readily adaptable to essentially any cancer, or other chemotherapeutic target. Molecular targets (e.g., interacting with a binding moiety) used to target a particular cell or tissue can be selected based upon their presence in the target cell or tissue and/or their relative abundance in the target cell or tissue (e.g., disease-related versus normal cells).

SDC-TRAP molecules of the present invention represent a new class of drugs. One particular advantage of SDC-TRAPs is that they can be designed to selectively deliver an effector moiety (e.g., a chemotherapeutic drug) into a targeted cell because of the relative overexpression or presence of a binding moiety's molecular target in the cell. After the binding moiety binds the molecular target, the effector moiety is thereafter available (e.g., through cleavage of a linker moiety joining the binding moiety and the effector moiety) to act upon the cell. Accordingly, SDC-TRAPs employ a different mechanism from strategies currently used in the art, for example delivering an Hsp90 inhibitor to a cell using HPMA copolymer-Hsp90i conjugates, Hsp90i prodrugs, nanoparticle-Hsp90i conjugates, or micellar methodologies.

SDC-TRAPs can also described by the formula:

Binding moiety-L-E where "binding moiety" is a protein interacting binding moiety; L is a conjugation or linking moiety (e.g., a bond or a linking group); and E is an effector moiety. These elements are discussed in the context of additional illustrative examples below. However, while features of each element may be discussed separately, design and selection of an SDC-TRAP can involve the interplay and/or cumulative effect of features of each element (e.g., diffusion, binding, and effect).

Once SDC-TRAP molecules of the invention enter a target cell the effector molecule is released from the SDC-TRAP. In one embodiment, the effector molecule has no activity until it is released from the SDC-TRAP. Accordingly, once the SDC-TRAP molecules enter a target cell an equilibrium exists between free and bound SDC-TRAP molecules. In one embodiment, the effector moiety is only released from the SDC-TRAP when the SDC-TRAP is not associated with the target protein. For example, when an SDC-TRAP molecule is not bound intracellular enzymes can access the linker region thereby freeing the effector moiety. Alternatively, when free SDC-TRAP molecules may be able to release effector molecules through, for example, hydrolysis of the bond or linker that connects the binding moiety and effector moiety.

Accordingly, the rate of effector molecule release and the amount of effector molecule released can be controlled by using binding moieties that bind to the target protein with different affinities. For example, binding moieties that bind to the target protein with lower affinity will be free, resulting in higher concentrations of unbound intracellular SDC-TRAP, and thereby resulting in higher concentrations of free effector molecule. Therefore, in at least one embodiment, irreversibly-binding binding moieties are incompatible with certain aspects of the invention, e.g., those embodiments where effector molecule release is based on free intracellular SDC-TRAP molecules.

In one embodiment, SDC-TRAPs have favorable safety profiles, for example, when compared to, for example, the binding moiety or effector molecule alone. One reason for the increased safety profile is the rapid clearance of SDC-TRAP molecules that do not enter into a target cell.

A number of exemplary SDC-TRAP molecules are set forth in the examples. Specifically a number of Hsp90-specific SDC-TRAP molecules are described and used to demonstrate the efficacy of SDC-TRAP molecules.

Binding Moieties

A primary role of a binding moiety is to ensure that the SDC-TRAP delivers its payload—the effector moiety—to its target by binding to a molecular target in or on a target cell or tissue. In this respect, it is not necessary that the binding moiety also have an effect on the target (e.g., in the case of an Hsp90-targeting moiety, to inhibit Hsp90 in the manner that Hsp90is are known to do, that is, exhibit pharmacological activity or interfere with its function), but in some embodiments, the binding moiety does have an effect on the target. Accordingly, in various embodiments, an activity of the SDC-TRAP is due solely to the effector moiety exerting a pharmacological effect on the target cell(s), which has been better facilitated by the pharmaceutical conjugate targeting the target cell(s). In other embodiments, an activity of the SDC-TRAP is due in part to the binding moiety—that is, the binding moiety can have an effect beyond targeting.

The molecular target of a binding moiety may or may not be part of a complex or structure of a plurality of biological molecules, e.g., lipids, where the complexes or structures may include lipoproteins, lipid bilayers, and the like. However, in many embodiments, the molecular target to which the binding moiety binds will be free (e.g., cytoplasmic globular protein and/or not be part of a macromolecular assembly or aggregation). The present invention can exploit the selectively high presence of a molecular target in locations of high physiological activity (e.g., Hsp90 in oncological processes). For example, where a drug target is an intracellular drug target, a corresponding molecular target (e.g., Hsp90) can be present in the cell. Likewise, where a drug target is an extracellular drug target, a corresponding molecular target (e.g., Hsp90) can be extracellular, proximal, or associated with the extracellular cell membrane of the target cell or tissue.

In various embodiments, a binding moiety can effect a target cell or tissue (e.g., in the case of an Hsp90-targeting moiety that in fact inhibits Hsp90, for example, Hsp90i). In such embodiments, a pharmacological activity of the binding moiety contributes to, complements, or augments, the pharmacological activity of the effector moiety. Such embodiments go beyond the advantages combination therapies (e.g., a cancer combination therapy of Hsp90i and a second drug such as ganetespib or crizotinib) by providing a therapy that can be carried out by administration of a single SDC-TRAP that realizes both the benefits of the combination therapy and targeting. Other examples of such SDC-TRAPs include conjugates of an Hsp90i (such as ganetespib) and a second cancer drug such as docetaxel or paclitaxel (e.g., in NSCLC); BEZ235 (e.g., in melanoma, prostate and/or NSCLC); temsirolimus (e.g., renal cell carcinoma (RCC), colon, breast and/or NSCLC); PLX4032 (e.g., in melanoma); cisplatin (e.g., colon, breast cancer); AZD8055 (e.g., in NSCLC); and crizotinib (e.g., ALK+ NSCLC).

A range of pharmaceutical activities can be achieved by judicious selection of a binding moiety and an effector moiety. For example, for treating solid tumors, e.g., colon cancer, high continuous doses of antimetabolites such as capecitabine or gemcitabine tend to be required in combination with other drugs. A conjugate having an Hsp90-targeting moiety with lower binding affinity or inhibitory activity to Hsp90, e.g., as determined by a HER2 degradation assay, can be designed to meet this need. Such a conjugate can comprise an effector moiety that is a strong, potent antimetabolite such as 5-FU, to afford a high dose of the conjugate that may be dosed relatively frequently. Such an approach not only achieves the aim of providing a high dose of an antimetabolite fragment at the tumor, but also lowers the toxicity of administering the drug on its own, owing to the plasma stability of SDC-TRAPs of the invention, and the ability of the Hsp90-targeting moiety to deliver the antimetabolite to the desired cells or tissues.

In embodiments where solid tumors such as SCLC or colorectal cancer are to be treated with drugs such as topotecan or irinotecan, only low doses of the drug may be dosed. Due to the very high intrinsic activity of these drugs, an SDC-TRAP should be designed to provide a low dose of such drugs at the target tissue. In this scenario, for example, an Hsp90-targeting moiety having a higher binding affinity or inhibitory activity to Hsp90 (e.g., as determined by a HER2 degradation assay) can sufficiently maintain the presence of the drug in the tissue at a very high level, to ensure that enough of the drug reaches and is retained by the desired target tissue due to the low dosing.

In various illustrative embodiments where a molecular target of a binding moiety is Hsp90, the binding moiety can be an Hsp90-targeting moiety, for example a triazole/resorcinol-based compound that binds Hsp90, or a resorcinol amide-based compound that binds Hsp90, e.g., ganetespib, AUY-922 or AT-13387. In another embodiment, the binding moiety may advantageously be an Hsp90-binding compound of formula (I):

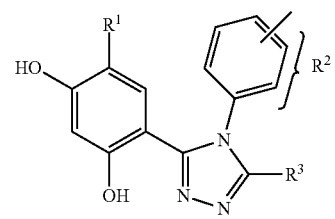

Formula I wherein
$R^1$ may be alkyl, aryl, halide, carboxamide or sulfonamide; $R^2$ may be alkyl, cycloalkyl, aryl or heteroaryl, wherein when $R^2$ is a 6 membered aryl or heteroaryl, $R^2$ is substituted at the 3- and 4-positions relative to the connection point on the triazole ring, through which a linker L is attached; and $R^3$ may be SH, OH, —CONHR$^4$, aryl or heteroaryl, wherein when $R^3$ is a 6 membered aryl or heteroaryl, $R^3$ is substituted at the 3 or 4 position.

In another embodiment, the binding moiety may advantageously be an Hsp90-binding (e.g. Hsp90-targeting) compound of formula (II):

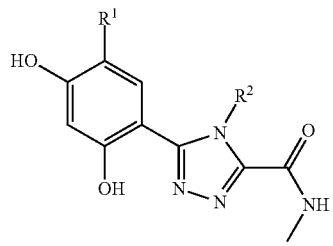

Formula II wherein
$R^1$ may be alkyl, aryl, halo, carboxamido, sulfonamido; and $R^2$ may be optionally substituted alkyl, cycloalkyl, aryl or heteroaryl. Examples of such compounds include 5-(2,4-dihydroxy-5-isopropylphenyl)-N-(2-morpholinoethyl)-4-(4-(morpholinomethyl)phenyl)-4H-1,2,4-triazole-3-carboxamide and 5-(2,4-dihydroxy-5-isopropylphenyl)-4-(4-(4-methylpiperazin-1-yl)phenyl)-N-(2,2,2-trifluoroethyl)-4H-1,2,4-triazole-3-carboxamide.

In another embodiment, the binding moiety may advantageously be an Hsp90-binding compound of formula (III):

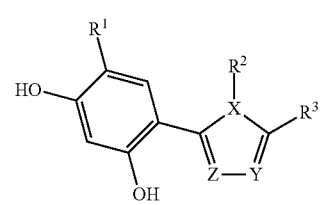

Formula III wherein
X, Y, and Z may independently be CH, N, O or S (with appropriate substitutions and satisfying the valency of the corresponding atoms and aromaticity of the ring); $R^1$ may be alkyl, aryl, halide, carboxamido or sulfonamido; $R^2$ may be substituted alkyl, cycloalkyl, aryl or heteroaryl, where a linker L is connected directly or to the extended substitutions on these rings; R³ may be SH, OH, NR⁴R⁵ AND —CONHR⁶, to which an effector moiety may be connected; R⁴ and R⁵ may independently be H, alkyl, aryl, or heteroaryl; and R⁶ may be alkyl, aryl, or heteroaryl, having a minimum of one functional group to which an effector moiety may be connected. Examples of such compounds include AUY-922:

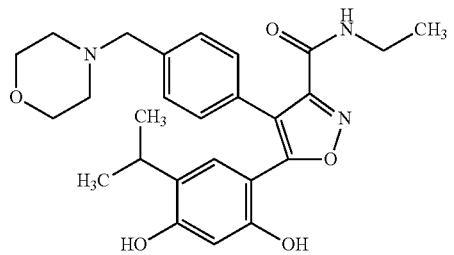 [SMILES: CCNC(=O)c1noc(-c2cc(C(C)C)c(O)cc2O)c1-c1ccc(CN2CCOCC2)cc1]

In another embodiment, the binding moiety may advantageously be an Hsp90-binding compound of formula (IV):

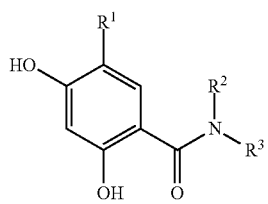

Formula IV wherein
R¹ may be alkyl, aryl, halo, carboxamido or sulfonamido; R² and R³ are independently C₁-C₅ hydrocarbyl groups optionally substituted with one or more of hydroxy, halogen, C₁-C₂ alkoxy, amino, mono- and di-C₁-C₂ alkylamino; 5- to 12-membered aryl or heteroaryl groups; or, R² and R³, taken together with the nitrogen atom to which they are attached, form a 4- to 8-membered monocyclic heterocyclic group, of which up to 5 ring members are selected from O, N and S. Examples of such compounds include AT-13387:

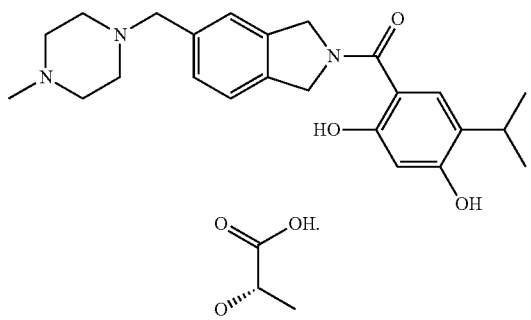

In certain embodiments, to enhance the bioavailability or delivery of the pharmaceutical conjugate, the binding moiety may be a prodrug of the Hsp90-binding compound. FIG. 1 shows how the illustrated Hsp90-targeting moiety may be suitably modified at one or more positions to enhance the physical, pharmacokinetic or pharmacodynamic properties of the conjugate.

Specific examples of suitable Hsp90-targeting moieties include geldanamycins, e.g., IPI-493

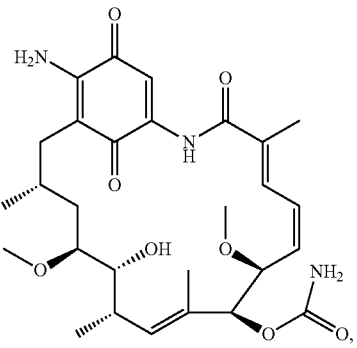 [SMILES: CO[C@H]1/C=C\C=C(/C)C(=O)NC2=CC(=O)C(N)=C(C[C@@H](C)C[C@H](OC)[C@H](O)[C@@H](C)/C=C(\C)[C@@H]1OC(N)=O)C2=O]

macbecins, tripterins, tanespimycins, e.g., 17-AAG

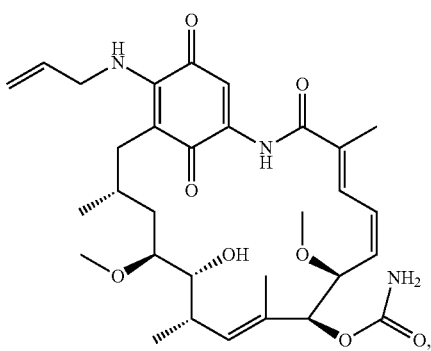 [SMILES: C=CCNC1=C2C[C@@H](C)C[C@H](OC)[C@H](O)[C@@H](C)/C=C(\C)[C@H](OC(N)=O)[C@@H](OC)/C=C\C=C(/C)C(=O)NC(=CC1=O)C2=O]

KF-55823

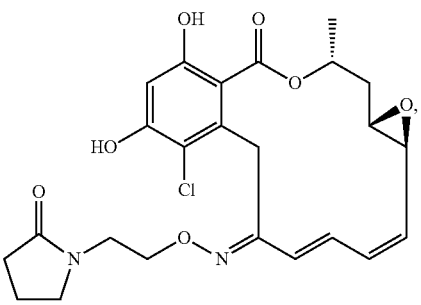 [SMILES: C[C@@H]1C[C@@H]2O[C@H]2\C=C/C=C/C(=N/OCCN2CCCC2=O)Cc2c(Cl)c(O)cc(O)c2C(=O)O1]

radicicols, KF-58333

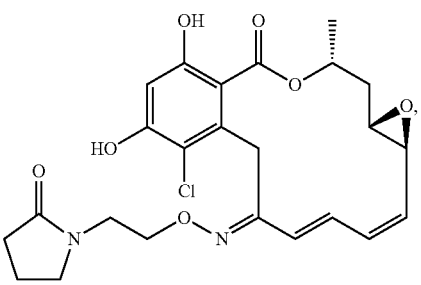 [SMILES: C[C@@H]1C[C@@H]2O[C@H]2\C=C/C=C/C(=N/OCCN2CCCC2=O)Cc2c(Cl)c(O)cc(O)c2C(=O)O1]

KF-58332
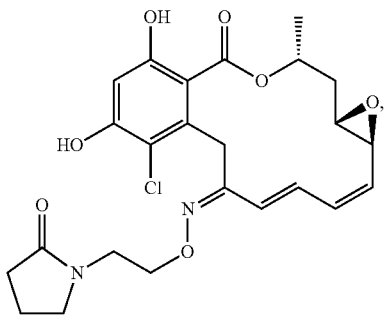 [SMILES: C[C@@H]1C[C@@H]2O[C@H]2\C=C/C=C/C(=N\OCCN2CCCC2=O)Cc2c(Cl)c(O)cc(O)c2C(=O)O1]
17-DMAG
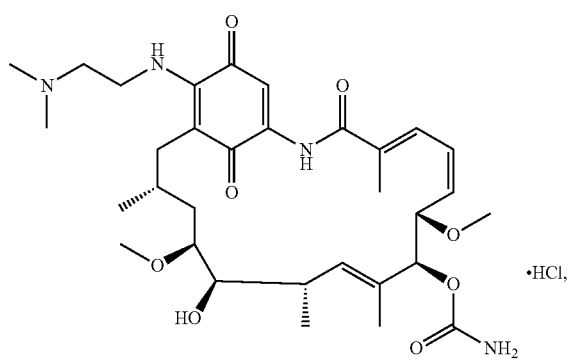 [SMILES: CO[C@H]1/C=C\C=C(/C)C(=O)NC2=CC(=O)C(NCCN(C)C)=C(C[C@@H](C)C[C@H](OC)[C@H](O)[C@@H](C)/C=C(\C)[C@@H]1OC(N)=O)C2=O]
•HCl,
IPI-504
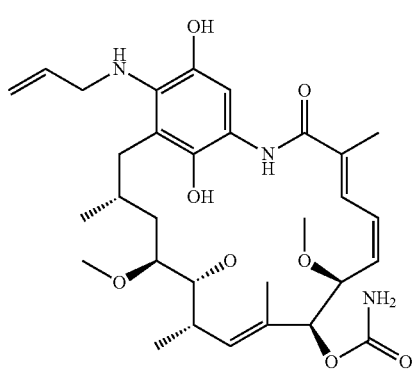
•HCl,
BIIB-021
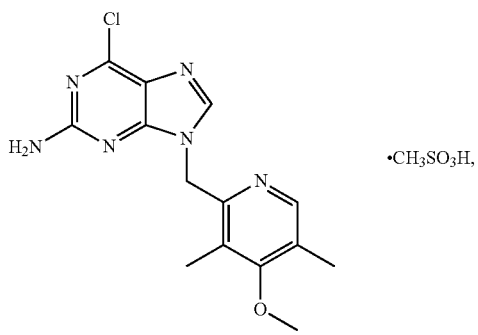 [SMILES: COc1c(C)cnc(Cn2cnc3c(Cl)nc(N)nc32)c1C]
•CH₃SO₃H,
BIIB-028, PU-H64
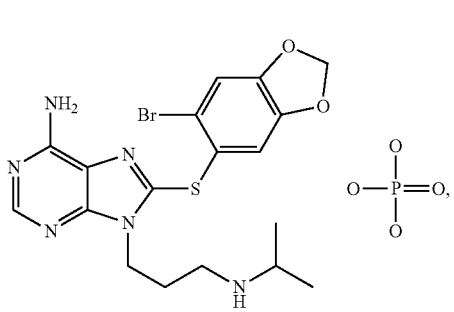 [SMILES: CC(C)NCCCn1c(Sc2cc3c(cc2Br)OCO3)nc2c(N)ncnc21 ; O=P(O)(O)O]
PU-H71
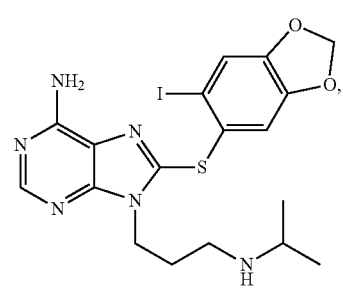 [SMILES: CC(C)NCCCn1c(Sc2cc3c(cc2I)OCO3)nc2c(N)ncnc21]
PU-DZ8
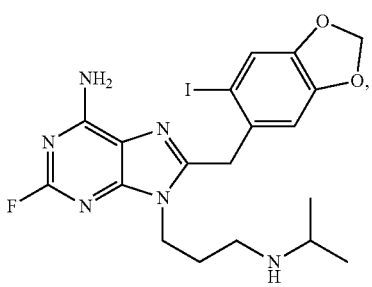
PU-HZ151
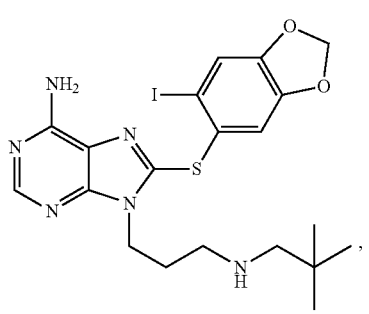

SNX-2112
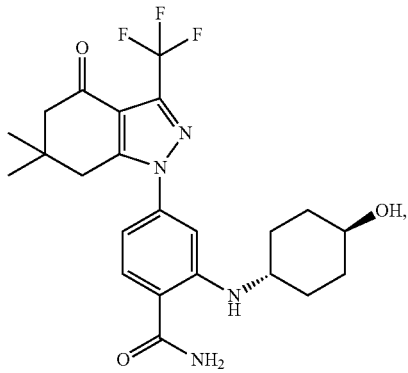 [SMILES: CC1(C)CC(=O)c2c(C(F)(F)F)nn(-c3ccc(C(N)=O)c(N[C@H]4CC[C@H](O)CC4)c3)c2C1]
SNX-8891, SNX-0723
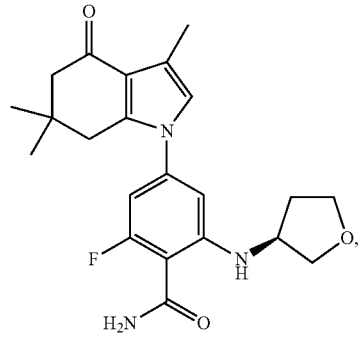
SNX-2321
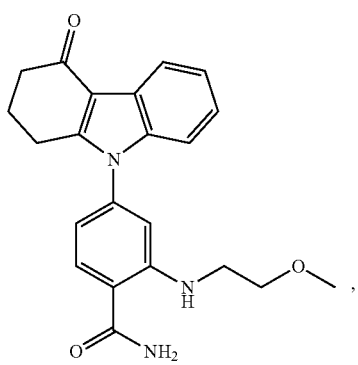 [SMILES: COCCNc1cc(-n2c3c(c4ccccc42)C(=O)CCC3)ccc1C(N)=O]
SAR-567530, ABI-287, ABI-328, AT-13387
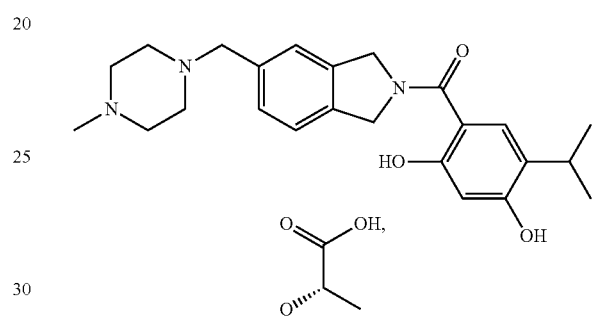
SNX-5422
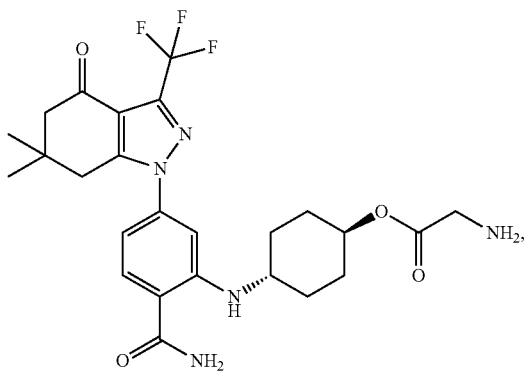 [SMILES: CC1(C)CC(=O)c2c(C(F)(F)F)nn(-c3ccc(C(N)=O)c(N[C@H]4CC[C@H](OC(=O)CN)CC4)c3)c2C1]
NSC-113497
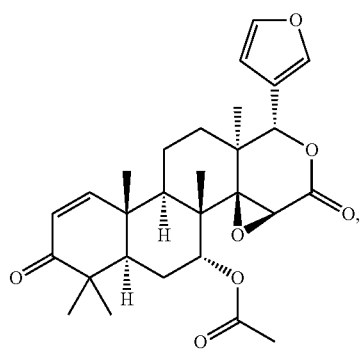
SNX-7081
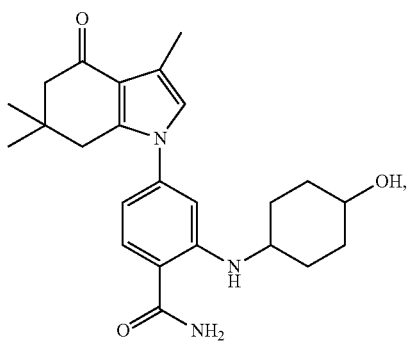 [SMILES: Cc1cn(-c2ccc(C(N)=O)c(NC3CCC(O)CC3)c2)c2c1C(=O)CC(C)(C)C2]
PF-3823863
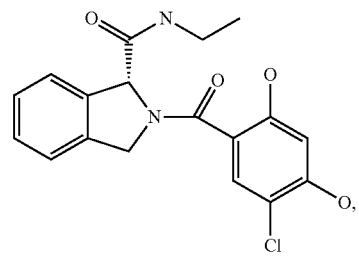

PF-4470296
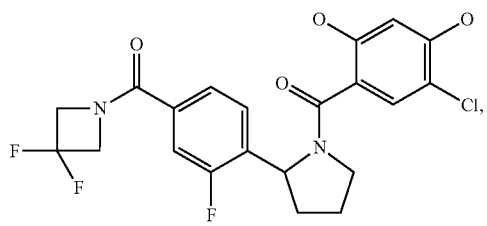 [SMILES: O=C(c1ccc(C2CCCN2C(=O)c2cc(Cl)c(O)cc2O)c(F)c1)N1CC(F)(F)C1]
EC-102, EC-154, ARQ-250-RP, BC-274
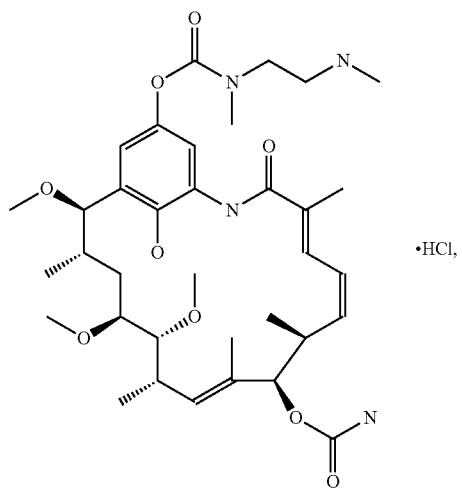
·HCl,
VER-50589
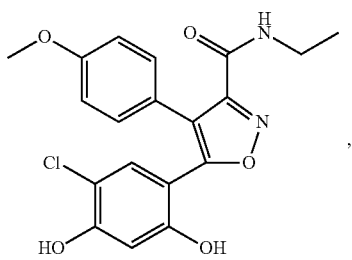 [SMILES: CCNC(=O)c1noc(-c2cc(Cl)c(O)cc2O)c1-c1ccc(OC)cc1]
KW-2478
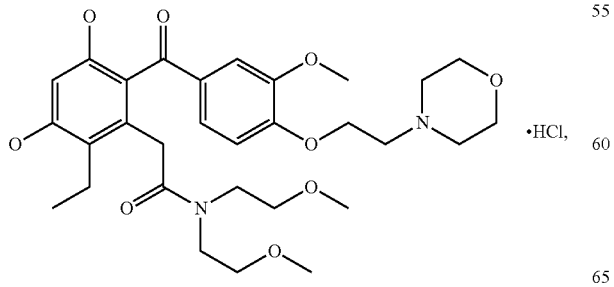
·HCl,
BHI-001, AUY-922
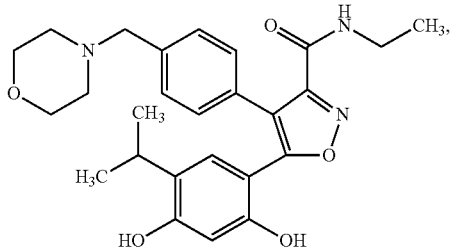 [SMILES: CCNC(=O)c1noc(-c2cc(C(C)C)c(O)cc2O)c1-c1ccc(CN2CCOCC2)cc1]
EMD-614684
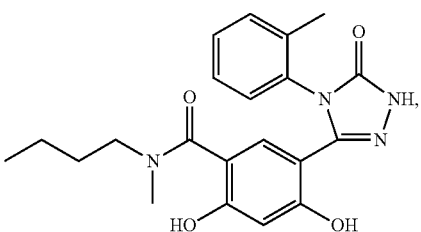 [SMILES: CCCCN(C)C(=O)c1cc(-c2n[nH]c(=O)n2-c2ccccc2C)c(O)cc1O]
EMD-683671, XL-888, VER-51047
KOS-2484, KOS-2539, CUDC-305
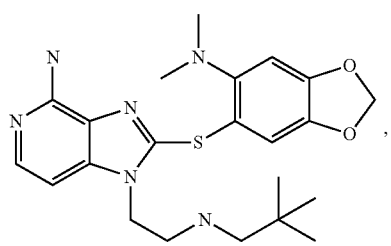 [SMILES: CN(C)c1cc2c(cc1Sc1nc3c(N)nccc3n1CCNCC(C)(C)C)OCO2]
MPC-3100
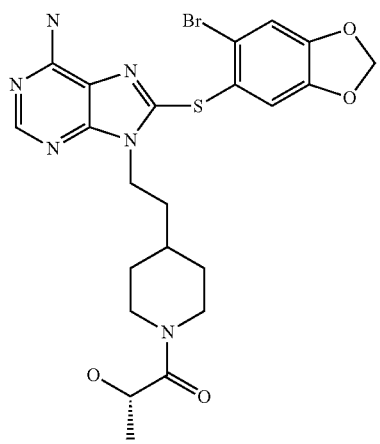

63
CH-5164840
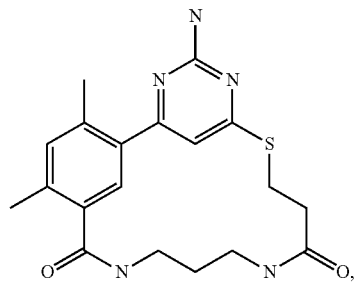 [SMILES: Cc1cc(C)c2cc1C(=O)NCCCNC(=O)CCSc1cc-2nc(N)n1]
PU-DZ13
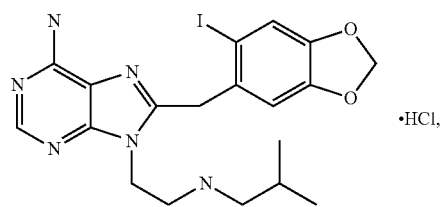 [SMILES: CC(C)CNCCn1c(Cc2cc3c(cc2I)OCO3)nc2c(N)ncnc21]
•HCl,
PU-HZ151
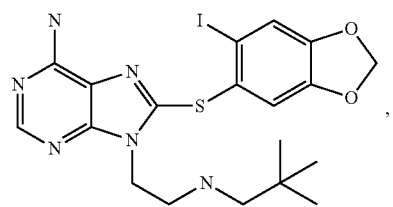 [SMILES: CC(C)(C)CNCCn1c(Sc2cc3c(cc2I)OCO3)nc2c(N)ncnc21]
,
PU-DZ13
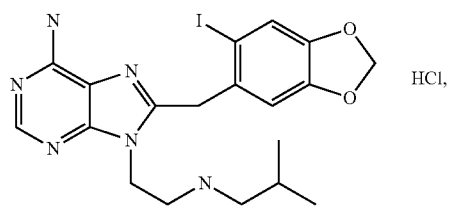 [SMILES: CC(C)CNCCn1c(Cc2cc3c(cc2I)OCO3)nc2c(N)ncnc21]
HCl,
VER-82576
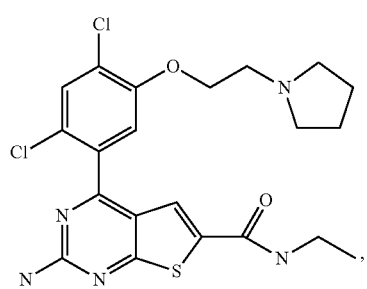 [SMILES: CCNC(=O)c1cc2c(-c3cc(OCCN4CCCC4)c(Cl)cc3Cl)nc(N)nc2s1]
,
64
VER-82160
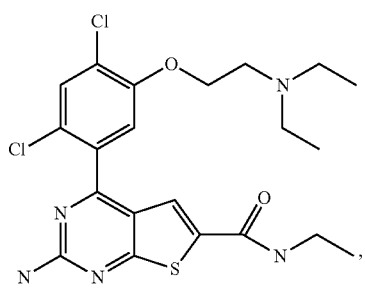 [SMILES: CCNC(=O)c1cc2c(-c3cc(OCCN(CC)CC)c(Cl)cc3Cl)nc(N)nc2s1]
,
VER-82576
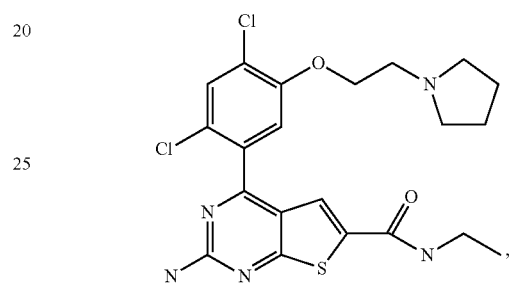
,
VER-82160
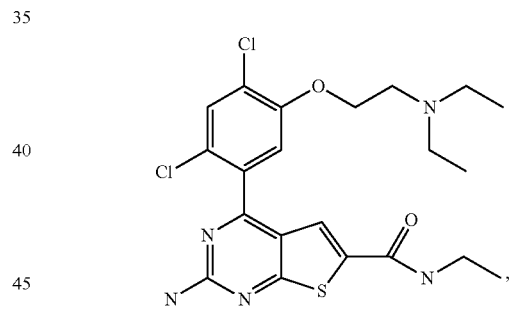
,
NXD-30001
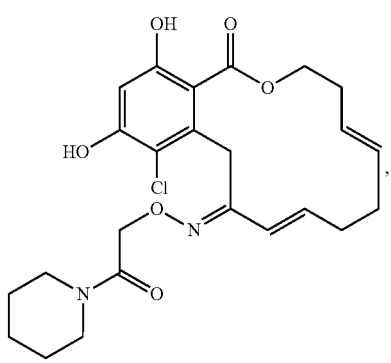 [SMILES: O=C1OCC/C=C/CC/C=C/C(=N/OCC(=O)N2CCCCC2)Cc2c(Cl)c(O)cc(O)c21]
,

NVP-HSP990

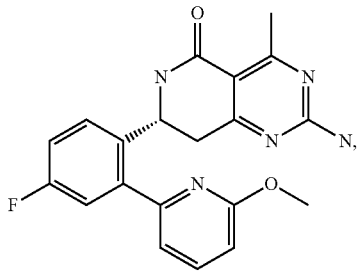

SST-0201CL1

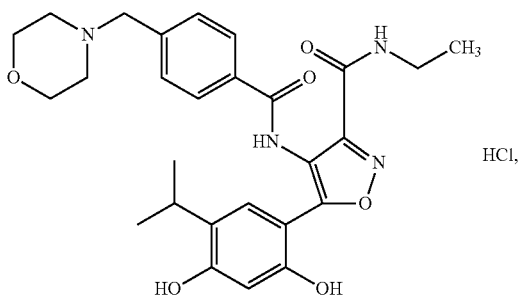 [SMILES: CCNC(=O)c1noc(-c2cc(C(C)C)c(O)cc2O)c1NC(=O)c1ccc(CN2CCOCC2)cc1]

SST-0115AA1

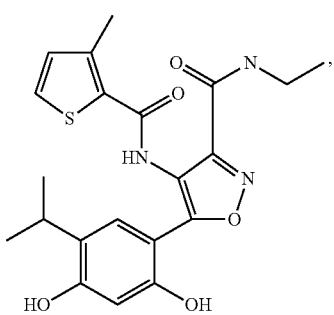 [SMILES: CCNC(=O)c1noc(-c2cc(C(C)C)c(O)cc2O)c1NC(=O)c1sccc1C]

SST-0221AA1

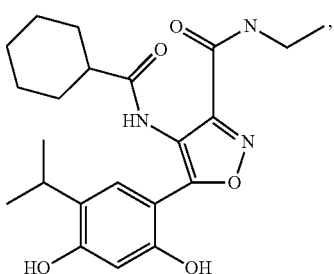 [SMILES: CCNC(=O)c1noc(-c2cc(C(C)C)c(O)cc2O)c1NC(=O)C1CCCCC1]

SST-0223AA1

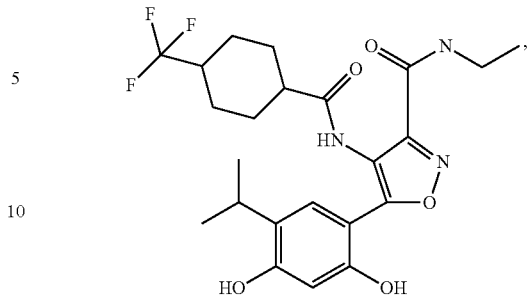

novobiocin (a C-terminal Hsp90i.). The selection of other Hsp90-targeting moieties will be within the grasp of one of ordinary skill in the art. Likewise, the selection of binding moieties suitable for other molecular targets and/or other applications will be within the ability of one of ordinary skill in the art.

Additionally Hsp90 targeting moieties can be used to construct SDC-TRAP molecules for the treatment of inflammation. For example, binding moieties comprising the compounds shown in Tables 5, 6, and 7 of U.S. Patent Publication 2010/0280032, which is incorporated herein by reference in its entirety, or compounds of any formula therein, or tautomers, pharmaceutically acceptable salts, solvates, clathrates, hydrates, polymorphs or prodrugs thereof, inhibit the activity of Hsp90 and, thereby cause the degradation of Hsp90 client proteins. Any of these compounds may be coupled to an effector molecule to form an SDC-TRAP. The glucocorticoid receptor is a client protein of Hsp90 and binds to Hsp90 when it is in the conformation that is able to bind glucocorticoid ligands such as cortisol. Once a glucocorticoid binds to GR, the receptor disassociates with Hsp90 and translocates to the nucleus where it modulates gene expression to reduce inflammatory responses such as proinflammatory cytokine production. Thus, glucocorticoids may be given to patients in need of immunosuppression and patients with inflammatory and autoimmune disorders. Unfortunately, although glucocorticoids are effective at relieving inflammation, they have a number of severe side effects including osteoporosis, muscle wasting, hypertension, insulin resistance, truncal obesity and fat redistribution, and inhibition of wound repair. Inhibition of Hsp90 causes changes in GR activity which results in reduction of inflammatory responses similar to those seen for glucocorticoids. However, since the mechanism for reducing inflammation is different than that of glucocorticoids, it is expected that some or all of the side effects of glucocorticoid treatment will be reduced or eliminated.

In an embodiment, the binding moiety, e.g. the Hsp90 targeting moiety, may include compounds of the following general formula V:

Formula V

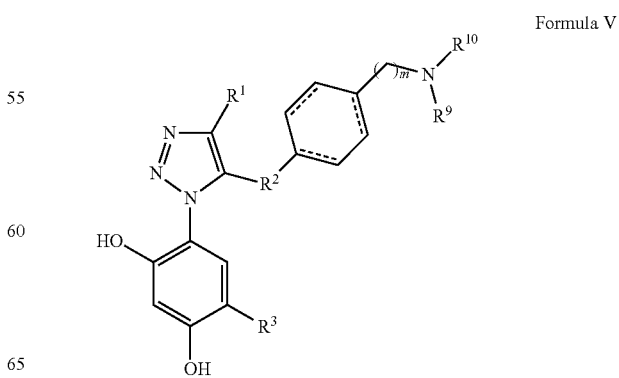

wherein:

$R^1$ is H, or $CONR^4R^5$;

$R^5$ is H, $(C_1-C_6)$-alkyl, or $(C_3-C_{10})$-cycloalkyl, each being optionally substituted once or more with OH, OMe, Cl, or F;

$R^4$ is H, $(C_1-C_4)$-alkyl, or $CH(R^{11})COR^{12}$; or $R^4$ and $R^5$, taken together with the nitrogen atom to which they are attached, form a three- to seven-membered heterocycle optionally containing a further heteroatom selected from the group consisting of N, O and S; and wherein the heterocycle is optionally substituted once or more by OH, OMe, $(C_1-C_4)$-alkyl, optionally substituted phenyl, or benzyl;

$R^{11}$ is a side chain of a natural o-amino acid;

$R^{12}$ is OH, amino, alkylamino or dialkylamino;

$R^2$ is a bond, —NH(CO)—, —N($R^7$)— or —N($R^7$)CH$_2$—;

$R^7$ is H, $(C_1-C_4)$-alkyl or $CO_2R^8$;

$R^8$ is $(C_1-C_4)$-alkyl or benzyl;

the endocyclic symbols ==== are, for each single compound, all double bonds or all single bonds; m is an integer comprised between 0 and 3;

$R^9$ and $R^{10}$ are, independently from each other, $(C_1-C_4)$-alkyl optionally substituted with OH, cycloalkyl, heterocycloalkyl, OMe, amino, $(C_1-C_6)$-alkylamino or $(C_1-C_{10})$-dialkylamino; heterocycloalkyl optionally substituted once or more by alkyl, amino, $(C_1-C_6)$-alkylamino or $(C_1-C_6)$-dialkylamino; cycloalkyl; or $R^9$ and $R^{10}$, taken together with the nitrogen atom to which they are attached, form a heterocycle ring chosen from the group consisting of piperidyl, pyrrolidinyl, piperazinyl and morpholinyl, each of them being optionally substituted once or more by F, Cl, Br, OH, OMe, amino, $(C_1-C_6)$-alkylamino, $(C_1-C_6)$-dialkylamino, $(C_1-C_4)$-alkyl, hydroxyalkyl, optionally substituted phenyl, or benzyl; or an imidazole unsaturated heterocycle;

$R^3$ is Cl, Et or i-Pr;

their tautomers, their geometrical isomers, their optically active forms such as enantiomers, diastereomers and their racemate forms, as well as their pharmaceutically acceptable salts thereof.

Particular examples of such compounds include 4-isopropyl-6-[5-(4-(morpholin-4-ylmethyl-phenyl)-[1,2,3]-triazol-1-yl)benzene-1,3-diol;

4-{5-[4-(3-hydroxy-piperidin-1-ylmethyl)-phenyl]-[1,2,3]triazol-1-yl}-6-isopropyl-benzene-1,3-diol;

4-{5-[4-(4-benzyl-piperazin-1-ylmethyl)-phenyl]-[1,2,3]triazol-1-yl}-6-isopropyl-benzene-1,3-diol;

4-isopropyl-6-{5-[4-(4-phenyl-piperazin-1-ylmethyl)-phenyl]-[1,2,3]triazol-1-yl}-benzene-1,3-diol;

1-(2,4-dihydroxy-5-isopropyl-phenyl)-5-(4-morpholin-4-ylmethyl-phenyl)-1H-[1,2,3]triazole-4-carboxylic ethyl amide;

(R,S)-1-(2,4-dihydroxy-5-isopropyl-phenyl)-5-[4-(3-hydroxy-piperidin-1-ylmethyl)-phenyl]-1H-[1,2,3]triazole-4-carboxylic acid ethylamide;

1-(2,4-dihydroxy-5-isopropyl-phenyl)-5-(4-{[ethyl-(2-hydroxy-ethyl)-amino]-methyl}-phenyl)-1H-[1,2,3]triazole-4-carboxylic acid ethylamide;

1-(2,4-dihydroxy-5-isopropyl-phenyl)-5-{4-[2-(2-hydroxy-ethyl)-piperidin-1-ylmethyl]-phenyl}-1H-[1,2,3]triazole-4-carboxylic acid ethylamide;

1-(2,4-dihydroxy-5-isopropyl-phenyl)-5-(4-piperidin-1-ylmethyl-phenyl)-1H-[1,2,3]triazole-4-carboxylic acid ethylamide;

5-(4-diethylaminomethyl-phenyl)-1-(2,4-dihydroxy-5-isopropyl-phenyl)-1H-[1,2,3]triazole-4-carboxylic acid ethylamide;

1-(2,4-dihydroxy-5-isopropyl-phenyl)-5-[4-(4-methyl-piperazin-1-ylmethyl)-phenyl]-1H-[1,2,3]triazole-4-carboxylic acid ethylamide;

1-(2,4-dihydroxy-5-isopropylphenyl)-5-(4-piperazin-1-ylmethyl-phenyl)-1H-[1,2,3]triazole-4-carboxylic acid ethylamide;

1-(2,4-dihydroxy-5-isopropyl-phenyl)-5-[4-(4-dimethylamino-piperidin-1-ylmethyl)-phenyl]-1H-[1,2,3]triazole-4-carboxylic acid ethylamide;

1-(2,4-dihydroxy-5-isopropyl-phenyl)-5-{4-[(2-morpholin-4-yl-ethylamino)-methyl]-phenyl}-1H-[1,2,3]triazole-4-carboxylic acid ethylamide;

5-{4-[(cyclohexylmethyl-amino)methyl]-phenyl}-1-(2,4-dihydroxy-5-isopropyl-phenyl)-1H-1,2,3]triazole-4-carboxylic acid ethylamide;

5-(4-cyclohexylaminomethyl-phenyl)-1-(2,4-dihydroxy-5-isopropyl-phenyl)-1H-[1,2,3]triazole-4-carboxylic acid ethylamide;

5-{4-[(2-diethylaminoethylamino)-methyl]-phenyl}-1-(2,4-dihydroxy-5-isopropyl-phenyl)-1H-[1,2,3]triazole-4-carboxylic acid ethylamide;

5-{4-[(3-diethylamino-propylamino)-methyl]-phenyl}-1-(2,4-dihydroxy-5-isopropyl-phenyl)-1H-[1,2,3]triazole-4-carboxylic acid ethylamide;

1-(2,4-dihydroxy-5-isopropyl-phenyl)-5-{4-[(1-methyl-piperidin-4-ylamino)-methyl]-phenyl}-1H-[1,2,3]triazole-4-carboxylic acid ethylamide;

1-(2,4-dihydroxy-5-isopropyl-phenyl)-5-[4-((S)-3-dimethylamino-pyrrolidin-1-ylmethyl)-5 phenyl]-1H-[1,2,3]triazole-4-carboxylic acid ethylamide;

1-(2,4-dihydroxy-5-isopropyl-phenyl)-5-(4-pyrrolidin-1-ylmethyl-phenyl)-1H-[1,2,3]triazole-4-carboxylic acid ethylamide;

1-(2,4-dihydroxy-5-isopropyl-phenyl)-5-(4-imidazol-1-ylmethylphenyl)-1H-[1,2,3]triazole-4-carboxylic acid ethylamide;

4-isopropyl-6-[5-(4-morpholin-4-yl-phenylamino)-[1,2,3]triazol-1-yl]-benzene-1,3-diol;

(4-morpholin-4-yl-benzylamino)-[1,2,3]triazol-1-yl]-benzene-1,3-diol;

4-isopropyl-6-[5-1-(2,4-dihydroxy-5-isopropyl-phenyl)-5-(4-morpholin-4-yl-phenylamino)-1H-[1,2,3]triazole-4-carboxylic acid ethylamide;

1-(2,4-dihydroxy-5-isopropyl-phenyl)-5-(4-morpholin-4-yl-benzylamino)-H-[1,2,3]triazole-4-carboxylic acid ethylamide;

1-(2,4-dihydroxy-5-isopropyl-phenyl)-5-(4-morpholin-4-yl-methyl-phenyl)-1H-[1,2,3]triazole-4-carboxylic acid hexylamide;

1-(2,4-dihydroxy-5-isopropyl-phenyl)-5-(4-morpholin-4-yl-methyl-phenyl)-1H-[1,2,3]triazole-4-carboxylic acid cyclopentylamide;

1-(2,4-dihydroxy-5-isopropyl-phenyl)-5-(4-morpholin-4-yl-methyl-phenyl)-1H-[1,2,3]triazole-4-carboxylic acid cyclohexylamide;

[1-(2,4-dihydroxy-5-isopropylphenyl)-5-(4-morpholin-4-yl-methyl-phenyl)-1H-[1,2,3]triazol-4-yl]-morpholin-4-yl-methanone;

(S)-2-{[1-(2,4-dihydroxy-5-isopropyl-phenyl)-5-(4-morpholin-4-ylmethylphenyl)-1H-[1,2,3]triazole-4-carbonyl]-amino}-3-methyl-butyric acid;

4-isopropyl-6-[5-(4-pyrrolidin-1-ylmethyl-phenyl)-[1,2,3]triazol-1-yl]-benzene-1,3-diol;

4-isopropyl-6-[5-(4-isoxazolidin-2-ylmethyl-phenyl)-[1,2,3]triazol-1-yl]-benzene-1,3-diol;

1-(2,4-dihydroxy-5-isopropyl-phenyl)-5-(4-isoxazolidin-2-ylmethyl-phenyl)-1H-[1,2,3]triazole-4-carboxylic acid ethylamide;
1-(2,4-dihydroxy-5-isopropyl-phenyl)-5-[4-(4-phenyl-piperazin-1-ylmethyl)-phenyl]-1H-[1,2,3]triazole-4-carboxylic acid ethylamide;
4-[5-(4-{[ethyl-(2-hydroxy-ethyl)-amino]-methyl}-phenyl)-[1,2,3]triazol-1-yl]-6-isopropyl-benzene-1,3-diol;
4-(5-{4-[2-(2-Hydroxy-ethyl)-piperidin-1-ylmethyl]-phenyl}-[1,2,3]triazol-1-yl)-6-isopropyl-benzene-1,3-diol;
4-isopropyl-6-[5-(4-piperidin-1-ylmethyl-phenyl)-[1,2,3]triazol-1-yl]-benzene-1,3-diol;
4-[5-(4-diethylaminomethyl-phenyl)-[1,2,3]triazol-1-yl]-6-isopropyl-benzene-1,3-diol;
N-[3-(2,4-dihydroxy-5-isopropyl-phenyl)-3H-[1,2,3]triazol-4-yl]-4-morpholin-4-yl-benzamide;
1-(2,4-dihydroxy-5-isopropyl-phenyl)-5-(4-morpholin-4-yl-benzoylamino)-1H-[1,2,3]triazole-4-carboxylic acid ethylamide;
N-[3-(2,4-dihydroxy-5-isopropyl-phenyl)-3H-[1,2,3]triazol-4-yl]-4-piperidin-1-yl-benzamide;
1-(2,4-dihydroxy-5-isopropyl-phenyl)-5-(4-piperidin-1-yl-benzoylamino)-1H-[1,2,3]triazole-4-carboxylic acid ethylamide;
N-[3-(2,4-dihydroxy-5-isopropyl-phenyl)-3H-[1,2,3]triazol-4-yl]-4-(3-hydroxy-piperidin-1-yl)-benzamide;
1-(2,4-dihydroxy-5-isopropyl-phenyl)-5-[4-(3-hydroxy-piperidin-1-yl)-benzoylamino]-1H-[1,2,3]triazole-4-carboxylic acid ethylamide;
N-[3-(2,4-dihydroxy-5-isopropyl-phenyl)-3H-[1,2,3]triazol-4-yl]-4-morpholin-4-ylmethyl-benzamide;
1-(2,4-dihydroxy-5-isopropyl-phenyl)-5-(4-morpholin-4-ylmethyl-benzoylamino)-1H-[1,2,3]triazole-4-carboxylic acid ethylamide;
4-morpholin-4-ylmethyl-cyclohexanecarboxylic acid [3-(2,4-dihydroxy-5-isopropyl-phenyl)-3H-[1,2,3]triazol-4-yl]-amide;
1-(2,4-dihydroxy-5-isopropyl-phenyl)-5-[(4-morpholin-4-ylmethyl-cyclohexanecarbonyl)-amino]-1H-[1,2,3]triazole-4-carboxylic acid ethylamide;
4-isopropyl-6-{5-[4-(4-methyl-piperazin-1-ylmethyl)-phenyl]-[1,2,3]triazol-1-yl}-benzene-1,3-diol;
4-isopropyl-6-[5-(4-morpholin-4-ylmethyl-phenyl)-[1,2,3]triazol-1-yl]-benzene-1,3-diol;
1-(2,4-dihydroxy-5-isopropyl-phenyl)-5-(4-morpholin-4-ylmethyl-phenyl)-1H-[1,2,3]triazole-4-carboxylic acid ethylamide;
5-[4-(4-benzyl-piperazin-1-ylmethyl)-phenyl]-1-(2,4-dihydroxy-5-isopropyl-phenyl)-1H-[1,2,3]triazole-4-carboxylic acid ethylamide;
N-[3-(2,4-dihydroxy-5-isopropyl-phenyl)-3H-[1,2,3]triazol-4-yl]-4-pyrrolidin-1-yl-benzamide;
1-(2,4-dihydroxy-5-isopropyl-phenyl)-5-(4-pyrrolidin-1-yl-benzoylamino)-1H-[1,2,3]triazole-4-carboxylic acid ethylamide;
1-(2,4-dihydroxy-5-isopropylphenyl)-5-(4-morpholin-4-ylmethyl-phenyl)-1H-[1,2,3]triazole-4-carboxylic acid (2-chloro-ethyl)-amide;

In another embodiment, the binding moiety, e.g. the Hsp90 targeting moiety, may include compounds of the following general formula VI:

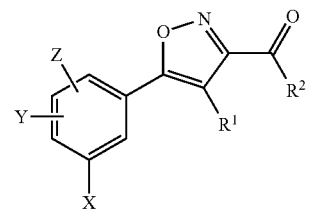

Formula VI wherein:
X is halogen, alkyl, alkenyl, haloalkyl, aryl, heteroaryl, benzyl, amino, alkylamino, or aminocarbonyl;
Y and Z, the same or different, are halogen, nitro, haloalkyl, $R^3$, $OR^3$, amino, alkylamino, or aminocarbonyl;
$R^3$ is hydrogen or alkyl;
$R^1$ is NHC(=D)E$R^4$ or NR$^5$R$^6$;
D is O or S;
E is O, NR$^7$ or is absent;
$R^7$ is hydrogen or alkyl;
$R^4$ is alkyl optionally substituted once with alkoxy or amino; alkenyl, aryl optionally substituted once or more with alkoxy, halo or heterocycloalkylalkyl; cycloalkyl optionally substituted once or more with alkyl, haloalkyl, alkoxy, amino or aminoalkyl; norbornyl, adamantyl, heteroaryl optionally substituted once or more with alkyl, alkylaminocarbonyl; heterocycloalkyl optionally substituted once or more with alkyl; or heterocycloalkylalkyl optionally substituted once or more with alkyl;
$R^5$ and $R^6$ independently are hydrogen, alkyl, cycloalkyl, heterocycloalkyl optionally substituted once or more with alkyl; alkenyl, benzyl, aryl, arylalkyl optionally substituted with alkoxy; heteroaryl, heteroarylalkyl optionally substituted once or more with alkyl, hydroxyalkyl, alkoxy, alkoxycarbonyl; or $R^5$ and $R^6$, taken together with the nitrogen atom to which they are attached, form an optionally substituted five to seven-membered heterocycle ring, which optional substitution being halogen, hydroxyl, alkoxyl, alkyl, aryl, arylalkyl, alkylcarbonyl or aminocarbonyl;
$R^2$ is NR$^8$R$^9$;
$R^8$ and $R^9$ are the same or different, and are chosen from H, alkyl optionally substituted with halogen, haloalkyl, aryl, cycloalkyl, heterocycloalkyl and heteroaryl; or $R^8$ and $R^9$, taken together with the nitrogen atom to which they are attached, form a heterocycle that may contain one or two further heteroatoms selected from O, S or N and which can optionally be substituted once or twice with alkyl or halogen; and their tautomers, their geometrical isomers, their optically active forms such as enantiomers, diastereomers and their racemate forms, as well as their pharmaceutically acceptable salts thereof.

Particular examples of such compounds include
4-acetylamino-5-(5-chloro-2,4-dihydroxy-phenyl)-isoxazole-3-carboxylic acid ethylamide;
5-(5-chloro-2,4-dihydroxy-phenyl)-4-(4-methoxy-benzoylamino)-isoxazole-3-carboxylic acid ethylamide;
5-(5-chloro-2,4-dihydroxy-phenyl)-4-(3,4-dimethoxy-benzoylamino)-isoxazole-3-carboxylic acid ethylamide;
5-(5-chloro-2,4-dihydroxy-phenyl)-4-(3,4,5-trimethoxy-benzoylamino)-isoxazole-3-carboxylic acid ethylamide;
5-(5-chloro-2,4-dihydroxy-phenyl)-4-(2,2-dimethyl-propionylamino)-isoxazole-3-carboxylic acid ethylamide;
4-[(adamantane-1-carbonyl)-amino]-5-(5-chloro-2,4-dihydroxy-phenyl)-isoxazole-3-carboxylic acid ethylamide;

4-acryloylamino-5-(5-chloro-2,4-dihydroxy-phenyl)-isoxazole-3-carboxylic acid ethylamide;
5-(5-chloro-2,4-dihydroxy-phenyl)-4-[(3-methyl-thiophene-2-carbonyl)-amino]-isoxazole-3-carboxylic acid ethylamide;
5-(5-chloro-2,4-dihydroxy-phenyl)-4-(3-morpholin-4-yl-propionylamino)-isoxazole-3-carboxylic acid ethylamide;
4-(4-bromo-benzoyl amino)-5-(5-chloro-2,4-dihydroxy-phenyl)-isoxazole-3-carboxylic acid ethylamide;
5-(2,4-dihydroxy-5-isopropyl-phenyl)-4-(4-methoxy-benzoylamino)-isoxazole-3-carboxylic acid ethylamide;
4-acetylamino-5-(2,4-dihydroxy-5-isopropyl-phenyl)-isoxazole-3-carboxylic acid ethylamide;
5-(2,4-dihydroxy-5-isopropyl-phenyl)-4-(2,2-dimethyl-propionylamino)-isoxazole-3-carboxylic acid ethylamide;
5-(2,4-dihydroxy-5-isopropyl-phenyl)-4-[(3-methyl-thiophene-2-carbonyl)-amino]-isoxazole-3-carboxylic acid ethylamide;
5-(2,4-dihydroxy-5-isopropyl-phenyl)-4-(3-morpholin-4-yl-propionylamino)-isoxazole-3-carboxylic acid ethylamide;
4-(3-(4-methylpiperazin-1-yl)propanamido)-N-ethyl-5-(2,4-dihydroxy-5-isopropylphenyl)-isoxazole-3-carboxamide;
1H-indole-6-carboxylic acid [5-(2,4-dihydroxy-5-isopropyl-phenyl)-3-ethyl carbamoyl-isoxazol-4-yl]-amide;
5-(2,4-dihydroxy-5-isopropyl-phenyl)-4-(4-morpholin-4-yl-methyl-benzoyl amino)-isoxazole-3-carboxylic acid ethylamide hydrochloride;
4-(cyclohexanecarbonyl-amino)-5-(2,4-dihydroxy-5-isopropyl-phenyl)-isoxazole-3-carboxylic acid ethylamide;
5-(2,4-dihydroxy-5-isopropyl-phenyl)-4-[(trans-4-pentyl-cyclohexanecarbonyl)-amino]-isoxazole-3-carboxylic acid ethylamide;
5-(2,4-dihydroxy-5-isopropyl-phenyl)-4-[(4-trifluoromethyl-cyclohexane carbonyl)-amino]-isoxazole-3-carboxylic acid ethylamide;
$N^5$-(3-(ethylcarbamoyl)-5-(2,4-dihydroxy-5-isopropylphenyl)-isoxazol-4-yl)-$N^3$-ethylisoxazole-3,5-dicarboxamide;
5-(2,4-dihydroxy-5-isopropyl-phenyl)-4-[(4-methoxy-cyclohexanecarbonyl)-amino]-isoxazole-3-carboxylic acid ethylamide;
4-[(4-tert-butyl-cyclohexanecarbonyl)-amino]-5-(2,4-dihydroxy-5-isopropyl-1-phenyl)-isoxazole-3-carboxylic acid ethylamide;
4-[(4-amino-cyclohexanecarbonyl)-amino]-5-(2,4-dihydroxy-5-isopropyl-phenyl)-isoxazole-3-carboxylic acid ethylamide;
4-[(4-aminomethyl-cyclohexanecarbonyl)-amino]-5-(2,4-dihydroxy-5-isopropyl-phenyl)-isoxazole-3-carboxylic acid ethylamide;
4-(4-methoxybenzylamino)-5-(5-chloro-2,4-di hydroxyphenyl)-N-ethylisoxazole-3-carboxamide;
4-((3-methylthiophen-2-yl)methylamino)-5-(5-chloro-2,4-dihydroxyphenyl)-N-ethylisoxazole-3-carboxamide;
5-(5-chloro-2,4-dihydroxyphenyl)-4-(cyclohexylamino)-N-ethylisoxazole-3-carboxamide;
4-(1-methylpiperidin-4-ylamino)-5-(5-chloro-2,4-dihydroxyphenyl)-N-ethylisoxazole-3-carboxamide;
methyl 5-((3-(ethylcarbamoyl)-5-(5-chloro-2,4-di hydroxyphenyl)isoxazol-4-ylamino-)methyl)isoxazole-3-carboxylate;
4-((3-(hydroxymethyl)isoxazol-5-yl)methylamino)-5-(5-chloro-2,4-dihydroxy-phenyl)-N-ethylisoxazole-3-carboxamide;
4-(4-methoxybenzamido)-5-(5-chloro-2,4-dihydroxyphenyl)-N-(2,2,2-trifluoroethyl)-isoxazole-3-carboxamide;
4-(4-methoxybenzamido)-5-(5-chloro-2,4-dihydroxyphenyl)-isoxazol-3-yl)-(3,3-difluoroazetidinyl)-methanone;
5-(5-chloro-2,4-dihydroxy-phenyl)-4-(4-methoxy-benzoylamino)-isoxazol-3-yl)-(4-methylpiperazin-1-yl)-methanone;
5-(2,4-dihydroxy-5-isopropyl-phenyl)-4-(3,4-dimethoxybenzoylamino)-isoxazole-3-carboxylic acid ethylamide;
5-(2,4-dihydroxy-5-isopropyl-phenyl)-4-(3,4,5-trimethoxybenzoyl amino)-isoxazole-3-carboxylic acid ethylamide;
4-[(adamantane-1-carbonyl)-amino]-5-(2,4-dihydroxy-5-isopropyl-phenyl)-isoxazole-3-carboxylic acid ethylamide;
4-acryloylamino-5-(2,4-dihydroxy-5-isopropyl-phenyl)-isoxazole-3-carboxylic acid ethylamide;
4-(4-bromo-benzoylamino)-5-(2,4-dihydroxy-5-isopropyl-phenyl)-isoxazole-3-carboxylic acid ethylamide;
5-(2,4-di hydroxy-5-isopropyl-phenyl)-4-(4-methoxy-benzenesulfonylamino)-isoxazole-3-carboxylic acid ethylamide;
4-amino-5-(2,4-dihydroxy-5-isopropyl-phenyl)-isoxazole-3-carboxylic acid ethylamide;
5-(2,4-dihydroxy-5-isopropyl-phenyl)-4-(toluene-4-sulfonylamino)]-isoxazole-3-carboxylic acid ethylamide; and
5-(2,4-dihydroxy-5-isopropyl-phenyl)-4-[bis-(toluene-4-sulfonyl amino)]-isoxazole-3-carboxylic acid ethylamide.

In yet another embodiment, the targeting moiety may include compounds of the following formula:

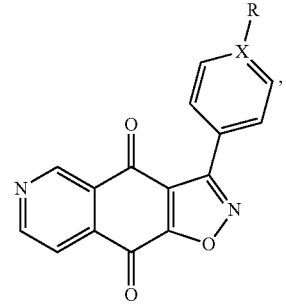

wherein X=C, R is F, OCH$_3$, or

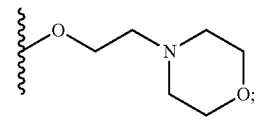 [SMILES: *OCCN1CCOCC1]

or, X=N, and R is absent.

In other various embodiments, the binding moiety comprises:

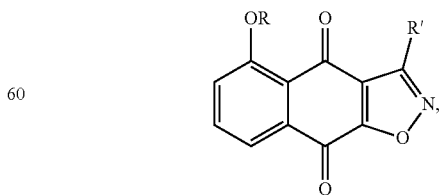

wherein R is H, CH$_3$, or Ac; and R' is 4-pyridyl, or 4-fluorophenyl.

In other various embodiments, the binding moiety comprises:

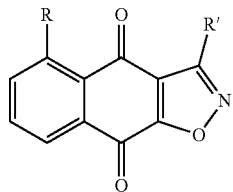

wherein:
R is H, OH, OCH$_3$, or OAc; and
R' is

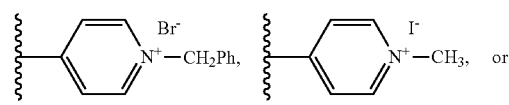

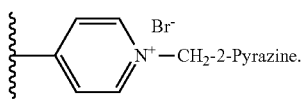

In other various embodiments, the binding moiety comprises:

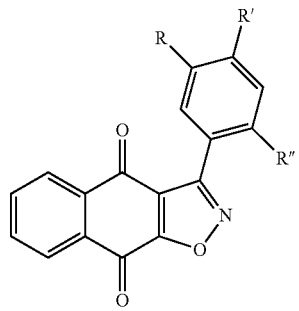

wherein:
R is H, or C$_1$;
R' is H, F, OH, OCH$_3$, or

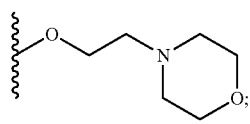 [SMILES: *OCCN1CCOCC1]

and
R" is H, OH, or OCH$_3$.

In other various embodiments, the binding moiety comprises:

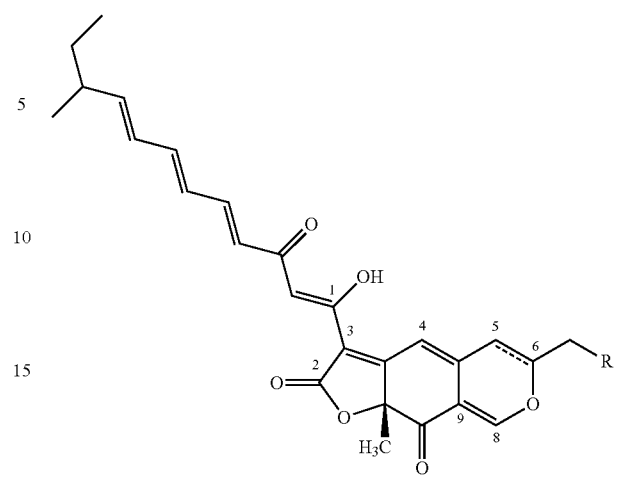

wherein:
R is H, and C$_5$-C$_6$ is a single bond or a double bond; or
R is OH, and C$_5$-C$_6$ is a single bond.

In other various embodiments, the binding moiety comprises:

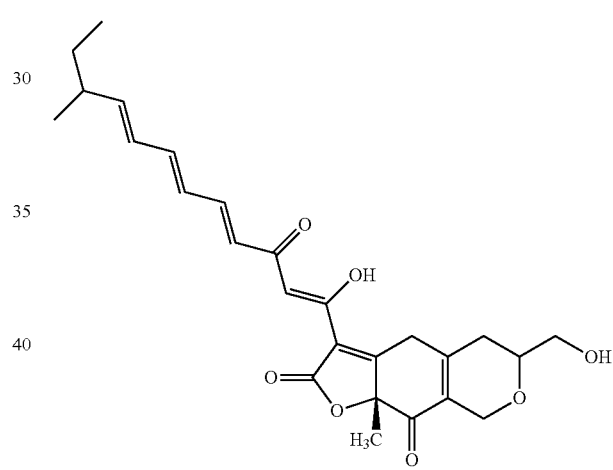

In other various embodiments, the binding moiety comprises:

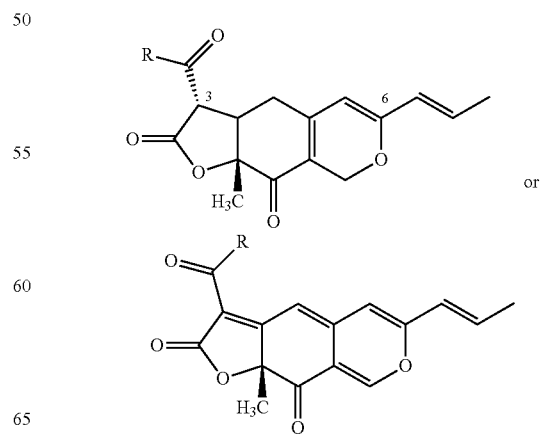

wherein R is —C$_7$H$_{15}$, or —C$_5$H$_{11}$.

In other various embodiments, the binding moiety comprises:

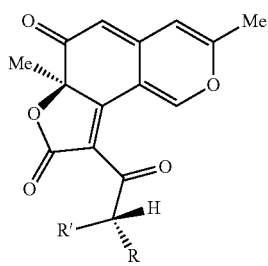

wherein R is —C$_6$H$_{13}$, —C$_8$H$_{17}$, or —C$_{10}$H$_{21}$, and R' is H or CH$_3$.

Effector Moieties

An effector moiety can be any therapeutic or imaging agent that can be conjugated to a binding moiety and, in a thus conjugated state, delivered to a molecular target of the binding moiety. An effector molecule can, in some cases, require a linking moiety for conjugation (e.g., cannot be directly conjugated to a binding moiety). Similarly, an effector molecule can, in some cases, impede or reduce the ability of the binding moiety and/or SDC-TRAP to reach a target as long as the SDC-TRAP can still effect the target. However, in preferred embodiments, an effector moiety is readily conjugatable and may benefits delivery to, and effecting, of the target.

In various embodiments, an SDC-TRAP, via an effector moiety, can have other ways of cell penetration than simple passive diffusion. Such an example is an SDC-TRAP including an antifolate or fragments thereof (e.g., temozolamide, mitozolamide, nitrogen mustards, estramustine, or chloromethine) as the effector moiety. In this case, a conjugate of a binding moiety (e.g., Hsp90 inhibitor) with pemetrexed (or its folate-recognizing fragment) can undergo folate receptor mediated endocytosis rather than passive diffusion. Once in a target cell, the SDC-TRAP can bind the molecular target (e.g., Hsp90 protein) via its binding moiety (e.g., Hsp90 inhibitor).

As described in greater detail below, an effector moiety can comprise a region that can be modified and/or participate in covalent linkage to a binding moiety without substantially adversely affecting the binding moiety's ability to bind to its target. An effector moiety can be a pharmaceutical molecule or a derivative thereof, which essentially retains activity while conjugated to a binding moiety. It will be appreciated that drugs with otherwise good and desirable activity can prove challenging to administer conventionally (e.g., due to poor bioavailability or undesirable side-effects in vivo prior to reaching their target)—such drugs can be "reclaimed" for use as effector moieties in the SDC-TRAPs of the present invention.

Examples of effector moieties include: peptidyl-prolyl isomerase ligands, e.g., FK506; rapamycin, cyclosporin A and the like; steroid hormone receptor ligands, e.g., naturally occurring steroid hormones, such as estrogen, progestin, testosterone, and the like, as well as synthetic derivatives and mimetics thereof; binding moieties that bind to cytoskeletal proteins, e.g., antimitotic agents, such as taxanes, colchicine, colcemid, nocadozole, vinblastine, and vincristine, actin binding agents, such as cytochalasin, latrunculin, phalloidin, and the like; lenalidomide, pomalidomide, camptothecins including SN-38

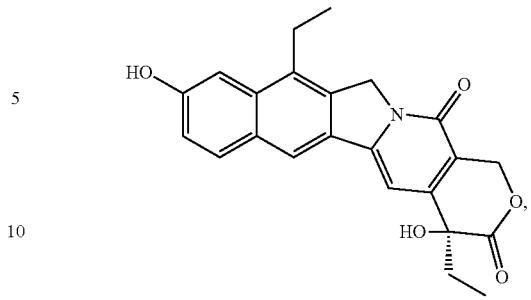

topotecan, combretastatins, capecitabine, gemcitabine, vinca alkaloids, platinum-containing compounds, metformin, HDAC inhibitors (e.g., suberoylanilidehydroxamic acid (SAHA)), thymidylate synthase inhibitors such as methotrexate, pemetrexed, and raltitrexed; nitrogen mustards such as bendamustine and melphalan; 5-fluorouracil (5-FU) and its derivatives; and agents used in ADC drugs, such as vedotin and DM1.

Figure 2:
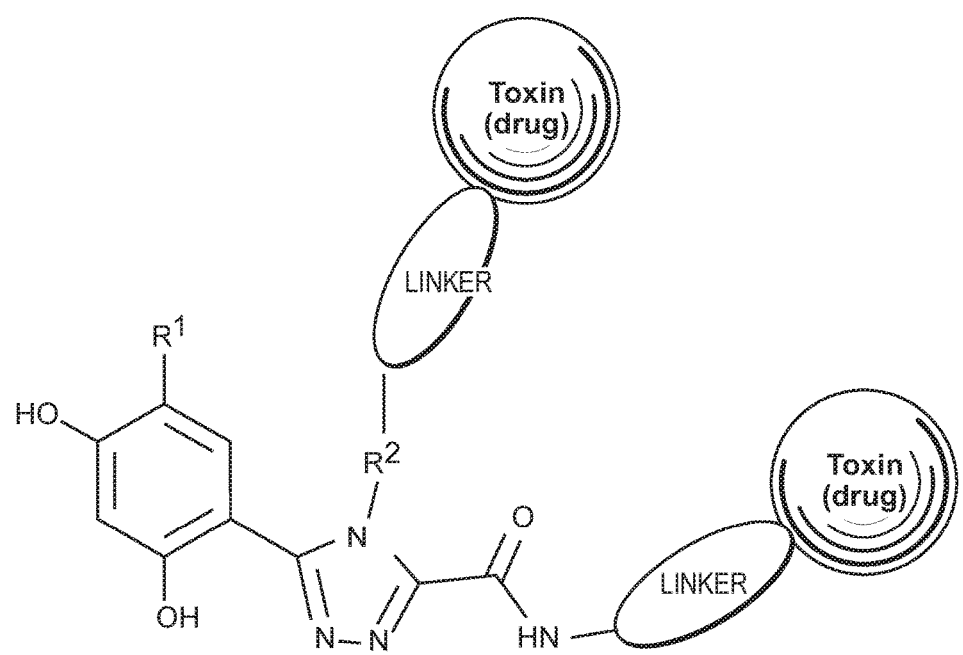
FIG. 2 illustrates an embodiment of a pharmaceutical conjugate having two effector moieties.

The effector moiety may be obtained from a library of naturally occurring or synthetic molecules, including a library of compounds produced through combinatorial means, i.e., a compound diversity combinatorial library. When obtained from such libraries, the effector moiety employed will have demonstrated some desirable activity in an appropriate screening assay for the activity. It is contemplated that in other embodiments, the pharmaceutical conjugate may include more than one effector moiety(ies), providing the medicinal chemist with more flexibility. The number of effector moieties linked to the binding moiety (e.g., Hsp90-targeting moiety) will generally only be limited by the number of sites on the binding moiety (e.g., Hsp90-targeting moiety) and/or any linking moiety available for linking to an effector moiety; the steric considerations, e.g., the number of effector moieties than can actually be linked to the binding moiety (e.g., Hsp90-targeting moiety); and that the ability of the pharmaceutical conjugate to bind to the molecular target (e.g., Hsp90 protein) is preserved. An example of a two-effector moiety pharmaceutical conjugate can be seen in FIG. 2.

Specific drugs from which the effector moiety may be derived include: psychopharmacological agents, such as central nervous system depressants, e.g., general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines, etc.), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs, etc.), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.); central nervous system stimulants, e.g., analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics; psychopharmacological/psychotropics, e.g., anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives, etc.), antidepressants (tricyclic compounds, MAO inhibitors, etc.);

respiratory tract drugs, e.g., central antitussives (opium alkaloids and their derivatives); immunosuppressive agents; pharmacodynamic agents, such as peripheral nervous system drugs, e.g., local anesthetics (ester derivatives, amide derivatives); drugs acting at synaptic or neuroeffector junctional sites, e.g., cholinergic agents, cholinergic blocking agents, neuromuscular blocking agents, adrenergic agents, antiadrenergic agents; smooth muscle active drugs, e.g., spasmolytics (anticholinergics, musculotropic spasmolytics), vasodilators, smooth muscle stimulants; histamines and antihistamines, e.g., histamine and derivative thereof (betazole), antihistamines ($H_1$-antagonists, $H_2$-antagonists), histamine metabolism drugs; cardiovascular drugs, e.g., cardiotonics (plant extracts, butenolides, pentadienolids, alkaloids from erythrophleum species, ionophores, -adrenoceptor stimulants, etc.), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemostyptics; chemotherapeutic agents, such as anti-infective agents, e.g., ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and cytostatics, i.e., antineoplastic agents or cytotoxic drugs, such as alkylating agents, e.g., Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Myleran), Thiotepa (Triethylenethiophosphoramide), Carmustine (BiCNU, BCNU), Lomustine (CeeNU, CCNU), Streptozocin (Zanosar) and the like; plant alkaloids, e.g., Vincristine (Oncovin), Vinblastine (Velban, Velbe), Paclitaxel (Taxol), and the like; antimetabolites, e.g., Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA) and the like; antibiotics, e.g., Dactinomycin (Actinomycin D, Cosmegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g., Hydroxyurea (Hydrea), Procarbazine (Mutalane), Dacarbazine (DTIC-Dome), Cisplatin (Platinol) Carboplatin (Paraplatin), Asparaginase (Elspar) Etoposide (VePesid, VP-16-213), Amsarcrine (AMSA, m-AMSA), Mitotane (Lysodren), Mitoxantrone (Novatrone), and the like;

anti-inflammatory agents; antibiotics, such as: aminoglycosides, e.g., amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g., azidamfenicol, chloramphenicol, florfenicol, and theimaphenicol; ansamycins, e.g., rifamide, rifampin, rifamycin, rifapentine, rifaximin; β-lactams, e.g., carbacephems, carbapenems, cephalosporins, cehpamycins, monobactams, oxaphems, penicillins; lincosamides, e.g., clinamycin, lincomycin; macrolides, e.g., clarithromycin, dirthromycin, erythromycin, etc.; polypeptides, e.g., amphomycin, bacitracin, capreomycin, etc.; tetracyclines, e.g., apicycline, chlortetracycline, clomocycline, etc.; synthetic antibacterial agents, such as 2,4-diaminopyrimidines, nitrofurans, quinolones and analogs thereof, sulfonamides, sulfones;

antifungal agents, such as: polyenes, e.g., amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g., butenafine, naftifine, terbinafine; imidazoles, e.g., bifonazole, butoconazole, chlordantoin, chlormidazole, etc., thiocarbamates, e.g., tolciclate, triazoles, e.g., fluconazole, itraconazole, terconazole;

anthelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.;

antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, dibasic sodium arsenate; and antiprotozoan agents, such as: acranil, tinidazole, ipronidazole, ethylstibamine, pentamidine, acetarsone, aminitrozole, anisomycin, nifuratel, tinidazole, benzidazole, suramin, and the like.

Conjugation and Linking Moieties

Binding moieties and effector moieties of the present invention can be conjugated, for example, through a linker or linking moiety L, where L may be either a bond or a linking group. For example, in various embodiments, a binding moiety and an effector moiety are bound directly or are parts of a single molecule. Alternatively, a linking moiety can provide a covalent attachment between a binding moiety and effector moiety. A linking moiety, as with a direct bond, can achieve a desired structural relationship between a binding moiety and effector moiety and or an SDC-TRAP and its molecular target. A linking moiety can be inert, for example, with respect to the targeting of a binding moiety and biological activity of an effector moiety.

Appropriate linking moieties can be identified using the affinity, specificity, and/or selectivity assays described herein. Linking moieties can be selected based on size, for example, to provide an SDC-TRAP with size characteristics as described above. In various embodiments, a linking moiety can be selected, or derived from, known chemical linkers. Linking moieties can comprise a spacer group terminated at either end with a reactive functionality capable of covalently bonding to the drug or ligand moieties. Spacer groups of interest include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linking moieties that may find use in the SDC-TRAPs include disulfides and stable thioether moieties.

In various embodiments, a linking moiety is cleavable, for example enzymatically cleavable. A cleavable linker can be used to release an effector moiety inside a target cell after the SDC-TRAP is internalized. The susceptibility of a linking moiety to cleavage can be used to control delivery of an effector molecule. For example, a linking moiety can be selected to provide extended or prolonged release of an effector moiety in a target cell over time (e.g., a carbamate linking moiety may be subject to enzymatic cleavage by a carboxylesterase via the same cellular process used to cleave other carbamate prodrugs like capecitabine or irinotecan). In these, and various other embodiments, a linking moiety can exhibit sufficient stability to ensure good target specificity and low systemic toxicity, but not so much stability that it results in lowering the potency and efficacy of the SDC-TRAP.

Exemplary linkers are described in U.S. Pat. No. 6,214,345 (Bristol-Myers Squibb), U.S. Pat. Appl. 2003/0096743 and U.S. Pat. Appl. 2003/0130189 (both to Seattle Genetics), de Groot et al., J. Med. Chem. 42, 5277 (1999); de Groot et al. J. Org. Chem. 43, 3093 (2000); de Groot et al., J. Med. Chem. 66, 8815, (2001); WO 02/083180 (Syntarga); Carl et al., J. Med. Chem. Lett. 24, 479, (1981); Dubowchik et al., Bioorg & Med. Chem. Lett. 8, 3347 (1998) and Doronina et al. Bio Conjug Chem. 2006; Doronina et al. Nat Biotech 2003.

Identification and Selection of Targets and Corresponding SDC-TRAPs

The present invention provides for a broad class of pharmacological compounds including an effector moiety conjugated to an binding moiety directing the effector moiety to a biological target of interest. While treating cancer using an Hsp90 inhibitor binding moiety conjugated to a cytotoxic agent effector moiety is one illustrative example of the present invention, SDC-TRAPs are fundamentally broader in terms of their compositions and uses.

In various embodiments, the broad class of SDC-TRAP pharmacological compounds that are directed to biological targets have the following properties: the biological target (a cell and/or tissue target of interest, e.g., a tumor) should be effectible by an effector moiety, and the effector moiety should be known or developed for the biological target (e.g., chemotherapeutic agent for the tumor); the biological target should be associated with a molecular target (e.g., biomolecule, capable of being specifically bound, that is uniquely represented in the biological target) that specifically interacts with a binding moiety, and the binding moiety should be known or developed for the molecular target (e.g., ligand for the biomolecule); the effector moiety and binding moiety should be amenable to coupling and should essentially retain their respective activity after coupling. Furthermore, the conjugate should be capable of reaching and interacting with the molecular target, and in clinical applications should be suitable for administration to a subject (e.g., a subject can tolerate a therapeutically effective dose).

Examples of therapeutic molecular targets (i.e., binding moiety binding partners) for various conditions/disease states are presented in the table below. A suitable binding moiety can be selected based upon a given molecular target and/or a suitable effector moiety can be selected based upon a given condition/disease. In some cases, an FDA approved therapeutic agent can be used as an effector moiety (i.e., where the FDA approved therapeutic agent is an effector moiety as described herein, for example, a binding moiety and not an antibody).

| Condition/Disease State | Molecular target(s) | FDA Approved Therapeutic Agent |
| --- | --- | --- |
| Acute allograft rejection (renal transplant) | CD3E | Muromonab |
| Acromegaly | somatostatin receptor 1 | Octreotide |
| Actinic Keratosis | toll-like receptor 7 | Imiquimod |
| Acute Coronary Syndrome | P2Y12 ADP-receptor | Brilinta |
| Acute Myocardial Infarction | plasminogen | Reteplase |
| alpha$_1$-proteinase inhibitor (A$_1$-PI) deficiency | elastase, neutrophil expressed | Alpha-1 proteinase inhibitor |
| Alzheimer's Disease | BACE1 | |
| Alzheimer's Disease | soluble APP α and APP β | |
| Anemia | erythropoietin receptor | Epoetin alfa |
| Angina, chronic stable | calcium channel, voltage-dependent, L type, alpha 1C subunit | Nicardipine |
| Angina, unstable | P2Y12 ADP-receptor | Brilinta |
| Angioedema, hereditary | kallikrein 1 | Ecallantide |
| Angioedema, acute hereditary | bradykinin B2 receptor | Firazyr |
| Ankylosing spondylitis | tumor necrosis factor | Infliximab |
| Anticoagulant | serpin peptidase inhibitor, clade D (heparin cofactor), member 1 | Ardeparin (withdrawn) |
| Arrhythmia (ventricular) | potassium voltage-gated channel, subfamily H (eag-related), member 2 | Propafenone |
| Arrhythmia | calcium channel, voltage-dependent, P/Q type, alpha 1A subunit | Bepridil |

-continued

| Condition/Disease State | Molecular target(s) | FDA Approved Therapeutic Agent |
|---|---|---|
| Arthritis/rheumatic disorders | dihydroorotate dehydrogenase (quinone) | Leflunomide |
| Arthritis/rheumatic disorders | interleukin 1 receptor, type I | Anakinra |
| Asthma | cysteinyl leukotriene receptor 1 | Nedocromil |
| Asthma | IgE antibodies | Omalizumab |
| Atypical hemolytic uremic syndrome (aHUS) | complement component 5 | Eculizumab |
| Baldness | steroid-5-alpha-reductase, alpha polypeptide 1 (3-oxo-5 alpha-steroid delta 4-dehydrogenase alpha 1) | Finasteride |
| Benign prostatic hyperplasia | steroid-5-alpha-reductase, alpha polypeptide 1 (3-oxo-5 alpha-steroid delta 4-dehydrogenase alpha 1) | Finasteride |
| Bone/vertebral fracture prevention | TGF-beta activated kinase 1/MAP3K7 binding protein 2 | — |
| Breast Cancer | ER (estrogen receptor) | |
| Breast Cancer | HER-2/neu | Trastuzumab (HER-2) |
| Breast Cancer | tubulin, beta 1 class VI | Paclitaxel |
| Breast Cancer | chromodomain helicase DNA binding protein 1 | Epirubicin |
| Breast Cancer | Tubulin | Halaven |
| Breast/Ovarian Cancer | BRCA genes | |
| Bronchitis, chronic | phosphodiesterase 4 (PDE4) inhibitors | Daliresp |
| Cardiac Ischemic Conditions | integrin, beta 3 (platelet glycoprotein IIIa, antigen CD61) | Abciximab |
| Cancer | CD74; Trop-2; CEACAM6 | |
| Cancer | EGFR | |
| Cardiovascular disease | Matrix Mettaloproteinases | |
| Cardiovascular disease | VKORC1 | |
| Cardiovascular disease | LDL | |
| Cervical Dystonia | vesicle-associated membrane protein 1 (synaptobrevin 1) | Botulinum toxin type B |
| Chemoprotectant | alkaline phosphatase, placental-like 2 | Amifostine |
| Chonic myelogenous leukemia | interferon (alpha, beta and omega) receptor 1 | Interferon alfa-2a |
| Chronic Obstructive Pulmonary Disorder | phosphodiesterase 4 (PDE4) inhibitors | Daliresp |
| Chronic spasticity due to upper motor disorders | ryanodine receptor 1 (skeletal) | Dantrolene |
| Colon Cancer | guanylate cyclase 2C | |
| Colorectal Cancer | EGFR | |
| Colorectal Cancer | KRAS | |
| Colorectal Cancer | CEA | |
| Congestive Heart Failure | B-type natriuretic peptide | |
| Congestive Heart Failure | plasminogen | Reteplase |
| Crohn's Disease | integrin, alpha 4 (antigen CD49D, alpha 4 subunit of VLA-4 receptor) | Natalizumab |
| Cryopyrin-associated periodic syndromes | interleukin 1, beta | Canakinumab |
| Cryopyrin-associated periodic syndromes | interleukin 1, alpha | Rilonacept |
| Depression | 5HT1A receptor (a serotonin reuptake inhibitor) | Viibryd |
| Diabetes | dipeptidyl peptidase-4 (DPP-4) enzyme | Tradjenta |
| Diabetes | protein kinase, AMP-activated, beta 1 non-catalytic subunit | Metformin |
| Diabetes | amylase, alpha 2A (pancreatic) | Acarbose |
| Diabetes | peroxisome proliferator-activated receptor gamma | Troglitazone (withdrawn) |
| Diabetes | glucagon-like peptide 1 receptor | Exenatide |
| Diabetes | receptor (G protein-coupled) activity modifying protein 1 | Pramlintide |
| Diabetes | dipeptidyl-peptidase 4 | Sitagliptin |
| Edema | potassium voltage-gated channel, Isk-related family, member 1 | Indapamide |
| Edema | solute carrier family 12 (sodium/potassium/chloride transporters), member 2 | Bumetanide |
| Factor XIII (FXIII) deficiency, congenital | enzyme replacement therapy (FactorXIII) | Corifact |
| Familial cold autoinflammatory syndrome | interleukin 1, beta | Canakinumab |
| Familial cold autoinflammatory syndrome | interleukin 1, alpha | Rilonacept |
| Gaucher Disease, type I | UDP-glucose ceramide glucosyltransferase | Miglustat |
| GI stromal tumors (GIST), metastatic malignant | Bcr-Abl tyrosine kinase (an abnormal tyrosine kinase) | |

-continued

| Condition/Disease State | Molecular target(s) | FDA Approved Therapeutic Agent |
|---|---|---|
| Glaucoma | prostaglandin F receptor (FP) | Latanoprost |
| Granulomatous disease, chronic | interferon gamma receptor 1 | Interferon gamma-1b |
| Growth disorder | insulin-like growth factor 1 receptor | Mecasermin |
| Growth hormone deficiency | growth hormone releasing hormone receptor | Sermorelin |
| Hairy cell leukemia | interferon (alpha, beta and omega) receptor 1 | Interferon alfa-2a |
| Hairy cell leukemia | adenosine deaminase | Pentostatin |
| Heartburn (Gastric reflux) | 5-hydroxytryptamine (serotonin) receptor 4, G protein-coupled | Cisapride (withdrawn) |
| Hemophilia (prevent bleeding) | plasminogen activator, tissue | Tranexamic acid |
| Hepatitis C | interferon (alpha, beta and omega) receptor 1 | Interferon alfa-2a |
| Hepatitis C (genotype 1) | hepatitis C virus non-structural protein 3 (NS3) serine protease | Victrelis |
| Hepatitis C (genotype 1) | hepatitis C virus non-structural protein 3 (NS3)/4A serine protease | Incivek |
| Hepatocellular Carcinoma | α-fetoprotein | |
| HIV | chemokine (C-C motif) receptor 5 (gene/pseudogene) | Maraviroc |
| HIV | HIV-1 reverse transcriptase | Edurant |
| Hyperammonemia | carbamoyl-phosphate synthase 1, mitochondrial | Carglumic acid |
| Hypercalcemia in patients with parathyroid carcinoma | calcium-sensing receptor | Cinacalcet |
| Hypercholesterolemia | 3-hydroxy-3-methylglutaryl-CoA reductase | Lovastatin |
| Hyperlipidemia | NPC1 (Niemann-Pick disease, type C1, gene)-like 1 | Ezetimibe |
| Hyperplasia | steroid-5-alpha-reductase, alpha polypeptide 1 (3-oxo-5 alpha-steroid delta 4-dehydrogenase alpha 1) | Finasteride |
| Hypertension | adrenoceptor alpha 1D | Terazosin |
| Hypertension | calcium channel, voltage-dependent, P/Q type, alpha 1A subunit | Bepridil |
| Hypertension | calcium channel, voltage-dependent, N type, alpha 1B subunit | Amlodipine |
| Hypertension | angiotensin II receptor, type | Losartan |
| Hypertension | renin | Aliskiren |
| Hypertension | AT1 subtype angiotensin II receptor | Edarbi |
| Hypertension | membrane metallo-endopeptidase | Candoxatril |
| Increase bone density, prevent bone fracture | parathyroid hormone 1 receptor | Teriparatide |
| Infections, acute skin and skin structure | penicillin-binding proteins | Teflaro |
| Infections, bacterial | dipeptidase 1 (renal) | Cilastatin (adjuvant) |
| Infections (bone marrow transplant, etc.) | colony stimulating factor 3 receptor (granulocyte) | Filgrastim |
| Infections, immunomodulatory agents | colony stimulating factor 2 receptor, alpha, low-affinity (granulocyte-macrophage) | Sargramostim |
| Infertility | follicle stimulating hormone receptor | Urofollitropin |
| Inflammation | C Reactive Protein | |
| Interstitial cystitis, bladder pain/discomfort due to | fibroblast growth factor 1 (acidic) | Pentosan polysulfate |
| Irritable Bowel Syndrome | chloride channel, voltage-sensitive 2 | Lubiprostone |
| Kaposi's sarcoma, AIDS-related | interferon (alpha, beta and omega) receptor 1 | Interferon alfa-2a |
| Leukemia/Lymphoma | CD20 Antigen | |
| Leukemia/Lymphoma | CD30 | |
| Leukemia/Lymphoma | PML/RAR alpha | |
| Leukemia, chronic myeloid | proto-oncogene tyrosine-protein kinase Src | Dasatinib |
| Leukemia, myeloid | CD33, Myeloid cell surface antigen CD33 | Gemtuzumab ozogamicin (withdrawn) |
| Lipodystrophy | human GRF receptors | Egrifta |
| Lung Cancer | ALK | |
| Lung Cancer | CD98; fascin; 14-3-3 eta | |
| Lymphocytic leukemia, B-cell chronic | polymerase (DNA directed), alpha 1, catalytic subunit | Fludarabine |
| Lymphocytic leukemia, B-cell chronic | CD52 (CAMPATH-1 antigen precursor) | Alemtuzumab |
| Lymphocytic leukemia, chronic | membrane-spanning 4-domains, subfamily A, member 1 | Rituximab |
| Lymphoma, Hodgkin's | chemokine (C—X—C motif) receptor 4 | Plerixafor |
| Lymphoma, Hodgkin's | CD30 | Adcetris |
| Lymphoma, mantle cell | proteasome (prosome, macropain) subunit, beta type, 1 | Bortezomib |
| Lymphoma, systemic anaplastic large cell | CD30 | Adcetris |
| Lymphocytic leukemia, T-cell | histone deacetylase 1 | Vorinostat |
| Melanoma | S100 protein | |

| Condition/Disease State | Molecular target(s) | FDA Approved Therapeutic Agent |
| --- | --- | --- |
| Melanoma, metastatic (with BRAFV600E mutation) | mutated form of BRAf that facilitates cell growth | Zelboraf |
| Melanoma, metastatic | CTLA-4 | Yervoy |
| Migrane Headache | carbonic anhydrase II | Topiramate |
| Muckle-Wells syndrome | interleukin 1, beta | Canakinumab |
| Muckle-Wells syndrome | interleukin 1, alpha | Rilonacept |
| Multiple Sclerosis | sphingosine-1-phosphate receptor 1 | Fingolimod |
| Myeloma, multiple | chemokine (C—X—C motif) receptor 4 | Plerixafor |
| Myeloma, multiple | proteasome (prosome, macropain) subunit, beta type, 1 | Bortezomib |
| Myocardial Infarction | Troponin I | |
| Myocardial Infarction, non-ST-elevation | P2Y12 ADP-receptor | Brilinta |
| Myocardial Infarction, ST-elevation | P2Y12 ADP-receptor | Brilinta |
| N-acetylglutamate synthase (NAGS) deficiency | carbamoyl-phosphate synthase 1, mitochondrial | Carglumic acid |
| Nausea/vomiting | 5-hydroxytryptamine (serotonin) receptor 3A, ionotropic | Ondansetron |
| Nausea/vomiting | tachykinin receptor 1 | Aprepitant |
| Nausea/vomiting (severe) | cannabinoid receptor 1 (brain) | Marinol |
| Non-Hodgkin's Lymphoma | membrane-spanning 4-domains, subfamily A, member 1 | Rituximab |
| Non-small cell lung cancer | phosphoribosylglycinamide formyltransferase, phosphoribosylglycinamide synthetase, phosphoribosylaminoimidazole synthetase | Pemetrexed |
| Non-small cell lung cancer | epidermal growth factor receptor | Gefitinib |
| Non-small cell lung cancer (that is ALK-positive) | the ATP-binding pocket of target protein kinases | Xalkori |
| Obesity | lipase, gastric/pancreatic lipase | Orlistat |
| Ovarian Cancer | IGF-II; leptin; osteopontin; prolactin | |
| Oral mucositis | fibroblast growth factor receptor 2 | Palifermin |
| Organ rejection prophylaxsis | FK506 binding protein 1A, 12 kDa | Tacrolimus |
| Organ rejection prophylaxsis | IMP (inosine 5'-monophosphate) dehydrogenase 2 | Mycophenolate mofetil |
| Organ rejection prophylaxsis | interleukin 2 receptor, alpha | Daclizumab |
| Organ rejection prophylaxsis | FK506 binding protein 12-rapamycin associated protein 1 | Sirolimus |
| Organ rejection prophylaxsis | protein phosphatase 3, regulatory subunit B, beta | Cyclosporine |
| Organ rejection prophylaxsis | CD80 and CD86, blocks CD28 mediated costimulation of T lymphocytes | Nulojix |
| Osteoporosis | interferon gamma receptor 1 | Interferon gamma-1b |
| Osteoporosis (prophylaxsis) | TGF-beta activated kinase 1/MAP3K7 binding protein 2 | Denosumab |
| Paget's Disease | farnesyl diphosphate synthase | Pamidronate |
| Pancreatic Cancer | CA19-9 | |
| Parkinson's Disease | catechol-O-methyltransferase | Tolcapone (withdrawn) |
| Parkinson's Disease | monoamine oxidase B | Selegiline |
| Paroxysmal nocturnal hemoglobinuria | complement component 5 | Eculizumab |
| Pneumonia, susceptible bacterial community-acquired | penicillin-binding proteins | Teflaro |
| Poisoning, ethylene glycol or methanol | alcohol dehydrogenase 1B (class I), beta polypeptide | Fomepizole |
| Psoriasis, plaque | interleukin 12B (natural killer cell stimulatory factor 2, cytotoxic lymphocyte maturation factor 2, p40) | Ustekinumab |
| Psoriasis, plaque | integrin, alpha L (antigen CD11A (p180), lymphocyte function-associated antigen 1; alpha polypeptide) | Efalizumab (withdrawn) |
| Psoriasis, chronic plaque | T-cell surface antigen CD2 precursor | Alefacept |
| Psoriatic Arthritis | tumor necrosis factor | Infliximab |
| Prostate Cancer | PSA (prostate specific antigen) | |
| Prostate hyperplasia, benign | adrenoceptor alpha 1D | Terazosin |
| Pulmonary embolism | Factor Xa | Xarelto |
| Pulmonary hypertension | endothelin receptor type B | Bosentan |
| Renal cell carcinoma | v-raf-1 murine leukemia viral oncogene homolog 1 | Sorafenib |
| Renal cell carcinoma | fms-related tyrosine kinase 1 (vascular endothelial growth factor/vascular permeability factor receptor) | Sunitinib |
| Renal cell carcinoma | vascular endothelial growth factor A | Bevacizumab |
| Rheumatoid arthritis | TNF-α | |
| Rheumatoid arthritis | IL-6 | |
| Rheumatoid arthritis | inhibitor of kappa light polypeptide gene enhancer in B-cells, kinase beta | Auranofin |

| Condition/Disease State | Molecular target(s) | FDA Approved Therapeutic Agent |
|---|---|---|
| Rheumatoid arthritis | tumor necrosis factor | Infliximab |
| Rheumatoid arthritis | CD80 (T-lymphocyte activation antigen CD80) | Abatacept |
| Rheumatoid arthritis | interleukin 6 receptor | Tocilizumab |
| Rheumatoid arthritis | CEP-1 | |
| Schizophrenia | CYP2D6 | |
| Scorpion stings | venom toxins | Anascorp |
| Seizures | carbonic anhydrase II | Topiramate |
| Seizures | solute carrier family 6 (neurotransmitter transporter, GABA), member 1 | Tiagabine |
| Seizures | 4-aminobutyrate aminotransferase | Divalproex sodium |
| Seizures | Gamma-amino butyric acid (GABA) | |
| Sepsis, severe | coagulation factor VIII (Factors Va and VIIIa), procoagulant component | Drotrecogin alfa |
| Small Cell Lung Cancer | topoisomerase (DNA) II alpha 170 kDa | Etoposide |
| Small Cell Lung Cancer | topoisomerase (DNA) I | Topotecan |
| Stroke | thrombin | Pradaxa |
| Stroke | Factor Xa | Xarelto |
| Stroke, thrombotic | purinergic receptor P2Y, G-protein coupled, 12 | Ticlopidine |
| Systemic embolism | Factor Xa | Xarelto |
| systemic embolism in non-valvular atrial fibrillation | thrombin | Pradaxa |
| Systemic lupus erythematosus | human B lymphocyte stimulator protein (BLyS) | Benlysta |
| Testicular Cancer | LDH | |
| Throid Cancer Metastasis | Thyro-globulin | |
| Thrombocythemia | phosphodiesterase 4B, cAMP-specific | Amrinone |
| Thrombocytopenia | myeloproliferative leukemia virus oncogene expression product | Romiplostim |
| Thrombocytopenia | interleukin 11 receptor, alpha | Oprelvekin |
| Thrombosis, Deep vein | Factor Xa | Xarelto |
| Thyroid Cancer | protein kinases of the VEGF, EGFR, and/or RET pathways | Caprelsa |
| Tyrosinemia type I, hereditary | 4-hydroxyphenylpyruvate dioxygenase | Nitisinone |
| Ulcer (anti-ulcer agent) | ATPase, H+/K+ exchanging, alpha polypeptide | Omeprazole |
| Ulcers, diabetic neuropathic | platelet-derived growth factor receptor, beta polypeptide | Becaplermin |
| Urothelial Cell Carcinoma | Bladder Tumor Antigen | |

Examples of imaging/diagnostic molecular targets (i.e., binding moiety binding partners) for various conditions/disease states are presented in the table below. A suitable binding moiety can be selected based upon a given molecular target and/or a suitable effector moiety can be selected based upon a given condition/disease. In some cases, an FDA approved imaging/diagnostic agent can be used as an effector moiety (i.e., where the FDA approved imaging/diagnostic agent is an effector moiety as described herein, for example, a binding moiety and not an antibody).

| Condition/Disease State | Molecular target(s) | FDA Approved Imaging/Diagnostic |
|---|---|---|
| Alzheimer's disease, stroke, schizophrenia | cerebral blood flow (hemoglobin) | |
| Alzheimer's disease | β-amyloid protein (can be used to monitor progression of the disease) | |
| Diagnostic (screening test for exocrine pancreatic insufficiency and to monitor the adequacy of supplemental pancreatic therapy) | pancreatic lipase | Bentiromide |
| Diagnostic for bone density | parathyroid hormone 1 receptor | Teriparatide |
| Diagnostic/imaging | proteasome (prosome, macropain) subunit, alpha type, 6 pseudogene 1 | Capromab |
| Diagnostic for MRI to visualize blood brain barrier/abnormal vascularity of the CNS (to diagnose disorders of the brain and spine) | Paramagnetic macrocyclic contrast agent | Gadavist |
| General Cognitive Decline (Dementia, Alzheimer's Disease, Parkinson's Disease, etc.) | thining of the cerebral cortex | |
| Inflammation/tumor progression | (radiolabeled) 18F-fludeoxyglucose | |

| Condition/Disease State | Molecular target(s) | FDA Approved Imaging/Diagnostic |
|---|---|---|
| Osteoarthritis | cartilage (collagen and proteoglycan) degeneration | |
| Parkinson's syndrome | Dopamine receptors (diagnostic that detects dopamine receptors) | DaTscan |
| Thyroid Cancer | thyroid stimulating hormone receptor | Thyrotropin alfa |

Imaging Moieties, and Diagnostic and Research Applications

In various embodiments, the effector moiety is an imaging moiety—that is, a molecule, compound, or fragment thereof that facilitates a technique and/or process used to create images or take measurements of a cell, tissue, and/or organism (or parts or functions thereof) for clinical and/or research purposes. An imaging moiety can produce, for example, a signal through emission and/or interaction with electromagnetic, nuclear, and/or mechanical (e.g., acoustic as in ultrasound) energy. An imaging moiety can be used, for example, in various radiology, nuclear medicine, endoscopy, thermography, photography, spectroscopy, and microscopy methods.

Imaging studies can be used, for example, in a clinical or research setting to diagnose a subject, select a subject for therapy, select a subject for participation in a clinical trial, monitor the progression of a disease, monitor the effect of therapy, to determine if a subject should discontinue or continue therapy, to determine if a subject has reached a clinical end point, and to determine recurrence of a disease. Imaging studies can be used, for example, to conduct research to identify effective interacting moieties and/or effector moieties and/or combinations thereof, to identify effective dosing and dose scheduling, to identify effective routes of administration, and to identify suitable targets (e.g., diseases susceptible to particular treatment).

Methods of Making Pharmaceutical Conjugates

The pharmaceutical conjugates, i.e., SDC-TRAPs, of the invention may be prepared using any convenient methodology. In a rational approach, the pharmaceutical conjugates are constructed from their individual components, binding moiety, in some cases a linker, and effector moiety. The components can be covalently bonded to one another through functional groups, as is known in the art, where such functional groups may be present on the components or introduced onto the components using one or more steps, e.g., oxidation reactions, reduction reactions, cleavage reactions and the like. Functional groups that may be used in covalently bonding the components together to produce the pharmaceutical conjugate include: hydroxy, sulfhydryl, amino, and the like. The particular portion of the different components that are modified to provide for covalent linkage will be chosen so as not to substantially adversely interfere with that components desired binding activity, e.g., for the effector moiety, a region that does not affect the target binding activity will be modified, such that a sufficient amount of the desired drug activity is preserved. Where necessary and/or desired, certain moieties on the components may be protected using blocking groups, as is known in the art, see, e.g., Green & Wuts, Protective Groups in Organic Synthesis (John Wiley & Sons) (1991).

Alternatively, the pharmaceutical conjugate can be produced using known combinatorial methods to produce large libraries of potential pharmaceutical conjugates which may then be screened for identification of a bifunctional, molecule with the pharmacokinetic profile. Alternatively, the pharmaceutical conjugate may be produced using medicinal chemistry and known structure-activity relationships for the targeting moiety and the drug. In particular, this approach will provide insight as to where to join the two moieties to the linker.

A number of exemplary methods for preparing SDC-TRAP molecules are set forth in the examples. As one of skill in the art will understand, the exemplary methods set forth in the examples can be modified to make other SDC-TRAP molecules.

Methods of Use, Pharmaceutical Preparations, and Kits

The pharmaceutical conjugates find use in treatment of a host condition, e.g., a disease condition. In these methods, an effective amount of the pharmaceutical conjugate is administered to the host, where "effective amount" means a dosage sufficient to produce the desired result, e.g., an improvement in a disease condition or the symptoms associated therewith. In many embodiments, the amount of drug in the form of the pharmaceutical conjugate that need be administered to the host in order to be an effective amount will vary from that which must be administered in free drug form. The difference in amounts may vary, and in many embodiments may range from two-fold to ten-fold. In certain embodiments, e.g., where the resultant modulated pharmacokinetic property or properties result(s) in enhanced activity as compared to the free drug control, the amount of drug that is an effective amount is less than the amount of corresponding free drug that needs to be administered, where the amount may be two-fold, usually about four-fold and more usually about ten-fold less than the amount of free drug that is administered.

The pharmaceutical conjugate may be administered to the host using any convenient means capable of producing the desired result. Thus, the pharmaceutical conjugate can be incorporated into a variety of formulations for therapeutic administration. More particularly, the pharmaceutical conjugate of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the pharmaceutical conjugate can be achieved in various ways, including oral, buccal, rectal, parenteral, intraperitoneal, intradermal, transdermal, intracheal, etc., administration. In pharmaceutical dosage forms, the pharmaceutical conjugate may be administered alone or in combination with other pharmaceutically active compounds.

The subject methods find use in the treatment of a variety of different disease conditions. In certain embodiments, of particular interest is the use of the subject methods in disease conditions where an active agent or drug having desired activity has been previously identified, but which active agent or drug does not bind to its target with desired affinity and/or specificity. With such active agents or drugs, the subject methods can be used to enhance the binding affinity and/or specificity of the agent for its target.

The specific disease conditions treatable by with the subject bifunctional compounds are as varied as the types of drug moieties that can be present in the pharmaceutical conjugate. Thus, disease conditions include cellular proliferative diseases, such as neoplastic diseases, autoimmune diseases, central nervous system or neurodegenerative diseases, cardiovascular diseases, hormonal abnormality diseases, infectious diseases, and the like.

By treatment is meant at least an amelioration of the symptoms associated with the disease condition afflicting the host, where amelioration is used in a broad sense to refer to at least a reduction in the magnitude of a parameter, e.g., symptom, associated with the pathological condition being treated, such as inflammation and pain associated therewith. As such, treatment also includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition.

Methods of use of the invention extend beyond strict treatment of a disease. For example, the invention includes uses in a clinical or research setting to diagnose a subject, select a subject for therapy, select a subject for participation in a clinical trial, monitor the progression of a disease, monitor the effect of therapy, to determine if a subject should discontinue or continue therapy, to determine if a subject has reached a clinical end point, and to determine recurrence of a disease. The invention also includes uses in conducting research to identify effective interacting moieties and/or effector moieties and/or combinations thereof, to identify effective dosing and dose scheduling, to identify effective routes of administration, and to identify suitable targets (e.g., diseases susceptible to particular treatment).

A variety of hosts are treatable according to the subject methods. Generally such hosts are "mammals" or "mammalian," where these terms are used broadly to describe organisms which are within the class Mammalia, including the orders carnivore (e.g., dogs and cats), rodentia (e.g., mice, guinea pigs, and rats), and primates (e.g., humans, chimpanzees, and monkeys). In many embodiments, the hosts will be humans.

The invention provides kits for treating a subject in need thereof comprising at least one SDC-TRAP and instruction for administering a therapeutically effective amount of the at least one SDC-TRAP to the subject, thereby treating the subject. The invention also provides kits for imaging, diagnosing, and/or selecting a subject comprising at least one SDC-TRAP and instruction for administering an effective amount of at least one SDC-TRAP to the subject, thereby imaging, diagnosing, and/or selecting the subject.

Kits with unit doses of the pharmaceutical conjugate, usually in oral or injectable doses and often in a storage stable formulation, are provided. In such kits, in addition to the containers containing the unit doses, an informational package insert describing the use and attendant benefits of the drugs in treating pathological condition of interest will be included. Preferred compounds and unit doses are those described herein above.

The invention also provides methods for treatment of a disease or disorder in which the subject to be treated is selected for treatment based on the presence of, or the overexpression of, a particular protein. For example, subjects may be selected for treatment of cancer based on the presence of greater the normal levels of Hsp90. In this case, subjects would be administered an SDC-TRAP that comprises a binding moiety that selectively binds to Hsp90.

The invention provides methods of treating or preventing an inflammatory disorder in a subject, comprising administering to the subject an effective amount of a compound represented by any one of formula (I) through (LXXII), or any embodiment thereof, or a compound shown in Table 5, 6, or 7 as disclosed in U.S. Patent Publication 2010/0280032. In one embodiment, the compound or binding moiety or SDC-TRAP may be administered to a human to treat or prevent an inflammatory disorder. In another embodiment, the inflammatory disorder is selected from the group consisting of transplant rejection, skin graft rejection, arthritis, rheumatoid arthritis, osteoarthritis and bone diseases associated with increased bone resorption; inflammatory bowel disease, ileitis, ulcerative colitis, Barrett's syndrome, Crohn's disease; asthma, adult respiratory distress syndrome, chronic obstructive airway disease; corneal dystrophy, trachoma, onchocerciasis, uveitis, sympathetic ophthalmitis, endophthalmitis; gingivitis, periodontitis; tuberculosis; leprosy; uremic complications, glomerulonephritis, nephrosis; sclerodermatitis, psoriasis, eczema; chronic demyelinating diseases of the nervous system, multiple sclerosis, AIDS-related neurodegeneration, Alzheimer's disease, infectious meningitis, encephalomyelitis, Parkinson's disease, Huntington's disease, amyotrophic lateral sclerosis viral or autoimmune encephalitis; autoimmune disorders, immune-complex vasculitis, systemic lupus and erythematodes; systemic lupus erythematosus (SLE); cardiomyopathy, ischemic heart disease hypercholesterolemia, atherosclerosis, preeclampsia; chronic liver failure, brain and spinal cord trauma. In another embodiment, an SDC-TRAP, or a compound shown in Table 5, 6, or 7 as disclosed in U.S. Patent Publication 2010/0280032, is administered with an additional therapeutic agent. In another embodiment, the additional therapeutic agent may an anti-inflammatory agent.

In one embodiment, an SDC-TRAP that is administered to a subject but does not enter a target cell is rapidly cleared from the body. In this embodiment, the SDC-TRAP that does not enter a target cell is rapidly cleared in order to reduce the toxicity due to the components of the SDC-TRAP, the degradation products of the SDC-TRAP or the SDC-TRAP molecule. Clearance rate can be determined by measuring the plasma concentration of the SDC-TRAP molecule as a function of time.

Likewise, SDC-TRAP molecules that enter non-targeted cells by passive diffusion rapidly exit the non-targeted cell or tissue and are either eliminated from the subject or proceed to enter and be retained a targeted cell or tissue. For example, an SDC-TRAP that is intended to treat tumor cells and is targeted to tumor cells that overexpress, for example, Hsp90 will accumulate selectively in tumor cells that overexpress Hsp90. Accordingly, very low levels of this exemplary SDC-TRAP will be present in non-tumor tissue such as normal lung tissue, heart, kidney, and the like. In one embodiment, the safety of the SDC-TRAP molecules of the invention can be determined by their lack of accumulation in non-targeted tissue. Conversely, the safety of the SDC-TRAP molecules of the invention can be determined by their selective accumulation in the targeted cells and/or tissue.

EXAMPLES

The following examples, which are briefly summarized and then discussed in turn below, are offered by way of illustration and not by way of limitation.

Example 1 presents the synthesis of exemplary SDC-TRAPs.

Example 2 presents the targeted delivery of exemplary SDC-TRAPs.

Example 3 presents an exemplary assay for selecting binding moieties.

Example 4 presents the cytotoxicity of exemplary SDC-TRAPs.

Example 5 presents the stability of exemplary SDC-TRAPs in plasma.

Example 6 presents a detailed schematic for the synthesis of an exemplary SDC-TRAP.

Example 7 presents results of tests using the SDC-TRAP of Example 6.

Example 8 presents the synthesis and testing of a lenalidomide-based SDC-TRAP.

Examples 9 and 10 present examples of $IC_{50}$ value determinations.

Example 11 presents an exemplary Hsp90α binding assay.

Example 12 presents an exemplary HER2 degradation assay.

Example 13 presents an exemplary cytotoxicity assay.

Example 14 presents an exemplary plasma stability protocol.

Example 15 presents an exemplary tissue distribution extraction procedure.

Example 16 presents an exemplary tissue distribution study.

Examples 17 and 18 present examples of SDC-TRAP stability in mouse plasma and cell culture media.

Examples 19-33 present synthesis and $IC_{50}$ data for different exemplary SDC-TRAPs. Within examples 19-33, exemplary synthetic schemes are set forth. It is to be understood that the additional exemplary compounds were synthesized according to the methods described for the exemplary synthetic schemes.

Example 34 sets forth the identification and use of SDC-TRAPs for prevention and treatment of chronic bronchitis and asthma.

Example 35 sets forth the identification and use of SDC-TRAPs for prevention and treatment of skin cancers and actinic keratosis.

Example 36 set forth experiments for determining the permeability of SDC-TRAP molecules.

Example 1

SDC-TRAPs of an exemplary embodiment may be prepared in the following manner:

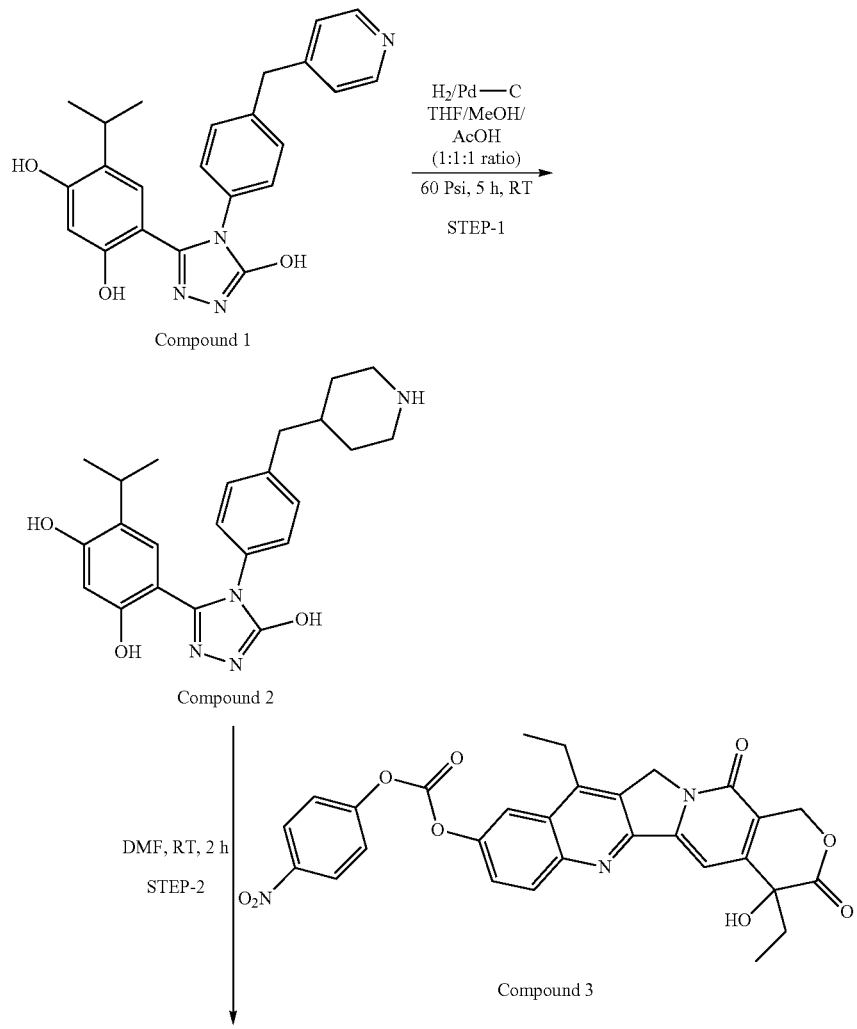

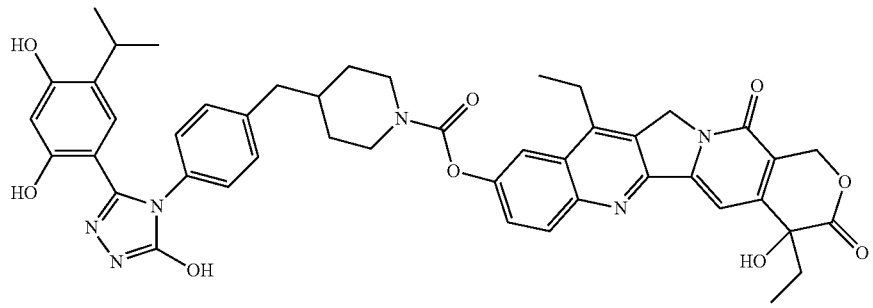

The synthesis of Compound 1 and Compound 3 are discussed in WO 2007/139968 and WO 2004/012661, respectively.

Synthesis of Compound 2 (STEP-1): To a solution of 1.0 g (2.48 mmols) of Compound 1 in 60 mL of 1:1:1-Methanol:Tetrahydrofuran:Acetic acid was added 75 mg of 10% Palladium on charcoal (wet Degussa type) and the contents of the flask was deoxygenated by vacuum and hydrogen purge. It was then pressurized to 60 Psi with hydrogen and stirred for 5 h at room temperature. The flask was then thoroughly flushed with argon and filtered the solids through a short pad of celite. Evaporation and recrystallization of the crude product afforded 900 mg (88%) of the Compound 2 in pure form as an off-white solid. ESMS calculated for $C_{23}H_{28}N_4O_3$: 408.22; Found: 409.1 (M+).

Synthesis: To a stirred solution of 0.1 g (0.245 mmols) of Compound 2 in 5 mL of anhydrous N,N-Dimethylformamide was added in portion 0.13 g (0.245 mmols) of Compound 3 (4,11-diethyl-4-hydroxy-3,14-dioxo-3,4,12,14-tetrahydro-1H-pyrano[3',4':6,7]indolizino[1,2-b]quinolin-9-yl (4-nitrophenyl) carbonate) and the mixture was stirred at room temperature for 2 h. After confirming the completion of the reaction by LC-MS, 30 mL of water was added to the flask and stirred for 5 mins. The resultant precipitate was filtered, thoroughly washed with water (10 mL×3) and dried. The solids were dissolved in 25 mL of 95:5-dichloromethane:methanol and dried over anhydrous $Na_2SO_4$. Evaporation followed by column chromatography afforded the conjugate 1 which was further purified by crystallization in methanol to remove minor impurities (mostly SN-38) and the procedure afforded 130 mg (65%) of the pure Conjugate 1. $^1$H NMR (400 MHz, DMSO-$d_6$), δ (ppm): 11.93 (bs, 1H), 9.57 (bs, 1H), 9.45 (bs, 1H), 8.18 (d, J=8 Hz, 1H), 7.98 (s, 1H), 7.66 (dd, J=4.0, 8.0 Hz, 1H). 7.34 (s, 1H), 7.24 (d, J=8 Hz, 2H), 7.13 (d, J=8 Hz, 2H), 6.77 (s, 1H), 6.54 (bs, 1H), 6.28 (s, 1H), 5.44 (s, 2H), 5.34 (s, 2H), 3.21-3.18 (m, 2H), 3.10-2.96 (m, 3H), 2.59 (d, J=8 Hz, 2H), 1.91-1.76 (m, 3H), 1.67 (bs, 2H), 1.30 (t, J=8 Hz, 3H), 0.95 (d, J=8 Hz, 6H), 0.89 (d, J=8 Hz, 3H). ESMS calculated for $C_{46}H_{46}N_6O_9$: 826.33; Found: 827.3 (M+).

Additional SDC-TRAPs made according to the general scheme noted above include the following:

Compound SDC-TRAP-0008

4,11-diethyl-4-hydroxy-3,14-dioxo-3,4,12,14-tetrahydro-1H-pyrano[3',4':6,7]indolizino[1,2-b]quinolin-9-yl (2-(5-(3-(2,4-dihydroxy-5-isopropylphenyl)-5-hydroxy-4H-1,2,4-triazol-4-yl)-1H-indol-1-yl)ethyl) carbamate

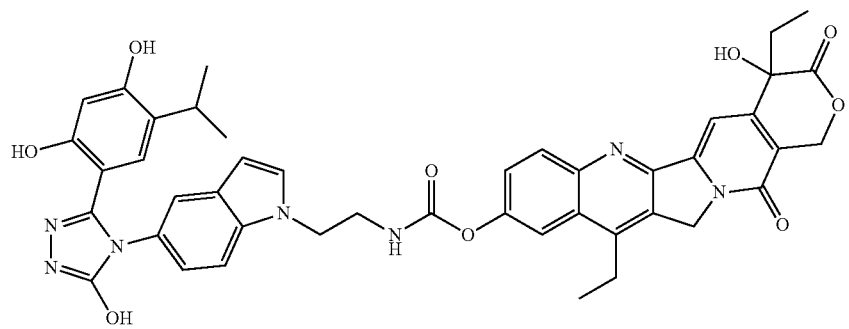 [SMILES: CCc1c2c(nc3ccc(OC(=O)NCCn4ccc5cc(-n6c(O)nnc6-c6cc(C(C)C)c(O)cc6O)ccc54)cc13)-c1cc3c(c(=O)n1C2)COC(=O)C3(O)CC]

ESMS calculated for $C_{44}H_{41}N_7O_9$: 811.30; Found: 812.3 (M+).

SDC-TRAP-0015

N1-(2-(2-(5-(3-(2,4-dihydroxy-5-isopropylphenyl)-5-hydroxy-4H-1,2,4-triazol-4-yl)-1H-indol-1-yl)ethoxy)ethyl)-N5-(2-(2,6-dixopiperidin-3-yl)-1-oxoisoindolin-4-yl)glutaramide

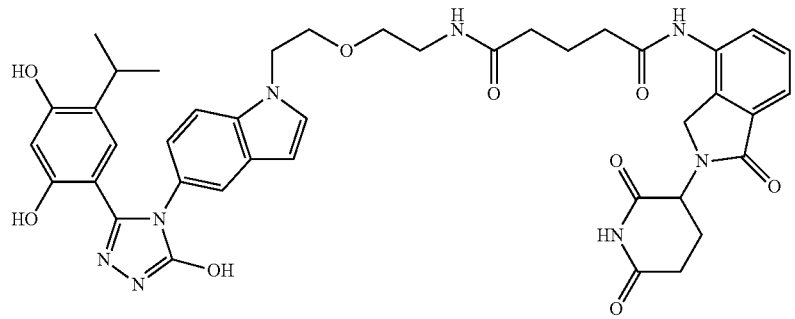 [SMILES: CC(C)c1cc(-c2nnc(O)n2-c2ccc3c(ccn3CCOCCNC(=O)CCCC(=O)Nc3cccc4c3CN(C3CCC(=O)NC3=O)C4=O)c2)c(O)cc1O]

ESMS calculated for $C_{41}H_{44}N_8O_9$: 792.32; Found: 793.3 (M+).

SDC-TRAP-0016

4,11-diethyl-4-hydroxy-3,14-dioxo-3,4,12,14-tetrahydro-1H-pyrano[3',4':6,7]indolizino[1,2-b]quinolin-9-yl (2-(2-(5-(3-(2,4-dihydroxy-5-isopropylphenyl)-5-hydroxy-4H-1,2,4-triazol-4-yl)-1H-indol-1-yl)ethoxy)ethyl)carbamate

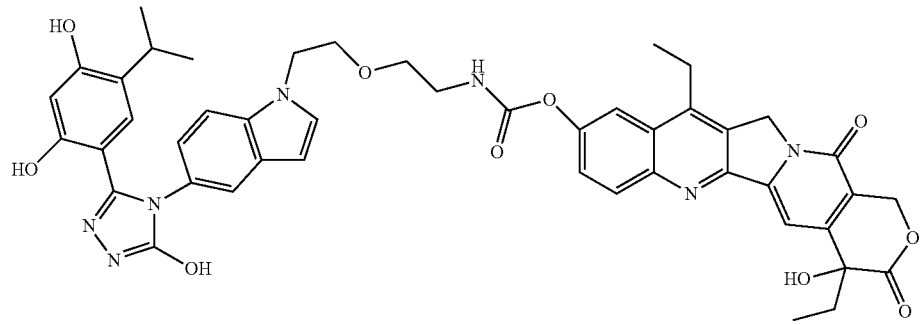 [SMILES: CCc1c2c(nc3ccc(OC(=O)NCCOCCn4ccc5cc(-n6c(O)nnc6-c6cc(C(C)C)c(O)cc6O)ccc54)cc13)-c1cc3c(c(=O)n1C2)COC(=O)C3(O)CC]

ESMS calculated for $C_{46}H_{45}N_7O_{10}$: 855.32; Found: 856.3 (M+).

SDC-TRAP-0017

3-(5-(3-(2,4-dihydroxy-5-isopropylphenyl)-5-hydroxy-4H-1,2,4-triazol-4-yl)-1H-indol-1-yl)-N-(2-(2,6-dioxopiperidin-3-yl)-1-oxoisoindolin-4-yl)propanamide

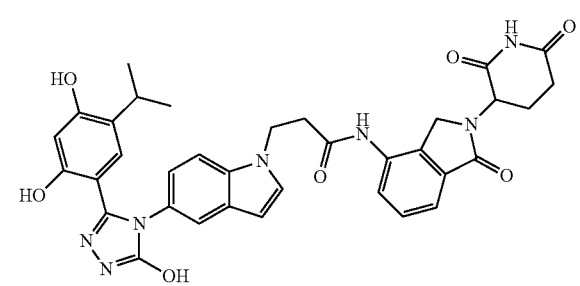 [SMILES: CC(C)c1cc(-c2nnc(O)n2-c2ccc3c(ccn3CCC(=O)Nc3cccc4c3CN(C3CCC(=O)NC3=O)C4=O)c2)c(O)cc1O]

ESMS calculated for $C_{35}H_{33}N_7O_7$: 663.24; Found: 664.3 (M+).

SDC-TRAP-0018

N1-(2-(5-(3-(2,4-dihydroxy-5-isopropylphenyl)-5-hydroxy-4H-1,2,4-triazol-4-yl)-1H-indol-1-yl)ethyl)-N5-(2-(2,6-dioxopiperidin-3-yl)-1-oxoisoindolin-4-yl)-N1-methylglutaramide

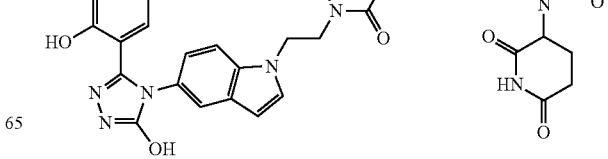

ESMS calculated for $C_{40}H_{42}N_8O_8$: 762.31; Found: 763.3 (M+).

SDC-TRAP-0019

4-(2-(2-amino-4-oxo-4,7-dihydro-3H-pyrrolo[2,3-d]pyrimidin-5-yl)ethyl)-N-(2-(5-(3-(2,4-dihydroxy-5-isopropylphenyl)-5-hydroxy-4H-1,2,4-triazol-4-yl)-1H-indol-1-yl)ethyl)-N-methylbenzamide

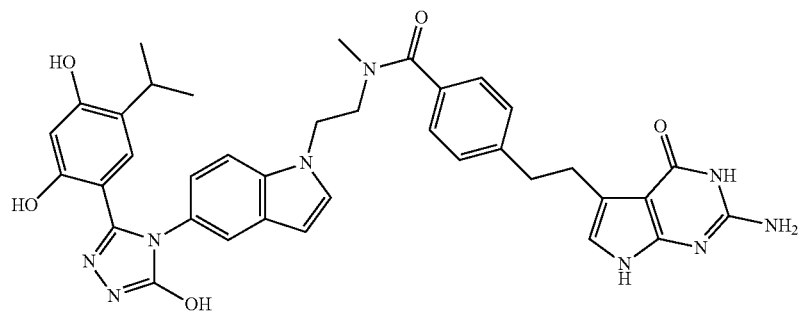 [SMILES: CC(C)c1cc(-c2nnc(O)n2-c2ccc3c(ccn3CCN(C)C(=O)c3ccc(CCc4c[nH]c5nc(N)[nH]c(=O)c45)cc3)c2)c(O)cc1O]

$^1$H NMR (300 MHz, DMSO-d6), d (ppm): 11.86 (s, 1H); 10.61 (s, 1H); 10.14 (s, 1H); 9.51 (s, 1H); 9.47 (s, 1H); 7.59-7.45 (m, 2H); 7.28-6.96 (m, 5H); 6.72 (m, 2H); 6.47 (s, 1H); 6.32 (s, 1H); 6.24 (s, 1H); 6.00 (bs, 2H); 4.46-4.28 (m, 2H); 3.75-3.49 (m, 2H); 2.96-2.80 (m, 5H); 2.61 (s, 3H); 0.81 (d, J=6.9 Hz, 6). ESMS calculated for $C_{37}H_{37}N_9O_5$; Found: 687.29; Found: 688.2 (M).

SDC-TRAP-0020

4-(2-(2-amino-4-oxo-4,7-dihydro-3H-pyrrolo[2,3-d]pyrimidin-5-yl)ethyl)-N-(2-(2-(5-(3-(2,4-dihydroxy-5-isopropylphenyl)-5-hydroxy-4H-1,2,4-triazol-4-yl)-1H-indol-1-yl)ethoxy)ethyl)benzamide

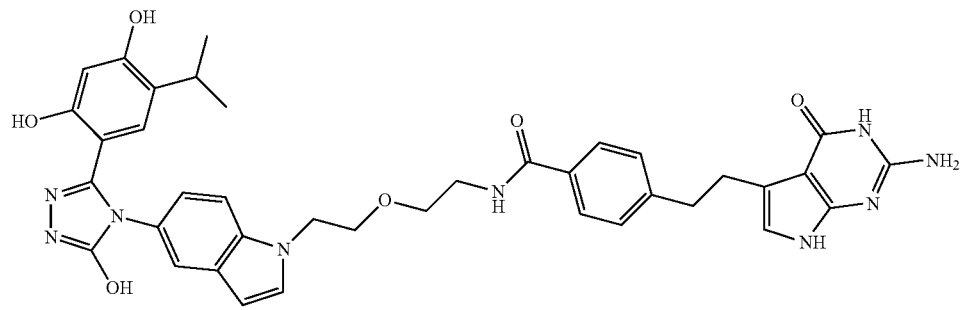 [SMILES: CC(C)c1cc(-c2nnc(O)n2-c2ccc3c(ccn3CCOCCNC(=O)c3ccc(CCc4c[nH]c5nc(N)[nH]c(=O)c45)cc3)c2)c(O)cc1O]

ESMS calculated for $C_{38}H_{39}N_9O_6$: 717.3; Found: 718.3 (M+).

SDC-TRAP-0021

2-(3-(2-(5-(3-(2,4-dihydroxy-5-isopropylphenyl)-5-hydroxy-4H-1,2,4-triazol-4-yl)-1H-indol-1-yl)ethyl)-3-methylureido)-N-(2-(2,6-dioxopiperidin-3-yl)-1-oxoisoindolin-4-yl)acetamide

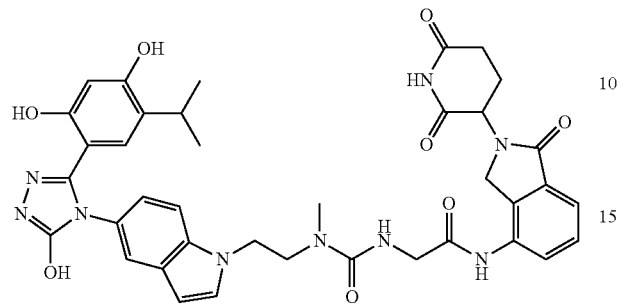

ESMS calculated for $C_{38}H_{39}N_9O_8$: 749.29; Found: 750.3 $(M^+)$.

SDC-TRAP-0022

4,11-diethyl-4-hydroxy-3,14-dioxo-3,4,12,14-tetrahydro-1H-pyrano[3',4':6,7]indolizino[1,2-b]quinolin-9-yl (2-(5-(3-(2,4-dihydroxy-5-isopropylphenyl)-5-hydroxy-4H-1,2,4-triazol-4-yl)-1H-indol-1-yl)ethyl)(methyl)carbamate

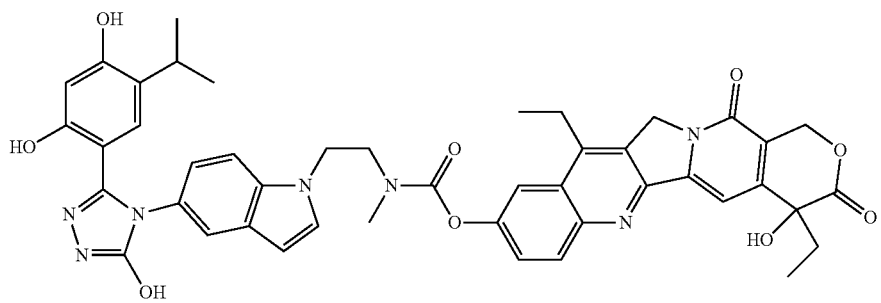 [SMILES: CCc1c2c(nc3ccc(OC(=O)N(C)CCn4ccc5cc(-n6c(O)nnc6-c6cc(C(C)C)c(O)cc6O)ccc54)cc13)-c1cc3c(c(=O)n1C2)COC(=O)C3(O)CC]

ESMS calculated for $C_{45}H_{43}N_7O_9$: 825.31; Found: 826.3 $(M^+)$.

SDC-TRAP-0010

4,11-diethyl-4-hydroxy-3,14-dioxo-3,4,12,14-tetrahydro-1H-pyrano[3',4':6,7]indolizino[1,2-b]quinolin-9-yl (2-(5-(3-(2,4-dihydroxy-5-isopropylphenyl)-5-hydroxy-4H-1,2,4-triazol-4-yl)-N,1-dimethyl-1H-indole-2-carboxamido)ethyl)(methyl)carbamate

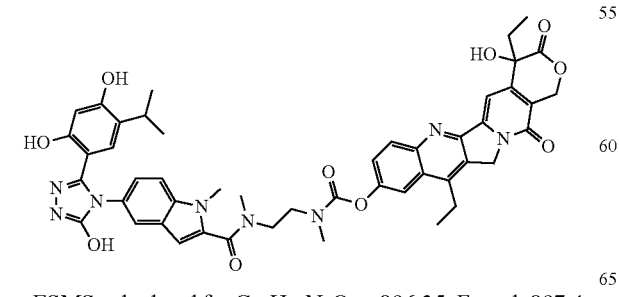

ESMS calculated for $C_{48}H_{48}N_8O_{10}$: 896.35; Found: 897.4 $(M^+)$.

SDC-TRAP-0023

2-((4,11-diethyl-4-hydroxy-3,14-dioxo-3,4,12,14-tetrahydro-1H-pyrano[3',4':6,7]indolizino[1,2b]quinolin-9-yl)oxy)-N-(2-(5-(3-(2,4-dihydroxy-5-isopropylphenyl)-5-hydroxy-4H-1,2,4-triazol-4-yl)-1H-indol-1-yl)ethyl)acetamide

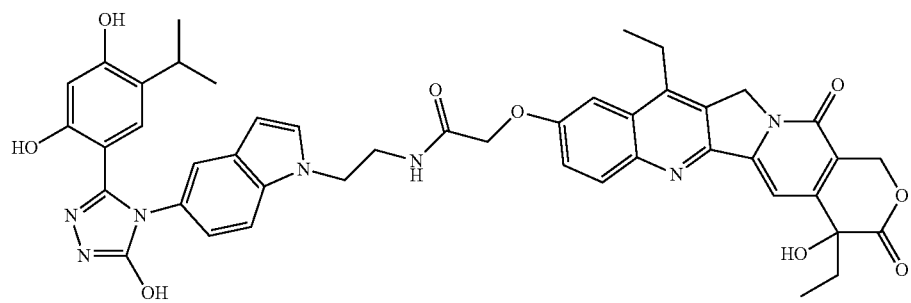 [SMILES: CCc1c2c(nc3ccc(OCC(=O)NCCn4ccc5cc(-n6c(O)nnc6-c6cc(C(C)C)c(O)cc6O)ccc54)cc13)-c1cc3c(c(=O)n1C2)COC(=O)C3(O)CC]

ESMS calculated for $C_{45}H_{43}N_7O_9$: 825.31; Found: 826.3 (M$^+$).

SDC-TRAP-0027

2-((4,11-diethyl-4-hydroxy-3,14-dioxo-3,4,12,14-tetrahydro-1H-pyrano[3',4':6,7]indolizino[1,2-b]quinolin-9-yl)oxy)-N-(2-(5-(3-(2,4-dihydroxy-5-isopropylphenyl)-5-hydroxy-4H-1,2,4-triazol-4-yl)-1H-indol-1-yl)ethyl)-N-methylacetamide

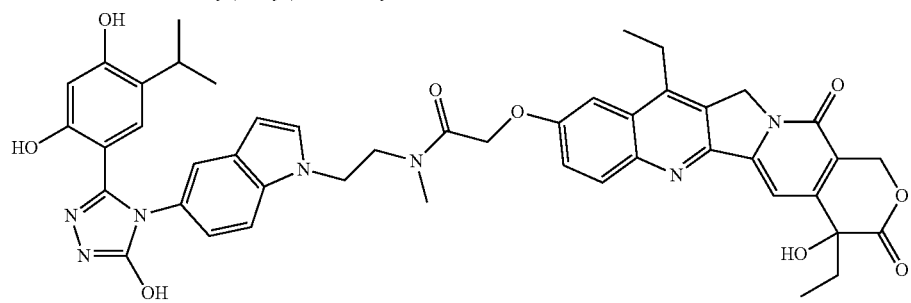

ESMS calculated for $C_{46}H_{45}N_7O_9$: 839.33; Found: 840.4 (M$^+$).

SDC-TRAP-0028

2-((4,11-diethyl-4-hydroxy-3,14-dioxo-3,4,12,14-tetrahydro-1H-pyrano[3',4':6,7]indolizino[12-b]quinolin-9-yl)oxy)-N-(2-(2-(5-(3-(2,4-dihydroxy-5-isopropylphenyl)-5-hydroxy-4H-1,2,4-triazol-4-yl)-1H-indol-1-yl)ethoxy)ethyl)-N-methylacetamide

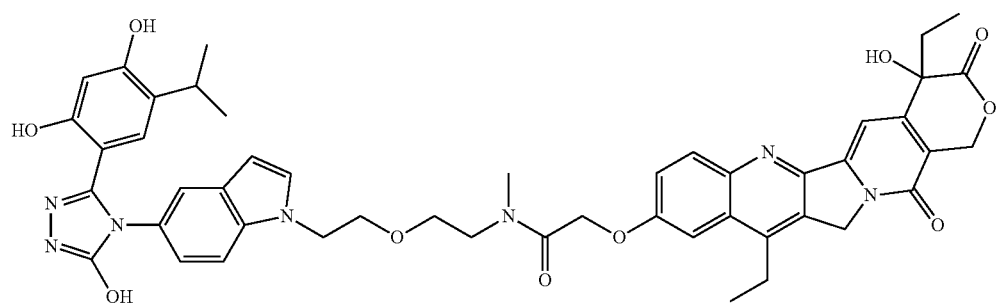 [SMILES: CCc1c2c(nc3ccc(OCC(=O)N(C)CCOCCn4ccc5cc(-n6c(O)nnc6-c6cc(C(C)C)c(O)cc6O)ccc54)cc13)-c1cc3c(c(=O)n1C2)COC(=O)C3(O)CC]

SDC-TRAP-0029

4,11-diethyl-4-hydroxy-3,14-dioxo-3,4,12,14-tetrahydro-1H-pyrano[3',4':6,7]indolizino[1,2-b]quinolin-9-yl (2-(2-(5-(3-(2,4-dihydroxy-5-isopropylphenyl)-5-hydroxy-4H-1,2,4-triazol-4-yl)-1H-indol-1-yl)ethoxy)ethyl)(methyl)carbamate ESMS calculated for $C_{48}H_{49}N_7O_{10}$: 883.35; Found: 884.4 (M+).

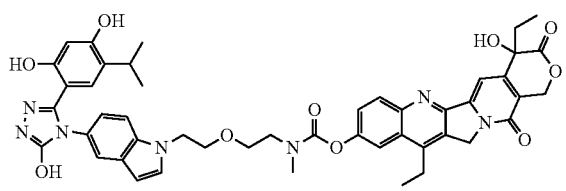 [SMILES: CCc1c2c(nc3ccc(OC(=O)N(C)CCOCCn4ccc5cc(-n6c(O)nnc6-c6cc(C(C)C)c(O)cc6O)ccc54)cc13)-c1cc3c(c(=O)n1C2)COC(=O)C3(O)CC]

ESMS calculated for $C_{47}H_{47}N_7O_{10}$: 869.34; Found: 870.4 (M+).

SDC-TRAP-0031

4,11-diethyl-4-hydroxy-3,14-dioxo-3,4,12,14-tetrahydro-1H-pyrano[3',4':6,7]indolizino[1,2-b]quinolin-9-yl 4-(4-(3-(2,4-dihydroxy-5-isopropylphenyl)-5-hydroxy-4H-1,2,4-triazol-4-yl)benzyl)piperidine-1-carboxylate

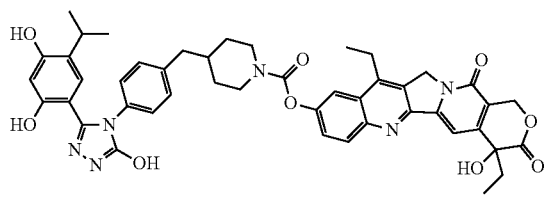 [SMILES: CCc1c2c(nc3ccc(OC(=O)N4CCC(Cc5ccc(-n6c(O)nnc6-c6cc(C(C)C)c(O)cc6O)cc5)CC4)cc13)-c1cc3c(c(=O)n1C2)COC(=O)C3(O)CC]

$^1$H NMR (400 MHz, DMSO-$d_6$), d (ppm): 11.93 (bs, 1H), 9.57 (bs, 1H), 9.45 (bs, 1H), 8.18 (d, J=8 Hz, 1H), 7.98 (s, 1H), 7.66 (dd, J=4.0, 8.0 Hz, 1H). 7.34 (s, 1H), 7.24 (d, J=8 Hz, 2H), 7.13 (d, J=8 Hz, 2H), 6.77 (s, 1H), 6.54 (bs, 1H), 6.28 (s, 1H), 5.44 (s, 2H), 5.34 (s, 2H), 3.21-3.18 (m, 2H), 3.10-2.96 (m, 3H), 2.59 (d, J=8 Hz, 2H), 1.91-1.76 (m, 3H), 1.67 (bs, 2H), 1.30 (t, J=8 Hz, 3H), 0.95 (d, J=8 Hz, 6H), 0.89 (d, J=8 Hz, 3H). ESMS calculated for $C_{46}H_{46}N_6O_9$: 826.33; Found: 827.3 (M+).

SDC-TRAP-0024

4,11-diethyl-9-hydroxy-3,14-dioxo-3,4,12,14-tetrahydro-1H-pyrano[3',4':6,7] indolizino[1,2-b]quinolin-4-yl 4-(5-(3-(2,4-dihydroxy-5-isopropylphenyl)-5-hydroxy-4H-1,2,4-triazol-4-yl)-1-methyl-1H-indole-2-carboxamido)butanoate

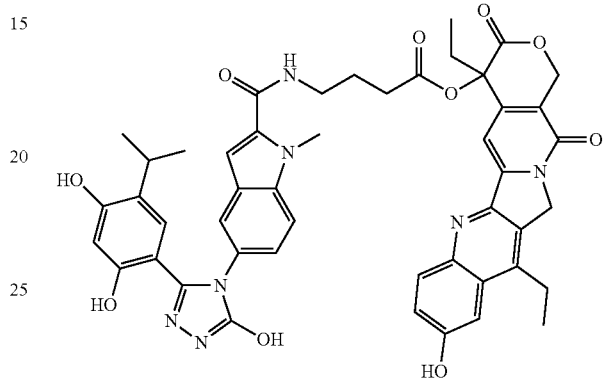

$^1$H NMR (400 MHz, CH$_3$OD) δ 7.88 (d, J=8.0 Hz, 1H), 7.44 (s, 1H), 7.35-7.27 (m, 4H), 7.16-7.14 (m, 1H), 6.73 (s, 1H), 6.67 (s, 1H), 6.26 (s, 1H), 5.62 (d, J=16 Hz, 1H), 5.44 (d, J=16 Hz, 1H), 5.05 (d, J=16 Hz, 1H), 3.58 (s, 3H), 3.48-3.33 (m, 3H), 3.09-3.04 (m, 1H), 2.96-2.86 (m, 2H), 2.75-2.71 (m, 2H), 2.25-2.13 (m, 2H), 2.05-1.94 (m, 2H), 1.29 (t, J=8.0 Hz, 3H), 1.01 (t, J=8.0 Hz, 3H), 0.78-0.72 (m, 6H); ESMS calculated for $C_{47}H_{45}N_7O_{10}$: 867.3; found: 868.3 (M+H).

SDC-TRAP-0025

2-(5-(3-(2,4-dihydroxy-5-isopropylphenyl)-5-hydroxy-4H-1,2,4-triazol-4-yl)-1H-indol-1-yl)ethyl (5-fluoro-2-oxo-1,2-dihydropyrimidin-4-yl) carbamate

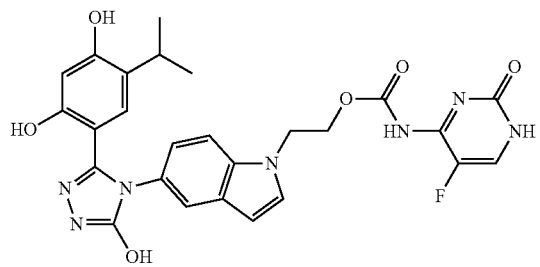 [SMILES: CC(C)c1cc(-c2nnc(O)n2-c2ccc3c(ccn3CCOC(=O)Nc3nc(=O)[nH]cc3F)c2)c(O)cc1O]

ESMS calculated $C_{26}H_{24}FN_7O_6$: 549.18; found: 550.1 (M+H).

SDC-TRAP-0033

N1-(2-(2-(5-(3-(2,4-dihydroxy-5-isopropylphenyl)-5-hydroxy-4H-1,2,4-triazol-4-yl)-1H-indol-1-yl)ethoxy)ethyl)-N4-(2-(2,6-dioxopiperidin-3-yl)-1-oxoisoindolin-4-yl)-N1-methylsuccinamide

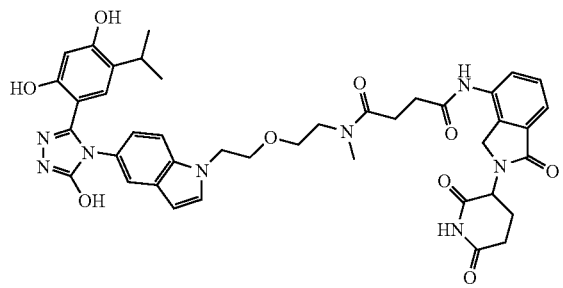 [SMILES: CC(C)c1cc(-c2nnc(O)n2-c2ccc3c(ccn3CCOCCN(C)C(=O)CCC(=O)Nc3cccc4c3CN(C3CCC(=O)NC3=O)C4=O)c2)c(O)cc1O]

ESMS calculated for $C_{41}H_{44}N_8O_9$: 792.32; found: 793.3 (M+H).

SDC-TRAP-0037

4,11-diethyl-9-hydroxy-3,14-dioxo-3,4,12,14-tetrahydro-1H-pyrano[3',4':6,7]indolizino[1,2-b]quinolin-4-yl (2-(2-(5-(3-(2,4-dihydroxy-5-isopropylphenyl)-5-hydroxy-4H-1,2,4-triazol-4-yl)-1H-indol-1-yl)ethoxy)ethyl) (methyl)carbamate

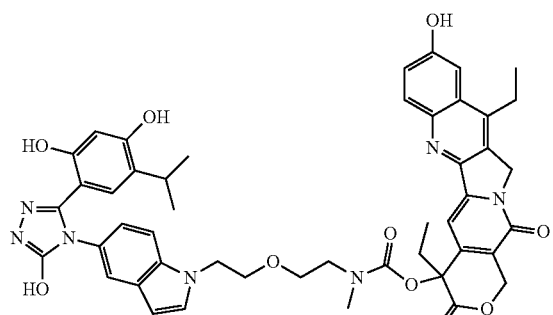

ESMS calculated for $C_{47}H_{47}N_7O_{10}$: 869.34; found: 870.3 (M+H).

SDC-TRAP-0038

4,11-diethyl-9-hydroxy-3,14-dioxo-3,4,12,14-tetrahydro-1H-pyrano[3',4':6,7]indolizino[1,2-b]quinolin-4-yl (2-(5-(3-(2,4-dihydroxy-5-isopropylphenyl)-5-hydroxy-4H-1,2,4-triazol-4-yl)-1H-indol-1-yl)ethyl)(methyl)carbamate

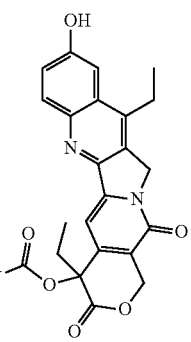

ESMS calculated for $C_{45}H_{43}N_7O_9$: 825.31; found: 826.3 (M+H).

SDC-TRAP-0039

4-(5-(bis(2-chloroethyl)amino)-1-methyl-1H-benzo[d]imidazol-2-yl)-N-(2-(5-(3-(2,4-dihydroxy-5-isopropylphenyl)-5-hydroxy-4H-1,2,4-triazol-4-yl)-1H-indol-1-yl)ethyl)-N-methylbutanamide

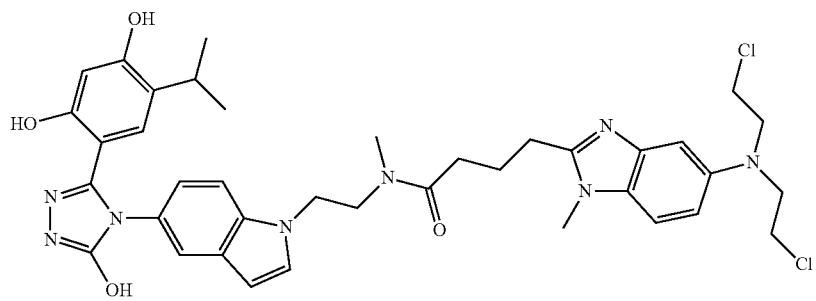 [SMILES: CC(C)c1cc(-c2nnc(O)n2-c2ccc3c(ccn3CCN(C)C(=O)CCCc3nc4cc(N(CCCl)CCCl)ccc4n3C)c2)c(O)cc1O]

ESMS calculated for $C_{38}H_{44}Cl_2N_8O_4$: 746.29; found: 747.3 (M+H).

SDC-TRAP-0040

4-(5-(bis(2-chloroethyl)amino)-1-methyl-1H-benzo[d]imidazol-2-yl)-N-(2-(2-(5-(3-(2,4-dihydroxy-5-isopropylphenyl)-5-hydroxy-4H-1,2,4-triazol-4-yl)-1H-indol-1-yl)ethoxy)ethyl)-N-methylbutanamide

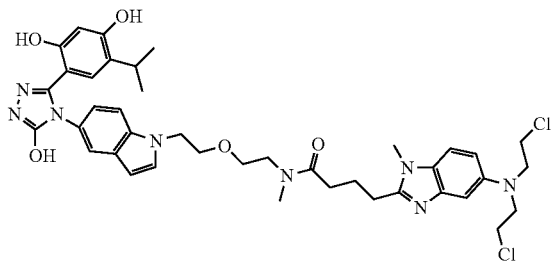 [SMILES: CC(C)c1cc(-c2nnc(O)n2-c2ccc3c(ccn3CCOCCN(C)C(=O)CCCc3nc4cc(N(CCCl)CCCl)ccc4n3C)c2)c(O)cc1O]

ESMS calculated for $C_{40}H_{48}Cl_2N_8O_5$: 790.31; found: 791.3 (M+H).

SDC-TRAP-0041

5-(4-(4-(3-(2,4-dihydroxy-5-isopropylphenyl)-5-hydroxy-4H-1,2,4-triazol-4-yl)benzyl)piperazin-1-yl)-N-(2-(2,6-dioxopiperidin-3-yl)-1-oxoisoindolin-4-yl)-5-oxopentanamide

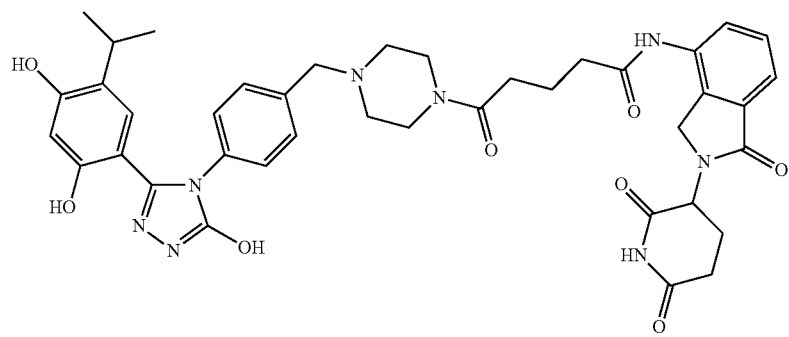 [SMILES: CC(C)c1cc(-c2nnc(O)n2-c2ccc(CN3CCN(C(=O)CCCC(=O)Nc4cccc5c4CN(C4CCC(=O)NC4=O)C5=O)CC3)cc2)c(O)cc1O]

ESMS calculated for $C_{40}H_{44}N_8O_8$: 764.33; found: 765.3 (M+H).

SDC-TRAP-0042

4,11-diethyl-9-hydroxy-3,14-dioxo-3,4,12,14-tetrahydro-1H-pyrano[3',4':6,7]indolizino[1,2-b]quinolin-4-yl 4-(4-(4-(3-(2,4-dihydroxy-5-isopropylphenyl)-5-hydroxy-4H-1,2,4-triazol-4-yl)benzyl)piperidin-1-yl)-4-oxobutanoate

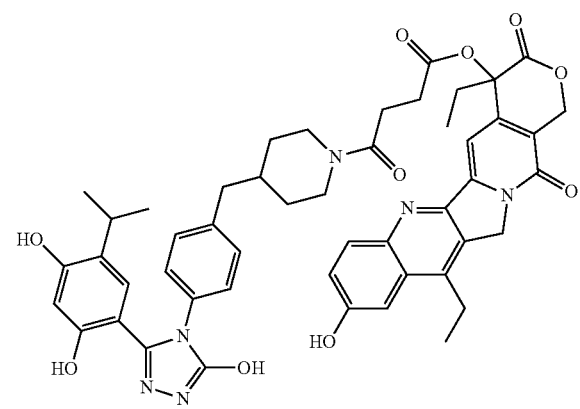 [SMILES: CCc1c2c(nc3ccc(O)cc13)-c1cc3c(c(=O)n1C2)COC(=O)C3(CC)OC(=O)CCC(=O)N1CCC(Cc2ccc(-n3c(O)nnc3-c3cc(C(C)C)c(O)cc3O)cc2)CC1]

ESMS calculated for $C_{49}H_{50}N_6O_{10}$: 882.36; found: 883.3 (M+H).

SDC-TRAP-0043

4,11-diethyl-9-hydroxy-3,14-dioxo-3,4,12,14-tetrahydro-1H-pyrano[3',4':6,7]indolizino[1,2-b]quinolin-4-yl 4-(4-(4-(3-(2,4-dihydroxy-5-isopropylphenyl)-5-hydroxy-4H-1,2,4-triazol-4-yl)benzyl)piperazin-1-yl)-4-oxobutanoate

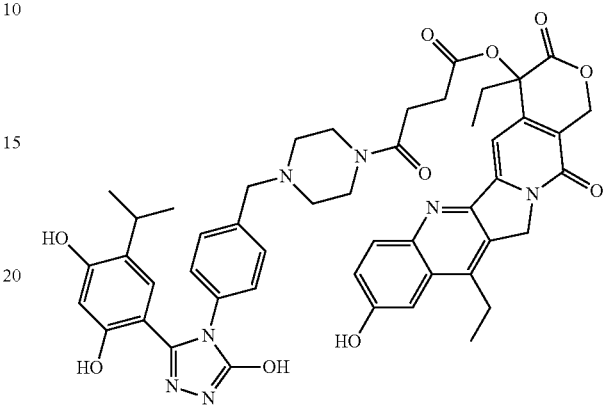

ESMS calculated for $C_{48}H_{49}N_7O_{10}$: 883.35; found: 884.3 (M+H).

SDC-TRAP-0044

4,11-diethyl-4-hydroxy-3,14-dioxo-3,4,12,14-tetrahydro-1H-pyrano[3',4':6,7]indolizino[1,2-b]quinolin-9-yl (4-(4-(4-(3-(2,4-dihydroxy-5-isopropylphenyl)-5-hydroxy-4H-1,2,4-triazol-4-yl)benzyl)piperazin-1-yl)butyl)(methyl)carbamate

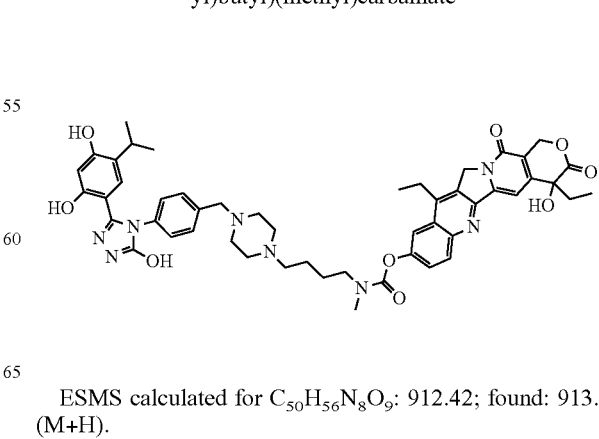

ESMS calculated for $C_{50}H_{56}N_8O_9$: 912.42; found: 913.4 (M+H).

SDC-TRAP-0045

4,11-diethyl-4-hydroxy-3,14-dioxo-3,4,12,14-tetrahydro-1H-pyrano[3',4':6,7]indolizino[1,2-b]quinolin-9-yl 4-(4-(3-(2,4-dihydroxy-5-isopropylphenyl)-5-hydroxy-4H-1,2,4-triazol-4-yl)phenyl)piperazine-1-carboxylate

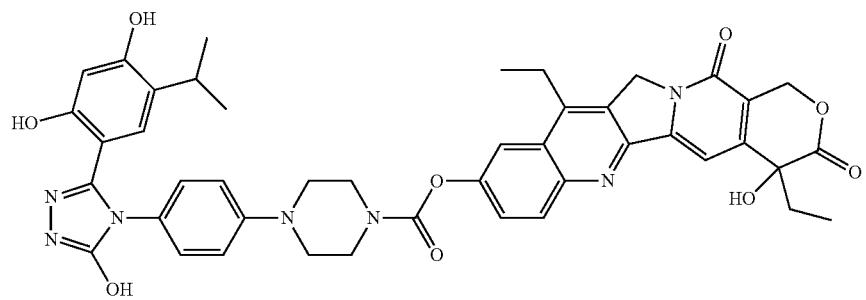 [SMILES: CCc1c2c(nc3ccc(OC(=O)N4CCN(c5ccc(-n6c(O)nnc6-c6cc(C(C)C)c(O)cc6O)cc5)CC4)cc13)-c1cc3c(c(=O)n1C2)COC(=O)C3(O)CC]

ESMS calculated for $C_{44}H_{43}N_7O_9$: 813.31; found: 814.3 (M+H).

SDC-TRAP-0046

4,11-diethyl-4-hydroxy-3,14-dioxo-3,4,12,14-tetrahydro-1H-pyrano[3',4':6,7]indolizino[1,2-b]quinolin-9-yl 4-(4-(3-(2,4-dihydroxy-5-isopropylphenyl)-5-hydroxy-4H-1,2,4-triazol-4-yl)benzyl)piperazine-1-carboxylate

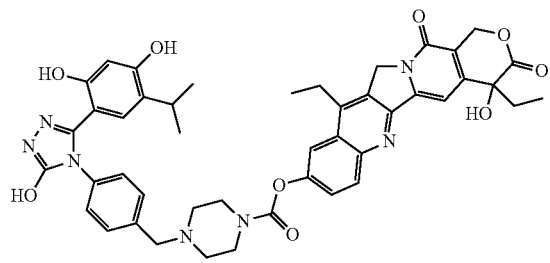 [SMILES: CCc1c2c(nc3ccc(OC(=O)N4CCN(Cc5ccc(-n6c(O)nnc6-c6cc(C(C)C)c(O)cc6O)cc5)CC4)cc13)-c1cc3c(c(=O)n1C2)COC(=O)C3(O)CC]

ESMS calculated for $C_{45}H_{45}N_7O_9$: 827.33; found: 828.3 (M+H).

SDC-TRAP-0047

4,11-diethyl-9-hydroxy-3,14-dioxo-3,4,12,14-tetrahydro-1H-pyrano[3',4':6,7]indolizino[1,2-b]quinolin-4-yl 4-(4-(3-(2,4-dihydroxy-5-isopropylphenyl)-5-hydroxy-4H-1,2,4-triazol-4-yl)benzyl)piperazine-1-carboxylate

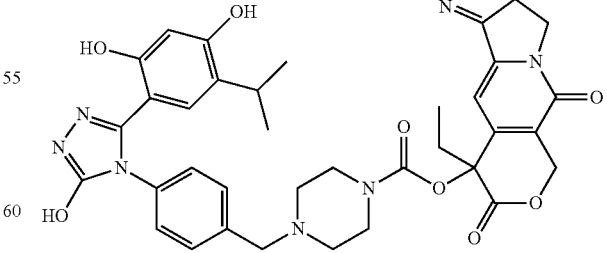

ESMS calculated for $C_{45}H_{45}N_7O_9$: 827.33; found: 828.3 (M+H).

SDC-TRAP-0048

N-(2-(2-(5-(3-(2,4-dihydroxy-5-isopropylphenyl)-5-hydroxy-4H-1,2,4-triazol-4-yl)-1H-indol-1-yl)ethoxy)ethyl)-3-(5-fluoro-2,4-dioxo-3,4-dihydropyrimidin-1(2H)-yl)propanamide

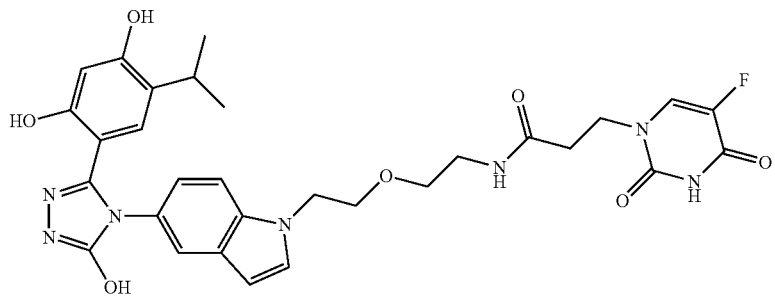 [SMILES: CC(C)c1cc(-c2nnc(O)n2-c2ccc3c(ccn3CCOCCNC(=O)CCn3cc(F)c(=O)[nH]c3=O)c2)c(O)cc1O]

ESMS calculated for $C_{30}H_{32}FN_7O_7$: 621.23; found: 622.2 (M+H).

SDC-TRAP-0049

1-(3-(4-(4-(3-(2,4-dihydroxy-5-isopropylphenyl)-5-hydroxy-4H-1,2,4-triazol-4-yl)benzyl)piperazin-1-yl)-3-oxopropyl)-5-fluoropyrimidine-2,4(1H,3H)-dione

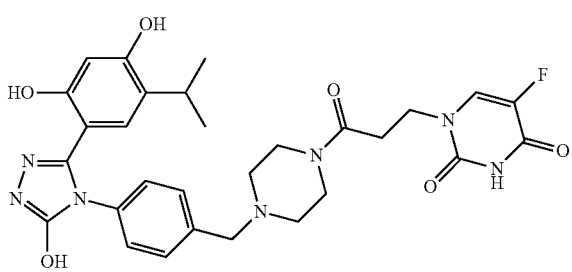 [SMILES: CC(C)c1cc(-c2nnc(O)n2-c2ccc(CN3CCN(C(=O)CCn4cc(F)c(=O)[nH]c4=O)CC3)cc2)c(O)cc1O]

ESMS calculated for $C_{29}H_{32}FN_7O_6$: 593.24; found: 594.2 (M+H).

SDC-TRAP-0050

N-(2-(2-(5-(3-(2,4-dihydroxy-5-isopropylphenyl)-5-hydroxy-4H-1,2,4-triazol-4-yl)-1H-indol-1-yl)ethoxy)ethyl)-3-(5-fluoro-2,4-dioxo-3,4-dihydropyrimidin-1(2H)-yl)-N-methylpropanamide

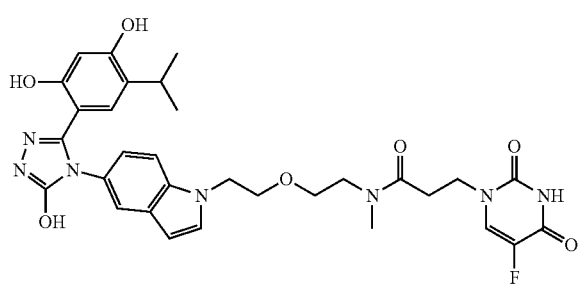 [SMILES: CC(C)c1cc(-c2nnc(O)n2-c2ccc3c(ccn3CCOCCN(C)C(=O)CCn3cc(F)c(=O)[nH]c3=O)c2)c(O)cc1O]

ESMS calculated for $C_{31}H_{34}FN_7O_7$: 635.64; found: 636.6 (M+H).

SDC-TRAP-0051

N-(2-(5-(3-(2,4-dihydroxy-5-isopropylphenyl)-5-hydroxy-4H-1,2,4-triazol-4-yl)-1H-indol-1-yl)ethyl)-3-(5-fluoro-2,4-dioxo-3,4-dihydropyrimidin-1(2H)-yl)-N-methylpropanamide

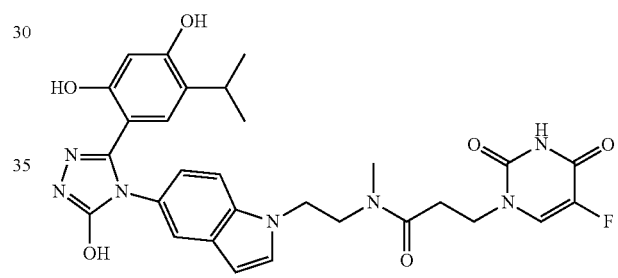

ESMS calculated for $C_{29}H_{30}FN_7O_6$: 591.22; found: 592.2 (M+H).

Example 2

The ability of Hsp90-targeting moieties to penetrate solid tumors and exhibit rapid clearance from normal tissues for reduced toxicity is illustrated in the following tissue distribution study with a compound, ganetespib, which may be used as an Hsp90 binding moiety.

Tissue distribution of ganetespib in female CD-1 nu/nu mice bearing RERF human NSCLC xenografts Objectives:

To confirm the distribution of ganetespib in blood, livers, kidneys, brains, hearts, lungs and tumors after IV administration of ganetespib to female CD-1 nu/nu mice bearing RERF human NSCLC xenografts, and to examine metabolic profiles of ganetespib in plasma, red blood cells, and above tissues.

Study Outline:
Test Articles: ganetespib
Animals: female CD-1 nu/nu mice bearing RERF human NSCLC xenografts (N=3/group)
Route: IV
Dosage: 50 mg/kg
Dose level: 10 mL/kg Formulation: 10% DMSO, 18% Cremophor RH40, 3.6% dextrose solution (DRD)

Bleeding time points: 5 min, 6, 24 hr

Collected tissues: blood (plasma and red blood cells (RBC)), liver, kidneys, brain, heart, lung, tumor Method Sample Preparation Plasma and RBC Protein precipitation: 50 µL of 10 times diluted plasma or RBC+150 µL ACN (10 mM NH$_4$OAc), vortexed and centrifuged at 10000 rpm for 8 min; 150 µL supernatant+150 µL water (10 mM NH$_4$OAc)

Other Tissues

Protein precipitation: 100 µL homogenized tissue (1:3 tissue: PBS buffer)+100 µL ACN (10 mM NH$_4$OAc), vortexed and centrifuged at 10000 rpm for 8 min Bioanalysis HPLC (ChemStation)

Column: Agilent Zorbax Eclipse XDB-C18, 4.6×150 mm, 5 µm

Mobile phase: A: water containing 10 mM NH$_4$OAc; B: 95% ACN containing 10 mM NH$_4$OAc Gradient: 95/5 A/B to 5/95 A/B in 10 min, total run time 15 min Flow rate: 1 mL/min Column temp.: 40° C.

Wavelength: 254 nm

Injection volume: 100 µL

Calibration Curve Range:

Plasma: 1-50 µM (linear regression; $R^2$=0.9901); LLOQ=1 µM

RBC: 1-50 µM (linear regression; $R^2$=0.9987); LLOQ=1 µM

Kidney: 1-100 µM (linear regression; $R^2$=1.0000); LLOQ=1 µM

Lung: 1-100 µM (linear regression; $R^2$=1.0000); LLOQ=1 µM

Heart: 1-100 µM (linear regression; $R^2$=0.9998); LLOQ=1 µM

Liver: 1-100 µM (linear regression; $R^2$=1.0000); LLOQ=1 µM

Tumor: 0.1-10 µM (linear regression; $R^2$=1.0000); LLOQ=0.1 µM

LC-MS/MS (Q-Trap4000)

Polarity: positive (ESI)

Column: Phenomenex Synergi, 2.1×50 mm, 4 µm

Mobile phase: A: water containing 0.1% HCOOH; B: ACN containing 0.1% HCOOH

Gradient: 60/40 A/B to 5/95 A/B in 0.5 min, total run time 4 min

Flow rate: 0.5 mL/min

Column temp.: room temperature

Injection volume: 20 µL

Calibration Curve Range:

Plasma: 2.5-500 nM (linear regression; $R^2$=0.9994); LLOQ=2.5 nM

RBC: 2.5-500 nM (linear regression; $R^2$=0.9998); LLOQ=2.5 nM

Kidney: 2.5-500 nM (linear regression; $R^2$=0.9993); LLOQ=2.5 nM

Lung: 2.5-500 nM (linear regression; $R^2$=0.9993); LLOQ=2.5 nM

Heart: 2.5-500 nM (linear regression; $R^2$=0.9997); LLOQ=2.5 nM

Liver: 2.5-500 nM (linear regression; $R^2$=1.0000); LLOQ=2.5 nM 0.5-5 µM (linear regression; $R^2$=0.9970); LLOQ=0.5 µM Brain: 2.5-500 nM (linear regression; $R^2$=0.9998); LLOQ=2.5 nM 0.5-5 µM (linear regression; $R^2$=0.9992); LLOQ=0.5 µM Results Formulations The dosing solution was confirmed to have 98.1% accuracy by HPLC.

Tissue Distribution

The concentrations of ganetespib in plasma, RBC and the tissues are summarized in Table 1 and FIG. 1 at each time point.

The mean plasma concentration of ganetespib at 5 min after IV injection was 160 µM, highest among all the tissues studied. Thereafter, the plasma ganetespib concentration declined quickly and at 6 hr, it was 0.12 µM. At 24 hr, it was below the lower limit of quantitation (LLOQ, <2.5 nM).

After IV injection, ganetespib was widely distributed to the normal tissues analyzed. At 5 min, the highest concentration of ganetespib among the tissues was observed in kidney (57.8 µM), followed by liver (46.3 µM) and heart (36.2 µM). In brain, 0.53 µM of ganetespib was detected at 5 min, which was the lowest among the tissues. In all the normal tissues, the concentrations of ganetespib decreased quickly.

Although the concentration of ganetespib in tumor at 5 min (2.35 M) was lower than that in plasma and most of the other tissues studied, it remained relatively constant up to 24 hr (0.85 µM at 24 hr). However, the in vitro IC$_{50}$ values of ganetespib are small, and the tumor concentration of ganetespib at 24 hr was significantly higher than IC$_{50}$ of in vitro HER2 assays (~30 nM). Thus, the prolonged efficacy is expected even after ganetespib was cleared from the blood stream.

Figure 3:
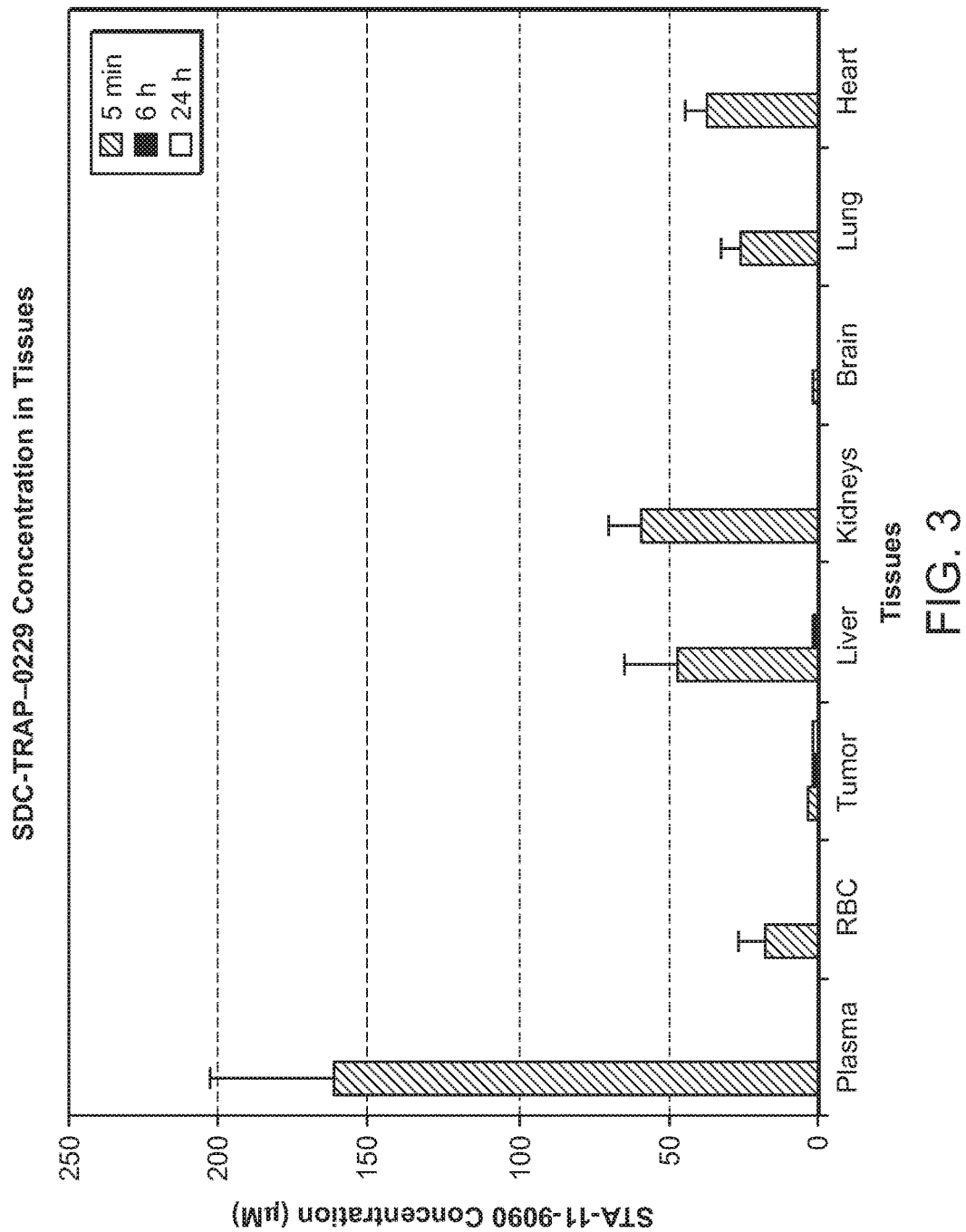
FIG. 3 illustrates an example where the mean concentration of ganetespib in plasma is about 10 times higher than that in RBC at 5 min time point.

The mean concentration of ganetespib in plasma was about 10 times higher than that in RBC at 5 min time point, indicating that ganetespib tends to stay in plasma rather than in RBCs. See FIG. 3.

Conclusion

Ganetespib appeared to persist longer in tumor than in plasma or any other tissues studied. The results from this study suggest that ganetespib also has a higher binding affinity to Hsp90 from tumor cells than Hsp90 from normal cells, and that it is possible for ganetespib to modulate relative protein concentrations of Hsp90 and its client proteins selectively in tumors. The plasma concentrations of ganetespib did not correlate to the concentrations in tumor.

TABLE 1

Concentrations of ganetespib in tissues:

Test Articles: ganetespib

Structure

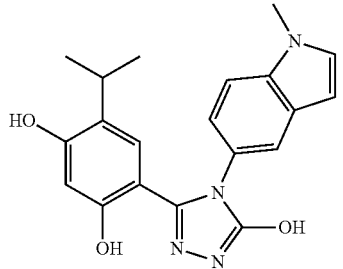 [SMILES: CC(C)c1cc(-c2nnc(O)n2-c2ccc3c(ccn3C)c2)c(O)cc1O]

| | |
|---|---|
| Species | CD-1-nu/nu female mice |
| Tumor | RERF human NSCLC |
| Route | IV |
| Dosage | 50 mg/kg |
| Formulation | DRD |

| Time | plasma (µg/mL) | RBC (µg/mL) | tumor (µg/g) | liver (µg/g) | kidneys (µg/g) | brain (µg/g) | heart (µg/g) | lung (µg/g) |
|---|---|---|---|---|---|---|---|---|
| 5 min | 58.4 | 6.00 | 0.86 | 16.9 | 21.1 | 0.19 | 13.2 | 9.24 |
| 6 hr | 0.04 | No data | 0.29 | 0.14 | 0.06 | 0.07 | 0.05 | 0.05 |
| 24 hr | <LLOQ | 0.003 | 0.31 | 0.005 | 0.01 | 0.04 | 0.00 | 0.00 |

| Time | plasma (µM) | RBC (µM) | tumor (µM) | liver (µM) | kidneys (µM) | brain (µM) | heart (µM) | lung (µM) |
|---|---|---|---|---|---|---|---|---|
| 5 min | 160 | 16.5 | 2.35 | 46.3 | 57.8 | 0.53 | 36.2 | 25.4 |
| 6 hr | 0.12 | N/A | 0.80 | 0.39 | 0.15 | 0.18 | 0.13 | 0.14 |
| 24 hr | <LLOQ | 0.007 | 0.85 | 0.01 | 0.02 | 0.12 | 0.00 | 0.005 |

Summary

Ganetespib was widely distributed to various tissues. The compound was accumulated in tumor relative to the plasma and other tissues, indicating the higher binding affinity of this compound to Hsp90 in tumor than Hsp90 in other tissues. The metabolite M2, which was previously thought to be human-specific, was also detected in mouse liver, kidney, heart and lung, but not in plasma. M2 does not seem to be excreted into blood stream in mice and possibly in other species as well.

Example 3

This example illustrates how a HER2 degradation assay may be used as a test to determine and select Hsp90-targeting moieties suitable for use in SDC-TRAPs of the invention, and further illustrates the ability of SDC-TRAPs to target cells preferentially expressing Hsp90. Such a test may further be used to determine the Hsp90 binding ability of SDC-TRAPs of the invention, as well as through competitive binding assays and cell-based Hsp90 client protein degradation assays known in the art.

Degradation of HER2 in Cells after Treatment with an SDC-TRAP of the Invention

Method 1:

BT-474 cells are treated with 0.5 µM, 2 µM, or 5 µM of 17-AAG (a positive control) or 0.5 µM, 2 µM, or 5 µM of an Hsp90-targeting moiety or conjugate of the invention overnight in DMEM medium. After treatment, each cytoplasmic sample is prepared from 1×10⁶ cells by incubation of cell lysis buffer (#9803, Cell Signaling Technology) on ice for 10 minutes. The resulting supernatant used as the cytosol fractions is dissolved with sample buffer for SDS-PAGE and run on a SDS-PAGE gel, blotted onto a nitrocellulose membrane by using semi-dry transfer. Non-specific binding to nitrocellulose is blocked with 5% skim milk in TBS with 0.5% Tween at room temperature for 1 hour, then probed with anti-HER2/ErB2 mAb (rabbit IgG, #2242, Cell Signaling) and anti-Tubulin (T9026, Sigma) as housekeeping control protein. HRP-conjugated goat anti-rabbit IgG (H+L) and HRP-conjugated horse anti-mouse IgG (H+L) are used as secondary Ab (#7074, #7076, Cell Signaling) and LumiGLO reagent, 20× Peroxide (#7003, Cell Signaling) is used for visualization. The Hsp90 client protein HER2 is degraded when cells are treated with Hsp90-targeting moieties or SDC-TRAPs of the invention. 0.5 µM of 17-AAG, a known Hsp90 inhibitor used as a positive control, causes partial degradation of HER2.

Method 2:

BT-474 cells are plated in the interior 60 wells of a 96 well black clear bottom plate (20,000 cells/well) in DMEM medium, with DMEM media in the surrounding 36 wells, and incubated at 37° C. with 5% CO₂ overnight. On the second day, concentration response curve source plates are produced (10 point, 3-fold dilution of compounds in DMSO) followed by a 1:30 dilution in an intermediate dilution plate containing DMEM. Compound is transferred from the intermediate plate to the cell plate at a dilution of 1:10. The cells are then incubated at 37° C. with 5% CO₂ for 24 hours.

Cells are then fixed in 4% phosphate-buffered paraformaldehyde for 30 minutes at room temperature and then permeabilized by washing five times with 0.1% Triton X-100 in PBS for 5 minutes at room temperature on a shaker. Cells are blocked with Odyssey Blocking Buffer (LI-COR, #927-40000) on a shaker at room temperature for 1.5 hours, followed by incubation with HER2 antibody (CST, #2165)

diluted 1:400 in blocking buffer overnight on a shaker at 4° C. Cells are washed five times with 0.1% Tween-20 in PBS for 5 minutes at room temperature on a shaker and incubated with fluorescently-labeled secondary antibody (LI-COR, #926-32211) diluted 1:1000 in blocking buffer, and DRAQ5 nuclear stain (Biostatus Limited, #DRAQ5) diluted 1:10,000, at room temperature on a shaker for 1 hour. Cells are washed 5 times with 0.1% Tween-20 in PBS for 5 minutes at room temperature on a shaker and imaged on a LI-COR Odyssey imaging station. The raw data is normalized to DRAQ5 and the HER2 $EC_{50}$ is calculated using XLfit™.

The above procedures were utilized to generate the following HER2 degradation data, which show the ability of these exemplary SDC-TRAPs to target cells preferentially expressing Hsp90:

| HER2 ($IC_{50}$, nM) | SDC-TRAP |
|---|---|
| 2347 | SDC-TRAP-0015 |
| >5000 | SDC-TRAP-0017 |
| >5000 | SDC-TRAP-0018 |
| 4419 | SDC-TRAP-0019 |
| >5000 | SDC-TRAP-0020 |
| >5000 | SDC-TRAP-0021 |
| >5000 | SDC-TRAP-0022 |
| >5000 | SDC-TRAP-0010 |
| 4300 | SDC-TRAP-0023 |
| >5000 | SDC-TRAP-0027 |
| >5000 | SDC-TRAP-0028 |
| 1603 | SDC-TRAP-0029 |
| 2916 | SDC-TRAP-0031 |
| >5000 | SDC-TRAP-0024 |
| 395 | SDC-TRAP-0025 |
| >5000 | SDC-TRAP-0033 |
| 2112 | SDC-TRAP-0037 |
| >5000 | SDC-TRAP-0038 |
| 2935 | SDC-TRAP-0039 |
| 4741 | SDC-TRAP-0040 |
| >5000 | SDC-TRAP-0041 |
| 1057 | SDC-TRAP-0042 |
| 2135 | SDC-TRAP-0043 |
| 602 | SDC-TRAP-0044 |
| 464 | SDC-TRAP-0045 |
| 246 | SDC-TRAP-0046 |
| 875 | SDC-TRAP-0047 |

Example 4

This example illustrates a method of assessing the cytotoxicity of SDC-TRAPs of the invention.

Cell Lines.

Human H3122 NSCLC cells were obtained and grown in RPMI in the presence of fetal bovine serum (10%), 2 mM L-glutamine and antibiotics (100 IU/ml penicillin and 100 µg/ml streptomycin, Sigma Aldrich.) Cells were maintained at 37° C., 5% $CO_2$ atmosphere.

Cell Viability Assays.

Cell viability was measured using the CellTiter-Glo® assay (Promega). In brief, cells were plated in 96-well plates in triplicate at optimal seeding density (determined empirically) and incubated at 37° C., 5% $CO_2$ atmosphere for 24 hr prior to the addition of drug or vehicle (0.3% DMSO) to the culture medium. At the end of the assay, CellTiter-Glo was added to the wells per manufacturer's recommendation, shaken for two minutes and incubated for 10 minutes at room temperature. Luminescence (0.1 sec) was measured with a Victor II microplate reader (Perkin Elmer) and the resulting data were used to calculate cell viability, normalized to vehicle control.

Cells as described above were treated with exemplary SDC-TRAPs and their viability determined as above as well. The following table illustrates the results.

| SDC-TRAP Number | $IC_{50}$ (H3122) (nM) |
|---|---|
| SDC-TRAP-0010 | 234 |
| SDC-TRAP-0015 | 1273 |
| SDC-TRAP-0017 | >3000 |
| SDC-TRAP-0018 | 620 |
| SDC-TRAP-0019 | 393 |
| SDC-TRAP-0020 | 1737 |
| SDC-TRAP-0021 | 717 |
| SDC-TRAP-0022 | 492 |
| SDC-TRAP-0023 | 137 |
| SDC-TRAP-0024 | 99 |
| SDC-TRAP-0027 | 1354 |
| SDC-TRAP-0028 | 909 |
| SDC-TRAP-0029 | 125 |

Example 5

This example illustrates a method for assessing the stability of SDC-TRAP of the invention in human and mouse plasma.

SDC-TRAP-0022 and SDC-TRAP-0028 were incubated in human and mouse plasma for 2 h at 37° C. and assayed for integrity at 0.25, 0.5, 1 and 2 h. The values reported below are the remaining of the parent compound at the end of the 2 h incubation period.

| Conjugate ID | Concentration | % Remaining 2 h (37° C.) | |
|---|---|---|---|
| | | HU | MO |
| SDC-TRAP-0022 | 1 µM | 29% | 32% |
| | 10 µM | 30% | 31% |
| SDC-TRAP-0028 | 1 µM | 51% | 53% |
| | 10 µM | 65% | 47% |

Example 6

A Detailed Schematic for the Synthesis of SDC-TRAP-0063

A detailed scheme of the synthesis of SDC-TRAP-0063 is provided. The person of ordinary skill in the art would be able, without undue experimentation, to adapt this synthetic scheme for making other targeting molecule conjugates within the scope of the invention.

As explained hereinabove, SDC-TRAP-0063 is essentially a conjugate of the binding moiety ganetespib and the effector moiety irinotecan. SDC-TRAP-0063 is: 4,11-diethyl-4-hydroxy-3,14-dioxo-3,4,12,14-tetrahydro-1H-pyrano[3',4':6,7]indolizino[1,2-b]quinolin-9-yl 4-(2-(5-(3-(2,4-dihydroxy-5-isopropylphenyl)-5-hydroxy-4H-1,2,4-triazol-4-yl)-1H-indol-1-yl)ethyl)piperidine-1-carboxylate.

SDC-TRAP-0063 was synthesized according to the following scheme:

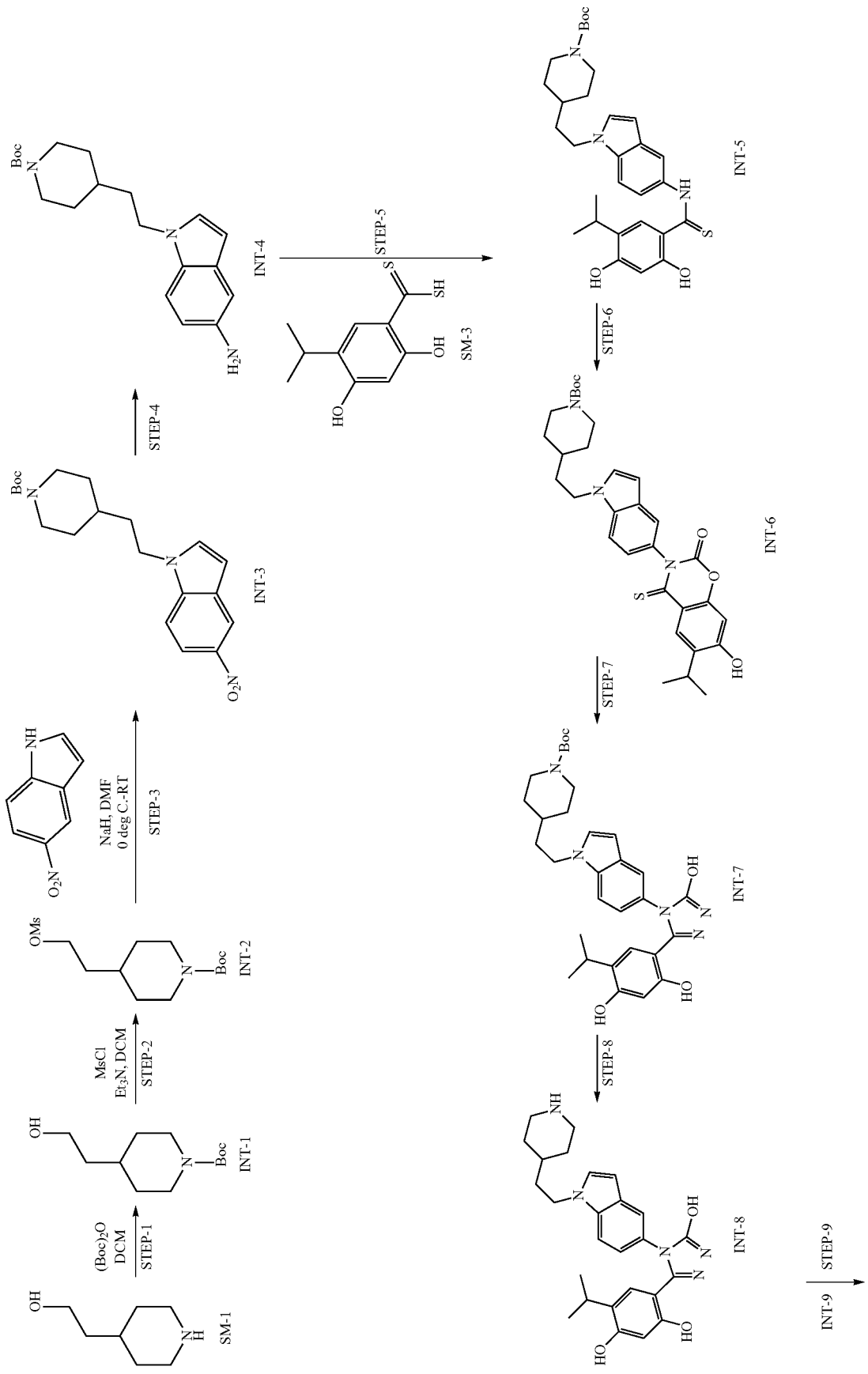

-continued
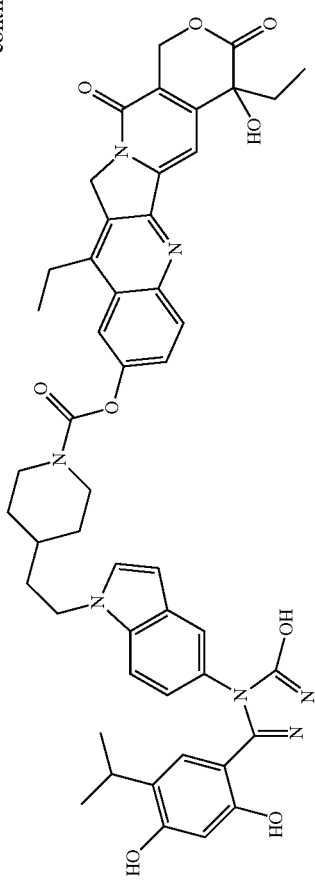
SDC-TRAP-0063
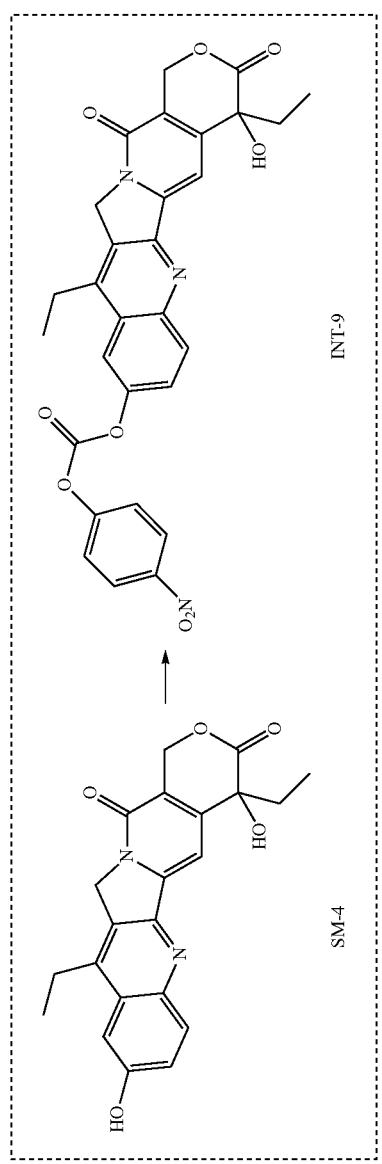

Synthesis of each of the above intermediates (INT) is detailed as follows.

Preparation of tert-butyl 4-(2-hydroxyethyl)piperidine-1-carboxylate (INT-1)

To a stirred solution of 2-(piperidin-4-yl)ethanol (30 g, 0.2322 mmol) in 1,2-dichloromethane (200 ml) was added in portions di-tert-butyl dicarbonate (53 g, 0.24 mmol). The resultant mixture was stirred at room temperature overnight. After confirming reaction completion by thin-layer chromatography, the reaction mixture was washed with water and concentrated to yield compound INT-1 (52 g).

Preparation of tert-butyl 4-(2-((methyl sulfonyl)oxy)ethyl)piperidine-1-carboxylate (INT-2)

To a stirred solution of INT-1 (52 g, 0.23 mmol), 4-dimethylamino pyridine (4.2 g, 3.41 mmol) and triethylamine (92 g, 908 mmol) in 1,2-dichloroethane was added to methanesulfonyl chloride drop wise at 0° C., and the mixture was stirred at room temperature overnight. After confirming reaction completion by thin-layer chromatography, the mixture was washed with water and concentrated to yield compound INT-2 (67 g).

Preparation of tert-butyl 4-(2-(5-nitro-1H-indol-1-yl)ethyl)piperidine-1-carboxylate (INT-3)

To a stirred solution of 5-nitro-1H-indole (SM-2, above, 30 g, 185 mmol) in N,N-dimethylformamide (200 ml), sodium hydride (13 g, 325.5 mmol) was added in portions at 0° C. and the mixture was stirred at room temperature for 30 min. INT-2 (67 g, 217 mmol) was added at 0° C. and the resultant mixture was stirred at room temperature overnight. The mixture was carefully poured into ice water while a yellow precipitate was observed. The mixture was extracted with ethyl acetate followed drying and concentration to afford the crude product, which was then purified by silica gel chromatography to yield INT-3 as a yellow solid (80 g).

Preparation of Compound tert-butyl 4-(2-(5-amino-1H-indol-1-yl)ethyl) piperidine-1-carboxylate (INT-4)

To a solution of INT-3 (80 g, 215 mmol) in a mixture of ethanol (200 ml) and tetrahydrofuran (350 ml) was added Raney nickel (10 g). The resultant mixture was stirred at room temperature overnight under hydrogen atmosphere. The contents then were filtered to remove the solids and concentrated to yield INT-4 (70 g).

Preparation of Compound tert-butyl 4-(2-(5-(2,4-dihydroxy-5-isopropylphenylthioamido)-1H-indol-1-yl)ethyl)piperidine-1-carboxylate (INT-5)

A mixture of 2,4-dihydroxy-5-isopropylbenzodithioic acid (SM-3, 46.5 g, 204 mmol), sodium 2-chloroacetate (38 g, 326.4 mmol) and sodium bicarbonate (52.0 g, 612 mmol) in N,N-dimethylformamide (350 ml) was degassed using nitrogen gas to remove oxygen. The reaction mixture then was stirred at 25° C. for 3 hours. The second reactant, INT-4 (70.0 g, 204 mmol) in N,N-dimethylformamide (150 ml) was added slowly to the reaction mixture through a syringe. The reaction mixture was stirred at 80° C. for 3 hours. After reaction completion, the reaction mixture was extracted with ethyl acetate, washed with water, then brine, and dried. Concentration by flash chromatography yielded INT-5 (58 g).

Preparation of tert-butyl 4-(2-(5-(7-hydroxy-6-isopropyl-2-oxo-4-thioxo-2H-benzo[e][1,3]oxazin-3(4H)-yl)-1H-indol-1-yl)ethyl)piperidine-1-carboxylate (INT-6)

To a stirred solution of compound INT-5 (27 g, 50.86 mmol) in tetrahydrofuran (200 ml), carbonyldiimidazole (16.5 g, 101.7 mmol) was added in portions. The resulting mixture was stirred at room temperature for 3 hours under nitrogen atmosphere, then poured into water and extracted with ethyl acetate. The organic layer was dried over anhydrous $Na_2SO_4$ and concentrated to yield INT-6 (28 g).

Preparation of tert-butyl 4-(2-(5-(3-(2,4-dihydroxy-5-isopropylphenyl)-5-hydroxy-4H-1,2,4-triazol-4-yl)-1H-indol-1-yl)ethyl)piperidine-1-carboxylate (INT-7)

To a stirred solution of compound INT-6 (28 g, 50.86 mmol) in anhydrous ethanol (200 mL) was added hydrazine hydrate (5 ml, 102.2 mmol), and the resulting mixture was stirred overnight at room temperature under argon atmosphere. The reaction product was filtered over a short pad of silica gel, followed by concentration and thorough drying yielding INT-7 (16.4 g.)

Preparation of 4-(5-hydroxy-4-(1-(2-(piperidin-4-yl)ethyl)-1H-indol-5-yl)-4H-1,2,4-triazol-3-yl)-6-isopropylbenzene-1,3-diol (INT-8)

To a solution of compound INT-7 (8 g, 14.3 mmol) in methanol (40 mL) was added a solution of 1.0 M HCl in methanol (100 ml). The resulting mixture was stirred at room temperature overnight. The resultant solids were concentrated, then washed with methanol to yield INT-8 as a hydrochloride salt (4.8 g.)

To a 0° C. stirred suspension of 4-(5-hydroxy-4-(1-(2-(piperidin-4-yl)ethyl)-1H-indol-5-yl)-4H-1,2,4-triazol-3-yl)-6-isopropylbenzene-1,3-diol hydrochloride (INT-8, 3.0 mmol) and (S)-4,11-diethyl-4-hydroxy-3,14-dioxo-3,4,12,14-tetrahydro-1H-pyrano[3',4':6,7]indolizino[1,2-b]quinolin-9-yl (4-nitrophenyl) carbonate (INT-9, 3.0 mmol) in dimethylformamide (40 mL) was added triethylamine (4.0 mmol) dropwise, and the mixture was stirred at 0° C. for 1 hour. 50 mL water then was poured into the mixture. The yellow suspension was stirred at room temperature for 1 hour, then filtered. The filter cake was washed with water (10 mL×2) and purified by column chromatography to yield SDC-TRAP-0063 as a white solid (2.20 g, 2.5 mmol).

$^1$H NMR (400 MHz, Chloroform-d) δ 8.21 (d, J=9.2 Hz, 1H), 7.84 (d, J=2.5 Hz, 1H), 7.68 (s, 1H), 7.64-7.56 (m, 2H), 7.47 (d, J=8.7 Hz, 1H), 7.24-7.12 (m, 2H), 6.55 (dd, J=3.2, 0.8 Hz, 1H), 6.37 (d, J=4.2 Hz, 2H), 5.73 (d, J=16.3 Hz, 1H), 5.36-5.24 (m, 3H), 4.41 (d, J=13.5 Hz, 1H), 4.29 (q, J=9.3, 7.5 Hz, 3H), 3.17 (q, J=7.7 Hz, 2H), 3.06 (t, J=12.7 Hz, 1H), 2.96-2.77 (m, 2H), 2.42 (s, 2H), 1.90 (dq, J=14.2, 7.1 Hz, 6H), 1.45-1.33 (m, 5H), 1.31-1.22 (m, 1H), 1.04 (t, J=7.3 Hz, 3H), 0.50 (d, J=6.8 Hz, 6H). ppm; ESMS calculated for $C_{49}H_{49}N_7O_9$: 879.4; found: 880.2 (M+H$^+$).

Example 7

The following example uses a number of assays to characterize SDC-TRAP-0063 (described in Example 6.)

In vitro activity as determined by the HER2 degradation and Hsp90 binding assay is set forth below. Protocols for the HER2 degradation assay and Hsp90 binding assay are provided in Examples 11 and 12 respectively.

| $IC_{50}$ (HER2 degradation assay) | $EC_{50}$ (Hsp90 binding assay) |
|---|---|
| 793 nM | 157 nM |

In order to determine the stability of SDC-TRAP-006 in plasma, the compound was exposed to mouse plasma and the percent of the compound remaining at 1 hour was determined. After 1 hour 11.1% of SDC-TRAP-0063 remained. As shown below, SDC-TRAP-0063 breaks down into degradation product 1 (DP-1, an Hsp90 inhibitor fragment) and SN-38.

FIGS. 15A-C. The data demonstrate that SDC-TRAP-0063 selectively targets and accumulates in tumor cells, as does the degradation products of SDC-TRAP-0063 including the chemotherapeutic SN-38.

| Compound ID | SDC-TRAP-0063 |
|---|---|
| Lot | 1 |
| Dose | 50 mg/10 mL/kg |
| Species | Female SCID Mouse (H1975) |
| Route | IV |
| Formulation | DRD |

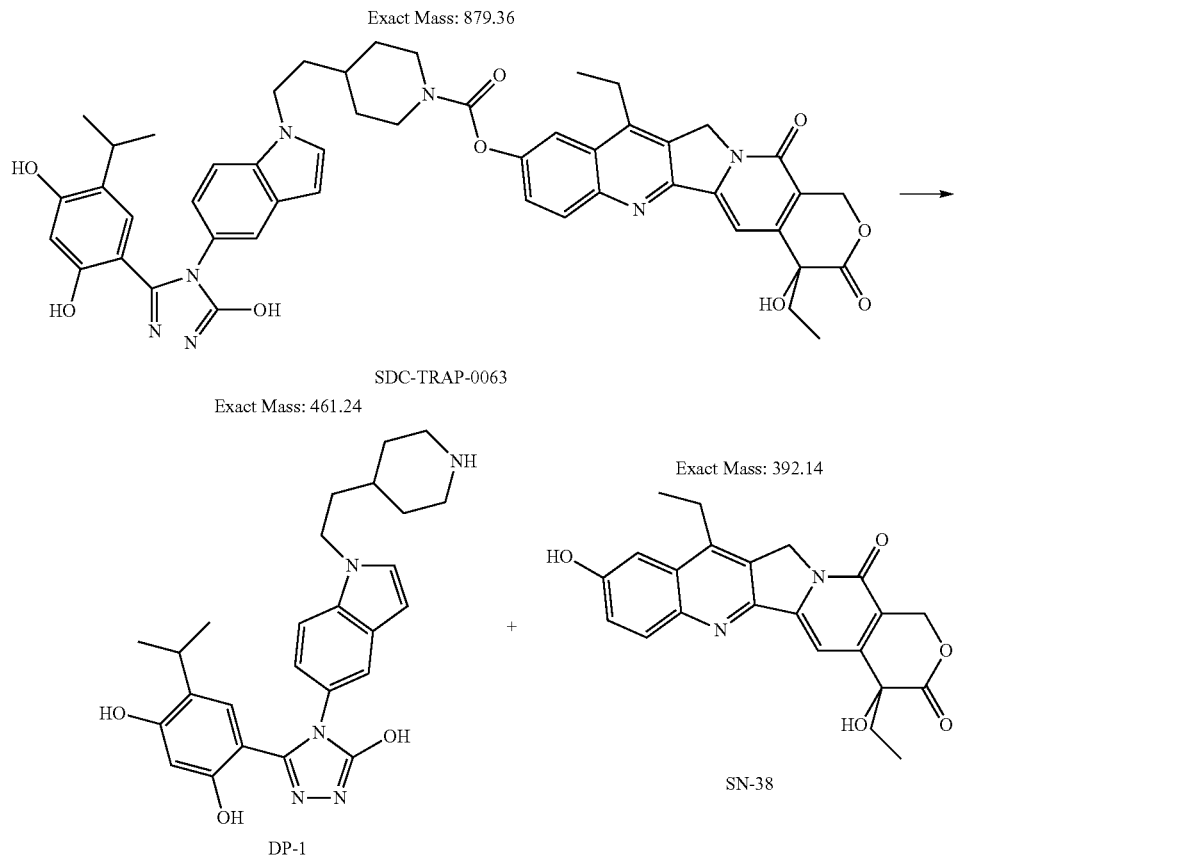

The degradation of SDC-TRAP-0063 was followed in mouse plasma. The release profile of fragment DP-1 and payload (SN-38) was determined according to the protocols provided in Examples 16-18.

| MOUSE PLASMA (MO) Peak Area Ratio Time (h) | | | | |
|---|---|---|---|---|
| | 0 | 0.25 | 0.5 | 1 |
| SDC-TRAP-0063 | 17.9 | 15.6 | 7.77 | 1.98 |
| DP-1 | 0.00133 | 0.00268 | 0.0190 | 0.113 |
| SN-38 | 0.0616 | 1.37 | 4.13 | 4.46 |

In order to determine if SDC-TRAP-0063 is targeting tumor cells selectively, the tissue distribution of SDC-TRAP-0063 and its degradation products DP-1 and SN-38 was monitored in mouse plasma, tumor and heart. Data from these experiments are presented in the table below and in -continued

| Appearance | N/A | | |
|---|---|---|---|
| Accuracy | N/A | | |
| Analyte Target | SDC-TRAP-0063 | DP-1 | SN-38 |
| Time (h) | Plasma Conc. (μM) | | |
| 0.083 | 526 | 0.0662 | 20.4 |
| 6 | 1.69 | 0.0397 | 0.0509 |
| 24 | 0.00675 | 0.0175 | 0.0240 |
| 48 | BQL | 0.00793 | 0.00524 |
| Time (h) | Tumor Conc. (nmol/g of tissue) | | |
| 0.083 | 6.43 | 0.00758 | 1.47 |
| 6 | 1.61 | 0.111 | 0.730 |
| 24 | 0.203 | 0.404 | 0.618 |
| 48 | 0.0188 | 1.06 | 0.296 |

-continued

| Time (h) | Heart Conc. (nmol/g of tissue) | | |
|---|---|---|---|
| 0.083 | 79.1 | 0.0271 | 0.927 |
| 6 | 0.536 | 0.207 | BQL |
| 24 | BQL | 0.0855 | BQL |
| 48 | BQL | 0.0238 | BQL |

Mouse Xenograft Efficacy Data in an HCT-116 Colon Cancer Model

A xenograft tumor model was used to evaluate the anti-tumor efficacy of SDC-TRAP-0063. The tumor model was established by transplanting HCT-116 tumor cells into mice and testing the effect of SDC-TRAP-0063 on tumor volume and change in tumor volume.

HCT 116 human colorectal adenocarcinoma tumor cells were purchased from ATCC. The cells were maintained in vitro as a monolayer culture in McCoy's 5a Medium. Fetal bovine serum was then be added to the medium. The final concentration of fetal bovine serum was 10%. Cells were cultured at 37° C. and 5% $CO_2$. The tumor cells were routinely sub-cultured twice weekly by trypsin-EDTA treatment. Cells in an exponential growth phase were harvested and counted for tumor inoculation.

100 18-22 g, 5-7 week old, female BALB/cA nude mice were inoculated with the HCT 116 cells ($2.0 \times 10^6$, 1:1 with Matrigel) subcutaneously on the back of each animal (0.1 mL/mouse). When the average tumor volume reached about 150-250 mm³, 60 of the inoculated mice was selected based on tumor growth and randomly grouped into 6 treatment groups (10 mice per group) according to the following table. Mice that were not put on treatment were euthanized. Animals were sourced through Shanghai SINO-British SIPPR/BK Lab Animal Ltd, Shanghai, China. Mice were treated as set forth in the table below:

Treatment Groups

| Groups | Animal Number | Treatment | Dosage (mg/kg) | Dosage Conc. (mg/mL) | Dosage Vol. (mL/kg) | Route of Adm. | Dosing Schedule |
|---|---|---|---|---|---|---|---|
| 1 | 10 | Vehicle | NA | NA | 10 | IV | Q7D × 3 |
| 2 | 10 | SDC-TRAP-0063 | 200 | 20 | 10 | IV | Q7D × 3 |
| 3 | 10 | SDC-TRAP-0063 | 100 | 10 | 10 | IV | Q7D × 3 |
| 4 | 10 | SDC-TRAP-0046 | 94 | 9.4 | 10 | IV | Q7D × 3 |
| 5 | 10 | irinotecan | 67 | 6.7 | 10 | IV | Q7D × 3 |
| 6 | 10 | irinotecan | 67 | 6.7 | 10 | IV | Q7D × 3 |
| 7 |  | SYN-01 | 100 | 10 | 10 | IV | Q7D × 3 |

Dose Preparation & Treatment Schedule

The dosing solutions of SDC-TRAP-0063, SDC-TRAP-0046, SYN-01(ganetespib) and irinotecan were prepared according to the DRD formulation protocol (10% dimethyl sulfoxide (DMSO), 18% Cremophore RH40, 3.6% dextrose, 68.4% sterile water and the clearly dissolved drug was added at desired concentration in DMSO). The administrations were made with 27-gauge IV needle.

Evaluation of Anti-Tumor Activity

Figure 4:
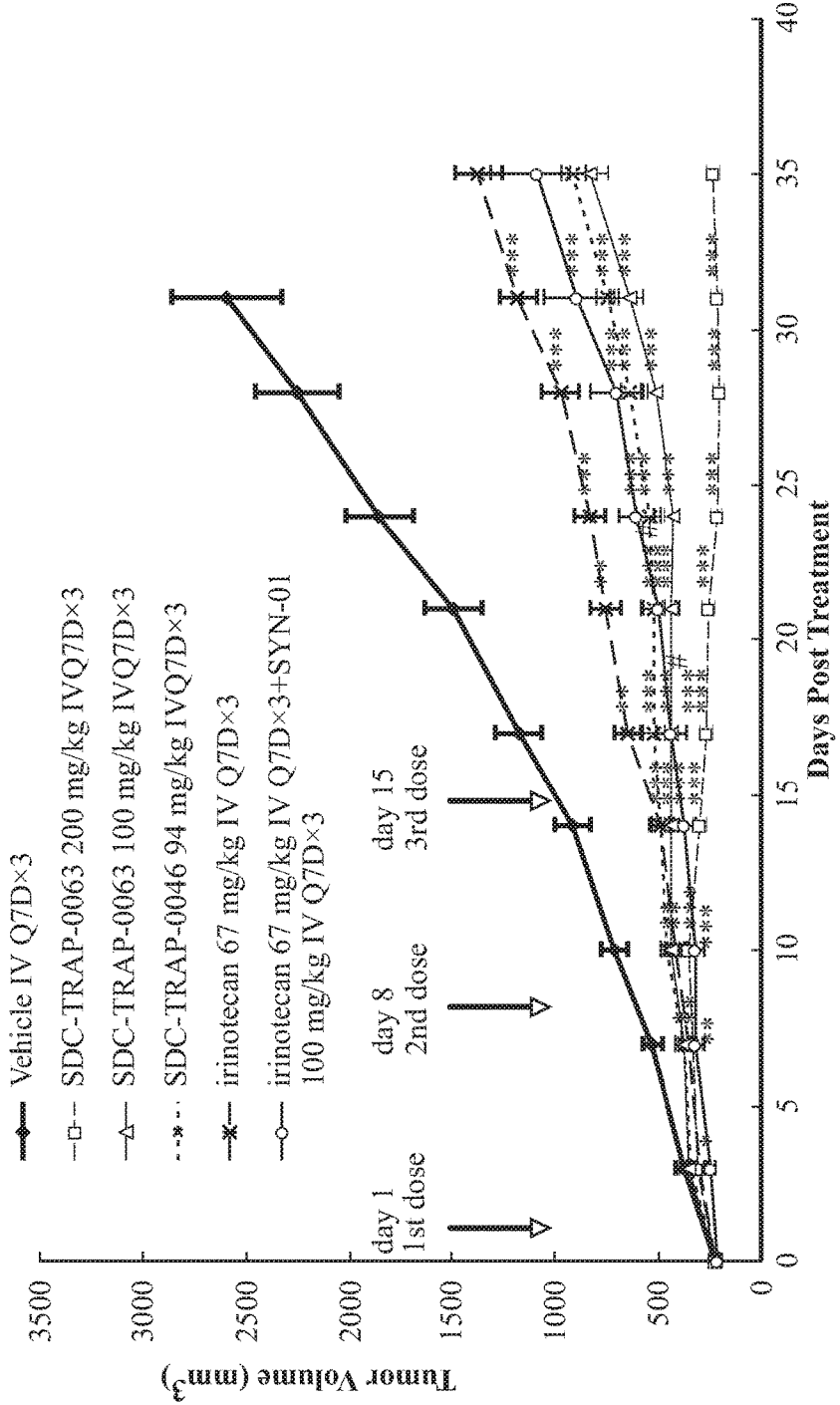
FIG. 4 shows the change in tumor volume following treatment with SDC-TRAP-0063, compared to effector moiety irinotecan and vehicle control in an HCT-116 colon cancer model.
Figure 5:
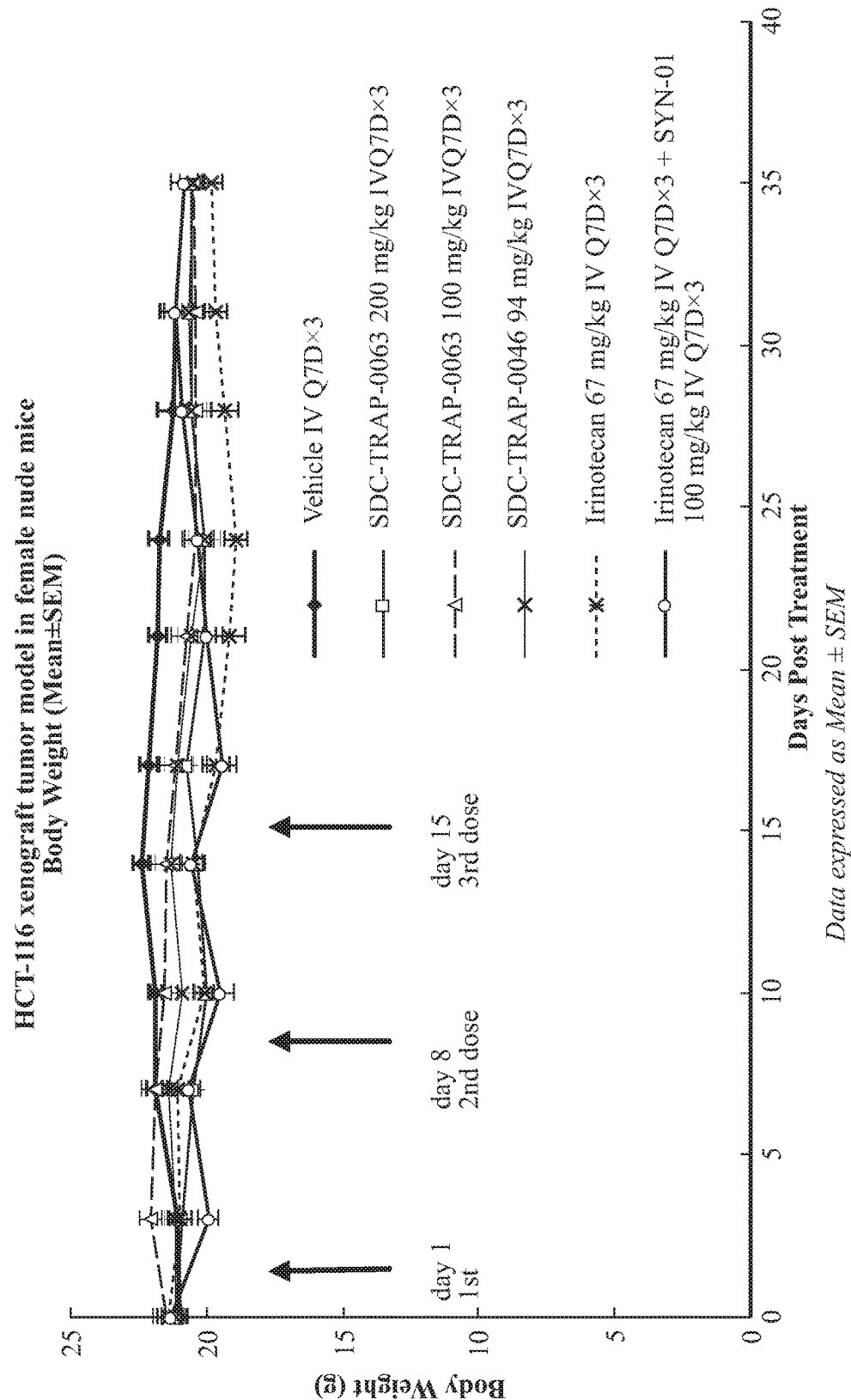
FIG. 5 shows the change in animal body weight following treatment with SDC-TRAP-0063, compared to effector moiety irinotecan and vehicle control in an HCT-116 colon cancer model.

During the treatment period, the implanted tumors were measured by caliper twice per week. The tumors were measured for the maximum width (X) and length (Y) and the tumor volumes (V) were calculated using the formula: $V=(X^2Y)/2$. The differences in the tumor volume between the control and treatment groups were analyzed for significance using the unpaired two-tailed Student's t-test. $P<0.05$ was considered to be statistically significant. The animal body weights were also weighed and recorded twice per week. The changes in tumor volume in the days following compound treatment are shown in FIG. 4. The changes in animal body weight in the days following compound treatment are shown in FIG. 5.

Mouse Xenograft Efficacy Data in an MCF-7 Breast Cancer Model

A xenograft tumor model to evaluate the anti-tumor efficacy of SDC-TRAP-0063 was established by transplanting MCF-7 breast cancer cells into mice and testing the effect of SDC-TRAP-0063 on tumor volume and change in tumor volume.

MCF-7 breast cancer cells were purchased from ATCC. The cells were maintained in vitro as a monolayer culture in McCoy's 5a Medium. Fetal bovine serum was then added to the medium. The final concentration of fetal bovine serum was 10%. Cells were cultured at 37° C. and 5% $CO_2$. The tumor cells were routinely sub-cultured twice weekly by trypsin-EDTA treatment. Cells in an exponential growth phase were harvested and counted for tumor inoculation.

75 24-30 g, 10-13 week old, female CD-1 nude mice were inoculated with the MCF-7 cells ($5.0 \times 10^6$/mouse) orthotopically in mammary fat pad (0.1 mL/mouse). 60 days estrogen pellets was implanted the day prior to cell implantations. When the average tumor volume reached about 100-225 mm³, 40 of the inoculated mice were selected based on tumor growth and randomly grouped into 5 treatment groups (8 mice per group) according to the following table. Mice that were not put on treatment were euthanized. Animals were sourced through CRL (Wilmington, Mass.). Animals were treated as set forth in the table below.

| Group | Animal Number | Treatment | Dosage (mg/kg) | Dosage Conc. (mg/mL) | Dosage Vol. (mL/kg) | Roe Adm. | Dosing Schedule |
|---|---|---|---|---|---|---|---|
| 1 | 8 | Vehicle | NA | NA | 10 | IV | Q7D × 3 |
| 2 | 8 | SDC-TRAP-0063 | 150 | 15 | 10 | IV | Q7D × 3 |
| 3 | 8 | SDC-TRAP-0063 | 100 | 10 | 10 | IV | Q7D × 3 |
| 5 | 8 | Irinotecan | 67 | 6.7 | 10 | IV | Q7D × 3 |
| 6 | 8 | Irinotecan | 67 | 6.7 | 10 | IV | Q7D × 3 |
|  |  | ganetespib | 42 | 10 | 10 | IV | Q7D × 3 |

Dose Preparation & Treatment Schedule

The dosing solutions of SDC-TRAP-0063, ganetespib and irinotecan were prepared in a standard DRD formulation (10% DMSO, 18% Cremophor RH40, 3.6% dextrose, 68.4% sterile water, while clearly dissolved drug substances were added in DMSO.) The administrations were made with a 27-gauge IV needle. In the combo group, irinotecan was dosed 2 hours after ganetespib.

Evaluation of Anti-Tumor Activity

Figure 6:
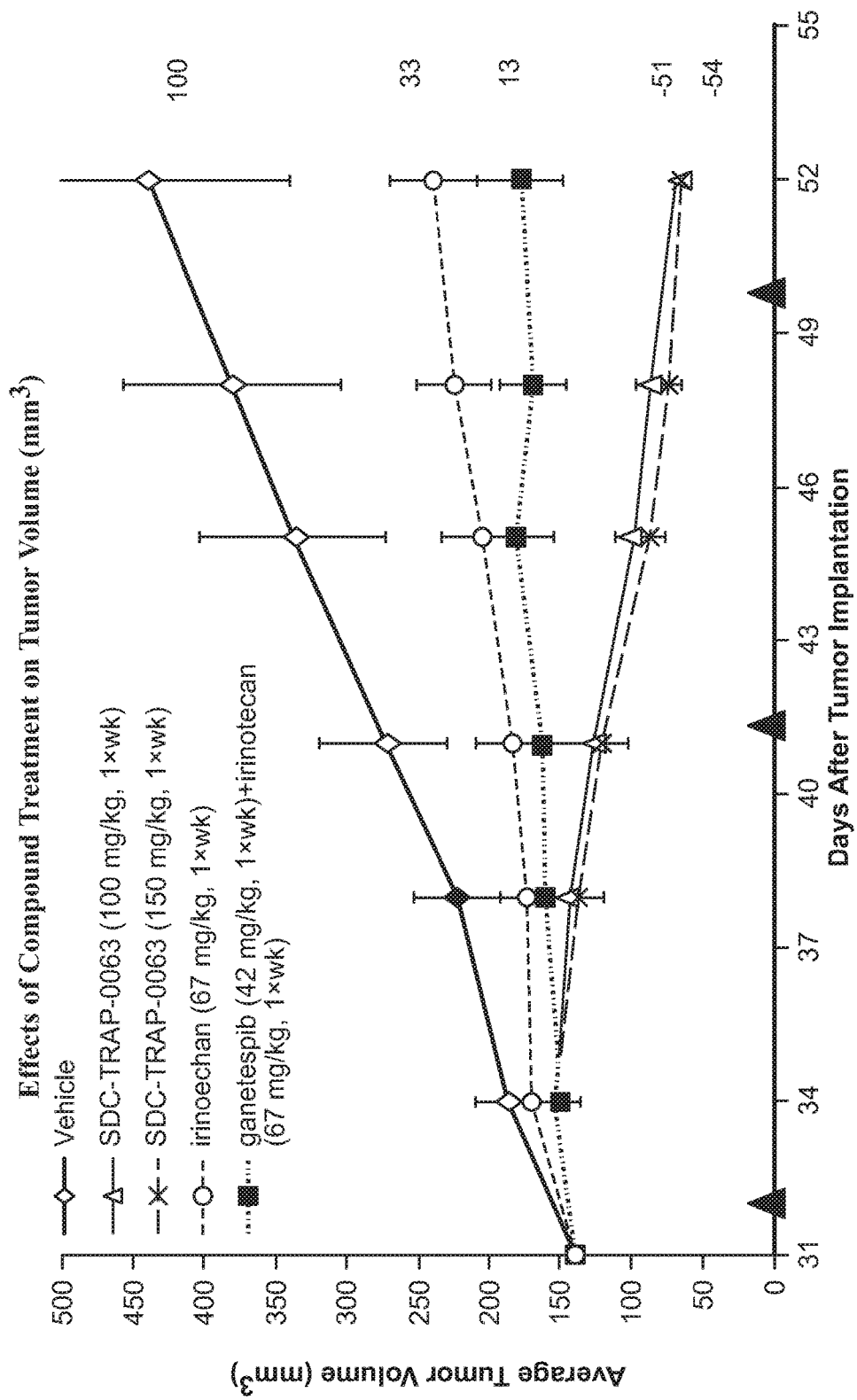
FIG. 6 shows the change in tumor volume following treatment with SDC-TRAP-0063, compared to effector moiety irinotecan and vehicle control in an MCF-7 breast cancer model.
Figure 7:
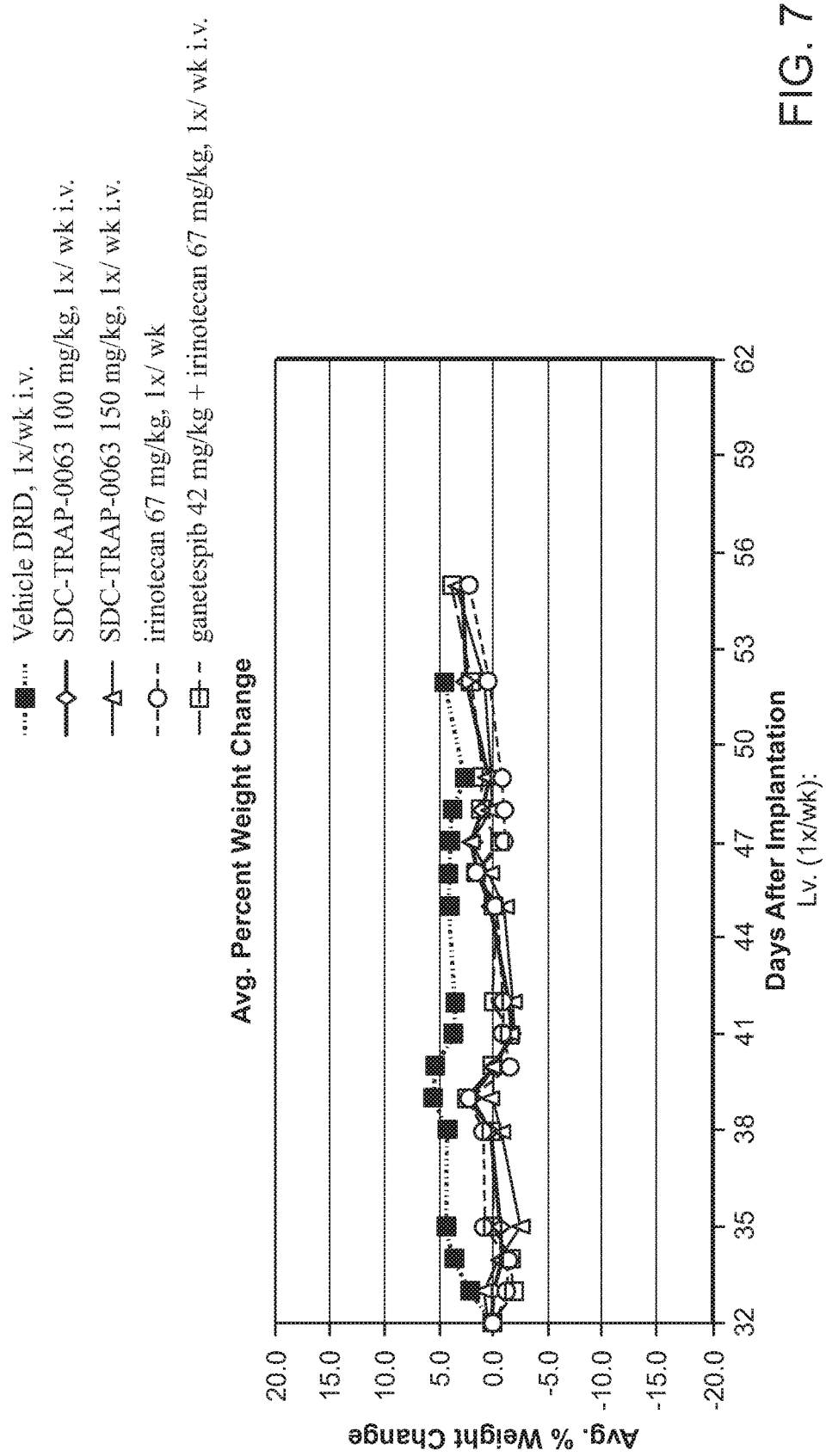
FIG. 7 shows the change in animal body weight following treatment with SDC-TRAP-0063, compared to effector moiety irinotecan and vehicle control in an MCF-7 breast cancer model.

During the treatment period, the implanted tumors were measured by caliper twice per week. The tumors were measured for the maximum width (X) and length (Y) and height (Z), the tumor volumes (V) were calculated using the formula:

V=0.5236*X*Y*Z. The differences in the tumor volume between the control and treatment groups were analyzed for significance using % T/C value. Animal body weights were also weighed and recorded 5× per week. The changes in tumor volume in the days following compound treatment are shown in FIG. 6. The changes in animal body weight in the days following compound treatment are shown in FIG. 7.

Figure 8:
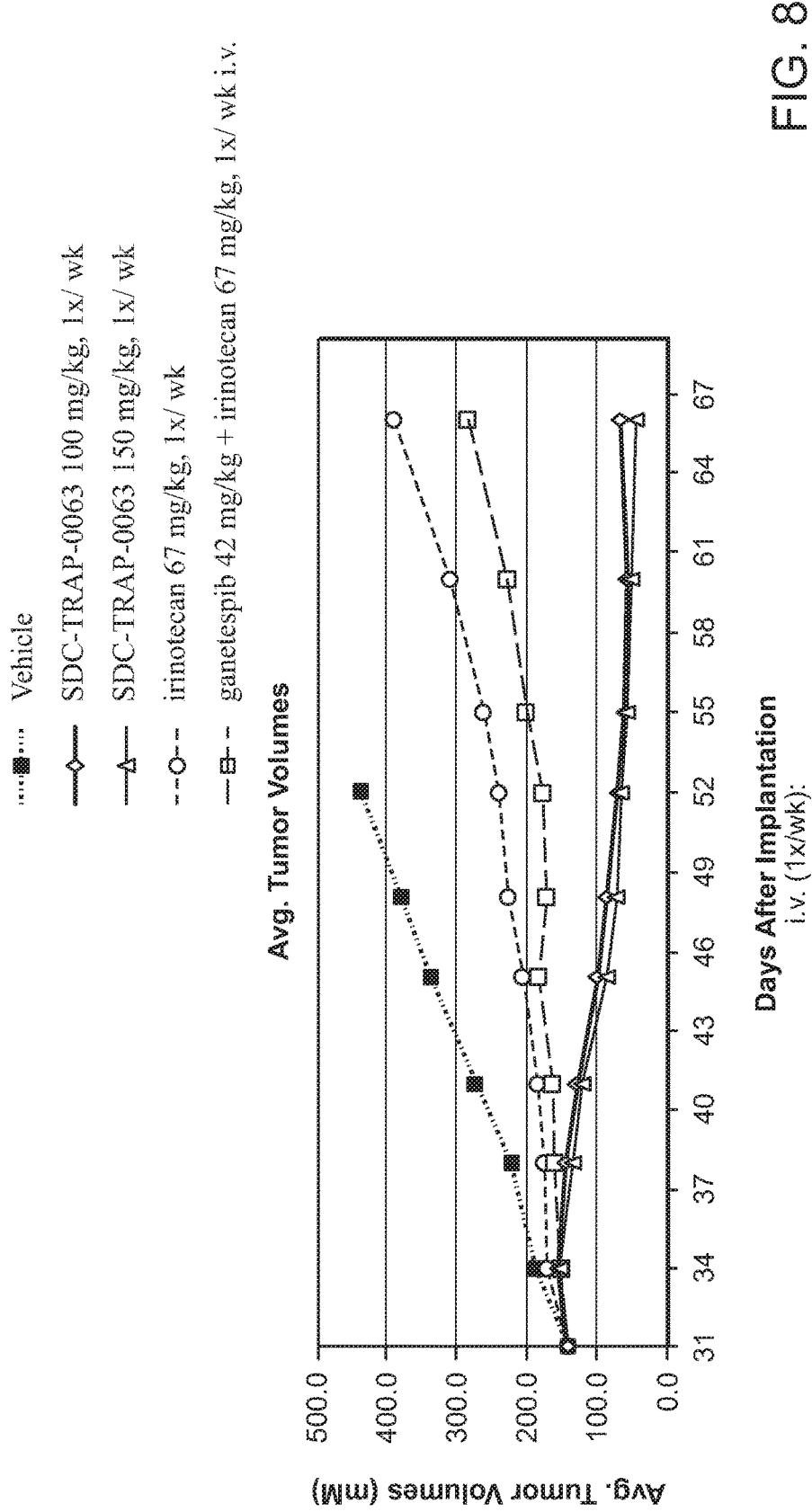
FIG. 8 demonstrates a dose-dependent decrease in tumor volume compared to binding moiety or effector moiety alone.

Preliminary Toxicological Evaluation Data (TK Analysis, Biomarker Analysis for Myelosuppression at Various Dose Levels in Rats):

The data presented in FIG. 8 indicates that a higher dose (150 mg/kg/1×wk) of conjugate SDC-TRAP-0063 appears to prolong the suppression of increase in tumor volume compared to a lower dose (100 mg/kg/1×wk). Either dose of SDC-TRAP-0063 has greater tumor growth suppression than effector moiety irinotecan alone, or unconjugated binding moiety ganetespib and effector moiety irinotecan administered together.

Example 8

Synthesis and Testing of Lenalidomide Conjugate SDC-TRAP-0178

Synthesis and testing of SDC-TRAP-0178, which is a conjugate of HSP90 inhibitor fragment 3 and lenalidomide, is exemplified below.

Synthesis and Structure of Lenalidomide Conjugate SDC-TRAP-0178:

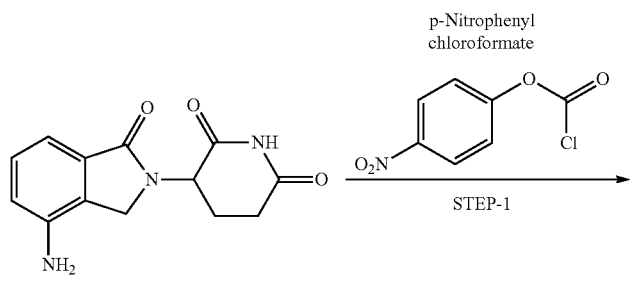

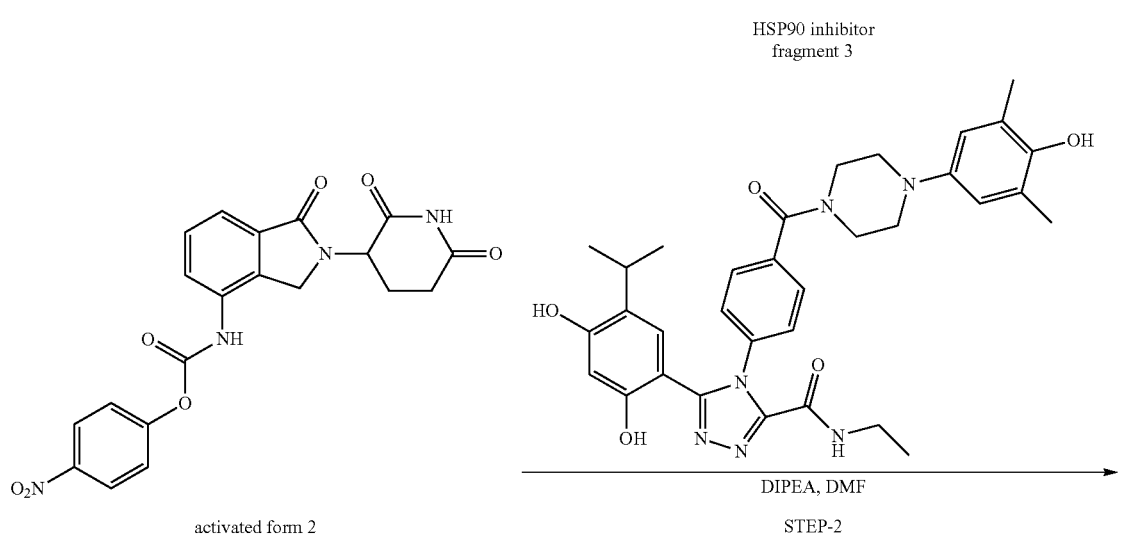

-continued

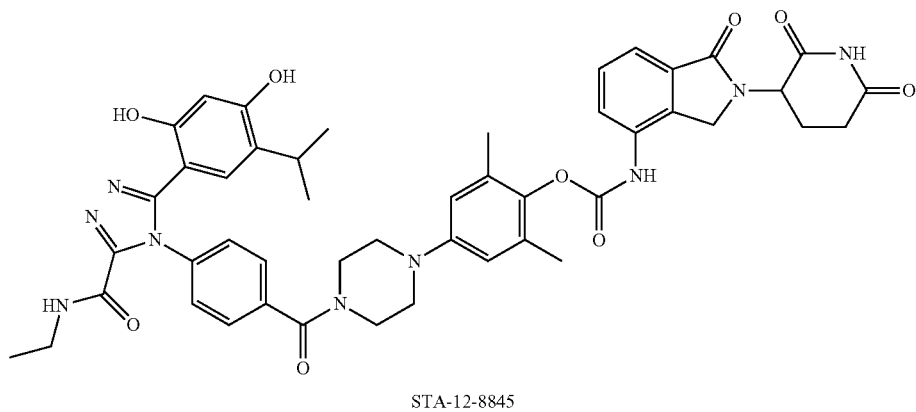

STA-12-8845

STEP-1: To a stirred suspension of lenalidomide 1 (520 mg, 2 mmol) in dry THF (70 mL) was added 4-nitrophenylchloroformate (605 mg, 3 mmol). The reaction mixture was refluxed for 2 h, concentrated to approximately 40 mL, and triturated with ethyl acetate to yield a white precipitate. The solid was collected by filtration and washed with ethyl acetate to give carbamate 2 (650 mg, 77%).

STEP-2: Diisopropylethylamine (33 mg, 0.25 mmol) was added to a stirred solution of Hsp90 inhibitor fragment 3 (120 mg, 0.2 mmol) and the activated lenalidomide 2 (86 mg, 0.2 mmol) in anhydrous DMF (5 mL). The reaction mixture was stirred at room temperature for 18 h; then diluted with water (5 mL) and extracted with ethyl acetate (100 mL). The organic phase was dried (sodium sulfate), filtered and evaporated, followed by flash chromatography (hexane-ethyl acetate 1:1 and ethyl acetate-methanol 98:2) to give SDC-TRAP-0178 (95 mg, 53%) as a white solid.

$^1$H NMR (400 MHz, DMSO-$d_6$) δ 11.02 (s, 1H), 10.22 (s, 1H), 10.17 (s, 1H), 9.74 (s, 1H), 9.02 (t, J=5.9 Hz, 1H), 7.86-7.77 (m, 1H), 7.58-7.46 (m, 4H), 7.45-7.37 (m, 2H), 6.73 (d, J=11.9 Hz, 3H), 6.33 (s, 1H), 5.13 (dd, J=13.2, 5.1 Hz, 1H), 4.50 (d, J=17.6 Hz, 1H), 4.41 (d, J=17.6 Hz, 1H), 3.76 (s, 2H), 3.48 (s, 2H), 3.25-3.13 (m, 4H), 3.02-2.85 (m, 2H), 2.66-2.57 (m, 1H), 2.45-2.31 (m, 1H), 2.14 (s, 6H), 2.04-2.02 (m, 1H), 1.06 (t, J=7.2 Hz, 3H), 0.91 (d, J=6.9 Hz, 6H).

ESMS calculated for $C_{47}H_{49}N_9O_9$: 883.37; Found: 884.1 (M+H)$^+$.

SDC-TRAP-0178 was tested in the HER2 degredation assays described in Example 12. There results are set forth in the table below.

SDC-TRAP-0178 HER2 Degradation Assay

| SDC-TRAP# | HER2 Degradation IC50 (nM) |
|---|---|
| SDC-TRAP-0178 | 91 nM |

SDC-TRAP-0178 Mouse Plasma Stability Assay

The percentage of a 10 μmole (μM) intravenous dose of SDC-TRAP-0178 remaining in plasma of a mouse after 1 hour was determined by the protocol set forth in Example 16:

| Compound ID | % Remaining (1 h, 10 μM) |
|---|---|
| SDC-TRAP-0178 | 82.0% |

SDC-TRAP-0178 Tissue Distribution

Tissue distribution of SDC-TRAP-0178 in plasma and tumor was determined following the protocol set forth in Example 14. Data therefrom are set forth in the table below:

| Analyte | Plasma Conc. (μM) | | | Tumor Conc. (nmol/g of tissue) | | | Tumor/Plasma Ratio | | |
|---|---|---|---|---|---|---|---|---|---|
| Target Time (h) | SDC-TRAP-0178 | SDC-TRAP-0183 | Lenalidomide | SDC-TRAP-0178 | SDC-TRAP-0183 | Lenalidomide | SDC-TRAP-0178 | SDC-TRAP-0183 | Lenalidomide |
| 0.083 | 918 | N/A | 1.39 | 16.4 | 0.320 | 0.623 | 0.0179 | — | 0.449 |
| 1 | 217 | N/A | 0.963 | 12.8 | 0.316 | 0.629 | 0.0589 | — | 0.653 |
| 6 | 4.51 | N/A | 0.00447 | 7.17 | 0.418 | 0.0532 | 1.59 | — | 11.9 |
| 24 | 0.0280 | N/A | BQL | 2.81 | 0.556 | BQL | 100 | — | — |
| 48 | 0.241 | N/A | BQL | 1.01 | 0.508 | BQL | — | — | — |

Determination of Cytotoxicity of Additional SDC-TRAP Molecules

The cytotoxicity of additional SDC-TRAP molecules was determined in BT-474, SW780 and RT-112 cancer cell lines. Cytotoxicity was determined following the protocol set forth in Example 13. Results are presented in the table below.

| Compounds | Payload | Cytotoxicity (IC$_{50}$, nM) | | |
|---|---|---|---|---|
| | | BT-474 | RT-112 | SW-780 |
| SDC-TRAP-0069 | Bendamustine | 914 | 909 | 1,342 |
| SDC-TRAP-0211 | Bendamustine | 249 | 110 | 2,341 |
| SDC-TRAP-0098 | VDA | 41 | 22 | 257 |
| SDC-TRAP-0198 | Doxorubicin | 786 | 297 | >10,000 |
| SDC-TRAP-0199 | Doxorubicin | 29 | 29 | 2,299 |
| SDC-TRAP-0219 | Doxorubicin | >10,000 | 973 | >10,000 |
| SDC-TRAP-0200 | Doxorubicin | 32 | 16 | 651 |
| SDC-TRAP-0068 | Pemetrexed fragment | 70 | 74 | 202 |
| SDC-TRAP-0093 | Pemetrexed fragment | 1,540 | 1287 | >10,000 |
| SDC-TRAP-0117 | Vorinostat | 452 | 152 | 284 |
| SDC-TRAP-0201 | SN-38 | 1406 | 72 | 1,097 |
| SDC-TRAP-0204 | SN-38 | 8062 | 1314 | >10,000 |
| SDC-TRAP-0046 | SN-38 | 205 | 20 | 489 |
| SDC-TRAP-0063 | SN-38 | 320 | 83 | 261 |
| SDC-TRAP-0171 | Lenalidomide | 58 | 20 | 275 |
| SDC-TRAP-0178 | Lenalidomide | 37 | 29 | >10,000 |
| SDC-TRAP-0196 | Lenalidomide | 17 | 31 | >10,000 |
| Lenalidomide | | >10,000 | >10,000 | >10,000 |
| (17-AAG) | | 42 | 44 | 161 |
| (SN-38) | | >10,000 | <10 | 38 |

Example 9

Determination of IC$_{50}$ by Assessing the Effects of Various SDC-TRAPs on Tumor Shrinkage H3122 cells were seeded into in 96-well plates at 7,500 cells/90 µL/well, and were incubated for 24 hours. 14 SDC-TRAPs, plus ganetespib as a control, were serially diluted in dimethylsulfoxide (DMSO) into each of six wells of each 96-well plate according to the graphic in FIG. 16, where each cell represents a well in the plate.

To each well of plates #1 and 3 (continuous plates), 145 µL of media was added, and the cells were incubated. The wells of plates #2 and 4 (pulsed plates) were incubated for 1 hour, then the wells were rinsed 2× with fresh media to remove the conjugate, and 145 µL of media was then added to each washed well. IC$_{50}$ was determined visually under a microscope after 48 hours and 72 hours drug-exposure. Also at the 72 hour time point, 50 µL of the cell culture supernatant was mixed with 50 µL of CellTiter-Glo and the luminescence was determined, from which an IC$_{50}$ for each conjugate was calculated.

The data demonstrating the tumor effect of these SDC-TRAPs are set forth in FIGS. 4-8.

Example 10

IC$_{50}$ of Continuous and Pulsed Exposure to SDC-TRAPs

IC$_{50}$ toxicity was determined for 72 hour continuous exposure to 14 SDC-TRAPs run in triplicate, and for duplicate pulse exposure (1 hour "pulse" exposure to conjugate compound, followed by 72 hour incubation in conjugate-free media) using H3211 cells, according to the protocol set forth in Example 9. The experimental data are set forth in the table below.

| compound | 72 h-continuous | 72 h-continuous | 72 h-continuous | 1 h-pulse/ 71 h-compound free | 1 h-pulse/ 71 h-compound free |
|---|---|---|---|---|---|
| H 3211 NSLC cells (7.5 × 10^3 cells/well), plate #1 (continuous), #2 (pulse), n = 1 | | | | | |
| SDC-TRAP-0223 | 12> | 12> | 12> | 82 | 88 |
| SDC-TRAP-0003 | >3000 | >3000 | >3000 | >3000 | >3000 |
| SDC-TRAP-0004 | 22 | 60 | 40 | 624 | 1748 |
| SDC-TRAP-0005 | >3000 | >3000 | >3000 | >3000 | >3000 |
| SDC-TRAP-0006 | 21 | 49 | 27 | >3000 | 756 |
| SDC-TRAP-0010 | 144 | 327 | 232 | 291 | >3000 |
| SDC-TRAP-0015 | 796 | 2227 | 796 | >3000 | >3000 |
| SDC-TRAP-0017 | >3000 | >3000 | >3000 | >3000 | >3000 |
| SDC-TRAP-0018 | 287 | 839 | 735 | >3000 | >3000 |
| SDC-TRAP-0019 | 209 | 713 | 258 | >3000 | >3000 |
| SDC-TRAP-0020 | 587 | 2615 | 2009 | >3000 | >3000 |
| SDC-TRAP-0021 | 431 | 817 | 902 | >3000 | >3000 |
| SDC-TRAP-0022 | 193 | 823 | 460 | >3000 | >3000 |
| SDC-TRAP-0023 | 59 | 239 | 113 | >3000 | >3000 |
| SDC-TRAP-0024 | 76 | 118 | 104 | 697 | 2211 |
| H 3211 NSLC cells (7.5 × 10^3 cells/well), plate #3 (continuous), #4 (pulse), n = 1 | | | | | |
| SDC-TRAP-0223 | >12 | 12> | 12> | 49 | 116 |
| SDC-TRAP-0027 | 984 | 1743 | 1335 | >3000 | >3000 |
| SDC-TRAP-0028 | 468 | 1761 | 499 | >3000 | >3000 |
| SDC-TRAP-0029 | 79 | 191 | 106 | >3000 | >3000 |
| SDC-TRAP-0030 | 53 | 38 | 53 | >3000 | >3000 |
| SDC-TRAP-0032 | 250 | 407 | 333 | >3000 | >3000 |
| SDC-TRAP-0034 | 587 | 1167 | 2046 | >3000 | >3000 |
| SDC-TRAP-0035 | 260 | 830 | 787 | >3000 | >3000 |

-continued

| compound | 72 h-continuous | 72 h-continuous | 72 h-continuous | 1 h-pulse/71 h-compound free | 1 h-pulse/71 h-compound free |
|---|---|---|---|---|---|
| SDC-TRAP-0036 | 139 | 265 | 96 | >3000 | >3000 |
| SDC-TRAP-0224 | >3000 | >3000 | >3000 | >3000 | >3000 |
| SDC-TRAP-0225 | 12> | 12> | 12> | 108 | 1481 |
| SDC-TRAP-0226 | 152 | 292 | 232 | 1089 | 2901 |
| SDC-TRAP-0227 | >3000 | >3000 | >3000 | >3000 | >3000 |
| SDC-TRAP-0228 | >3000 | >3000 | >3000 | >3000 | >3000 |
| SDC-TRAP-0223 | >12 | 12> | 12> | 60 | 111 |

Example 11

Hsp90$^\alpha$ Binding Assay Protocol

An Hsp90$^\alpha$ fluorescence assay kit from BPS Bioscience (Cat #50294) containing Hsp90 recombinant enzyme, FITC-labeled geldanamycin, assay buffer and a low binding 384-well plate was used to assay Hsp90$^\alpha$ binding. Dithiothreitol (DTT) (Cat #D0643) and bovine serum albumin (BSA) (Cat #A2153) were obtained from Sigma-Aldrich. Fluorescence polarization was measured using a PHERAstar microplate reader (BMG LABTECH GmbH, Ortenberg, Germany.)

The compounds were diluted to 1 mM in DMSO and loaded into a compound dilution plate to make 3-fold dilutions yielding a total of 8 concentrations. 1 µL of compound was transferred from the dilution plate to the low binding assay plate provided in the assay kit. 5 mL of Hsp90$^\alpha$ binding solution was prepared having a final concentration of 7 ng/µL Hsp90$^\alpha$, 5 nM FITC-labeled geldanamycin, 2 mM DTT and 0.1 mg/mL BSA. 49 µL of binding solution was added to each microplate well, incubated at room temperature for 1 hour, then read using the PHERAstar microplate reader. The high control sample contained no compound plus Hsp90$^\alpha$; the low control sample contained no compound and no Hsp90$^\alpha$. Percent inhibition was calculated using high control as 100% and low control as 0% inhibition. The IC$_{50}$ was calculated using GraphPad Prism 4 software.

Example 12

HER2 Degradation Assay with BT-474 Cell Line

HER2 has emerged as a key target for anticancer drugs due to its intrinsic involvement in the phosphatidylinositol-3-kinase-Akt/protein kinase B (PI3K-Akt) and the mitogen-activated protein kinase (MAPK) pathways, both of which suppress apoptosis and promote tumor cell survival, gene transcription, angiogenesis, cellular proliferation, migration, mitosis, and differentiation. The degradation of HER2 is a measure of efficacy of anticancer therapeutics that target Hsp90. Accordingly, the SDC-TRAP molecules of the invention that comprise a binding moiety that binds Hsp90 were tested in the following HER2 degradation assay.

BT-474 cells (human breast cancer cell line ATCC HTB-20) were obtained from ATCC and seeded into 12-well tissue culture plates at 0.2×10$^6$/1.8 mL/well. The cells were incubated for more than 6 hours at 37° C. in DMEM+10% FBS, +1% P/S, +1.5 g/L sodium bicarbonate. Each test compound was titrated in 4-fold dilutions from 5 µM to 78 nM with DMSO and 200 µL of the titration was added to each well of the cell plate. The DMSO final concentration was 0.2%. Cells were incubated overnight at 37° C. in 5% CO$_2$.

Media was decanted from the plate, cells were washed 1× in PBS. 400 µL trypsin (EDTA) per well was added, and the cells were incubated for 2 to 3 minutes. Cells were collected into FACS tubes containing 1 ml culture medium to neutralize the trypsin and were centrifuged for 5 minutes at 1200 rpm. Supernatant was decanted and the cells were resuspended in 5 µL FITC (anti HER2/nu)/200 µL staining buffer (1×PBS+1% FBS+0.05% Sodium Azide)/tube. Controls were 5 L IgG isotype control and staining buffer only. Tubes were incubated for 30 minutes in the dark at room temperature. 1 mL staining buffer was added to each tube and the tubes were centrifuged for 6 minutes at 1200 rpm. The supernatant was decanted and 300 µL staining buffer was added to each tube, which was store at 4° C. for FACS (cytometer) analysis. The cytometer readout was normalized and the potency of each compound is evaluated with IC$_{50}$ calculated with XLfit™ software.

Example 13

Cytotoxicity Assay with Cancer Cell Lines

Cytotoxicity of SDC-TRAP molecules was determined in three cancer cell lines. 5000 cells/100 µL/well of human breast cancer cell line BT-474 (ATCC #HTB-20) and human urinary bladder cancer cell line SW780 (ATCC# CRL-2169) and 5000 cells/well of human urinary bladder cancer cell line RT-112 were seeded into 96-well flat-bottom tissue cultures plates and incubated overnight at 37° C. in 5% CO$_2$. BT-474 and SW780 cells were cultured in DMEM+10% FBS, +1% P/S, +1.5 g/L sodium bicarbonate; RT-112 cells were cultured in EMEM+10% FBS, +1% P/S. SDC-TRAP-0178 was titrated by 10-fold dilutions from 10 µM to 10 nM and added to the plate at 10 µL/well. Final concentration of DMSO in the cell plate was 0.25%. The plates were incubated for 72 hours at 37° C. in 5% CO$_2$. 80 µL of CellTiter-Glo was added to each well, followed by room temperature incubation in the dark for 15 minutes. Cell was determined by luminescence. IC$_{50}$ was calculated using XLfit™ software.

Example 14

Tissue Distribution Extraction Procedure for SDC-TRAP Tumor Samples

SDC-TRAP molecules have the ability to be specifically targeted to desired cells. For example, SDC-TRAP molecules can be targeted to tumors and tumor cells in order to treat cancer. This example sets forth a protocol to extract the SDC-TRAP molecules of the invention from tumor samples.

A 150 ng/mL solution of SDC-TRAP-0002 in methanol was prepared using an internal spiking solution (500 µg/mL SDC-TRAP-0002 in DMSO). Using the 10 mM stock solutions of the SDC-TRAP molecule and its Hsp90i binding moiety and effector moiety in DMSO, spiking solutions were prepared at 0.025, 0.05, 0.1, 0.5, 1, 5, 10, 50, 100, 250, and 500 µM in DMSO. 5 µL of each spiking solution was added to a 96-deep well plate.

Quality control standards were prepared from 5 µL of 0.1, 1, and 10 µM calibration standard spiking solution added in triplicate into 96-deep well plate and adding 50 µL of matrix (plasma or homogenized tumor).

To prepare test samples, test plasma was diluted as needed using blank plasma. Tumor samples were pulverized in liquid nitrogen, weighed, and homogenized in PBS at 5× volume to sample weight. 50 µL of unknown plasma or homogenized tumor sample was mixed with 5 µL of DMSO. The samples were extracted by precipitating calibration standards, QC standards, and unknown samples with 200 µL of internal standard solution. The samples were mixed by vortex at room temperature for approximately 1.5 minutes, then centrifuge at 2-8° C. 150 µL of supernatant was collected and 25 µL of water added. Samples were mixed and analyzed by LC-MS/MS.

Example 15

SDC-TRAP-0063 Tissue Distribution Study in Mice

The following experiment was conducted in order to demonstrate the ability of SDC-TRAP molecules to specifically target desired tissues. An exemplary SDC-TRAP molecule, SDC-TRAP-0063, was administered to mice according to the protocol below and tissue samples were collected to evaluate tissue distribution.

Samples of plasma, heart and tumor were excised from a euthanized mouse, homogenized in PBS at 5 times tissue weight and diluted in 5 µL DMSO/50 µL sample. Prior to analysis, 55 µL samples and calibration standards were precipitated in 200 µL methanol in 96-well plates. Samples were mixed on a vortex mixer for 1.5 minutes at 1500 rpm at room temperature, then centrifuged at 4400 rpm for 10 minutes at 8° C. 150 µL of each supernatant was transferred to a well of a new 96-well plate, and 25 µL of water was added and mixed with the sample. The samples were analyzed by LCMS/MS using a Phenomenex Kinetex 2.6 µm C18 100 A, 30×2.1 mm column at 0.5 mL/minute for 3.5 minutes with a TIS detector. For the analysis of samples from female SCID mice, a gradient of solvent A (water/0.1% formic acid) and B (acetonitrile/0.1% formic acid) was used as in Table A below. The solvent gradient used to analyze the tissues from male SD and CD-1 mice is shown in Table B below.

TABLE A

| Time (min) | A | B |
|---|---|---|
| 0 | 80 | 20 |
| 1.7 | 5 | 95 |
| 2 | 5 | 95 |
| 2.1 | 80 | 20 |
| 3.5 | 80 | 20 |

TABLE B

| Time (min) | A | B |
|---|---|---|
| 0 | 95 | 5 |
| 1.7 | 5 | 95 |
| 2 | 5 | 95 |
| 2.1 | 95 | 5 |
| 3.5 | 95 | 5 |

Figure 11:
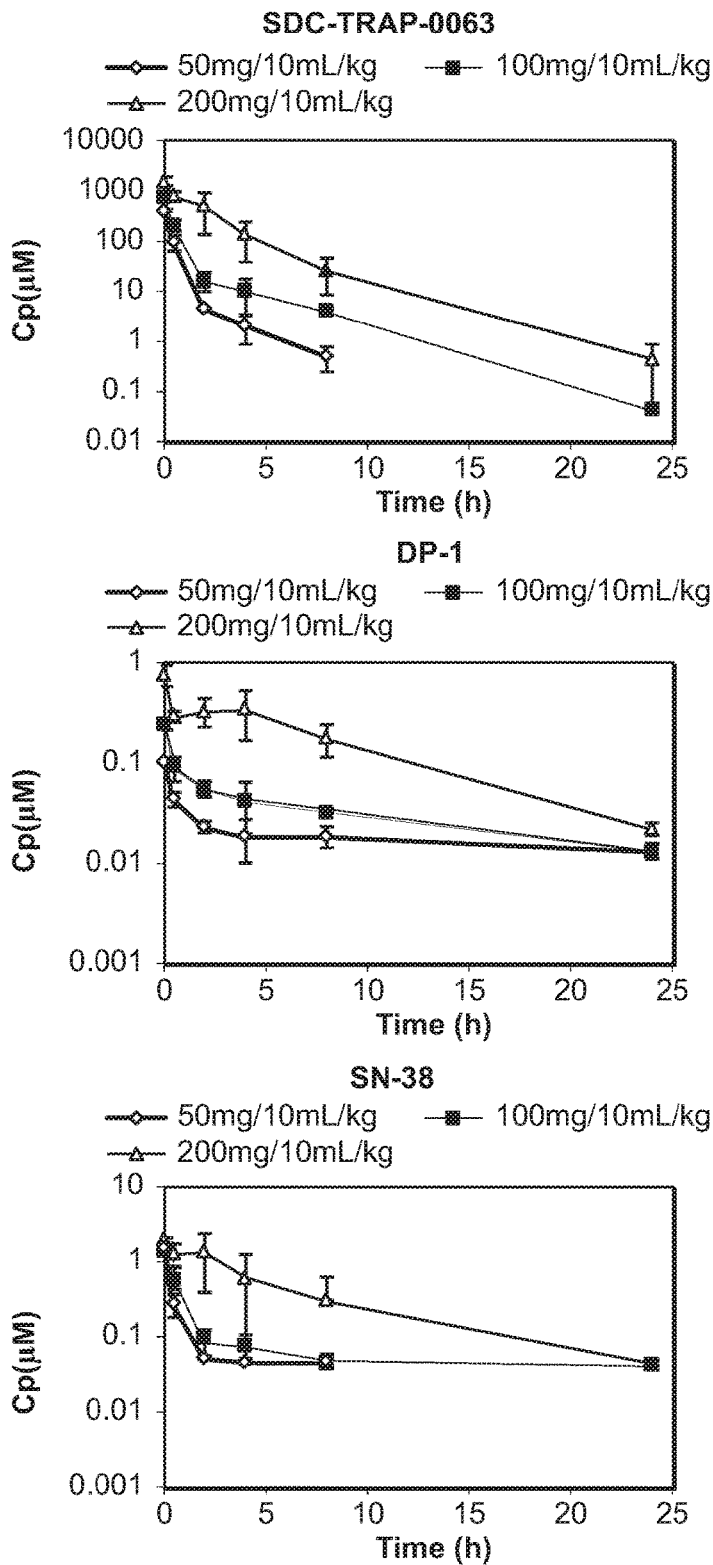
FIG. 11 shows the results of SDC-TRAP-0063 tissue distribution studies in male CD-1 mice.

The distribution of SDC-TRAP-0063 and its expected degradants, DP-1, (ganetespib) and effector moiety SN-38 (irinotecan) in plasma, tumor and heart of female SCID mice at the illustrated time points following injection are shown in the tables below and in FIG. 9. Similar data were collected from male SD mice (FIG. 10) and male CD-1 mice (FIG. 11.) Tabular data are not shown. In each case, data collected over 48 hours post-treatment indicate that binding moiety and effector moiety accumulate and persist in tumor, but rapidly diminish in plasma and heart, demonstrating the efficacy of the SDC-TRAP molecules.

| Compound ID | SDC-TRAP-0063 | | |
|---|---|---|---|
| Lot | 1 | | |
| Dose | 50 mg/10 mL/kg | | |
| Species | Female SCID Mouse (H1975) | | |
| Route | IV | | |
| Formulation | DRD | | |
| Appearance | N/A | | |
| Accuracy | N/A | | |
| Analyte Target | SDC-TRAP-0063 | DP-1 | SN-38 |

| Time (h) | Plasma Conc. (µM) | | |
|---|---|---|---|
| 0.083 | 526 | 0.0662 | 20.4 |
| 6 | 1.69 | 0.0397 | 0.0509 |
| 24 | 0.00675 | 0.0175 | 0.0240 |
| 48 | BQL | 0.00793 | 0.00524 |

| Time (h) | Tumor Conc. (nmol/g of tissue) | | |
|---|---|---|---|
| 0.083 | 6.43 | 0.00758 | 1.47 |
| 6 | 1.61 | 0.111 | 0.730 |
| 24 | 0.203 | 0.404 | 0.618 |
| 48 | 0.0188 | 1.06 | 0.296 |

| Time (h) | Heart Conc. (nmol/g of tissue) | | |
|---|---|---|---|
| 0.083 | 79.1 | 0.0271 | 0.927 |
| 6 | 0.536 | 0.207 | BQL |
| 24 | BQL | 0.0855 | BQL |
| 48 | BQL | 0.0238 | BQL |

| Time (h) | Tumor/Plasma Ratio | | |
|---|---|---|---|
| 0.083 | 0.0122 | 0.114 | 0.0721 |
| 6 | 0.958 | 2.79 | 14.3 |
| 24 | 30.1 | 23.1 | 25.8 |
| 48 | — | 134 | 56.4 |

| Time (h) | Heart/Plasma Ratio | | |
|---|---|---|---|
| 0.083 | 0.151 | 0.409 | 0.0454 |
| 6 | 0.318 | 5.21 | — |
| 24 | — | 4.90 | — |
| 48 | — | 3.00 | — |

The tissue distribution of SDC-TRAP-0056 and SDC-TRAP-0052 as well as SN-38 and irinotecan was evaluated in female SCID mice as set forth above for SDC-TRAP-0063, DP-1 and SN-38. In each case, the data demonstrate that SDC-TRAP molecule and the effector moiety accumulate and persist in tumor, but rapidly diminish from the plasma, demonstrating the efficacy of the SDC-TRAP molecules. The data is shown in the table below.

| Compound ID | SDC-TRAP-0046 | SDC-TRAP-0052 | | Irinotecan | | |
|---|---|---|---|---|---|---|
| Lot | 2 | 1 | | RCN-102 | | |
| Dose | 50 mg/10 mL/kg | 25 mg/10 mL/kg | | 24 mg/10 mL/kg | | |
| Species | | | Female SCID Mouse (H1975) | | | |
| Route | IV | | | IV | IV | |
| Formulation | DRD | | | DRD | DRD | |
| Appearance | Clear | | | Clear | Clear | |
| Accuracy | 81.6% | | | 97.2% | 97.1% | |
| Analyte Target | SDC-TRAP-0046 | SDC-TRAP-0052 | SN-38 | SDC-TRAP-0052 | Irinotecan | SN-38 |
| Time (h) | | | Plasma Conc. (µM) | | | |
| 0.083 | 360 | 0.0782 | 2.29 | — | — | — |
| 6 | 5.88 | 0.0917 | 0.0773 | 58.7 | 2.24 | 1.42 |
| 12 | 2.37 | 0.0612 | 0.0389 | — | — | — |
| 24 | 0.0542 | 0.0364 | 0.00955 | 0.0223 | BQL | BQL |
| 48 | BQL | 0.0107 | BQL | — | — | — |
| Time (h) | | | Tumor Conc. (nmol/g of tissue) | | | |
| 0.083 | 6.94 | BQL | 0.298 | — | — | — |
| 6 | 4.97 | 0.241 | 0.448 | 13.9 | 13.1 | 1.44 |
| 12 | 5.21 | 0.407 | 0.344 | — | — | — |
| 24 | 2.19 | 1.71 | 1.01 | 5.33 | 0.0307 | BQL |
| 48 | 0.188 | 1.01 | BQL | — | — | — |
| Time (h) | | | Tumor/Plasma Ratio | | | |
| 0.083 | 0.0193 | — | 0.130 | — | — | — |
| 6 | 0.844 | 2.63 | 5.80 | 0.236 | 5.82 | 1.01 |
| 12 | 2.20 | 6.65 | 8.83 | — | — | — |
| 24 | 40.3 | 46.9 | 105 | 238 | — | — |
| 48 | — | 94.4 | — | — | — | — |

Example 16

Plasma Stability Protocol for SDC-TRAP Compounds 150 ng/mL solution of SDC-TRAP-0002 in methanol was prepared using the internal standard spiking solution. This solution was used to precipitate all plasma samples in the study. 200 µL was pipetted into a 96 deepwell plate over dry ice. 10 µL of 1 mM stock in DMSO was added to a 1.5 mL microfuge tube, then 990 µL of plasma. Samples were mixed by vortex, then 50 µL of each sample was added in triplicate to a 96-well plate containing internal standard solution. This was designated the 0 hour time point sample. 250 µL of the remaining plasma sample was added to each of four 96 deepwell plates—one per time point. Samples were incubated at 37° C. with gentle shaking for 0.25, 0.5, and 1 hour. After each time point, one plate of each sample was removed from the shaker and placed on wet ice for approximately 2 minutes. 50 µL plasma aliquots (in triplicate) were added to the deepwell plate containing internal standard solution. After the last time point was extracted, the 96 deepwell plate was vortexed, then centrifuged at 2-8° C. 150 µL of supernatant was collected and 25 µL of water was added. Samples were mixed and analyzed by LC-MS/MS.

Example 17

SDC-TRAP Stability in Mouse Plasma

The stability of seven SDC-TRAP types in mouse plasma was measured as follows. 990 µL mouse plasma aliquots from a common stock were spiked with 10 µL of 1 mM stock of one of seven SDC-TRAP samples identified in the table below. Each sample was mixed and divided into 250 µL aliquots, each representing time points 0, 15 minutes, 30 minutes or 1 hour. At the prescribed time point, 3×50 µL samples were each mixed with 200 µL of methanol containing internal standard and held on dry ice until all time point samples were extracted. The samples collectively were vortex mixed for 1.5 minutes at 1500 rpm, then centrifuged at 4400 rpm for 10 minutes at 8° C. 150 µL of each supernatant was transferred to a new 96-well plate, 25 µL of water added and mixed, then each sample was analyzed by LCMS/MS as described in Example 16. The data collected at one hour are set forth in the table below.

| Compound ID | % Remaining (1 h) |
|---|---|
| SDC-TRAP-0063 | 11.1% |
| SDC-TRAP-0064 | 91.5% |
| SDC-TRAP-0172 | 74.7% |
| SDC-TRAP-0180 | 72.4% |
| SDC-TRAP-0184 | 18.0% |
| SDC-TRAP-0185 | 68.1% |
| SDC-TRAP-0186 | 57.9% |

Figure 12:
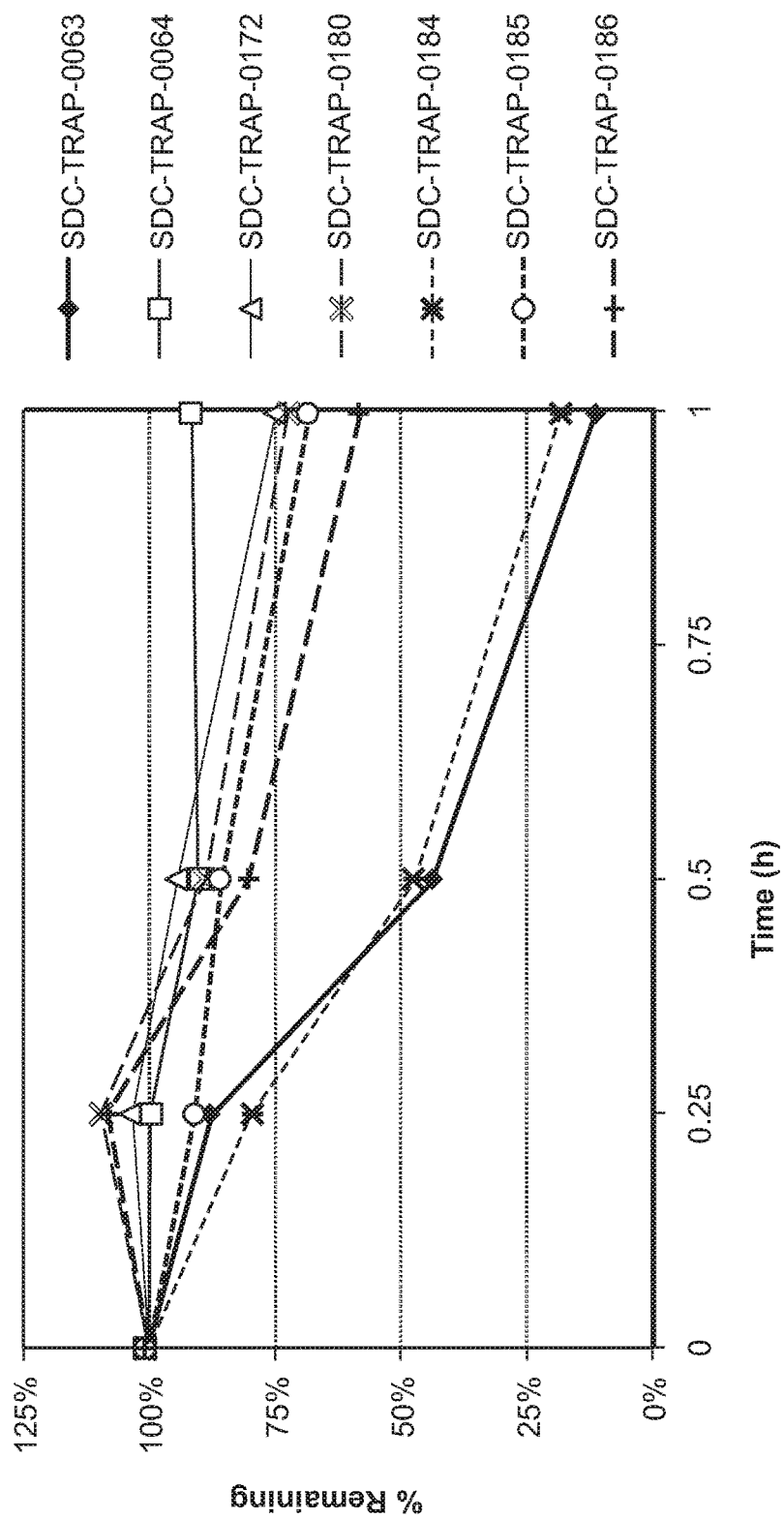
FIG. 12 illustrates the stability of seven SDC-TRAP species in mouse plasma.
Figure 13:
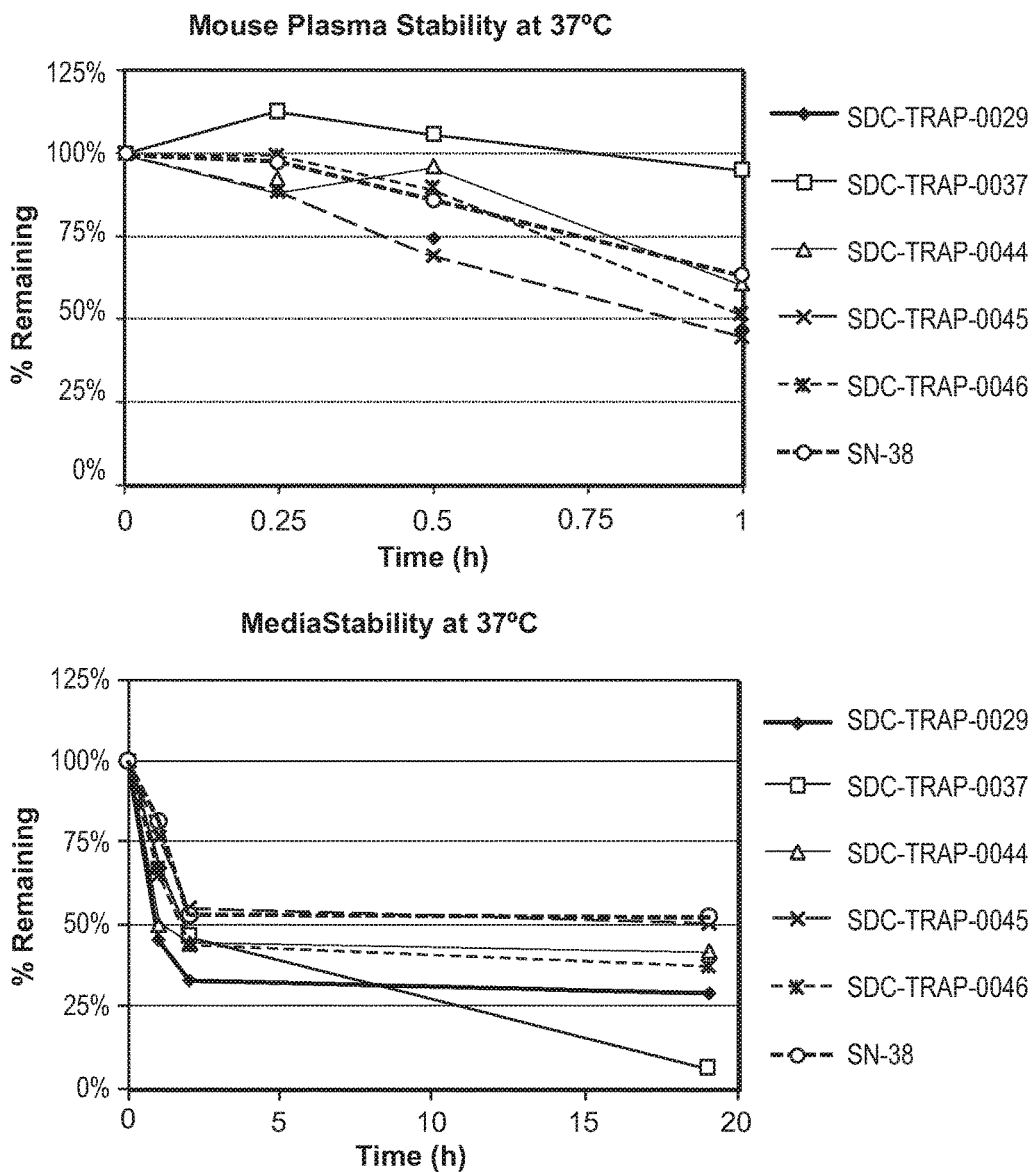
FIG. 13 illustrates the stability of five additional SDC-TRAP species plus effector moiety SN-38 in mouse plasma and cell culture media.
Figure 14:
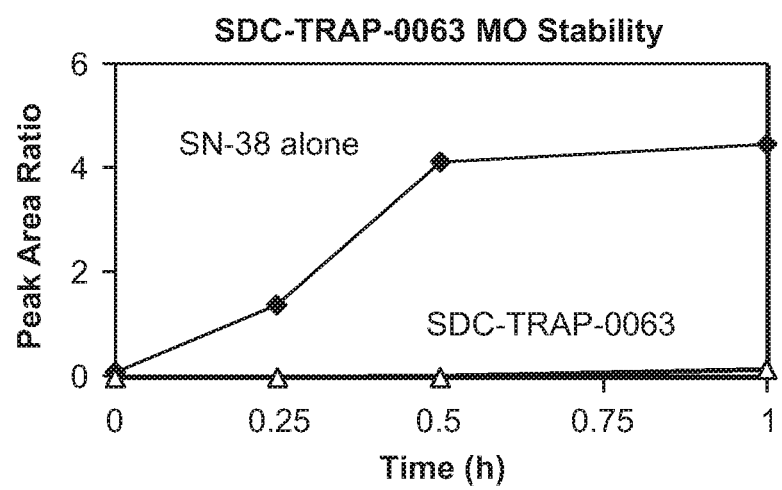
FIG. 14 depicts the stability of SDC-TRAP-0063 and SN-38 alone.

These and data taken at times 0, 15 minutes, 30 minutes and 1 hour are presented graphically in FIG. 12. As indicated in FIG. 12, the SDC-TRAP molecules of the invention are stable in mouse plasma.

Example 18

SDC-TRAP Stability in Mouse Plasma and Cell Culture Media

The stability of six SDC-TRAP molecules with a variety of binding moieties and a particular effector moiety (SN-38/irinotecan) in mouse plasma and cell culture media was assessed. Mouse plasma samples were prepared according to Example 16. 98 µL of DMEM+10% FBS, +1% P/S, +1.5 g/L sodium bicarbonate cell culture media was mixed with 2 µL of DMSO and aliquotted into 96-well plates at 250 µL per 0, 1, 2, and 18 hour time point. Plasma samples were mixed at 150 rpm for the required time and extracted and processed for analysis according to Example 16.

3×50 µL media samples in 96 were held in 96-well plates at −80° C. until the last time point was extracted. 200 µL of methanol containing IS was added and mixed by vortex at 1500 rpm for 1.5 minutes at room temperature. The samples were centrifuged at 4400 rpm for 10 minutes at 8° C. 150 µL of supernatant was transferred to a new 96-well plate; 25 µL of water was added to each well; and mixed and the samples were analyzed according to the procedure described in Example 16.

| SDC-TRAP-# | Mouse (10 μM) % Remaining 1 h (37° C.)§ | Mouse (10 μM) % Remaining 1 h (37° C.)* | Media (5 μM) % Remaining 1 h (37° C.)§ | Media (5 μM) % Remaining 1 h (37° C.)* | Media (5 μM) % Remaining 19 h (37° C.) |
|---|---|---|---|---|---|
| SDC-TRAP-0029 | 44% | 47% | 43% | 46% | 29% |
| SDC-TRAP-0037 | — | 95% | — | 67% | 6% |
| SDC-TRAP-0044 | — | 61% | — | 50% | 41% |
| SDC-TRAP-0045 | 34% | 45% | 72% | 77% | 50% |
| SDC-TRAP-0046 | 50% | 52% | 62% | 65% | 37% |
| SN-38 | — | 64% | — | 82% | 52% |

§Data from single parent peak. No double peak for SDC-TRAP-0044 plasma and media or SDC-TRAP-0037 plasma. SN-38 only integrated for double peaks.
*Double peaks observed in parent chromatogram. Data calculated with sum of both peaks.

Example 19: SDC-TRAPs Comprising Vorinostat

SDC-TRAP-0117

N1-((4-(4-(3-(2,4-dihydroxy-5-isopropylphenyl)-5-hydroxy-4H-1,2,4-triazol-4-yl) benzyl)piperazine-1-carbonyl)oxy)-N8-phenyloctanediamide

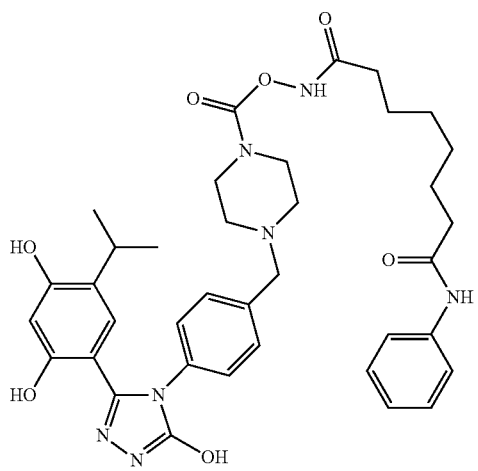 [SMILES: CC(C)c1cc(-c2nnc(O)n2-c2ccc(CN3CCN(C(=O)ONC(=O)CCCCCCC(=O)Nc4ccccc4)CC3)cc2)c(O)cc1O]

$^1$H NMR (400 MHz, DMSO-$d_6$) δ 11.91 (s, 1H), 11.40 (s, 1H), 9.83 (s, 1H), 9.58 (s, 1H), 9.39 (s, 1H), 7.62-7.54 (m, 2H), 7.35-7.23 (m, 4H), 7.18-7.10 (m, 2H), 7.05-6.96 (m, 1H), 6.78 (s, 1H), 6.26 (s, 1H), 3.48 (s, 2H), 3.40 (s, 4H), 2.97 (p, J=6.9 Hz, 1H), 2.40-2.24 (m, 6H), 2.07 (t, J=7.3 Hz, 2H), 1.54 (dt, J=22.8, 7.3 Hz, 4H), 1.36-1.25 (m, 4H), 0.95 (d, J=6.9 Hz, 6H); ESMS calculated for $C_{37}H_{45}N_7O_7$: 699.34; Found: 700.3 (M+H)$^+$.

SDC-TRAP-0118

N1-((4-(2-(5-(3-(2,4-dihydroxy-5-isopropylphenyl)-5-hydroxy-4H-1,2,4-triazol-4-yl)-1H-indol-1-yl)ethyl)piperidine-1-carbonyl)oxy)-N8-phenyloctanediamide

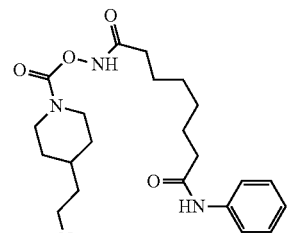

$^1$H NMR (400 MHz, DMSO-$d_6$) δ 11.88 (s, 1H), 11.37 (s, 1H), 9.84 (s, 1H), 9.53 (d, J=19.5 Hz, 2H), 7.58 (dt, J=7.3, 1.0 Hz, 2H), 7.52-7.39 (m, 3H), 7.32-7.22 (m, 2H), 7.06-6.90 (m, 2H), 6.69 (s, 1H), 6.43 (d, J=3.1 Hz, 1H), 6.23 (s, 1H), 4.22 (t, J=7.1 Hz, 2H), 3.91 (s, 2H), 2.95-2.80 (m, 3H), 2.29 (t, J=7.4 Hz, 2H), 2.07 (t, J=7.3 Hz, 2H), 1.79-1.64 (m, 4H), 1.54 (dt, J=24.2, 6.6 Hz, 5H), 1.43 (s, 1H), 1.37-1.25 (m, 4H), 1.16 (q, J=12.3, 9.7 Hz, 4H), 0.80 (d, J=6.8 Hz, 6H); ESMS calculated for $C_{41}H_{49}N_7O_7$: 751.37; Found: 752.3 (M+H)$^+$.

in vitro activity was determined for these compounds using the HER2 degradation assay set forth herein:

| SDC-TRAP# | HER2 degradation IC$_{50}$ (nM) |
|---|---|
| SDC-TRAP-0117 | 1095 |
| SDC-TRAP-0118 | 2352 |

Example 20: SDC-TRAPs Comprising 5-FU

Exemplary Synthetic Protocol:

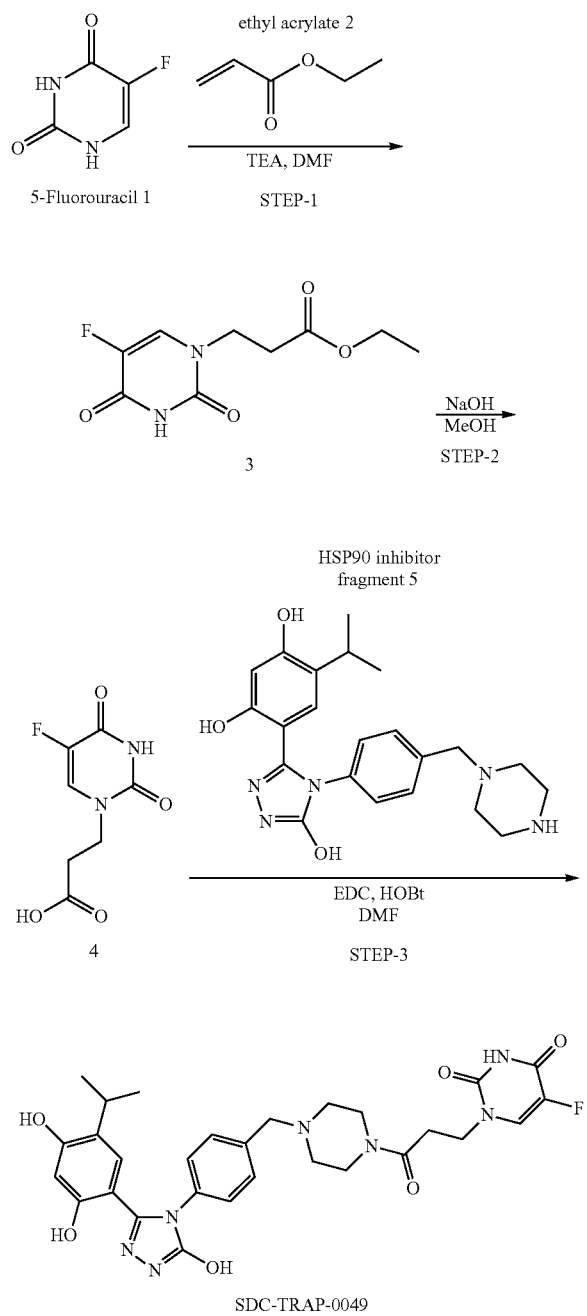

STEP-1: To a solution of 5-fluorouracil 1 (650 mg, 5 mmol) in anhydrous DMF (8 mL), triethylamine (100 mg, 1 mmol) was added while stirring. After 5 min, methyl acrylate 2 (1 g, 10 mmol) was added dropwise. Stirring was continued for 36 h. The solvent was evaporated under reduced pressure, and the residue was purified on chromatographic column (95:5 CH$_2$Cl$_2$/MeOH) to give compound 3 (860 mg, 75%).

STEP-2: A solution of compound 3 (800 mg, 3.47 mmol) in a mixture of MeOH (4 mL) and 2N aqueous solution NaOH (3 mL) was heated for 4 h at 60° C. The solvent was removed under reduced pressure, and the residue was subjected to acidification to pH2, using a solution of 10% HCl, resulting in acid 4 as white crystals. $^1$H NMR (400 MHz, DMSO-d$_6$) δ: 12.43 (s, 1H); 11.78 (s, 1H); 8.06 (d, J=7.2 Hz, 1H); 3.82 (t, J=6.9 Hz, 2H); 2.63 (t, J=6.9 Hz, 2H).

STEP-3: To a solution of acid 4 (42 mg, 0.2 mmol) and amine 5 (82 mg, 0.2 mmol) in anhydrous DMF (4 mL) was added EDC (60 mg, 0.3 mmol) and HOBT (27 mg, 0.2 mmol). The reaction mixture was stirred at room temperature for 5 h. The reaction mixture was diluted with 5 mL water and extracted with 100 mL of ethyl acetate. The organic phase was dried with sodium sulfate, filtered and evaporated, followed by flash chromatography (hexane-ethyl acetate 1:1 and ethyl acetate-methanol 98:2) to give SDC-TRAP-0049 (95 mg, 80%) as a white solid.

$^1$H NMR (400 MHz, DMSO-d$_6$) δ 11.94 (s, 1H), 11.75 (s, 1H), 9.62 (s, 1H), 9.42 (s, 1H), 8.04 (d, J=6.9 Hz, 1H), 7.32-7.30 (m, 2H), 7.15-7.12 (m, 2H), 6.77 (s, 1H), 6.27 (s, 1H), 3.82 (t, J=6.8 Hz, 2H), 3.54-3.33 (m, 6H), 2.90 (ddt, J=13.9, 9.7, 5.3 Hz, 1H), 2.73-2.60 (m, 2H), 2.34-2.29 (m, 4H), 0.94 (dd, J=11.8, 6.9 Hz, 6H); ESMS calculated for C$_{29}$H$_{32}$FN$_7$O$_6$: 593.24; Found: 594.2 (M+H)$^+$.

The following compounds were made in the same general manner as above:

SDC-TRAP-0051

N-(2-(5-(3-(2,4-dihydroxy-5-isopropylphenyl)-5-hydroxy-4H-1,2,4-triazol-4-yl)-1H-indol-1-yl)ethyl)-3-(5-fluoro-2,4-dioxo-3,4-dihydropyrimidin-1(2H)-yl)-N-methylpropanamide

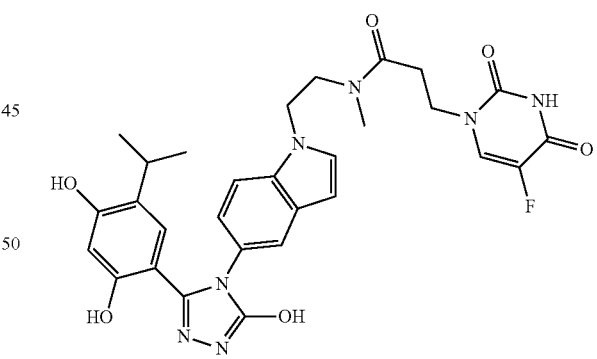

$^1$H NMR (400 MHz, DMSO-d$_6$) δ 11.90 (s, 1H), 11.75 (s, 1H), 9.56 (s, 1H), 9.47 (d, J=14.3 Hz, 1H), 8.04 (d, J=6.9 Hz, 1H), 7.54-7.35 (m, 3H), 6.95 (td, J=8.9, 2.0 Hz, 1H), 6.74 (d, J=13.6 Hz, 1H), 6.47-6.40 (m, 1H), 6.23 (d, J=4.1 Hz, 1H), 4.37 (t, J=6.0 Hz, 1H), 4.28 (t, J=6.5 Hz, 1H), 3.82 (t, J=6.8 Hz, 1H), 3.60 (q, J=6.8 Hz, 3H), 3.54-3.33 (m, 6H), 2.90 (ddt, J=13.9, 9.7, 5.3 Hz, 1H), 2.73-2.60 (m, 5H), 2.34 (t, J=6.7 Hz, 1H), 0.84 (dd, J=11.8, 6.9 Hz, 6H); ESMS calculated for C$_{29}$H$_{30}$FN$_7$O$_6$: 591.22; Found: 592.1 (M+H)$^+$.

SDC-TRAP-0048

N-(2-(2-(5-(3-(2,4-dihydroxy-5-isopropylphenyl)-5-hydroxy-4H-1,2,4-triazol-4-yl)-1H-indol-1-yl)ethoxy)ethyl)-3-(5-fluoro-2,4-dioxo-3,4-dihydropyrimidin-1(2H)-yl) propanamide

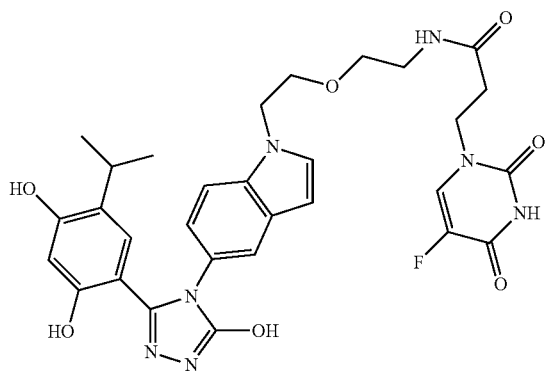 [SMILES: CC(C)c1cc(-c2nnc(O)n2-c2ccc3c(ccn3CCOCCNC(=O)CCn3cc(F)c(=O)[nH]c3=O)c2)c(O)cc1O]

$^1$H NMR (400 MHz, DMSO-d$_6$) δ 11.88 (s, 1H), 11.77 (s, 1H), 9.56 (s, 1H), 9.48 (s, 1H), 8.00 (t, J=5.6 Hz, 1H), 7.93 (d, J=6.8 Hz, 1H), 7.50 (d, J=8.7 Hz, 1H), 7.41 (t, J=2.1 Hz, 2H), 6.93 (dd, J=8.6, 2.1 Hz, 1H), 6.73 (s, 1H), 6.43 (d, J=3.2 Hz, 1H), 6.23 (s, 1H), 4.31 (t, J=5.3 Hz, 2H), 3.81 (t, J=6.6 Hz, 2H), 3.67 (t, J=5.4 Hz, 2H), 3.57 (s, 1H), 3.48-3.31 (m, 13H), 3.15 (q, J=5.6 Hz, 2H), 2.90 (p, J=6.8 Hz, 1H), 2.45 (t, J=6.7 Hz, 2H), 0.83 (d, J=6.9 Hz, 6H); ESMS calculated for C$_{30}$H$_{32}$FN$_7$O$_7$: 621.23; Found: 622.2 (M+H)$^+$.

SDC-TRAP-0050

N-(2-(2-(5-(3-(2,4-dihydroxy-5-isopropylphenyl)-5-hydroxy-4H-1,2,4-triazol-4-yl)-1H-indol-1-yl)ethoxy)ethyl)-3-(5-fluoro-2,4-dioxo-3,4-dihydropyrimidin-1 (2H)-yl)-N-methylpropanamide

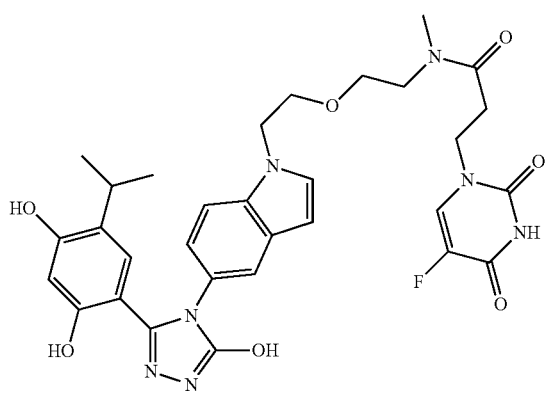 [SMILES: CC(C)c1cc(-c2nnc(O)n2-c2ccc3c(ccn3CCOCCN(C)C(=O)CCn3cc(F)c(=O)[nH]c3=O)c2)c(O)cc1O]

$^1$H NMR (400 MHz, DMSO-d$_6$) δ 11.88 (s, 1H), 11.76 (s, 1H), 9.56 (s, 1H), 9.49 (d, J=3.0 Hz, 1H), 8.03 (d, J=6.8 Hz, 1H), 7.49 (d, J=8.7 Hz, 1H), 7.45-7.32 (m, 2H), 6.92 (dd, J=8.6, 2.1 Hz, 1H), 6.73 (d, J=1.6 Hz, 1H), 6.41 (dd, J=13.7, 3.1 Hz, 1H), 6.23 (s, 1H), 4.32 (q, J=5.2 Hz, 2H), 3.88 (s, 2H), 3.80 (td, J=6.9, 3.6 Hz, 2H), 3.71-3.63 (m, 2H), 3.47 (dd, J=19.9, 8.3 Hz, 7H), 2.90 (hept, J=7.0 Hz, 1H), 2.80 (s, 2H), 2.76-2.60 (m, 4H), 0.84 (d, J=6.9 Hz, 6H); ESMS calculated for C$_{31}$H$_{34}$FN$_7$O$_7$: 635.25; Found: 636.2 (M+H)$^+$.

SDC-TRAP-0009

1-(2-(5-(3-(2,4-dihydroxy-5-isopropylphenyl)-5-hydroxy-4H-1,2,4-triazol-4-yl)-1H-indol-1-yl)ethyl)-3-(5-fluoro-2-oxo-1,2-dihydropyrimidin-4-yl)urea

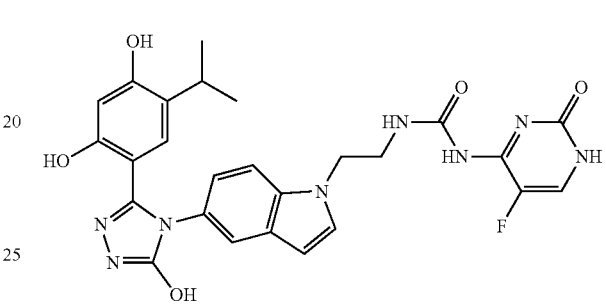

$^1$H NMR (400 MHz, DMSO-d$_6$) δ 11.86 (s, 1H), 9.52 (s, 1H), 9.46 (d, J=4.8 Hz, 1H), 8.10-7.82 (m, 2H), 7.59-7.39 (m, 3H), 6.95 (t, J=7.7 Hz, 1H), 6.73 (d, J=9.6 Hz, 1H), 6.44 (dd, J=16.8, 3.3 Hz, 1H), 6.22 (s, 1H), 4.31 (dt, J=12.6, 6.4 Hz, 2H), 3.57-3.48 (m, 2H), 2.90 (h, J=7.1 Hz, 1H), 0.84 (t, J=7.8 Hz, 6H); ESMS calculated (C$_{26}$H$_{25}$FN$_8$O$_5$): 548.2; found: 549.1 (M+H).

SDC-TRAP-0025

2-(5-(3-(2,4-dihydroxy-5-isopropylphenyl)-5-hydroxy-4H-1,2,4-triazol-4-yl)-1H-indol-1-yl)ethyl (5-fluoro-2-oxo-1,2-dihydropyrimidin-4-yl)carbamate

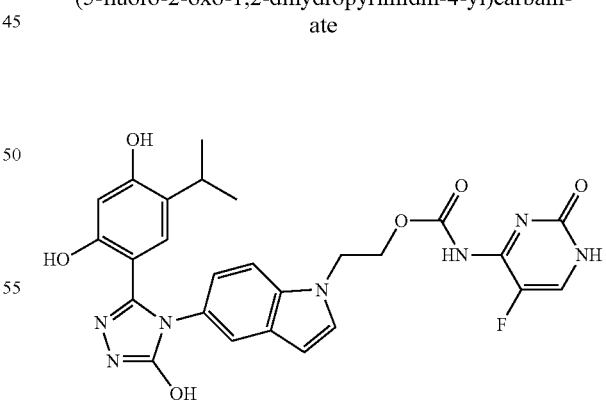

$^1$H NMR (400 MHz, Methanol-d$_4$) δ 7.77 (d, J=5.3 Hz, 1H), 7.61 (d, J=8.6 Hz, 1H), 7.51 (d, J=2.0 Hz, 1H), 7.42 (t, J=3.9 Hz, 1H), 7.07 (dd, J=8.7, 2.1 Hz, 1H), 6.51 (q, J=3.4 Hz, 2H), 6.26 (d, J=2.7 Hz, 1H), 4.57-4.47 (m, 4H), 2.84 (q, J=6.8 Hz, 1H), 0.61 (d, J=6.8 Hz, 6H); ESMS calculated (C$_{26}$H$_{24}$FN$_7$O$_6$): 549.2; found: 550.2 (M+H).

SDC-TRAP-0013

N-(2-(5-(3-(2,4-dihydroxy-5-isopropylphenyl)-5-hydroxy-4H-1,2,4-triazol-4-yl)-1H-indol-1-yl)ethyl)-2-(5-fluoro-2,4-dioxo-3,4-dihydropyrimidin-1(2H)-yl) acetamide

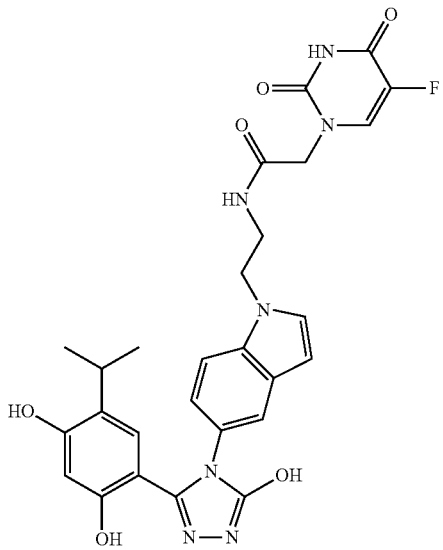 [SMILES: CC(C)c1cc(-c2nnc(O)n2-c2ccc3c(ccn3CCNC(=O)Cn3cc(F)c(=O)[nH]c3=O)c2)c(O)cc1O]

$^1$H NMR (400 MHz, DMSO-d$_6$) δ 11.85 (s, 2H), 9.53 (s, 1H), 9.45 (s, 1H), 8.34 (t, J=5.6 Hz, 1H), 7.96 (d, J=6.7 Hz, 1H), 7.51-7.38 (m, 3H), 6.95 (dd, J=8.6, 2.1 Hz, 1H), 6.78 (s, 1H), 6.43 (d, J=3.1 Hz, 1H), 6.22 (s, 1H), 4.23 (d, J=7.9 Hz, 3H), 3.46-3.34 (m, 2H), 3.35-3.26 (m, 1H), 2.98-2.88 (m, 1H), 0.88 (d, J=6.9 Hz, 6H). ppm; ESMS calculated for C$_{27}$H$_{26}$FN$_7$O$_6$: 563.2; found: 563.9 (M+H$^+$).

SDC-TRAP-0137

1-(2-(4-(2-(5-(3-(2,4-dihydroxy-5-isopropylphenyl)-5-hydroxy-4H-1,2,4-triazol-4-yl)-1H-indol-1-yl)ethyl)piperidin-1-yl)-2-oxoethyl)-5-fluoropyrimidine-2,4(1H,3H)-dione

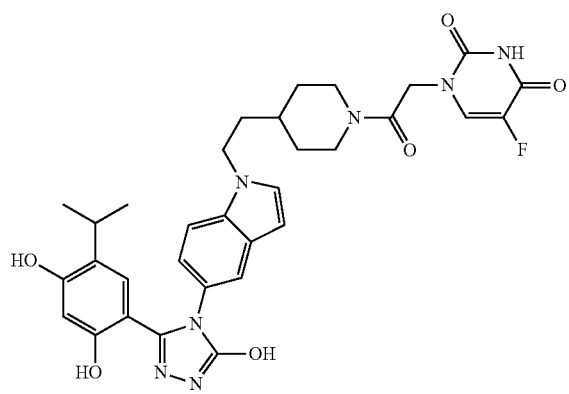 [SMILES: CC(C)c1cc(-c2nnc(O)n2-c2ccc3c(ccn3CCC3CCN(C(=O)Cn4cc(F)c(=O)[nH]c4=O)CC3)c2)c(O)cc1O]

$^1$H NMR (400 MHz, Chloroform-d) δ 7.57 (d, J=2.4 Hz, 1H), 7.44 (dt, J=6.5, 3.1 Hz, 1H), 7.40-7.28 (m, 3H), 7.19 (q, J=3.3 Hz, 1H), 7.12 (dq, J=8.6, 3.8, 3.0 Hz, 1H), 6.52 (q, J=3.3 Hz, 1H), 6.44-6.27 (m, 2H), 4.74-4.35 (m, 2H), 4.34-4.16 (m, 2H), 4.09 (ddt, J=19.4, 7.6, 3.9 Hz, 1H), 3.43-3.28 (m, 1H), 3.18-2.96 (m, 2H), 2.84 (qd, J=8.1, 5.3 Hz, 1H), 2.63 (t, J=12.4 Hz, 1H), 1.93-1.68 (m, 4H), 1.45-1.06 (m, 3H), 0.48 (dt, J=6.4, 3.0 Hz, 6H). ppm; ESMS calculated for C$_{32}$H$_{34}$FN$_7$O$_6$: 631.3; found: 632.2 (M+H$^+$).

in vitro activity was determined for these compounds using the HER2 degradation assay set forth herein:

| SDC-TRAP-# | HER2 degradation IC$_{50}$ (nM) |
|---|---|
| SDC-TRAP-0049 | >5000 |
| SDC-TRAP-0048 | >5000 |
| SDC-TRAP-0050 | >5000 |
| SDC-TRAP-0051 | >5000 |
| SDC-TRAP-0013 | >5000 |
| SDC-TRAP-0137 | >5000 |

Example 21: SDC-TRAPs Comprising Abiraterone

SDC-TRAP-0150

(3S,8R,9S,10R,13S,14S)-10,13-dimethyl-17-(pyridin-3-yl)-2,3,4,7,8,9,10,11,12,13,14,15-dodecahydro-1H-cyclopenta[a]phenanthren-3-yl 4-(4-(3-(2,4-dihydroxy-5-isopropylphenyl)-5-hydroxy-4H-1,2,4-triazol-4-yl)benzyl) piperazine-1-carboxylate

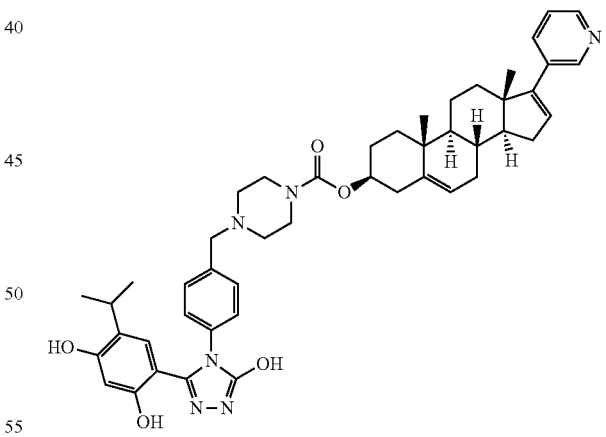

$^1$H NMR (400 MHz, DMSO-d$_6$) δ 11.94 (s, 1H), 9.61 (s, 1H), 9.41 (s, 1H), 8.59 (dd, J=2.3, 0.9 Hz, 1H), 8.43 (dd, J=4.8, 1.6 Hz, 1H), 7.76 (dt, J=8.1, 1.9 Hz, 1H), 7.38-7.27 (m, 3H), 7.18-7.10 (m, 2H), 6.78 (s, 1H), 6.26 (s, 1H), 6.12 (s, 1H), 5.38 (d, J=4.9 Hz, 1H), 4.34 (tt, J=10.8, 4.8 Hz, 1H), 3.47 (s, 2H), 2.97 (p, J=6.9 Hz, 1H), 2.36-2.16 (m, 7H), 2.05 (dt, J=15.2, 8.2 Hz, 3H), 1.82-1.46 (m, 8H), 1.40 (td, J=12.2, 5.0 Hz, 1H), 1.03 (d, J=5.6 Hz, 8H), 0.95 (d, J=6.8 Hz, 6H); ESMS calculated for C$_{47}$H$_{56}$N$_6$O$_5$: 784.43; Found: 785.3 (M+H)$^+$.

SDC-TRAP-0151

(3S,8R,9S,10R,13S,14S)-10,13-dimethyl-17-(pyridin-3-yl)-2,3,4,7,8,9,10,11,12,13,14,15-dodecahydro-1H-cyclopenta[a]phenanthren-3-yl (2-(2-(5-(3-(2,4-dihydroxy-5-isopropylphenyl)-5-hydroxy-4H-1,2,4-triazol-4-yl)-1H-indol-1-yl)ethoxy)ethyl) carbamate

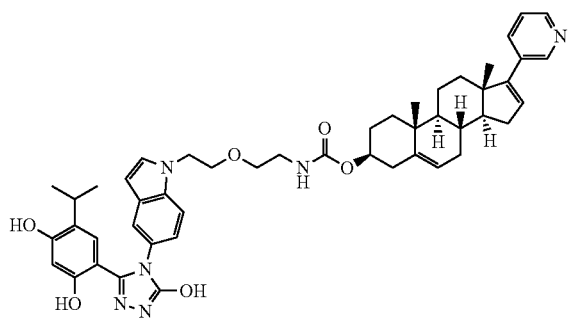

$^1$H NMR (400 MHz, DMSO-d$_6$) δ 11.88 (s, 1H), 9.55 (s, 1H), 9.47 (s, 1H), 8.60 (d, J=2.4 Hz, 1H), 8.44 (dd, J=4.7, 1.6 Hz, 1H), 7.77 (dt, J=8.2, 1.9 Hz, 1H), 7.50 (d, J=8.7 Hz, 1H), 7.44-7.30 (m, 3H), 7.06 (q, J=6.4, 5.7 Hz, 1H), 6.91 (dd, J=8.7, 2.0 Hz, 1H), 6.73 (s, 1H), 6.40 (d, J=3.1 Hz, 1H), 6.22 (s, 1H), 6.12 (dd, J=3.3, 1.8 Hz, 1H), 5.38 (d, J=4.9 Hz, 1H), 4.32 (q, J=5.8, 5.3 Hz, 3H), 3.67 (t, J=5.3 Hz, 2H), 3.08 (q, J=5.8 Hz, 2H), 2.96-2.84 (m, 1H), 2.33-2.17 (m, 3H), 2.11-1.96 (m, 3H), 1.87-1.35 (m, 8H), 1.12-1.00 (m, 8H), 0.83 (d, J=6.9 Hz, 6H); ESMS calculated for C$_{48}$H$_{56}$N$_6$O$_6$: 812.43; Found: 813.3 (M+H)$^+$.

SDC-TRAP-0153

(3S,8R,9S,10R,13S,14S)-10,13-dimethyl-17-(pyridin-3-yl)-2,3,4,7,8,9,10,11,12,13,14,15-dodecahydro-1H-cyclopenta[a]phenanthren-3-yl 4-(4-(3-(2,4-dihydroxy-5-isopropylphenyl)-5-hydroxy-4H-1,2,4-triazol-4-yl)benzyl) piperidine-1-carboxylate

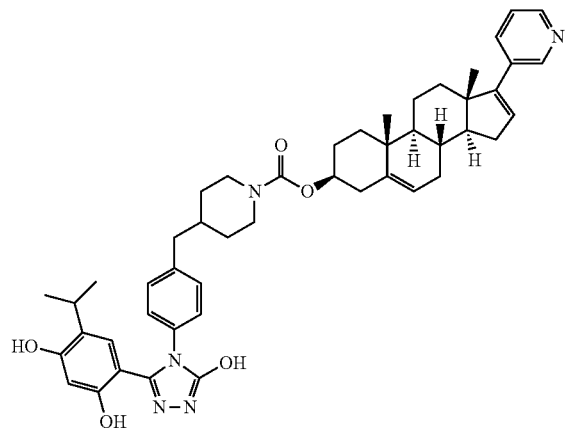

$^1$H NMR (400 MHz, DMSO-d$_6$) δ 11.93 (s, 1H), 9.61 (s, 1H), 9.43 (s, 1H), 8.59 (s, 1H), 8.43 (dd, J=4.8, 1.6 Hz, 1H), 7.76 (dt, J=8.2, 2.0 Hz, 1H), 7.38-7.29 (m, 1H), 7.18 (d, J=8.6 Hz, 2H), 7.14-7.06 (m, 2H), 6.75 (s, 1H), 6.27 (s, 1H), 6.12 (dd, J=3.1, 1.7 Hz, 1H), 5.38 (s, 1H), 4.33 (tt, J=10.9, 4.7 Hz, 1H), 3.94 (d, J=12.6 Hz, 2H), 2.96 (p, J=6.8 Hz, 1H), 2.67 (s, 2H), 2.37-2.16 (m, 3H), 2.04 (td, J=14.7, 13.8, 4.7 Hz, 3H), 1.87-1.60 (m, 6H), 1.53 (d, J=12.9 Hz, 5H), 1.40 (td, J=12.2, 5.0 Hz, 1H), 1.13-0.90 (m, 15H); ESMS calculated for C$_{48}$H$_{57}$N$_5$O$_5$: 783.44; Found: 784.5 (M+H)$^+$.

in vitro activity was determined for these compounds using the HER2 degradation assay set forth herein:

| SDC-TRAP-# | HER2 degradation IC$_{50}$ (nM) |
|---|---|
| SDC-TRAP-0150 | 1407 |
| SDC-TRAP-0151 | 1194 |
| SDC-TRAP-0153 | 6336 |

Mouse Plasma Stability Data

| SDC-TRAP-# | % Remaining (1 h) |
|---|---|
| SDC-TRAP-0150 | 103% |

Example 22: SDC-TRAPs Comprising Bendamustine

SDC-TRAP-0211 4-(5-(bis(2-chloroethyl)amino)-1-methyl-1H-benzo[d]imidazol-2-yl)-N-(2-(2,4-dihydroxy-5-isopropylbenzoyl)isoindolin-5-yl)butanamide

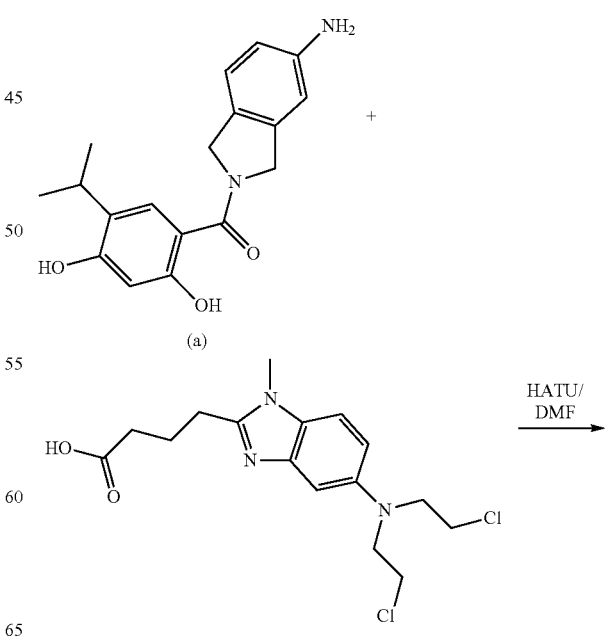

-continued

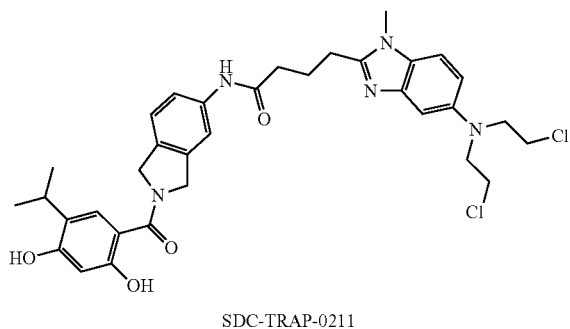

SDC-TRAP-0211

A mixture of (5-aminoisoindolin-2-yl)(2,4-dihydroxy-5-isopropylphenyl) methanone (a, 0.1 mmol), bendamustine (b, 0.1 mmol) and HATU (0.1 mmol) in DMF (2 mL) was stirred at room temperature for 16 h. The mixture was diluted with 50 mL of water and extracted with 50 mL×2 EtOAc, and the organic layers were combined, concentrated and purified by column to yield SDC-TRAP-0211 as a white solid (25 mg, 0.04 mmol).

$^1$H NMR (400 MHz, Chloroform-d) δ 7.62 (s, 1H), 7.41 (s, 1H), 7.28 (s, 1H), 7.20 (t, J=9.3 Hz, 2H), 6.96 (d, J=2.3 Hz, 1H), 6.80 (dd, J=8.9, 2.4 Hz, 1H), 6.38 (d, J=2.5 Hz, 1H), 5.00 (d, J=5.3 Hz, 4H), 3.77-3.68 (m, 6H), 3.61 (t, J=6.7 Hz, 4H), 3.25 (p, J=6.9 Hz, 1H), 2.97 (t, J=6.8 Hz, 2H), 2.49 (d, J=14.8 Hz, 4H), 2.20 (dq, J=20.9, 7.1 Hz, 2H), 1.31-1.17 (m, 6H); ESMS calculated for $C_{34}H_{39}Cl_2N_5O_4$: 651.2; found: 652.0 (M+H$^+$).

SDC-TRAP-0039

4-(5-(bis(2-chloroethyl)amino)-1-methyl-1H-benzo[d]imidazol-2-yl)-N-(2-(5-(3-(2,4-dihydroxy-5-isopropylphenyl)-5-hydroxy-4H-1,2,4-triazol-4-yl)-1H-indol-1-yl)ethyl)-N-methylbutanamide

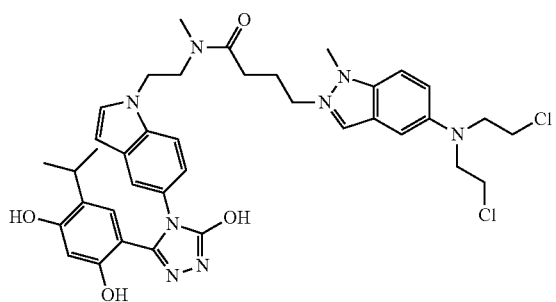

$^1$H NMR (400 MHz, DMSO-d$_6$) δ 11.85 (d, J=1.9 Hz, 1H), 9.61 (s, 1H), 9.58 (s, 1H), 7.50-7.32 (m, 4H), 6.92-6.74 (m, 4H), 6.42 (s, 1H), 6.22 (d, J=1.6 Hz, 1H), 4.38-4.30 (m, 2H), 3.71-3.58 (m, 14H), 2.95-2.73 (m, 3H), 2.40-2.35 (m, 2H), 1.90-1.98 (m, 2H), 0.84 (dd, J=6.9, 4.4 Hz, 6H); ESMS calculated for $C_{38}H_{44}Cl_2N_8O_4$: 746.29; Found: 747.3 (M+H)$^+$.

SDC-TRAP-0040

4-(5-(bis(2-chloroethyl)amino)-1-methyl-1H-benzo[d]imidazol-2-yl)-N-(2-(2-(5-(3-(2,4-dihydroxy-5-isopropylphenyl)-5-hydroxy-4H-1,2,4-triazol-4-yl)-1H-indol-1-yl)ethoxy)ethyl)-N-methylbutanamide

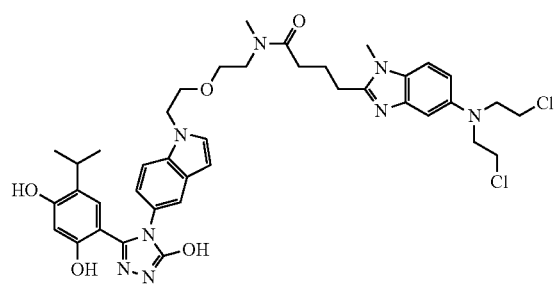 [SMILES: CC(C)c1cc(-c2nnc(O)n2-c2ccc3c(ccn3CCOCCN(C)C(=O)CCCc3nc4cc(N(CCCl)CCCl)ccc4n3C)c2)c(O)cc1O]

$^1$H NMR (400 MHz, DMSO-d$_6$) δ 11.86 (d, J=1.9 Hz, 1H), 9.60 (s, 1H), 9.55 (s, 1H), 7.49-7.28 (m, 4H), 6.95-6.87 (m, 2H), 6.73-6.70 (m, 2H), 6.39 (s, 1H), 6.24 (d, J=1.6 Hz, 1H), 4.30 (dt, J=16.3, 5.2 Hz, 2H), 3.73-3.62 (m, 13H), 2.86-2.73 (m, 6H), 2.41-2.35 (m, 2H), 1.93 (dd, J=10.0, 5.1 Hz, 2H), 0.84 (dd, J=6.9, 4.4 Hz, 6H); ESMS calculated for $C_{40}H_{48}Cl_2N_8O_5$: 790.31; Found: 791.3 (M+H)$^+$.

SDC-TRAP-0069

4-(5-(bis(2-chloroethyl)amino)-1-methyl-1H-benzo[d]imidazol-2-yl)-1-(4-(4-(3-(2,4-dihydroxy-5-isopropylphenyl)-5-hydroxy-4H-1,2,4-triazol-4-yl)benzyl) piperazin-1-yl)butan-1-one

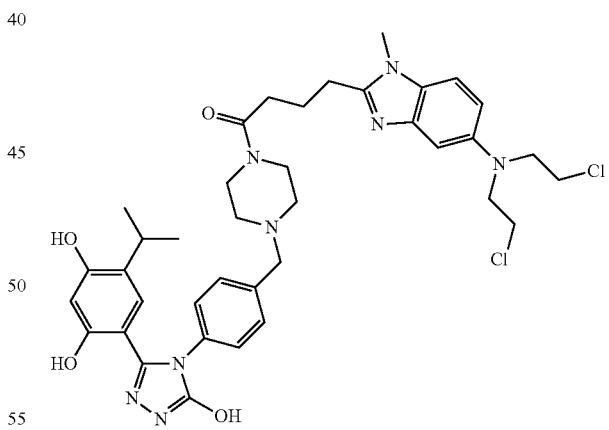

$^1$H NMR (400 MHz, DMSO-d$_6$) δ 11.93 (s, 1H), 9.61 (s, 1H), 9.41 (s, 1H), 7.31 (dd, J=8.5, 4.6 Hz, 3H), 7.18-7.10 (m, 2H), 6.91 (d, J=2.3 Hz, 1H), 6.82-6.74 (m, 2H), 6.27 (s, 1H), 3.71-3.68 (m, 10H), 3.65 (s, 3H), 3.43 (dd, J=12.5, 7.2 Hz, 6H), 2.96 (h, J=6.9 Hz, 1H), 2.82 (t, J=7.4 Hz, 2H), 2.44 (t, J=7.2 Hz, 2H), 2.31 (dt, J=26.0, 5.1 Hz, 4H), 1.97 (d, J=11.4 Hz, 2H), 0.94 (d, J=6.8 Hz, 6H); ESMS calculated for $C_{38}H_{46}Cl_2N_8O_4$: 748.30; Found: 749.1 (M+H)$^+$.

In vitro activity was determined for these compounds using the HER2 degradation assay set forth herein:

| SDC-TRAP-# | HER2 degradation IC$_{50}$ (nM) |
|---|---|
| SDC-TRAP-0039 | 2925 |
| SDC-TRAP-0040 | 4741 |
| SDC-TRAP-0069 | 1232 |
| SDC-TRAP-0211 | 289 |

Example 23: SDC-TRAPs Comprising Crizotinib

SDC-TRAP-0134 preparation: (R)-4-(4-((4-(4-(4-(6-amino-5-(1-(2,6-dichloro-3-fluorophenyl)ethoxy)pyridin-3-yl)-1H-pyrazol-1-yl)piperidine-1-carbonyl)piperidin-1-yl)methyl)phenyl)-5-(2,4-dihydroxy-5-isopropylphenyl)-N-ethyl-4H-1,2,4-triazole-3-carboxamide A mixture of 1-(4-(3-(2,4-dihydroxy-5-isopropylphenyl)-5-(ethylcarbamoyl)-4H-1,2,4-triazol-4-yl)benzyl)piperidine-4-carboxylic acid (a, 25 mg, 0.05 mmol), crizotinib (23 mg, 0.05 mmol), DMAP (0.1 mmol) and T3P (0.10 mmol) in 5 mL THF was heated in a microwave reactor at 80° C. for 1 h. The mixture was diluted with 100 mL each of 1M NaHCO$_3$ solution and EtOAc. The organic layer was separated, dried, concentrated and purified by column chromatography to give (R)-4-(4-((4-(4-(4-(6-amino-5-(1-(2,6-dichloro-3-fluorophenyl)ethoxy)pyridin-3-yl)-1H-pyrazol-1-yl)piperidine-1-carbonyl)piperidin-1-yl)methyl)phenyl)-5-(2,4-dihydroxy-5-isopropylphenyl)-N-ethyl-4H-1,2,4-triazole-3-carboxamide (SDC-TRAP-0134, 20 mg) as white solid.

$^1$H-NMR (CDCl$_3$) δδ 7.7 (d, 1H, J=4), 7.5 (m, 4H), 7.4 (m, 1H), 7.3 (m, 3H), 7.0 (t, 1H, J=8), 6.9 (d, 1H, J=$), 6.54 (s, 1H), 6.50 (s, 1H), 6.1 (q, 1H, t=8), 4.95 (s, 2H), 4.8 (m, 1H), 4.4 (m, 1H), 4.1 (m, 1H), 3.57 (s, 1H), 3.4 (m, 1H), 2.8 (m, 1H), 2.6 (m, 1H), 1.8-2.2 (m, 12H), 1.9 (d, 3H, J=8), 1.7 (m, 1H), 1.2 (m, 6H), 0.7 (d, 6H, J=8) ppm; ESMS calculated for C$_{48}$H$_{53}$C$_{12}$FN$_{10}$O$_5$: 938.4; found: 939.4 (M+H$^+$).

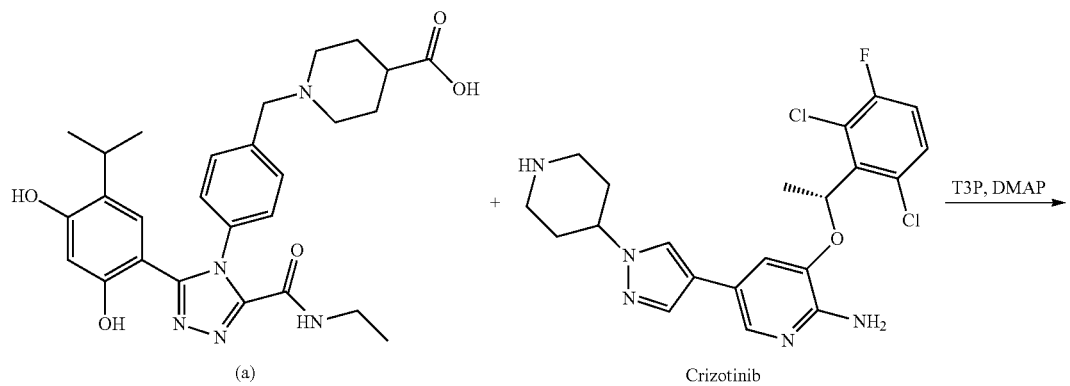

(a) + Crizotinib  T3P, DMAP →

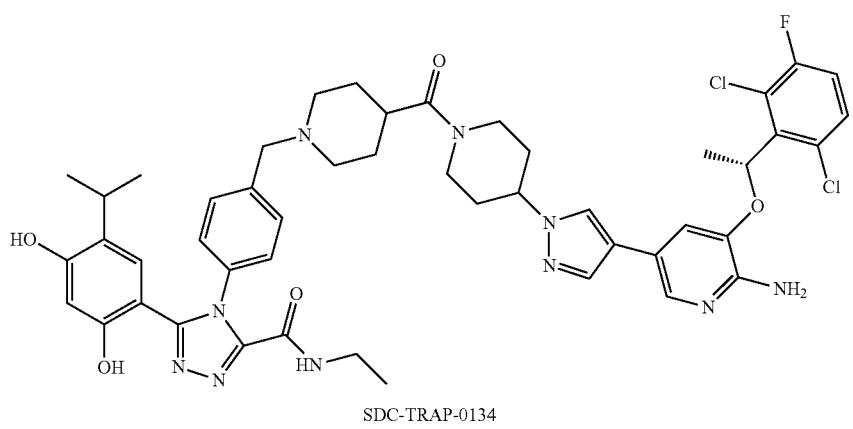

SDC-TRAP-0134

157

SDC-TRAP-0139

(R)-4-(4-((2-(4-(4-(6-amino-5-(1-(2,6-dichloro-3-fluorophenyl)ethoxy)pyridin-3-yl)-1H-pyrazol-1-yl)piperidin-1-yl)-2-oxoethyl)(methyl)carbamoyl)phenyl)-5-(2,4-dihydroxy-5-isopropylphenyl)-N-ethyl-4H-1,2,4-triazole-3-carboxamide

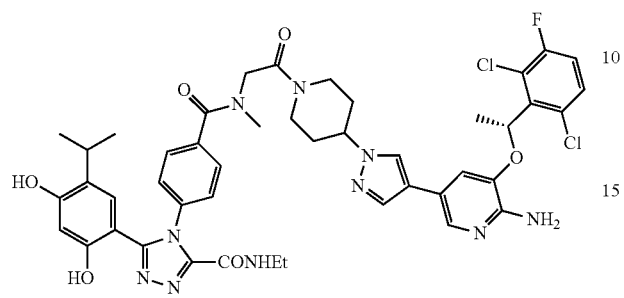

158

$^1$H-NMR (CDCl$_3$) δ 7.7 (m, 3H), 7.57 (s, 1H), 7.53 (s, 1H), 7.4 (m, 3H), 7.3 (m, 1H), 7.0 (t, 1H, J=8), 6.89 (s, 1H), 6.51 (s, 1H), 6.45 (s, 1H), m 6.1 (t, 1H, J=8), 4.89 (s, 2H), 4.7 (m, 1H), 4.4 (m, 2H), 4.1 (m, 1H), 3.4 (m, 2H), 3.2 (m, 2H), 2.9 (m, 2H), 2.2-2.4 (m, 2H), 2.1 (m, 2H), 1.9 (d, 3H, J=8), 1.2 (m, 6H), 0.7 (d, 6H, J=8) ppm; ESMS calculated for C$_{45}$H$_{47}$C$_{12}$FN$_{10}$O$_6$: 912.3; found: 913.3 (M+H$^+$).

SDC-TRAP-0138

(R)-(4-(4-(6-amino-5-(1-(2,6-dichloro-3-fluorophenyl)ethoxy)pyridin-3-yl)-1H-pyrazol-1-yl)piperidin-1-yl)(4-(4-(3-(2,4-dihydroxy-5-isopropylphenyl)-5-hydroxy-4H-1,2,4-triazol-4-yl)phenyl)piperazin-1-yl)methanone

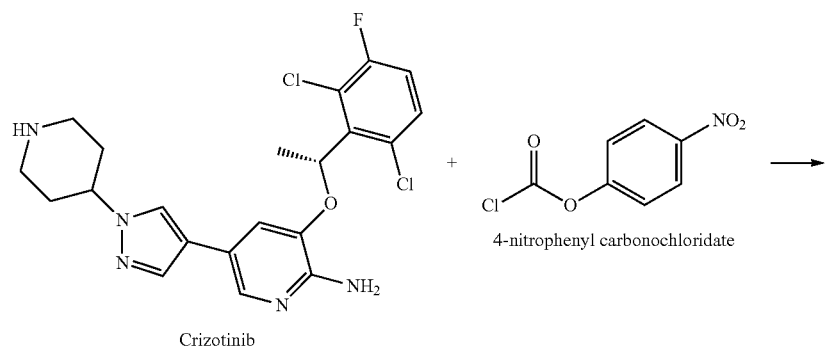

Crizotinib 4-nitrophenyl carbonochloridate

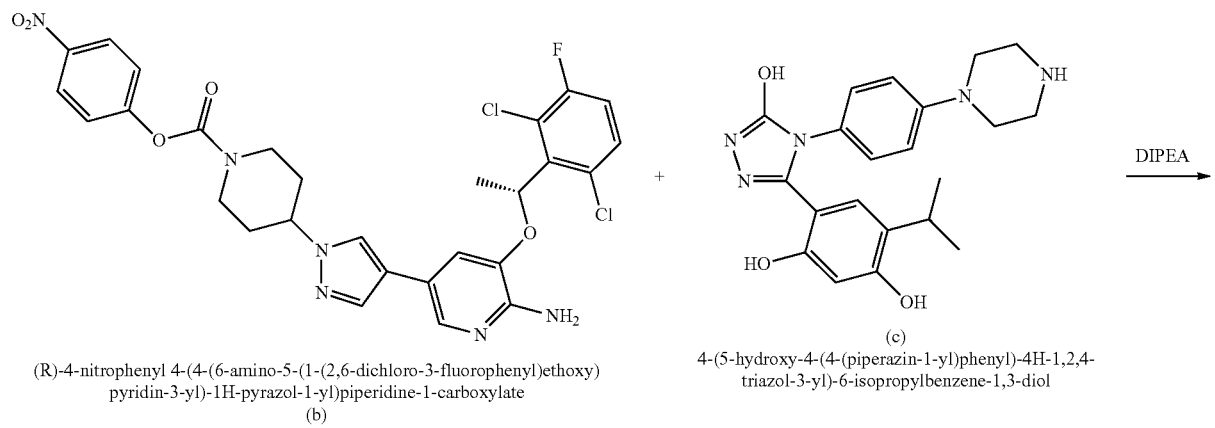

(R)-4-nitrophenyl 4-(4-(6-amino-5-(1-(2,6-dichloro-3-fluorophenyl)ethoxy)pyridin-3-yl)-1H-pyrazol-1-yl)piperidine-1-carboxylate
(b)

4-(5-hydroxy-4-(4-(piperazin-1-yl)phenyl)-4H-1,2,4-triazol-3-yl)-6-isopropylbenzene-1,3-diol
(c)

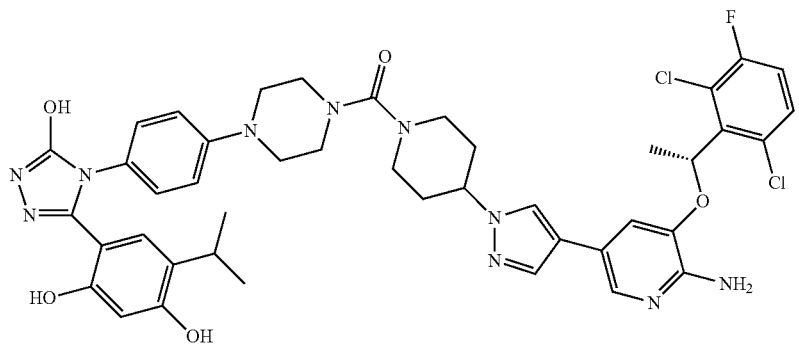

STA-12-8777

To a mixture of crizotinib (22 mg, 0.05 mmol) and 4-nitrophenyl carbonochloridate (10 mg, 0.05 mmol) was added 2 mL $CHCl_3$ whereafter the mixture was stirred for 1 h. Solvent was removed to yield crude (R)-4-nitrophenyl 4-(4-(6-amino-5-(1-(2,6-dichloro-3-fluorophenyl)ethoxy) pyridin-3-yl)-1H-pyrazol-1-yl)piperidine-1-carboxylate (b, 0.05 mmol).

To the above crude solids was added a solution of 4-(5-hydroxy-4-(4-(piperazin-1-yl)phenyl)-4H-1,2,4-triazol-3-yl)-6-isopropylbenzene-1,3-diol (c, 20 mg, 0.05 mmol) in DMF (2 mL), and the mixture was heated to 110° C. for 10 h. The mixture was diluted in 100 mL each of water and EtOAc. The organic layer was separated, dried, concentrated and purified by column chromatography to give (R)-(4-(4-(6-amino-5-(1-(2,6-dichloro-3-fluorophenyl) ethoxy)pyridin-3-yl)-1H-pyrazol-1-yl)piperidin-1-yl)(4-(4-(3-(2,4-dihydroxy-5-isopropylphenyl)-5-hydroxy-4H-1,2,4-triazol-4-yl)phenyl)piperazin-1-yl)methanone (SDC-TRAP-0138, 4 mg) as a white solid.

$^1$H-NMR ($CD_3OD$) δ 7.7 (m, 1H), 7.6 (m, 2H), 7.4 (m, 3H), 7.2 (m, 2H), 7.1 (m, 3H), 6.9 (m, 1H), 6.53 (s, 1H), 6.48 (s, 1H), 6.1 (m, 1H), 4.3 (m, 1H), 3.9 (m, 1H), 3.2-3.8 (m, 7H), 3.0 (m, 2H), 1.8-2.3 (m, 8H), 1.3 (3H, d, J=8), 0.8 (d, 6H, J=8) ppm; ESMS calculated for $C_{43}H_{45}Cl_2FN_{10}O_5$: 870.3; found: 871.3 (M+H$^+$).

in vitro activity was determined for these compounds using the HER2 degradation assay set forth herein:

| No | SDC-TRAP-# | HER2 IC$_{50}$ (nM) |
|---|---|---|
| 1 | SDC-TRAP-0134 | 77 |
| 2 | SDC-TRAP-0138 | 707 |
| 3 | SDC-TRAP-0139 | 1000-2000 |

Hsp90$^\alpha$ Binding Activity Data:

| No | SDC-TRAP-# | Binding EC$_{50}$ (nM) |
|---|---|---|
| 1 | SDC-TRAP-0134 | 95.42 nM |

Hsp90$^\alpha$ Binding Data:

| SDC-TRAP-# | EC$_{50}$ (nM) |
|---|---|
| SDC-TRAP-0134 | 95.42 nM |

Mouse Plasma Stability Data:

| SDC-TRAP-# | % Remaining (1 h) |
|---|---|
| SDC-TRAP-0143 | 89.9% |
| SDC-TRAP-0144 | 96.2% |

Example 24: SDC-TRAPs Comprising Doxorubicin

Exemplary Synthesis:

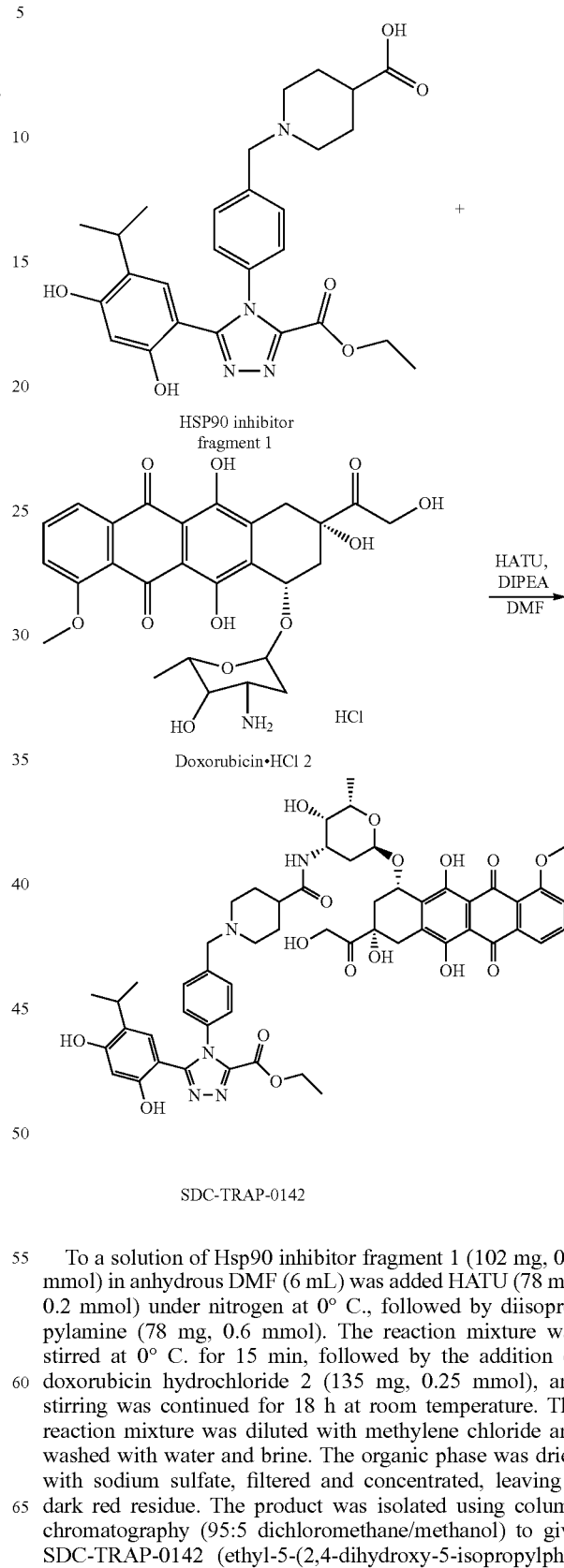

SDC-TRAP-0142

To a solution of Hsp90 inhibitor fragment 1 (102 mg, 0.2 mmol) in anhydrous DMF (6 mL) was added HATU (78 mg, 0.2 mmol) under nitrogen at 0° C., followed by diisopropylamine (78 mg, 0.6 mmol). The reaction mixture was stirred at 0° C. for 15 min, followed by the addition of doxorubicin hydrochloride 2 (135 mg, 0.25 mmol), and stirring was continued for 18 h at room temperature. The reaction mixture was diluted with methylene chloride and washed with water and brine. The organic phase was dried with sodium sulfate, filtered and concentrated, leaving a dark red residue. The product was isolated using column chromatography (95:5 dichloromethane/methanol) to give SDC-TRAP-0142 (ethyl-5-(2,4-dihydroxy-5-isopropylphenyl)-4-(4-((4-(((2S,3S,4S,6R)-3-hydroxy-2-methyl-6-(((1S,3S)-3,5,12-trihydroxy-3-(2-hydroxyacetyl)-10-methoxy-6,11-dioxo-1,2,3,4,6,11-hexahydrotetracen-1-yl)oxy)tetrahydro-2H-pyran-4-yl)carbamoyl)piperidin-1-yl)methyl)phenyl)-4H-1,2,4-triazole-3-carboxylate, 115 mg, 55%) as a red solid.

$^1$H NMR (400 MHz, DMSO-d$_6$) δ 14.02 (s, 1H), 13.27 (s, 1H), 10.62 (s, 1H), 9.76 (s, 1H), 8.93 (t, J=5.9 Hz, 1H), 7.90 (d, J=4.8 Hz, 2H), 7.64 (p, J=3.8 Hz, 1H), 7.44 (d, J=8.1 Hz, 1H), 7.35 (d, J=8.0 Hz, 2H), 7.27 (d, J=8.0 Hz, 2H), 6.55 (s, 1H), 6.33 (s, 1H), 5.44 (s, 1H), 5.22 (d, J=3.4 Hz, 1H), 4.94 (t, J=4.4 Hz, 1H), 4.85 (t, J=5.9 Hz, 1H), 4.72 (d, J=5.8 Hz, 1H), 4.57 (d, J=5.9 Hz, 2H), 4.16 (q, J=6.7 Hz, 1H), 4.08-3.93 (m, 3H), 3.41 (d, J=17.4 Hz, 3H), 3.15 (p, J=7.0 Hz, 2H), 3.05-2.77 (m, 5H), 2.24-2.06 (m, 3H), 1.95-1.79 (m, 3H), 1.60-1.36 (m, 5H), 1.15 (dd, J=23.9, 6.7 Hz, 2H), 1.02 (t, J=7.1 Hz, 3H), 0.77 (d, J=6.8 Hz, 6H). ESMS calculated for C$_{54}$H$_{59}$N$_5$O$_{16}$: 1033.40; Found: 1033.8 (M+H)$^+$.

The following compounds were made in the same general manner as above:

SDC-TRAP-0198

1-(1-(4-(3-(2,4-dihydroxy-5-isopropylphenyl)-5-(ethylcarbamoyl)-4H-1,2,4-triazol-4-yl)benzyl)piperidine-4-carbonyl)-N-((2S,3S,4S,6R)-3-hydroxy-2-methyl-6-(((1S,3S)-3,5,12-trihydroxy-3-(2-hydroxyacetyl)-10-methoxy-6,11-dioxo-1,2,3,4,6,11-hexahydrotetracen-1-yl)oxy)tetrahydro-2H-pyran-4-yl)piperidine-4-carboxamide $^1$H NMR (400 MHz, DMSO-d$_6$) δ 14.04 (s, 1H), 13.28 (s, 1H), 10.61 (s, 1H), 9.79 (s, 1H), 8.96 (t, J=5.8 Hz, 1H), 7.91 (d, J=4.8 Hz, 2H), 7.69-7.61 (m, 1H), 7.55 (d, J=8.1 Hz, 1H), 7.36 (d, J=8.0 Hz, 2H), 7.28 (d, J=7.9 Hz, 2H), 6.57 (s, 1H), 6.34 (s, 1H), 5.47 (s, 1H), 5.22 (d, J=3.4 Hz, 1H), 4.96-4.83 (m, 2H), 4.77 (t, J=6.0 Hz, 1H), 4.57 (d, J=5.9 Hz, 2H), 4.33-4.16 (m, 2H), 3.98 (s, 3H), 3.46 (s, 2H), 3.21-3.09 (m, 2H), 3.05-2.84 (m, 4H), 2.82-2.39 (m, 2H), 2.24-2.08 (m, 2H), 1.85 (t, J=12.1 Hz, 1H), 1.61 (s, 3H), 1.54 (s, 4H), 1.41-1.26 (m, 3H), 1.16-0.98 (m, 8H), 0.79 (d, J=6.8 Hz, 6H); ESMS calculated for C$_{60}$H$_{69}$N$_7$O$_{16}$: 1143.48; Found: 1144.2 (M+H)$^+$.

SDC-TRAP-0199

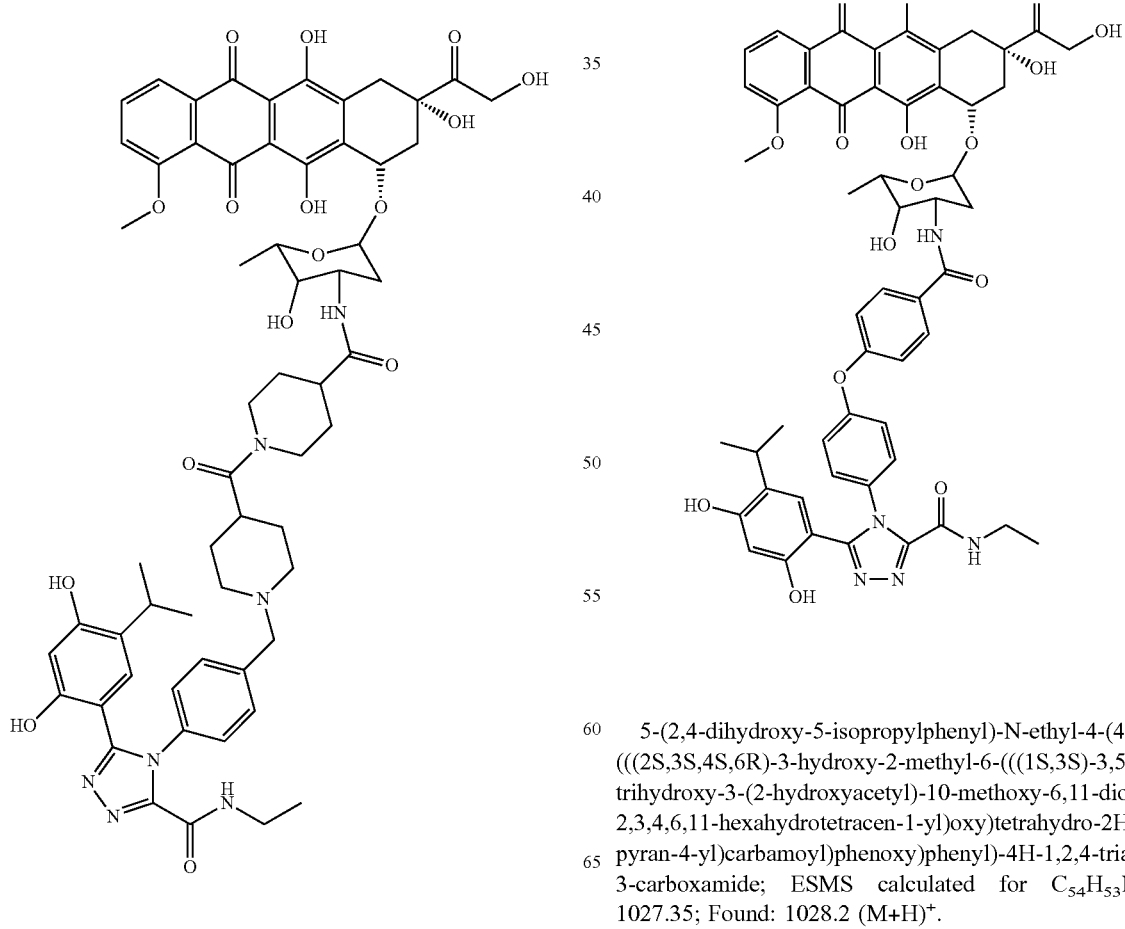

5-(2,4-dihydroxy-5-isopropylphenyl)-N-ethyl-4-(4-(4-(((2S,3S,4S,6R)-3-hydroxy-2-methyl-6-(((1S,3S)-3,5,12-trihydroxy-3-(2-hydroxyacetyl)-10-methoxy-6,11-dioxo-1,2,3,4,6,11-hexahydrotetracen-1-yl)oxy)tetrahydro-2H-pyran-4-yl)carbamoyl)phenoxy)phenyl)-4H-1,2,4-triazole-3-carboxamide; ESMS calculated for C$_{54}$H$_{53}$N$_5$O$_{16}$: 1027.35; Found: 1028.2 (M+H)$^+$.

SDC-TRAP-0199

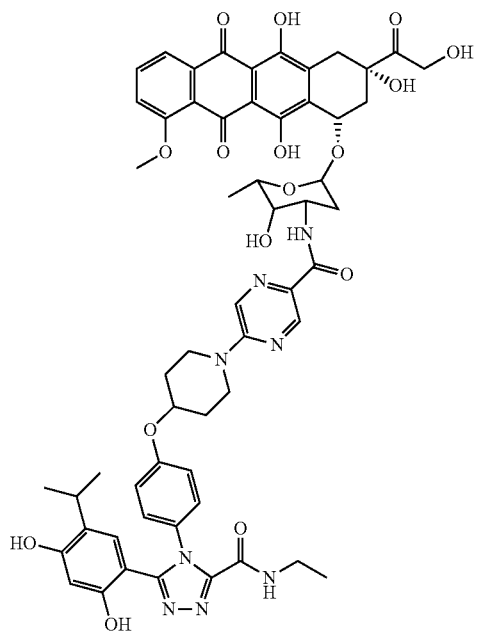

5-(4-(4-(3-(2,4-dihydroxy-5-isopropylphenyl)-5-(ethyl-carbamoyl)-4H-1,2,4-triazol-4-yl)phenoxy)piperidin-1-yl)-N-((2S,3S,4S,6R)-3-hydroxy-2-methyl-6-(((1S,3S)-3,5,12-trihydroxy-3-(2-hydroxyacetyl)-10-methoxy-6,11-dioxo-1,2,3,4,6,11-hexahydrotetracen-1-yl)oxy)tetrahydro-2H-pyran-4-yl)pyrazine-2-carboxamide; ESMS calculated for $C_{57}H_{60}N_8O_{16}$: 1112.41; Found: 1113.2 (M+H)$^+$.

SDC-TRAP-0219

(E)-N'-(1-((2S,4S)-4-(((2R,4S,5S,6S)-4-amino-5-hydroxy-6-methyltetrahydro-2H-pyran-2-yl)oxy)-2,5,12-trihydroxy-7-methoxy-6,11-dioxo-1,2,3,4,6,11-hexahydrotetracen-2-yl)-2-hydroxyethylidene)-3-(5-(3-(2,4-dihydroxy-5-isopropylphenyl)-5-hydroxy-4H-1,2,4-triazol-4-yl)-1H-indol-1-yl)propanehydrazide ESMS calculated for $C_{49}H_{51}N_7O_{14}$: 961.35; Found: 962.2 (M+H)$^+$.

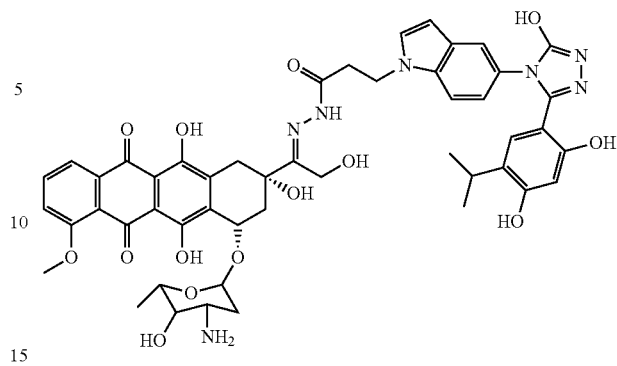

in vitro activity was determine or these compounds using the HER2 degradation assay set forth herein:

| SDC-TRAP-# | HER2 degradation IC$_{50}$ (nM) |
|---|---|
| SDC-TRAP-0142 | >10,000 |
| SDC-TRAP-0198 | >10,000 |
| SDC-TRAP-0199 | >10,000 |
| SDC-TRAP-0200 | >10,000 |

Hsp90$^\alpha$ Binding Assay Data

| SDC-TRAP-# | EC$_{50}$ (nM) |
|---|---|
| SDC-TRAP-0198 | 93.32 |
| SDC-TRAP-0199 | 136.3 |
| SDC-TRAP-0200 | 252.6 |

Example 25: SDC-TRAPs Comprising Lenalidomide

Exemplary Synthesis:

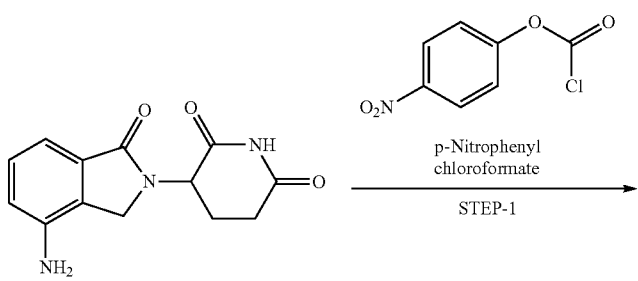

Lenalidomide 1 → p-Nitrophenyl chloroformate, STEP-1

-continued

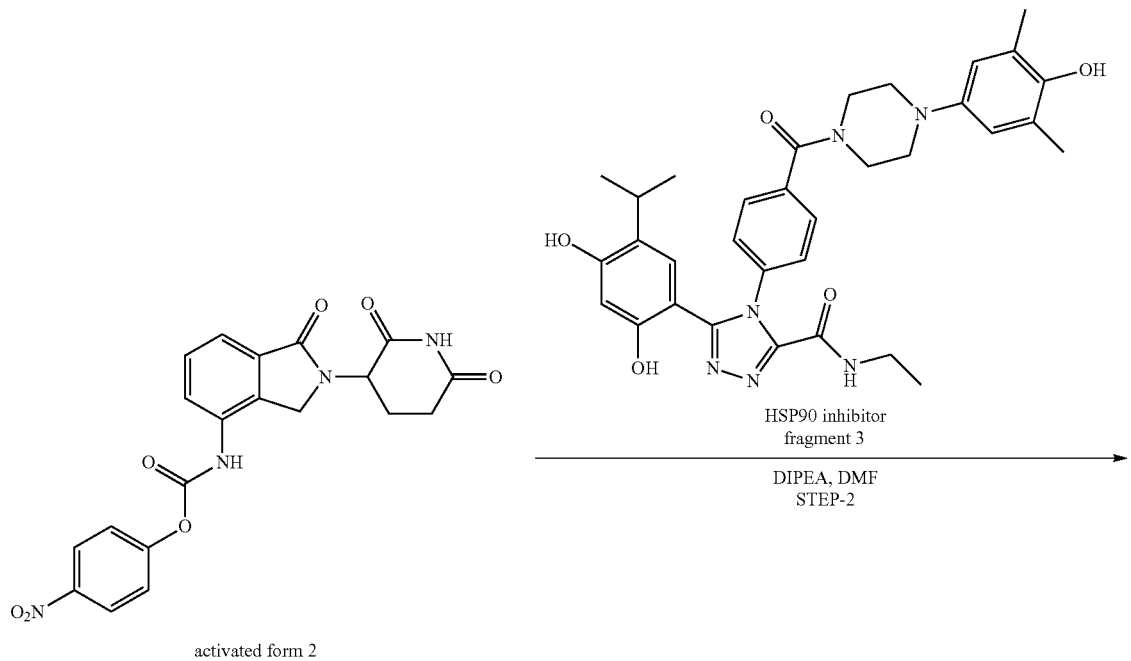

activated form 2

HSP90 inhibitor fragment 3

DIPEA, DMF
STEP-2

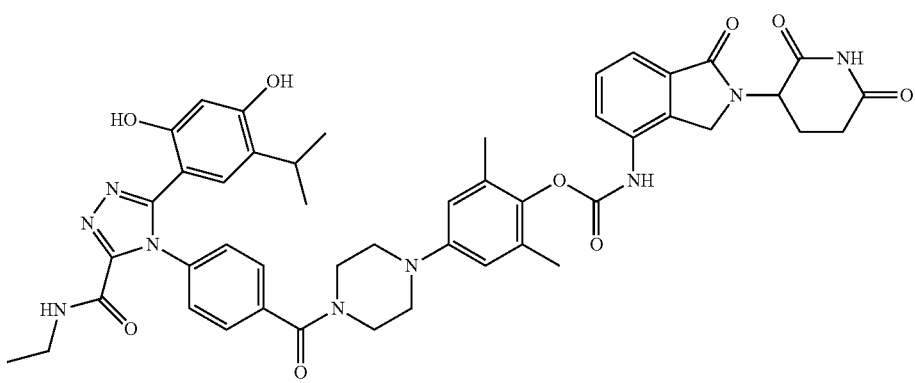

SDC-TRAP-0178

STEP-1: To a stirred suspension of lenalidomide 1 (520 mg, 2 mmol) in dry THF (70 mL) was added 4-nitrophenylchloroformate (605 mg, 3 mmol). The reaction mixture was refluxed for 2 h, concentrated to approximately 40 mL and triturated with ethyl acetate to yield a white precipitate. The solid was collected by filtration and washed with ethyl acetate to give activated lenalidomide 2 (650 mg, 77%).

STEP-2: Diisopropylethylamine (33 mg, 0.25 mmol) was added to a stirred solution of Hsp90 inhibitor fragment 3 (120 mg, 0.2 mmol) and the activated lenalidomide 2 (86 mg, 0.2 mmol) in anhydrous DMF (5 mL). The reaction mixture was stirred at room temperature for 18 h. The reaction mixture was diluted with water (5 mL) and extracted with ethyl acetate (100 mL). Organic phase was dried (sodium sulfate) filtered and evaporation, followed by flash chromatography (hexane-ethyl acetate 1:1 and ethyl acetate-methanol 98:2) gave SDC-TRAP-0178 (95 mg, 53%) as a white solid.

$^1$H NMR (400 MHz, DMSO-$d_6$) δ 11.02 (s, 1H), 10.22 (s, 1H), 10.17 (s, 1H), 9.74 (s, 1H), 9.02 (t, J=5.9 Hz, 1H), 7.86-7.77 (m, 1H), 7.58-7.46 (m, 4H), 7.45-7.37 (m, 2H), 6.73 (d, J=11.9 Hz, 3H), 6.33 (s, 1H), 5.13 (dd, J=13.2, 5.1 Hz, 1H), 4.50 (d, J=17.6 Hz, 1H), 4.41 (d, J=17.6 Hz, 1H), 3.76 (s, 2H), 3.48 (s, 2H), 3.25-3.13 (m, 4H), 3.02-2.85 (m, 2H), 2.66-2.57 (m, 1H), 2.45-2.31 (m, 1H), 2.14 (s, 6H), 2.04-2.02 (m, 1H), 1.06 (t, J=7.2 Hz, 3H), 0.91 (d, J=6.9 Hz, 6H). ESMS calculated for $C_{47}H_{49}N_9O_9$: 883.37; Found: 884.1 (M+H)$^+$.

SDC-TRAP-0105

1-(2-(4-(4-(3-(2,4-dihydroxy-5-isopropylphenyl)-5-hydroxy-4H-1,2,4-triazol-4-yl) benzyl)piperazin-1-yl)ethyl)-3-(2-(2,6-dioxopiperidin-3-yl)-1-oxoisoindolin-4-yl)-1-methylurea

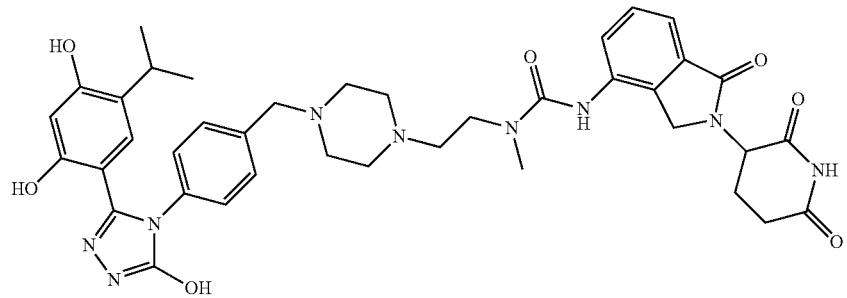 [SMILES: CC(C)c1cc(-c2nnc(O)n2-c2ccc(CN3CCN(CCN(C)C(=O)Nc4cccc5c4CN(C4CCC(=O)NC4=O)C5=O)CC3)cc2)c(O)cc1O]

$^1$H NMR (400 MHz, Chloroform-d) δ 7.69 (dd, J=8.9, 6.4 Hz, 1H), 7.49 (dp, J=6.6, 3.6 Hz, 3H), 7.42-7.22 (m, 4H), 6.43 (dd, J=40.6, 2.5 Hz, 1H), 5.17 (dd, J=13.7, 5.6 Hz, 1H), 4.41 (d, J=19.5 Hz, 2H), 4.13 (tt, J=8.7, 4.3 Hz, 1H), 3.35 (d, J=17.6 Hz, 2H), 3.00 (p, J=4.9, 4.0 Hz, 4H), 2.93-2.31 (m, 11H), 2.21 (d, J=13.0 Hz, 1H), 2.12-1.99 (m, 2H), 1.28 (qd, J=7.5, 2.9 Hz, 3H), 0.92 (td, J=10.3, 9.7, 4.7 Hz, 1H), 0.75 (td, J=7.2, 2.7 Hz, 6H). ppm; ESMS calculated for $C_{39}H_{45}N_9O_7$: 751.3; found: 752.3 (M+H$^+$).

SDC-TRAP-0108

4-(4-(3-(2,4-dihydroxy-5-isopropylphenyl)-5-hydroxy-4H-1,2,4-triazol-4-yl)phenethyl)-N-(2-(2,6-dioxopiperidin-3-yl)-1-oxoisoindolin-4-yl) piperidine-1-carboxamide $^1$H NMR (400 MHz, Chloroform-d) δ 8.05-7.97 (m, 1H), 7.63 (ddd, J=12.2, 7.1, 3.1 Hz, 1H), 7.53-7.39 (m, 1H), 7.37-7.30 (m, 1H), 7.27-7.19 (m, 2H), 6.43 (d, J=29.7 Hz, 1H), 5.14 (td, J=12.9, 5.2 Hz, 1H), 4.58-4.29 (m, 2H), 4.22-4.01 (m, 2H), 3.59 (s, 2H), 3.37 (dt, J=3.4, 1.7 Hz, 1H), 3.10-2.65 (m, 6H), 2.53-2.11 (m, 2H), 1.85 (d, J=14.3 Hz, 2H), 1.62 (tdd, J=18.4, 9.2, 5.3 Hz, 3H), 1.37-1.14 (m, 3H), 0.75 (d, J=6.8 Hz, 6H). ppm; ESMS calculated for $C_{38}H_{41}N_7O_7$: 707.3; found: 708.2 (M+H$^+$).

SDC-TRAP-0126

4-(4-(4-(3-(2,4-dihydroxy-5-isopropylphenyl)-5-hydroxy-4H-1,2,4-triazol-4-yl)phenyl)piperazin-1-yl)-N-(2-(2,6-dioxopiperidin-3-yl)-1-oxoisoindolin-4-yl) butanamide

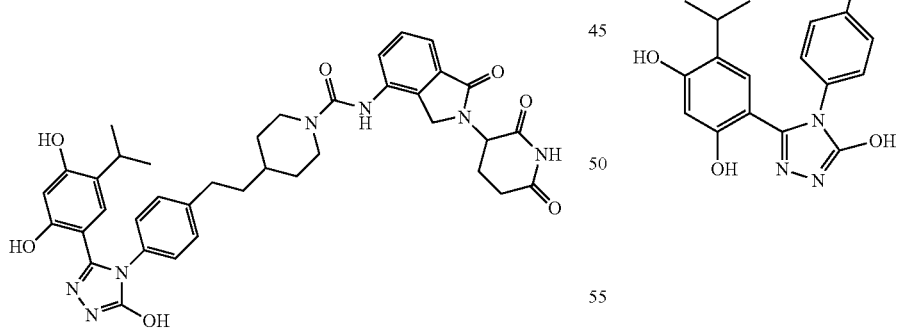

$^1$H NMR (400 MHz, Methanol-d$_4$) δ 7.76 (d, J=7.9 Hz, 1H), 7.70 (d, J=7.5 Hz, 1H), 7.51 (d, J=7.8 Hz, 1H), 7.48 (s, 3H), 7.28-7.18 (m, 2H), 7.09-7.02 (m, 2H), 6.55 (s, 1H), 6.37 (s, 1H), 5.16 (dd, J=13.3, 5.1 Hz, 1H), 4.50 (s, 2H), 3.39 (s, 2H), 3.36 (p, J=1.6 Hz, 4H), 2.99 (p, J=6.8 Hz, 2H), 2.93-2.82 (m, 2H), 2.64 (t, J=6.9 Hz, 2H), 2.55-2.33 (m, 1H), 2.22 (dp, J=12.9, 4.4 Hz, 1H), 2.09 (dt, J=13.7, 6.7 Hz, 3H), 0.80 (d, J=6.9 Hz, 6H). ppm; ESMS calculated for $C_{38}H_{42}N_8O_7$: 722.3; found: 723.3 (M+H$^+$).

SDC-TRAP-0132

3-(2-(4-(3-(2,4-dihydroxy-5-isopropylphenyl)-5-hydroxy-4H-1,2,4-triazol-4-yl)phenyl)-N-methylacetamido)propyl(2-(2, 6-dioxopiperidin-3-yl)-1-oxoisoindolin-4-yl)carbamate

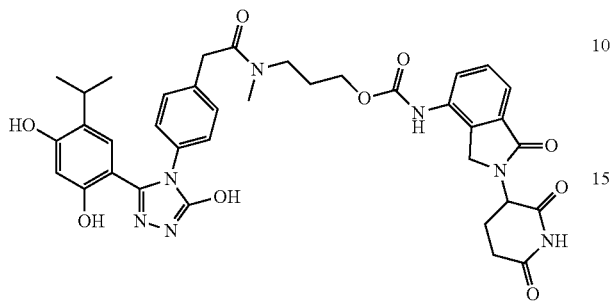

ESMS calculated for $C_{37}H_{39}N_7O_9$: 725.3; found: 726.2 (M+H$^+$).

SDC-TRAP-0127

2-(2-(4-(3-(2,4-di hydroxy-5-isopropylphenyl)-5-hydroxy-4H-1,2,4-triazol-4-yl)phenyl)-N-methylacetamido)ethyl(2-(2,6-dioxopiperidin-3-yl)-1-oxoisoindolin-4-yl)carbamate

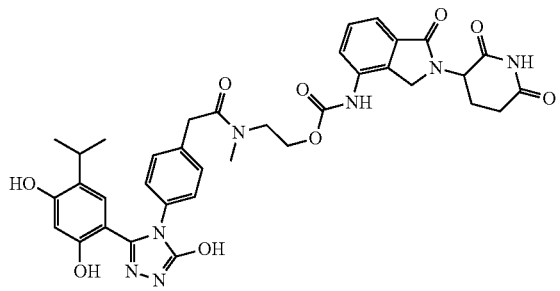 [SMILES: CC(C)c1cc(-c2nnc(O)n2-c2ccc(CC(=O)N(C)CCOC(=O)Nc3cccc4c3CN(C3CCC(=O)NC3=O)C4=O)cc2)c(O)cc1O]

$^1$H NMR (400 MHz, DMSO-61 (s, 1H), 11.00 (s, 1H), 9.75-9.28 (m, 3H), 7.70 (d, J=20.2 Hz, 1H), 7.57-7.38 (m, 3H), 7.21 (d, J=8.1 Hz, 2H), 7.15-7.05 (m, 2H), 6.82 (d, J=2.2 Hz, 1H), 6.25 (s, 1H), 5.12 (dd, J=13.3, 5.2 Hz, 1H), 4.55-4.11 (m, 4H), 3.89-3.48 (m, 4H), 3.07 (s, 1H), 3.03-2.79 (m, 1H), 2.74-2.55 (m, 1H), 2.50 (s, 3H), 0.98 (dd, J=7.0, 5.2 Hz, 6H). ppm; ESMS calculated for $C_{36}H_{37}N_7O_9$: 711.3; found: 712.1 (M+H$^+$).

SDC-TRAP-0133

2-(4-(3-(2,4-dihydroxy-5-isopropylphenyl)-5-(ethylcarbamoyl)-4H-1,2,4-triazol-4-yl)-N-methylbenzamido)ethyl(2-(2, 6-dioxopiperidin-3-yl)-1-oxoisoindolin-4-yl)carbamate

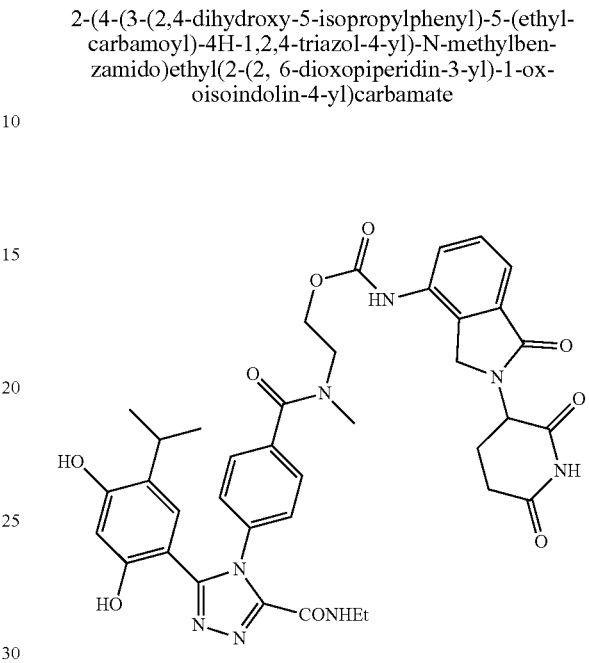

$^1$H NMR (400 MHz, DMSO-d$_6$) δ 11.01 (s, 1H), 10.21 (d, J=17.5 Hz, 1H), 9.72 (s, 1H), 9.60 (s, 1H), 9.01 (t, J=5.9 Hz, 1H), 7.70 (d, J=36.6 Hz, 1H), 7.57-7.28 (m, 6H), 6.71 (s, 1H), 6.32 (s, 1H), 5.12 (dd, J=13.2, 5.1 Hz, 1H), 4.52-4.16 (m, 4H), 3.77 (s, 1H), 3.52 (s, 1H), 3.18 (qd, J=7.3, 4.7 Hz, 2H), 3.10-2.79 (m, 5H), 2.75-2.55 (m, 1H), 2.45-2.23 (m, 1H), 2.12-1.91 (m, 1H), 1.05 (t, J=7.2 Hz, 3H), 0.88 (d, J=6.8 Hz, 6H). ppm; ESMS calculated for $C_{38}H_{40}N_8O_9$: 752.3; found: 753.3 (M+H$^+$).

SDC-TRAP-0135

3-(4-(3-(2,4-dihydroxy-5-isopropylphenyl)-5-(ethylcarbamoyl)-4H-1,2,4-triazol-4-yl)-N-methylbenzamido)propyl(2-(2,6-dioxopiperidin-3-yl)-1-oxoisoindolin-4-yl)carbamate

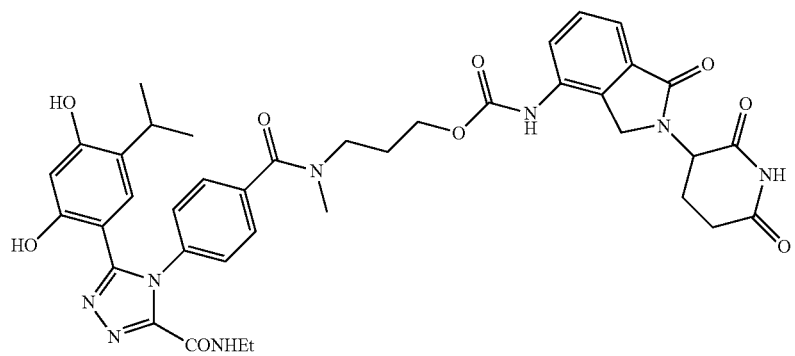

¹H NMR (400 MHz, DMSO-d₆) δ 11.01 (s, 1H), 10.18 (s, 1H), 9.71 (s, 1H), 9.57 (s, 1H), 9.00 (t, J=5.9 Hz, 1H), 7.77 (s, 1H), 7.51-7.43 (m, 5H), 7.41-7.34 (m, 2H), 6.73 (s, 1H), 6.32 (s, 1H), 5.12 (dd, J=13.3, 5.1 Hz, 1H), 4.41 (q, J=17.1, 16.2 Hz, 2H), 4.19 (s, 2H), 3.58 (s, 2H), 3.31 (s, 2H), 3.18 (s, 3H), 3.02-2.84 (m, 3H), 2.60 (dt, J=15.7, 3.3 Hz, 1H), 2.34 (d, J=13.0 Hz, 2H), 1.05 (t, J=7.4 Hz, 3H), 0.90 (d, J=6.8 Hz, 6H). ppm; ESMS calculated for $C_{39}H_{42}N_8O_9$: 766.3; found: 767.3 (M+H⁺).

SDC-TRAP-0140

2-(1-(4-(3-(2,4-dihydroxy-5-isopropylphenyl)-5-(ethylcarbamoyl)-4H-1,2,4-triazol-4-yl)benzoyl)piperidin-4-yl)ethyl(2-(2,6-dioxopiperidin-3-yl)-1-oxoisoindolin-4-yl)carbamate

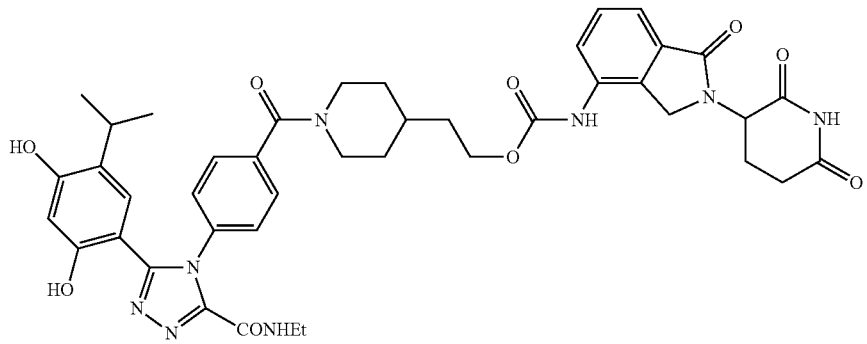

¹H NMR (400 MHz, DMSO-d₆) δ 11.03 (s, 1H), 10.30 (s, 1H), 9.75 (s, 1H), 9.54 (s, 1H), 9.01 (t, J=5.9 Hz, 1H), 7.77 (dt, J=7.7, 3.8 Hz, 1H), 7.54-7.36 (m, 6H), 6.68 (s, 1H), 6.33 (s, 1H), 5.13 (dd, J=13.3, 5.1 Hz, 1H), 4.40 (q, J=17.6 Hz, 3H), 4.17 (t, J=6.5 Hz, 2H), 3.56 (s, 1H), 3.24-3.13 (m, 2H), 3.07 (s, 1H), 2.92 (ddd, J=17.1, 13.5, 5.8 Hz, 2H), 2.78 (s, 1H), 2.67-2.57 (m, 1H), 2.35 (qd, J=13.2, 4.4 Hz, 1H), 2.08-1.97 (m, 1H), 1.71 (m, 4H), 1.62 (q, J=6.6 Hz, 2H), 1.22 (d, J=13.2 Hz, 2H), 1.06 (t, J=7.2 Hz, 3H), 0.88 (d, J=6.9 Hz, 6H). ppm; ESMS calculated for $C_{42}H_{46}N_8O_9$: 806.3; found: 807.3 (M+H⁺).

SDC-TRAP-0136

(1-(4-(3-(2,4-dihydroxy-5-isopropylphenyl)-5-(ethylcarbamoyl)-4H-1,2,4-triazol-4-yl)benzoyl)piperidin-4-yl)methyl (2-(2,6-dioxopiperidin-3-yl)-1-oxoisoindolin-4-yl)carbamate

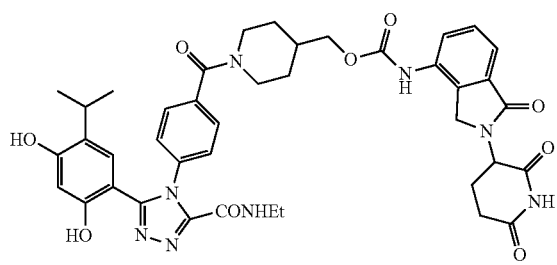

¹H NMR (400 MHz, DMSO-d₆) δ 10.88 (s, 1H), 10.16 (s, 1H), 9.60 (s, 1H), 9.40 (s, 1H), 8.87 (t, J=5.8 Hz, 1H), 7.63 (dd, J=6.7, 2.4 Hz, 1H), 7.39-7.22 (m, 6H), 6.53 (s, 1H), 6.19 (s, 1H), 4.99 (dd, J=13.2, 5.1 Hz, 1H), 4.35-4.17 (m, 2H), 3.94-3.81 (m, 3H), 3.10-2.98 (m, 2H), 2.85-2.70 (m, 2H), 2.67 (s, 1H), 2.51-2.42 (m, 1H), 1.93-1.81 (m, 4H), 1.52 (s, 2H), 1.03 (t, J=7.1 Hz, 3H), 0.91 (t, J=7.2 Hz, 3H), 0.73 (d, J=6.9 Hz, 6H). ppm; ESMS calculated for $C_{41}H_{44}N_8O_9$: 792.3; found: 793.2 (M+H⁺).

SDC-TRAP-0231

3-(1-(4-(3-(2,4-dihydroxy-5-isopropylphenyl)-5-(ethylcarbamoyl)-4H-1,2,4-triazol-4-yl)benzyl)-N-methylpiperidine-4-carboxamido)propyl (2-(2,6-dioxopiperidin-3-yl)-1-oxoisoindolin-4-yl)carbamate

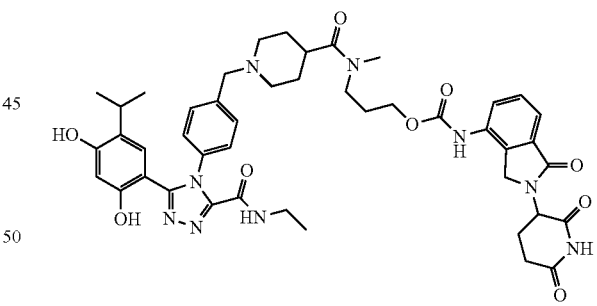

¹H NMR (400 MHz, Chloroform-d) δ 73.88 (d, J=8.1 Hz, 1H), 7.61 (t, J=6.8 Hz, 2H), 7.57-7.49 (m, 2H), 7.51-7.41 (m, 2H), 7.32 (d, J=8.3 Hz, 2H), 6.57-6.40 (m, 2H), 5.19 (dd, J=13.2, 5.1 Hz, 1H), 4.55-4.31 (m, 2H), 4.13 (td, J=6.2, 3.0 Hz, 2H), 3.71-3.46 (m, 5H), 3.46-3.30 (m, 3H), 3.08 (s, 3H), 3.01-2.72 (m, 4H), 2.29-2.14 (m, 1H), 2.06 (dd, J=11.8, 6.7 Hz, 2H), 1.87 (dp, J=13.0, 7.6, 6.9 Hz, 4H), 1.70 (d, J=13.3 Hz, 2H), 1.41-1.12 (m, 6H), 0.71 (dd, J=13.5, 6.9 Hz, 6H). ppm; ESMS calculated for $C_{45}H_{53}N_9O_9$: 863.4; found: 864.3 (M+H⁺).

173

SDC-TRAP-0147

5-(2,4-dihydroxy-5-isopropylphenyl)-4-(4-((2-((2-(2,6-dioxopiperidin-3-yl)-1-oxoisoindolin-4-yl)amino)-2-oxoethyl)(methyl)carbamoyl) phenyl)-N-ethyl-4H-1,2,4-triazole-3-carboxamide

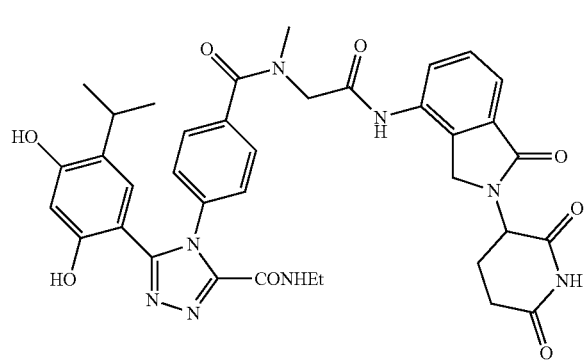

ESMS calculated for $C_{37}H_{38}N_8O_8$: 722.3; found: 723.2 (M+H$^+$).

174

SDC-TRAP-0165

5-(2,4-dihydroxy-5-isopropylphenyl)-4-(4-((3-((2-(2,6-dioxopiperidin-3-yl)-1-oxoisoindolin-4-yl)amino)-3-oxopropyl)(methyl)carbamoyl) phenyl)-N-(2,2,2-trifluoroethyl)-4H-1,2,4-triazole-3-carboxamide ESMS calculated for $C_{38}H_{37}F_3N_8O_8$: 790.3; found: 791.1 (M+H$^+$).

SDC-TRAP-0163

1-(4-(3-(2,4-dihydroxy-5-isopropylphenyl)-5-(ethyl-carbamoyl)-4H-1,2,4-triazol-4-yl)benzyl)-N-((2S)-1-((2-(2,6-dioxopiperidin-3-yl)-1-oxoisoindolin-4-yl)amino)-3-methyl-1-oxobutan-2-yl)piperidine-4-carboxamide $^1$H NMR (400 MHz, Methanol-d$_4$) δ 7.80 (ddd, J=26.0, 8.0, 1.0 Hz, 1H), 7.70 (ddd, J=7.6, 4.3, 1.0 Hz, 1H), 7.59-7.43 (m, 3H), 7.41 (s, 1H), 7.38-7.31 (m, 2H), 6.50 (s, 1H), 6.43 (s, 1H), 5.15 (ddd, J=13.3, 5.1, 3.6 Hz, 1H), 4.60-4.22 (m, 3H), 3.63 (s, 2H), 3.43-3.28 (m, 3H), 3.09-2.77 (m, 5H), 2.52-2.01 (m, 6H), 1.94-1.70 (m, 4H), 1.32-1.13 (m, 4H), 1.03 (dd, J=12.4, 6.7 Hz, 6H), 0.98-0.83 (m, 1H), 0.75 (d, J=6.9 Hz, 6H). ppm; ESMS calculated for $C_{45}H_{53}N_9O_8$: 847.4; found: 848.3 (M+H$^+$).

SDC-TRAP-0164

5-(2,4-dihydroxy-5-isopropylphenyl)-4-(4-((4-((2S)-2-((2-(2,6-dioxopiperidin-3-yl)-1-oxoisoindolin-4-yl)carbamoyl)pyrrolidine-1-carbonyl) piperidin-1-yl) methyl)phenyl)-N-ethyl-4H-1,2,4-triazole-3-carboxamide

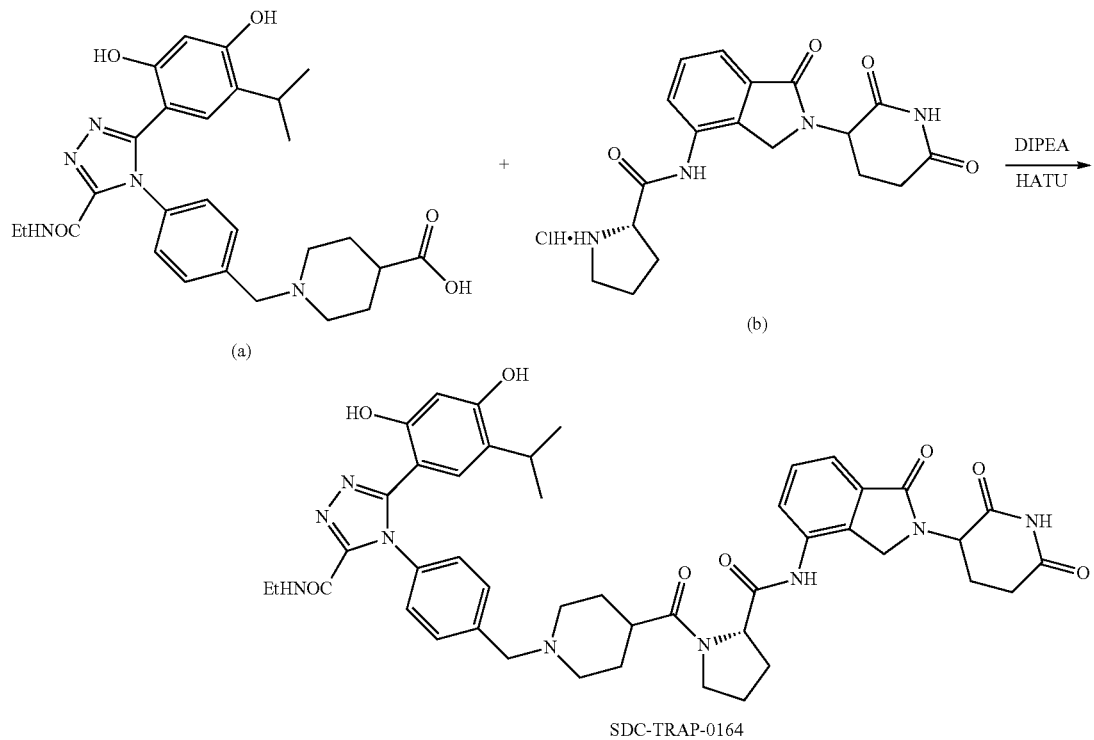

To a mixture of 1-(4-(3-(2,4-dihydroxy-5-isopropylphenyl)-5-(ethylcarbamoyl)-4H-1,2,4-triazol-4-yl)benzyl)piperidine-4-carboxylic acid (a, 0.90 mmol), (2S)—N-(2-(2,6-dioxopiperidin-3-yl)-1-oxoisoindolin-4-yl) pyrrolidine-2-carboxamide hydrochloride (b, 0.80 mmol) and HATU (1.0 mmol) in DMF (10 mL) at room temperature was added DIPEA (3.0 mmol) and the mixture was stirred at room temperature for 16 h. The mixture was added to a solution of NaHCO$_3$ (200 mL, 0.1M) and stirred for 30 min before filtering. The yellow filter cake was purified by column to yield SDC-TRAP-0164 as a white solid (0.25 g, 0.29 mmol).

$^1$H NMR (400 MHz, DMSO-d$_6$) δ 11.06 (d, J=6.8 Hz, 1H), 10.69-10.60 (m, 1H), 9.90 (s, 1H), 9.77 (s, 1H), 8.97 (t, J=5.9 Hz, 1H), 7.81-7.72 (m, 1H), 7.60-7.46 (m, 2H), 7.42-7.27 (m, 4H), 6.57 (d, J=9.4 Hz, 1H), 6.34 (s, 1H), 5.19-5.11 (m, 1H), 4.47 (d, J=8.3 Hz, 1H), 4.33 (t, J=12.4 Hz, 2H), 3.68 (s, 1H), 3.61 (s, 1H), 3.49 (s, 2H), 3.21-3.13 (m, 2H), 2.90 (d, J=18.7 Hz, 5H), 2.63 (s, 1H), 2.00 (s, 7H), 1.67 (s, 2H), 1.58 (s, 3H), 1.03 (td, J=7.2, 3.1 Hz, 4H), 0.79 (ddd, J=17.0, 6.9, 2.3 Hz, 6H). ppm; ESMS calculated for C$_{45}$H$_{51}$N$_9$O$_8$: 845.4; found: 846.2 (M+H$^+$).

SDC-TRAP-0166

5-(2,4-dihydroxy-5-isopropylphenyl)-4-(4-(((2S)-1-((2-(2,6-dioxopiperidin-3-yl)-1-oxoisoindolin-4-yl) amino)-1-oxopropan-2-yl)carbamoyl)phenyl)-N-ethyl-4H-1,2,4-triazole-3-carboxamide $^1$H NMR (400 MHz, Chloroform-d) δ 8.09-7.98 (m, 2H), 7.92-7.76 (m, 1H), 7.71 (dd, J=7.6, 2.4 Hz, 1H), 7.56-7.39 (m, 3H), 6.40 (dd, J=5.6, 1.5 Hz, 2H), 5.17 (ddd, J=13.5, 5.2, 1.7 Hz, 1H), 4.93-4.75 (m, 1H), 4.58-4.28 (m, 2H), 3.49-3.30 (m, 3H), 3.30-3.10 (m, 5H), 2.88 (dddd, J=26.5, 12.7, 6.1, 2.9 Hz, 3H), 2.53-2.33 (m, 1H), 2.32-2.08 (m, 1H), 1.70-1.53 (m, 3H), 1.34-1.11 (m, 4H), 0.72 (dd, J=6.9, 3.6 Hz, 6H). ppm; ESMS calculated for $C_{37}H_{38}N_8O_8$: 722.3; found: 723.1 (M+H$^+$).

SDC-TRAP-0188

5-(2,4-dihydroxy-5-isopropylphenyl)-4-(4-(((2S)-1-((2-(2,6-dioxopiperidin-3-yl)-1-oxoisoindolin-4-yl)amino)-3-methyl-1-oxobutan-2-yl)carbamoyl) phenyl)-N-ethyl-4H-1,2,4-triazole-3-carboxamide

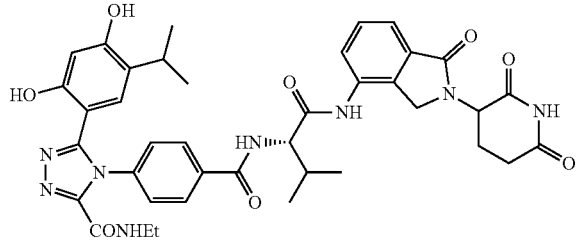

$^1$H NMR (400 MHz, Methanol-d$_4$) δ 8.07 (ddd, J=8.9, 4.5, 2.1 Hz, 2H), 7.90-7.64 (m, 2H), 7.58-7.41 (m, 3H), 6.46-6.28 (m, 2H), 5.17 (dd, J=13.3, 5.1 Hz, 1H), 4.67-4.35 (m, 3H), 3.45-3.26 (m, 4H), 3.04-2.67 (m, 3H), 2.52-2.14 (m, 3H), 1.58 (dq, J=19.9, 7.5 Hz, 1H), 1.30-1.17 (m, 5H), 1.18-1.03 (m, 5H), 1.04-0.90 (m, 1H), 0.72 (dt, J=7.1, 1.4 Hz, 6H). ppm; ESMS calculated for $C_{39}H_{42}N_8O_8$: 750.3; found: 751.1 (M+H$^+$).

SDC-TRAP-0189

5-(2,4-dihydroxy-5-isopropylphenyl)-4-(4-(((2S)-1-((2-(2,6-dioxopiperidin-3-yl)-1-oxoisoindolin-4-yl)amino)-4-methyl-1-oxopentan-2-yl) carbamoyl)phenyl)-N-ethyl-4H-1,2,4-triazole-3-carboxamide

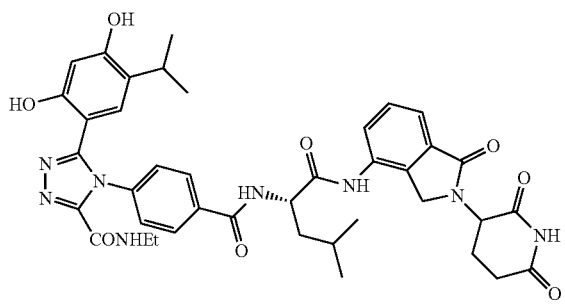

$^1$H NMR (400 MHz, Chloroform-d) δ 8.13-8.01 (m, 2H), 7.95-7.77 (m, 1H), 7.74-7.63 (m, 1H), 7.56-7.39 (m, 3H), 6.41 (d, J=2.0 Hz, 1H), 6.35 (d, J=5.0 Hz, 1H), 5.17 (ddd, J=13.3, 5.1, 2.2 Hz, 1H), 5.01-4.78 (m, 1H), 4.59-4.26 (m, 2H), 3.47-3.25 (m, 4H), 2.98-2.79 (m, 3H), 2.53-2.11 (m, 2H), 1.91-1.67 (m, 3H), 1.24 (dt, J=17.9, 7.2 Hz, 4H), 1.08-0.95 (m, 6H), 0.70 (ddd, J=7.0, 4.2, 1.3 Hz, 6H). ppm; ESMS calculated for $C_{40}H_{44}N_8O_8$: 764.3; found: 765.1 (M+H$^+$).

SDC-TRAP-0190

5-(2,4-dihydroxy-5-isopropylphenyl)-4-(4-((2S)-2-((2-(2,6-dioxopiperidin-3-yl)-1-oxoisoindolin-4-yl)carbamoyl)pyrrolidine-1-carbonyl)phenyl)-N-ethyl-4H-1,2,4-triazole-3-carboxamide

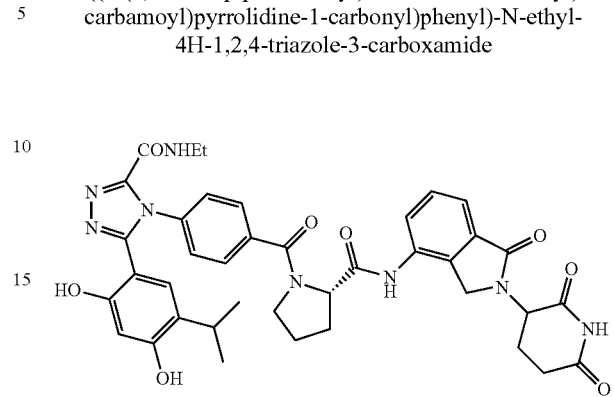

$^1$H NMR (400 MHz, DMSO-d$_6$) δ 11.04 (s, 1H), 10.20 (d, J=3.7 Hz, 1H), 10.03 (d, J=3.1 Hz, 1H), 9.72 (s, 1H), 9.03 (t, J=5.9 Hz, 1H), 7.80 (dd, J=7.6, 1.6 Hz, 1H), 7.69-7.58 (m, 2H), 7.60-7.47 (m, 2H), 7.41 (d, J=8.0 Hz, 3H), 6.72 (s, 1H), 6.31 (d, J=1.3 Hz, 1H), 5.15 (dd, J=13.3, 5.1 Hz, 1H), 4.66 (t, J=6.5 Hz, 1H), 4.50-4.29 (m, 2H), 3.56 (ddd, J=22.5, 9.7, 5.7 Hz, 2H), 3.19 (p, J=6.8 Hz, 2H), 2.92 (qt, J=14.8, 7.4 Hz, 3H), 2.61 (d, J=17.0 Hz, 1H), 2.35 (t, J=11.7 Hz, 3H), 2.15-1.80 (m, 4H), 1.06 (t, J=7.2 Hz, 3H), 0.90 (dd, J=7.3, 2.1 Hz, 6H). ppm; ESMS calculated for $C_{39}H_{40}N_8O_8$: 748.3; found: 749.1 (M+H$^+$).

SDC-TRAP-0191

5-(2,4-dihydroxy-5-isopropylphenyl)-4-(4-(4-(((2S)-1-((2-(2,6-dioxopiperidin-3-yl)-1-oxoisoindolin-4-yl)amino)-4-methyl-1-oxopentan-2-yl)carbamoyl)phenoxy)phenyl)-N-ethyl-4H-1,2,4-triazole-3-carboxamide

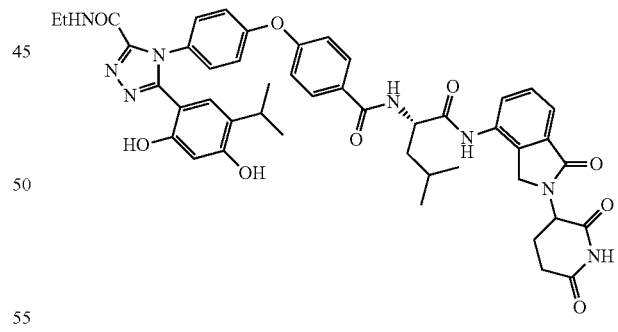

$^1$H NMR (400 MHz, Methanol-d$_4$) δ 7.98-7.80 (m, 4H), 7.68 (ddd, J=7.7, 5.3, 1.0 Hz, 1H), 7.48 (td, J=7.8, 3.4 Hz, 1H), 7.36 (d, J=6.9 Hz, 1H), 7.24-7.13 (m, 4H), 6.55 (s, 1H), 6.45 (s, 1H), 5.16 (ddd, J=13.3, 5.1, 1.8 Hz, 1H), 4.86 (ddp, J=8.7, 5.2, 2.5 Hz, 1H), 4.64-4.23 (m, 2H), 3.49-3.27 (m, 3H), 3.04 (p, J=6.9 Hz, 1H), 2.85 (ddt, J=9.4, 5.1, 2.3 Hz, 2H), 2.51-2.29 (m, 1H), 2.20 (ddd, J=13.5, 6.9, 3.7 Hz, 1H), 1.89-1.74 (m, 3H), 1.25 (dt, J=13.4, 7.2 Hz, 5H), 1.12-1.00 (m, 6H), 1.00-0.91 (m, 1H), 0.87 (d, J=6.9 Hz, 6H). ppm; ESMS calculated for $C_{46}H_{48}N_8O_9$: 856.4; found: 857.1 (M+H$^+$).

SDC-TRAP-0192

5-(2,4-dihydroxy-5-isopropylphenyl)-4-(4-(4-((2S)-2-((2-(2,6-dioxopiperidin-3-yl)-1-oxoisoindolin-4-yl)carbamoyl)pyrrolidine-1-carbonyl)phenoxy)phenyl)-N-ethyl-4H-1,2,4-triazole-3-carboxamide

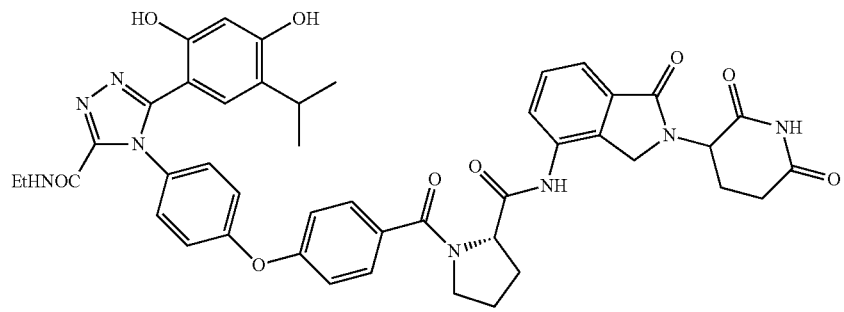

$^1$H NMR (400 MHz, Methanol-$d_4$) δ 7.94 (ddd, J=25.0, 8.1, 1.0 Hz, 1H), 7.81 (dt, J=8.3, 4.1 Hz, 1H), 7.72-7.58 (m, 3H), 7.48 (td, J=7.8, 6.2 Hz, 1H), 7.42-7.30 (m, 1H), 7.23-7.11 (m, 4H), 6.54 (d, J=1.7 Hz, 1H), 6.44 (s, 1H), 5.14 (dd, J=13.3, 5.1 Hz, 1H), 4.87 (dt, J=8.1, 5.3 Hz, 1H), 4.56-4.33 (m, 2H), 3.75-3.65 (m, 3H), 3.52-3.29 (m, 4H), 3.03 (p, J=6.8 Hz, 1H), 2.83 (ddd, J=10.6, 5.5, 2.8 Hz, 2H), 2.53-2.09 (m, 7H), 1.97 (dtd, J=15.5, 8.2, 7.2, 4.7 Hz, 1H), 1.25 (dt, J=13.5, 7.2 Hz, 4H), 0.87 (d, J=6.9 Hz, 6H). ppm; ESMS calculated for $C_{45}H_{44}N_8O_9$: 840.3; found: 841.1 (M+H$^+$).

SDC-TRAP-0193

1-(4-(3-(2,4-dihydroxy-5-isopropylphenyl)-5-(ethylcarbamoyl)-4H-1,2,4-triazol-4-yl)benzyl)-N-((2S)-1-((2-(2,6-dioxopiperidin-3-yl)-1-oxoisoindolin-4-yl)amino)-4-methyl-1-oxopentan-2-yl)piperidine-4-carboxamide

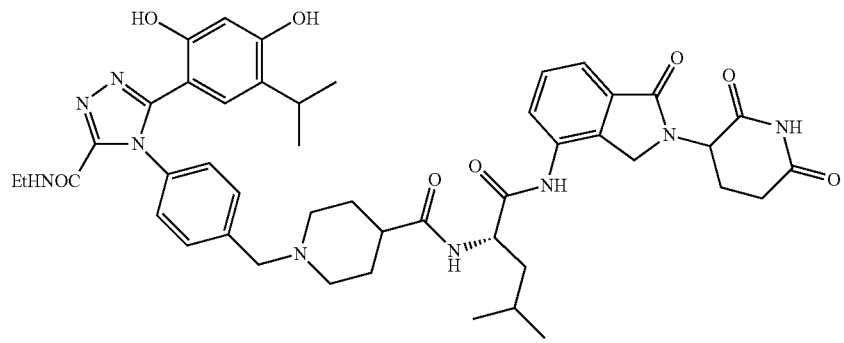

$^1$H NMR (400 MHz, Chloroform-d) δ 7.93-7.83 (m, 1H), 7.68 (d, J=7.5 Hz, 1H), 7.62-7.41 (m, 4H), 7.32 (dd, J=8.2, 2.7 Hz, 2H), 6.51-6.45 (m, 1H), 6.43 (d, J=1.8 Hz, 1H), 5.16 (ddd, J=13.9, 9.4, 5.1 Hz, 1H), 4.67-4.52 (m, 1H), 4.53-4.20 (m, 2H), 3.68-3.49 (m, 2H), 3.46-3.28 (m, 3H), 3.07-2.72 (m, 6H), 2.35-2.25 (m, 4H), 2.05 (d, J=6.5 Hz, 1H), 1.91-1.53 (m, 6H), 1.34-1.14 (m, 6H), 1.05-0.92 (m, 6H), 0.71 (dt, J=6.9, 2.9 Hz, 6H). ppm; ESMS calculated for $C_{46}H_{55}N_9O_8$: 861.4; found: 862.2 (M+H$^+$).

SDC-TRAP-0122

2-(5-(3-(2,4-dihydroxy-5-isopropylphenyl)-5-hydroxy-4H-1,2,4-triazol-4-yl)-1H-indol-1-yl)ethyl (2-(2,6-dioxopiperidin-3-yl)-1-oxoisoindolin-4-yl) carbamate

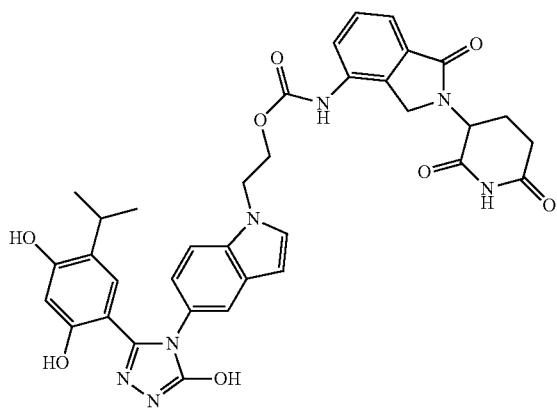 [SMILES: CC(C)c1cc(-c2nnc(O)n2-c2ccc3c(ccn3CCOC(=O)Nc3cccc4c3CN(C3CCC(=O)NC3=O)C4=O)c2)c(O)cc1O]

$^1$H NMR (400 MHz, DMSO-d$_6$) δ 11.87 (s, 1H), 11.02 (s, 1H), 9.56 (d, J=14.1 Hz, 2H), 9.46 (s, 1H), 7.65 (s, 1H), 7.54 (d, J=8.7 Hz, 1H), 7.52-7.39 (m, 4H), 6.95 (dd, J=8.7, 2.0 Hz, 1H), 6.74 (d, J=1.7 Hz, 1H), 6.46 (d, J=3.1 Hz, 1H), 6.21 (s, 1H), 5.11 (dd, J=13.4, 5.0 Hz, 1H), 4.49 (t, J=5.2 Hz, 2H), 4.44-4.25 (m, 4H), 2.84-2.85 (m, 2H), 2.65-2.56 (m, 1H), 2.33 (td, J=13.4, 8.7 Hz, 1H), 2.03-1.95 (m, 1H), 0.83 (dd, J=7.1, 1.7 Hz, 6H); ESMS calculated (C$_{35}$H$_{33}$N$_7$O$_8$): 679.2; found: 680.2 (M+H).

SDC-TRAP-0123

1-(1-(4-(3-(2,4-Dihydroxy-5-isopropylphenyl)-5-(ethylcarbamoyl)-4H-1,2,4-triazol-4-yl)benzyl)piperidine-4-carbonyl)piperidin-4-yl (2-(2,6-dioxopiperidin-3-yl)-1-oxoisoindolin-4-yl)carbamate

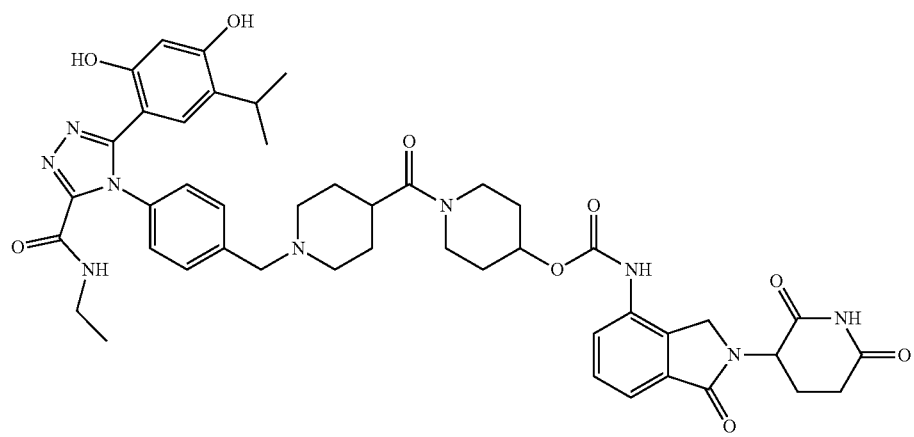 [SMILES: CCNC(=O)c1nnc(-c2cc(C(C)C)c(O)cc2O)n1-c1ccc(CN2CCC(C(=O)N3CCC(OC(=O)Nc4cccc5c4CN(C4CCC(=O)NC4=O)C5=O)CC3)CC2)cc1]

$^1$H NMR (400 MHz, DMSO-d$_6$) δ 11.01 (s, 1H), 10.62 (s, 1H), 9.76 (s, 1H), 9.55 (s, 1H), 8.96 (t, J=5.9 Hz, 1H), 7.77 (dd, J=6.6, 2.6 Hz, 1H), 7.54-7.44 (m, 2H), 7.42-7.35 (m, 2H), 7.34-7.26 (m, 2H), 6.58 (s, 1H), 6.35 (s, 1H), 5.13 (dd, J=13.3, 5.1 Hz, 1H), 4.93-4.86 (m, 1H), 4.40 (q, J=17.6 Hz, 2H), 4.10 (q, J=5.3 Hz, 1H), 3.92 (s, 1H), 3.77 (s, 1H), 3.49 (s, 2H), 3.30 (s, 2H), 3.20-3.13 (m, 5H), 2.96-2.83 (m, 4H), 2.67-2.60 (m, 2H), 2.39-2.29 (m, 1H), 2.06-1.89 (m, 5H), 1.90 (s, 1H), 1.53-1.47 (m, 1H), 1.04 (t, J=7.2 Hz, 3H), 0.81 (d, J=6.9 Hz, 6H); ESMS calculated (C$_{46}$H$_{53}$N$_9$O$_9$): 875.4; found: 876.4 (M+H).

SDC-TRAP-0124

(1-(1-(4-(3-(2,4-Dihydroxy-5-isopropylphenyl)-5-(ethylcarbamoyl)-4H-1,2,4-triazol-4-yl)benzyl)piperidine-4-carbonyl)piperidin-4-yl)methyl (2-(2,6-dioxopiperidin-3-yl)-1-oxoisoindolin-4-yl)carbamate

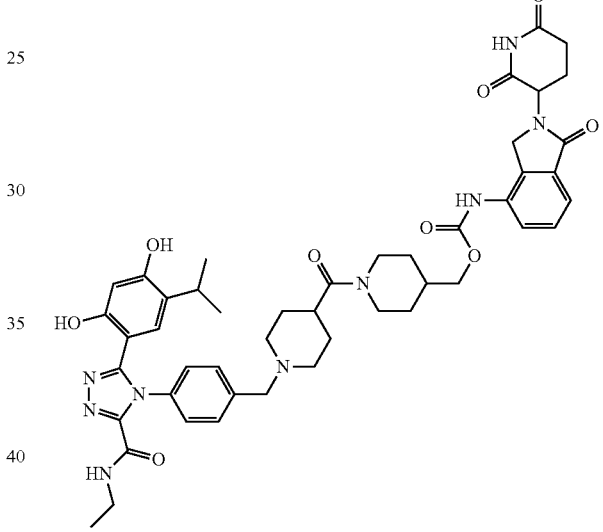

ESMS calculated (C$_{47}$H$_{55}$N$_9$O$_9$): 889.4; found: 890.3 (M+H).

SDC-TRAP-0125

(1-(4-(4-(3-(2,4-Dihydroxy-5-isopropylphenyl)-5-(ethylcarbamoyl)-4H-1,2,4-triazol-4-yl)phenoxy)benzoyl)piperidin-4-yl)methyl (2-(2,6-dioxopiperidin-3-yl)-1-oxoisoindolin-4-yl)carbamate

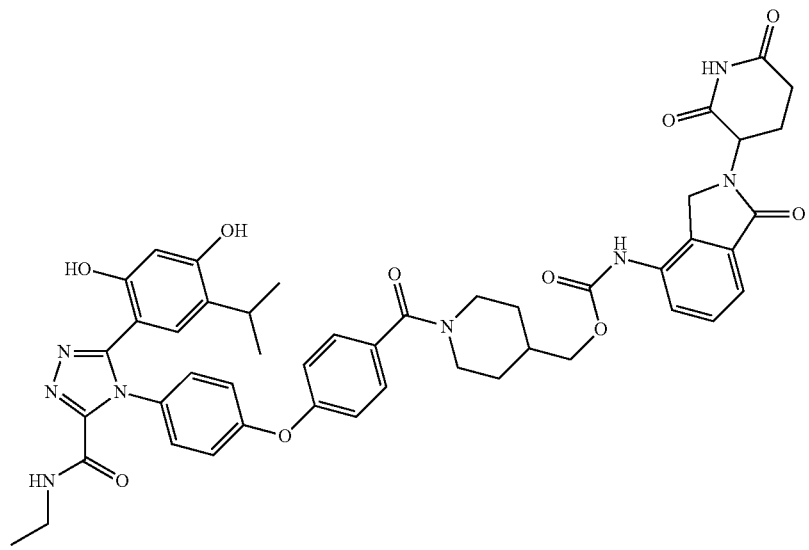 [SMILES: CCNC(=O)c1nnc(-c2cc(C(C)C)c(O)cc2O)n1-c1ccc(Oc2ccc(C(=O)N3CCC(COC(=O)Nc4cccc5c4CN(C4CCC(=O)NC4=O)C5=O)CC3)cc2)cc1]

$^1$H NMR (400 MHz, DMSO-d$_6$) δ 11.03 (s, 1H), 10.41 (s, 1H), 9.77 (s, 1H), 9.55 (s, 1H), 8.99 (t, J=5.9 Hz, 1H), 7.77 (d, J=6.8 Hz, 1H), 7.54-7.42 (m, 4H), 7.41-7.34 (m, 2H), 7.14-7.04 (m, 4H), 6.68 (s, 1H), 6.35 (s, 1H), 5.13 (dd, J=13.3, 5.1 Hz, 1H), 4.39 (q, J=17.6 Hz, 2H), 4.03 (q, J=7.1 Hz, 2H), 3.19 (p, J=6.9 Hz, 2H), 3.03-2.85 (m, 2H), 2.60 (d, J=16.8 Hz, 1H), 2.36-2.29 (m, 1H), 1.99 (s, 3H), 1.75 (s, 2H), 1.29-1.13 (m, 5H), 1.06 (t, J=7.2 Hz, 3H), 0.92 (d, J=6.9 Hz, 6H); ESMS calculated (C$_{47}$H$_{48}$N$_8$O$_{10}$): 884.3; found: 885.3 (M+H).

SDC-TRAP-0155

(1-((5-(3-(2,4-dihydroxy-5-isopropylphenyl)-5-hydroxy-4H-1,2,4-triazol-4-yl)-1-methyl-1H-indol-2-yl)methyl)piperidin-4-yl)methyl (2-(2,6-dioxopiperidin-3-yl)-1-oxoisoindolin-4-yl)carbamate

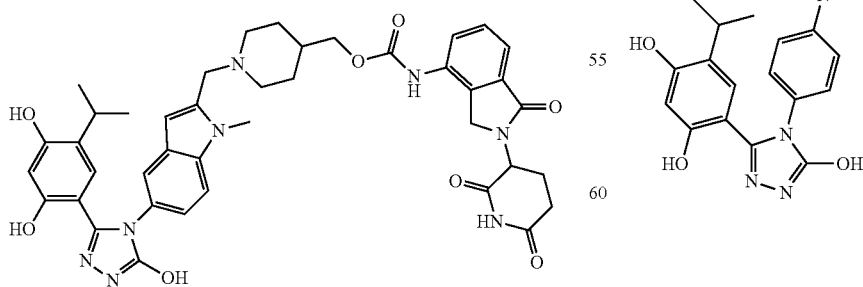

ESMS calculated (C$_{41}$H$_{44}$N$_8$O$_8$): 776.3; found: 777.3 (M+H).

SDC-TRAP-0156

4-(4-(4-(3-(2,4-Dihydroxy-5-isopropylphenyl)-5-hydroxy-4H-1,2,4-triazol-4-yl)phenyl)piperazine-1-carbonyl)benzyl (2-(2,6-dioxopiperidin-3-yl)-1-oxoisoindolin-4-yl)carbamate

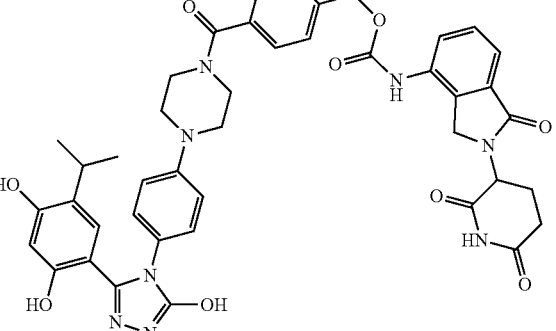

ESMS calculated (C$_{43}$H$_{42}$N$_8$O$_9$) 814.3; found: 815.0 (M+H).

185

SDC-TRAP-0157

4-(4-(4-(3-(2,4-dihydroxy-5-isopropylphenyl)-5-hydroxy-4H-1,2,4-triazol-4-yl)-2-fluorobenzyl)piperazine-1-carbonyl)benzyl (2-(2,6-dioxopiperidin-3-yl)-1-oxoisoindolin-4-yl)carbamate

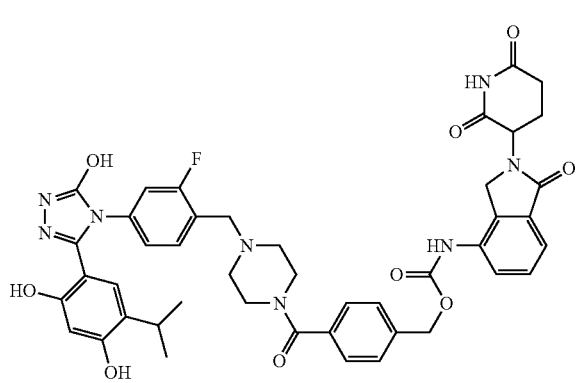 [SMILES: CC(C)c1cc(-c2nnc(O)n2-c2ccc(CN3CCN(C(=O)c4ccc(COC(=O)Nc5cccc6c5CN(C5CCC(=O)NC5=O)C6=O)cc4)CC3)c(F)c2)c(O)cc1O]

ESMS calculated ($C_{44}H_{43}N_8O_9$): 846.3; found: 847.2 (M+H).

186

SDC-TRAP-0160

5-(4-(4-(3-(2,4-dihydroxy-5-isopropylphenyl)-5-hydroxy-4H-1,2,4-triazol-4-yl)-2-fluorobenzyl)piperazine-1-carbonyl)-N-(2-(2,6-dioxopiperidin-3-yl)-1-oxoisoindolin-4-yl)pyrazine-2-carboxamide

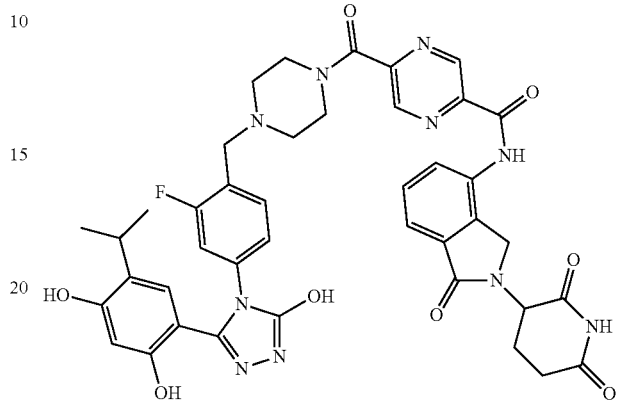

ESMS calculated ($C_{41}H_{39}FN_{10}O_8$): 818.3; found: 819.2 (M+H).

SDC-TRAP-0167

4-(4-(3-(2,4-dihydroxy-5-isopropylphenyl)-5-(ethylcarbamoyl)-4H-1,2,4-triazol-4-yl)phenoxy)phenyl(2-(((2-(2,6-dioxopiperidin-3-yl)-1-oxoisoindolin-4-yl)carbamoyl)oxy)ethyl)(methyl)carbamate

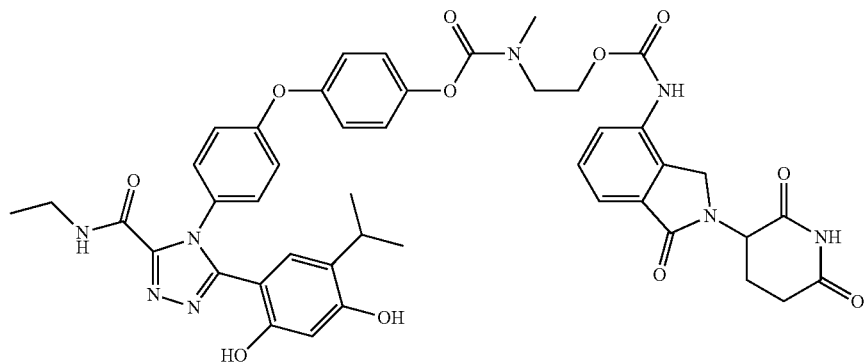 [SMILES: CCNC(=O)c1nnc(-c2cc(C(C)C)c(O)cc2O)n1-c1ccc(Oc2ccc(OC(=O)N(C)CCOC(=O)Nc3cccc4c3CN(C3CCC(=O)NC3=O)C4=O)cc2)cc1]

ESMS calculated ($C_{44}H_{44}N_8O_{11}$): 860.3; found: 861.1 (M+H).

187
SDC-TRAP-0168

4-(4-(4-(3-(2,4-dihydroxy-5-isopropylphenyl)-5-hydroxy-4H-1,2,4-triazol-4-yl)-2-fluorobenzyl)piperazine-1-carbonyl)-2,6-dimethylphenyl (2-(2,6-dioxopiperidin-3-yl)-1-oxoisoindolin-4-yl)carbamate

188
SDC-TRAP-0170

5-(4-(4-(3-(2,4-dihydroxy-5-isopropylphenyl)-5-hydroxy-4H-1,2,4-triazol-4-yl)-2-fluorobenzyl)piperazin-1-yl)-N-(2-(2,6-dioxopiperidin-3-yl)-1-oxoisoindolin-4-yl)pyrazine-2-carboxamide

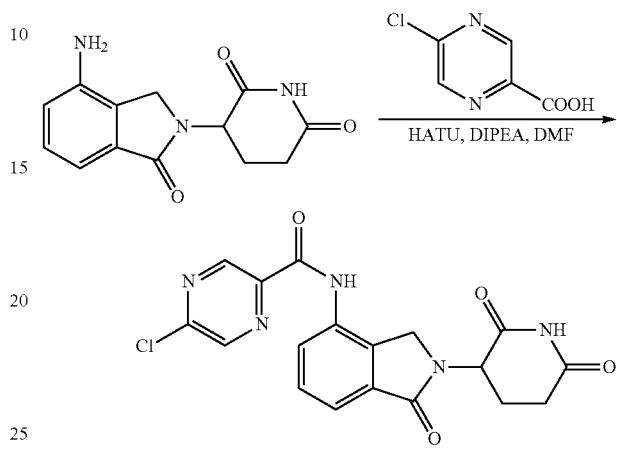

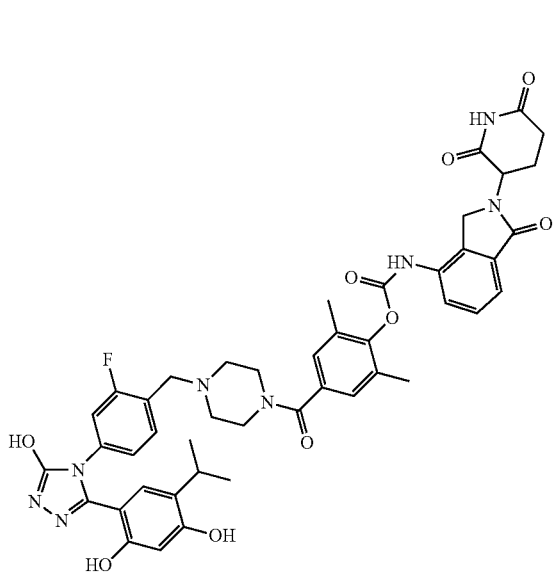 [SMILES: Cc1cc(C(=O)N2CCN(Cc3ccc(-n4c(O)nnc4-c4cc(C(C)C)c(O)cc4O)cc3F)CC2)cc(C)c1OC(=O)Nc1cccc2c1CN(C1CCC(=O)NC1=O)C2=O]

ESMS calculated ($C_{45}H_{45}FN_8O_9$): 860.3; found: 861.2 (M+H).

To a solution of lenalidomide (0.2 g, 0.77 mmol) in DMF (4 mL) was added 5-chloropyrazine-2-carboxylic acid (0.15 g, 0.95 mmol), HATU, (0.29 g, 0.77 mmol), and DIPEA (0.27 mL, 1.54 mmol). The reaction was stirred at room temperature for 1 hr before it was quenched with saturated $NH_4Cl$ (5 mL). The mixture was extracted with EtOAc (10 mL×3), and the combined organic phase was dried over $Na_2SO_4$ and concentrated. Column chromatography gave 5-chloro-N-(2-(2,6-dioxopiperidin-3-yl)-1-oxoisoindolin-4-yl)pyrazine-2-carboxamide (0.1 g, 33%).

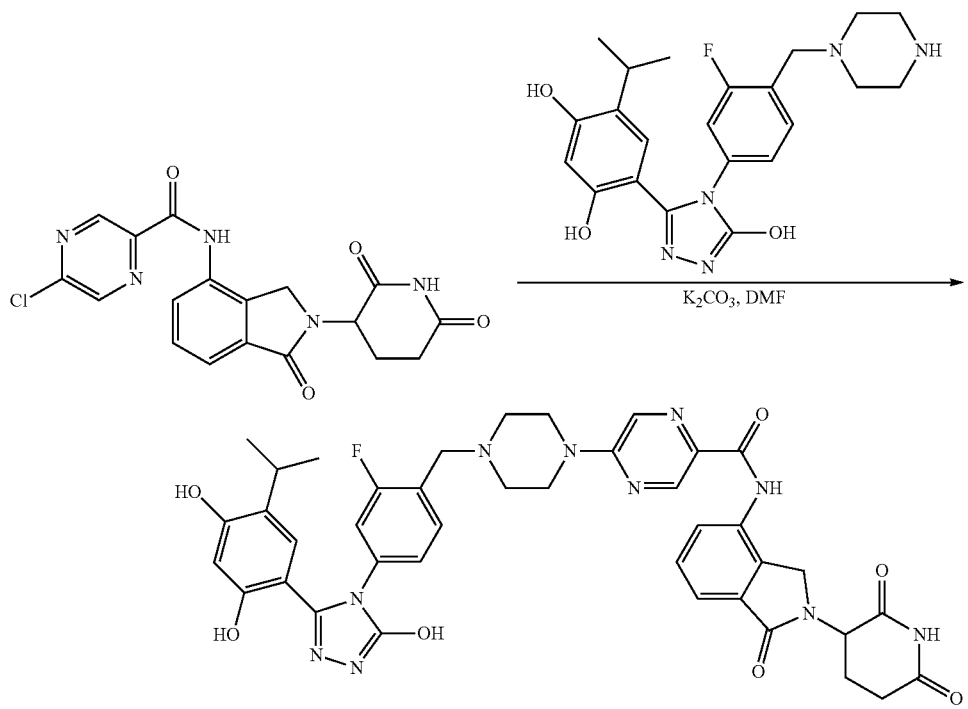

SDC-TRAP-0170

The solution of 5-chloro-N-(2-(2,6-dioxopiperidin-3-yl)-1-oxoisoindolin-4-yl) pyrazine-2-carboxamide (0.05 g, 0.13 mmol), 4-(4-(3-fluoro-4-(piperazin-1-ylmethyl)phenyl)-5-hydroxy-4H-1,2,4-triazol-3-yl)-6-isopropylbenzene-1,3-diol (0.06 g, 0.13 mmol), and K₂CO₃ (0.07 g, 0.51 mmol) in DMF (3 mL) was heated in a microwave at 50° C. for 1 hr. The solution was diluted with saturated NH₄Cl (5 mL), extracted with EtOAc (10 mL×3) and the combined organic phase was dried over Na₂SO₄ and concentrated. Column chromatography gave SDC-TRAP-0170 (0.86 g, 87%).

¹H NMR (400 MHz, DMSO-$d_6$) δ 12.00 (s, 1H), 11.00 (s, 1H), 10.29 (s, 1H), 9.64 (s, 1H), 9.41 (s, 1H), 8.73 (d, J=1.2 Hz, 1H), 8.34 (d, J=1.4 Hz, 1H), 7.85 (dd, J=7.6, 1.4 Hz, 1H), 7.62-7.50 (m, 2H), 7.44 (t, J=8.2 Hz, 1H), 7.09 (dd, J=10.8, 2.0 Hz, 1H), 6.99 (dd, J=8.2, 2.0 Hz, 1H), 6.87 (s, 1H), 6.27 (s, 1H), 5.14 (dd, J=13.3, 5.1 Hz, 1H), 4.55-4.38 (m, 2H), 3.74 (t, J=4.8 Hz, 4H), 3.59 (s, 2H), 3.33 (s, 2H), 3.17 (d, J=5.3 Hz, 1H), 3.06-2.83 (m, 2H), 2.63-2.53 (m, 2H), 2.48-2.32 (m, 1H), 2.03-1.95 (m, 1H), 1.00 (d, J=6.9 Hz, 6H); ESMS calculated ($C_{40}H_{39}FN_{10}O_7$): 790.3; found: 791.2 (M+H).

SDC-TRAP-0171

4-((((2-(2,6-dioxopiperidin-3-yl)-1-oxoisoindolin-4-yl)carbamoyl)oxy) methyl)phenyl-4-(4-(3-(2,4-dihydroxy-5-isopropylphenyl)-5-hydroxy-4H-1,2,4-triazol-4-yl)-2-fluorobenzyl)piperazine-1-carboxylate

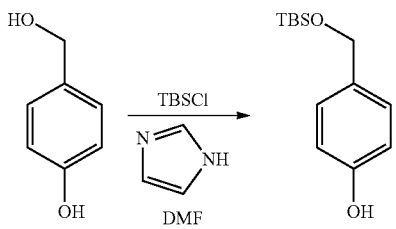

To a solution of 4-(hydroxymethyl)phenol (2 g, 16.1 mmol) in DMF (20 mL) was added TBSCl (2.7 g, 17.9 mmol) and imidazole (2.2 g, 32.3 mmol). The reaction was stirred at room temperature for 2 hr. The reaction was diluted with EtOAc (100 mL) and washed with 0.1 N HCl (50 mL×3). The organic phase was dried over Na₂SO₄ and concentrated. Column chromatography gave 4-(((tert-butyldimethylsilyl)oxy)methyl)phenol (2.6 g, 68%).

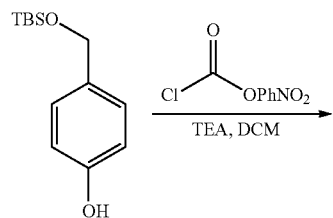

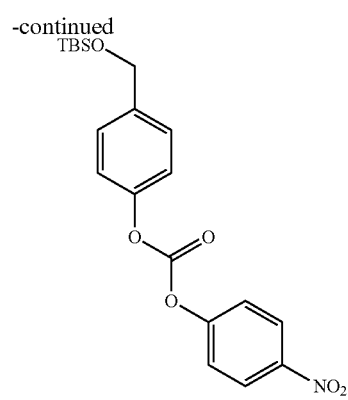

To the solution of 4-(((tert-butyldimethylsilyl)oxy)methyl)phenol (1.0 g, 4.2 mmol) in DCM (15 mL) was added 4-nitrophenyl chloroformate (1.0 g, 4.96 mmol) followed by TEA (1.8 mL, 12.9 mmol). The reaction was stirred at room temperature overnight. The reaction solution was concentrated and column chromatography gave 4-(((tert-butyldimethylsilyl)oxy)methyl)phenyl (4-nitrophenyl) carbonate (1.44 g, 85%).

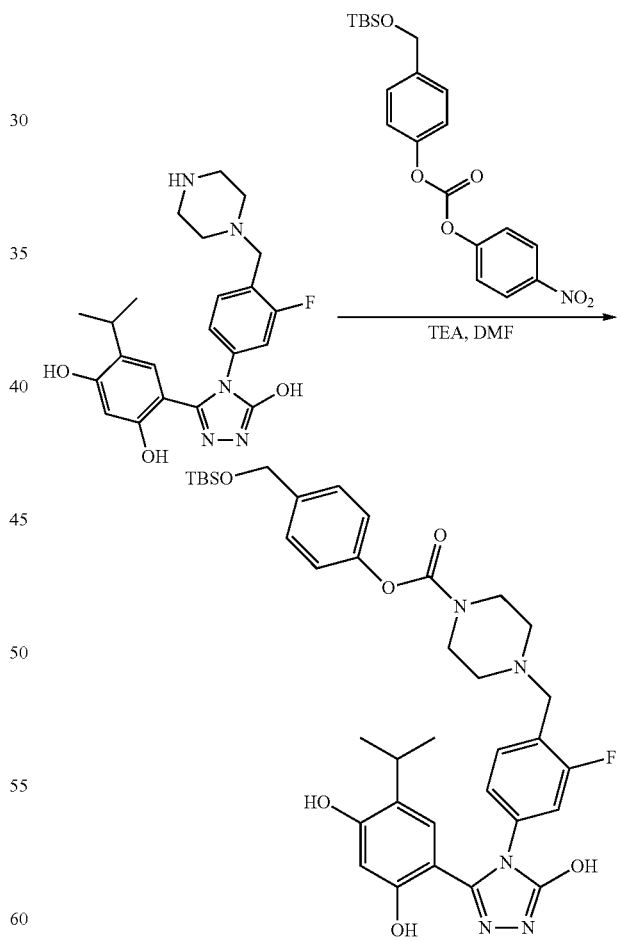

To a solution of 4-(4-(3-fluoro-4-(piperazin-1-ylmethyl)phenyl)-5-hydroxy-4H-1,2,4-triazol-3-yl)-6-isopropylbenzene-1,3-diol (0.32 g, 0.75 mmol) in DMF (5 mL) was added 4-(((tert-butyldimethylsilyl)oxy)methyl)phenyl (4-nitrophenyl) carbonate (0.36 g, 0.89 mmol) and TEA (0.31 mL, 2.22 mmol). The reaction was stirred at room temperature for 1 hr before it was quenched with saturated NH$_4$Cl (10 mL). The mixture was extracted with EtOAc (20 mL×2) and the combined organic phase was dried over Na$_2$SO$_4$ and concentrated. Column chromatography gave 4-(((tert-butyldimethylsilyl)oxy)methyl)phenyl 4-(4-(3-(2,4-dihydroxy-5-isopropylphenyl)-5-hydroxy-4H-1,2,4-triazol-4-yl)-2-fluorobenzyl)piperazine-1-carboxylate (0.38 g, 75%).

A solution of 4-(4-(3-(2,4-dihydroxy-5-isopropylphenyl)-5-hydroxy-4H-1,2,4-triazol-4-yl)-2-fluorobenzyl)piperazine-1-carboxylate (0.38 g, 0.55 mmol) and TBAF (0.29 g, 1.10 mmol) was heated at 40° C. for 30 min. The solution was concentrated and column chromatography gave 4-(hydroxymethyl)phenyl 4-(4-(3-(2,4-dihydroxy-5-isopropylphenyl)-5-hydroxy-4H-1,2,4-triazol-4-yl)-2-fluorobenzyl)piperazine-1-carboxylate (0.22 g, 70%).

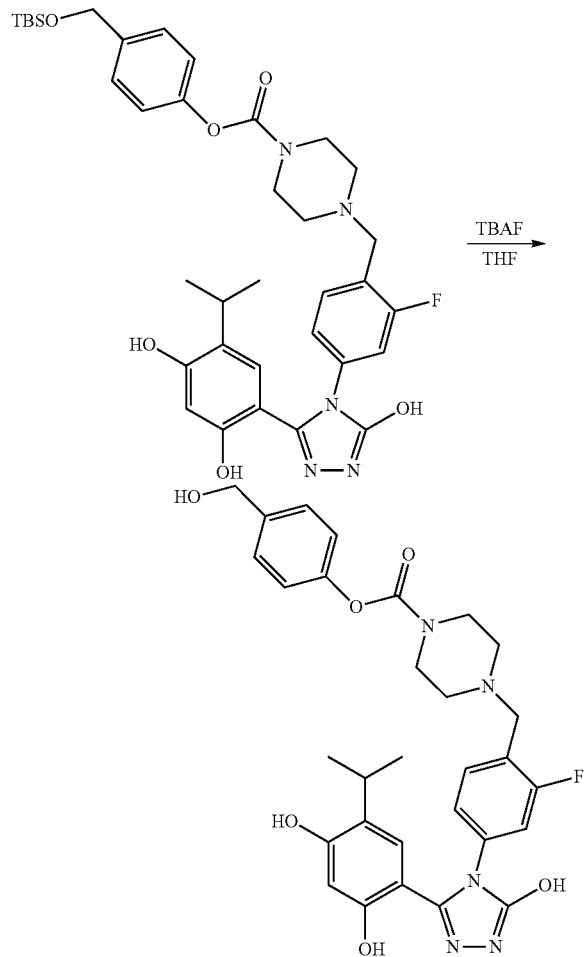

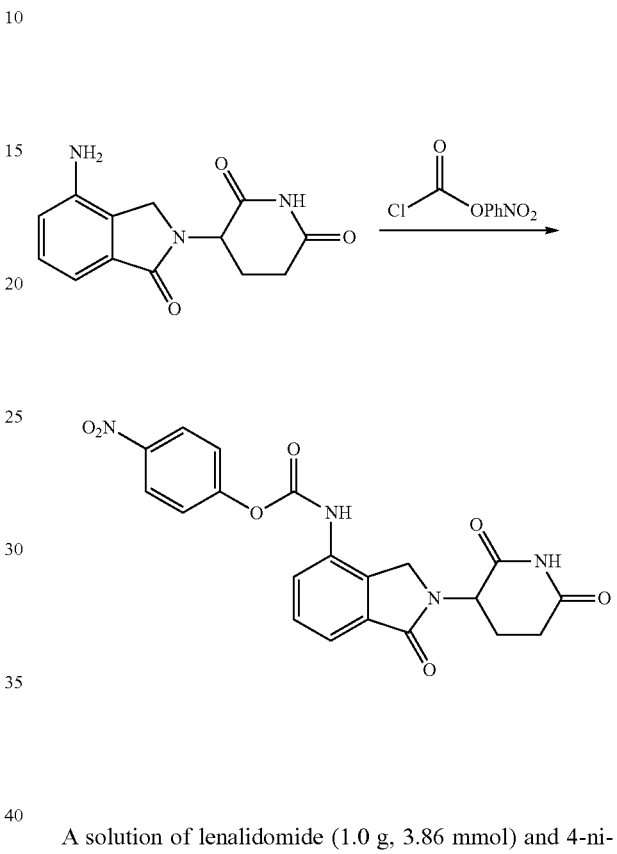

A solution of lenalidomide (1.0 g, 3.86 mmol) and 4-nitrophenyl chloroformate (1.15 g, 5.70 mmol) was heated at 65° C. for 1 hr. The solution was allowed to cool to room temperature, then filtered. The solid was dried and used for the next step without further purification.

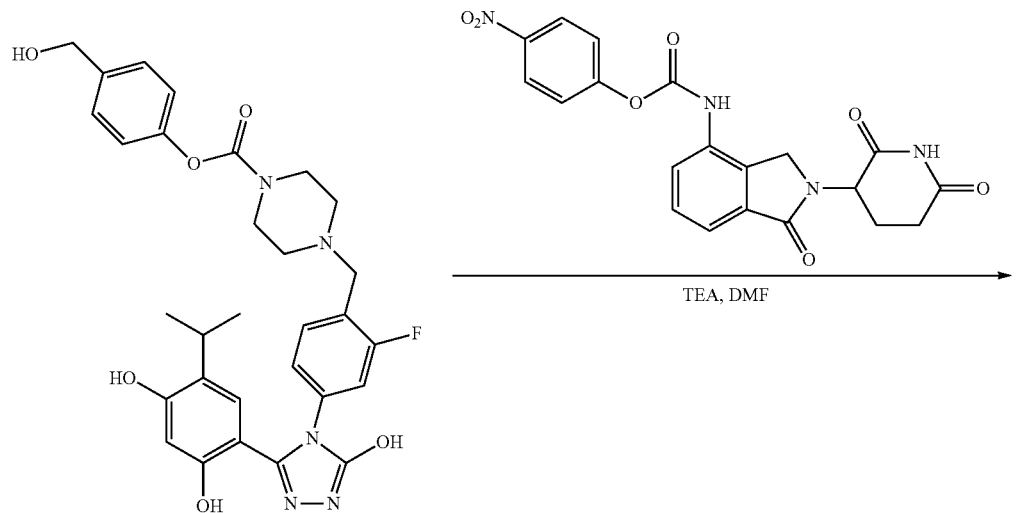

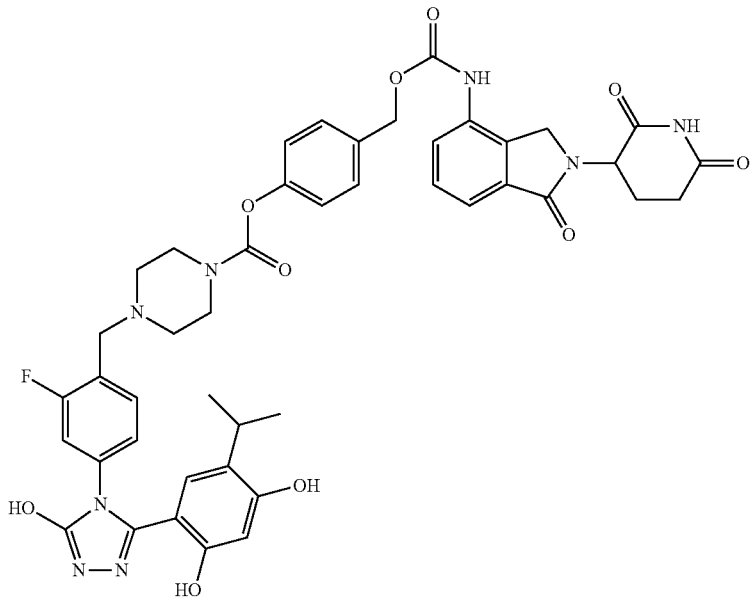

SDC-TRAP-0171

To the solution of 4-(hydroxymethyl)phenyl 4-(4-(3-(2,4-dihydroxy-5-isopropylphenyl)-5-hydroxy-4H-1,2,4-triazol-4-yl)-2-fluorobenzyl)piperazine-1-carboxylate (0.23 g, 0.39 mmol) in DMF (4 mL) was added 4-nitrophenyl (2-(2,6-dioxopiperidin-3-yl)-1-oxoisoindolin-4-yl)carbamate (0.27 g, 0.62 mmol) and TEA (0.17 mL, 1.17 mmol). The reaction was stirred at room temperature overnight before it was quenched with NH$_4$Cl (5 mL). The mixture was extracted with EtOAc (20 mL×2) and combined organic phase was dried over Na$_2$SO$_4$ and concentrated. Column chromatography gave SDC-TRAP-0171 (0.21 g, 65%) as an off-white solid.

$^1$H NMR (400 MHz, DMSO-d$_6$) δ 11.96 (s, 1H), 10.98 (s, 1H), 9.65 (s, 1H), 9.59 (s, 1H), 9.37 (s, 1H), 7.79 (dd, J=6.5, 2.5 Hz, 1H), 7.54-7.37 (m, 5H), 7.18-7.04 (m, 3H), 6.99 (dd, J=8.1, 2.0 Hz, 1H), 6.87 (s, 1H), 6.27 (s, 1H), 5.19-5.06 (m, 3H), 4.38 (q, J=17.6 Hz, 2H), 4.11-3.98 (m, 1H), 3.57 (s, 3H), 3.41 (d, J=7.6 Hz, 1H), 3.28 (s, 1H), 3.17 (d, J=5.3 Hz, 1H), 3.07-2.83 (m, 2H), 2.60 (d, J=17.3 Hz, 1H), 2.45 (s, 3H), 2.39-2.24 (m, 1H), 2.04-1.99 (m, 1H), 1.00 (d, J=6.9 Hz, 6H); ESMS calculated (C$_{44}$H$_{43}$FN$_8$O$_{10}$): 862.3; found: 863.2 (M+H).

SDC-TRAP-0182

4-((((2-(2,6-dioxopiperidin-3-yl)-1-oxoisoindolin-4-yl)carbamoyl)oxy)methyl)-2,6-dimethylphenyl 4-(4-(3-(2,4-dihydroxy-5-isopropylphenyl)-5-hydroxy-4H-1,2,4-triazol-4-yl)-2-fluorobenzyl)piperazine-1-carboxylate

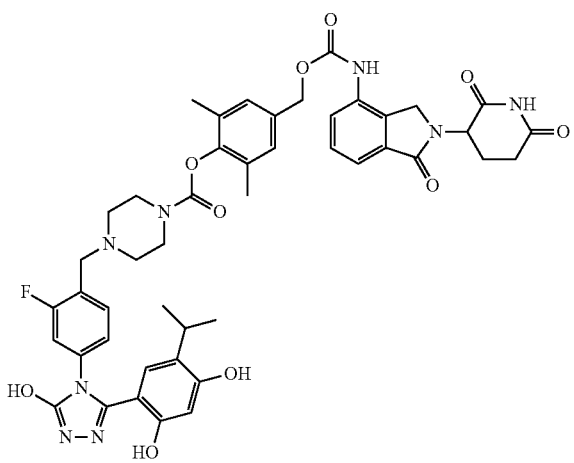 [SMILES: Cc1cc(COC(=O)Nc2cccc3c2CN(C2CCC(=O)NC2=O)C3=O)cc(C)c1OC(=O)N1CCN(Cc2ccc(-n3c(O)nnc3-c3cc(C(C)C)c(O)cc3O)cc2F)CC1]

$^1$H NMR (400 MHz, DMSO-d$_6$) δ 11.99 (s, 1H), 11.02 (s, 1H), 9.65 (d, J=13.1 Hz, 2H), 9.41 (s, 1H), 7.79 (dd, J=6.8, 2.3 Hz, 1H), 7.54-7.38 (m, 3H), 7.16 (s, 2H), 7.08 (dd, J=11.0, 2.0 Hz, 1H), 6.99 (dd, J=8.2, 2.0 Hz, 1H), 6.88 (s, 1H), 6.27 (s, 1H), 5.17-5.06 (m, 3H), 4.47-4.29 (m, 2H), 3.72-3.61 (m, 2H), 3.56 (s, 2H), 3.44 (d, J=6.5 Hz, 2H), 3.07-2.84 (m, 2H), 2.65-2.55 (m, 1H), 2.45 (s, 4H), 2.38-2.23 (m, 1H), 2.10 (s, 6H), 2.05-1.96 (m, 1H), 1.01 (d, J=6.9 Hz, 6H); ESMS calculated ($C_{46}H_{47}FN_8O_{10}$): 890.3; found: 891.2 (M+H).

SDC-TRAP-0187

4-((((2-(2,6-dioxopiperidin-3-yl)-1-oxoisoindolin-4-yl)carbamoyl)oxy) methyl)-2, 6-dimethylphenyl 4-(4-(3-(2,4-dihydroxy-5-isopropylphenyl)-5-(ethyl-carbamoyl)-4H-1,2,4-triazol-4-yl)phenoxy)piperidine-1-carboxylate

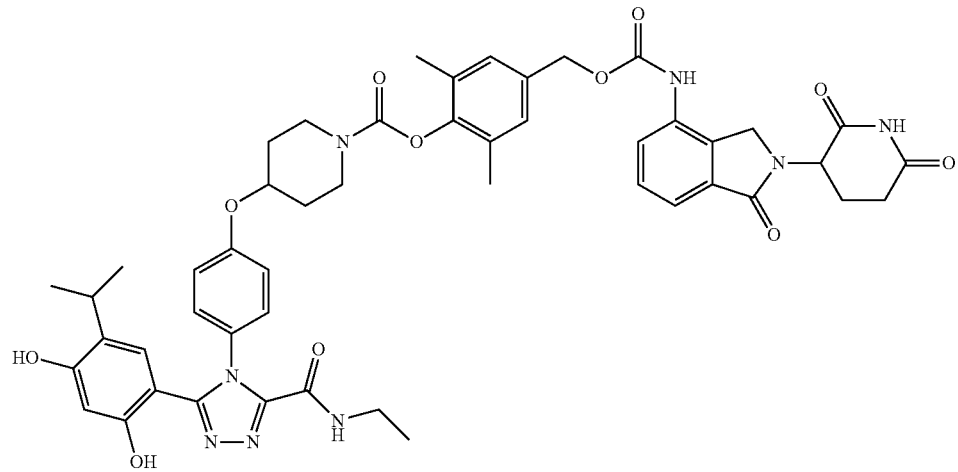 [SMILES: CCNC(=O)c1nnc(-c2cc(C(C)C)c(O)cc2O)n1-c1ccc(OC2CCN(C(=O)Oc3c(C)cc(COC(=O)Nc4cccc5c4CN(C4CCC(=O)NC4=O)C5=O)cc3C)CC2)cc1]

ESMS calculated ($C_{49}H_{52}N_8O_{11}$): 928.4; found: 929.1 (M+H).

SDC-TRAP-0017

3-(5-(3-(2,4-dihydroxy-5-isopropylphenyl)-5-hydroxy-4H-1,2,4-triazol-4-yl)-1H-indol-1-yl)-N-(2-(2,6-dioxopiperidin-3-yl)-1-oxoisoindolin-4-yl)propanamide

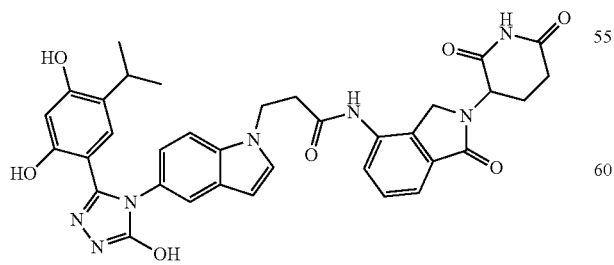

ESMS calculated for $C_{35}H_{33}N_7O_7$: 663.24; Found: 664.2 (M+H)$^+$.

SDC-TRAP-0015

N1-(2-(2-(5-(3-(2,4-dihydroxy-5-isopropylphenyl)-5-hydroxy-4H-1,2,4-triazol-4-yl)-1H-indol-1-yl)ethoxy)ethyl)-N5-(2-(2, 6-dioxopiperidin-3-yl)-1-oxoisoindolin-4-yl)glutaramide

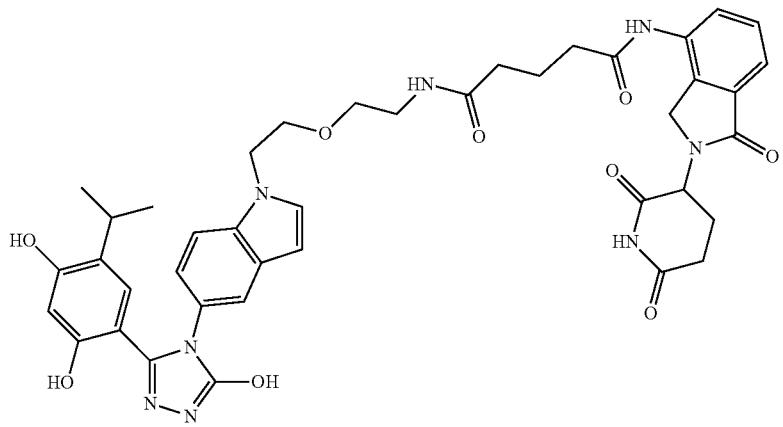 [SMILES: CC(C)c1cc(-c2nnc(O)n2-c2ccc3c(ccn3CCOCCNC(=O)CCCC(=O)Nc3cccc4c3CN(C3CCC(=O)NC3=O)C4=O)c2)c(O)cc1O]

¹H NMR (400 MHz, DMSO-d₆) δ 11.87 (s, 1H), 11.02 (s, 1H), 9.90 (s, 1H), 9.52 (s, 1H), 9.47 (s, 1H), 7.97-7.83 (m 2H), 7.55-7.38 (m, 4H), 6.92 (d, J=8.7 Hz, 1H), 6.73 (s, 1H), 6.41 (s, 1H), 6.23 (s, 1H), 5.13 (d, J=13.6 Hz, 1H), 4.37 (dd, J=26.6, 17.5 Hz, 4H), 3.70-3.39 (m, 6H), 2.91 (q, J=12.5, 11.7 Hz, 3H), 2.37 (d, J=8.9 Hz, 4H), 2.13 (t, J=7.3 Hz, 2H), 2.06-1.96 (m, 2H), 1.86-1.77 (m, 2H), 1.22-0.90 (m, 2H), 0.83 (d, J=6.7 Hz, 6H). ESMS calculated for $C_{41}H_{44}N_8O_9$: 792.32; Found: 793.2 (M+H)⁺.

SDC-TRAP-0018

N1-(2-(5-(3-(2,4-dihydroxy-5-isopropylphenyl)-5-hydroxy-4H-1,2,4-triazol-4-yl)-1H-indol-1-yl)ethyl)-N5-(2-(2, 6-dioxopiperidin-3-yl)-1-oxoisoindolin-4-yl)-N1-methylglutaramide

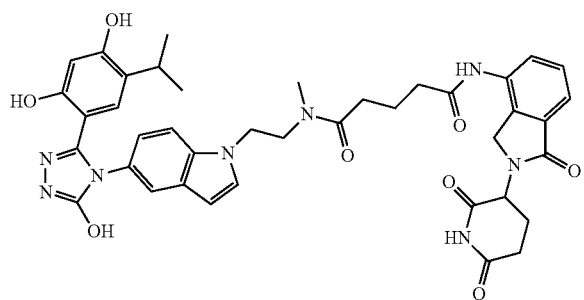 [SMILES: CC(C)c1cc(-c2nnc(O)n2-c2ccc3c(ccn3CCN(C)C(=O)CCCC(=O)Nc3cccc4c3CN(C3CCC(=O)NC3=O)C4=O)c2)c(O)cc1O]

¹H NMR (400 MHz, DMSO-d₆) δ 11.94 (bs, 1H), 11.01 (s, 1H), 9.79 (s, 1H), 9.45 (d, J=7.0 Hz, 2H), 7.79 (dd, J=18.5, 7.1 Hz, 1H), 7.50-7.38 (m, 5H), 6.94 (t, J=7.6 Hz, 1H), 6.74 (d, J=9.7 Hz, 1H), 6.44 (s, 1H), 6.23 (s, 1H), 5.14 (dd, J=12.6, 6.1 Hz, 1H), 4.49-4.24 (m, 4H), 3.65-3.54 (m, 4H), 3.17 (d, J=4.6 Hz, 1H), 2.89 (d, J=12.7 Hz, 5H), 2.76 (s, 2H), 2.45-2.24 (m, 4H), 2.13-1.97 (m, 4H), 1.80 (d, J=13.2 Hz, 2H), 1.60-1.52 (m, 1H), 0.82 (d, J=7.9 Hz, 6H). ESMS calculated for $C_{40}H_{42}N_8O_8$: 762.31; Found: 763.2 (M+H)⁺.

SDC-TRAP-0021

2-(3-(2-(5-(3-(2,4-dihydroxy-5-isopropylphenyl)-5-hydroxy-4H-1,2,4-triazol-4-yl)-1H-indol-1-yl)ethyl)-3-methylureido)-N-(2-(2,6-dioxopiperidin-3-yl)-1-oxoisoindolin-4-yl)acetamide

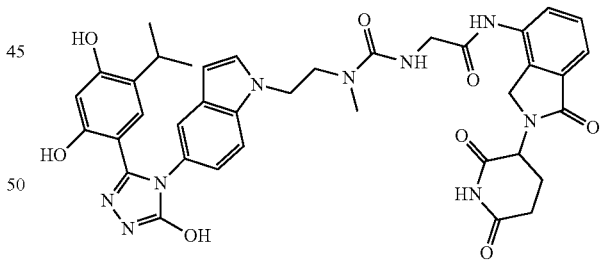

¹H NMR (400 MHz, DMSO-d₆) δ 11.87 (s, 1H), 11.01 (s, 1H), 9.83 (s, 1H), 9.53 (s, 1H), 9.47 (s, 1H), 7.86 (dd, J=6.3, 2.7 Hz, 1H), 7.58-7.46 (m, 3H), 7.41 (dd, J=8.3, 2.6 Hz, 2H), 6.94 (dd, J=8.7, 2.0 Hz, 1H), 6.82-6.70 (m, 2H), 6.43 (dd, J=3.2, 0.8 Hz, 1H), 6.23 (s, 1H), 5.14 (dd, J=13.3, 5.1 Hz, 1H), 4.46-4.26 (m, 4H), 3.91-3.84 (m, 2H), 3.59-3.50 (m, 2H), 2.97-2.83 (m, 2H), 2.59 (s, 4H), 2.36-2.20 (m, 1H), 1.99 (s, 1H), 0.82 (d, J=6.8 Hz, 6H). ESMS calculated for $C_{38}H_{39}N_9O_8$: 749.29; Found: 750.2 (M+H)⁺.

SDC-TRAP-0033

N1-(2-(2-(5-(3-(2,4-dihydroxy-5-isopropylphenyl)-5-hydroxy-4H-1,2,4-triazol-4-yl)-1H-indol-1-yl)ethoxy)ethyl)-N4-(2-(2, 6-dioxopiperidin-3-yl)-1-oxoisoindolin-4-yl)-N1-methylsuccinamide

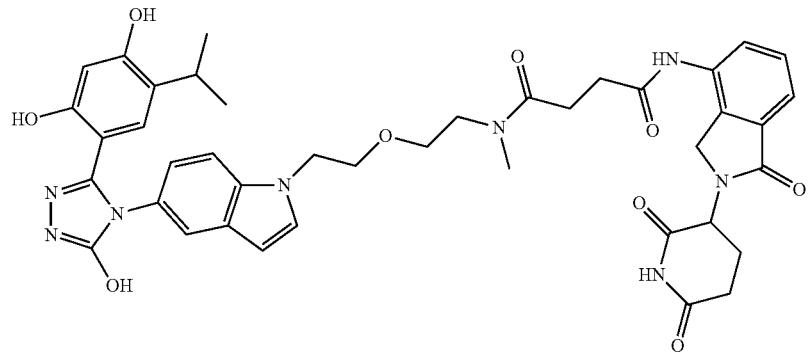 [SMILES: CC(C)c1cc(-c2nnc(O)n2-c2ccc3c(ccn3CCOCCN(C)C(=O)CCC(=O)Nc3cccc4c3CN(C3CCC(=O)NC3=O)C4=O)c2)c(O)cc1O]

$^1$H NMR (400 MHz, DMSO-d$_6$) δ 11.89 (m, 1H), 11.03 (s, 1H), 9.86 (s, 1H), 9.58 (s, 1H), 9.50 (s, 1H), 7.94-7.81 (m, 2H), 7.74-7.30 (m, 7H), 6.93 (d, J=8.7 Hz, 1H), 6.74 (s, 1H), 6.42 (d, J=7.5 Hz, 1H), 6.24 (s, 1H), 5.15 (d, J=12.7 Hz, 1H), 4.51-4.37 (m, 4H), 3.86-3.42 (m, 5H), 3.19 (m, 1H), 2.90-2.51 (m, 9H), 2.31-2.04 (m, 4H), 0.84 (d, J=5.9 Hz, 6H). ESMS calculated for C$_{41}$H$_{44}$N$_8$O$_9$: 792.32; Found: 793.3 (M+H)$^+$.

SDC-TRAP-0041

5-(4-(4-(3-(2,4-dihydroxy-5-isopropylphenyl)-5-hydroxy-4H-1,2,4-triazol-4-yl)benzyl)piperazin-1-yl)-N-(2-(2,6-dioxopiperidin-3-yl)-1-oxoisoindolin-4-yl)-5-oxopentanamide

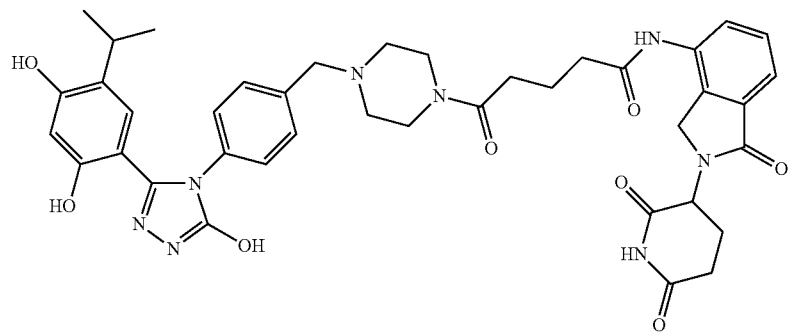 [SMILES: CC(C)c1cc(-c2nnc(O)n2-c2ccc(CN3CCN(C(=O)CCCC(=O)Nc4cccc5c4CN(C4CCC(=O)NC4=O)C5=O)CC3)cc2)c(O)cc1O]

$^1$H NMR (400 MHz, DMSO-d$_6$) δ 11.94 (s, 1H), 11.03 (s, 1H), 9.80 (s, 1H), 9.62 (s, 1H), 9.42 (s, 1H), 7.83 (dd, J=6.9, 2.1 Hz, 1H), 7.50 (d, J=7.1 Hz, 2H), 7.31 (d, J=8.0 Hz, 2H), 7.15 (d, J=7.9 Hz, 2H), 6.78 (s, 1H), 6.27 (s, 1H), 5.15 (dd, J=13.2, 5.1 Hz, 1H), 4.45-4.29 (m, 2H), 3.62-3.54 (m, 1H), 3.44 (dd, J=14.8, 8.9 Hz, 8H), 3.03-2.85 (m, 2H), 2.60 (dd, J=22.9, 8.3 Hz, 2H), 2.49-2.25 (m, 10H), 2.08-1.97 (m, 1H), 1.82 (p, J=7.4 Hz, 2H), 0.95 (d, J=6.9 Hz, 6H). ESMS calculated for C$_{40}$H$_{44}$N$_8$O$_8$: 764.33; Found: 765.3 (M+H)$^+$.

201

SDC-TRAP-0109

4-(4-(3-(2,4-dihydroxy-5-isopropylphenyl)-5-hydroxy-4H-1,2,4-triazol-4-yl)benzyl)-N-(2-(2,6-dioxopiperidin-3-yl)-1-oxoisoindolin-4-yl)piperazine-1-carboxamide

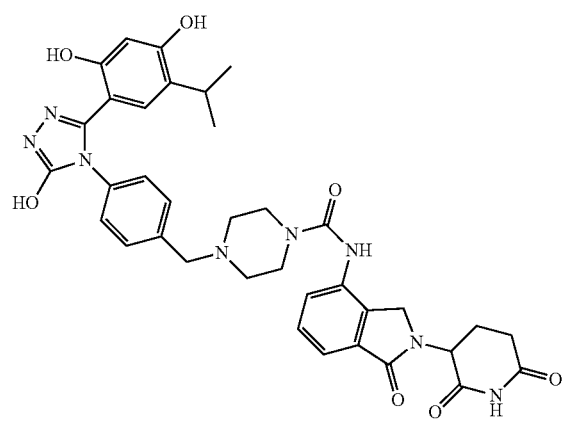 [SMILES: CC(C)c1cc(-c2nnc(O)n2-c2ccc(CN3CCN(C(=O)Nc4cccc5c4CN(C4CCC(=O)NC4=O)C5=O)CC3)cc2)c(O)cc1O]

$^1$H NMR (400 MHz, DMSO-d$_6$) δ 11.94 (s, 1H), 10.99 (s, 1H), 9.61 (s, 1H), 9.42 (s, 1H), 8.57 (s, 1H), 7.53-7.39 (m, 3H), 7.33 (d, J=8.0 Hz, 2H), 7.15 (d, J=8.0 Hz, 2H), 6.77 (s, 1H), 6.27 (s, 1H), 5.12 (dd, J=13.2, 5.2 Hz, 1H), 4.36-4.30 (m, 2H), 3.53-3.41 (m, 6H), 3.38 (s, 1H), 2.92 (ddd, J=31.5, 15.9, 6.1 Hz, 2H), 2.64-2.54 (m, 1H), 2.47-2.35 (m, 5H), 0.94 (d, J=6.9 Hz, 6H). ESMS calculated for C$_{36}$H$_{38}$N$_8$O$_7$: 694.29; Found: 695.2 (M+H)$^+$.

SDC-TRAP-0110

2-(4-(4-(3-(2,4-dihydroxy-5-isopropylphenyl)-5-hydroxy-4H-1,2,4-triazol-4-yl)phenyl)piperazin-1-yl)-N-(2-(2,6-dioxopiperidin-3-yl)-1-oxoisoindolin-4-yl)acetamide

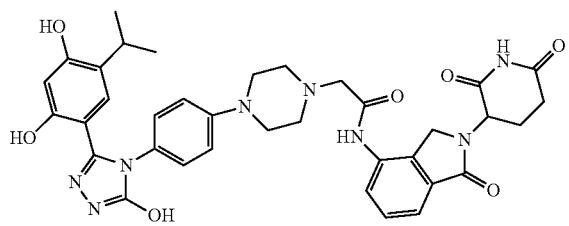 [SMILES: CC(C)c1cc(-c2nnc(O)n2-c2ccc(N3CCN(CC(=O)Nc4cccc5c4CN(C4CCC(=O)NC4=O)C5=O)CC3)cc2)c(O)cc1O]

$^1$H NMR (400 MHz, DMSO-d$_6$) δ 11.83 (s, 1H), 11.00 (s, 1H), 9.77 (s, 1H), 9.57 (s, 1H), 9.44 (s, 1H), 7.80 (dd, J=7.5, 1.5 Hz, 1H), 7.58-7.47 (m, 2H), 7.06-6.98 (m, 2H), 6.97-6.89 (m, 2H), 6.78 (s, 1H), 6.27 (s, 1H), 5.12 (dd, J=13.3, 5.1 Hz, 1H), 4.47-4.32 (m, 2H), 3.23 (d, J=5.8 Hz, 6H), 3.03-2.83 (m, 3H), 2.76-2.55 (m, 6H), 2.47-2.32 (m, 1H), 2.02 (td, J=7.5, 3.9 Hz, 1H), 0.96 (d, J=6.9 Hz, 6H).

ESMS calculated for C$_{36}$H$_{38}$N$_8$O$_7$: 694.29; Found: 695.2 (M+H)$^+$.

202

SDC-TRAP-0114

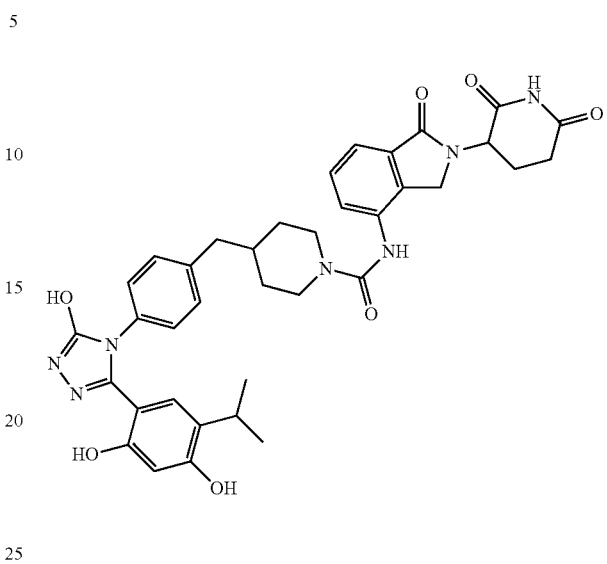

4-(4-(3-(2,4-dihydroxy-5-isopropylphenyl)-5-hydroxy-4H-1,2,4-triazol-4-yl)benzyl)-N-(2-(2,6-dioxopiperidin-3-yl)-1-oxoisoindolin-4-yl)piperidine-1-carboxamide ESMS calculated for C$_{37}$H$_{39}$N$_7$O$_7$: 693.29; Found: 694.2 (M+H)$^+$.

SDC-TRAP-0115

N-(2-(2,6-dioxopiperidin-3-yl)-1-oxoisoindolin-4-yl)-1-(4-(3-(2-hydroxy-5-isopropyl-4-methoxyphenyl)-5-(isopropylcarbamoyl)-4H-1,2,4-triazol-4-yl)benzyl)piperidine-4-carboxamide

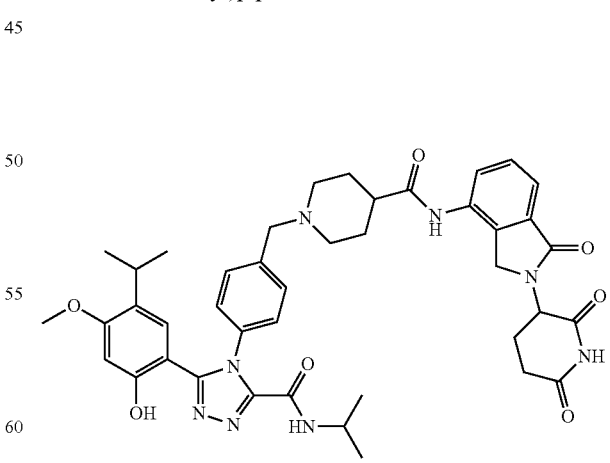

ESMS calculated for C$_{42}$H$_{48}$N$_8$O$_7$: 776.36; Found: 777.3 (M+H)$^+$.

SDC-TRAP-0116

2-(4-(4-(3-(2,4-dihydroxy-5-isopropylphenyl)-5-hydroxy-4H-1,2,4-triazol-4-yl)benzyl)piperidin-1-yl)-N-(2-(2,6-dioxopiperidin-3-yl)-1-oxoisoindolin-4-yl)acetamide

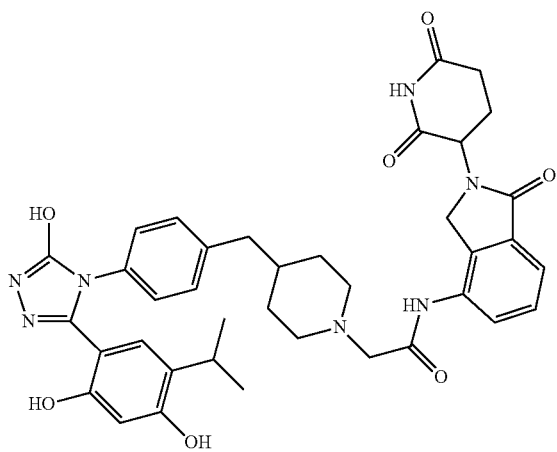 [SMILES: CC(C)c1cc(-c2nnc(O)n2-c2ccc(CC3CCN(CC(=O)Nc4cccc5c4CN(C4CCC(=O)NC4=O)C5=O)CC3)cc2)c(O)cc1O]

$^1$H NMR (400 MHz, DMSO-d$_6$) δ 11.91 (s, 1H), 11.01 (s, 1H), 9.69 (s, 1H), 9.58 (s, 1H), 9.42 (s, 1H), 7.77 (dd, J=7.5, 1.5 Hz, 1H), 7.58-7.46 (m, 2H), 7.18 (d, J=8.4 Hz, 2H), 7.14-7.06 (m, 2H), 6.74 (s, 1H), 6.27 (s, 1H), 5.13 (dd, J=13.2, 5.1 Hz, 1H), 4.45-4.30 (m, 2H), 3.20-3.09 (m, 3H), 3.03-2.83 (m, 4H), 2.60 (ddd, J=17.4, 4.3, 2.4 Hz, 1H), 2.37 (qd, J=12.5, 11.8, 5.9 Hz, 1H), 2.14-1.96 (m, 3H), 1.60-1.44 (m, 3H), 1.38-1.24 (m, 2H), 0.92 (d, J=6.9 Hz, 6H).

ESMS calculated for C$_{38}$H$_{41}$N$_7$O$_7$: 707.31; Found: 708.2 (M+H)$^+$.

SDC-TRAP-0119

4-(2-(5-(3-(2,4-dihydroxy-5-isopropylphenyl)-5-hydroxy-4H-1,2,4-triazol-4-yl)-1H-indol-1-yl)ethyl)-N-(2-(2,6-dioxopiperidin-3-yl)-1-oxoisoindolin-4-yl)piperidine-1-carboxamide

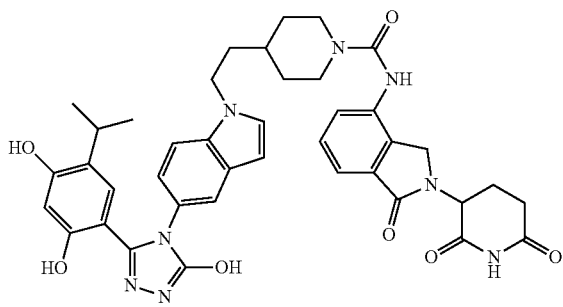 [SMILES: CC(C)c1cc(-c2nnc(O)n2-c2ccc3c(ccn3CCC3CCN(C(=O)Nc4cccc5c4CN(C4CCC(=O)NC4=O)C5=O)CC3)c2)c(O)cc1O]

$^1$H NMR (400 MHz, DMSO-d$_6$) δ 11.90 (s, 1H), 10.99 (s, 1H), 9.54 (d, J=17.1 Hz, 2H), 8.50 (s, 1H), 7.53-7.41 (m, 6H), 6.95 (d, J=8.7 Hz, 1H), 6.69 (s, 1H), 6.47-6.41 (m, 1H), 6.25 (s, 1H), 5.12 (dd, J=13.1, 5.2 Hz, 1H), 4.33 (s, 2H), 4.24 (t, J=6.9 Hz, 2H), 4.11-3.99 (m, 2H), 2.90 (td, J=13.9, 6.3 Hz, 2H), 2.75 (t, J=12.8 Hz, 2H), 2.60-2.55 (m, 1H), (2.45-2.34 (m, 1H), 2.00 (d, J=8.5 Hz, 1H), 1.74 (d, J=13.1 Hz, 4H), 1.43 (s, 1H), 1.21-1.07 (m, 2H), 0.80 (d, J=6.8 Hz, 6H).

ESMS calculated for C$_{40}$H$_{42}$N$_8$O$_7$: 746.32; Found: 747.3 (M+H)$^+$.

SDC-TRAP-0120

N1-(2-(2-(5-(3-(2,4-dihydroxy-5-isopropylphenyl)-5-hydroxy-4H-1,2,4-triazol-4-yl)-1H-indol-1-yl)ethoxy)ethyl)-N5-(2-(2,6-dioxopiperidin-3-yl)-1-oxoisoindolin-4-yl)-N1-methylglutaramide

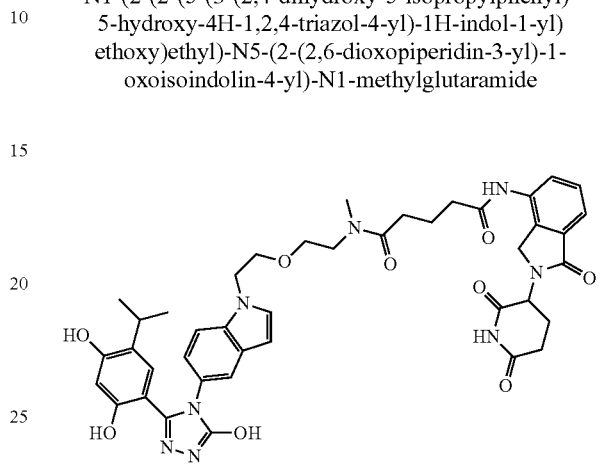

$^1$H NMR (400 MHz, DMSO-d$_6$) δ 11.87 (s, 1H), 11.02 (s, 1H), 9.80 (d, J=4.4 Hz, 1H), 9.54 (s, 1H), 9.47 (s, 1H), 7.82 (dt, J=7.4, 2.1 Hz, 1H), 7.54-7.31 (m, 5H), 6.91 (dd, J=8.7, 2.0 Hz, 1H), 6.73 (d, J=2.1 Hz, 1H), 6.40 (dd, J=7.0, 3.1 Hz, 1H), 6.22 (s, 1H), 5.19-5.09 (m, 1H), 4.45-4.26 (m, 4H), 3.70-3.63 (m, 2H), 3.49-3.33 (m, 4H), 2.98-2.80 (m, 4H), 2.75 (s, 1H), 2.60 (ddd, J=17.1, 4.3, 2.3 Hz, 1H), 2.35 (ddd, J=31.6, 15.2, 7.4 Hz, 5H), 1.80 (p, J=7.4 Hz, 2H), 0.83 (dd, J=6.9, 2.1 Hz, 6H). ESMS calculated for C$_{42}$H$_{46}$N$_8$O$_9$: 806.34; Found: 807.3 (M+H)$^+$.

SDC-TRAP-0121

2-(4-(4-(3-(2,4-dihydroxy-5-isopropylphenyl)-5-hydroxy-4H-1,2,4-triazol-4-yl)benzyl)piperazin-1-yl)-2-oxoethyl(2-(2,6-dioxopiperidin-3-yl)-1-oxoisoindolin-4-yl)carbamate

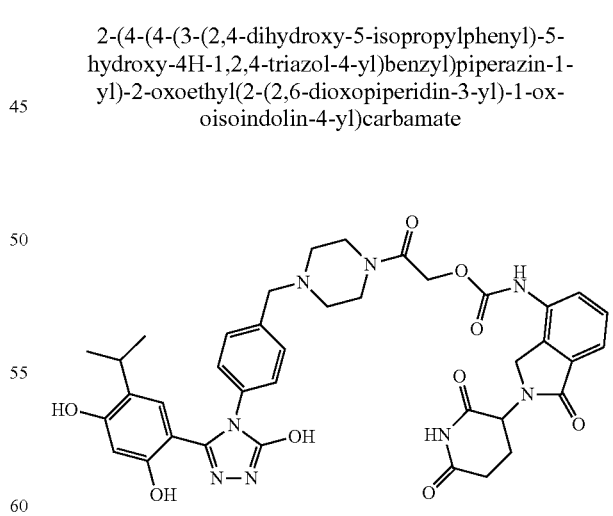

$^1$H NMR (400 MHz, DMSO-d$_6$) δ 11.93 (s, 1H), 11.01 (s, 1H), 9.77 (s, 1H), 9.60 (s, 1H), 9.40 (s, 1H), 7.77 (dt, J=7.0, 3.6 Hz, 1H), 7.56-7.46 (m, 2H), 7.32 (d, J=8.0 Hz, 2H), 7.15 (d, J=7.8 Hz, 2H), 6.78 (s, 1H), 6.27 (s, 1H), 5.12 (dd, J=13.3, 5.1 Hz, 1H), 4.85 (s, 2H), 4.45-4.35 (m, 2H), 3.49 (s, 2H), 3.44 (s, 3H), 3.03-2.84 (m, 2H), 2.61 (d, J=17.6 Hz,

1H), 2.42-2.26 (m, 6H), 2.07-1.99 (m, 1H), 0.95 (d, J=6.9 Hz, 6H). ESMS calculated for $C_{38}H_{40}N_8O_9$: 752.29; Found: 753.3 (M+H)$^+$.

SDC-TRAP-0128

2-(4-(4-(3-(2,4-dihydroxy-5-isopropylphenyl)-5-hydroxy-4H-1,2,4-triazol-4-yl)benzyl)piperazin-1-yl)-N-(2-(2,6-dioxopiperidin-3-yl)-1-oxoisoindolin-4-yl)acetamide

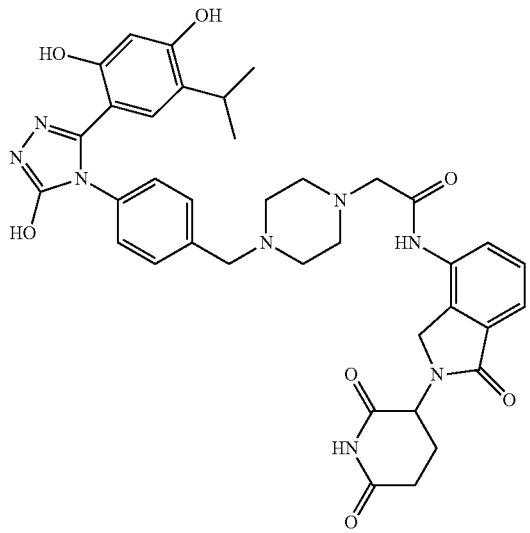 [SMILES: CC(C)c1cc(-c2nnc(O)n2-c2ccc(CN3CCN(CC(=O)Nc4cccc5c4CN(C4CCC(=O)NC4=O)C5=O)CC3)cc2)c(O)cc1O]

$^1$H NMR (400 MHz, DMSO-d$_6$) δ 11.92 (s, 1H), 11.01 (s, 1H), 9.71 (s, 1H), 9.59 (s, 1H), 9.40 (s, 1H), 7.79 (dd, J=7.4, 1.5 Hz, 1H), 7.58-7.46 (m, 2H), 7.30 (d, J=8.0 Hz, 2H), 7.13 (d, J=8.0 Hz, 2H), 6.77 (s, 1H), 6.26 (s, 1H), 5.12 (dd, J=13.2, 5.1 Hz, 1H), 4.45-4.29 (m, 2H), 3.46 (s, 2H), 3.16 (s, 2H), 3.02-2.84 (m, 2H), 2.65-2.50 (m, 5H), 2.47-2.32 (m, 5H), 1.99 (m, 1H), 0.94 (d, J=6.9 Hz, 6H). ESMS calculated for $C_{37}H_{40}N_8O_7$: 708.30; Found: 709.3 (M+H)$^+$.

SDC-TRAP-0129

2-(4-(2-(5-(3-(2,4-dihydroxy-5-isopropylphenyl)-5-hydroxy-4H-1,2,4-triazol-4-yl)-1H-indol-1-yl)ethyl)piperidin-1-yl)-N-(2-(2,6-dioxopiperidin-3-yl)-1-oxoisoindolin-4-yl)acetamide

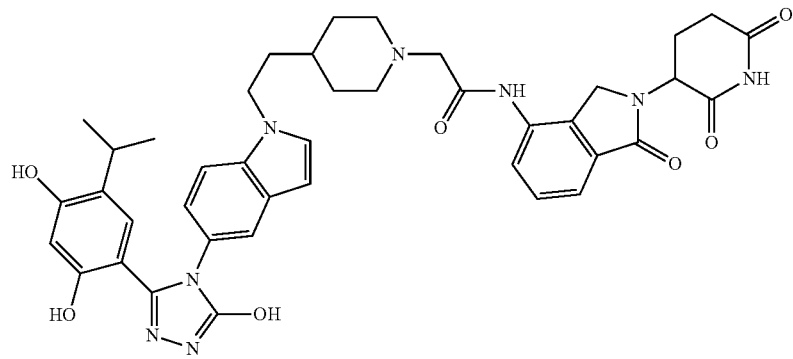 [SMILES: CC(C)c1cc(-c2nnc(O)n2-c2ccc3c(ccn3CCC3CCN(CC(=O)Nc4cccc5c4CN(C4CCC(=O)NC4=O)C5=O)CC3)c2)c(O)cc1O]

$^1$H NMR (400 MHz, DMSO-d$_6$) δ 11.89 (s, 1H), 11.00 (s, 1H), 9.70 (s, 1H), 9.54 (d, J=14.6 Hz, 2H), 7.77 (dd, J=7.4, 1.5 Hz, 1H), 7.58-7.40 (m, 5H), 6.94 (dd, J=8.7, 2.1 Hz, 1H), 6.67 (s, 1H), 6.43 (d, J=3.1 Hz, 1H), 6.24 (s, 1H), 5.12 (dd, J=13.2, 5.1 Hz, 1H), 4.45-4.29 (m, 2H), 4.22 (t, J=7.2 Hz, 2H), 3.12 (s, 2H), 2.87 (q, J=6.9 Hz, 4H), 2.59 (d, J=17.3 Hz, 1H), 2.46-2.33 (m, 1H), 2.09-2.04 (m, 5H), 1.69 (d, J=6.9 Hz, 4H), 1.36-1.25 (m, 2H), 0.78 (d, J=6.8 Hz, 6H). ESMS calculated for $C_{41}H_{44}N_8O_7$: 760.33; Found: 761.2 (M+H)$^+$.

SDC-TRAP-0131

2-(4-(4-(3-(2,4-dihydroxy-5-isopropylphenyl)-5-hydroxy-4H-1,2,4-triazol-4-yl)benzyl)piperidin-1-yl)-2-oxoethyl(2-(2,6-dioxopiperidin-3-yl)-1-oxoisoindolin-4-yl)carbamate

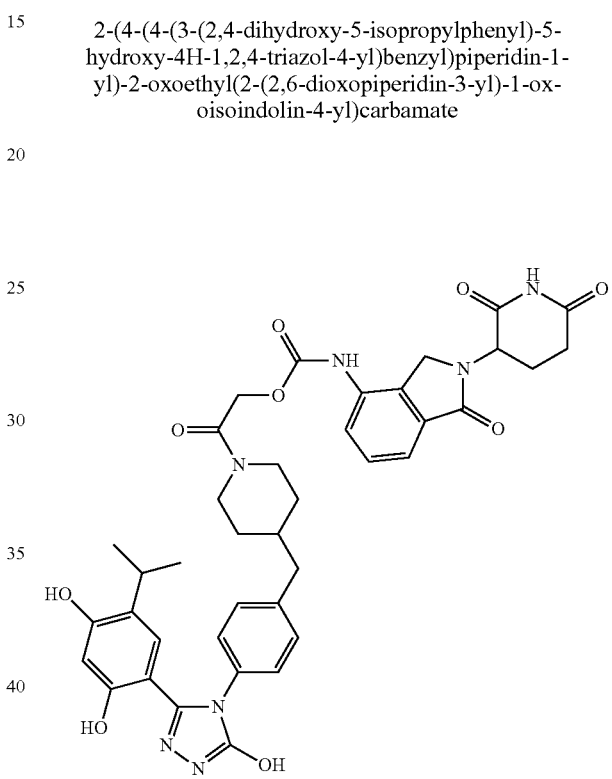

$^1$H NMR (400 MHz, DMSO-d$_6$) δ 11.91 (s, 1H), 11.01 (s, 1H), 9.75 (s, 1H), 9.60 (s, 1H), 9.42 (s, 1H), 7.81-7.74 (m,

1H), 7.54-7.46 (m, 2H), 7.19 (d, J=8.0 Hz, 2H), 7.10 (d, J=7.8 Hz, 2H), 6.75 (s, 1H), 6.27 (s, 1H), 5.12 (dd, J=13.2, 5.2 Hz, 1H), 4.90-4.75 (m, 2H), 4.45 (d, J=17.6 Hz, 1H), 4.40-4.24 (m, 2H), 3.69 (d, J=13.1 Hz, 1H), 3.02-2.84 (m, 3H), 2.61 (d, J=17.6 Hz, 2H), 2.34 (td, J=14.4, 9.8 Hz, 1H), 2.08-1.96 (m, 2H), 1.75 (s, 1H), 1.59 (t, J=12.0 Hz, 2H), 1.26-1.08 (m, 2H), 1.01 (s, 1H), 0.94 (d, J=6.9 Hz, 6H). ESMS calculated for $C_{39}H_{41}N_7O_9$: 751.30; Found: 752.2 (M+H)$^+$.

SDC-TRAP-0149

1-(4-(3-(2,4-dihydroxy-5-isopropylphenyl)-5-(ethylcarbamoyl)-4H-1,2,4-triazol-4-yl)benzyl)-N-(2-(2,6-dioxopiperidin-3-yl)-1-oxoisoindolin-4-yl)piperidine-4-carboxamide

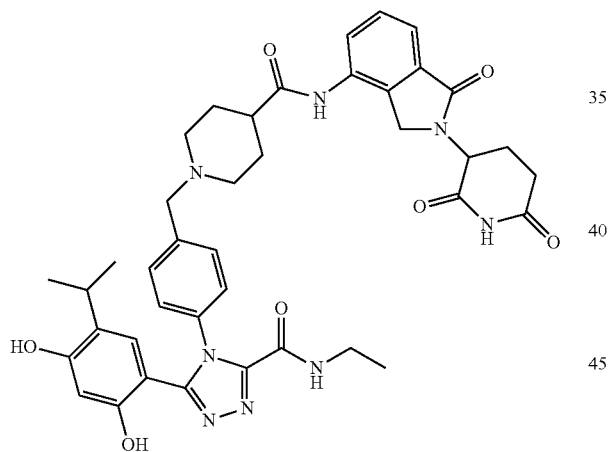

$^1$H NMR (400 MHz, DMSO-d$_6$) δ 11.03 (s, 1H), 10.61 (s, 1H), 9.76 (d, J=9.5 Hz, 2H), 8.97 (t, J=5.9 Hz, 1H), 7.82 (dd, J=7.2, 1.9 Hz, 1H), 7.55-7.44 (m, 2H), 7.40 (d, J=8.3 Hz, 2H), 7.35-7.27 (m, 2H), 6.59 (s, 1H), 6.35 (s, 1H), 5.15 (dd, J=13.3, 5.1 Hz, 1H), 4.44-4.28 (m, 2H), 3.51 (s, 2H), 3.31 (s, 1H), 3.23-3.11 (m, 2H), 2.92 (dq, J=13.4, 7.5, 6.4 Hz, 4H), 2.61 (d, J=17.6 Hz, 1H), 2.39 (dtt, J=26.4, 13.3, 6.3 Hz, 2H), 2.01 (dd, J=12.9, 8.7 Hz, 3H), 1.81 (d, J=12.2 Hz, 2H), 1.70 (q, J=11.4 Hz, 2H), 1.04 (t, J=7.1 Hz, 3H), 0.82 (d, J=6.9 Hz, 6H). ESMS calculated for $C_{40}H_{44}N_8O_7$: 748.33; Found: 749.3 (M+H)$^+$.

SDC-TRAP-0152

4-(4-(4-(3-(2,4-dihydroxy-5-isopropylphenyl)-5-(ethylcarbamoyl)-4H-1,2,4-triazol-4-yl)benzoyl)piperazin-1-yl)phenyl(2-(2,6-dioxopiperidin-3-yl)-1-oxoisoindolin-4-yl)carbamate

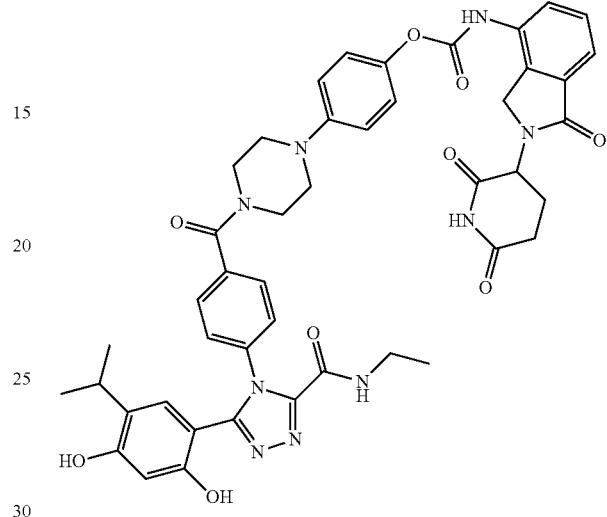

ESMS calculated for $C_{45}H_{45}N_9O_9$: 855.33; Found: 856.2 (M+H)$^+$.

SDC-TRAP-0168

4-(4-(4-(3-(2,4-dihydroxy-5-isopropylphenyl)-5-hydroxy-4H-1,2,4-triazol-4-yl)-2-fluorobenzyl)piperazine-1-carbonyl)-2, 6-dimethylphenyl(2-(2,6-dioxopiperidin-3-yl)-1-oxoisoindolin-4-yl)carbamate

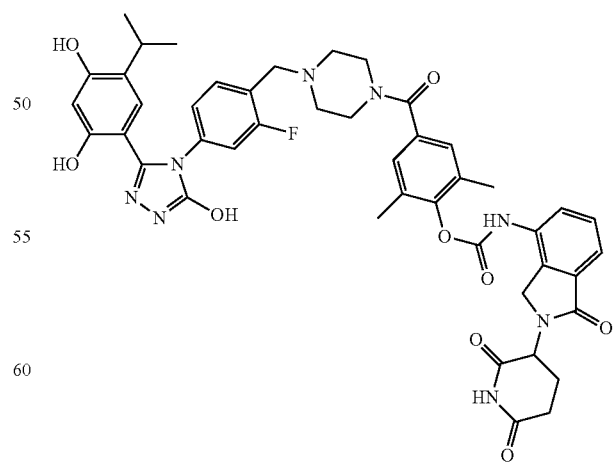

ESMS calculated for $C_{45}H_{45}FN_8O_9$: 860.33; Found: 861.2 (M+H)$^+$.

SDC-TRAP-0173

4-(4-(4-(3-(2,4-dihydroxy-5-isopropylphenyl)-5-(ethyl carbamoyl)-4H-1,2,4-triazol-4-yl)benzoyl)piperazin-1-yl)-2-methoxyphenyl(2-(2,6-dioxopiperidin-3-yl)-1-oxoisoindolin-4-yl)carbamate

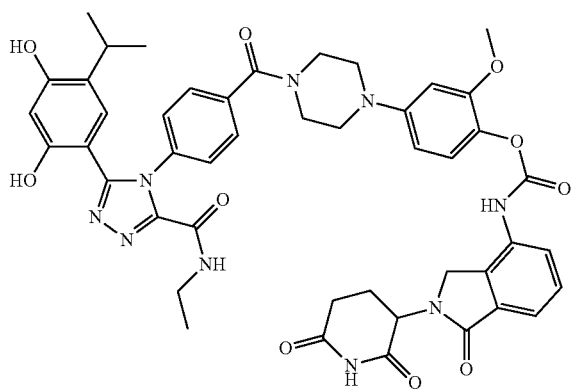 [SMILES: CCNC(=O)c1nnc(-c2cc(C(C)C)c(O)cc2O)n1-c1ccc(C(=O)N2CCN(c3ccc(OC(=O)Nc4cccc5c4CN(C4CCC(=O)NC4=O)C5=O)c(OC)c3)CC2)cc1]

$^1$H NMR (400 MHz, DMSO-d$_6$) δ 11.04 (s, 1H), 10.22 (s, 1H), 10.08 (s, 1H), 9.75 (s, 1H), 9.03 (t, J=6.2 Hz, 1H), 7.80 (s, 1H), 7.50-7.41 (m, 6H), 7.04 (d, J=8.5 Hz, 1H), 6.73 (d, J=11.0 Hz, 2H), 6.56-6.49 (m, 1H), 6.33 (s, 1H), 5.15 (dd, J=13.3, 5.1 Hz, 1H), 4.44-4.28 (m, 2H), 3.79 (s, 3H), 3.29-3.13 (m, 8H), 2.95-2.55 (m, 2H), 2.36 (d, J=14.6 Hz, 1H), 2.11-2.02 (m, 1H), 1.06 (t, J=7.4 Hz, 3H), 0.91 (d, J=6.9 Hz, 6H). ESMS calculated for C$_{46}$H$_{47}$N$_9$O$_{10}$: 885.34; Found: 886.3 (M+H)$^+$.

SDC-TRAP-0174

4-(4-(4-(3-(2,4-dihydroxy-5-isopropylphenyl)-5-hydroxy-4H-1,2,4-triazol-4-yl)-2-fluorobenzyl)piperazine-1-carbonyl)-3-fluorobenzyl (2-(2,6-dioxopiperidin-3-yl)-1-oxoisoindolin-4-yl)carbamate

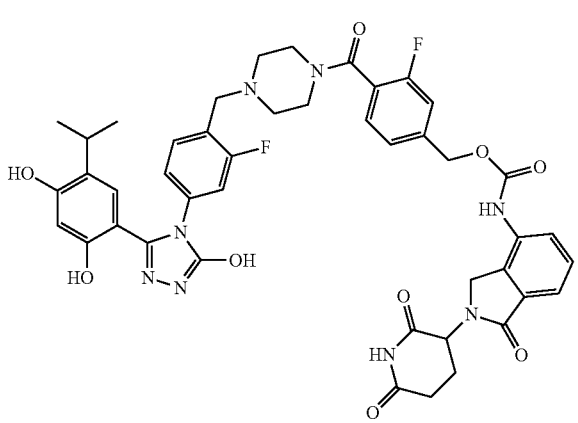 [SMILES: CC(C)c1cc(-c2nnc(O)n2-c2ccc(CN3CCN(C(=O)c4ccc(COC(=O)Nc5cccc6c5CN(C5CCC(=O)NC5=O)C6=O)cc4F)CC3)c(F)c2)c(O)cc1O]

ESMS calculated for C$_{44}$H$_{42}$FN$_8$O$_9$: 864.30; Found: 865.2 (M+H)$^+$.

SDC-TRAP-0175

4-(4-(5-(3-(2,4-dihydroxy-5-isopropylphenyl)-5-hydroxy-4H-1,2,4-triazol-4-yl)pyridin-2-yl)piperazine-1-carbonyl)benzyl (2-(2,6-dioxopiperidin-3-yl)-1-oxoisoindolin-4-yl)carbamate

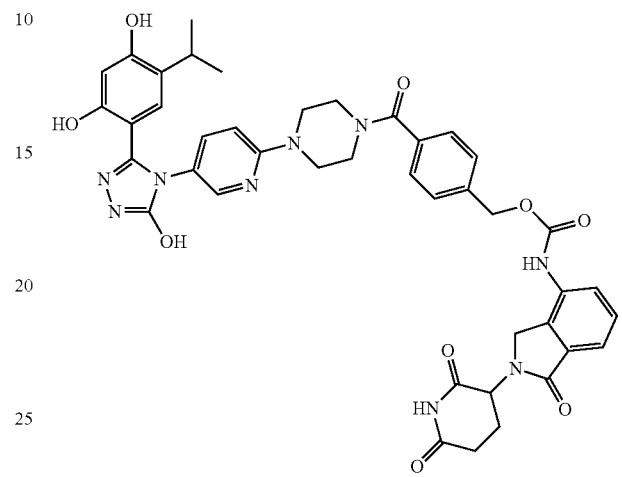

ESMS calculated for C$_{42}$H$_{41}$N$_9$O$_9$: 815.30; Found: 816.1 (M+H)$^+$.

SDC-TRAP-0176

4-(4-(4-(3-(2,4-dihydroxy-5-isopropylphenyl)-5-(ethylcarbamoyl)-4H-1,2,4-triazol-4-yl)benzoyl)piperazin-1-yl)-2-methylphenyl (2-(2,6-dioxopiperidin-3-yl)-1-oxoisoindolin-4-yl)carbamate

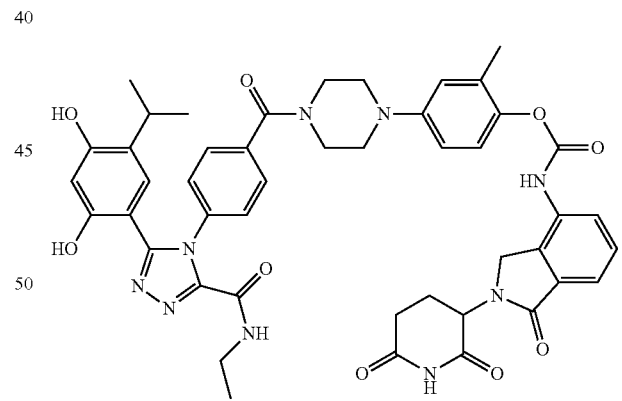

$^1$H NMR (400 MHz, DMSO-d$_6$) δ 11.03 (s, 1H), 10.25 (s, 1H), 10.11 (s, 1H), 9.75 (s, 1H), 9.02 (t, J=6.1 Hz, 1H), 7.81 (p, J=3.5 Hz, 1H), 7.58-7.46 (m, 4H), 7.42 (d, J=7.9 Hz, 2H), 7.04 (d, J=8.7 Hz, 1H), 6.92 (d, J=2.7 Hz, 1H), 6.84 (dd, J=8.8, 2.9 Hz, 1H), 6.72 (s, 1H), 6.34 (s, 1H), 5.14 (dd, J=13.2, 5.1 Hz, 1H), 4.51 (d, J=17.7 Hz, 1H), 4.42 (d, J=17.7 Hz, 1H), 3.78 (s, 2H), 3.50 (s, 2H), 3.18 (dt, J=20.9, 11.0 Hz, 6H), 2.94 (dp, J=18.6, 6.2, 4.7 Hz, 2H), 2.53-2.47 (m, 2H), 2.46-2.30 (m, 1H), 2.18 (s, 3H), 2.04 (dd, J=11.6, 5.9 Hz, 1H), 1.07 (t, J=7.2 Hz, 3H), 0.91 (d, J=6.8 Hz, 6H). ESMS calculated for C$_{46}$H$_{47}$N$_9$O$_9$: 869.35; Found: 870.1 (M+H)$^+$.

SDC-TRAP-0177

4-(4-(4-(3-(2,4-dihydroxy-5-isopropylphenyl)-5-(ethylcarbamoyl)-4H-1,2,4-triazol-4-yl)benzoyl)piperazine-1-carbonyl)benzyl (2-(2,6-dioxopiperidin-3-yl)-1-oxoisoindolin-4-yl)carbamate

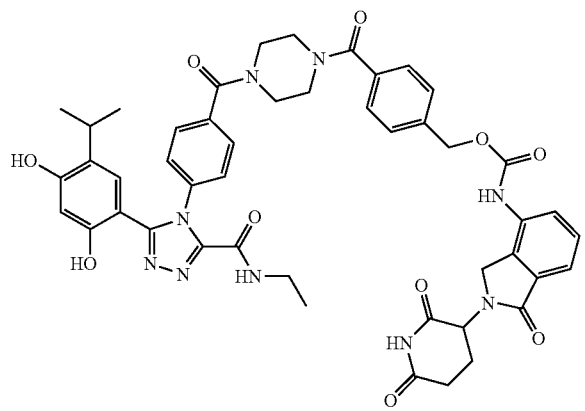 [SMILES: CCNC(=O)c1nnc(-c2cc(C(C)C)c(O)cc2O)n1-c1ccc(C(=O)N2CCN(C(=O)c3ccc(COC(=O)Nc4cccc5c4CN(C4CCC(=O)NC4=O)C5=O)cc3)CC2)cc1]

$^1$H NMR (400 MHz, DMSO-d$_6$) δ 11.03 (s, 1H), 10.19 (s, 1H), 9.73 (s, 2H), 9.02 (t, J=6.0 Hz, 1H), 7.84-7.77 (m, 1H), 7.50 (dq, J=11.4, 6.5 Hz, 8H), 7.40 (d, J=6.8 Hz, 2H), 6.70 (s, 1H), 6.33-6.28 (m, 1H), 5.23 (s, 2H), 5.13 (dd, J=13.2, 5.1 Hz, 1H), 4.40 (d, J=17.8 Hz, 2H), 3.68 (d, J=24.7 Hz, 4H), 3.22-3.12 (m, 2H), 2.93 (d, J=12.6 Hz, 2H), 2.65-2.55 (m, 1H), 2.30-2.25 (m, 1H), 2.02 (dd, J=15.0, 7.1 Hz, 1H), 1.05 (t, J=7.1 Hz, 3H), 0.88 (d, J=7.5 Hz, 6H). ESMS calculated for C$_{47}$H$_{47}$N$_9$O$_{10}$: 897.34; Found: 898.1 (M+H)$^+$.

SDC-TRAP-0178

4-(4-(4-(3-(2,4-dihydroxy-5-isopropylphenyl)-5-(ethyl carbamoyl)-4H-1,2,4-triazol-4-yl)benzoyl)piperazin-1-yl)-2,6-dimethylphenyl (2-(2,6-dioxopiperidin-3-yl)-1-oxoisoindolin-4-yl)carbamate

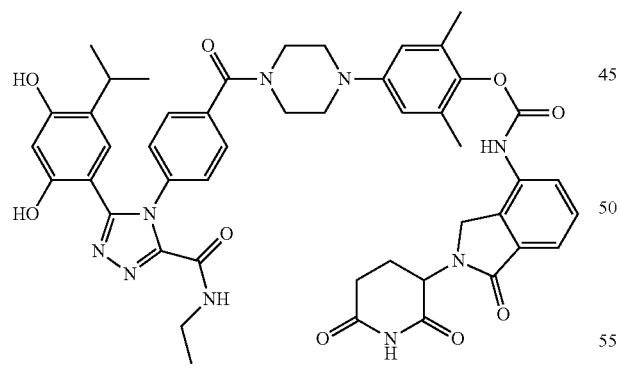

$^1$H NMR (400 MHz, DMSO-d$_6$) δ 11.02 (s, 1H), 10.22 (s, 1H), 10.17 (s, 1H), 9.74 (s, 1H), 9.02 (t, J=5.9 Hz, 1H), 7.86-7.77 (m, 1H), 7.58-7.46 (m, 4H), 7.45-7.37 (m, 2H), 6.73 (d, J=11.9 Hz, 3H), 6.33 (s, 1H), 5.13 (dd, J=13.2, 5.1 Hz, 1H), 4.50 (d, J=17.6 Hz, 1H), 4.41 (d, J=17.6 Hz, 1H), 3.76 (s, 2H), 3.48 (s, 2H), 3.25-3.13 (m, 4H), 3.02-2.85 (m, 2H), 2.66-2.57 (m, 1H), 2.45-2.31 (m, 1H), 2.14 (s, 6H), 2.04-2.02 (m, 1H), 1.06 (t, J=7.2 Hz, 3H), 0.91 (d, J=6.9 Hz, 6H). ESMS calculated for C$_{47}$H$_{49}$N$_9$O$_9$: 883.37; Found: 884.1 (M+H)$^+$.

SDC-TRAP-0194

4-(2-(4-(4-(3-(2,4-dihydroxy-5-isopropylphenyl)-5-hydroxy-4H-1,2,4-triazol-4-yl)-2-fluorobenzyl)piperazin-1-yl)-2-oxoethyl)benzyl (2-(2,6-dioxopiperidin-3-yl)-1-oxoisoindolin-4-yl)carbamate

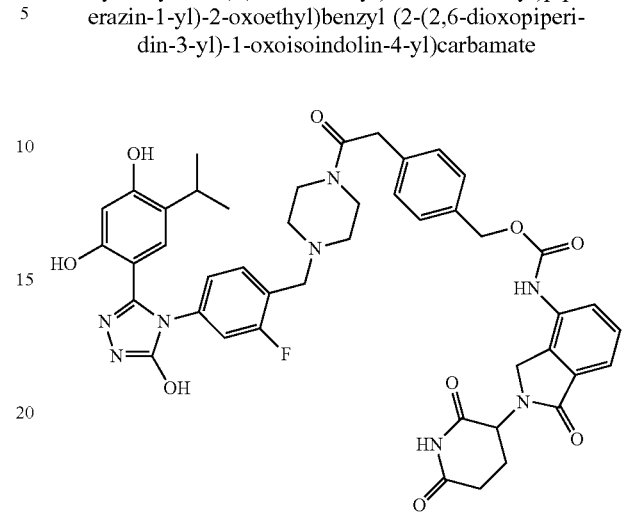

$^1$H NMR (400 MHz, DMSO-d$_6$) δ 12.04 (s, 1H), 11.06 (s, 1H), 9.70 (d, J=7.6 Hz, 2H), 9.45 (s, 1H), 7.88-7.81 (m, 1H), 7.59-7.49 (m, 2H), 7.42 (d, J=8.2 Hz, 3H), 7.31-7.24 (m, 2H), 7.12 (dd, J=10.5, 2.1 Hz, 1H), 7.02 (dd, J=8.1, 2.1 Hz, 1H), 6.92 (s, 1H), 6.33 (s, 1H), 5.22-5.12 (m, 3H), 4.56-4.35 (m, 2H), 3.73 (d, J=15.5 Hz, 2H), 3.57-3.46 (m, 6H), 3.13-2.89 (m, 2H), 2.71-2.61 (m, 1H), 2.37 (h, J=6.4, 5.4 Hz, 5H), 2.12-1.99 (m, 1H), 1.05 (d, J=6.9 Hz, 6H). ESMS calculated for C$_{45}$H$_{45}$FN$_8$O$_9$: 860.33; Found: 861.2 (M+H)$^+$.

SDC-TRAP-0195

4-(4-(1-(4-(3-(2,4-dihydroxy-5-isopropylphenyl)-5-(ethylcarbamoyl)-4H-1,2,4-triazol-4-yl)benzyl)piperidine-4-carbonyl)piperazin-1-yl)-2,6-dimethylphenyl (2-(2,6-dioxopiperidin-3-yl)-1-oxoisoindolin-4-yl)carbamate

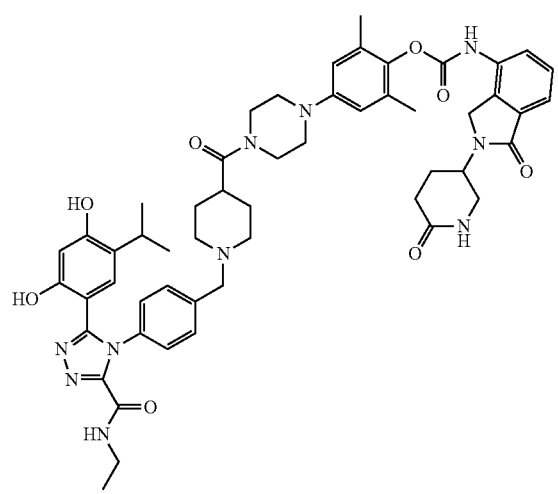 [SMILES: CCNC(=O)c1nnc(-c2cc(C(C)C)c(O)cc2O)n1-c1ccc(CN2CCC(C(=O)N3CCN(c4cc(C)c(OC(=O)Nc5cccc6c5CN(C5CCC(=O)NC5)C6=O)c(C)c4)CC3)CC2)cc1]

ESMS calculated for C$_{53}$H$_{60}$N$_{10}$O$_9$: 980.45; Found: 981.3 (M+H)$^+$.

SDC-TRAP-0196

4-((5-(3-(2,4-dihydroxy-5-isopropylphenyl)-5-(ethyl carbamoyl)-4H-1,2,4-triazol-4-yl)isoindolin-2-yl) methyl)-2,6-dimethoxyphenyl (2-(2,6-dioxopiperi- din-3-yl)-1-oxoisoindolin-4-yl)carbamate

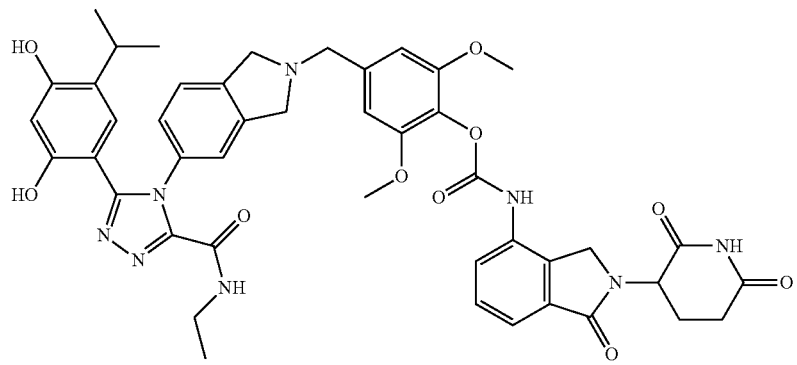 [SMILES: CCNC(=O)c1nnc(-c2cc(C(C)C)c(O)cc2O)n1-c1ccc2c(c1)CN(Cc1cc(OC)c(OC(=O)Nc3cccc4c3CN(C3CCC(=O)NC3=O)C4=O)c(OC)c1)C2]

$^1$H NMR (400 MHz, DMSO-d$_6$) δ 11.03 (s, 1H), 10.56 (s, 1H), 10.15 (s, 1H), 9.77 (s, 1H), 8.99 (t, J=5.9 Hz, 1H), 7.82 (dd, J=5.7, 3.2 Hz, 1H), 7.52 (q, J=4.1, 3.4 Hz, 2H), 7.36-7.24 (m, 2H), 7.17 (dd, J=7.9, 2.1 Hz, 1H), 6.79 (s, 2H), 6.57 (s, 1H), 6.33 (s, 1H), 5.14 (dd, J=13.2, 5.2 Hz, 1H), 4.49 (d, J=17.7 Hz, 1H), 4.40 (d, J=17.6 Hz, 1H), 3.90 (d, J=16.3 Hz, 5H), 3.79 (s, 6H), 3.17 (p, J=7.0 Hz, 2H), 2.92 (tt, J=12.5, 6.2 Hz, 2H), 2.62 (d, J=16.8 Hz, 1H), 2.42-2.31 (m, 1H), 2.10-2.01 (m, 1H), 1.05 (t, J=7.1 Hz, 3H), 0.85 (d, J=6.9 Hz, 6H). ESMS calculated for C$_{45}$H$_{46}$N$_8$O$_{10}$: 858.33; Found: 859.2 (M+H)$^+$.

in vitro activity was determined for these compounds using the HER2 degradation assay set forth herein:

| SDC-TRAP-# | HER2 Degradation IC$_{50}$ (nM) |
|---|---|
| SDC-TRAP-0015 | 2347 |
| SDC-TRAP-0017 | >10,000 |
| SDC-TRAP-0018 | 8205 |
| SDC-TRAP-0021 | >5000 |
| SDC-TRAP-0033 | >5000 |
| SDC-TRAP-0041 | >10000 |
| SDC-TRAP-0109 | >10000 |
| SDC-TRAP-0110 | >10000 |
| SDC-TRAP-0114 | 4,311 |
| SDC-TRAP-0115 | 1890 |
| SDC-TRAP-0116 | 967 |
| SDC-TRAP-0105 | >10000 |
| SDC-TRAP-0119 | >10,000 |
| SDC-TRAP-0108 | >10,000 |
| SDC-TRAP-0122 | >10000 |
| SDC-TRAP-0121 | 3,000 |
| SDC-TRAP-0128 | 6,909 |
| SDC-TRAP-0129 | 4,519 |
| SDC-TRAP-0126 | 8,636 |
| SDC-TRAP-0132 | >5000 |
| SDC-TRAP-0127 | 8,086 |
| SDC-TRAP-0131 | >5,000 |
| SDC-TRAP-0123 | 657 |
| SDC-TRAP-0135 | 9667 |
| SDC-TRAP-0133 | >10000 |
| SDC-TRAP-0136 | >5000 |
| SDC-TRAP-0140 | >5000 |
| SDC-TRAP-0149 | 1692 |
| SDC-TRAP-0231 | 696 |
| SDC-TRAP-0152 | 254 |
| SDC-TRAP-0124 | 358 |

-continued

| SDC-TRAP-# | HER2 Degradation IC$_{50}$ (nM) |
|---|---|
| SDC-TRAP-0125 | 312 |
| SDC-TRAP-0156 | 3495 |
| SDC-TRAP-0157 | 696 |
| SDC-TRAP-0167 | 2861 |
| SDC-TRAP-0168 | 276 |
| SDC-TRAP-0173 | 323 |
| SDC-TRAP-0174 | 693 |
| SDC-TRAP-0160 | 239 |
| SDC-TRAP-0170 | 296 |
| SDC-TRAP-0171 | 199 |
| SDC-TRAP-0162 | >5,000 |
| SDC-TRAP-0147 | 4329 |
| SDC-TRAP-0175 | 2,629 |
| SDC-TRAP-0178 | 170 91 |
| SDC-TRAP-0176 | 178 |
| SDC-TRAP-0177 | 4,352 |
| SDC-TRAP-0182 | 359 |
| SDC-TRAP-0194 | 2,121 |
| SDC-TRAP-0166 | >5,000 |
| SDC-TRAP-0188 | 3,950 |
| SDC-TRAP-0189 | 1,091 |
| SDC-TRAP-0195 | 49 |
| SDC-TRAP-0163 | 885 |
| SDC-TRAP-0164 | 493 |
| SDC-TRAP-0190 | >5000 |
| SDC-TRAP-0191 | 1,177 |
| SDC-TRAP-0192 | >5000 |
| SDC-TRAP-0196 | 89 |
| SDC-TRAP-0187 | 72 |
| SDC-TRAP-0193 | 266 |
| SDC-TRAP-0155 | 1190 |

Hsp90$^\alpha$ Binding Assay Data

| No | STA | Binding EC$_{50}$ (nM) |
|---|---|---|
| 1 | SDC-TRAP-0196 | 93.11 |
| 2 | SDC-TRAP-0115 | 203.2 |
| 3 | SDC-TRAP-0116 | 158.8 |
| 4 | SDC-TRAP-0127 | 102.2 |

Mouse Plasma Stability Data

| Compound ID | % Remaining (1 h, 10 μM) |
|---|---|
| SDC-TRAP-0187 | 102% |
| SDC-TRAP-0196 | 66.2% |
| SDC-TRAP-0147 | 98.1% |
| SDC-TRAP-0167 | 51.2% |
| SDC-TRAP-0163 | 93.0% |
| SDC-TRAP-0164 | 98.0% |
| SDC-TRAP-0171 | 17.7% |
| SDC-TRAP-0178 | 82.0% |
| SDC-TRAP-0195 | 98.4% |
| SDC-TRAP-0115 | 85.9% |
| SDC-TRAP-0116 | 91.1% |
| SDC-TRAP-0121 | 89.1% |
| SDC-TRAP-0127 | 87.3% |
| SDC-TRAP-0124 | 112% |
| SDC-TRAP-0125 | 99.4% |
| SDC-TRAP-0231 | 98.3% |
| SDC-TRAP-0156 | 90.3% |
| SDC-TRAP-0157 | 81.4% |

Tissue Distribution Data for SDC-TRAP-0116

| Analyte Target Time (h) | Plasma Conc. (μM) | | Tumor Conc. (nmol/g of tissue) | | Tumor/Plasma Ratio | |
|---|---|---|---|---|---|---|
| | SDC-TRAP-0116 | Lenalidomide | SDC-TRAP-0116 | Lenalidomide | SDC-TRAP-0116 | Lenalidomide |
| 0.083 | 693 | 0.560 | 17.7 | 0.0856 | 0.03 | 0.15 |
| 1 | 65.2 | 1.76 | 13.7 | 0.736 | 0.21 | 0.42 |
| 6 | 0.595 | 0.113 | 6.09 | 0.120 | 10.2 | 1.07 |
| 24 | 0.0111 | BQL | 2.78 | BQL | 251 | — |
| 48 | 0.0315 | BQL | 1.46 | BQL | 46.5 | — |

Tissue Distribution Data for SDC-TRAP-0171

| Analyte Target Time (h) | Plasma Conc. (μM) | | | Tumor Conc. (nmol/g of tissue) | | | Tumor/Plasma Ratio | | |
|---|---|---|---|---|---|---|---|---|---|
| | SDC-TRAP-0171 | SDC-TRAP-0080 | Lenalidomide | SDC-TRAP-0171 | SDC-TRAP-0080 | Lenalidomide | SDC-TRAP-0171 | SDC-TRAP-0080 | Lenalidomide |
| 0.083 | 618 | 0.0312 | 3.23 | 0.083 | 618 | 0.0312 | 0.0164 | 3.80 | 0.613 |
| 1 | 32.2 | 0.258 | 2.03 | 1 | 32.2 | 0.258 | 0.249 | 0.636 | 1.06 |
| 6 | 1.21 | 0.153 | 0.252 | 6 | 1.21 | 0.153 | 3.10 | 2.09 | 1.16 |
| 24 | 0.00162 | 0.0574 | BQL | 24 | 0.00162 | 0.0574 | 407 | 6.91 | — |
| 48 | BQL | 0.0143 | BQL | 48 | BQL | 0.0143 | — | 26.8 | — |

Tissue Distribution Data for SDC-TRAP-0178

| Analyte Target Time (h) | Plasma Conc. (μM) | | | Tumor Conc. (nmol/g of tissue) | | | Tumor/Plasma Ratio | | |
|---|---|---|---|---|---|---|---|---|---|
| | SDC-TRAP-0178 | SDC-TRAP-0183 | Lenalidomide | SDC-TRAP-0178 | SDC-TRAP-0183 | Lenalidomide | SDC-TRAP-0178 | SDC-TRAP-0183 | Lenalidomide |
| 0.083 | 918 | N/A | 1.39 | 16.4 | 0.320 | 0.623 | 0.0179 | — | 0.449 |
| 1 | 217 | N/A | 0.963 | 12.8 | 0.316 | 0.629 | 0.0589 | — | 0.653 |
| 6 | 4.51 | N/A | 0.00447 | 7.17 | 0.418 | 0.0532 | 1.59 | — | 11.9 |
| 24 | 0.0280 | N/A | BQL | 2.81 | 0.556 | BQL | 100 | — | — |
| 48 | 0.241 | N/A | BQL | 1.01 | 0.508 | BQL | — | — | — |

Tissue Distribution Data for SDC-TRAP-0195

| Analyte Target Time (h) | Plasma Conc. (μM) | | | Tumor Conc. (nmol/g of tissue) | | | Tumor/Plasma Ratio | | |
|---|---|---|---|---|---|---|---|---|---|
| | SDC-TRAP-0195 | SDC-TRAP-0197 | Lenalidomide | SDC-TRAP-0195 | SDC-TRAP-0197 | Lenalidomide | SDC-TRAP-0195 | SDC-TRAP-0197 | Lenalidomide |
| 0.083 | 1220 | N/A | 0.923 | 17.1 | 0.206 | 0.477 | 0.0140 | — | 0.517 |
| 1 | 211 | N/A | 0.511 | 23.0 | 0.305 | 0.402 | 0.109 | — | 0.786 |
| 6 | 7.23 | N/A | 0.00316 | 17.1 | 0.662 | 0.0458 | 2.36 | — | 14.51 |

| Analyte | Plasma Conc. (µM) | | | Tumor Conc. (nmol/g of tissue) | | | Tumor/Plasma Ratio | | |
|---|---|---|---|---|---|---|---|---|---|
| Target Time (h) | SDC-TRAP-0195 | SDC-TRAP-0197 | Lena-lidomide | SDC-TRAP-0195 | SDC-TRAP-0197 | Lena-lidomide | SDC-TRAP-0195 | SDC-TRAP-0197 | Lena-lidomide |
| 24 | 2.03 | N/A | BQL | 11.2 | 1.60 | BQL | 5.50 | — | — |
| 48 | BQL | N/A | BQL | 12.6 | 2.64 | BQL | — | — | — |

Example 26: SDC-TRAPs Comprising Pemetrexed Fragment

Exemplary Synthesis of SDC-TRAPs:

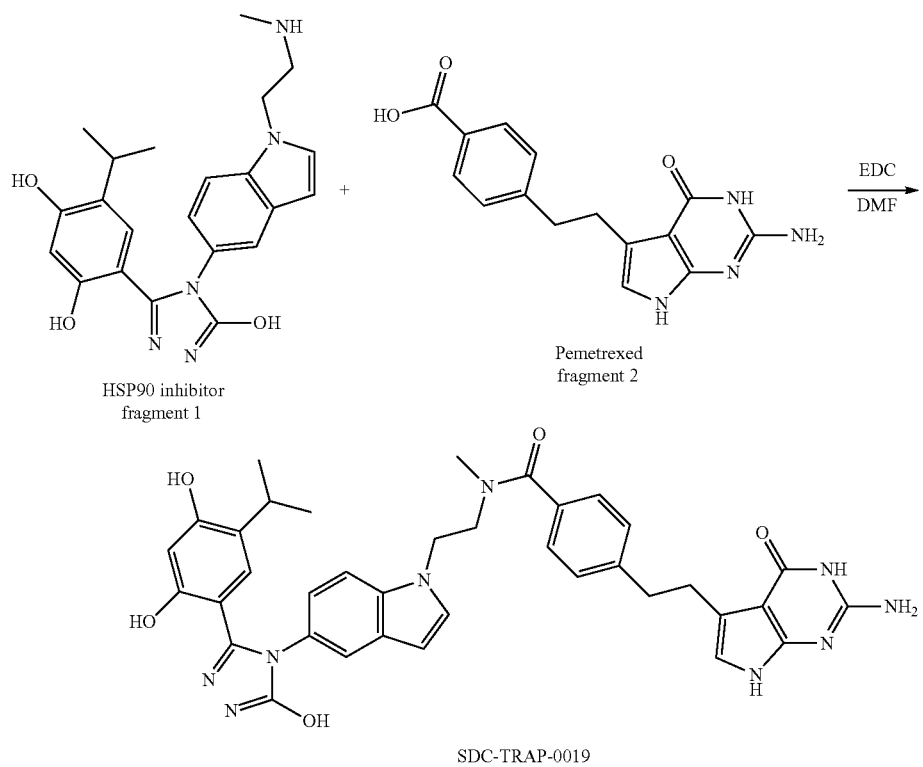

SDC-TRAP-0019

To a solution of pemetrexed-fragment 2 (60 mg, 0.2 mmol) and amine SDC-TRAP-0004 (82 mg, 0.2 mmol) in anhydrous DMF (3 mL) was added EDC (60 mg, 0.3 mmol). The reaction mixture was stirred at room temperature for 18 h. The reaction mixture was then diluted with water (5 mL) and extracted with ethyl acetate (100 mL). The organic phase was dried with sodium sulfate, filtered and evaporated, followed by flash chromatography (hexane-ethyl acetate 1:1 and ethyl acetate-methanol 98:2) to give SDC-TRAP-0019 (95 mg, 70%) as a white solid.

4-(2-(2-amino-4-oxo-4,7-dihydro-3H-pyrrolo[2,3-d]pyrimidin-5-yl)ethyl)-N-(2-(5-(3-(2,4-dihydroxy-5-isopropylphenyl)-5-hydroxy-4H-1,2,4-triazol-4-yl)-1H-indol-1-yl)ethyl)-N-methylbenzamide $^1$H NMR (400 MHz, DMSO-d$_6$) δ: 11.86 (s, 1H); 10.61 (s, 1H); 10.14 (s, 1H); 9.51 (s, 1H); 9.47 (s, 1H); 7.59-7.45 (m, 2H); 7.28-6.96 (m, 5H); 6.72 (m, 2H); 6.47 (s, 1H); 6.32 (s, 1H); 6.24 (s, 1H); 6.00 (bs, 2H); 4.46-4.28 (m, 2H); 3.75-3.49 (m, 2H); 2.96-2.80 (m, 5H); 2.61 (s, 3H); 0.81 (d, J=6.9 Hz, 6H). ESMS calculated for $C_{37}H_{37}N_9O_5$: 687.29; Found: 688.2 (M+H)$^+$.

SDC-TRAP-0020

4-(2-(2-amino-4-oxo-4,7-dihydro-3H-pyrrolo[2,3-d]pyrimidin-5-yl)ethyl)-N-(2-(2-(5-(3-(2,4-dihydroxy-5-isopropylphenyl)-5-hydroxy-4H-1,2,4-triazol-4-yl)-1H-indol-1-yl)ethoxy)ethyl)benzamide

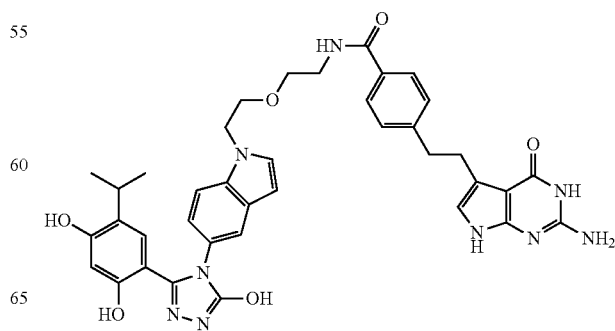

¹H NMR (400 MHz, DMSO-d₆), δ (ppm): 11.86 (s, 1H); 10.61 (s, 1H); 10.14 (s, 1H); 9.51 (s, 1H); 9.47 (s, 1H); 7.59-7.45 (m, 2H); 7.28-6.96 (m, 5H); 6.72 (m, 2H); 6.47 (s, 1H); 6.32 (s, 1H); 6.24 (s, 1H); 6.01 (s, 2H); 4.33 (d, J=6.5 Hz, 2H), 3.73 (d, J=6.3 Hz, 2H), 3.54-3.46 (m, 2H); 3.00-2.82 (m, 7H); 0.81 (d, J=6.9 Hz, 6H); ESMS calculated for $C_{38}H_{39}N_9O_6$: 717.30; Found: 718.2 (M+H)⁺.

SDC-TRAP-0068

2-amino-5-(4-(4-(4-(3-(2,4-dihydroxy-5-isopropyl-phenyl)-5-hydroxy-4H-1,2,4-triazol-4-yl)benzyl)piperazine-1-carbonyl)phenethyl)-3H-pyrrolo[2,3-d]pyrimidin-4(7H)-one

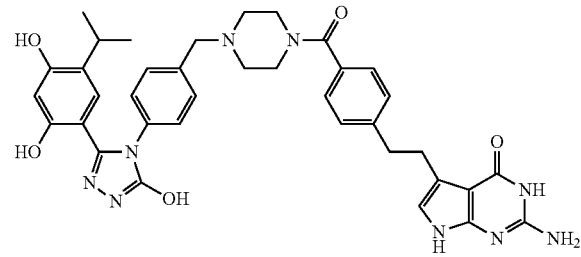 [SMILES: CC(C)c1cc(-c2nnc(O)n2-c2ccc(CN3CCN(C(=O)c4ccc(CCc5c[nH]c6nc(N)[nH]c(=O)c56)cc4)CC3)cc2)c(O)cc1O]

¹H NMR (400 MHz, DMSO-d₆) δ 11.92 (s, 1H), 10.62 (d, J=2.2 Hz, 1H), 10.15 (s, 1H), 9.60 (s, 1H), 9.38 (s, 1H), 7.34-7.22 (m, 6H), 7.17-7.10 (m, 2H), 6.79 (s, 1H), 6.33 (d, J=2.2 Hz, 1H), 6.26 (s, 1H), 6.00 (s, 2H), 3.48 (s, 2H), 3.33 (s, 2H), 3.03-2.88 (m, 3H), 2.84 (dd, J=9.5, 5.7 Hz, 2H), 2.37-2.34 (m, 4H), 0.95 (d, J=6.9 Hz, 6H); ESMS calculated for $C_{37}H_{39}N_9O_5$: 689.31; Found: 690.1 (M+H)⁺.

SDC-TRAP-0078

2-amino-5-(4-(4-(4-(3-(2,4-dihydroxy-5-isopropyl-phenyl)-5-hydroxy-4H-1,2,4-triazol-4-yl)-2-fluorobenzyl)piperazine-1-carbonyl)phenethyl)-3H-pyrrolo[2,3-d]pyrimidin-4(7H)-one

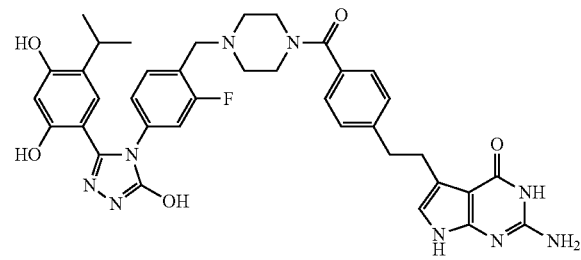 [SMILES: CC(C)c1cc(-c2nnc(O)n2-c2ccc(CN3CCN(C(=O)c4ccc(CCc5c[nH]c6nc(N)[nH]c(=O)c56)cc4)CC3)c(F)c2)c(O)cc1O]

¹H NMR (400 MHz, DMSO-d₆) δ 11.97 (s, 1H), 10.63 (d, J=2.3 Hz, 1H), 10.15 (s, 1H), 9.63 (s, 1H), 9.39 (s, 1H), 7.96 (s, 1H), 7.40 (t, J=8.1 Hz, 1H), 7.27 (s, 4H), 7.06 (dd, J=10.9, 2.1 Hz, 1H), 6.97 (dd, J=8.2, 2.0 Hz, 1H), 6.88 (s, 1H), 6.34 (d, J=2.2 Hz, 1H), 6.26 (s, 1H), 6.00 (s, 2H), 3.54 (bs, 4H), 3.07-2.80 (m, 3H), 2.74 (s, 2H), 2.40 (bs, 4H), 1.01 (d, J=6.9 Hz, 6H). ESMS calculated for $C_{37}H_{38}FN_9O_5$: 707.30; Found: 708.2 (M+H)⁺.

SDC-TRAP-0082

2-amino-5-(4-(4-(4-(3-(2,4-dihydroxy-5-isopropyl-phenyl)-5-hydroxy-4H-1,2,4-triazol-4-yl)phenyl)piperazine-1-carbonyl)phenethyl)-3H-pyrrolo[2,3-d]pyrimidin-4(7H)-one

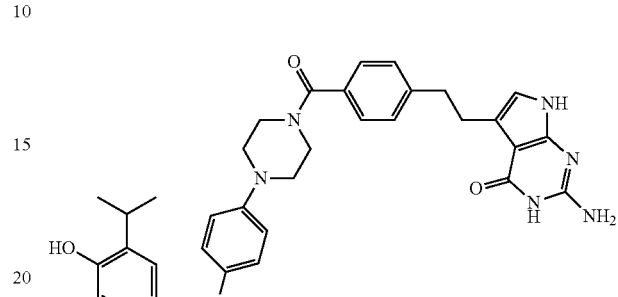

¹H NMR (400 MHz, DMSO-d₆) δ 11.85 (s, 1H), 10.63 (d, J=2.1 Hz, 1H), 10.15 (s, 1H), 9.59 (s, 1H), 9.44 (s, 1H), 7.37-7.25 (m, 4H), 7.04 (d, J=8.6 Hz, 2H), 6.97-6.90 (m, 2H), 6.81 (s, 1H), 6.35 (d, J=2.2 Hz, 1H), 6.27 (s, 1H), 6.01 (s, 2H), 3.69 (s, 2H), 3.52 (s, 2H), 3.18 (s, 4H), 3.04-2.90 (m, 3H), 2.86 (dd, J=9.5, 5.8 Hz, 2H), 0.98 (d, J=6.9 Hz, 6H); ESMS calculated for $C_{36}H_{37}N_9O_5$: 675.29; Found: 676.2 (M+H)⁺.

SDC-TRAP-0093

2-amino-5-(4-(5-(3-(2,4-dihydroxy-5-isopropylphenyl)-5-hydroxy-4H-1,2,4-triazol-4-yl)isoindoline-2-carbonyl)phenethyl)-3H-pyrrolo[2,3-d]pyrimidin-4(7H)-one

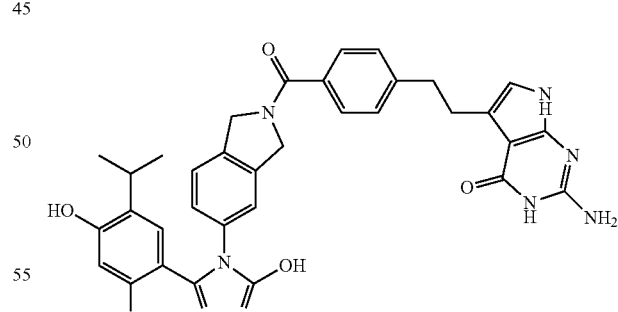

¹H NMR (400 MHz, DMSO-d₆) δ 11.91 (s, 1H), 10.64 (s, 1H), 10.23 (s, 1H), 9.62 (s, 1H), 9.38 (s, 1H), 7.51 (dd, J=8.2, 3.4 Hz, 2H), 7.40-7.17 (m, 4H), 7.07-6.96 (m, 1H), 6.91 (s, 1H), 6.36 (s, 1H), 6.25 (s, 1H), 6.06 (s, 2H), 4.78 (dd, J=31.3, 14.1 Hz, 4H), 3.07-2.93 (m, 3H), 2.87 (dd, J=9.5, 5.8 Hz, 2H), 1.02 (dd, J=10.8, 6.8 Hz, 6H); ESMS calculated for $C_{34}H_{32}N_8O_5$: 632.25; Found: 633.1 (M+H)⁺.

SDC-TRAP-0102

2-amino-5-(4-(4-(5-(3-(2,4-dihydroxy-5-isopropylphenyl)-5-hydroxy-4H-1,2,4-triazol-4-yl)-1-methyl-1H-benzo[d]imidazol-2-yl)piperidine-1-carbonyl)phenethyl)-3H-pyrrolo[2,3-d]pyrimidin-4(7H)-one

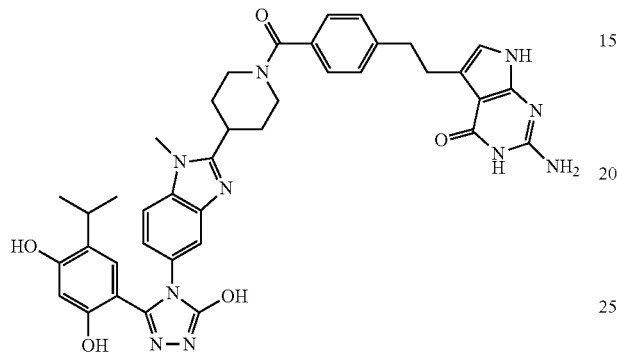

$^1$H NMR (400 MHz, DMSO-d$_6$) δ 11.86 (s, 1H), 10.66-10.60 (m, 1H), 10.17 (s, 1H), 9.57 (s, 1H), 9.36 (s, 1H), 7.48 (d, J=8.7 Hz, 1H), 7.40-7.25 (m, 4H), 7.06-6.99 (m, 1H), 6.86 (s, 1H), 6.35 (d, J=2.3 Hz, 1H), 6.20 (s, 1H), 6.02 (s, 2H), 4.53 (s, 1H), 3.79 (s, 3H), 3.02-2.81 (m, 5H), 1.95 (s, 2H), 1.76 (q, J=11.9 Hz, 2H), 0.96 (d, J=6.7 Hz, 6H); ESMS calculated for C$_{39}$H$_{40}$N$_{10}$O$_5$: 728.32; Found: 729.2 (M+H)$^+$.

SDC-TRAP-0103

2-amino-5-(4-(4-((4-(4-(3-(2,4-dihydroxy-5-isopropylphenyl)-5-hydroxy-4H-1,2,4-triazol-4-yl)benzyl)piperidin-1-yl)methyl)piperidine-1-carbonyl)phenethyl)-3H-pyrrolo[2,3-d]pyrimidin-4(7H)-one

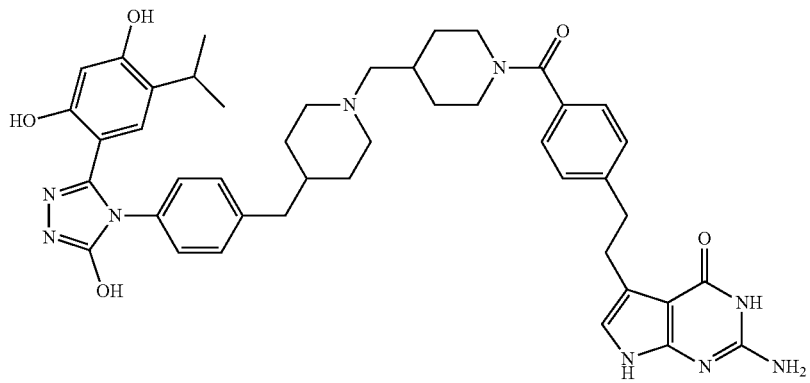 [SMILES: CC(C)c1cc(-c2nnc(O)n2-c2ccc(CC3CCN(CC4CCN(C(=O)c5ccc(CCc6c[nH]c7nc(N)[nH]c(=O)c67)cc5)CC4)CC3)cc2)c(O)cc1O]

$^1$H NMR (400 MHz, DMSO-d$_6$) δ 11.93 (s, 1H), 10.63 (s, 1H), 10.20 (s, 1H), 9.69 (s, 1H), 9.49 (s, 1H), 7.20 (d, J=39.7 Hz, 6H), 7.08 (d, J=8.0 Hz, 2H), 6.73 (s, 1H), 6.31 (d, J=19.5 Hz, 2H), 6.04 (s, 2H), 4.42 (s, 1H), 3.58 (s, 1H), 2.95 (dt, J=13.8, 7.4 Hz, 4H), 2.85 (d, J=8.1 Hz, 2H), 2.77 (d, J=10.7 Hz, 3H), 2.08 (d, J=6.7 Hz, 2H), 1.76-1.59 (m, 6H), 1.51-1.43 (m, 3H), 1.12-0.89 (m, 6H); ESMS calculated for C$_{44}$H$_{51}$N$_9$O$_5$: 785.40; Found: 786.3 (M+H)$^+$.

SDC-TRAP-0130

2-amino-5-(4-(4-(2-(5-(3-(2,4-dihydroxy-5-isopropylphenyl)-5-hydroxy-4H-1,2,4-triazol-4-yl)-1H-indol-1-yl)ethyl)piperidine-1-carbonyl)phenethyl)-3H-pyrrolo[2,3-d]pyrimidin-4(7H)-one

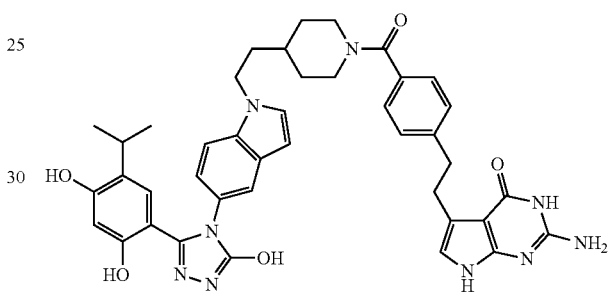

$^1$H NMR (400 MHz, DMSO-d$_6$) δ 11.88 (s, 1H), 10.62 (s, 1H), 10.17-10.11 (m, 1H), 9.53 (dd, J=20.0, 2.8 Hz, 2H), 7.52-7.39 (m, 3H), 7.25 (d, J=2.8 Hz, 4H), 6.97-6.89 (m, 1H), 6.68 (d, J=2.7 Hz, 1H), 6.42 (t, J=3.1 Hz, 1H), 6.33 (d, J=2.8 Hz, 1H), 6.23 (d, J=2.8 Hz, 1H), 6.00 (s, 2H), 4.41 (s, 1H), 4.21 (t, J=7.4 Hz, 2H), 2.98-2.80 (m, 6H), 1.76-1.66 (m, 4H), 1.47 (bs, 2H), 1.20-1.10 (m, 3H), 0.78 (dd, J=7.1, 2.7 Hz, 6H); ESMS calculated for C$_{41}$H$_{43}$N$_9$O$_5$: 741.34; Found: 742.3 (M+H)$^+$.

in vitro activity was determined for these compounds using the HER2 degradation assay set forth herein:

| SDC-TRAP-# | HER2 degradation IC$_{50}$ (nM) |
|---|---|
| SDC-TRAP-0020 | >5000 |
| SDC-TRAP-0019 | 4419 |
| SDC-TRAP-0068 | 262 |
| SDC-TRAP-0078 | 1005 |
| SDC-TRAP-0082 | 1042 |
| SDC-TRAP-0093 | >5,000 |
| SDC-TRAP-0102 | >5,000 |
| SDC-TRAP-0103 | 245 |
| SDC-TRAP-0130 | 1829 |

Mouse Plasma Stability

| SDC-TRAP-# | % Remaining (1 h) |
|---|---|
| SDC-TRAP-0068 | 96.5% |
| SDC-TRAP-0141 | 101% |

Example 27: SDC-TRAPs Comprising SN-38

SDC-TRAP-0011

(S)-4,11-diethyl-4-hydroxy-3,14-dioxo-3,4,12,14-tetrahydro-1H-pyrano[3',4':6,7]indolizino[1,2-b]quinolin-9-yl 4-(4-(3-(2,4-dihydroxy-5-isopropyl-phenyl)-5-hydroxy-4H-1,2,4-triazol-4-yl)phenoxy)piperidine-1-carboxylate

SDC-TRAP-0012

(S)-4,11-diethyl-9-hydroxy-3,14-dioxo-3,4,12,14-tetrahydro-1H-pyrano [3',4':6,7]indolizino[1,2-b]quinolin-4-yl-4-(4-(3-(2,4-dihydroxy-5-isopropyl-phenyl)-5-hydroxy-4H-1,2,4-triazol-4-yl)phenoxy)piperidine-1-carboxylate hydrochloride

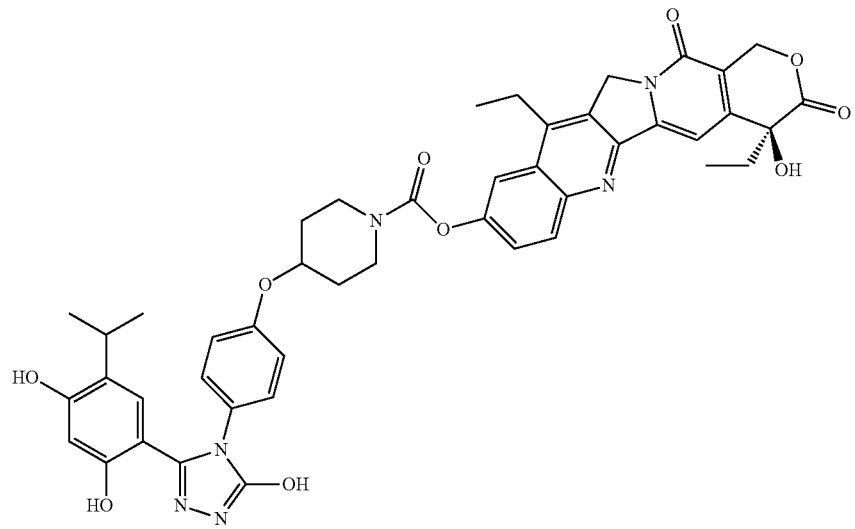 [SMILES: CCc1c2c(nc3ccc(OC(=O)N4CCC(Oc5ccc(-n6c(O)nnc6-c6cc(C(C)C)c(O)cc6O)cc5)CC4)cc13)-c1cc3c(c(=O)n1C2)COC(=O)[C@]3(O)CC]

$^1$H NMR (400 MHz, DMSO-d$_6$) δ 10.02 (s, 3H), 8.17 (d, J=9.2 Hz, 1H), 8.01-7.93 (m, 1H), 7.74-7.62 (m, 2H), 7.18-7.01 (m, 4H), 6.70 (s, 1H), 6.40 (s, 1H), 6.05 (s, 1H), 5.44 (d, J=4.7 Hz, 1H), 5.25 (s, 2H), 4.92 (dd, J=11.8, 6.8 Hz, 1H), 4.69 (d, J=10.6 Hz, 2H), 4.03 (q, J=7.1 Hz, 1H), 3.79 (s, 1H), 3.59 (s, 1H), 3.17 (q, J=7.6 Hz, 2H), 3.03-2.87 (m, 2H), 2.55 (s, 1H), 2.21-1.96 (m, 2H), 1.73 (s, 2H), 1.30 (t, J=7.6 Hz, 3H), 1.01-0.81 (m, 9H) ppm; ESMS calculated for C$_{45}$H$_{44}$N$_6$O$_{10}$: 828.3; found: 829.1 (M+H$^+$).

$^1$H NMR (400 MHz, DMSO-d$_6$) δ 11.88 (s, 1H), 10.34 (s, 1H), 9.60 (s, 1H), 9.43 (s, 1H), 8.02 (t, J=10.0 Hz, 1H), 7.46-7.38 (m, 2H), 7.15-7.07 (m, 2H), 6.98 (d, J=15.2 Hz, 3H), 6.78 (s, 1H), 6.27 (s, 1H), 5.45 (d, J=3.6 Hz, 2H), 5.30 (d, J=2.4 Hz, 2H), 4.64 (d, J=9.6 Hz, 1H), 4.03 (m, 1H), 3.57 (s, 1H), 3.20 (s, 1H), 3.09 (q, J=7.6 Hz, 3H), 2.98 (q, J=6.9 Hz, 1H), 2.55 (s, 4H), 2.14 (q, J=11.2, 9.3 Hz, 3H), 1.46 (s, 1H), 1.29 (t, J=7.6 Hz, 3H), 0.99-0.87 (m, 9H). ppm; ESMS calculated for C$_{45}$H$_{44}$N$_6$O$_{10}$: 828.3; found: 829.0 (M+H$^+$).

SDC-TRAP-0014

(S)-4, 11-diethyl-9-hydroxy-3,14-dioxo-3,4,12,14-tetrahydro-1H-pyrano [3',4':6,7]indolizino[1,2-b]quinolin-4-yl 4-((4-(3-(2,4-dihydroxy-5-isopropyl-phenyl)-5-hydroxy-4H-1,2,4-triazol-4-yl)phenoxy)methyl)piperidine-1-carboxylate

SDC-TRAP-0063

(S)-4,11-diethyl-4-hydroxy-3,14-dioxo-3,4,12,14-tetrahydro-1H-pyrano[3',4':6,7]indolizino[1,2-b]quinolin-9-yl 4-(2-(5-(3-(2,4-dihydroxy-5-isopropyl-phenyl)-5-hydroxy-4H-1,2,4-triazol-4-yl)-1H-indol-1-yl)ethyl)piperidine-1-carboxylate

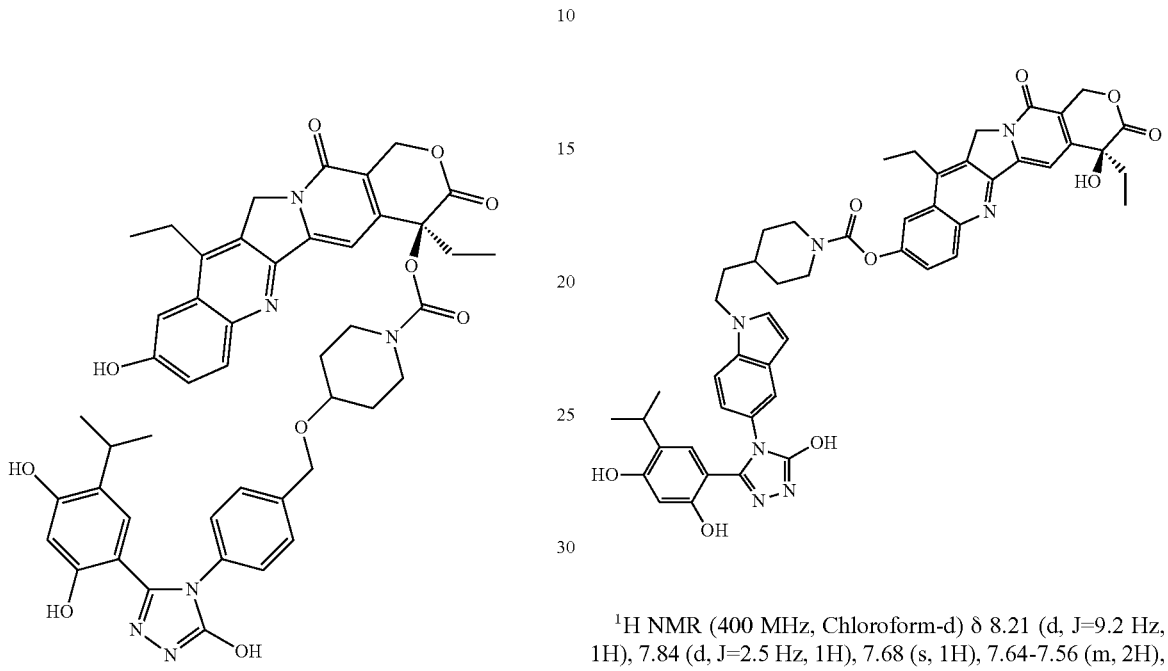

¹H NMR (400 MHz, Chloroform-d) δ 8.21 (d, J=9.2 Hz, 1H), 7.84 (d, J=2.5 Hz, 1H), 7.68 (s, 1H), 7.64-7.56 (m, 2H), 7.47 (d, J=8.7 Hz, 1H), 7.24-7.12 (m, 2H), 6.55 (dd, J=3.2, 0.8 Hz, 1H), 6.37 (d, J=4.2 Hz, 2H), 5.73 (d, J=16.3 Hz, 1H), 5.36-5.24 (m, 3H), 4.41 (d, J=13.5 Hz, 1H), 4.29 (q, J=9.3, 7.5 Hz, 3H), 3.17 (q, J=7.7 Hz, 2H), 3.06 (t, J=12.7 Hz, 1H), 2.96-2.77 (m, 2H), 2.42 (s, 2H), 1.90 (dq, J=14.2, 7.1 Hz, 6H), 1.45-1.33 (m, 5H), 1.31-1.22 (m, 1H), 1.04 (t, J=7.3 Hz, 3H), 0.50 (d, J=6.8 Hz, 6H). ppm; ESMS calculated for $C_{49}H_{49}N_7O_9$: 879.4; found: 880.2 (M+H⁺).

¹H NMR (400 MHz, Methanol-d₄) δ 8.07 (d, J=9.1 Hz, 1H), 7.91 (d, J=9.1 Hz, 1H), 7.52-7.36 (m, 4H), 7.35-7.16 (m, 2H), 7.04 (d, J=8.4 Hz, 1H), 6.94 (d, J=8.5 Hz, 1H), 6.57-6.49 (m, 1H), 6.37 (s, 1H), 5.67 (d, J=16.9 Hz, 1H), 5.42 (d, J=17.0 Hz, 1H), 4.45 (s, 2H), 4.12-4.00 (m, 1H), 3.88 (dd, J=17.8, 7.5 Hz, 1H), 3.78 (d, J=7.6 Hz, 1H), 3.39 (s, 2H), 3.14 (q, J=10.3, 6.7 Hz, 2H), 2.99 (dt, J=14.4, 7.1 Hz, 1H), 2.83 (d, J=14.9 Hz, 1H), 2.37-1.96 (m, 5H), 1.86 (d, J=13.2 Hz, 2H), 1.77 (d, J=13.5 Hz, 1H), 1.62 (td, J=27.9, 24.2, 13.8 Hz, 1H), 1.39 (t, J=7.6 Hz, 3H), 1.04 (t, J=7.5 Hz, 3H), 0.91-0.73 (m, 6H). ppm; ESMS calculated for $C_{46}H_{46}N_6O_{10}$: 842.3; found: 843.1 (M+H⁺).

SDC-TRAP-0064

(S)-4,11-diethyl-9-hydroxy-3,14-dioxo-3,4,12,14-tetrahydro-1H-pyrano[3',4':6,7]indolizino[1,2-b]quinolin-4-yl 4-(2-(5-(3-(2,4-dihydroxy-5-isopropyl-phenyl)-5-hydroxy-4H-1,2,4-triazol-4-yl)-1H-indol-1-yl)ethyl)piperidine-1-carboxylate

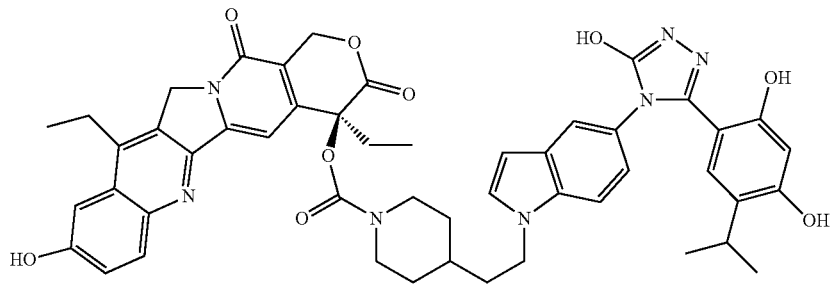 [SMILES: CCc1c2c(nc3ccc(O)cc13)-c1cc3c(c(=O)n1C2)COC(=O)[C@@]3(CC)OC(=O)N1CCC(CCn2ccc3cc(-n4c(O)nnc4-c4cc(C(C)C)c(O)cc4O)ccc32)CC1]

ESMS calculated for $C_{49}H_{49}N_7O_9$: 879.4; found: 880.1 (M+H⁺).

SDC-TRAP-0065

(S)-4,11-diethyl-4-hydroxy-3,14-dioxo-3,4,12,14-tetrahydro-1H-pyrano[3',4':6,7]indolizino[1,2-b]quinolin-9-yl (3-(4-(4-(3-(2,4-dihydroxy-5-isopropylphenyl)-5-hydroxy-4H-1,2,4-triazol-4-yl)benzyl)piperazin-1-yl)propyl)(methyl)carbamate

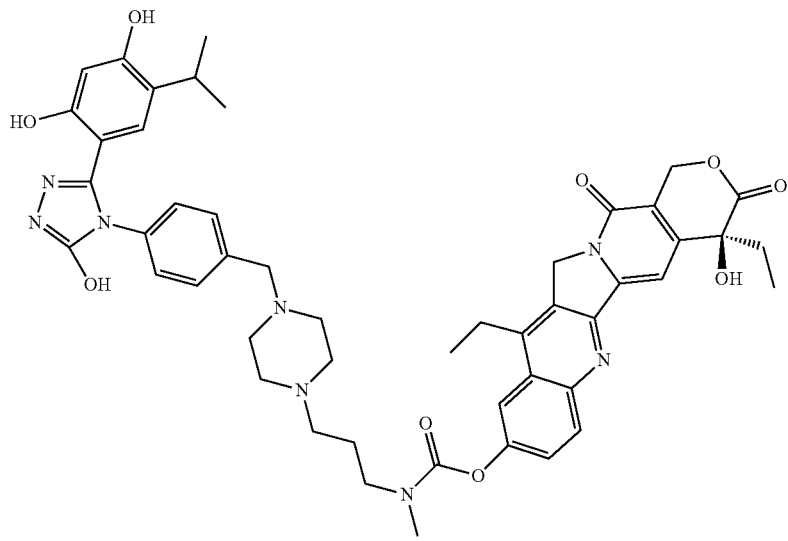 [SMILES: CCc1c2c(nc3ccc(OC(=O)N(C)CCCN4CCN(Cc5ccc(-n6c(O)nnc6-c6cc(C(C)C)c(O)cc6O)cc5)CC4)cc13)-c1cc3c(c(=O)n1C2)COC(=O)[C@]3(O)CC]

$^1$H NMR (400 MHz, Chloroform-d) δ 8.22 (dd, J=9.3, 2.0 Hz, 1H), 7.86 (dd, J=8.9, 2.6 Hz, 1H), 7.70 (d, J=2.2 Hz, 1H), 7.66-7.56 (m, 1H), 7.49 (d, J=7.9 Hz, 2H), 7.37-7.24 (m, 4H), 6.47 (d, J=16.0 Hz, 1H), 6.41-6.35 (m, 1H), 5.72 (dd, J=16.2, 2.2 Hz, 1H), 5.37-5.26 (m, 3H), 4.0 (m, 1H), 3.57 (d, J=4.1 Hz, 3H), 3.51-3.35 (m, 3H), 3.19 (d, J=8.4 Hz, 4H), 3.09 (d, J=2.2 Hz, 1H), 2.92 (dt, J=19.0, 7.0 Hz, 1H), 2.58-2.42 (m, 6H), 1.92 (dq, J=15.4, 7.4 Hz, 5H), 1.41 (tt, J=7.7, 4.1 Hz, 4H), 1.32-1.22 (m, 2H), 1.04 (t, J=7.4 Hz, 3H), 0.78-0.65 (m, 6H). ppm; ESMS calculated for $C_{49}H_{54}N_8O_9$: 898.4; found: 899.2 (M+H$^+$).

SDC-TRAP-0066

(S)-4,11-diethyl-4-hydroxy-3,14-dioxo-3,4,12,14-tetrahydro-1H-pyrano[3',4':6,7]indolizino[1,2-b]quinolin-9-yl (2-(4-(4-(3-(2,4-dihydroxy-5-isopropylphenyl)-5-hydroxy-4H-1,2,4-triazol-4-yl)benzyl)piperazin-1-yl)ethyl)(methyl)carbamate

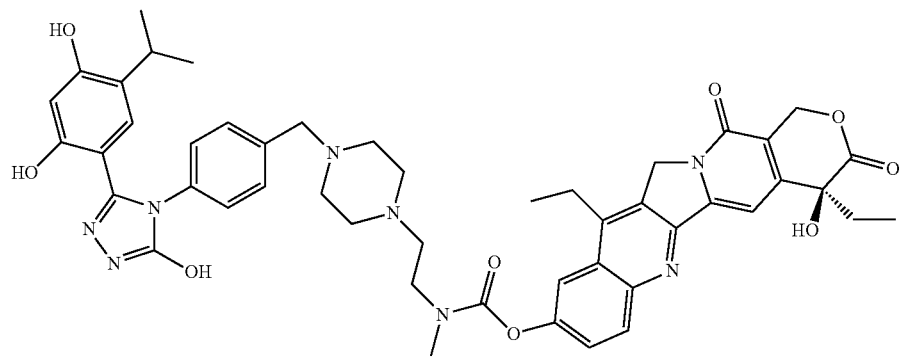 [SMILES: CCc1c2c(nc3ccc(OC(=O)N(C)CCN4CCN(Cc5ccc(-n6c(O)nnc6-c6cc(C(C)C)c(O)cc6O)cc5)CC4)cc13)-c1cc3c(c(=O)n1C2)COC(=O)[C@]3(O)CC]

$^1$H NMR (400 MHz, Chloroform-d) δ 8.22 (dd, J=9.2, 2.9 Hz, 1H), 7.87 (t, J=2.5 Hz, 1H), 7.70 (d, J=1.3 Hz, 1H), 7.62 (ddd, J=8.7, 5.9, 2.4 Hz, 1H), 7.51-7.44 (m, 2H), 7.31-7.23 (m, 2H), 6.47 (d, J=15.7 Hz, 1H), 6.39-6.31 (m, 1H), 5.70 (d, J=16.4 Hz, 1H), 5.37-5.26 (m, 3H), 3.61-3.53 (m, 3H), 3.43-3.33 (m, 3H), 3.25-3.13 (m, 3H), 3.10 (s, 1H), 2.96-2.84 (m, 1H), 2.77-2.60 (m, 5H), 2.55 (s, 4H), 1.99-1.85 (m, 2H), 1.41 (t, J=7.7 Hz, 3H), 1.03 (t, J=7.3 Hz, 3H), 0.77-0.65 (m, 6H). ppm; ESMS calculated for $C_{48}H_{52}N_8O_9$: 884.4; found: 885.1 (M+H$^+$).

SDC-TRAP-0084

(S)-4,11-diethyl-9-hydroxy-3,14-dioxo-3,4,12,14-tetrahydro-1H-pyrano[3',4':6,7]indolizino[1,2-b]quinolin-4-yl (3-(4-(4-(3-(2,4-dihydroxy-5-isopropylphenyl)-5-hydroxy-4H-1,2,4-triazol-4-yl)benzyl)piperazin-1-yl)propyl)(methyl)carbamate (m, 7H), 3.09 (d, J=16.2 Hz, 3H), 2.98 (p, J=6.8 Hz, 1H), 2.89 (s, 2H), 2.76 (s, 1H), 2.46 (s, 2H), 2.20-2.05 (m, 2H), 1.84 (t, J=8.2 Hz, 1H), 1.27 (td, J=7.7, 4.8 Hz, 3H), 1.02-0.85 (m, 9H). ppm; ESMS calculated for $C_{49}H_{54}N_8O_9$: 898.4; found: 899.3 (M+H$^+$).

SDC-TRAP-0086

(S)-4,11-diethyl-4-hydroxy-3,14-dioxo-3,4,12,14-tetrahydro-1H-pyrano[3',4':6,7]indolizino[1,2-b]quinolin-9-yl 4-(4-(3-(2,4-dihydroxy-5-isopropylphenyl)-5-hydroxy-4H-1,2,4-triazol-4-yl) phenethyl) piperidine-1-carboxylate

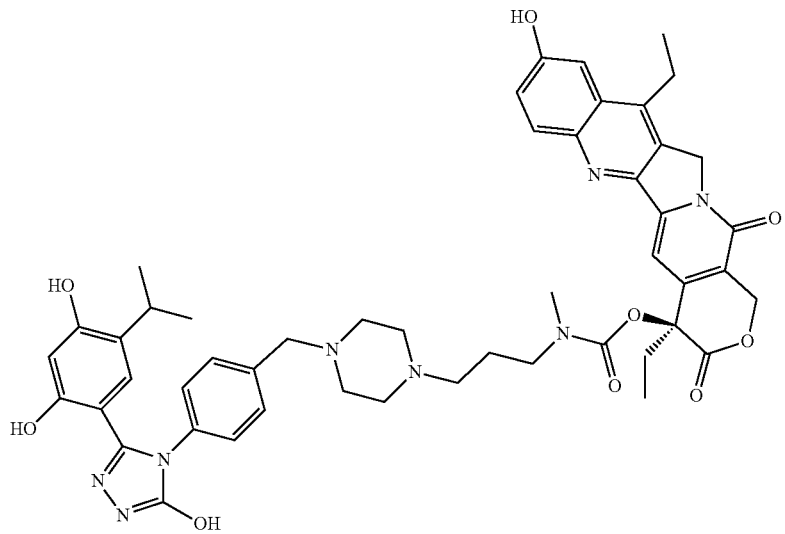 [SMILES: CCc1c2c(nc3ccc(O)cc13)-c1cc3c(c(=O)n1C2)COC(=O)[C@@]3(CC)OC(=O)N(C)CCCN1CCN(Cc2ccc(-n3c(O)nnc3-c3cc(C(C)C)c(O)cc3O)cc2)CC1]

$^1$H NMR (400 MHz, DMSO-d$_6$) δ 12.05 (s, 1H), 9.74 (s, 1H), 8.02 (dd, J=9.9, 6.7 Hz, 1H), 7.50 (t, J=7.7 Hz, 1H), 7.45-7.33 (m, 3H), 7.27-7.17 (m, 2H), 7.01 (d, J=5.8 Hz, 1H), 6.85 (d, J=2.3 Hz, 1H), 6.26 (d, J=3.2 Hz, 1H), 5.44 (d, J=2.4 Hz, 2H), 5.28 (s, 2H), 4.12 (d, J=16.9 Hz, 1H), 3.96 (s, 1H), 3.69 (s, 2H), 3.64 (s, 2H), 3.31-3.22 (m, 1H), 3.18

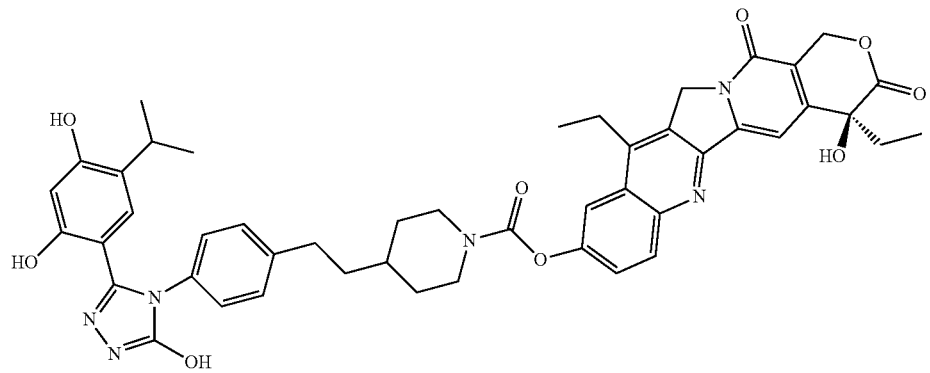 [SMILES: CCc1c2c(nc3ccc(OC(=O)N4CCC(CCc5ccc(-n6c(O)nnc6-c6cc(C(C)C)c(O)cc6O)cc5)CC4)cc13)-c1cc3c(c(=O)n1C2)COC(=O)[C@]3(O)CC]

$^1$H NMR (400 MHz, Chloroform-d) δ 8.21 (d, J=9.2 Hz, 1H), 7.85 (d, J=2.5 Hz, 1H), 7.69-7.57 (m, 2H), 7.37 (d, J=7.9 Hz, 2H), 7.28 (d, J=8.8 Hz, 2H), 6.44 (d, J=1.6 Hz, 1H), 6.37 (d, J=1.1 Hz, 1H), 5.74 (dt, J=16.3, 1.2 Hz, 1H), 5.36-5.24 (m, 3H), 4.42 (d, J=13.4 Hz, 1H), 4.31 (d, J=13.3 Hz, 1H), 3.23-3.03 (m, 3H), 2.94 (dq, J=14.0, 7.3 Hz, 2H), 2.76 (t, 1=7.7 Hz, 2H), 2.05 (d, J=0.9 Hz, 1H), 1.91 (dq, J=14.6, 7.4 Hz, 4H), 1.66 (d, J=7.7 Hz, 2H), 1.40 (q, J=9.8, 8.7 Hz, 5H), 1.08-0.89 (m, 3H), 0.74 (d, J=6.8 Hz, 6H). ppm; ESMS calculated for $C_{47}H_{48}N_6O_9$: 840.4; found: 841.2 ($M+H^+$).

SDC-TRAP-0088

(S)-4,11-diethyl-4-hydroxy-3,14-dioxo-3,4,12,14-tetrahydro-1H-pyrano[3',4':6,7]indolizino[1,2-b]quinolin-9-yl 4-((4-(4-(3-(2,4-dihydroxy-5-isopropylphenyl)-5-hydroxy-4H-1,2,4-triazol-4-yl)benzyl)piperazin-1-yl)methyl)piperidine-1-carboxylate

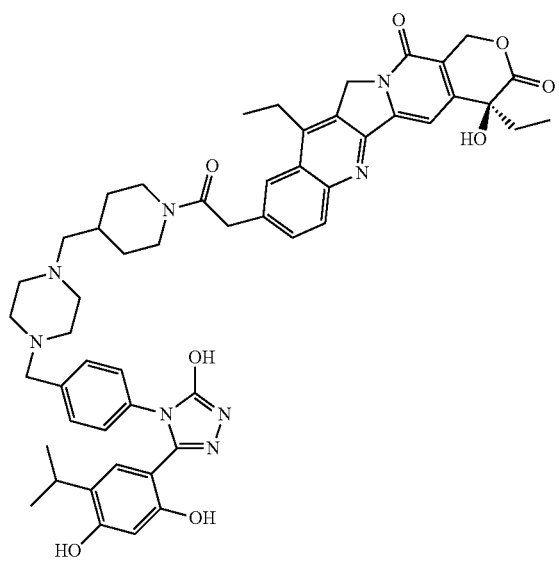 [SMILES: CCc1c2c(nc3ccc(CC(=O)N4CCC(CN5CCN(Cc6ccc(-n7c(O)nnc7-c7cc(C(C)C)c(O)cc7O)cc6)CC5)CC4)cc13)-c1cc3c(c(=O)n1C2)COC(=O)[C@]3(O)CC]

ESMS calculated for $C_{51}H_{56}N_8O_9$: 924.4; found: 925.4 ($M+H^+$).

SDC-TRAP-0087

(S)-4,11-diethyl-9-hydroxy-3,14-dioxo-3,4,12,14-tetrahydro-1H-pyrano[3',4':6,7]indolizino[1,2-b]quinolin-4-yl (2-(4-(4-(3-(2,4-dihydroxy-5-isopropylphenyl)-5-hydroxy-4H-1,2,4-triazol-4-yl)benzyl)piperazin-1-yl)ethyl)(methyl)carbamate

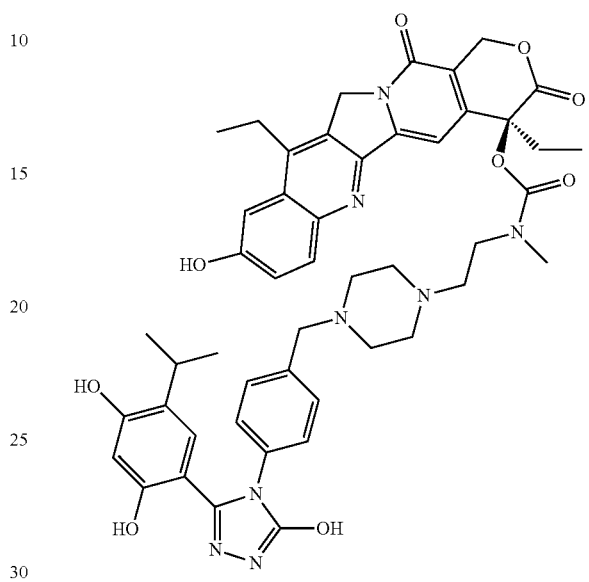

$^1$H NMR (400 MHz, Methanol-$d_4$) δ 8.54 (s, 1H), 8.20 (s, 1H), 7.90-7.50 (m, 4H), 7.41 (s, 1H), 7.28 (s, 1H), 6.90-6.20 (m, 2H), 5.70-5.30 (m, 6H), 4.40-4.10 (m, 7H), 3.98 (s, 2H), 3.77 (s, 2H), 3.71 (s, 2H), 3.59 (s, 2H), 3.37 (d, J=19.0 Hz, 5H), 3.05 (s, 1H), 2.94 (s, 1H), 1.44 (s, 2H), 1.05 (dd, J=19.6, 6.6 Hz, 6H), 0.96 (d, J=6.6 Hz, 6H). ppm; ESMS calculated for $C_{48}H_{52}N_8O_9$: 884.4; found: 885.3 ($M+H^+$).

SDC-TRAP-0089

(S)-4,11-diethyl-4-hydroxy-3,14-dioxo-3,4,12,14-tetrahydro-1H-pyrano[3',4':6,7]indolizino[1,2-b]quinolin-9-yl 4-(5-(3-(2,4-dihydroxy-5-isopropylphenyl)-5-hydroxy-4H-1,2,4-triazol-4-yl)isoindolin-2-yl)piperidine-1-carboxylate

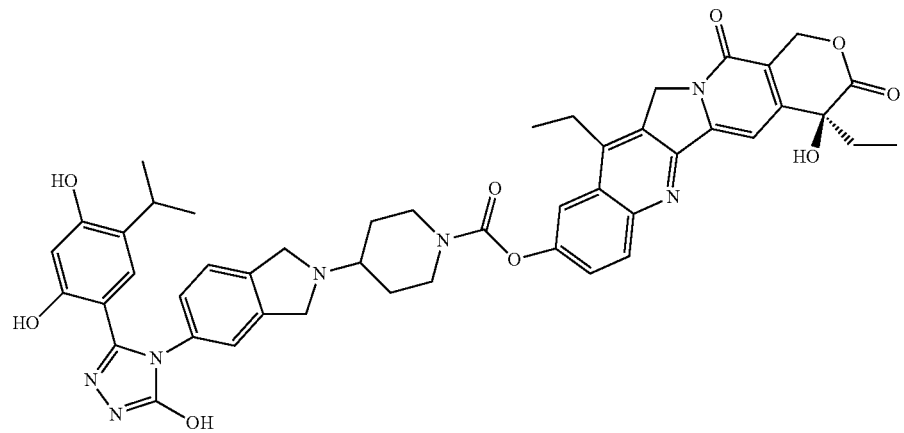 [SMILES: CCc1c2c(nc3ccc(OC(=O)N4CCC(N5Cc6ccc(-n7c(O)nnc7-c7cc(C(C)C)c(O)cc7O)cc6C5)CC4)cc13)-c1cc3c(c(=O)n1C2)COC(=O)[C@]3(O)CC]

¹H NMR (400 MHz, Chloroform-d) δ 8.22 (d, J=9.2 Hz, 1H), 7.87 (d, J=2.5 Hz, 1H), 7.69 (s, 1H), 7.62 (dd, J=9.2, 2.5 Hz, 1H), 7.39 (d, J=7.8 Hz, 1H), 7.20 (d, J=7.5 Hz, 2H), 6.49 (s, 1H), 6.36 (s, 1H), 5.71 (d, J=16.4 Hz, 1H), 5.36-5.25 (m, 3H), 4.31 (d, J=13.3 Hz, 1H), 4.18 (d, J=13.3 Hz, 1H), 4.11-4.03 (m, 4H), 3.42-3.30 (m, 1H), 3.19 (q, J=7.7 Hz, 1H), 3.00 (h, J=7.4, 6.9 Hz, 1H), 2.81-2.71 (m, 1H), 2.09-2.00 (m, 2H), 1.98-1.85 (m, 5H), 1.42 (t, J=7.7 Hz, 3H), 1.32-1.23 (m, 3H), 1.04 (t, J=7.4 Hz, 3H), 0.79 (d, J=6.8 Hz, 6H). ppm; ESMS calculated for $C_{47}H_{47}N_7O_9$: 853.3; found: 854.3 (M+H⁺).

SDC-TRAP-0090

(S)-4,11-diethyl-4-hydroxy-3,14-dioxo-3,4,12,14-tetrahydro-1H-pyrano[3',4':6,7]indolizino[1,2-b]quinolin-9-yl 4-(5-(3-(2,4-dihydroxy-5-isopropyl-phenyl)-5-hydroxy-4H-1,2,4-triazol-4-yl)pyridin-2-yl)piperazine-1-carboxylate

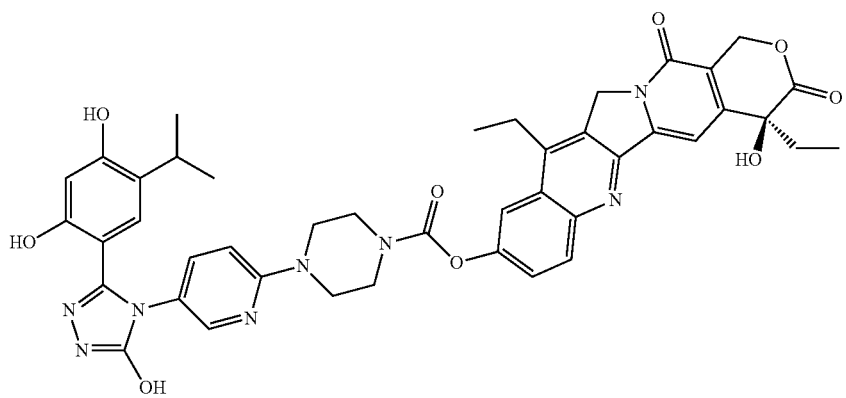 [SMILES: CCc1c2c(nc3ccc(OC(=O)N4CCN(c5ccc(-n6c(O)nnc6-c6cc(C(C)C)c(O)cc6O)cn5)CC4)cc13)-c1cc3c(c(=O)n1C2)COC(=O)[C@]3(O)CC]

¹H NMR (400 MHz, Chloroform-d) δ 8.25 (d, J=9.3 Hz, 1H), 8.12 (d, J=2.8 Hz, 1H), 7.91 (d, J=2.7 Hz, 1H), 7.78-7.57 (m, 2H), 7.51 (dd, J=9.1, 2.8 Hz, 1H), 6.85 (dd, J=9.4, 2.8 Hz, 1H), 6.62 (d, J=2.8 Hz, 1H), 6.39 (d, J=2.8 Hz, 1H), 5.71 (d, J=16.5 Hz, 1H), 5.39-5.22 (m, 4H), 4.07 (s, 1H), 3.98-3.68 (m, 4H), 3.21 (d, J=7.8 Hz, 2H), 3.12-2.95 (m, 1H), 2.06 (d, J=2.8 Hz, 2H), 2.01-1.86 (m, 2H), 1.61 (d, J=7.0 Hz, 1H), 1.44 (td, J=7.7, 2.8 Hz, 4H), 1.26 (d, J=3.4 Hz, 2H), 1.05 (td, J=7.3, 2.8 Hz, 3H), 0.94-0.80 (m, 6H). ppm; ESMS calculated for $C_{43}H_{42}N_8O_9$: 814.3; found: 815.2 (M+H⁺).

SDC-TRAP-0091

(S)-4,11-diethyl-9-hydroxy-3,14-dioxo-3,4,12,14-tetrahydro-1H-pyrano[3',4':6,7]indolizino[1,2-b]quinolin-4-yl 4-(5-(3-(2,4-dihydroxy-5-isopropylphenyl)-5-hydroxy-4H-1,2,4-triazol-4-yl)pyridin-2-yl)piperazine-1-carboxylate

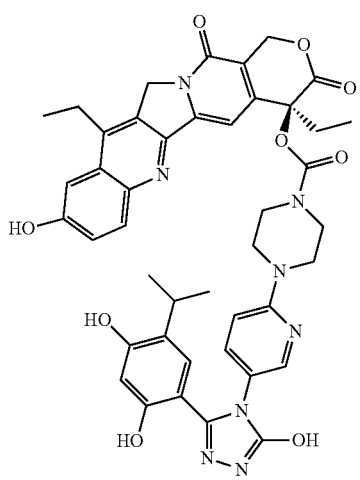 [SMILES: CCc1c2c(nc3ccc(O)cc13)-c1cc3c(c(=O)n1C2)COC(=O)[C@@]3(CC)OC(=O)N1CCN(c2ccc(-n3c(O)nnc3-c3cc(C(C)C)c(O)cc3O)cn2)CC1]

$^1$H NMR (400 MHz, DMSO-d$_6$) δ 11.93 (s, 1H), 9.64 (s, 1H), 9.48 (s, 1H), 7.99-7.87 (m, 2H), 7.49-7.37 (m, 3H), 7.04 (s, 1H), 6.98-6.91 (m, 2H), 6.28 (s, 1H), 5.53-5.38 (m, 2H), 5.29 (d, J=1.8 Hz, 2H), 3.78-3.60 (m, 4H), 3.51-3.34 (m, 4H), 3.14-2.95 (m, 3H), 2.14 (dd, J=14.3, 7.0 Hz, 2H), 1.38-1.21 (m, 3H), 1.04 (dd, J=6.9, 1.9 Hz, 6H), 0.92 (t, J=7.4 Hz, 3H). ppm; ESMS calculated for C$_{43}$H$_{42}$N$_8$O$_9$: 814.3; found: 815.2 (M+H$^+$).

SDC-TRAP-0092

(S)-4,11-diethyl-9-hydroxy-3,14-dioxo-3,4,12,14-tetrahydro-1H-pyrano[3',4':6,7]indolizino[1,2-b]quinolin-4-yl 4-(5-(3-(2,4-dihydroxy-5-isopropylphenyl)-5-hydroxy-4H-1,2,4-triazol-4-yl)isoindolin-2-yl)piperidine-1-carboxylate

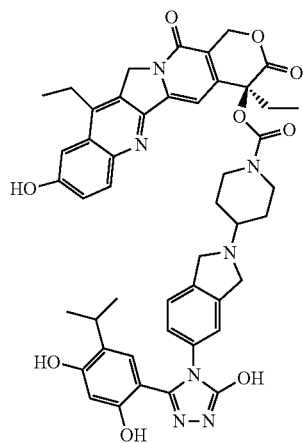 [SMILES: CCc1c2c(nc3ccc(O)cc13)-c1cc3c(c(=O)n1C2)COC(=O)[C@@]3(CC)OC(=O)N1CCC(N2Cc3ccc(-n4c(O)nnc4-c4cc(C(C)C)c(O)cc4O)cc3C2)CC1]

$^1$H NMR (400 MHz, Chloroform-d) δ 8.02 (d, J=9.1 Hz, 1H), 7.89 (d, J=9.1 Hz, 1H), 7.47-7.37 (m, 1H), 7.30-7.20 (m, 2H), 7.17 (dd, J=9.8, 2.6 Hz, 2H), 7.04 (s, 1H), 6.50 (d, J=27.1 Hz, 1H), 6.32 (d, J=4.2 Hz, 1H), 5.68 (d, J=16.9 Hz, 1H), 5.40 (d, J=16.9 Hz, 1H), 5.18-4.87 (m, 2H), 4.41-4.19 (m, 1H), 4.10-3.81 (m, 4H), 3.76-3.60 (m, 1H), 3.48-3.36 (m, 1H), 3.09-2.85 (m, 6H), 2.72 (s, 1H), 2.28 (dd, J=13.8, 7.5 Hz, 1H), 2.22-2.08 (m, 1H), 1.88 (d, J=10.1 Hz, 1H), 1.68-1.54 (m, 1H), 1.35-1.18 (m, 3H), 1.02 (dt, J=12.6, 6.1 Hz, 3H), 0.85-0.69 (m, 6H). ppm; ESMS calculated for C$_{47}$H$_{47}$N$_7$O$_9$: 853.3; found: 854.2 (M+H$^+$).

SDC-TRAP-0104

(S)-4,11-diethyl-9-hydroxy-3,14-dioxo-3,4,12,14-tetrahydro-1H-pyrano[3',4':6,7]indolizino[1,2-b]quinolin-4-yl 4-(4-(3-(2,4-dihydroxy-5-isopropylphenyl)-5-hydroxy-4H-1,2,4-triazol-4-yl)phenethyl)piperidine-1-carboxylate

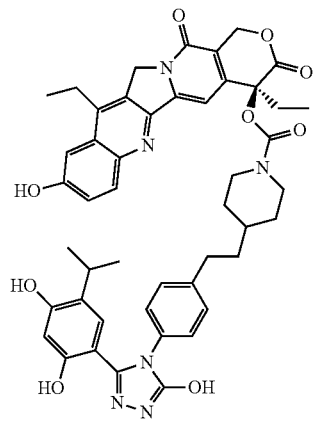 [SMILES: CCc1c2c(nc3ccc(O)cc13)-c1cc3c(c(=O)n1C2)COC(=O)[C@@]3(CC)OC(=O)N1CCC(CCc2ccc(-n3c(O)nnc3-c3cc(C(C)C)c(O)cc3O)cc2)CC1]

$^1$H NMR (400 MHz, Chloroform-d$_6$) δ 8.44 (d, J=9.2 Hz, 1H), 8.11-7.96 (m, 2H), 7.72 (s, 1H), 7.53 (d, J=9.2 Hz, 1H), 7.35 (s, 1H), 7.30-7.13 (m, 4H), 6.50-6.29 (m, 2H), 5.68 (d, J=17.3 Hz, 1H), 5.40 (d, J=17.3 Hz, 1H), 5.18 (t, J=5.4 Hz, 2H), 4.42 (dd, J=24.8, 13.2 Hz, 1H), 4.05-3.89 (m, 1H), 3.44 (s, 3H), 2.84-2.60 (m, 4H), 2.44-2.10 (m, 2H), 1.94-1.80 (m, 5H), 1.61 (dd, J=11.7, 3.7 Hz, 3H), 1.36 (dt, J=12.3, 4.9 Hz, 3H), 1.05 (dq, J=13.8, 7.0 Hz, 3H), 0.78-0.61 (m, 6H). ppm; ESMS calculated for C$_{47}$H$_{48}$N$_6$O$_9$: 840.4; found: 841.2 (M+H$^+$).

SDC-TRAP-0106

(S)-4, 11-diethyl-9-hydroxy-3,14-dioxo-3,4, 12, 14-tetrahydro-1H-pyrano[3',4':6,7]indolizino[1,2-b]quinolin-4-yl 2-(4-(4-(3-(2,4-dihydroxy-5-isopropylphenyl)-5-hydroxy-4H-1,2,4-triazol-4-yl)phenethyl)piperidin-1-yl)acetate

SDC-TRAP-0107

(S)-4,11-diethyl-9-hydroxy-3,14-dioxo-3,4,12,14-tetrahydro-1H-pyrano[3',4':6,7]indolizino[1,2-b]quinolin-4-yl 2-(4-(2-(5-(3-(2,4-dihydroxy-5-isopropylphenyl)-5-hydroxy-4H-1,2,4-triazol-4-yl)-1H-indol-1-yl)ethyl)piperidin-1-yl)acetate

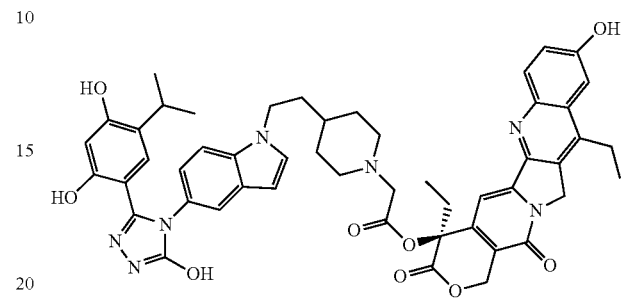

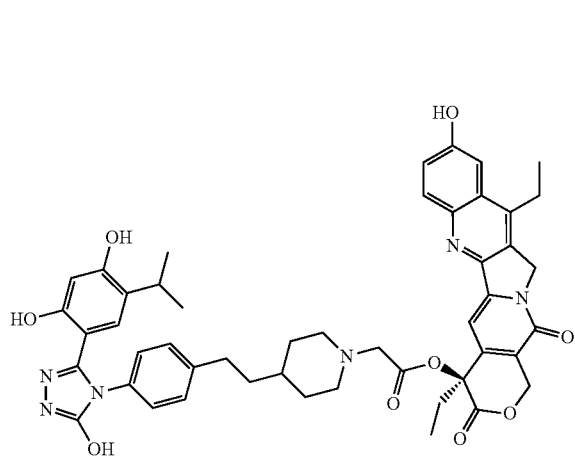 [SMILES: CCc1c2c(nc3ccc(O)cc13)-c1cc3c(c(=O)n1C2)COC(=O)[C@@]3(CC)OC(=O)CN1CCC(CCc2ccc(-n3c(O)nnc3-c3cc(C(C)C)c(O)cc3O)cc2)CC1]

$^1$H NMR (400 MHz, Chloroform-d) δ 8.00 (d, J=9.1 Hz, 1H), 7.39 (dd, J=5.2, 2.5 Hz, 1H), 7.31 (d, J=2.6 Hz, 1H), 7.29-7.14 (m, 4H), 6.40 (d, J=23.7 Hz, 2H), 5.68 (d, J=17.0 Hz, 1H), 5.42 (dd, J=17.0, 3.1 Hz, 1H), 5.22 (s, 2H), 3.11 (q, J=7.9 Hz, 2H), 2.98-2.81 (m, 2H), 2.59 (dt, J=10.3, 4.7 Hz, 2H), 2.45-2.08 (m, 6H), 1.80-1.44 (m, 4H), 1.44-1.19 (m, 6H), 0.99 (t, J=7.4 Hz, 3H), 0.70 (dd, J=6.8, 2.3 Hz, 6H). ppm; ESMS calculated for $C_{48}H_{50}N_6O_9$: 854.4; found: 855.3 (M+H$^+$).

$^1$H NMR (400 MHz, Chloroform-d) δ 8.07-7.92 (m, 1H), 7.54 (d, J=7.2 Hz, 1H), 7.36 (dq, J=5.9, 3.7 Hz, 5H), 7.30-7.19 (m, 1H), 7.19-6.99 (m, 2H), 6.47 (d, J=3.5 Hz, 1H), 6.41-6.27 (m, 2H), 5.75-5.59 (m, 1H), 5.41 (d, J=17.1 Hz, 1H), 5.21 (s, 2H), 4.26-3.94 (m, 2H), 3.51-3.24 (m, 5H), 3.11 (q, J=7.6 Hz, 2H), 2.93 (t, J=13.0 Hz, 2H), 2.80 (q, J=6.8 Hz, 1H), 2.23 (ddd, J=36.9, 13.1, 7.3 Hz, 4H), 1.71 (td, J=14.1, 13.5, 5.4 Hz, 4H), 1.48-1.15 (m, 5H), 1.05-0.89 (m, 3H), 0.52-0.32 (m, 6H). ppm; ESMS calculated for $C_{50}H_{51}N_7O_9$: 893.4; found: 894.3 (M+H$^+$).

SDC-TRAP-0145

(S)-4,11-diethyl-4-hydroxy-3,14-dioxo-3,4,12,14-tetrahydro-1H-pyrano[3',4':6,7]indolizino[1,2-b]quinolin-9-yl (4-(4-(3-(2,4-dihydroxy-5-isopropylphenyl)-5-(ethylcarbamoyl)-4H-1,2,4-triazol-4-yl)phenoxy)phenyl)(methyl)carbamate

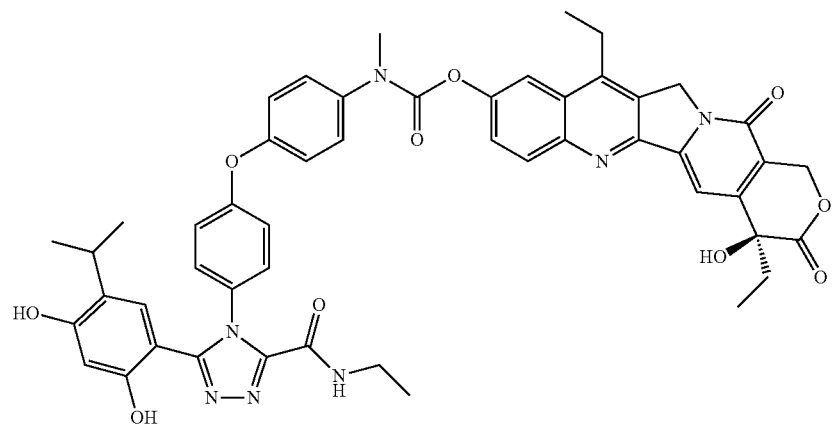 [SMILES: CCNC(=O)c1nnc(-c2cc(C(C)C)c(O)cc2O)n1-c1ccc(Oc2ccc(N(C)C(=O)Oc3ccc4nc5c(c(CC)c4c3)Cn3c-5cc4c(c3=O)COC(=O)[C@]4(O)CC)cc2)cc1]

ESMS calculated for $C_{50}H_{47}N_7O_{10}$: 905.3; found: 906.3 (M+H$^+$).

SDC-TRAP-0204

(S)—(S)4,11-diethyl-4-hydroxy-3,14-dioxo-3,4,12,14-tetrahydro-1H-pyrano[3',4':6,7]indolizino[1,2-b]quinolin-9-yl 2-(4-(4-(3-(2,4-dihydroxy-5-isopropylphenyl)-5-hydroxy-4H-1,2,4-triazol-4-yl)phenyl)piperazine-1-carbonyl)pyrrolidine-1-carbamate

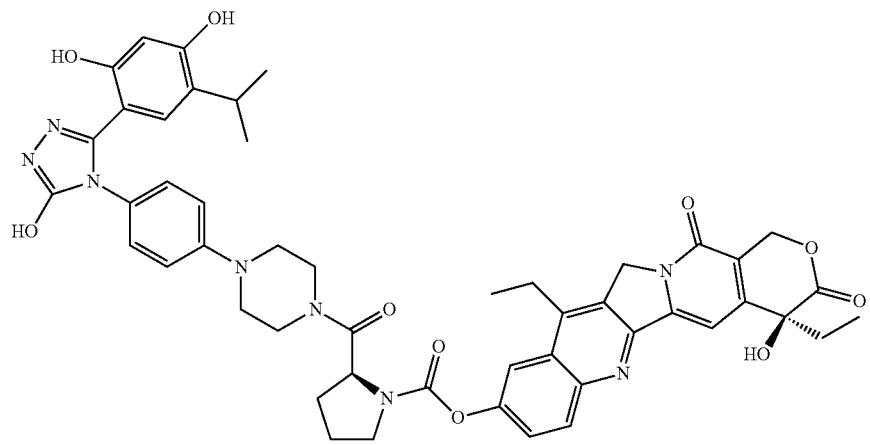 [SMILES: CCc1c2c(nc3ccc(OC(=O)N4CCC[C@H]4C(=O)N4CCN(c5ccc(-n6c(O)nnc6-c6cc(C(C)C)c(O)cc6O)cc5)CC4)cc13)-c1cc3c(c(=O)n1C2)COC(=O)[C@]3(O)CC]

$^1$H NMR (400 MHz, Chloroform-d) δ 8.20 (dd, J=9.2, 5.6 Hz, 1H), 7.86 (dd, J=42.0, 2.5 Hz, 1H), 7.72-7.50 (m, 2H), 7.22-7.08 (m, 2H), 6.95 (dd, J=35.5, 8.8 Hz, 2H), 6.49-6.25 (m, 2H), 5.72 (dd, J=16.4, 4.4 Hz, 1H), 5.42-5.23 (m, 3H), 5.05-4.79 (m, 1H), 4.05-3.51 (m, 5H), 3.39-3.02 (m, 5H), 2.67-2.20 (m, 5H), 2.15-2.00 (m, 2H), 1.90 (h, J=7.0 Hz, 2H), 1.50-1.31 (m, 4H), 1.26 (t, J=7.1 Hz, 2H), 1.03 (td, J=7.4, 2.6 Hz, 3H), 0.56 (ddd, J=73.4, 8.4, 6.9 Hz, 6H). ppm; ESMS calculated for $C_{49}H_{50}N_8O_{10}$: 910.4; found: 911.1 (M+H$^+$).

SDC-TRAP-0207

(S)-4,11-diethyl-4-hydroxy-3,14-dioxo-3,4,12,14-tetrahydro-1H-pyrano[3',4':6,7]indolizino[1,2-b]quinolin-9-yl (2-(4-(2-(5-(3-(2,4-dihydroxy-5-isopropylphenyl)-5-hydroxy-4H-1,2,4-triazol-4-yl)-1H-indol-1-yl)ethyl)piperidin-1-yl)-2-oxoethyl)(methyl)carbamate

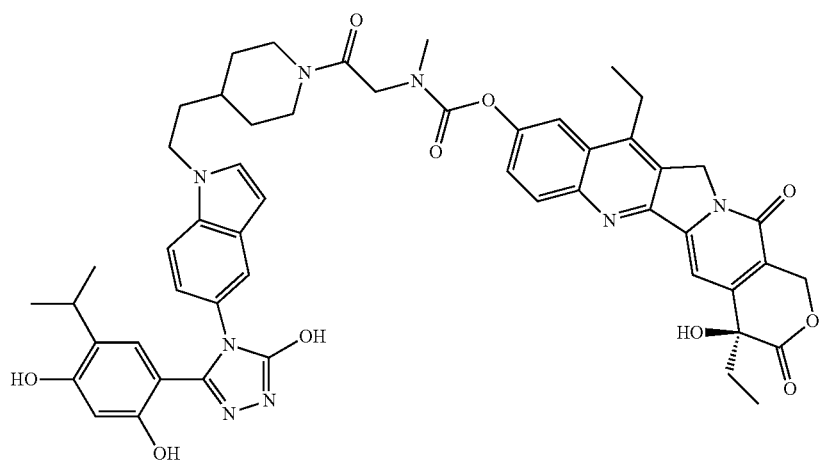 [SMILES: CCc1c2c(nc3ccc(OC(=O)N(C)CC(=O)N4CCC(CCn5ccc6cc(-n7c(O)nnc7-c7cc(C(C)C)c(O)cc7O)ccc65)CC4)cc13)-c1cc3c(c(=O)n1C2)COC(=O)[C@]3(O)CC]

¹H NMR (400 MHz, Chloroform-d) δ 8.19 (dd, J=9.2, 2.9 Hz, 1H), 7.95-7.78 (m, 1H), 7.71-7.49 (m, 3H), 7.38 (dd, J=28.1, 8.6 Hz, 1H), 7.18-7.05 (m, 2H), 6.50 (dd, J=15.3, 3.4 Hz, 1H), 6.37-6.15 (m, 2H), 5.72 (d, J=16.3 Hz, 1H), 5.38-5.09 (m, 3H), 4.49-4.02 (m, 5H), 3.78 (dd, J=12.7, 5.5 Hz, 1H), 3.27 (s, 2H), 3.23-2.95 (m, 4H), 2.86-2.55 (m, 2H), 2.00-1.68 (m, 6H), 1.67-1.48 (m, 2H), 1.47-1.13 (m, 6H), 1.08-0.83 (m, 4H), 0.53-0.19 (m, 6H). ppm; ESMS calculated for $C_{52}H_{54}N_8O_{10}$: 950.4; found: 951.2 (M+H⁺).

SDC-TRAP-0206

(S)-4,11-diethyl-4-hydroxy-3,14-dioxo-3,4,12,14-tetrahydro-1H-pyrano[3',4':6,7]indolizino[1,2-b]quinolin-9-yl (2-(4-(4-(3-(2,4-dihydroxy-5-isopropylphenyl)-5-(ethylcarbamoyl)-4H-1,2,4-triazol-4-yl)phenoxy)piperidin-1-yl)-2-oxoethyl)(methyl)carbamate

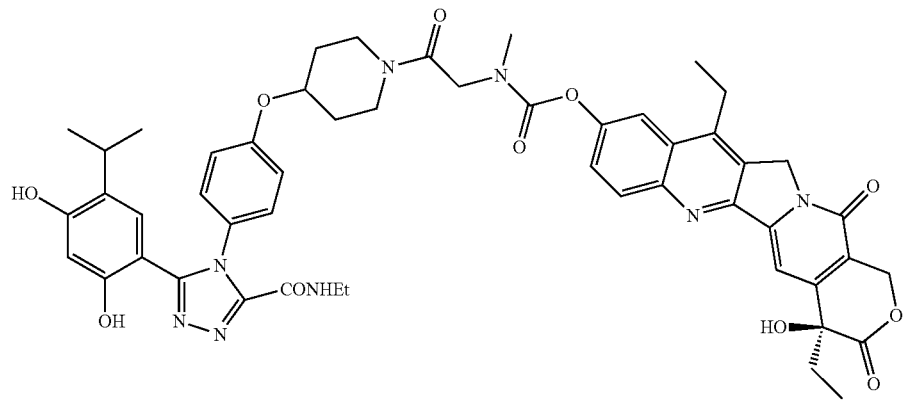

¹H NMR (400 MHz, Chloroform-d) δ 8.16 (t, J=8.8 Hz, 1H), 7.87 (dd, J=16.2, 2.5 Hz, 1H), 7.69-7.51 (m, 2H), 7.39 (t, J=5.9 Hz, 1H), 7.30-7.25 (m, 2H), 7.05 (dd, J=8.6, 5.3 Hz, 2H), 6.59-6.30 (m, 2H), 5.73 (dd, J=16.3, 2.6 Hz, 1H), 5.41-5.13 (m, 3H), 4.66 (s, 1H), 4.45-4.16 (m, 2H), 4.00-3.77 (m, 1H), 3.71 (d, J=15.5 Hz, 1H), 3.49 (d, J=13.3 Hz, 1H), 3.45-3.33 (m, 2H), 3.31 (s, 3H), 3.14 (d, J=9.0 Hz, 3H), 3.01-2.84 (m, 1H), 2.03-1.79 (m, 4H), 1.76-1.51 (m, 4H), 1.43-1.32 (m, 3H), 1.30-1.14 (m, 3H), 1.02 (td, J=7.4, 3.6 Hz, 3H), 0.98-0.89 (m, 1H), 0.76 (dd, J=6.8, 4.1 Hz, 6H). ppm; ESMS calculated for $C_{51}H_{54}N_8O_{11}$: 954.4; found: 955.2 (M+H⁺).

SDC-TRAP-0205

(S)-4,11-diethyl-4-hydroxy-3,14-dioxo-3,4,12,14-tetrahydro-1H-pyrano[3',4':6,7]indolizino[1,2-b]quinolin-9-yl 4-(2-(5-(3-(2,4-dihydroxy-5-isopropylphenyl)-5-(ethylcarbamoyl)-4H-1,2,4-triazol-4-yl)-1H-indol-1-yl)ethyl)piperidine-1-carboxylate

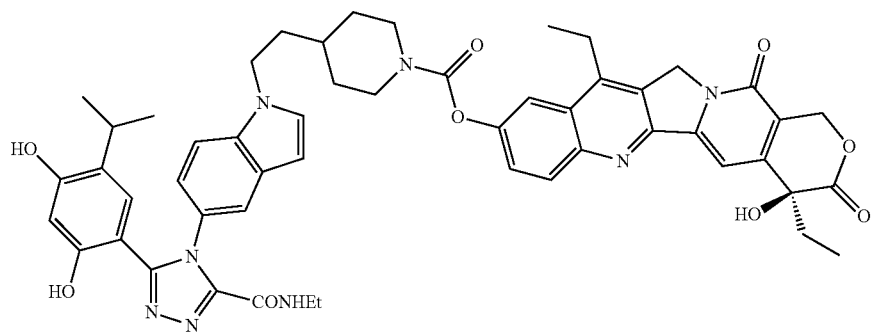

¹H NMR (400 MHz, Chloroform-d) δ 8.20 (d, J=9.2 Hz, 1H), 7.84 (d, J=2.5 Hz, 1H), 7.71-7.45 (m, 4H), 7.38 (t, J=5.9 Hz, 1H), 7.26-7.11 (m, 2H), 6.61-6.23 (m, 3H), 5.75 (d, J=16.3 Hz, 1H), 5.39-5.17 (m, 3H), 4.55-4.17 (m, 4H), 3.49-3.28 (m, 2H), 3.24-2.84 (m, 4H), 2.79 (p, J=6.9 Hz, 1H), 2.00-1.77 (m, 6H), 1.65-1.55 (m, 2H), 1.40 (q, J=7.5 Hz, 5H), 1.21 (t, J=7.3 Hz, 3H), 1.03 (t, J=7.3 Hz, 3H), 0.48 (ddd, J=58.3, 7.0, 4.0 Hz, 6H). ppm; ESMS calculated for $C_{52}H_{54}N_8O_9$: 934.4; found: 935.2 (M+H⁺).

SDC-TRAP-0208

(S)-4,11-diethyl-9-hydroxy-3,14-dioxo-3,4,12,14-tetrahydro-1H-pyrano[3',4':6,7]indolizino[1,2-b]quinolin-4-yl 4-(2-(5-(3-(2,4-dihydroxy-5-isopropylphenyl)-5-(ethylcarbamoyl)-4H-1,2,4-triazol-4-yl)-1H-indol-1-yl)ethyl)piperidine-1-carboxylate

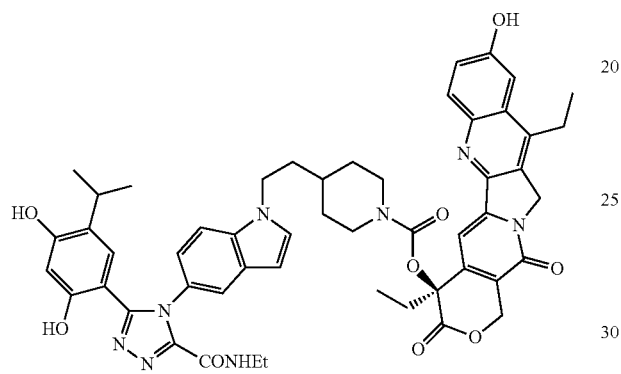

¹H NMR (400 MHz, DMSO-d₆) δ 10.84 (d, J=12.7 Hz, 1H), 10.08 (d, J=16.6 Hz, 1H), 8.75 (s, 1H), 7.75 (dd, J=51.2, 8.9 Hz, 1H), 7.44-7.13 (m, 4H), 7.13-6.64 (m, 3H), 6.40-6.02 (m, 3H), 5.35-4.86 (m, 4H), 4.09 (s, 3H), 3.56 (s, 1H), 3.05-2.71 (m, 5H), 2.69-2.39 (m, 2H), 2.00-1.85 (m, 2H), 1.44 (d, J=84.1 Hz, 5H), 1.14-0.99 (m, 4H), 0.82 (td, J=7.2, 4.4 Hz, 3H), 0.71 (q, J=10.2, 8.4 Hz, 4H), 0.32 (dd, J=19.9, 8.4 Hz, 6H). ppm; ESMS calculated for $C_{52}H_{54}N_8O_9$: 934.4; found: 935.1 (M+H⁺).

SDC-TRAP-0209

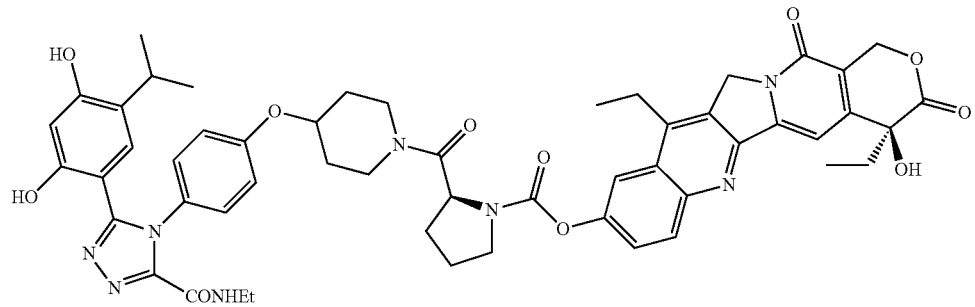

¹H NMR (400 MHz, Chloroform-d) δ 11.34 (s, 1H), 8.17-8.05 (m, 1H), 7.85 (dt, J=10.0, 2.6 Hz, 1H), 7.78-7.67 (m, 1H), 7.63-7.49 (m, 2H), 7.45-7.36 (m, 1H), 7.01 (d, J=8.5 Hz, 2H), 6.43-6.30 (m, 2H), 5.69 (tt, J=14.8, 5.9 Hz, 1H), 5.35-5.14 (m, 3H), 4.90 (d, J=7.9 Hz, 1H), 4.62 (s, 1H), 4.14-3.93 (m, 3H), 3.83 (dt, J=9.9, 7.1 Hz, 2H), 3.77-3.65 (m, 2H), 3.54 (d, J=12.6 Hz, 1H), 3.43-3.31 (m, 2H), 3.12 (q, J=8.5, 7.0 Hz, 2H), 2.99-2.82 (m, 1H), 2.45-2.19 (m, 2H), 2.11 (s, 1H), 2.09-1.99 (m, 2H), 1.88 (p, J=6.9 Hz, 2H), 1.75 (s, 2H), 1.44-1.15 (m, 7H), 1.06-0.89 (m, 4H), 0.88-0.60 (m, 6H); ESMS calculated for $C_{53}H_{56}N_8O_{11}$: 980.4; found: 980.1 (M+H⁺).

SDC-TRAP-0210

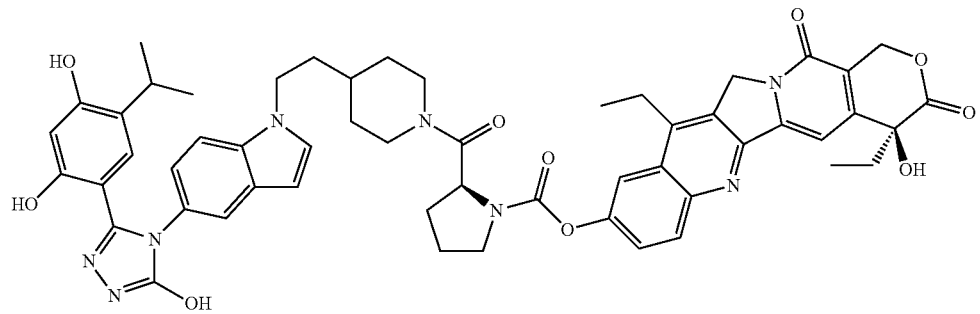 [SMILES: CCc1c2c(nc3ccc(OC(=O)N4CCC[C@H]4C(=O)N4CCC(CCn5ccc6cc(-n7c(O)nnc7-c7cc(C(C)C)c(O)cc7O)ccc65)CC4)cc13)-c1cc3c(c(=O)n1C2)COC(=O)[C@]3(O)CC]

$^1$H NMR (400 MHz, DMSO-d$_6$) 11.91-11.84 (m, 1H), 9.58-9.46 (m, 2H), 8.22-8.13 (m, 1H), 7.97 (d, J=2.6 Hz, 1H), 7.83 (dd, J=4.4, 2.4 Hz, 1H), 7.64 (ddd, J=8.2, 5.0, 2.4 Hz, 1H), 7.59-7.30 (m, 6H), 6.99-6.83 (m, 2H), 6.68 (d, J=7.8 Hz, 1H), 6.52 (d, J=7.3 Hz, 1H), 6.43 (dt, J=6.4, 3.2 Hz, 1H), 6.27-6.19 (m, 1H), 5.44 (s, 2H), 5.31 (d, J=15.6 Hz, 2H), 5.02 (q, J=7.9, 6.0 Hz, 1H), 4.83 (d, J=9.7 Hz, 1H), 4.44-4.28 (m, 2H), 4.22 (q, J=7.6 Hz, 2H), 4.08-3.91 (m, 4H), 3.73 (q, J=6.7 Hz, 1H), 3.52 (dq, J=11.4, 5.5, 4.8 Hz, 1H), 3.10 (ddt, J=49.9, 25.2, 10.0 Hz, 2H), 2.84 (ddt, J=32.9, 13.9, 6.6 Hz, 2H), 2.68-2.52 (m, 4H), 2.36 (d, J=8.3 Hz, 1H), 1.45 (s, 3H), 1.36-1.06 (m, 3H), 0.93-0.74 (m, 6H); ESMS calculated for $C_{54}H_{56}N_8O_{10}$: 976.4; found: 977.2 (M+H$^+$).

SDC-TRAP-0213

(S)-4,11-diethyl-4-hydroxy-3,14-dioxo-3,4,12,14-tetrahydro-1H-pyrano[3',4':6,7]indolizino[1,2-b]quinolin-9-yl 4-(4-(4-(3-(2,4-dihydroxy-5-isopropyl-phenyl)-5-(ethylcarbamoyl)-4H-1,2,4-triazol-4-yl)phenoxy)piperidine-1-carbonyl)-2-methylpiperidine-1-carboxylate

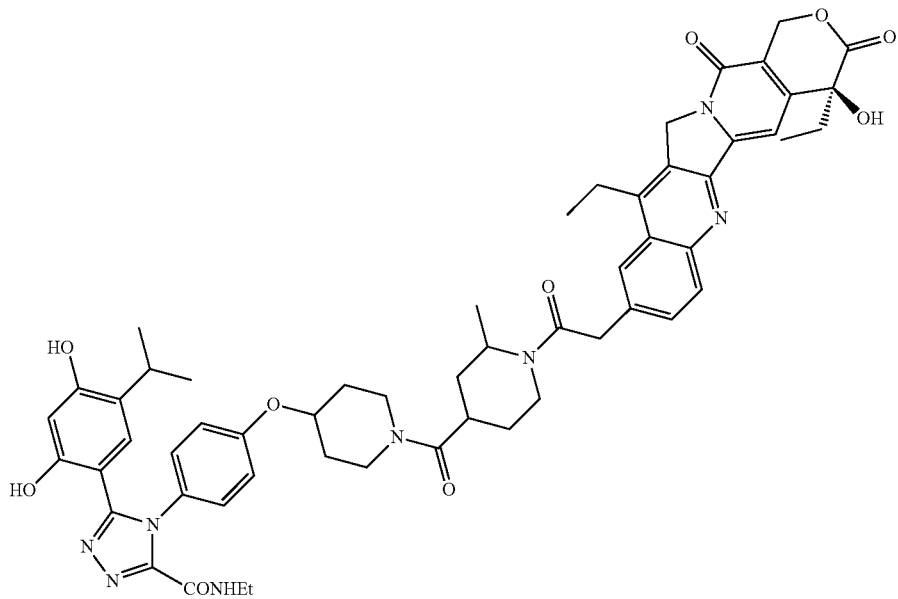

$^1$H NMR (400 MHz, Chloroform-d) δ 8.21 (d, J=9.2 Hz, 1H), 7.87 (s, 1H), 7.65 (s, 1H), 7.50 (m, 1H), 7.4 (m, 1H), 7.3 (m, 1H), 7.1 (d, J=1.2 Hz, 1H), 6.49 (s, 1H), 6.42 (s, 1H), 5.75 (d, J=16.3 Hz, 1H), 5.35-5.24 (m, 3H), 4.72 (s, 1H), 4.30 (m, 1H), 4.17-4.02 (m, 2H), 3.60-3.30 (m, 4H), 3.16 (q, J=7.8 Hz, 3H), 3.06 (s, 2H), 2.97 (s, 1H), 2.91 (p, J=7.3, 6.9 Hz, 1H), 1.90 (m, 5H), 1.72 (d, J=12.6 Hz, 3H), 1.67-1.53 (m, 1H), 1.39 (dt, J=13.1, 7.4 Hz, 4H), 1.30-1.16 (m, 6H), 1.03 (t, J=7.4 Hz, 3H), 0.99-0.77 (m, 1H), 0.77-0.69 (m, 6H). ppm; ESMS calculated for $C_{55}H_{60}N_8O_1$: 1008.4; found: 1009.4 (M+H$^+$).

SDC-TRAP-0214

(S)—(S)-4,11-diethyl-9-hydroxy-3,14-dioxo-3,4,12,
14-tetrahydro-1H-pyrano[3',4':6,7]indolizino[1,2-b]
quinolin-4-yl 2-(4-(4-(3-(2,4-dihydroxy-5-isopropyl-
phenyl)-5-(ethylcarbamoyl)-4H-1,2,4-triazol-4-yl)
phenoxy)piperidine-1-carbonyl)pyrrolidine-1-
carboxylate

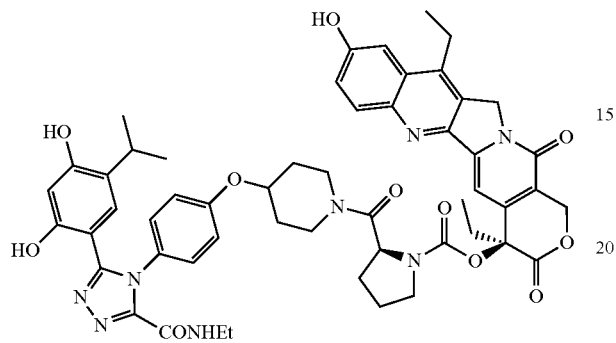

$^1$H NMR (400 MHz, DMSO-$d_6$) δ 10.75 (s, 1H), 10.23 (s, 2H), 9.78 (s, 1H), 8.92 (dt, J=11.8, 5.9 Hz, 1H), 7.98-7.90 (m, 1H), 7.41 (tq, J=5.0, 2.6 Hz, 2H), 7.36-7.22 (m, 2H), 7.17-6.95 (m, 3H), 6.63-6.50 (m, 1H), 6.40-6.30 (m, 1H), 5.48-5.19 (m, 3H), 4.99 (dd, J=8.4, 4.5 Hz, 1H), 4.87-4.73 (m, 1H), 4.66-4.57 (m, 1H), 4.02 (tt, J=12.8, 5.5 Hz, 1H), 3.50-3.34 (m, 1H), 3.25-3.04 (m, 4H), 2.41-2.32 (m, 1H), 2.16 (d, J=10.8 Hz, 2H), 2.13-1.76 (m, 6H), 1.73-1.63 (m, 2H), 1.60-1.46 (m, 1H), 1.40-1.14 (m, 3H), 1.10-0.99 (m, 3H), 0.95-0.76 (m, 6H), 0.71 (dd, J=6.8, 2.8 Hz, 3H). ppm; ESMS calculated for $C_{53}H_{56}N_8O_{11}$: 980.4; found: 981.2 (M+H$^+$).

SDC-TRAP-0215

(S)-4,11-diethyl-4-hydroxy-3,14-dioxo-3,4,12,14-
tetrahydro-1H-pyrano[3',4':6,7]indolizino[1,2-b]
quinolin-9-yl 2-(4-(2-(5-(3-(2,4-dihydroxy-5-isopro-
pylphenyl)-5-hydroxy-4H-1,2,4-triazol-4-yl)-1H-
indol-1-yl)ethyl)piperidine-1-carbonyl)piperidine-1-
carboxylate

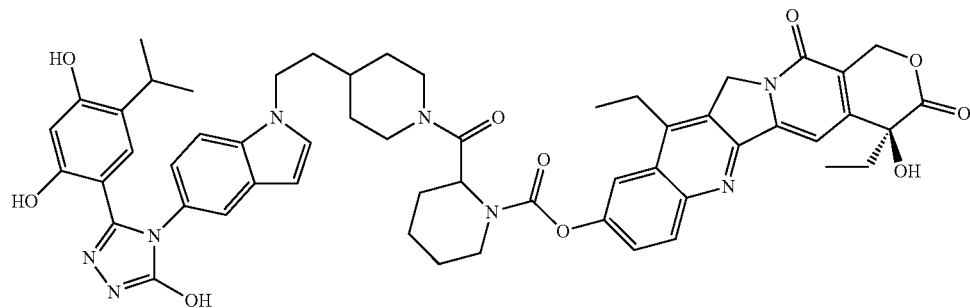 [SMILES: CCc1c2c(nc3ccc(OC(=O)N4CCCCC4C(=O)N4CCC(CCn5ccc6cc(-n7c(O)nnc7-c7cc(C(C)C)c(O)cc7O)ccc65)CC4)cc13)-c1cc3c(c(=O)n1C2)COC(=O)[C@]3(O)CC]

$^1$H NMR (400 MHz, Chloroform-d) δ 8.21 (d, J=9.5 Hz, 1H), 7.87 (s, 1H), 7.70 (s, 1H), 7.66-7.48 (m, 3H), 7.36 (s, 1H), 7.12 (d, J=31.7 Hz, 2H), 6.42 (d, J=60.7 Hz, 2H), 5.71 (d, J=16.5 Hz, 1H), 5.42-5.03 (m, 3H), 4.25 (m, 4H), 3.77 (d, J=14.9 Hz, 3H), 3.38 (dt, J=3.3, 1.7 Hz, 3H), 3.18 (s, 3H), 2.80-2.50 (m, 2H), 2.28 (t, J=7.7 Hz, 1H), 1.85 (d, J=64.6 Hz, 11H), 1.61 (s, 4H), 1.39 (d, J=7.9 Hz, 3H), 1.04 (t, J=7.4 Hz, 3H), 0.45 (d, J=21.7 Hz, 6H). ppm; ESMS calculated for $C_{55}H_{58}N_8O_{10}$: 990.4; found: 991.3 (M+H$^+$).

SDC-TRAP-0216

(S)-4,11-diethyl-4-hydroxy-3,14-dioxo-3,4,12,14-tetrahydro-1H-pyrano[3',4':6,7]indolizino[1,2-b]quinolin-9-yl 2-(4-(4-(3-(2,4-dihydroxy-5-isopropyl-phenyl)-5-(ethylcarbamoyl)-4H-1,2,4-triazol-4-yl)phenoxy)piperidine-1-carbonyl)piperidine-1-carboxylate

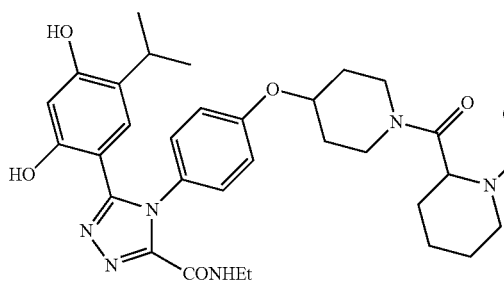

$^1$H NMR (400 MHz, Chloroform-d) δ 8.17 (t, J=9.0 Hz, 1H), 7.84 (d, J=2.6 Hz, 1H), 7.73-7.45 (m, 2H), 7.34 (t, J=5.9 Hz, 1H), 7.02 (d, J=8.2 Hz, 2H), 6.43 (s, 1H), 6.33 (s, 1H), 5.74 (d, J=16.8 Hz, 1H), 5.44-5.06 (m, 5H), 4.62 (s, 1H), 4.29 (d, J=12.8 Hz, 1H), 3.75 (d, J=98.1 Hz, 4H), 3.38 (p, J=7.0 Hz, 2H), 3.15 (q, J=7.3 Hz, 2H), 2.90 (s, 1H), 2.03-1.49 (m, 11H), 1.46-1.33 (m, 4H), 1.25-1.14 (m, 6H), 1.01 (q, J=7.3 Hz, 3H), 0.97-0.80 (m, 1H), 0.74 (d, J=6.5 Hz, 6H). ppm; ESMS calculated for $C_{54}H_{58}N_8O_{11}$: 994.4; found: 995.4 (M+H+).

SDC-TRAP-0217

(S)-4,11-diethyl-9-hydroxy-3,14-dioxo-3,4,12,14-tetrahydro-1H-pyrano[3',4':6,7]indolizino[1,2-b]quinolin-4-yl 4-(1-(4-(3-(2,4-dihydroxy-5-isopropyl-phenyl)-5-(ethylcarbamoyl)-4H-1,2,4-triazol-4-yl)benzyl)piperidine-4-carbonyl)-2-methylpiperazine-1-carboxylate

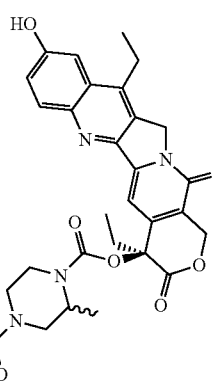
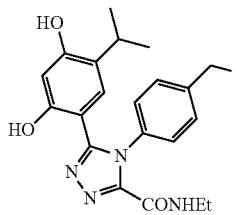

$^1$H NMR (400 MHz, Chloroform-d) δ 8.01 (s, 1H), 7.54 (s, 2H), 7.32 (s, 3H), 7.19 (s, 3H), 6.45 (dd, J=18.5, 11.0 Hz, 2H), 5.67 (s, 1H), 5.41 (s, 1H), 5.14 (s, 1H), 4.07 (tt, J=6.3, 2.8 Hz, 3H), 3.57 (s, 3H), 3.41 (d, J=16.0 Hz, 4H), 2.97 (d, J=56.0 Hz, 4H), 2.40-2.19 (m, 2H), 1.82-1.50 (m, 5H), 1.50-1.13 (m, 12H), 1.09-0.79 (m, 8H), 0.72 (s, 6H). ppm; ESMS calculated for $C_{55}H_{61}N_9O_{10}$: 1007.5; found: 1008.5 (M+H+).

SDC-TRAP-0218

(S)-4,11-diethyl-9-hydroxy-3,14-dioxo-3,4,12,14-tetrahydro-1H-pyrano[3',4':6,7]indolizino[1,2-b]quinolin-4-yl (2-(4-(4-(3-(2,4-dihydroxy-5-isopropy-lphenyl)-5-(ethylcarbamoyl)-4H-1,2,4-triazol-4-yl)phenoxy)piperidin-1-yl)-2-oxoethyl)(methyl)carbamate

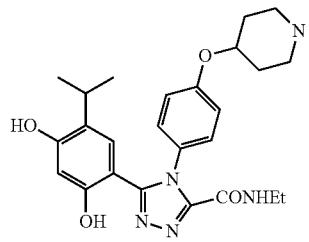

$^1$H NMR (400 MHz, Chloroform-d) δ 8.94 (s, 2H), 7.97 (d, J=9.2 Hz, 1H), 7.68 (dd, J=22.4, 7.6 Hz, 4H), 7.32 (t, J=2.5 Hz, 1H), 7.18 (s, 1H), 7.08 (s, 1H), 6.79-6.68 (m, 1H), 6.47 (d, J=8.8 Hz, 1H), 6.39 (d, J=15.8 Hz, 1H), 5.74 (dd, J=16.8, 3.4 Hz, 2H), 5.35 (dd, J=16.7, 2.7 Hz, 2H), 5.22 (d, J=3.0 Hz, 2H), 4.93-4.75 (m, 2H), 4.45 (s, 1H), 4.02 (s, 1H), 3.64-3.45 (m, 4H), 3.22 (d, J=11.8 Hz, 3H), 3.11-3.02 (m, 3H), 2.95-2.83 (m, 2H), 2.24-2.09 (m, 4H), 1.34 (td, J=7.1, 2.3 Hz, 6H), 1.12 (td, J=7.4, 4.3 Hz, 3H), 0.90-0.78 (m, 3H), 0.73 (d, J=6.9 Hz, 6H). ppm; ESMS calculated for $C_{51}H_{54}N_8O_{11}$: 954.4; found: 955.4 (M+H$^+$).

SDC-TRAP-0027

2-((4,11-diethyl-4-hydroxy-3,14-dioxo-3,4,12,14-tetrahydro-1H-pyrano[3',4':6,7]indolizino[1,2-b]quinolin-9-yl)oxy)-N-(2-(5-(3-(2,4-dihydroxy-5-isopropylphenyl)-5-hydroxy-4H-1,2,4-triazol-4-yl)-1H-indol-1-yl)ethyl)-N-methylacetamide

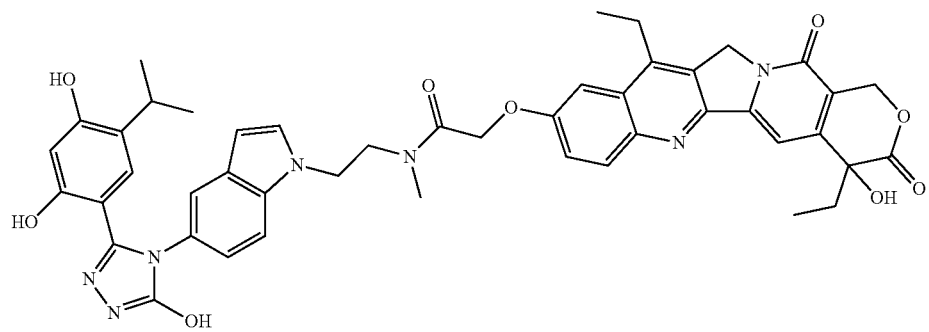 [SMILES: CCc1c2c(nc3ccc(OCC(=O)N(C)CCn4ccc5cc(-n6c(O)nnc6-c6cc(C(C)C)c(O)cc6O)ccc54)cc13)-c1cc3c(c(=O)n1C2)COC(=O)C3(O)CC]

$^1$H NMR (400 MHz, DMSO-d$_6$) δ 11.88 (s, 1H), 9.52 (s, 1H), 9.45 (d, J=11.1 Hz, 1H), 8.09 (dd, J=13.5, 9.1 Hz, 1H), 7.63-7.41 (m, 5H), 7.33 (dd, J=32.2, 3.0 Hz, 1H), 6.94 (ddd, J=8.7, 3.3, 2.0 Hz, 1H), 6.74 (d, J=13.7 Hz, 1H), 6.50 (s, 1H), 6.43 (dd, J=3.1, 0.8 Hz, 1H), 6.23 (d, J=2.1 Hz, 1H), 5.44 (s, 2H), 5.33-5.28 (m, 2H), 5.05 (s, 1H), 4.65 (s, 1H), 4.51 (d, J=6.3 Hz, 1H), 4.32 (t, J=6.5 Hz, 1H), 3.80 (t, J=6.2 Hz, 1H), 3.65 (t, J=6.5 Hz, 1H), 3.15 (dd, J=17.6, 8.3 Hz, 2H), 2.95-2.80 (m, 4H), 1.88 (hept, J=7.2 Hz, 2H), 1.28 (q, J=7.5 Hz, 3H), 0.93-0.78 (m, 9H).

ESMS calculated for $C_{46}H_{45}N_7O_9$: 839.33; Found: 840.1 (M+H)$^+$.

SDC-TRAP-0028

2-((4,11-diethyl-4-hydroxy-3,14-dioxo-3,4,12,14-tetrahydro-1H-pyrano[3',4':6,7]indolizino[1,2-b]quinolin-9-yl)oxy)-N-(2-(2-(5-(3-(2,4-dihydroxy-5-isopropylphenyl)-5-hydroxy-4H-1,2,4-triazol-4-yl)-1H-indol-1-yl)ethoxy)ethyl)-N-methylacetamide

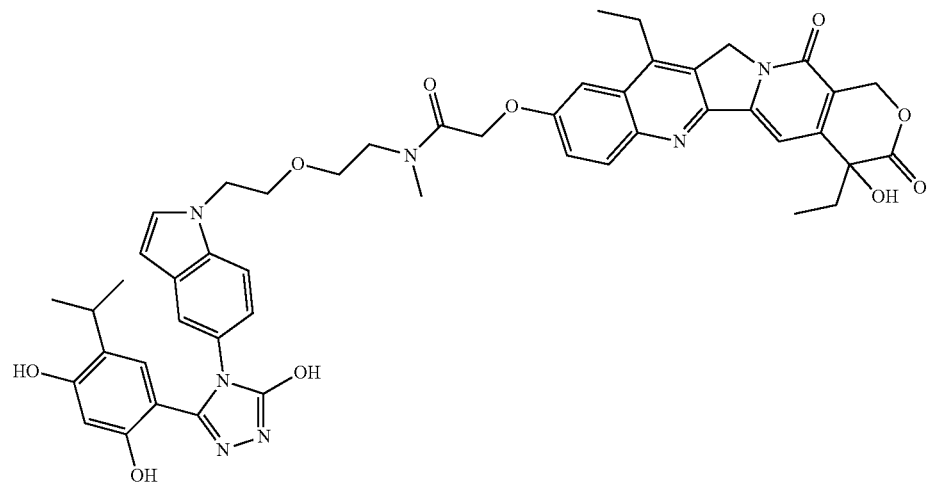 [SMILES: CCc1c2c(nc3ccc(OCC(=O)N(C)CCOCCn4ccc5cc(-n6c(O)nnc6-c6cc(C(C)C)c(O)cc6O)ccc54)cc13)-c1cc3c(c(=O)n1C2)COC(=O)C3(O)CC]

ESMS calculated for $C_{48}H_{49}N_7O_{10}$: 883.35; Found: 884.3 (M+H)$^+$.

SDC-TRAP-0029

4,11-diethyl-4-hydroxy-3,14-dioxo-3,4,12,14-tetrahydro-1H-pyrano[3',4':6,7]indolizino[1,2-b]quinolin-9-yl (2-(2-(5-(3-(2,4-dihydroxy-5-isopropylphenyl)-5-hydroxy-4H-1,2,4-triazol-4-yl)-1H-indol-1-yl)ethoxy)ethyl)(methyl)carbamate

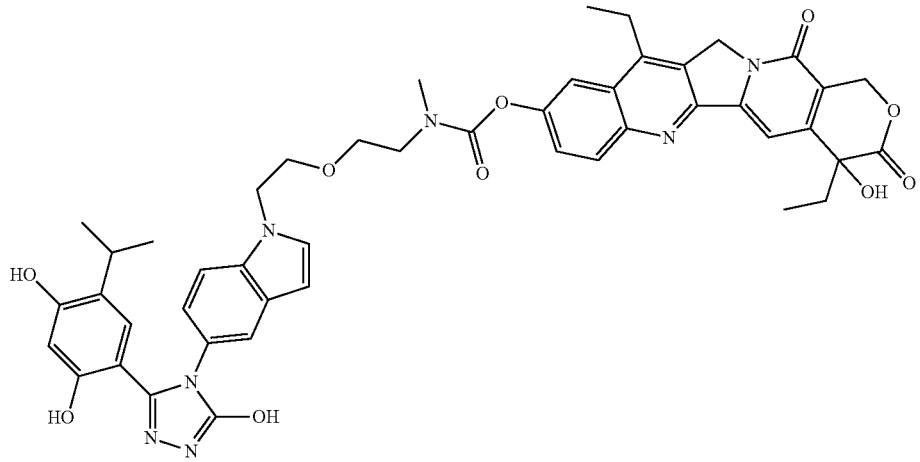 [SMILES: CCc1c2c(nc3ccc(OC(=O)N(C)CCOCCn4ccc5cc(-n6c(O)nnc6-c6cc(C(C)C)c(O)cc6O)ccc54)cc13)-c1cc3c(c(=O)n1C2)COC(=O)C3(O)CC]

$^1$H NMR (400 MHz, DMSO-d$_6$) δ 11.87 (s, 1H), 9.50 (d, J=19.6 Hz, 2H), 8.21-8.14 (m, 1H), 7.96 (d, J=9.5 Hz, 1H), 7.64 (d, J=8.3 Hz, 1H), 7.52 (s, 1H), 7.43 (d, J=7.0 Hz, 2H), 7.33 (s, 1H), 6.91 (dd, J=15.2, 8.5 Hz, 1H), 6.71 (d, J=8.6 Hz, 1H), 6.52 (s, 1H), 6.43 (d, J=13.7 Hz, 1H), 6.23 (s, 1H), 5.44 (s, 2H), 5.33 (s, 2H), 4.42-4.36 (m, 2H), 3.77 (d, J=11.5 Hz, 2H), 3.69-3.44 (m, 4H), 3.17 (t, J=7.3 Hz, 2H), 3.03 (s, 1H), 2.89 (d, J=13.3 Hz, 2H), 1.89 (dq, J=17.0, 9.1, 8.1 Hz, 2H), 1.27 (d, J=10.5 Hz, 3H), 0.85-0.74 (m, 9H). ESMS calculated for C$_{47}$H$_{47}$N$_7$O$_{10}$: 869.34; Found: 870.2 (M+H)$^+$.

SDC-TRAP-0037

4,11-diethyl-9-hydroxy-3,14-dioxo-3,4,12,14-tetrahydro-1H-pyrano[3',4':6,7]indolizino[1,2-b]quinolin-4-yl (2-(2-(5-(3-(2,4-dihydroxy-5-isopropylphenyl)-5-hydroxy-4H-1,2,4-triazol-4-yl)-1H-indol-1-yl)ethoxy)ethyl)(methyl)carbamate

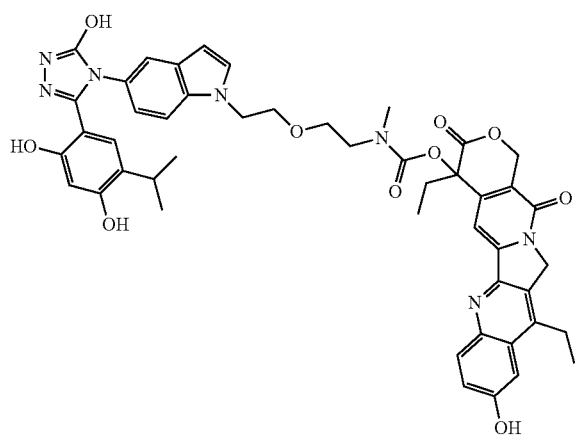 [SMILES: CCc1c2c(nc3ccc(O)cc13)-c1cc3c(c(=O)n1C2)COC(=O)C3(CC)OC(=O)N(C)CCOCCn1ccc2cc(-n3c(O)nnc3-c3cc(C(C)C)c(O)cc3O)ccc21]

$^1$H NMR (400 MHz, DMSO-d$_6$) δ 11.87 (s, 1H), 10.30 (s, 1H), 9.54 (s, 1H), 9.48 (s, 1H), 7.97 (t, J=9.4 Hz, 1H), 7.45-7.25 (m, 4H), 7.00 (d, J=23.6 Hz, 1H), 6.92-6.81 (m, 1H), 6.70 (d, J=2.3 Hz, 1H), 6.39 (d, J=3.0 Hz, 1H), 6.23 (d, J=3.2 Hz, 1H), 5.45 (s, 2H), 5.28 (s, 1H), 5.21 (d, J=6.9 Hz, 1H), 4.53-4.47 (m, 1H), 3.90 (d, J=6.3 Hz, 1H), 3.18-2.97 (m, 6H), 2.88 (dt, J=13.9, 7.0 Hz, 2H), 2.70 (s, 3H), 2.18-2.05 (m, 2H), 1.27 (dt, J=14.6, 7.3 Hz, 3H), 1.10-0.76 (m, 9H). ESMS calculated for C$_{47}$H$_{47}$N$_7$O$_{10}$: 869.34; Found: 870.3 (M+H)$^+$.

SDC-TRAP-0038

4,11-diethyl-9-hydroxy-3,14-dioxo-3,4,12,14-tetrahydro-1H-pyrano[3',4':6,7]indolizino[1,2-b]quinolin-4-yl (2-(5-(3-(2,4-dihydroxy-5-isopropylphenyl)-5-hydroxy-4H-1,2,4-triazol-4-yl)-1H-indol-1-yl)ethyl)(methyl)carbamate

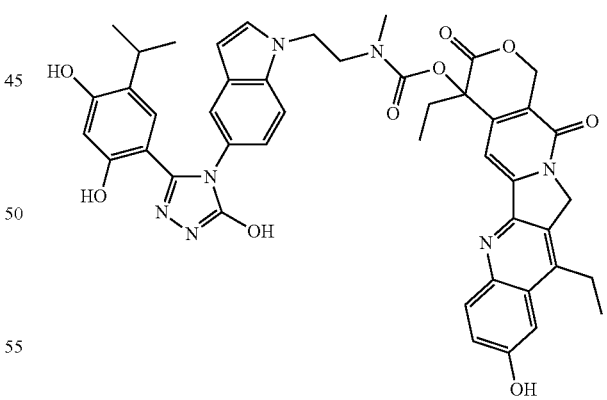

$^1$H NMR (400 MHz, DMSO-d$_6$) δ 11.94 (s, 1H), 10.33 (s, 1H), 9.52 (s, 1H), 9.44 (s, 1H), 8.01 (t, J=9.5 Hz, 1H), 7.67 (d, J=8.8 Hz, 1H), 7.55 (d, J=3.0 Hz, 1H), 7.41-7.25 (m, 4H), 7.13-7.08 (m, 1H), 7.04-6.94 (m, 2H), 6.73 (dd, J=7.0, 4.4 Hz, 1H), 6.22 (s, 1H), 5.44 (s, 2H), 5.34 (s, 2H), 4.56 (s, 1H), 3.91-3.84 (m, 2H), 3.59-3.50 (m, 2H), 2.97-2.83 (m, 2H), 2.59 (s, 3H), 2.31 (s, 1H), 2.14 (q, J=7.3 Hz, 2H), 1.30 (t, J=7.5 Hz, 3H), 1.01-0.86 (m, 9H). ESMS calculated for C$_{45}$H$_{43}$N$_7$O$_9$: 825.31; Found: 826.4 (M+H)$^+$.

SDC-TRAP-0046

4,11-diethyl-4-hydroxy-3,14-dioxo-3,4,12,14-tetrahydro-1H-pyrano[3',4':6,7]indolizino[1,2-b]quinolin-9-yl 4-(4-(3-(2,4-dihydroxy-5-isopropylphenyl)-5-hydroxy-4H-1,2,4-triazol-4-yl)benzyl)piperazine-1-carboxylate

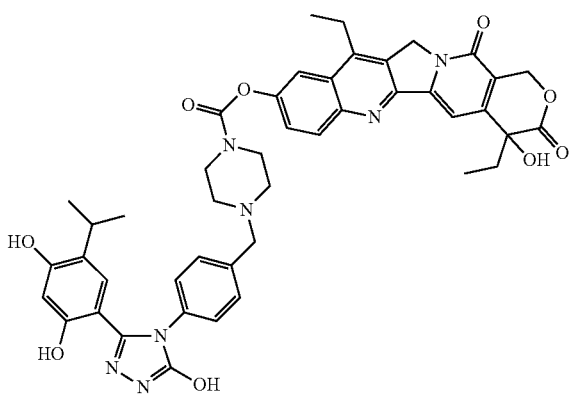 [SMILES: CCc1c2c(nc3ccc(OC(=O)N4CCN(Cc5ccc(-n6c(O)nnc6-c6cc(C(C)C)c(O)cc6O)cc5)CC4)cc13)-c1cc3c(c(=O)n1C2)COC(=O)C3(O)CC]

$^1$H NMR (400 MHz, DMSO-d$_6$) δ 11.95 (s, 1H), 9.62 (s, 1H), 9.43 (s, 1H), 8.18 (d, J=9.2 Hz, 1H), 8.00 (d, J=2.4 Hz, 1H), 7.67 (dd, J=9.1, 2.5 Hz, 1H), 7.40-7.31 (m, 3H), 7.18 (d, J=7.9 Hz, 2H), 6.80 (s, 1H), 6.53 (s, 1H), 6.28 (s, 1H), 5.44 (s, 2H), 5.34 (s, 2H), 3.69-3.46 (m, 4H), 3.19 (q, J=7.7 Hz, 2H), 2.99 (p, J=7.0 Hz, 1H), 1.88 (hept, J=7.1 Hz, 2H), 1.30 (t, J=7.5 Hz, 3H), 0.97 (d, J=6.9 Hz, 6H), 0.89 (t, J=7.3 Hz, 3H). ESMS calculated for C$_{45}$H$_{45}$N$_7$O$_9$: 827.33; Found: 828.2 (M+H)$^+$.

SDC-TRAP-0047

4,11-diethyl-9-hydroxy-3,14-dioxo-3,4,12,14-tetrahydro-1H-pyrano[3',4':6,7]indolizino[1,2-b]quinolin-4-yl 4-(4-(3-(2,4-dihydroxy-5-isopropylphenyl)-5-hydroxy-4H-1,2,4-triazol-4-yl)benzyl)piperazine-1-carboxylate

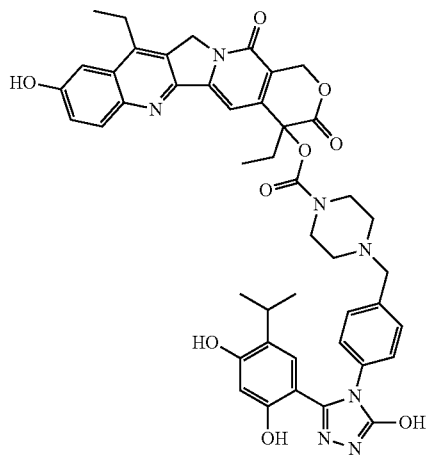 [SMILES: CCc1c2c(nc3ccc(O)cc13)-c1cc3c(c(=O)n1C2)COC(=O)C3(CC)OC(=O)N1CCN(Cc2ccc(-n3c(O)nnc3-c3cc(C(C)C)c(O)cc3O)cc2)CC1]

$^1$H NMR (400 MHz, DMSO-d$_6$) δ 11.94 (s, 1H), 10.34 (s, 1H), 9.60 (s, 1H), 9.41 (s, 1H), 8.08-8.00 (m, 1H), 7.47-7.39 (m, 2H), 7.32 (d, J=8.0 Hz, 3H), 7.15 (d, J=8.1 Hz, 2H), 6.96 (s, 1H), 6.78 (s, 1H), 6.27 (s, 1H), 5.44 (d, J=2.6 Hz, 2H), 5.32-5.27 (m, 2H), 3.71 (s, 1H), 3.62 (s, 1H), 3.56-3.47 (m, 2H), 3.39 (s, 5H), 3.37-3.23 (m, 6H), 3.09 (q, J=7.5 Hz, 2H), 2.97 (p, J=6.9 Hz, 1H), 2.31 (s, 1H), 2.22 (s, 1H), 2.14 (q, J=7.3 Hz, 2H), 1.30 (t, J=7.5 Hz, 3H), 1.01-0.86 (m, 9H). ESMS calculated for C$_{45}$H$_{45}$N$_7$O$_9$: 827.33; Found: 828.3 (M+H)$^+$.

SDC-TRAP-0067

4,11-diethyl-4-hydroxy-3,14-dioxo-3,4,12,14-tetrahydro-1H-pyrano[3',4':6,7]indolizino[1,2-b]quinolin-9-yl 4-((4-(4-(3-(2,4-dihydroxy-5-isopropylphenyl)-5-hydroxy-4H-1,2,4-triazol-4-yl)benzyl)piperidin-1-yl)methyl)piperidine-1-carboxylate

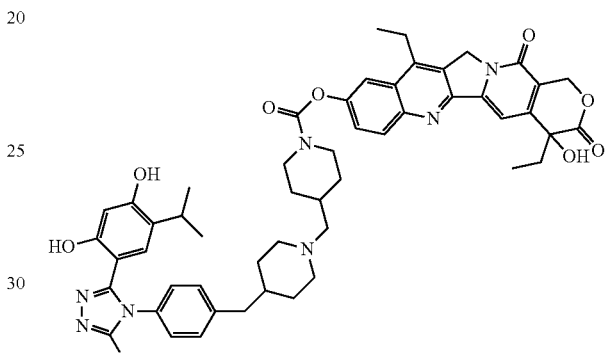

ESMS calculated for C$_{52}$H$_{57}$N$_7$O$_9$: 923.42; Found: 924.3 (M+H)$^+$.

SDC-TRAP-0070

4,11-diethyl-4-hydroxy-3,14-dioxo-3,4,12,14-tetrahydro-1H-pyrano[3',4':6,7]indolizino[1,2-b]quinolin-9-yl 4-(2-(4-(4-(3-(2,4-dihydroxy-5-isopropylphenyl)-5-hydroxy-4H-1,2,4-triazol-4-yl)phenyl)piperazin-1-yl)ethyl)piperidine-1-carboxylate

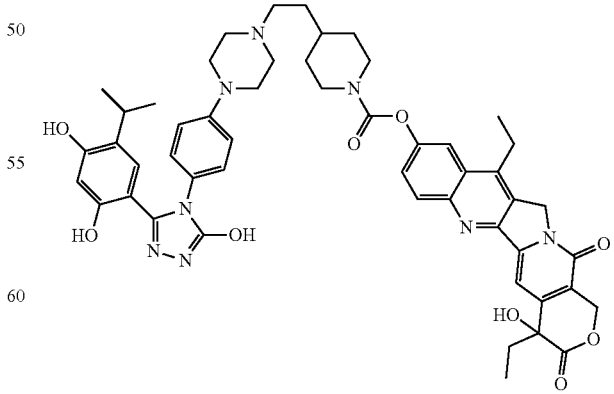

ESMS calculated for C$_{51}$H$_{56}$N$_8$O$_9$: 924.42; Found: 925.3 (M+H)$^+$.

SDC-TRAP-0077

9-(2-(4-(4-(3-(2,4-dihydroxy-5-isopropylphenyl)-5-hydroxy-4H-1,2,4-triazol-4-yl)benzyl)piperazin-1-yl)-2-oxoethoxy)-4,11-diethyl-4-hydroxy-1H-pyrano[3',4':6, 7]indolizino[1,2-b]quinoline-3,14(4H,12H)-dione

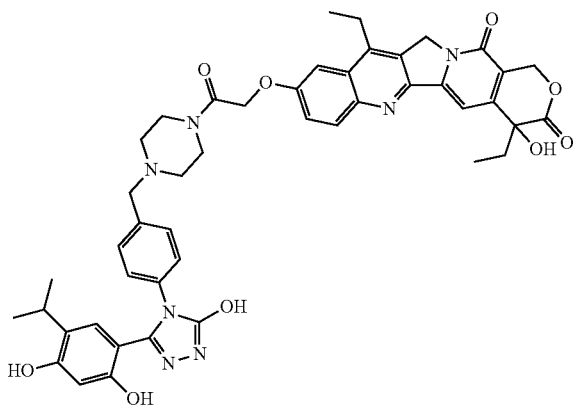 [SMILES: CCc1c2c(nc3ccc(OCC(=O)N4CCN(Cc5ccc(-n6c(O)nnc6-c6cc(C(C)C)c(O)cc6O)cc5)CC4)cc13)-c1cc3c(c(=O)n1C2)COC(=O)C3(O)CC]

$^1$H NMR (400 MHz, DMSO-d$_6$) δ 11.93 (s, 1H), 9.61 (s, 1H), 9.41 (s, 1H), 8.09 (d, J=9.2 Hz, 1H), 7.53 (dd, J=9.2, 2.7 Hz, 1H), 7.44 (d, J=2.8 Hz, 1H), 7.37-7.25 (m, 3H), 7.15 (d, J=8.3 Hz, 2H), 6.78 (s, 1H), 6.51 (s, 1H), 6.27 (s, 1H), 5.43 (s, 2H), 5.30 (s, 2H), 5.10 (s, 2H), 3.55 (s, 2H), 3.49 (d, J=9.1 Hz, 4H), 3.16 (q, J=7.6 Hz, 2H), 2.97 (p, J=6.9 Hz, 1H), 2.46 (d, J=5.8 Hz, 2H), 2.33 (s, 2H), 1.87 (hept, J=7.0 Hz, 2H), 1.29 (t, J=7.5 Hz, 3H), 0.98 (d, J=6.9 Hz, 6H), 0.89 (t, J=7.3 Hz, 3H). ESMS calculated for C$_{46}$H$_{47}$N$_7$O$_9$: 841.34; Found: 842.1 (M+H)$^+$.

SDC-TRAP-0079

4,11-diethyl-9-hydroxy-3,14-dioxo-3,4,12,14-tetrahydro-1H-pyrano[3',4':6,7]indolizino[1,2-b]quinolin-4-yl 4-(4-(3-(2,4-dihydroxy-5-isopropylphenyl)-5-hydroxy-4H-1,2,4-triazol-4-yl)-2-fluorobenzyl)piperazine-1-carboxylate

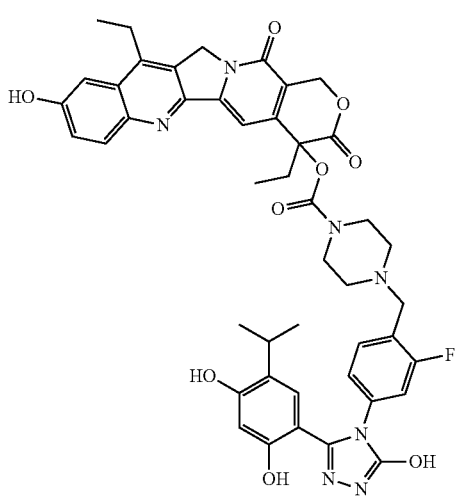 [SMILES: CCc1c2c(nc3ccc(O)cc13)-c1cc3c(c(=O)n1C2)COC(=O)C3(CC)OC(=O)N1CCN(Cc2ccc(-n3c(O)nnc3-c3cc(C(C)C)c(O)cc3O)cc2F)CC1]

$^1$H NMR (400 MHz, DMSO-d$_6$) δ 11.99 (s, 1H), 10.35 (s, 1H), 9.64 (s, 1H), 9.40 (s, 1H), 8.03 (d, J=9.1 Hz, 1H), 7.41 (d, J=6.9 Hz, 3H), 7.07 (d, J=10.8 Hz, 1H), 6.97 (d, J=9.8 Hz, 2H), 6.87 (s, 1H), 6.27 (s, 1H), 5.44 (s, 2H), 5.29 (s, 2H), 3.73 (d, J=13.4 Hz, 1H), 3.56 (d, J=16.6 Hz, 3H), 3.32-3.23 (m, 4H), 3.09 (d, J=8.0 Hz, 2H), 3.05-2.96 (m, 1H), 2.55 (s, 2H), 2.39-2.32 (m, 2H), 2.24 (s, 2H), 2.13 (d, J=7.7 Hz, 2H), 1.28 (q, J=13.0, 10.1 Hz, 3H), 0.96 (d, J=6.9 Hz, 6H), 0.89 (t, J=7.3 Hz, 3H). ESMS calculated for C$_{45}$H$_{44}$FN$_7$O$_9$: 845.32; Found: 846.2 (M+H)$^+$.

SDC-TRAP-0081

4,11-diethyl-9-hydroxy-3,14-dioxo-3,4, 12,14-tetrahydro-1H-pyrano[3',4':6,7]indolizino[1,2-b]quinolin-4-yl-4-(4-(3-(2,4-dihydroxy-5-isopropylphenyl)-5-hydroxy-4H-1,2,4-triazol-4-yl)phenyl)piperazine-1-carboxylate

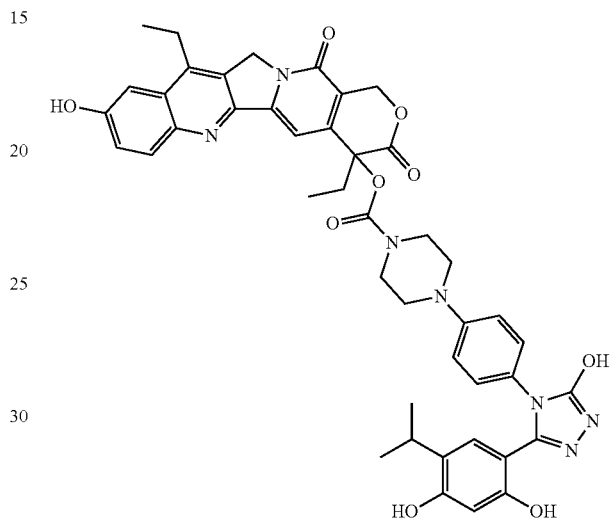

$^1$H NMR (400 MHz, DMSO-d$_6$) δ 11.94 (s, 1H), 10.38 (s, 1H), 9.66 (s, 1H), 9.51 (s, 1H), 7.99 (d, J=9.4 Hz, 1H), 7.46 (d, J=5.6 Hz, 2H), 7.21 (s, 1H), 7.12 (d, J=8.5 Hz, 2H), 7.04 (d, J=9.9 Hz, 3H), 6.84 (s, 1H), 6.33 (s, 1H), 5.52 (s, 2H), 5.35 (s, 2H), 3.91-3.83 (m, 4H), 3.20-3.09 (m, 6H), 3.02 (p, J=7.0 Hz, 1H), 2.23 (q, J=7.3 Hz, 2H), 1.35 (t, J=7.3 Hz, 3H), 1.07-0.91 (m, 9H). ESMS calculated for C$_{44}$H$_{43}$N$_7$O$_9$: 813.31; Found: 814.2 (M+H)$^+$.

SDC-TRAP-0083

4,11-diethyl-4-hydroxy-3,14-dioxo-3,4,12,14-tetrahydro-1H-pyrano[3',4':6,7]indolizino[1,2-b]quinolin-9-yl 5-(3-(2,4-dihydroxy-5-isopropylphenyl)-5-hydroxy-4H-1,2,4-triazol-4-yl)isoindoline-2-carboxylate

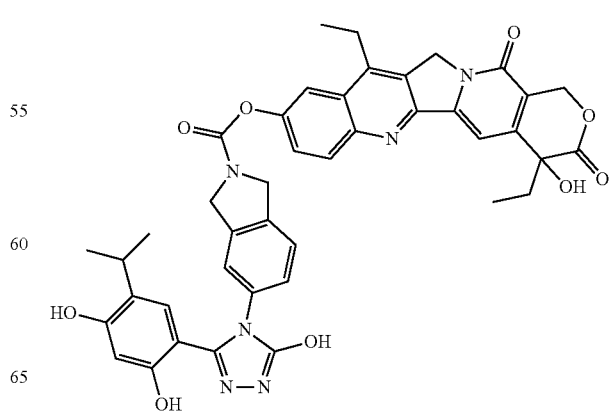

¹H NMR (400 MHz, DMSO-d₆) δ 12.01 (s, 1H), 9.66 (s, 1H), 9.45 (s, 1H), 8.27 (d, J=9.2 Hz, 1H), 8.15 (s, 1H), 7.85-7.77 (m, 1H), 7.48-7.35 (m, 3H), 7.15 (d, J=8.0 Hz, 1H), 6.99 (s, 1H), 6.60 (s, 1H), 6.32 (s, 1H), 5.50 (s, 2H), 5.41 (s, 2H), 5.03 (d, J=13.8 Hz, 2H), 4.80 (d, J=13.5 Hz, 2H), 3.29-3.20 (m, 2H), 3.09 (p, J=7.1 Hz, 1H), 1.94 (hept, J=7.2 Hz, 2H), 1.37 (t, J=7.4 Hz, 3H), 1.11 (d, J=6.9 Hz, 6H), 0.95 (t, J=7.3 Hz, 3H). ESMS calculated for C₄₂H₃₈N₆O₉: 770.27; Found: 771.2 (M+H)⁺.

SDC-TRAP-0094

4,11-diethyl-4-hydroxy-3,14-dioxo-3,4,12,14-tetrahydro-1H-pyrano[3',4':6,7]indolizino[1,2-b]quinolin-9-yl 4-(4-(4-(3-(2,4-dihydroxy-5-isopropylphenyl)-5-hydroxy-4H-1,2,4-triazol-4-yl)phenyl)piperazine-1-carbonyl)piperidine-1-carboxylate

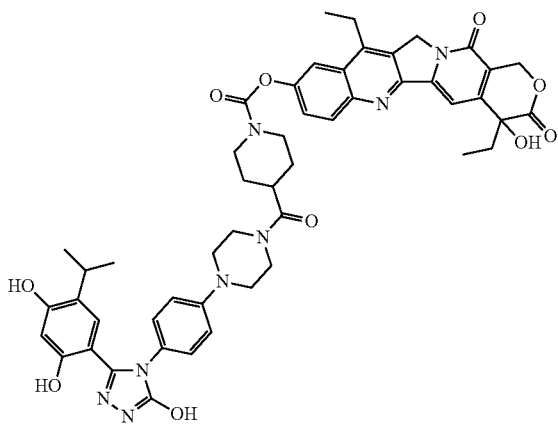 [SMILES: CCc1c2c(nc3ccc(OC(=O)N4CCC(C(=O)N5CCN(c6ccc(-n7c(O)nnc7-c7cc(C(C)C)c(O)cc7O)cc6)CC5)CC4)cc13)-c1cc3c(c(=O)n1C2)COC(=O)C3(O)CC]

ESMS calculated for C₅₀H₅₂N₈O₁₀: 924.38; Found: 925.1 (M+H)⁺.

SDC-TRAP-0095

4,11-diethyl-4-hydroxy-3,14-dioxo-3,4,12,14-tetrahydro-1H-pyrano[3',4':6,7]indolizino[1,2-b]quinolin-9-yl 4-(5-(3-(2,4-dihydroxy-5-isopropylphenyl)-5-hydroxy-4H-1,2,4-triazol-4-yl)-1-methyl-1H-benzo[d]imidazol-2-yl)piperidine-1-carboxylate

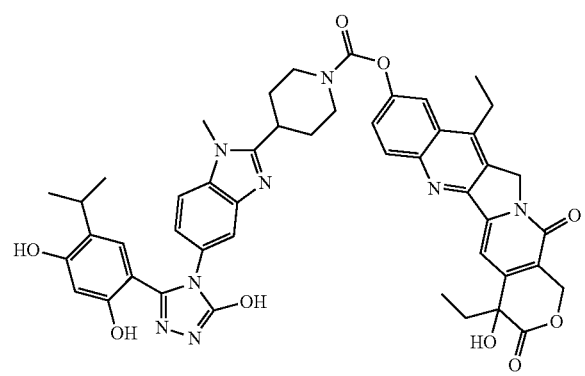 [SMILES: CCc1c2c(nc3ccc(OC(=O)N4CCC(c5nc6cc(-n7c(O)nnc7-c7cc(C(C)C)c(O)cc7O)ccc6n5C)CC4)cc13)-c1cc3c(c(=O)n1C2)COC(=O)C3(O)CC]

¹H NMR (400 MHz, DMSO-d₆) δ 11.87 (s, 1H), 9.53 (s, 1H), 9.34 (s, 1H), 8.19 (d, J=9.1 Hz, 1H), 8.04 (d, J=2.6 Hz, 1H), 7.71 (dd, J=9.2, 2.5 Hz, 1H), 7.51 (d, J=8.6 Hz, 1H), 7.39 (d, J=1.9 Hz, 1H), 7.34 (s, 1H), 7.05 (dd, J=8.6, 2.0 Hz, 1H), 6.87 (s, 1H), 6.54 (s, 1H), 6.21 (s, 1H), 5.45 (s, 2H), 5.35 (s, 2H), 4.37 (s, 1H), 4.18 (d, J=12.6 Hz, 1H), 3.83 (s, 3H), 3.43-3.28 (m, 4H), 3.27-3.15 (m, 4H), 2.97 (p, J=6.9 Hz, 1H), 1.88 (hept, J=7.2 Hz, 2H), 1.31 (t, J=7.6 Hz, 3H), 0.97 (d, J=6.9 Hz, 6H), 0.89 (t, J=7.3 Hz, 3H). ESMS calculated for C₄₇H₄₆N₈O₉: 866.34; Found: 867.2 (M+H)⁺.

SDC-TRAP-0101

4,11-diethyl-4-hydroxy-3,14-dioxo-3,4,12,14-tetrahydro-1H-pyrano[3',4':6,7]indolizino[1,2-b]quinolin-9-yl 4-(4-(4-(3-(2,4-dihydroxy-5-isopropylphenyl)-5-hydroxy-4H-1,2,4-triazol-4-yl)phenyl)piperazin-1-yl)piperidine-1-carboxylate

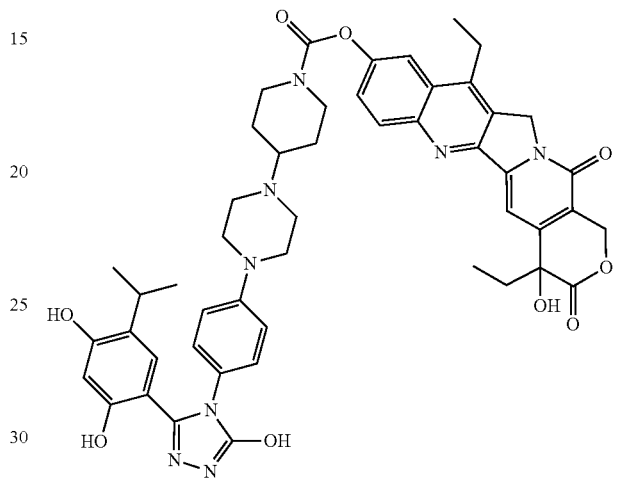

¹H NMR (400 MHz, DMSO-d₆) δ 11.74 (s, 1H), 9.50 (s, 1H), 9.37 (s, 1H), 8.05 (d, J=9.2 Hz, 1H), 7.87 (d, J=2.5 Hz, 1H), 7.55 (dd, J=9.1, 2.5 Hz, 1H), 7.20 (s, 1H), 6.90 (d, J=8.8 Hz, 2H), 6.80 (d, J=8.8 Hz, 2H), 6.65 (s, 1H), 6.42 (s, 1H), 6.16 (s, 1H), 5.32 (s, 2H), 5.21 (s, 2H), 4.15 (s, 1H), 4.00-3.85 (m, 1H), 3.12-3.00 (m, 7H), 2.84 (dq, J=12.6, 6.4, 5.9 Hz, 2H), 2.38 (p, J=1.8 Hz, 12H), 1.87 (s, 1H), 1.75 (hept, J=7.0, 6.5 Hz, 4H), 1.42 (s, 1H), 1.36 (s, 1H), 1.11 (dt, J=47.7, 7.3 Hz, 3H), 0.84 (d, J=6.8 Hz, 6H), 0.76 (t, J=7.2 Hz, 3H). ESMS calculated for C₄₉H₅₂N₈O₉: 896.39; Found: 897.3 (M+H)⁺.

SDC-TRAP-0220

4,11-diethyl-4-hydroxy-3,14-dioxo-3,4,12,14-tetrahydro-1H-pyrano[3',4':6,7]indolizino[1,2-b]quinolin-9-yl 4-(4-(3-(2,4-dihydroxy-5-isopropylphenyl)-5-hydroxy-4H-1,2,4-triazol-4-yl)benzyl)-2-methylpiperazine-1-carboxylate

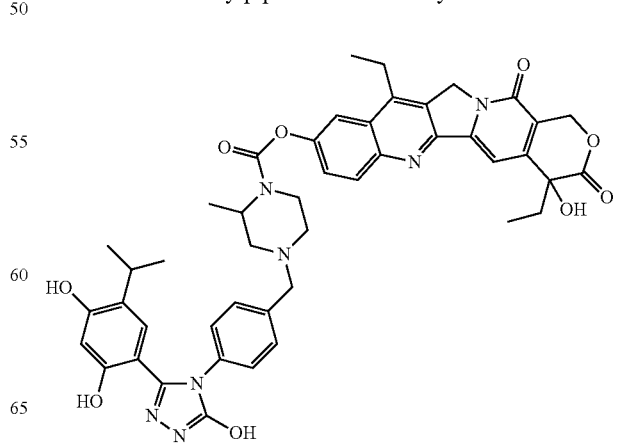

¹H NMR (400 MHz, DMSO-d₆) δ 11.77 (s, 1H), 9.44 (s, 1H), 9.25 (s, 1H), 8.01 (d, J=9.1 Hz, 1H), 7.83 (d, J=2.5 Hz, 1H), 7.50 (dd, J=9.1, 2.5 Hz, 1H), 7.24-7.14 (m, 3H), 7.01 (d, J=7.9 Hz, 2H), 6.63 (s, 1H), 6.36 (s, 1H), 6.11 (s, 1H), 5.27 (s, 2H), 5.17 (s, 2H), 4.18 (s, 1H), 3.41 (d, J=13.7 Hz, 1H), 3.32 (d, J=13.6 Hz, 1H), 3.14 (d, J=11.5 Hz, 3H), 3.03 (q, J=7.8 Hz, 2H), 2.82 (p, J=6.9 Hz, 1H), 2.69 (d, J=10.9 Hz, 1H), 2.07 (s, 1H), 1.93 (s, 1H), 1.71 (hept, J=7.2 Hz, 2H), 1.24-1.08 (m, 6H), 0.80 (d, J=6.9 Hz, 6H), 0.72 (t, J=7.3 Hz, 3H). ESMS calculated for $C_{46}H_{47}N_7O_9$: 841.34; Found: 842.4 (M+H)⁺.

SDC-TRAP-0010

4,11-diethyl-4-hydroxy-3,14-dioxo-3,4,12,14-tetrahydro-1H-pyrano[3',4':6,7]indolizino[1,2-b]quinolin-9-yl (2-(5-(3-(2,4-dihydroxy-5-isopropylphenyl)-5-hydroxy-4H-1,2,4-triazol-4-yl)-N,1-dimethyl-1H-indole-2-carboxamido)ethyl)(methyl)carbamate

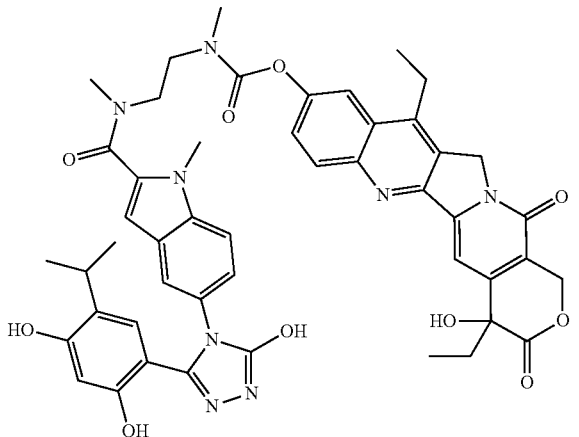 [SMILES: CCc1c2c(nc3ccc(OC(=O)N(C)CCN(C)C(=O)c4cc5cc(-n6c(O)nnc6-c6cc(C(C)C)c(O)cc6O)ccc5n4C)cc13)-c1cc3c(c(=O)n1C2)COC(=O)C3(O)CC]

ESMS calculated ($C_{48}H_{48}N_8O_{10}$): 896.4; found: 897.2 (M+H).

SDC-TRAP-0023

2-((4,11-diethyl-4-hydroxy-3,14-dioxo-3,4,12,14-tetrahydro-1H-pyrano[3',4':6,7]indolizino[1,2-b]quinolin-9-yl)oxy)-N-(2-(5-(3-(2,4-dihydroxy-5-isopropylphenyl)-5-hydroxy-4H-1,2,4-triazol-4-yl)-1H-indol-1-yl)ethyl)acetamide

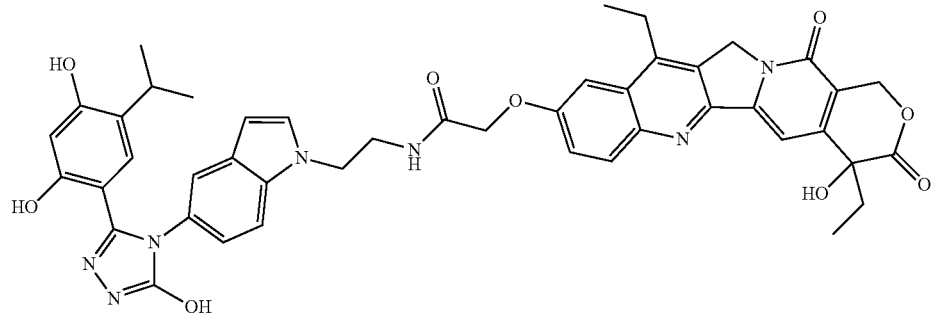 [SMILES: CCc1c2c(nc3ccc(OCC(=O)NCCn4ccc5cc(-n6c(O)nnc6-c6cc(C(C)C)c(O)cc6O)ccc54)cc13)-c1cc3c(c(=O)n1C2)COC(=O)C3(O)CC]

ESMS calculated ($C_{45}H_{43}N_7O_9$): 825.3; found: 826.2 (M+H).

SDC-TRAP-0024

4,11-diethyl-9-hydroxy-3,14-dioxo-3,4,12,14-tetrahydro-1H-pyrano[3',4':6,7]indolizino[1,2-b]quinolin-4-yl-4-(5-(3-(2,4-dihydroxy-5-isopropylphenyl)-5-hydroxy-4H-1,2,4-triazol-4-yl)-1-methyl-1H-indole-2-carboxamido)butanoate

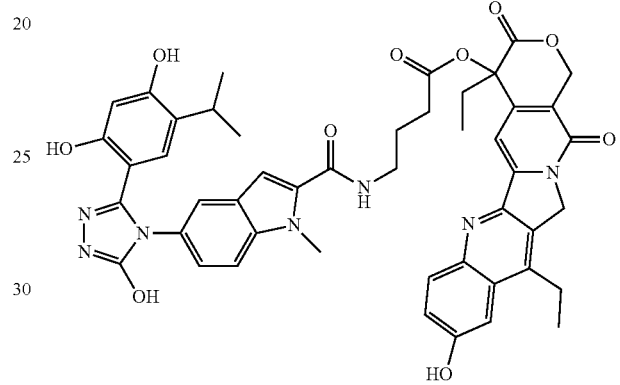

¹H NMR (400 MHz, Methanol-d₄) δ 7.88 (d, J=9.1 Hz, 1H), 7.44 (d, J=2.0 Hz, 1H), 7.38-7.24 (m, 4H), 7.15 (dd, J=8.8, 2.0 Hz, 1H), 6.74 (s, 1H), 6.67 (s, 1H), 6.26 (s, 1H), 5.62 (d, J=16.6 Hz, 1H), 5.44 (d, J=16.7 Hz, 1H), 5.05 (d, J=18.7 Hz, 1H), 4.81 (d, J=18.7 Hz, 1H), 3.58 (s, 3H), 3.49-3.42 (m, 1H), 3.40-3.32 (m, 1H), 3.10-2.96 (m, 1H), 2.96-2.83 (m, 2H), 2.73 (td, J=6.8, 2.5 Hz, 2H), 2.19 (ddt, J=18.2, 14.3, 7.2 Hz, 2H), 2.09-1.90 (m, 2H), 1.29 (t, J=7.6 Hz, 3H), 1.01 (t, J=7.4 Hz, 3H), 0.74 (dd, J=10.2, 6.8 Hz, 6H); ESMS calculated ($C_{47}H_{45}N_7O_{10}$): 867.3; found: 868.3 (M+H).

SDC-TRAP-0026

4,11-diethyl-9-hydroxy-3,14-dioxo-3,4,12,14-tetrahydro-1H-pyrano[3',4':6,7]indolizino[1,2-b]quinolin-4-yl-4-((2-(5-(3-(2,4-dihydroxy-5-isopropylphenyl)-5-hydroxy-4H-1,2,4-triazol-4-yl)-1H-indol-1-yl)ethyl)amino)-4-oxobutanoate

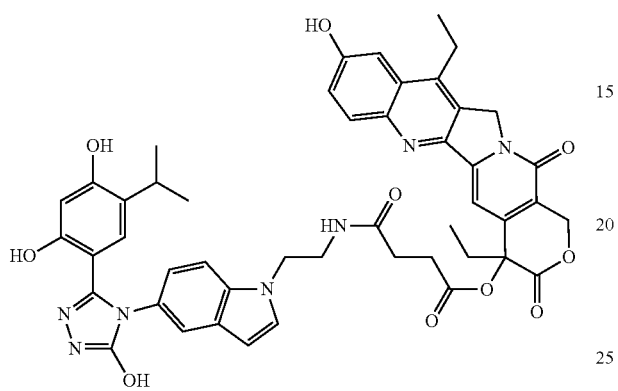

$^1$H NMR (400 MHz, Methanol-d$_4$) δ 8.00-7.88 (m, 2H), 7.42 (d, J=2.0 Hz, 1H), 7.37-7.23 (m, 3H), 7.02 (d, J=3.2 Hz, 1H), 6.87 (dd, J=8.7, 2.0 Hz, 1H), 6.45 (s, 1H), 6.33 (d, J=3.1 Hz, 1H), 6.23 (s, 1H), 5.61 (d, J=16.7 Hz, 1H), 5.44 (d, J=16.6 Hz, 1H), 5.06 (d, J=18.6 Hz, 1H), 4.89 (d, J=18.6 Hz, 1H), 4.58 (s, 1H), 4.08-3.97 (m, 1H), 3.45-3.40 (m, 1H), 3.35-3.29 (m, 1H), 2.99-2.74 (m, 5H), 2.51-2.40 (m, 2H), 2.27-2.12 (m, 2H), 1.36-1.18 (m, 3H), 1.02 (t, J=7.4 Hz, 3H), 0.58 (dd, J=6.9, 5.1 Hz, 6H); ESMS calculated (C$_{47}$H$_{45}$N$_7$O$_{10}$): 867.3; found: 868.3 (M+H).

SDC-TRAP-0042

4,11-diethyl-9-hydroxy-3,14-dioxo-3,4,12,14-tetrahydro-1H-pyrano[3',4':6,7]indolizino[1,2-b]quinolin-4-yl 4-(4-(4-(3-(2,4-dihydroxy-5-isopropylphenyl)-5-hydroxy-4H-1,2,4-triazol-4-yl)benzyl)piperidin-1-yl)-4-oxobutanoate

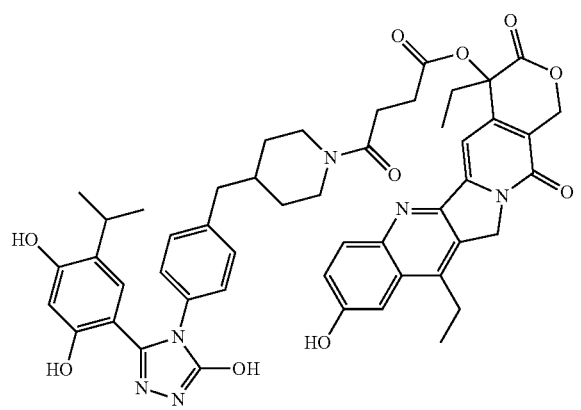

$^1$H NMR (400 MHz, Methanol-d$_4$) δ 7.99 (d, J=9.5 Hz, 1H), 7.45-7.33 (m, 3H), 7.27-7.05 (m, 4H), 6.64 (d, J=8.7 Hz, 1H), 6.26 (s, 1H), 5.60 (dd, J=16.7, 3.0 Hz, 1H), 5.51-5.40 (m, 1H), 5.24 (d, J=1.5 Hz, 2H), 4.48 (d, J=12.9 Hz, 1H), 3.88 (d, J=13.7 Hz, 1H), 3.34 (s, 2H), 3.13 (q, J=7.4 Hz, 2H), 3.02-2.83 (m, 3H), 2.83-2.63 (m, 3H), 2.55 (d, J=7.0 Hz, 1H), 2.46 (d, J=13.3 Hz, 2H), 2.21 (dp, J=21.6, 7.1 Hz, 2H), 1.70-1.56 (m, 2H), 1.36 (td, J=7.7, 3.6 Hz, 3H), 1.03 (td, J=7.5, 1.4 Hz, 3H), 0.88-0.79 (m, 6H); ESMS calculated (C$_{49}$H$_{50}$N$_6$O$_{10}$): 882.4; found: 883.3 (M+H).

SDC-TRAP-0043

4,11-diethyl-9-hydroxy-3,14-dioxo-3,4,12,14-tetrahydro-1H-pyrano[3',4':6,7]indolizino[1,2-b]quinolin-4-yl 4-(4-(4-(3-(2,4-dihydroxy-5-isopropylphenyl)-5-hydroxy-4H-1,2,4-triazol-4-yl)benzyl)piperazin-1-yl)-4-oxobutanoate

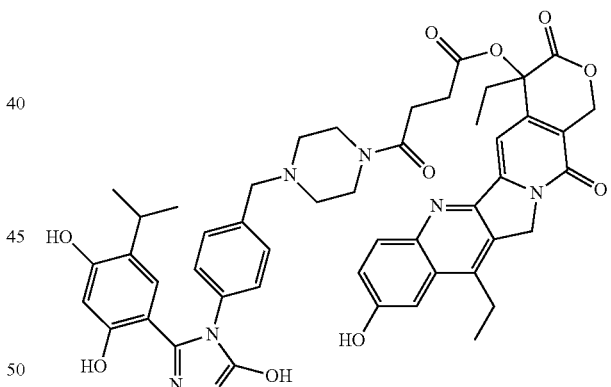

$^1$H NMR (400 MHz, Methanol-d$_4$) δ 7.99 (d, J=8.9 Hz, 1H), 7.43-7.28 (m, 5H), 7.26-7.17 (m, 2H), 6.68 (s, 1H), 6.24 (s, 1H), 5.59 (d, J=16.6 Hz, 1H), 5.45 (d, J=16.6 Hz, 1H), 5.24 (s, 2H), 3.59 (s, 2H), 3.54-3.31 (m, 4H), 3.13 (q, J=7.7 Hz, 2H), 3.02-2.83 (m, 2H), 2.81-2.62 (m, 3H), 2.45 (s, 1H), 2.35 (s, 1H), 2.30-2.10 (m, 4H), 1.40 (m, 3H), 1.03 (t, J=7.4 Hz, 3H), 0.84 (t, J=6.7 Hz, 6H); ESMS calculated (C$_{48}$H$_{49}$N$_7$O$_{10}$): 883.3; found: 884.3 (M+H).

SDC-TRAP-0044

4,11-diethyl-4-hydroxy-3,14-dioxo-3,4,12,14-tetrahydro-1H-pyrano[3',4':6,7]indolizino[1,2-b]quinolin-9-yl (4-(4-(4-(3-(2,4-dihydroxy-5-isopropylphenyl)-5-hydroxy-4H-1,2,4-triazol-4-yl)benzyl)piperazin-1-yl)butyl)(methyl)carbamate

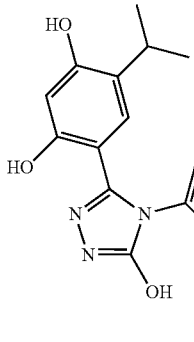
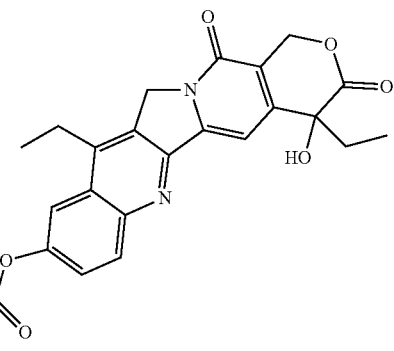

$^1$H NMR (400 MHz, Methanol-$d_4$) δ 8.13 (dd, J=9.9, 7.8 Hz, 1H), 7.93 (d, J=2.7 Hz, 1H), 7.66-7.59 (m, 2H), 7.45-7.40 (m, 2H), 7.26-7.20 (m, 2H), 6.66 (d, J=16.5 Hz, 1H), 6.27-6.19 (m, 1H), 5.58 (d, J=16.2 Hz, 1H), 5.38 (dd, J=16.2, 1.8 Hz, 1H), 5.27 (s, 2H), 4.85 (s, 1H), 3.64-3.52 (m, 3H), 3.48-3.40 (m, 1H), 3.17 (s, 3H), 3.05 (s, 1H), 3.01-2.87 (m, 2H), 2.70-2.49 (m, 9H), 1.99-1.91 (m, 2H), 1.80-1.64 (m, 5H), 1.37 (td, J=7.3, 2.1 Hz, 3H), 1.00 (td, J=7.3, 4.3 Hz, 3H), 0.95-0.77 (m, 6H); ESMS calculated ($C_{50}H_{56}N_8O_9$): 912.4; found: 913.3 (M+H).

SDC-TRAP-0045

4,11-diethyl-4-hydroxy-3,14-dioxo-3,4,12,14-tetrahydro-1H-pyrano[3',4':6,7]indolizino[1,2-b]quinolin-9-yl 4-(4-(3-(2,4-dihydroxy-5-isopropylphenyl)-5-hydroxy-4H-1,2,4-triazol-4-yl)phenyl)piperazine-1-carboxylate

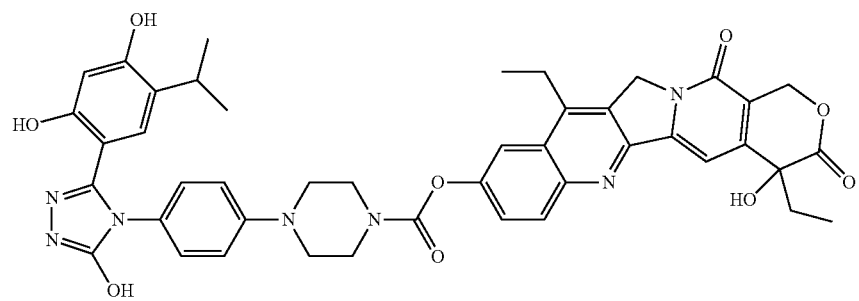 [SMILES: CCc1c2c(nc3ccc(OC(=O)N4CCN(c5ccc(-n6c(O)nnc6-c6cc(C(C)C)c(O)cc6O)cc5)CC4)cc13)-c1cc3c(c(=O)n1C2)COC(=O)C3(O)CC]

$^1$H NMR (400 MHz, DMSO-$d_6$) δ 11.88 (s, 1H), 9.62 (s, 1H), 9.46 (s, 1H), 8.19 (d, J=9.1 Hz, 1H), 8.04 (d, J=2.6 Hz, 1H), 7.71 (dd, J=9.2, 2.5 Hz, 1H), 7.33 (s, 1H), 7.07 (d, J=9.0 Hz, 2H), 7.00 (d, J=9.1 Hz, 2H), 6.82 (s, 1H), 6.56 (s, 1H), 6.27 (s, 1H), 5.44 (s, 2H), 5.35 (s, 2H), 3.81 (s, 2H), 3.72-3.52 (m, 4H), 3.48-3.19 (m, 4H), 2.99 (p, J=6.8 Hz, 1H), 1.87 (dt, J=14.9, 7.0 Hz, 2H), 1.30 (t, J=7.6 Hz, 3H), 0.99 (d, J=6.9 Hz, 6H), 0.88 (t, J=7.3 Hz, 3H); ESMS calculated ($C_{44}H_{43}N_7O_9$): 813.3; found: 814.3 (M+H).

SDC-TRAP-0055

4,11-diethyl-9-hydroxy-3,14-dioxo-3,4,12,14-tetrahydro-1H-pyrano[3',4':6,7]indolizino[1,2-b]quinolin-4-yl (4-(4-(4-(3-(2,4-dihydroxy-5-isopropylphenyl)-5-hydroxy-4H-1,2,4-triazol-4-yl)benzyl)piperazin-1-yl)butyl)(methyl)carbamate

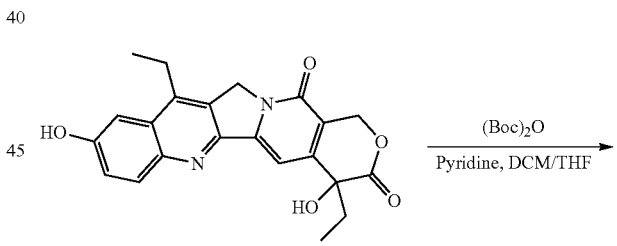

267

-continued

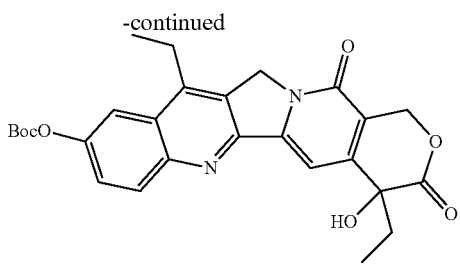

To a solution of SN-38 (3 g, 7.65 mmol) in DCM/THF (150 mL/150 mL) was added (Boc)$_2$O (2 g, 9.16 mmol) and pyridine (20 mL). The suspension was stirred at room temperature until the solution turned clear. The solution was diluted with DCM (100 mL) and washed with 2N HCl (100 mL×3). The organic phase was collected, dried over Na$_2$SO$_4$ and concentrated. The resulting crude product was used directly for the next step without purification.

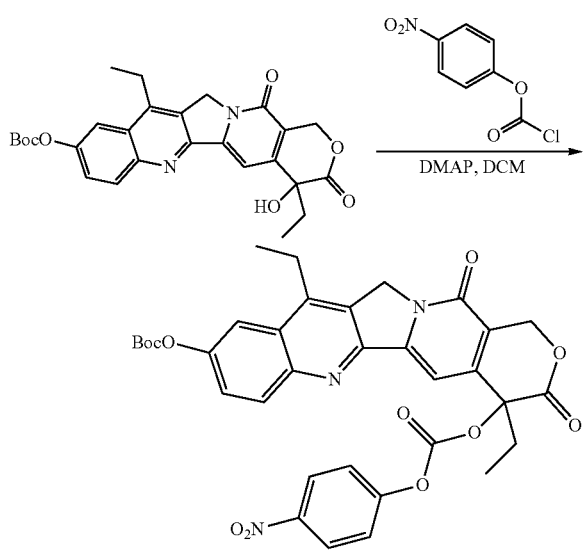

To the solution of SN-38-$^{10}$OBoc (1 g, 2.03 mmol) in DCM (50 mL) was added 4-nitrophenyl chloroformate (0.49 g, 2.44 mmol) followed by DMAP (0.74 g, 6.05 mmol). The reaction was stirred at room temperature for 1 hr before it was diluted with 100 mL of DCM. The reaction solution was washed with 0.1 N HCl (50 mL×3), dried over Na$_2$SO$_4$ and concentrated. The resulting solid was washed with Et$_2$O to remove excess 4-nitrophenyl chloroformate. The resulting crude product is used directly for the next step without purification.

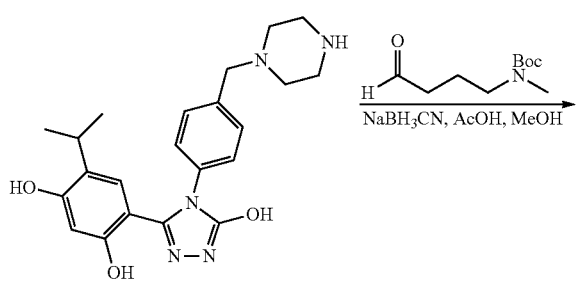

268

-continued

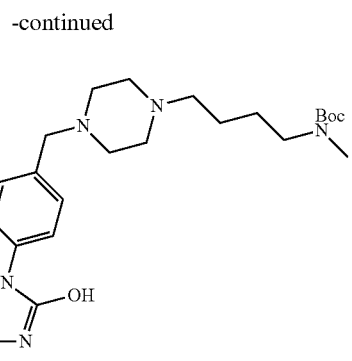

To the solution of 4-(5-hydroxy-4-(4-(piperazin-1-ylmethyl)phenyl)-4H-1,2,4-triazol-3-yl)-6-isopropylbenzene-1,3-diol (0.46 g, 1.12 mmol) in MeOH (10 mL) was added t-butyl methyl(4-oxobutyl)carbamate (0.45 g, 2.23 mmol) and acetic acid (3 drops) at room temperature. NaBH$_3$CN (0.28 g, 4.44 mmol) was added as two portions in 10 min. The resulting solution was stirred at room temperature for 30 min before it was concentrated. Column chromatography gave t-butyl-(4-(4-(4-(3-(2,4-dihydroxy-5-isopropylphenyl)-5-hydroxy-4H-1,2,4-triazol-4-yl)benzyl) piperazin-1-yl)butyl)(methyl)carbamate (0.48 g, 72%).

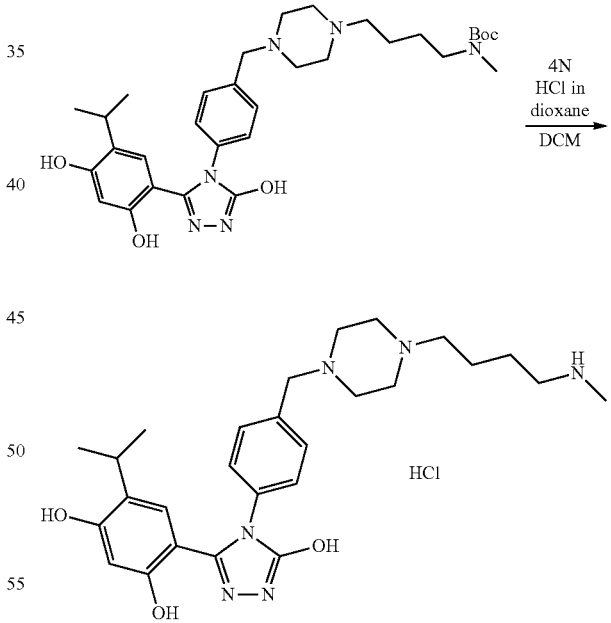

To the solution of t-butyl-(4-(4-(4-(3-(2,4-dihydroxy-5-isopropylphenyl)-5-hydroxy-4H-1,2,4-triazol-4-yl)benzyl) piperazin-1-yl)butyl)(methyl)carbamate (0.48 g, 0.81 mmol) in DCM (15 mL) was added 4N HCl in dioxane (5 mL). The reaction was stirred at room temperature for 3 hr before it was concentrated. The resulting crude product was used directly for the next step without purification.

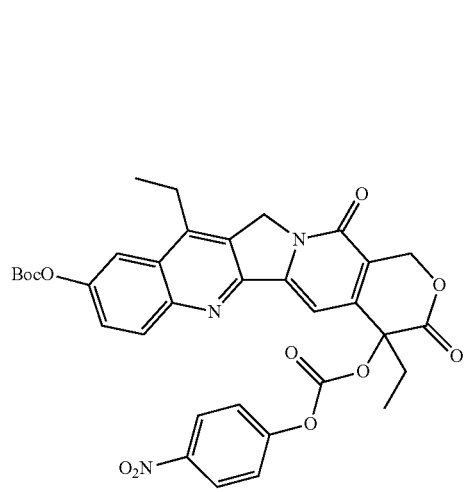
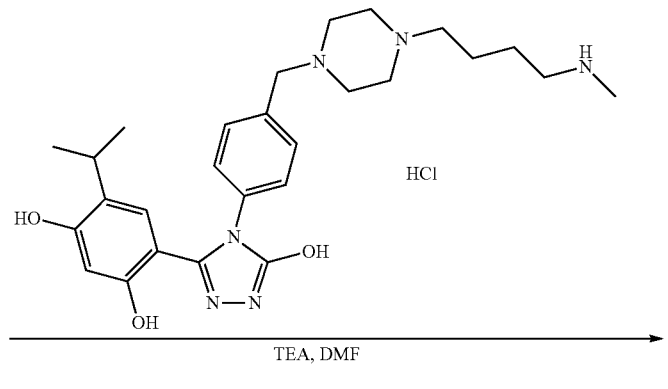

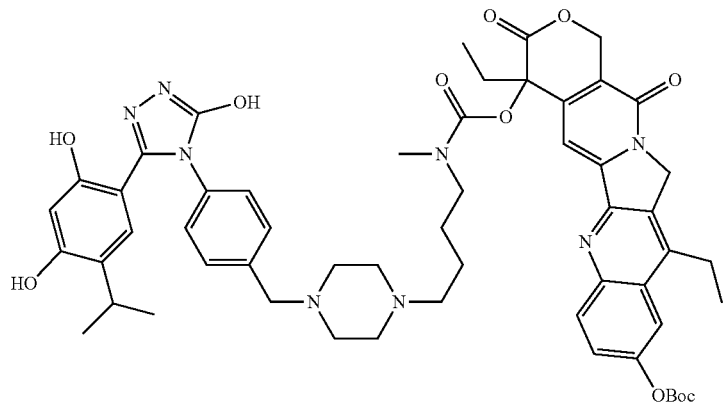

To the solution of 4-(5-hydroxy-4-(4-((4-(4-(methyl-amino)butyl) piperazin-1-yl)methyl)phenyl)-4H-1,2,4-triazol-3-yl)-6-isopropylbenzene-1,3-diol (HCl salt, 0.1 g, 0.19 mmol) in DMF (4 mL) was added t-butyl (4,11-diethyl-3,14-dioxo-3,4,12,14-tetrahydro-1H-pyrano[3',4':6,7]indolizino[1,2-b]quinoline-4,9-diyl) (4-nitrophenyl) dicarbonate (0.16 g, 0.24 mmol) and TEA (0.09 mL, 0.65 mmol). The reaction was stirred at room temperature for 2 hr before it was diluted with H$_2$O (20 mL) and EtOAc (20 mL). The organic phase was collected, dried over Na$_2$SO$_4$ and concentrated. Column chromatography gave 9-((t-butoxycarbonyl)oxy)-4,11-diethyl-3,14-dioxo-3,4,12,14-tetrahydro-1H-pyrano[3',4':6,7]indolizino[1,2-b]quinolin-4-yl (4-(4-(4-(3-(2,4-dihydroxy-5-isopropylphenyl)-5-hydroxy-4H-1,2,4-triazol-4-yl)benzyl)piperazin-1-yl)butyl)(methyl)carbamate (0.15 g, 75%).

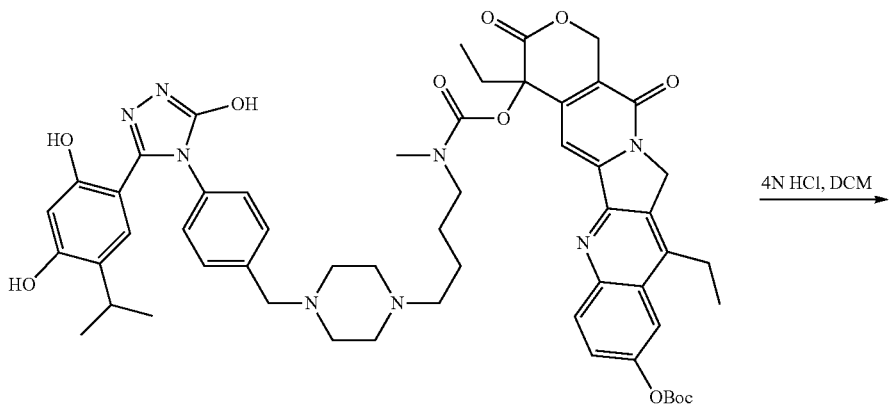

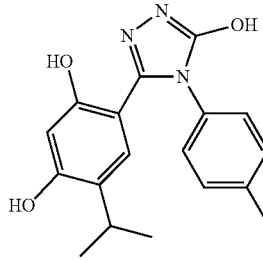
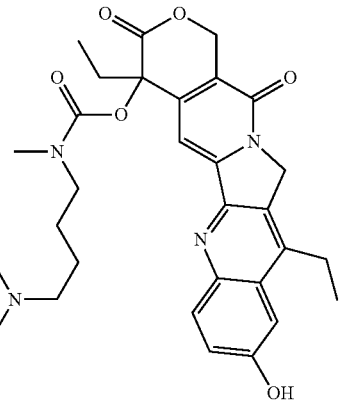

SDC-TRAP-0055

To the solution of 9-((t-butoxycarbonyl)oxy)-4,11-diethyl-3,14-dioxo-3,4,12,14-tetrahydro-1H-pyrano[3',4':6,7]indolizino[1,2-b]quinolin-4-yl (4-(4-(4-(3-(2,4-dihydroxy-5-isopropylphenyl)-5-hydroxy-4H-1,2,4-triazol-4-yl)benzyl)piperazin-1-yl)butyl)(methyl)carbamate (0.15 g, 0.15 mmol) in DCM (5 mL) was added 4N HCl in dioxane (5 mL). The reaction was stirred at room temperature for 3 hr before it was concentrated. Column chromatography gave SDC-TRAP-0055 (0.09 g, 66%) as yellow solid.

$^1$H NMR (400 MHz, Methanol-d$_4$) δ 7.93 (dd, J=9.5, 2.8 Hz, 1H), 7.40-7.28 (m, 4H), 7.26-7.13 (m, 3H), 6.63 (d, J=6.4 Hz, 1H), 6.17 (s, 1H), 5.48 (dd, J=16.7, 11.7 Hz, 1H), 5.41-5.27 (m, 1H), 5.17 (d, J=2.4 Hz, 2H), 3.57 (s, 1H), 3.45 (s, 1H), 3.25 (m, 5H), 3.15-3.00 (m, 8H), 2.92 (p, J=6.9 Hz, 3H), 2.75 (s, 1H), 2.10 (dp, J=21.9, 7.3 Hz, 2H), 1.82-1.46 (m, 5H), 1.28 (td, J=7.6, 1.9 Hz, 3H), 0.95 (dt, J=13.8, 7.4 Hz, 3H), 0.81 (dd, J=7.0, 2.0 Hz, 6H); ESMS calculated (C$_{50}$H$_{56}$N$_8$O$_9$): 912.4; found: 913.1 (M+H).

SDC-TRAP-0056

4,11-diethyl-9-hydroxy-3,14-dioxo-3,4,12,14-tetrahydro-1H-pyrano[3',4':6,7]indolizino[1,2-b]quinolin-4-yl 2-(4-(4-(3-(2,4-dihydroxy-5-isopropylphenyl)-5-hydroxy-4H-1,2,4-triazol-4-yl)phenyl)piperazin-1-yl)acetate

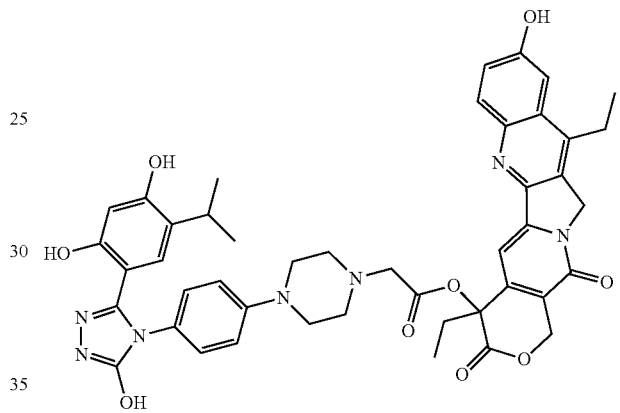

$^1$H NMR (400 MHz, DMSO-d$_6$) δ 11.84 (s, 1H), 10.32 (s, 1H), 9.57 (s, 1H), 9.44 (s, 1H), 8.00-7.92 (m, 1H), 7.40-7.37 (m, 2H), 6.99-6.97 (m, 3H), 6.90-6.83 (m, 2H), 6.76 (s, 1H), 6.25 (s, 1H), 5.50 (s, 2H), 5.30 (d, J=3.5 Hz, 2H), 3.58 (d, J=16.5 Hz, 1H), 3.42 (d, J=16.4 Hz, 1H), 3.18-3.07 (m, 6H), 2.95 (p, J=6.8 Hz, 1H), 2.65 (t, J=5.2 Hz, 4H), 2.15 (dt, J=9.4, 6.5 Hz, 2H), 1.29 (t, J=7.5 Hz, 3H), 0.93 (dd, J=6.8, 1.8 Hz, 9H); ESMS calculated (C$_{45}$H$_{45}$N$_7$O$_9$): 827.3; found: 828.0 (M+H).

SDC-TRAP-0057

9-(2-(4-(4-(3-(2,4-dihydroxy-5-isopropylphenyl)-5-hydroxy-4H-1,2,4-triazol-4-yl)phenyl)piperazin-1-yl)ethoxy)-4,11-diethyl-4-hydroxy-1H-pyrano[3',4':6,7]indolizino[1,2-b]quinoline-3,14(4H,12H)-dione

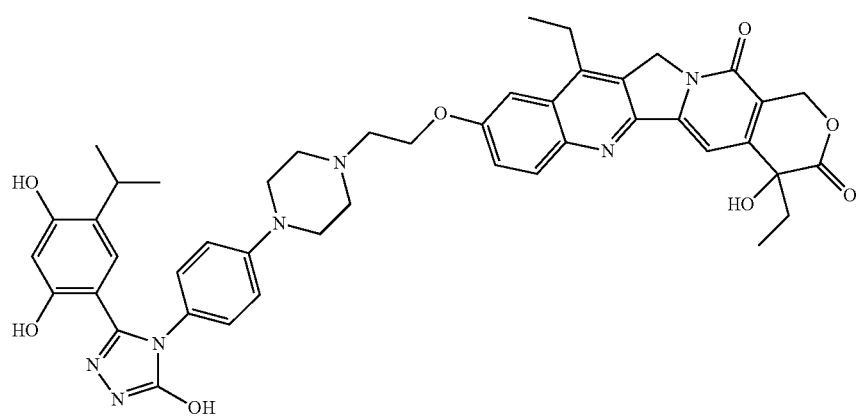 [SMILES: CCc1c2c(nc3ccc(OCCN4CCN(c5ccc(-n6c(O)nnc6-c6cc(C(C)C)c(O)cc6O)cc5)CC4)cc13)-c1cc3c(c(=O)n1C2)COC(=O)C3(O)CC]

ESMS calculated ($C_{45}H_{47}N_7O_8$): 813.3; found: 814.1 (M+H).

SDC-TRAP-0058

9-(2-(5-(3-(2,4-dihydroxy-5-isopropylphenyl)-5-hydroxy-4H-1,2,4-triazol-4-yl)-1H-indol-1-yl)ethoxy)-4,11-diethyl-4-hydroxy-1H-pyrano[3',4':6,7]indolizino[1,2-b]quinoline-3,14(4H,12H)-dione

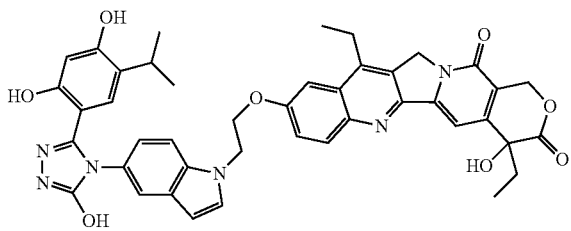 [SMILES: CCc1c2c(nc3ccc(OCCn4ccc5cc(-n6c(O)nnc6-c6cc(C(C)C)c(O)cc6O)ccc54)cc13)-c1cc3c(c(=O)n1C2)COC(=O)C3(O)CC]

ESMS calculated ($C_{43}H_{40}N_6O_8$): 768.3; found: 769.1 (M+H).

SDC-TRAP-0060

4,11-diethyl-9-hydroxy-3,14-dioxo-3,4,12,14-tetrahydro-1H-pyrano[3',4':6,7]indolizino[1,2-b]quinolin-4-yl 4-(3-(4-(3-(2,4-dihydroxy-5-isopropylphenyl)-5-hydroxy-4H-1,2,4-triazol-4-yl)phenyl)propanoyl)piperazine-1-carboxylate

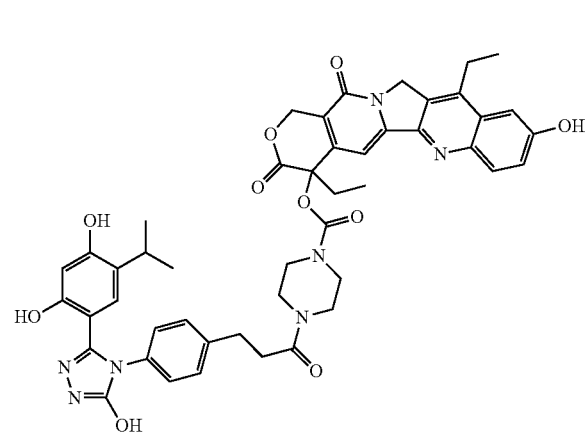 [SMILES: CCc1c2c(nc3ccc(O)cc13)-c1cc3c(c(=O)n1C2)COC(=O)C3(CC)OC(=O)N1CCN(C(=O)CCc2ccc(-n3c(O)nnc3-c3cc(C(C)C)c(O)cc3O)cc2)CC1]

ESMS calculated ($C_{47}H_{47}N_7O_{10}$): 869.3; found: 870.0 (M+H).

SDC-TRAP-0061

9-(3-(4-(4-(3-(2,4-dihydroxy-5-isopropylphenyl)-5-hydroxy-4H-1,2,4-triazol-4-yl)phenyl)piperazin-1-yl)propoxy)-4,11-diethyl-4-hydroxy-1H-pyrano[3',4':6,7]indolizino[1,2-b]quinoline-3,14(4H,12H)-dione

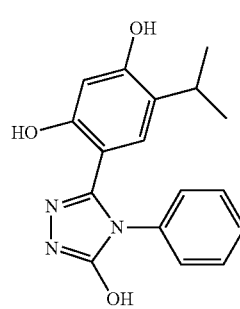

ESMS calculated ($C_{46}H_{49}N_7O_8$): 827.3; found: 828.1 (M+H).

SDC-TRAP-0071

4,11-diethyl-9-hydroxy-3,14-dioxo-3,4,12,14-tetrahydro-1H-pyrano[3',4':6,7]indolizino[1,2-b]quinolin-4-yl 2-(4-(4-(3-(2,4-dihydroxy-5-isopropylphenyl)-5-hydroxy-4H-1,2,4-triazol-4-yl)benzyl)piperidin-1-yl)acetate

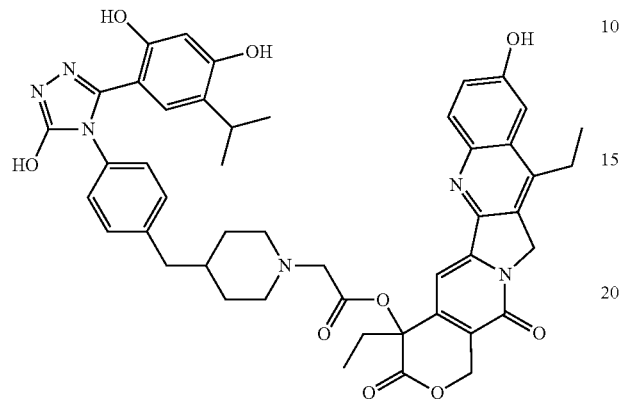

$^1$H NMR (400 MHz, Methanol-d$_4$) δ 7.86 (d, J=9.1 Hz, 1H), 7.32-7.21 (m, 2H), 7.18 (s, 1H), 7.15-7.06 (m, 2H), 7.06-6.98 (m, 2H), 6.49 (s, 1H), 6.16 (s, 1H), 5.52 (d, J=16.7 Hz, 1H), 5.35 (d, J=16.7 Hz, 1H), 5.08 (s, 2H), 3.49-3.31 (m, 2H), 2.99 (q, J=7.6 Hz, 2H), 2.87-2.66 (m, 3H), 2.42 (d, J=6.9 Hz, 2H), 2.21-2.00 (m, 4H), 1.54-1.33 (m, 3H), 1.28-1.15 (m, 5H), 0.93 (t, J=7.4 Hz, 3H), 0.66 (t, J=7.1 Hz, 6H); ESMS calculated (C$_{47}$H$_{48}$N$_6$O$_9$): 840.3; found: 841.2 (M+H).

SDC-TRAP-0072

4,11-diethyl-4-hydroxy-3,14-dioxo-3,4,12,14-tetrahydro-1H-pyrano[3',4':6,7]indolizino[1,2-b]quinolin-9-yl 4-(5-(3-(2,4-dihydroxy-5-isopropylphenyl)-5-hydroxy-4H-1,2,4-triazol-4-yl)-1-methyl-1H-indole-2-carbonyl)piperazine-1-carboxylate

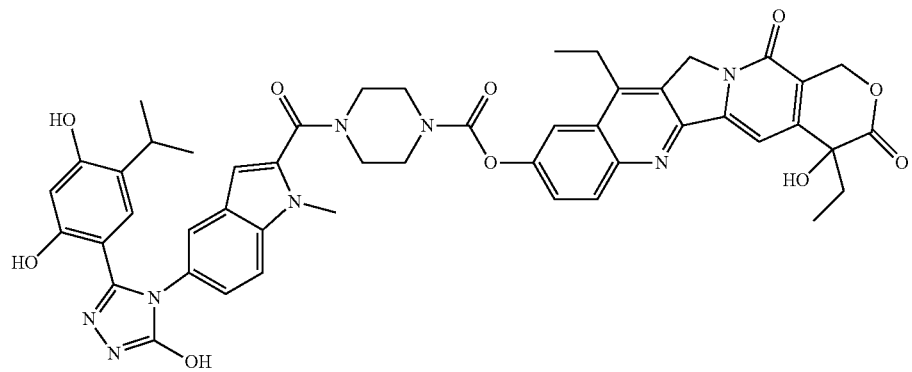 [SMILES: CCc1c2c(nc3ccc(OC(=O)N4CCN(C(=O)c5cc6cc(-n7c(O)nnc7-c7cc(C(C)C)c(O)cc7O)ccc6n5C)CC4)cc13)-c1cc3c(c(=O)n1C2)COC(=O)C3(O)CC]

$^1$H NMR (400 MHz, DMSO-d$_6$) δ 11.88 (s, 1H), 9.55 (s, 1H), 9.38 (s, 1H), 8.20 (d, J=9.1 Hz, 1H), 8.03 (d, J=2.6 Hz, 1H), 7.70 (dd, J=9.2, 2.5 Hz, 1H), 7.56-7.49 (m, 2H), 7.33 (s, 1H), 7.03 (dd, J=8.7, 2.1 Hz, 1H), 6.84 (s, 1H), 6.76 (s, 1H), 6.54 (s, 1H), 6.21 (s, 1H), 5.44 (s, 2H), 5.35 (s, 2H), 3.79 (brs, 7H), 3.60 (s, 2H), 3.25-3.14 (m, 3H), 2.95 (p, J=7.0 Hz, 1H), 1.95-1.79 (m, 3H), 1.30 (t, J=8.0 Hz, 3H), 0.94-0.85 (m, 9H); ESMS calculated (C$_{48}$H$_{46}$N$_8$O$_{10}$): 894.3; found: 895.0 (M+H).

SDC-TRAP-0073

4,11-diethyl-4-hydroxy-3,14-dioxo-3,4,12,14-tetrahydro-1H-pyrano[3',4':6,7]indolizino[1,2-b]quinolin-9-yl 4-((5-(3-(2,4-dihydroxy-5-isopropylphenyl)-5-hydroxy-4H-1,2,4-triazol-4-yl)-1-methyl-1H-indol-2-yl)methyl)piperazine-1-carboxylate

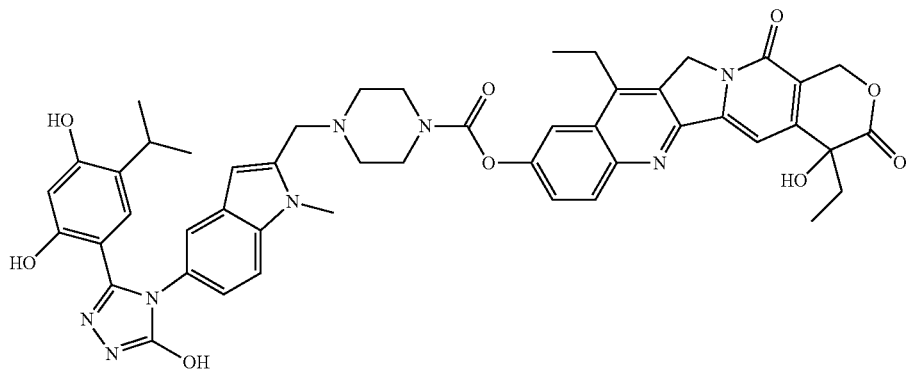 [SMILES: CCc1c2c(nc3ccc(OC(=O)N4CCN(Cc5cc6cc(-n7c(O)nnc7-c7cc(C(C)C)c(O)cc7O)ccc6n5C)CC4)cc13)-c1cc3c(c(=O)n1C2)COC(=O)C3(O)CC]

ESMS calculated ($C_{48}H_{48}N_8O_9$): 880.4; found: 881.1 (M+H).

SDC-TRAP-0074

9-acetoxy-4,11-diethyl-3,14-dioxo-3,4,12,14-tetrahydro-1H-pyrano[3',4':6,7]indolizino[1,2-b]quinolin-4-yl 4-(4-(3-(2,4-dihydroxy-5-isopropylphenyl)-5-hydroxy-4H-1, 2,4-triazol-4-yl)benzyl)piperazine-1-carboxylate

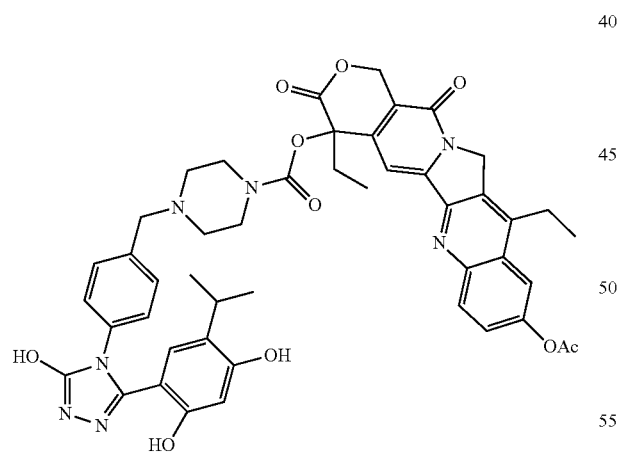

$^1$H NMR (400 MHz, DMSO-$d_6$) δ 11.94 (s, 1H), 9.61 (s, 1H), 9.42 (s, 1H), 8.21 (d, J=9.2 Hz, 1H), 8.03 (s, 1H), 7.68 (d, J=9.1 Hz, 1H), 7.32 (d, J=7.9 Hz, 2H), 7.14 (d, J=8.0 Hz, 2H), 7.05 (s, 1H), 6.78 (s, 1H), 6.26 (s, 1H), 5.46 (d, J=4.8 Hz, 2H), 5.35 (s, 2H), 3.73 (s, 1H), 3.62 (s, 1H), 3.52-3.44 (m, 3H), 3.28-3.13 (m, 4H), 2.97 (p, J=7.1 Hz, 1H), 2.38 (s, 3H), 2.30 (s, 1H), 2.24-2.10 (m, 4H), 1.28 (t, J=7.3 Hz, 3H), 0.92 (dd, J=19.9, 7.5 Hz, 9H); ESMS calculated ($C_{47}H_{47}N_7O_{11}$): 880.4; found: 881.1 (M+H).

SDC-TRAP-0075

4,11-diethyl-9-hydroxy-3,14-dioxo-3,4,12,14-tetrahydro-1H-pyrano[3',4':6,7]indolizino[1,2-b]quinolin-4-yl 4-((5-(3-(2,4-dihydroxy-5-isopropylphenyl)-5-hydroxy-4H-1,2,4-triazol-4-yl)-1-methyl-1H-indol-2-yl)methyl)piperazine-1-carboxylate

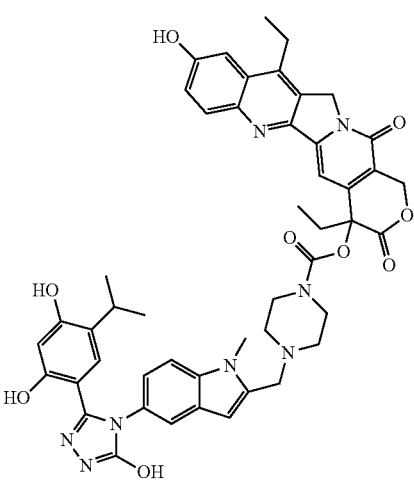 [SMILES: CCc1c2c(nc3ccc(O)cc13)-c1cc3c(c(=O)n1C2)COC(=O)C3(CC)OC(=O)N1CCN(Cc2cc3cc(-n4c(O)nnc4-c4cc(C(C)C)c(O)cc4O)ccc3n2C)CC1]

ESMS calculated ($C_{48}H_{48}N_8O_9$): 880.4; found: 881.2 (M+H).

279

SDC-TRAP-0076

4,11-diethyl-9-hydroxy-3,14-dioxo-3,4,12,14-tetrahydro-1H-pyrano[3',4':6,7]indolizino[1,2-b]quinolin-4-yl 1-(1-(4-(3-(2,4-dihydroxy-5-isopropylphenyl)-5-(ethylcarbamoyl)-4H-1,2,4-triazol-4-yl)benzyl)piperidine-4-carboxylate

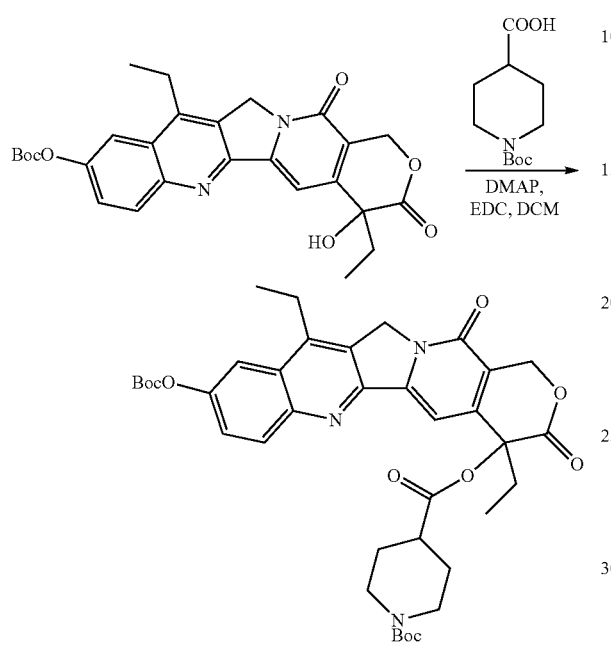

To the solution of SN-38-$^{10}$OBoc (0.85 g, 1.73 mmol) in DCM (50 mL) was added 1-(t-butoxycarbonyl)piperidine-4-carboxylic acid (0.48 g, 2.09 mmol) followed by DMAP (0.42 g, 3.44 mmol) and EDC (1 g, 5.2 mmol). The reaction was stirred at room temperature for 1 hr before it was diluted with DCM (100 mL). The organic phase was washed with 2N HCl (50 mL×2), dried over $Na_2SO_4$ and concentrated. Column chromatography gave 4-(9-((t-butoxycarbonyl)oxy)-4,11-diethyl-3,14-dioxo-3,4,12,14-tetrahydro-1H-pyrano[3',4':6,7] indolizino[1,2-b]quinolin-4-yl) 1-t-butyl piperidine-1,4-dicarboxylate (1.03 g, 85%).

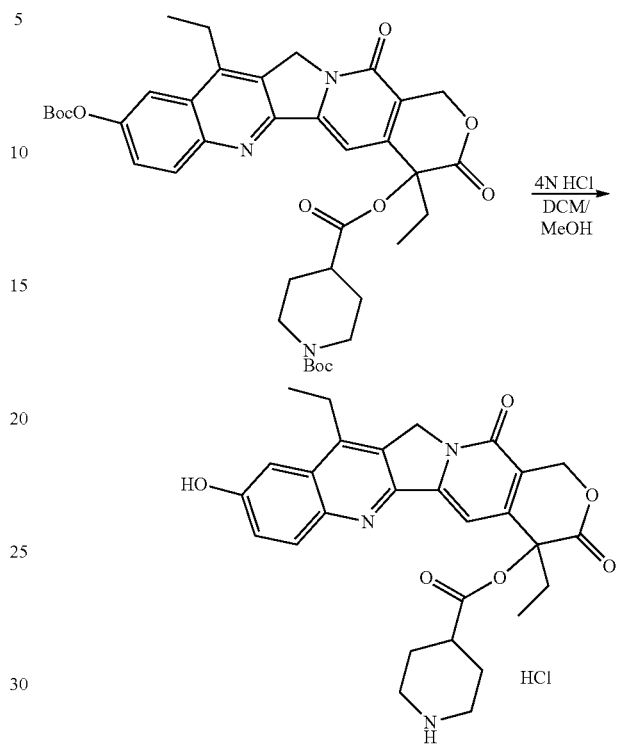

To the solution of 4-(9-((t-butoxycarbonyl)oxy)-4,11-diethyl-3,14-dioxo-3,4,12,14-tetrahydro-1H-pyrano[3',4':6,7]indolizino[1,2-b]quinolin-4-yl) 1-t-butyl piperidine-1,4-dicarboxylate (1.03 g, 1.46 mmol) in DCM (15 mL) was added 4N HCl in dioxane (10 mL). The reaction was heated at 45° C. for 30 min before it was concentrated. The resulting crude product is used directly for the next step without purification.

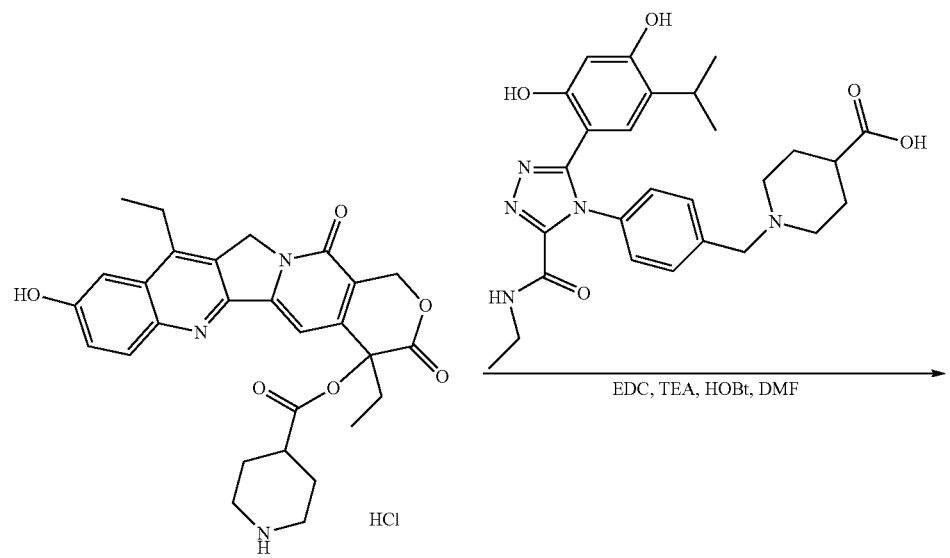

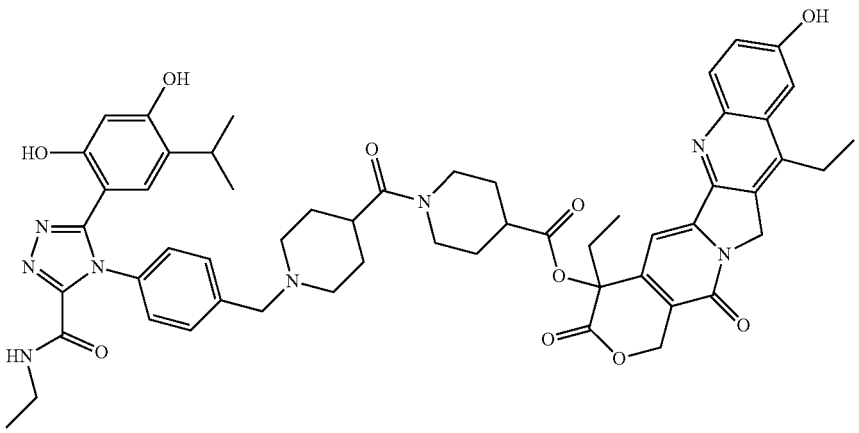

SDC-TRAP-0076

The suspension of 4,11-diethyl-9-hydroxy-3,14-dioxo-3,4,12,14-tetrahydro-1H-pyrano[3',4':6,7]indolizino[1,2-b]quinolin-4-yl piperidine-4-carboxylate (HCl salt, 0.35 g, 0.65 mmol) in DMF and TEA (20 mL/3 mL) was heated until it turned clear. To the resulting solution was added 1-(4-(3-(2,4-dihydroxy-5-isopropylphenyl)-5-(ethylcarbamoyl)-4H-1,2,4-triazol-4-yl)benzyl)piperidine-4-carboxylic acid (0.3 g, 0.6 mmol), EDC (0.35 g, 1.82 mmol), and HOBt (Cat.). The reaction was stirred at room temperature overnight before it was diluted with EtOAc (30 mL) and NH$_4$Cl (20 mL). The organic phase was collected, dried over Na$_2$SO$_4$ and concentrated. Column chromatography gave SDC-TRAP-0076 as a light yellow solid (0.28 g, 47%).

$^1$H NMR (400 MHz, DMSO-d$_6$) δ 10.63 (s, 1H), 10.32 (s, 1H), 9.75 (s, 1H), 8.94 (t, J=5.9 Hz, 1H), 8.01 (d, J=9.0 Hz, 1H), 7.45-7.34 (m, 4H), 7.33-7.26 (m, 2H), 6.93 (s, 1H), 6.56 (s, 1H), 6.34 (s, 1H), 5.49 (s, 2H), 5.29 (d, J=2.2 Hz, 2H), 4.14 (s, 1H), 3.87 (s, 1H), 3.47 (s, 2H), 3.25-3.05 (m, 4H), 2.92-2.82 (m, 5H), 2.59 (s, 1H), 2.22-2.11 (m, 2H), 2.04-1.88 (m, 4H), 1.56 (s, 5H), 1.27 (dd, J=16.8, 9.1 Hz, 5H), 1.03 (t, J=7.2 Hz, 3H), 0.97-0.83 (m, 3H), 0.79 (d, J=6.6 Hz, 6H); ESMS calculated (C$_{55}$H$_{60}$N$_8$O$_{10}$): 992.4; found: 993.5 (M+H).

SDC-TRAP-0097

4,11-diethyl-9-hydroxy-3,14-dioxo-3,4,12,14-tetrahydro-1H-pyrano[3',4':6,7]indolizino[1,2-b]quinolin-4-yl 1-(2-(4-(3-(2,4-dihydroxy-5-isopropylphenyl)-5-hydroxy-4H-1,2,4-triazol-4-yl)phenyl)acetyl)piperidine-4-carboxylate

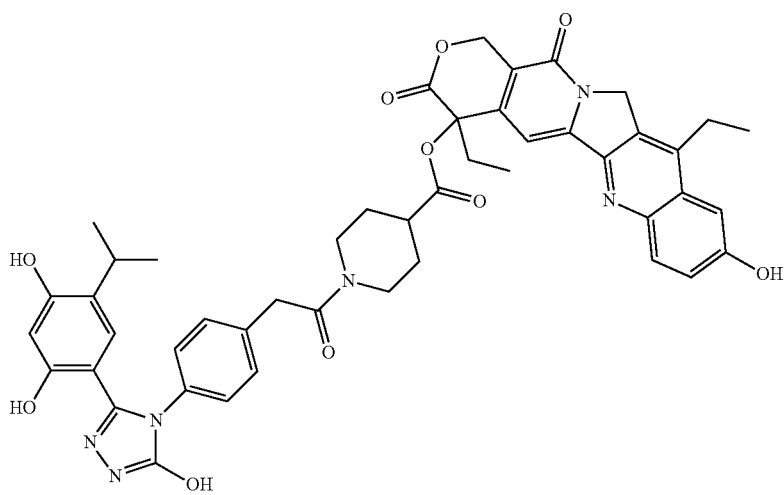 [SMILES: CCc1c2c(nc3ccc(O)cc13)-c1cc3c(c(=O)n1C2)COC(=O)C3(CC)OC(=O)C1CCN(C(=O)Cc2ccc(-n3c(O)nnc3-c3cc(C(C)C)c(O)cc3O)cc2)CC1]

¹H NMR (400 MHz, Methanol-d₄) δ 7.91 (d, J=9.5 Hz, 1H), 7.31 (d, J=7.7 Hz, 2H), 7.23 (t, J=5.6 Hz, 2H), 7.15 (d, J=4.2 Hz, 1H), 7.04 (dd, J=27.7, 8.1 Hz, 2H), 6.12 (d, J=6.1 Hz, 1H), 5.51 (d, J=16.4 Hz, 1H), 5.42-5.31 (m, 1H), 5.15 (d, J=15.5 Hz, 2H), 4.50 (s, 3H), 4.04 (s, 1H), 3.76 (s, 2H), 3.69 (d, J=16.0 Hz, 2H), 3.25 (s, 6H), 3.06 (d, J=13.2 Hz, 5H), 2.81 (d, J=13.5 Hz, 2H), 2.17-2.07 (m, 2H), 1.80 (s, 1H), 1.60 (s, 2H), 1.27 (q, J=7.8 Hz, 3H), 1.19 (s, 2H), 0.92 (q, J=6.8 Hz, 3H), 0.85-0.68 (m, 7H); ESMS calculated ($C_{47}H_{46}N_6O_{10}$): 854.3; found: 855.2 (M+H).

SDC-TRAP-0100

4,11-Diethyl-9-hydroxy-3,14-dioxo-3,4,12,14-tetrahydro-1H-pyrano[3',4':6,7]indolizino[1,2-b]quinolin-4-yl 3-(1-(4-(3-(2,4-dihydroxy-5-isopropylphenyl)-5-(ethylcarbamoyl)-4H-1,2,4-triazol-4-yl)benzyl)-N-methylpiperidine-4-carboxamido)propanoate

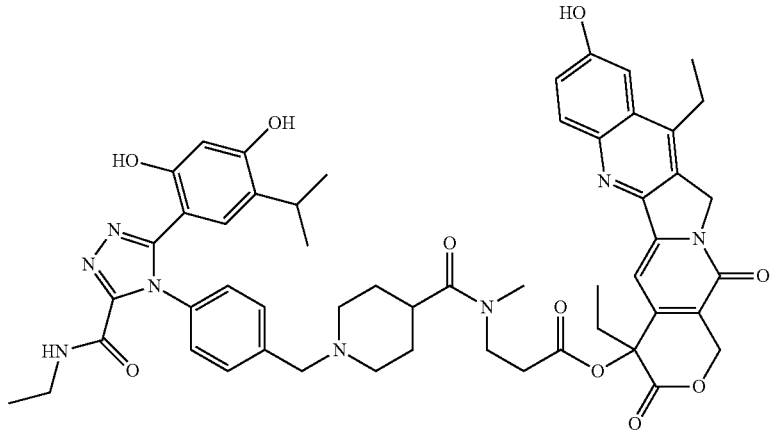 [SMILES: CCNC(=O)c1nnc(-c2cc(C(C)C)c(O)cc2O)n1-c1ccc(CN2CCC(C(=O)N(C)CCC(=O)OC3(CC)C(=O)OCc4c3cc3n(c4=O)Cc4c-3nc3ccc(O)cc3c4CC)CC2)cc1]

ESMS calculated ($C_{53}H_{58}N_8O_{10}$): 966.4; found: 967.4 (M+H).

SDC-TRAP-0111

4,11-Diethyl-9-hydroxy-3,14-dioxo-3,4,12,14-tetrahydro-1H-pyrano[3',4':6,7]indolizino[1,2-b]quinolin-4-yl 1-(2-(4-(4-(3-(2,4-dihydroxy-5-isopropylphenyl)-5-hydroxy-4H-1,2,4-triazol-4-yl)phenyl)piperazin-1-yl)acetyl)piperidine-4-carboxylate

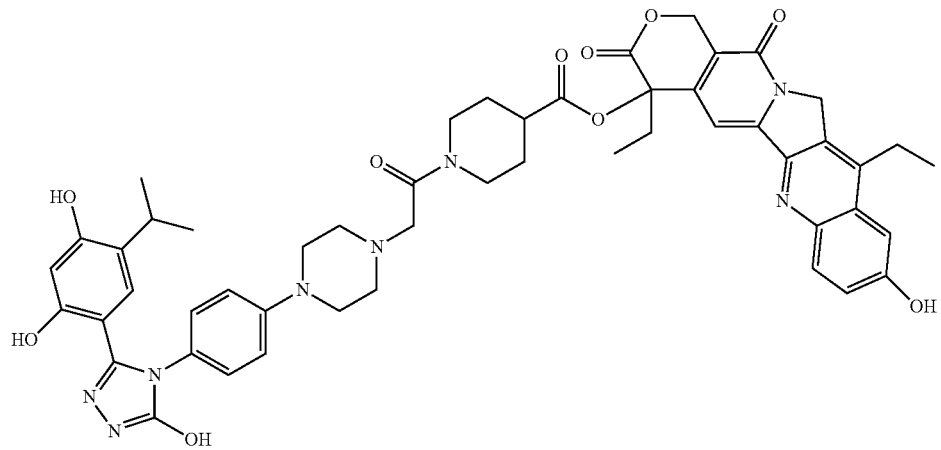 [SMILES: CCc1c2c(nc3ccc(O)cc13)-c1cc3c(c(=O)n1C2)COC(=O)C3(CC)OC(=O)C1CCN(C(=O)CN2CCN(c3ccc(-n4c(O)nnc4-c4cc(C(C)C)c(O)cc4O)cc3)CC2)CC1]

ESMS calculated ($C_{51}H_{54}N_8O_{10}$): 938.4; found: 939.4 (M+H).

SDC-TRAP-0112

4,11-Diethyl-4-hydroxy-3,14-dioxo-3,4,12,14-tetrahydro-1H-pyrano[3',4':6,7]indolizino[1,2-b]quinolin-9-yl (2-(5-(2,4-dihydroxy-5-isopropylphenyl)-4-(pyridin-3-yl)-4H-1,2,4-triazole-3-carboxamido)ethyl)(methyl)carbamate

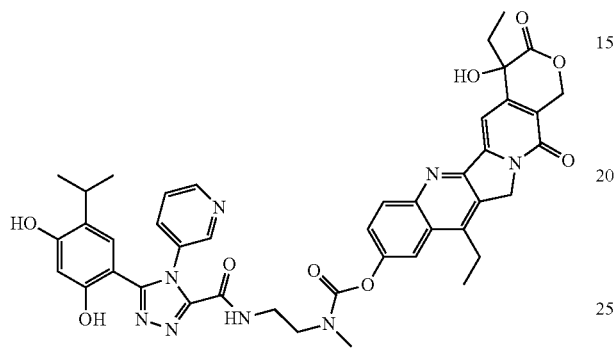

ESMS calculated ($C_{43}H_{42}N_8O_9$): 814.3; found: 815.2 (M+H).

SDC-TRAP-0113

4,11-diethyl-9-hydroxy-3,14-dioxo-3,4,12,14-tetrahydro-1H-pyrano[3',4':6,7]indolizino[1,2-b]quinolin-4-yl 1-(4-(3-(2,4-dihydroxy-5-isopropylphenyl)-5-(ethylcarbamoyl)-4H-1,2,4-triazol-4-yl)benzoyl)piperidine-4-carboxylate

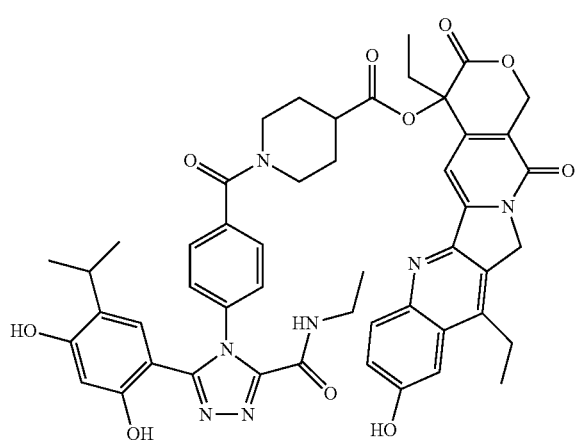 [SMILES: CCNC(=O)c1nnc(-c2cc(C(C)C)c(O)cc2O)n1-c1ccc(C(=O)N2CCC(C(=O)OC3(CC)C(=O)OCc4c3cc3n(c4=O)Cc4c-3nc3ccc(O)cc3c4CC)CC2)cc1]

$^1$H NMR (400 MHz, DMSO-$d_6$) δ 10.33 (s, 2H), 9.73 (s, 1H), 8.98 (t, J=6.0 Hz, 1H), 7.99 (s, 1H), 7.48-7.35 (m, 6H), 6.95 (s, 1H), 6.66 (s, 1H), 6.32 (s, 1H), 5.49 (s, 2H), 5.29 (d, J=2.6 Hz, 2H), 4.25 (s, 1H), 3.54 (s, 1H), 3.42-2.90 (m, 10H), 2.15 (t, J=7.7 Hz, 2H), 1.61 (s, 2H), 1.29 (t, J=7.6 Hz, 3H), 1.04 (t, J=7.2 Hz, 3H), 0.93 (t, J=7.4 Hz, 3H), 0.85 (d, J=6.8 Hz, 6H); ESMS calculated ($C_{49}H_{49}N_7O_{10}$): 895.4; found: 896.3 (M+H).

SDC-TRAP-0154

4,11-Diethyl-9-hydroxy-3,14-dioxo-3,4,12,14-tetrahydro-1H-pyrano[3',4':6,7]indolizino[1,2-b]quinolin-4-yl 1-(4-(4-(3-(2,4-dihydroxy-5-isopropylphenyl)-5-(ethylcarbamoyl)-4H-1,2,4-triazol-4-yl)phenoxy)benzoyl)piperidine-4-carboxylate

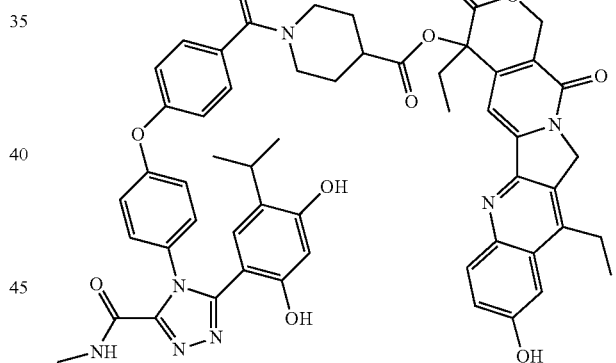

$^1$H NMR (400 MHz, DMSO-$d_6$) δ 10.41 (s, 1H), 10.34 (s, 1H), 9.76 (s, 1H), 8.98 (t, J=6.0 Hz, 1H), 8.00 (d, J=9.0 Hz, 1H), 7.49-7.33 (m, 6H), 7.14-7.01 (m, 4H), 6.95 (s, 1H), 6.68 (s, 1H), 6.34 (s, 1H), 5.49 (s, 2H), 5.30 (s, 2H), 3.18 (p, J=6.9 Hz, 4H), 3.08 (d, J=7.3 Hz, 3H), 2.95 (dd, J=15.7, 8.7 Hz, 3H), 2.16 (q, J=7.4 Hz, 2H), 1.96 (s, 2H), 1.60 (s, 2H), 1.28 (t, J=7.5 Hz, 3H), 1.05 (t, J=7.1 Hz, 3H), 0.92 (dd, J=11.6, 7.0 Hz, 9H); ESMS calculated ($C_{55}H_{53}N_7O_{11}$): 987.4; found: 988.4 (M+H).

SDC-TRAP-0169

4,11-diethyl-9-hydroxy-3,14-dioxo-3,4,12,14-tetrahydro-1H-pyrano[3',4':6,7]indolizino[1,2-b]quinolin-4-yl 3-(4-(4-(3-(2,4-dihydroxy-5-isopropylphenyl)-5-(ethylcarbamoyl)-4H-1,2,4-triazol-4-yl)phenoxy)-N-methylbenzamido)propanoate

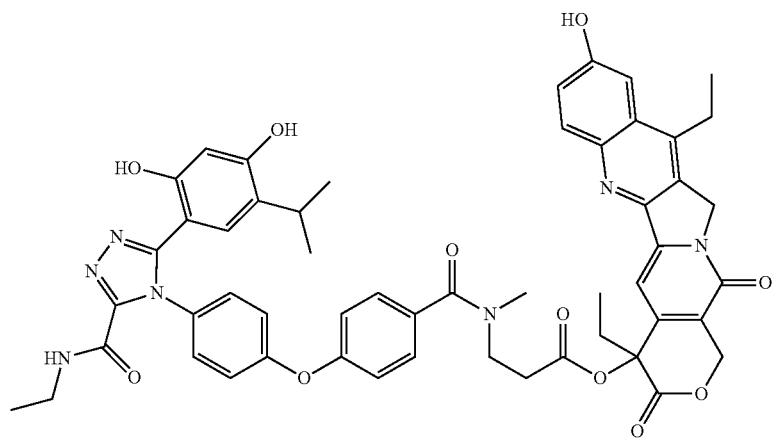 [SMILES: CCNC(=O)c1nnc(-c2cc(C(C)C)c(O)cc2O)n1-c1ccc(Oc2ccc(C(=O)N(C)CCC(=O)OC3(CC)C(=O)OCc4c3cc3n(c4=O)Cc4c-3nc3ccc(O)cc3c4CC)cc2)cc1]

ESMS calculated ($C_{53}H_{51}N_7O_{11}$): 961.4; found: 962.3 (M+H).

SDC-TRAP-0172

4,11-diethyl-4-hydroxy-3,14-dioxo-3,4,12,14-tetrahydro-1H-pyrano[3',4':6,7]indolizino[1,2-b]quinolin-9-yl (1-(1-(4-(3-(2,4-dihydroxy-5-isopropylphenyl)-5-(ethylcarbamoyl)-4H-1,2,4-triazol-4-yl)benzyl)piperidine-4-carbonyl)piperidin-4-yl)(methyl)carbamate

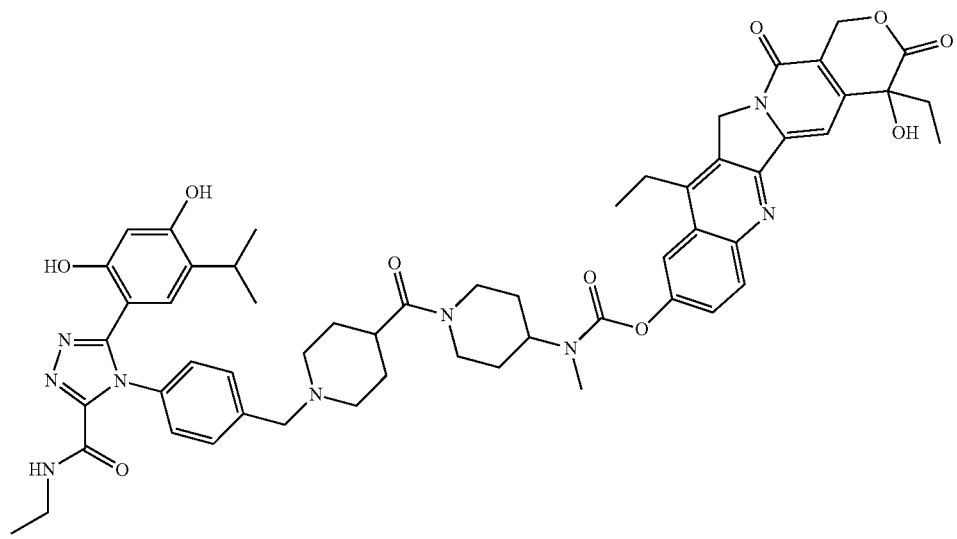 [SMILES: CCNC(=O)c1nnc(-c2cc(C(C)C)c(O)cc2O)n1-c1ccc(CN2CCC(C(=O)N3CCC(N(C)C(=O)Oc4ccc5nc6c(c(CC)c5c4)Cn4c-6cc5c(c4=O)COC(=O)C5(O)CC)CC3)CC2)cc1]

$^1$H NMR (400 MHz, DMSO-$d_6$) δ 10.62 (s, 1H), 9.77 (s, 1H), 8.97 (t, J=5.9 Hz, 1H), 8.18 (d, J=9.2 Hz, 1H), 8.01 (s, 1H), 7.68 (dd, J=9.2, 2.4 Hz, 1H), 7.39 (d, J=8.2 Hz, 2H), 7.35-7.27 (m, 3H), 6.56 (d, J=17.5 Hz, 2H), 6.35 (s, 1H), 5.44 (s, 2H), 5.35 (s, 2H), 4.56 (s, 1H), 4.07 (s, 1H), 3.50 (s, 2H), 3.31 (s, 4H), 3.20-3.13 (m, 4H), 3.00 (s, 2H), 2.95-2.83 (m, 4H), 2.68-2.60 (m, 2H), 2.04 (s, 2H), 1.87 (dt, J=14.8, 7.1 Hz, 3H), 1.61 (s, 5H), 1.30 (t, J=8.0 Hz, 3H), 1.04 (t, J=7.2 Hz, 3H), 0.88 (t, J=8.0 Hz, 3H), 0.81 (d, J=8.0 Hz, 6H); ESMS calculated ($C_{56}H_{63}N_9O_{10}$): 1021.5; found: 1022.5 (M+H).

SDC-TRAP-0180

4,11-Diethyl-4-hydroxy-3,14-dioxo-3,4,12,14-tetrahydro-1H-pyrano[3',4':6,7]indolizino[1,2-b]quinolin-9-yl (1-(4-(4-(3-(2,4-dihydroxy-5-isopropylphenyl)-5-(ethylcarbamoyl)-4H-1,2,4-triazol-4-yl)phenoxy)benzoyl)piperidin-4-yl)(methyl)carbamate

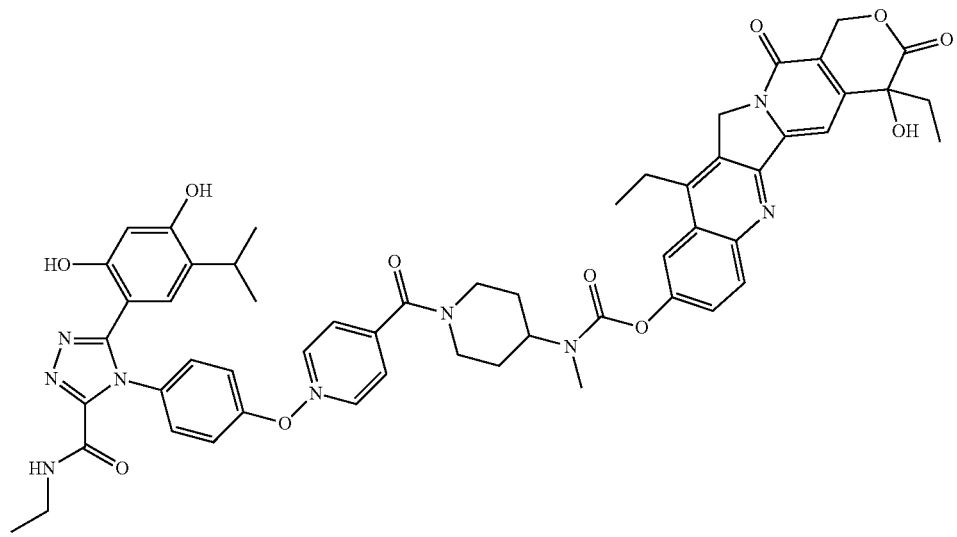

$^1$H NMR (400 MHz, DMSO-d$_6$) δ 10.42 (s, 1H), 9.77 (s, 1H), 8.98 (t, J=5.9 Hz, 1H), 8.18 (d, J=9.1 Hz, 1H), 8.01 (d, J=2.5 Hz, 1H), 7.68 (dd, J=9.1, 2.4 Hz, 1H), 7.53 (d, J=8.1 Hz, 2H), 7.44-7.35 (m, 2H), 7.33 (s, 1H), 7.16-7.06 (m, 4H), 6.69 (s, 1H), 6.53 (s, 1H), 6.35 (s, 1H), 5.44 (s, 2H), 5.34 (s, 2H), 4.62-4.22 (m, 2H), 3.77 (s, 1H), 3.26-3.14 (m, 5H), 3.05 (s, 2H), 2.98 (p, J=6.9 Hz, 1H), 2.90 (s, 2H), 1.91-1.80 (m, 6H), 1.34-1.21 (m, 3H), 1.07 (t, J=7.2 Hz, 3H), 0.93 (d, J=15.2, 8.0 Hz, 6H), 0.88 (t, J=8.0 Hz, 3H); ESMS calculated (C$_{56}$H$_{56}$N$_8$O$_{11}$): 1016.4; found: 1017.5 (M+H).

SDC-TRAP-0181

4-(((4-(4-(4-(3-(2,4-Dihydroxy-5-isopropylphenyl)-5-hydroxy-4H-1,2,4-triazol-4-yl)benzyl)piperazin-1-yl)butyl)(methyl)carbamoyl)oxy)-4,11-diethyl-3,14-dioxo-3,4,12,14-tetrahydro-1H-pyrano[3',4':6,7]indolizino[1,2-b]quinolin-9-yl acetate

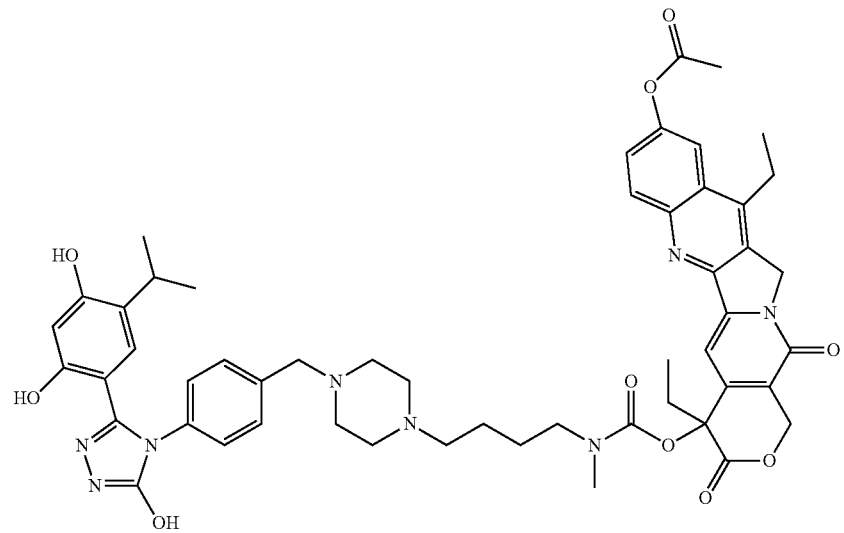 [SMILES: CCc1c2c(nc3ccc(OC(C)=O)cc13)-c1cc3c(c(=O)n1C2)COC(=O)C3(CC)OC(=O)N(C)CCCCN1CCN(Cc2ccc(-n3c(O)nnc3-c3cc(C(C)C)c(O)cc3O)cc2)CC1]

ESMS calculated ($C_{52}H_{58}N_8O_{10}$): 954.4; found: 955.3 (M+H).

SDC-TRAP-0184

4,11-diethyl-4-hydroxy-3,14-dioxo-3,4,12,14-tetrahydro-1H-pyrano[3',4':6,7]indolizino[1,2-b]quinolin-9-yl (1-(3-(5-(3-(2,4-dihydroxy-5-isopropylphenyl)-5-hydroxy-4H-1,2,4-triazol-4-yl)-1H-indol-1-yl)propanoyl)piperidin-4-yl)(methyl)carbamate

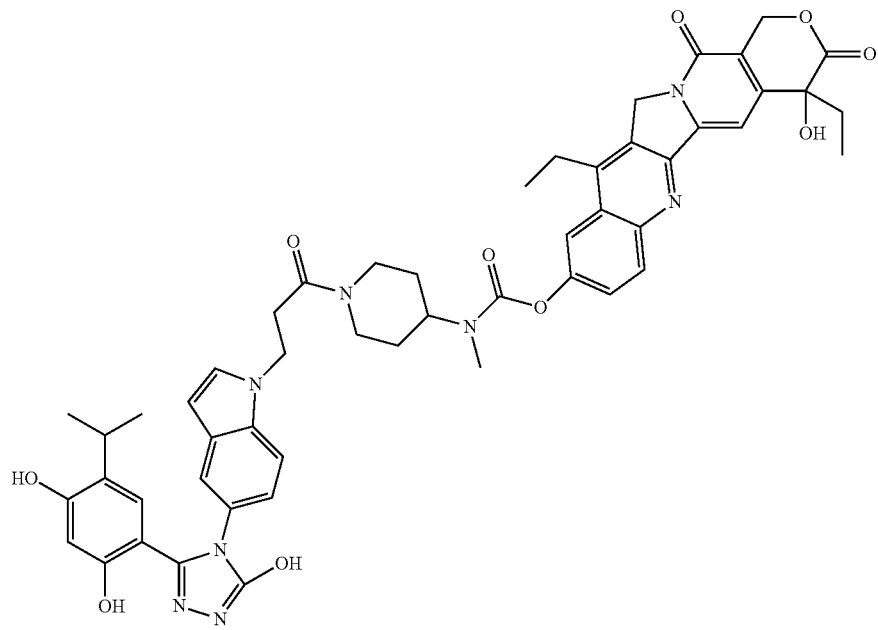 [SMILES: CCc1c2c(nc3ccc(OC(=O)N(C)C4CCN(C(=O)CCn5ccc6cc(-n7c(O)nnc7-c7cc(C(C)C)c(O)cc7O)ccc65)CC4)cc13)-c1cc3c(c(=O)n1C2)COC(=O)C3(O)CC]

$^1$H NMR (400 MHz, DMSO-d$_6$) δ 11.83 (s, 1H), 9.51 (s, 1H), 9.45 (s, 1H), 8.17 (d, J=9.1 Hz, 1H), 7.99 (s, 1H), 7.70-7.62 (m, 1H), 7.54-7.38 (m, 3H), 7.32 (s, 1H), 6.95 (dd, J=8.7, 2.0 Hz, 1H), 6.74 (s, 1H), 6.50 (s, 1H), 6.42 (d, J=3.1 Hz, 1H), 6.23 (s, 1H), 5.44 (s, 2H), 5.34 (s, 2H), 4.53 (s, 1H), 4.43 (t, J=6.8 Hz, 2H), 3.83 (s, 1H), 3.29 (s, 3H), 3.22-3.14 (m, 3H), 2.93-2.66 (s, 7H), 1.87 (p, J=7.1 Hz, 2H), 1.49 (s, 2H), 1.29 (t, J=8.0 Hz, 3H), 0.92-0.82 (m, 9H); ESMS calculated ($C_{51}H_{52}N_8O_{10}$): 936.4; found: 937.0 (M+H).

SDC-TRAP-0185

4,11-diethyl-4-hydroxy-3,14-dioxo-3,4,12,14-tetrahydro-1H-pyrano[3',4':6,7]indolizino[1,2-b]quinolin-9-yl 4-(1-(4-(3-(2,4-dihydroxy-5-isopropylphenyl)-5-(ethylcarbamoyl)-4H-1,2,4-triazol-4-yl)benzyl)piperidine-4-carbonyl)-2-methylpiperazine-1-carboxylate

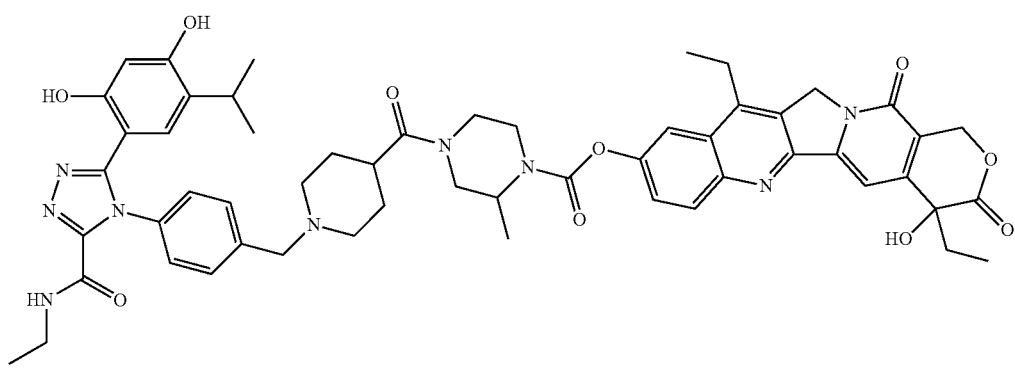 [SMILES: CCNC(=O)c1nnc(-c2cc(C(C)C)c(O)cc2O)n1-c1ccc(CN2CCC(C(=O)N3CCN(C(=O)Oc4ccc5nc6c(c(CC)c5c4)Cn4c-6cc5c(c4=O)COC(=O)C5(O)CC)C(C)C3)CC2)cc1]

¹H NMR (400 MHz, DMSO-d₆) δ 10.64 (d, J=1.8 Hz, 1H), 9.77 (s, 1H), 8.96 (t, J=5.9 Hz, 1H), 8.20 (d, J=9.2 Hz, 1H), 8.03 (d, J=2.5 Hz, 1H), 7.70 (dd, J=9.2, 2.5 Hz, 1H), 7.40 (d, J=8.2 Hz, 2H), 7.37-7.24 (m, 3H), 6.59 (s, 1H), 6.52 (s, 1H), 6.36 (s, 1H), 5.45 (s, 2H), 5.35 (s, 2H), 4.29 (d, J=17.9 Hz, 2H), 4.15-3.81 (m, 2H), 3.51 (s, 2H), 3.27-3.12 (m, 5H), 2.95-2.88 (m, 5H), 2.07 (s, 2H), 1.96-1.79 (m, 2H), 1.71-1.63 (m, 5H), 1.37-1.13 (m, 6H), 1.05 (t, J=7.2 Hz, 3H), 0.89 (t, J=7.3 Hz, 3H), 0.82 (d, J=6.9 Hz, 6H). ESMS calculated ($C_{55}H_{61}N_9O_{10}$): 1007.5; found: 1008.3 (M+H).

SDC-TRAP-0186

4,11-diethyl-4-hydroxy-3,14-dioxo-3,4,12,14-tetra-hydro-1H-pyrano[3',4':6,7]indolizino[1,2-b]quinolin-9-yl 4-((5-(3-(2,4-dihydroxy-5-isopropylphenyl)-5-hydroxy-4H-1,2,4-triazol-4-yl)-1H-indol-1-yl)methyl)piperidine-1-carboxylate

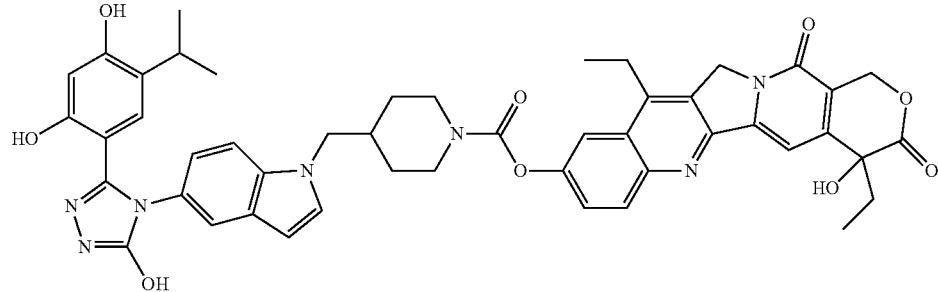 [SMILES: CCc1c2c(nc3ccc(OC(=O)N4CCC(Cn5ccc6cc(-n7c(O)nnc7-c7cc(C(C)C)c(O)cc7O)ccc65)CC4)cc13)-c1cc3c(c(=O)n1C2)COC(=O)C3(O)CC]

¹H NMR (400 MHz, DMSO-d₆) δ 11.91 (s, 1H), 9.57 (d, J=4.4 Hz, 2H), 8.17 (d, J=9.1 Hz, 1H), 7.97 (d, J=2.5 Hz, 1H), 7.69-7.56 (m, 2H), 7.46 (dd, J=4.9, 2.6 Hz, 2H), 7.32 (s, 1H), 6.98 (dd, J=8.7, 2.0 Hz, 1H), 6.67 (s, 1H), 6.53 (s, 1H), 6.47 (d, J=3.1 Hz, 1H), 6.25 (s, 1H), 5.44 (s, 2H), 5.34 (s, 2H), 4.25-4.07 (m, 4H), 3.22-3.14 (m, 2H), 3.01 (s, 1H), 2.88-2.85 (m, 2H), 2.09 (s, 1H), 1.87 (dt, J=14.7, 7.0 Hz, 2H), 1.58 (d, J=12.2 Hz, 2H), 1.33-1.21 (m, 5H), 0.88 (t, J=7.3 Hz, 3H), 0.77 (d, J=6.9 Hz, 6H); ESMS calculated ($C_{48}H_{47}N_7O_9$): 865.3; found: 866.0 (M+H).

SDC-TRAP-0201

4,11-Diethyl-4-hydroxy-3,14-dioxo-3,4,12,14-tetra-hydro-1H-pyrano[3',4':6,7]indolizino[1,2-b]quinolin-9-yl 4-(2-(5-(3-(2,4-dihydroxy-5-isopropylphenyl)-5-hydroxy-4H-1,2,4-triazol-4-yl)-1H-indol-1-yl)acetyl)-2-methylpiperazine-1-carboxylate

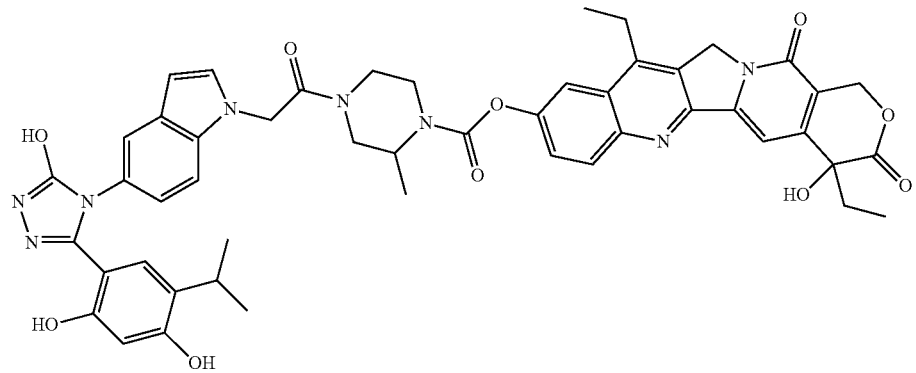 [SMILES: CCc1c2c(nc3ccc(OC(=O)N4CCN(C(=O)Cn5ccc6cc(-n7c(O)nnc7-c7cc(C(C)C)c(O)cc7O)ccc65)CC4C)cc13)-c1cc3c(c(=O)n1C2)COC(=O)C3(O)CC]

ESMS calculated ($C_{49}H_{48}N_8O_{10}$): 908.3; found: 909.0 (M+H).

SDC-TRAP-0202

4,11-diethyl-9-hydroxy-3,14-dioxo-3,4,12,14-tetrahydro-1H-pyrano[3',4':6,7]indolizino[1,2-b]quinolin-4-yl (2-(4-(4-(3-(2,4-dihydroxy-5-isopropylphenyl)-5-(ethylcarbamoyl)-4H-1,2,4-triazol-4-yl)benzoyl)piperazin-1-yl)-2-oxoethyl) carbonate

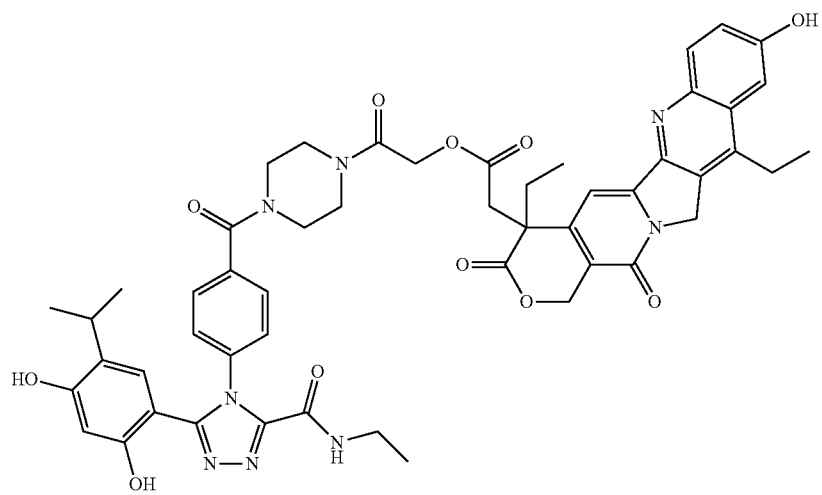 [SMILES: CCNC(=O)c1nnc(-c2cc(C(C)C)c(O)cc2O)n1-c1ccc(C(=O)N2CCN(C(=O)COC(=O)CC3(CC)C(=O)OCc4c3cc3n(c4=O)Cc4c-3nc3ccc(O)cc3c4CC)CC2)cc1]

ESMS calculated ($C_{50}H_{50}N_8O_{12}$): 954.4; found: 955.1 (M+H).

SDC-TRAP-0203

4,11-Diethyl-9-hydroxy-3,14-dioxo-3,4,12,14-tetrahydro-1H-pyrano[3',4':6,7]indolizino[1,2-b]quinolin-4-yl (1-(4-(4-(3-(2,4-dihydroxy-5-isopropylphenyl)-5-(ethylcarbamoyl)-4H-1,2,4-triazol-4-yl)phenoxy)benzoyl)piperidin-4-yl) carbonate

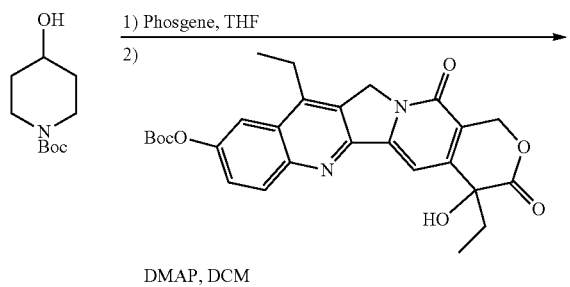

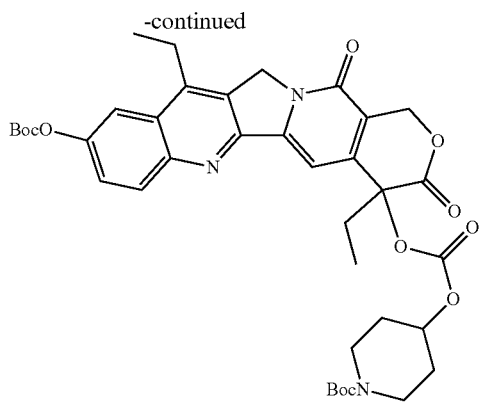

To a solution of tert-butyl 4-hydroxypiperidine-1-carboxylate (0.2 g, 1.0 mmol) in THF (4 mL) was added phosgene (15% wt in toluene, 0.66 mL). The reaction was stirred at room temperature for 1 hr. SN-38-[10]OBoc (0.2 g, 0.4 mmol) was added to the reaction solution, followed by DMAP (0.15 g, 1.2 mmol). The reaction was stirred at room temperature for 5 hr. The reaction was quenched with saturated NH$_4$Cl (10 mL) and extracted with EtOAc (15 mL×3). The organic phases were combined, dried over Na$_2$SO$_4$ and concentrated. Column chromatography gave tert-butyl 4-((((9-((tert-butoxycarbonyl)oxy)-4,11-diethyl-3,14-dioxo-3,4,12,14-tetrahydro-1H-pyrano[3',4':6,7]indolizino[1,2-b]quinolin-4-yl)oxy)carbonyl)oxy)piperidine-1-carboxylate (0.21 g, 73%).

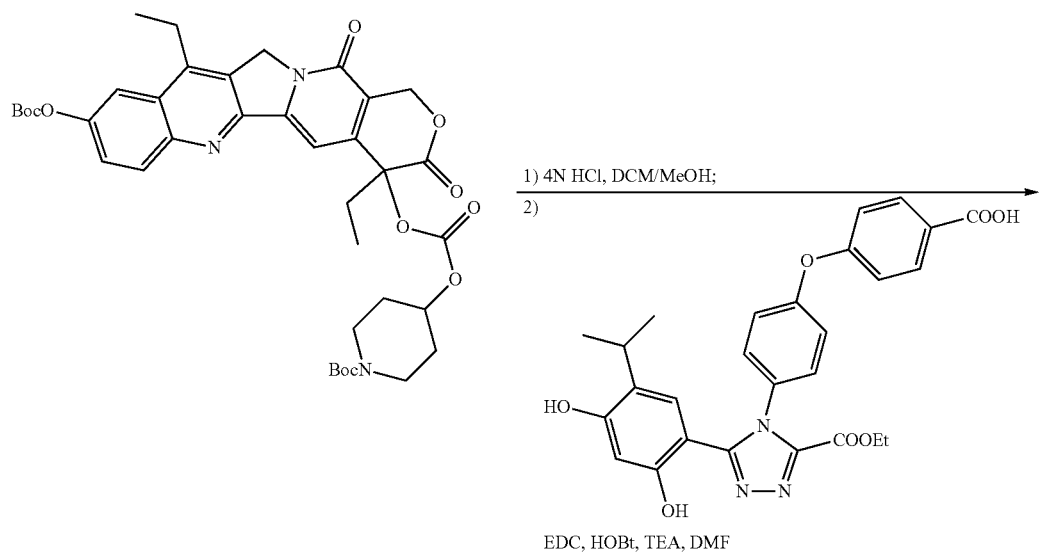

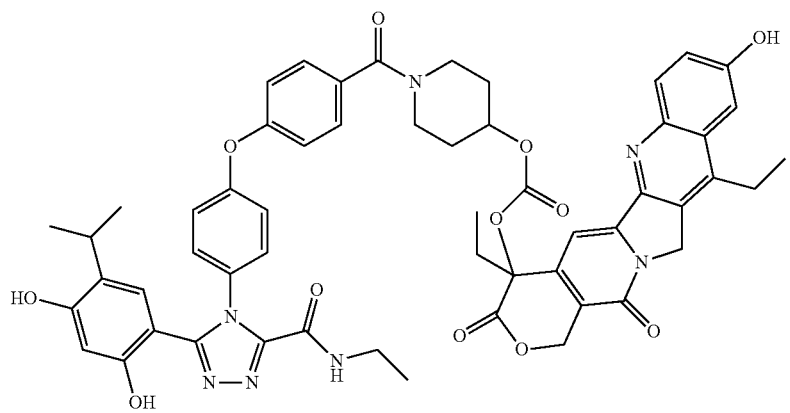

SDC-TRAP-0203

To the solution of 4-(((((9-((tert-butoxycarbonyl)oxy)-4,11-diethyl-3,14-dioxo-3,4,12,14-tetrahydro-1H-pyrano[3',4':6,7]indolizino[1,2-b]quinolin-4-yl)oxy)carbonyl)oxy)piperidine-1-carboxylate (0.2 g, 0.28 mmol) in DCM/MeOH (5 mL/4 mL) was added 4N HCl in dioxane (5 mL). The reaction was stirred at room temperature for 2 hr before it was concentrated. The resulting solid was dissolved in DMF (4 mL), and 4-(4-(3-(2,4-dihydroxy-5-isopropylphenyl)-5-(ethoxycarbonyl)-4H-1,2,4-triazol-4-yl)phenoxy)benzoic acid (0.14 g, 0.28 mmol), EDC (0.16 g, 0.83 mmol), TEA (1 mL), and HOBt (Cat.) were added. The reaction was stirred at room temperature overnight. The reaction was quenched with saturated NH$_4$Cl (10 mL) and extracted with EtOAc (15 mL×3). The combined organic phase was dried over Na$_2$SO$_4$ and concentrated. Column chromatography gave SDC-TRAP-0203 (0.15 g, 54%). ESMS calculated (C$_{55}$H$_{53}$N$_7$O$_{12}$): 1003.4; found: 1004.5 (M+H).

SDC-TRAP-0221

4,11-Diethyl-4-hydroxy-3,14-dioxo-3,4,12,14-tetra-hydro-1H-pyrano[3',4':6,7]indolizino[1,2-b]quinolin-9-yl (1-(4-(4-(3-(2,4-dihydroxy-5-isopropylphenyl)-5-(ethylcarbamoyl)-4H-1,2,4-triazol-4-yl)phenoxy)benzoyl)piperidin-4-yl)(ethyl)carbamate

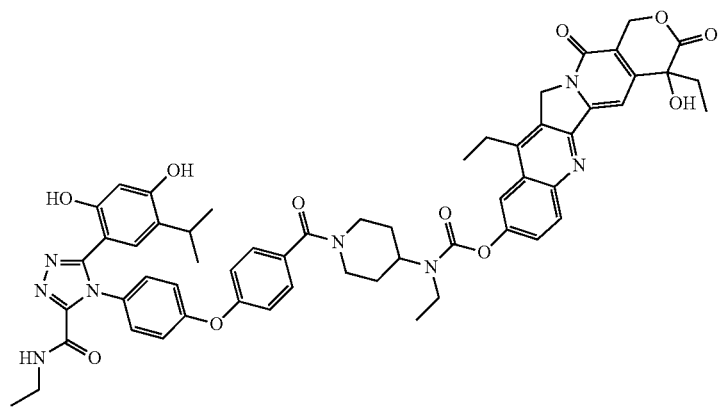 [SMILES: CCNC(=O)c1nnc(-c2cc(C(C)C)c(O)cc2O)n1-c1ccc(Oc2ccc(C(=O)N3CCC(N(CC)C(=O)Oc4ccc5nc6c(c(CC)c5c4)Cn4c-6cc5c(c4=O)COC(=O)C5(O)CC)CC3)cc2)cc1]

$^1$H NMR (400 MHz, DMSO-d$_6$) δ 10.43 (s, 1H), 9.80 (s, 1H), 8.97 (t, J=5.8 Hz, 1H), 8.19 (d, J=9.2 Hz, 1H), 8.00 (d, J=2.5 Hz, 1H), 7.67 (dd, J=9.2, 2.4 Hz, 1H), 7.52 (d, J=8.1 Hz, 2H), 7.43-7.31 (m, 3H), 7.16-7.05 (m, 4H), 6.68 (s, 1H), 6.54 (s, 1H), 6.35 (s, 1H), 5.44 (s, 2H), 5.34 (s, 2H), 4.59 (s, 1H), 4.13 (s, 1H), 3.52-3.35 (m, 4H), 3.20 (dt, J=13.1, 6.8 Hz, 4H), 2.98 (p, J=6.9 Hz, 1H), 1.93-1.80 (m, 6H), 1.30 (t, J=7.5 Hz, 6H), 1.22-1.13 (m, 1H), 1.07 (t, J=7.2 Hz, 3H), 0.96-0.84 (m, 9H); ESMS calculated (C$_{57}$H$_{58}$N$_8$O$_{11}$): 1030.4; found: 1031.5 (M+H).

SDC-TRAP-0222

4,11-Diethyl-4-hydroxy-3,14-dioxo-3,4,12,14-tetra-hydro-1H-pyrano[3',4':6,7]indolizino[1,2-b]quinolin-9-yl (1-(1-((4-(3-(2,4-dihydroxy-5-isopropylphenyl)-5-(ethylcarbamoyl)-4H-1,2,4-triazol-4-yl)phenyl)sulfonyl)piperidine-4-carbonyl)piperidin-4-yl)(methyl)carbamate

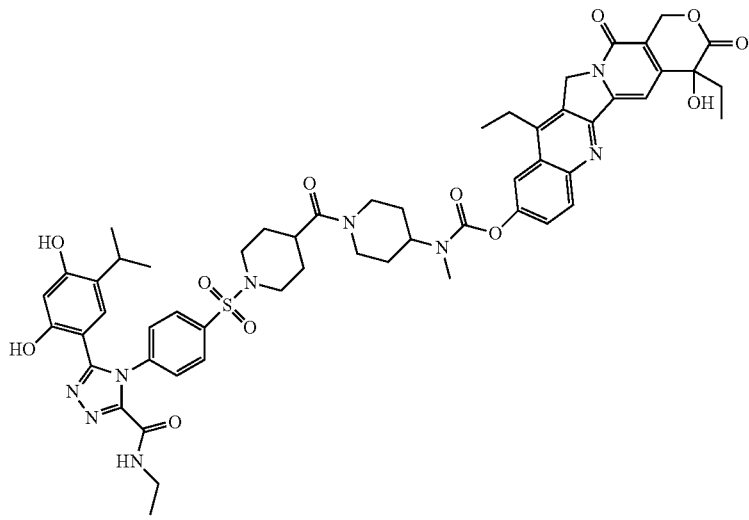 [SMILES: CCNC(=O)c1nnc(-c2cc(C(C)C)c(O)cc2O)n1-c1ccc(S(=O)(=O)N2CCC(C(=O)N3CCC(N(C)C(=O)Oc4ccc5nc6c(c(CC)c5c4)Cn4c-6cc5c(c4=O)COC(=O)C5(O)CC)CC3)CC2)cc1]

¹H NMR (400 MHz, DMSO-d₆) δ 9.91 (s, 1H), 9.69 (s, 1H), 9.05 (t, J=6.0 Hz, 1H), 8.18 (d, J=9.2 Hz, 1H), 8.00 (d, J=2.7 Hz, 1H), 7.81-7.73 (m, 2H), 7.67 (dd, J=9.2, 2.4 Hz, 1H), 7.59-7.52 (m, 2H), 7.32 (s, 1H), 6.74 (s, 1H), 6.51 (s, 1H), 6.28 (s, 1H), 5.75 (s, 1H), 5.44 (s, 2H), 5.34 (s, 2H), 4.53 (s, 1H), 4.06 (s, 2H), 3.70 (s, 2H), 3.25-3.14 (m, 6H), 3.02-2.93 (m, 3H), 2.84 (s, 1H), 2.67-2.32 (m, 3H), 1.87 (p, J=7.0 Hz, 2H), 1.74-1.55 (m, 7H), 1.29 (t, J=8.0 Hz, 3H), 1.08 (t, J=7.2 Hz, 3H), 0.95 (d, J=8.0 Hz, 6H), 0.88 (t, J=8.0 Hz, 3H); ESMS calculated ($C_{55}H_{61}N_9O_{12}S$): 1071.4; found: 1072.6 (M+H).

in vitro activity was determined for these compounds using the HER2 degradation assay set forth herein:

| SDC-TRAP-# | HER2 degradation IC$_{50}$ (nM) |
|---|---|
| SDC-TRAP-0016 | >5000 |
| SDC-TRAP-0027 | >5000 |
| SDC-TRAP-0028 | >5000 |
| SDC-TRAP-0030 | >5000 |
| SDC-TRAP-0031 | 1270 |
| SDC-TRAP-0022 | >5000 |
| SDC-TRAP-0023 | 4300 |
| SDC-TRAP-0010 | >5000 |
| SDC-TRAP-0038 | >5000 |
| SDC-TRAP-0037 | 2112 |
| SDC-TRAP-0026 | 1780 |
| SDC-TRAP-0029 | 1373 |
| SDC-TRAP-0046 | 246 |
| SDC-TRAP-0042 | 1057 |
| SDC-TRAP-0043 | 2135 |
| SDC-TRAP-0047 | 875 |
| SDC-TRAP-0044 | 602 |
| SDC-TRAP-0045 | 464 |
| SDC-TRAP-0054 | 1469 |
| SDC-TRAP-0059 | 184 |
| SDC-TRAP-0014 | >5000 |
| SDC-TRAP-0012 | >5000 |
| SDC-TRAP-0011 | >5000 |
| SDC-TRAP-0055 | 402 |
| SDC-TRAP-0056 | 1271 |
| SDC-TRAP-0057 | 449 |
| SDC-TRAP-0058 | 2929 |
| SDC-TRAP-0060 | >5000 |
| SDC-TRAP-0063 | 793 |
| SDC-TRAP-0067 | 196 |
| SDC-TRAP-0070 | 263 |
| SDC-TRAP-0064 | 1129 |
| SDC-TRAP-0065 | 661 |
| SDC-TRAP-0071 | 307 |
| SDC-TRAP-0072 | >5000 |
| SDC-TRAP-0073 | 478 |
| SDC-TRAP-0077 | 2791 |
| SDC-TRAP-0079 | 1430 |
| SDC-TRAP-0081 | 622 |
| SDC-TRAP-0083 | 1438 |
| SDC-TRAP-0094 | <78 953 |
| SDC-TRAP-0086 | >5,000 |
| SDC-TRAP-0084 | 1132 |
| SDC-TRAP-0095 | >5000 |
| SDC-TRAP-0101 | 280 |
| SDC-TRAP-0087 | 535 |
| SDC-TRAP-0090 | 4599 |
| SDC-TRAP-0089 | 1466 |
| SDC-TRAP-0088 | 221 |
| SDC-TRAP-0074 | 4120 |
| SDC-TRAP-0075 | 953 |
| SDC-TRAP-0076 | <78 227 |
| SDC-TRAP-0097 | >5,000 |
| SDC-TRAP-0091 | >5000 |
| SDC-TRAP-0104 | 350 |
| SDC-TRAP-0092 | 4706 |
| SDC-TRAP-0100 | 80 |
| SDC-TRAP-0111 | >5000 |
| SDC-TRAP-0112 | >5000 |
| SDC-TRAP-0154 | 191 |
| SDC-TRAP-0145 | 183 |
| SDC-TRAP-0146 | 1295 |
| SDC-TRAP-0169 | 611 |
| SDC-TRAP-0161 | 3694 |
| SDC-TRAP-0172 | <78 56 |
| SDC-TRAP-0180 | 325 |
| SDC-TRAP-0181 | 164 |
| SDC-TRAP-0185 | 38 |
| SDC-TRAP-0186 | 1,619 |
| SDC-TRAP-0184 | 4,002 |
| SDC-TRAP-0205 | 564 |
| SDC-TRAP-0206 | 321 |
| SDC-TRAP-0207 | >5,000 |
| SDC-TRAP-0204 | >10,000 |
| SDC-TRAP-0208 | 480 |
| SDC-TRAP-0209 | 1,130 |
| SDC-TRAP-0210 | >10,000 |
| SDC-TRAP-0213 | 248 |
| SDC-TRAP-0212 | 2,294 |
| SDC-TRAP-0201 | 4,670 |
| SDC-TRAP-0202 | >5,000 |
| SDC-TRAP-0214 | >5,000 |
| SDC-TRAP-0215 | 2,746 |
| SDC-TRAP-0220 | 474 445 |
| SDC-TRAP-0203 | 446 |

Hsp90ᵅ Binding Assay

| No | SDC-TRAP-# | Binding EC$_{50}$ (nM) |
|---|---|---|
| 1 | SDC-TRAP-0045 | 96.6 |
| 2 | SDC-TRAP-0046 | 101.8 |
| 3 | SDC-TRAP-0063 | 157.5 |
| 4 | SDC-TRAP-0064 | 122.2 |
| 5 | SDC-TRAP-0184 | 86.62 |
| 6 | SDC-TRAP-0204 | 82.59 |
| 7 | SDC-TRAP-0209 | 54.59 |
| 8 | SDC-TRAP-0210 | 91.03 |

Mouse Plasma Stability Data

| SDC-TRAP-# | % Remaining (1 h, 37° C.) |
|---|---|
| SDC-TRAP-0022 | 21% |
| SDC-TRAP-0028 | 41% |
| SDC-TRAP-0029 | 47% |
| SDC-TRAP-0037 | 95% |
| SDC-TRAP-0044 | 61% |
| SDC-TRAP-0045 | 45% |
| SDC-TRAP-0046 | 52% |
| SDC-TRAP-0054 | 41.0% |
| SDC-TRAP-0071 | 102% |
| SDC-TRAP-0076 | 96% |
| SDC-TRAP-0104 | 95.5% |
| SDC-TRAP-0063 | 11.1% |
| SDC-TRAP-0064 | 91.5% |
| SDC-TRAP-0172 | 74.7% |
| SDC-TRAP-0180 | 72.4% |
| SDC-TRAP-0184 | 18.0% |
| SDC-TRAP-0185 | 68.1% |
| SDC-TRAP-0186 | 57.9% |
| SDC-TRAP-0042 | 74% |
| SDC-TRAP-0047 | 89% |
| SDC-TRAP-0055 | 103% |
| SDC-TRAP-0056 | 78% |
| SDC-TRAP-0059 | 51% |
| SDC-TRAP-0145 | 14.1% |
| SDC-TRAP-0203 | 71.2% |
| SDC-TRAP-0215 | 77.2% |

| SDC-TRAP-# | % Remaining (1 h, 37° C.) |
|---|---|
| SDC-TRAP-0216 | 67.7% |
| SDC-TRAP-0220 | 78.3% |
| SDC-TRAP-0202 | 21.2% |
| SDC-TRAP-0205 | 58.4% |
| SDC-TRAP-0206 | 68.6% |
| SDC-TRAP-0208 | 86.1% |
| SDC-TRAP-0209 | 67.1% |
| SDC-TRAP-0213 | 74.7% |

Tissue Distribution Data for SDC-TRAP-0045

| Analyte | Plasma Conc. (µM) | | | Tumor Conc. (nmol/g of tissue) | | | Tumor/Plasma Ratio | | |
|---|---|---|---|---|---|---|---|---|---|
| Target Time (h) | SDC-TRAP-0045 | SDC-TRAP-0053 | SN-38 | SDC-TRAP-0045 | SDC-TRAP-0053 | SN-38 | SDC-TRAP-0045 | SDC-TRAP-0053 | SN-38 |
| 0.083 | 689 | 2.70 | 0.0716 | 4.30 | 0.0461 | 0.344 | 0.00624 | 0.0171 | 4.80 |
| 6 | 1.88 | 0.289 | 0.00471 | 2.55 | 0.590 | 0.473 | 1.35 | 2.04 | 101 |
| 12 | 0.141 | 0.0953 | BQL | 1.13 | 0.780 | 0.229 | 8.02 | 8.18 | — |
| 24 | 0.0113 | 0.0464 | BQL | BQL | 0.0622 | 0.0596 | — | 1.34 | — |
| 48 | BQL | 0.00618 | BQL | BQL | 0.764 | BQL | — | 124 | — |

Tissue Distribution Data for SDC-TRAP-0046

| Analyte | Plasma Conc. (µM) | | | Tumor Conc. (nmol/g of tissue) | | | Tumor/Plasma Ratio | | |
|---|---|---|---|---|---|---|---|---|---|
| Target Time (h) | SDC-TRAP-0046 | SDC-TRAP-0052 | SN-38 | SDC-TRAP-0046 | SDC-TRAP-0052 | SN-38 | SDC-TRAP-0046 | SDC-TRAP-0052 | SN-38 |
| 0.083 | 360 | 0.0782 | 2.29 | 6.94 | BQL | 0.298 | 0.0193 | — | 0.130 |
| 6 | 5.88 | 0.0917 | 0.0773 | 4.97 | 0.241 | 0.448 | 0.844 | 2.63 | 5.80 |
| 12 | 2.37 | 0.0612 | 0.0389 | 5.21 | 0.407 | 0.344 | 2.20 | 6.65 | 8.83 |
| 24 | 0.0542 | 0.0364 | 0.00955 | 2.19 | 1.71 | 1.01 | 40.3 | 46.9 | 105 |
| 48 | BQL | 0.0107 | BQL | 0.188 | 1.01 | BQL | — | 94.4 | — |

Tissue Distribution Data for SDC-TRAP-0056

| Analyte | Plasma Conc. (µM) | | | Tumor Conc. (nmol/g of tissue) | | | Tumor/Plasma Ratio | | |
|---|---|---|---|---|---|---|---|---|---|
| Target Time (h) | SDC-TRAP-0056 | SDC-TRAP-0096 | SN-38 | SDC-TRAP-0056 | SDC-TRAP-0096 | SN-38 | SDC-TRAP-0056 | SDC-TRAP-0096 | SN-38 |
| 0.083 | 1220 | 274 | 134 | 6.40 | 1.654 | 1.18 | 0.00525 | 0.00604 | 0.00881 |
| 6 | 2.06 | 0.510 | 0.483 | 2.65 | 0.726 | 0.490 | 1.28 | 1.42 | 1.02 |
| 12 | 0.382 | 0.151 | 0.176 | 0.746 | 0.252 | 0.152 | 1.95 | 1.67 | 0.86 |
| 24 | 0.0343 | 0.0130 | 0.0235 | BQL | BQL | 0.105 | — | — | 4.48 |
| 48 | BQL | BQL | BQL | BQL | 0.0581 | 0.0259 | — | — | — |

Tissue Distribution Data for SDC-TRAP-0063

| Analyte | Plasma Conc. (µM) | | | Tumor Conc. (nmol/g of tissue) | | | Tumor/Plasma Ratio | | |
|---|---|---|---|---|---|---|---|---|---|
| Target Time (h) | SDC-TRAP-0063 | DP-1 | SN-38 | SDC-TRAP-0063 | DP-1 | SN-38 | SDC-TRAP-0063 | DP-1 | SN-38 |
| 0.083 | 526 | 0.0662 | 20.4 | 6.43 | 0.00758 | 1.47 | 0.0122 | 0.114 | 0.0721 |
| 6 | 1.69 | 0.0397 | 0.0509 | 1.61 | 0.111 | 0.730 | 0.958 | 2.79 | 14.3 |
| 24 | 0.00675 | 0.0175 | 0.0240 | 0.203 | 0.404 | 0.618 | 30.1 | 23.1 | 25.8 |
| 48 | BQL | 0.00793 | 0.00524 | 0.0188 | 1.06 | 0.296 | — | 134 | 56.4 |

Tissue Distribution Data for SDC-TRAP-0076

| Analyte | Plasma Conc. (μM) | | Tumor Conc. (nmol/g of tissue) | | Tumor/Plasma Ratio | |
|---|---|---|---|---|---|---|
| Target Time (h) | SDC-TRAP-0076 | SN-38 | SDC-TRAP-0076 | SN-38 | SDC-TRAP-0076 | SN-38 |
| 0.083 | 671 | — 73.4 | 8.66 | — 0.503 | 0.01 | — 0.01 |
| 1 | 52.9 | — 8.60 | 9.12 | — 0.642 | 0.17 | — 0.07 |
| 6 | 4.00 | — 1.18 | 8.98 | — 0.670 | 2.25 | — 0.57 |
| 24 | 0.359 | — 0.0755 | 7.32 | — 0.572 | 20.4 | — 7.58 |
| 48 | 1.11 | — 0.160 | 7.60 | — 0.489 | 6.85 | — 3.06 |

Tissue Distribution Data for SDC-TRAP-0154

| Analyte | Plasma Conc. (μM) | | | Tumor Conc. (nmol/g of tissue) | | | Tumor/Plasma Ratio | | |
|---|---|---|---|---|---|---|---|---|---|
| Target Time (h) | SDC-TRAP-0154 | SDC-TRAP-0179 | SN-38 | SDC-TRAP-0154 | SDC-TRAP-0179 | SN-38 | SDC-TRAP-0154 | SDC-TRAP-0179 | SN-38 |
| 0.083 | 928 | 84.3 | 34.5 | 11.8 | 0.350 | 0.241 | 0.01 | 0.004 | 0.007 |
| 1 | 251 | 14.6 | 4.34 | 14.1 | 0.732 | 0.463 | 0.06 | 0.05 | 0.11 |
| 6 | 5.08 | 1.50 | 1.12 | 9.46 | 0.656 | 0.293 | 1.86 | 0.44 | 0.26 |
| 24 | 0.198 | 0.428 | 0.0198 | 2.35 | 0.115 | 0.0562 | 11.9 | 2.68 | 2.84 |
| 48 | 0.0218 | 0.00344 | BQL | 1.88 | 0.0921 | 0.0465 | 86.0 | 26.8 | — |

Example 28: SDC-TRAP Comprising Fulvestrant

SDC-TRAP-0148

(7R,8R,9S,13S,14S,17S)-17-hydroxy-13-methyl-7-(9-((4,4,5,5,5-pentafluoropentyl)sulfinyl)nonyl)-7,8,9,11,12,13,14,15,16,17-decahydro-6H-cyclopenta[a]phenanthren-3-yl 4-(4-(3-(2,4-dihydroxy-5-isopropylphenyl)-5-hydroxy-4H-1,2,4-triazol-4-yl)benzyl)piperazine-1-carboxylate

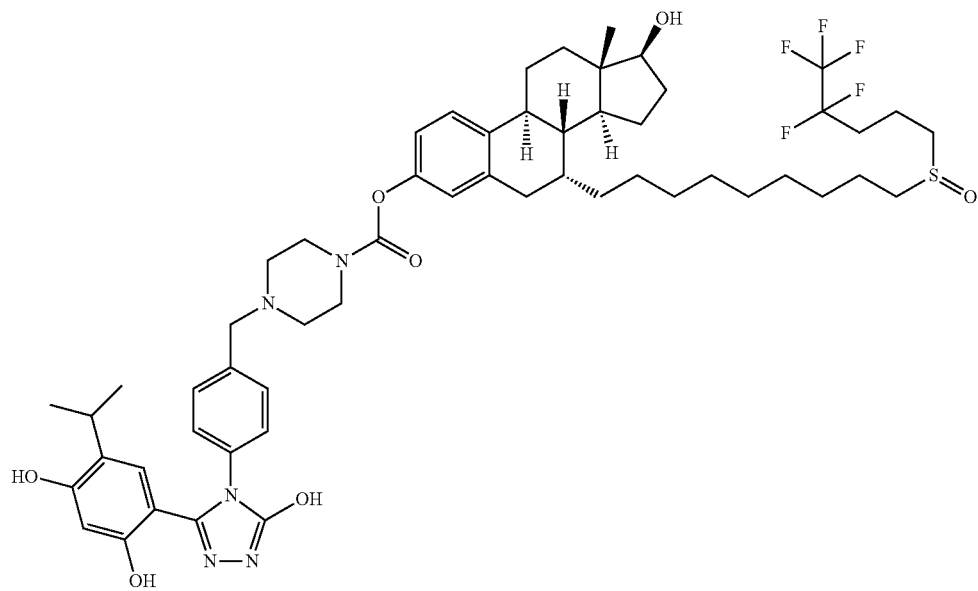

$^1$H NMR (400 MHz, DMSO-$d_6$) δ 11.94 (s, 1H), 9.61 (s, 1H), 9.42 (s, 1H), 7.30 (dd, J=25.2, 8.6 Hz, 3H), 7.18-7.11 (m, 2H), 6.88-6.75 (m, 3H), 6.26 (s, 1H), 4.51 (dd, J=4.6, 2.5 Hz, 1H), 3.53 (d, J=16.6 Hz, 5H), 2.97 (p, J=6.9 Hz, 1H), 2.91-2.58 (m, 8H), 2.43-2.22 (m, 6H), 2.04-1.77 (m, 7H$_1$), 1.66-1.44 (m, 4H), 1.42-1.13 (m, 18H), 0.92 (dd, J=22.4, 7.1 Hz, 6H), 0.67 (s, 3H); ESMS calculated for $C_{55}H_{72}F_5N_5O_7S$: 1041.51; Found: 1042.9 (M+H)$^+$.

Example 29: SDC-TRAP Comprising Topotecan

SDC-TRAP-0159

10-((dimethylamino)methyl)-4-ethyl-9-hydroxy-3,14-dioxo-3,4,12,14-tetrahydro-1H-pyrano[3',4':6,7]indolizino[1,2-b]quinolin-4-yl-1-(4-(4-(3-(2,4-dihydroxy-5-isopropylphenyl)-5-(ethyl carbamoyl)-4H-1,2,4-triazol-4-yl)phenoxy)benzoyl)piperidine-4-carboxylate

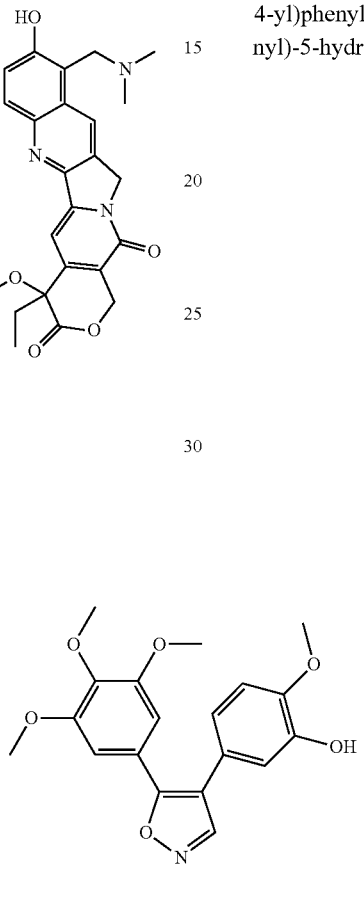

ESMS calculated ($C_{56}H_{56}N_8O_{11}$): 1016.4; found: 1017.6 (M+H).

Example 30: SDC-TRAPs Comprising VDAs (Vascular Disrupting Agents)

2-Methoxy-5-(5-(3,4,5-trimethoxyphenyl)isoxazol-4-yl)phenyl-4-(4-(3-(2,4-dihydroxy-5-isopropylphenyl)-5-hydroxy-4H-1,2,4-triazol-4-yl)benzyl)piperazine-1-carboxylate

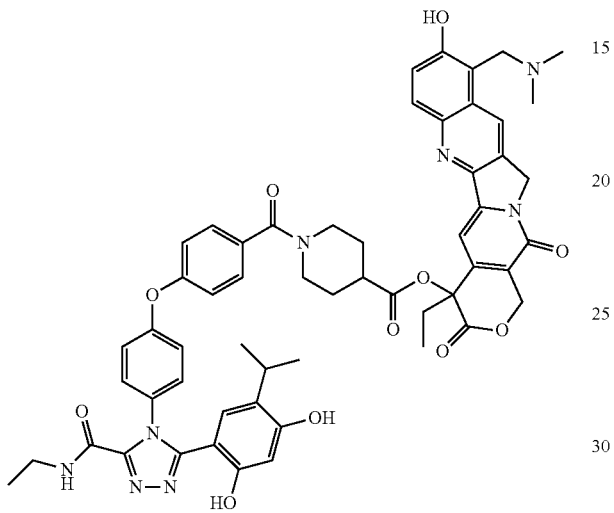

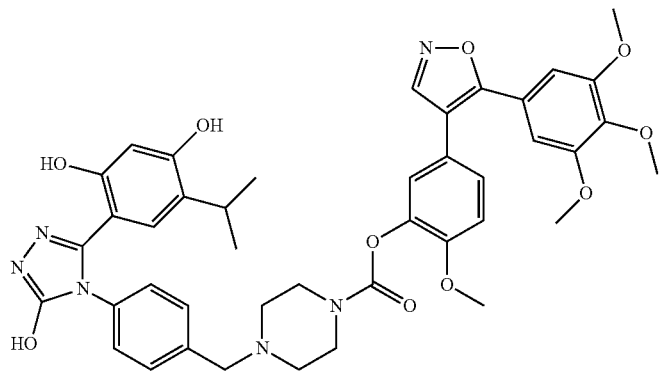

SDC-TRAP-098

To a solution of 2-methoxy-5-(5-(3,4,5-trimethoxyphenyl)isoxazol-4-yl) phenol (0.1 g, 0.28 mmol) in THF (4 mL) was added 4-nitrophenyl chloroformate (0.07 g, 0.35 mmol) and DIPEA (0.1 mL, 0.57 mmol). The reaction was stirred at room temperature for 30 min before adding a solution of 4-(5-hydroxy-4-(4-(piperazin-1-yl methyl)phenyl)-4H-1,2,4-triazol-3-yl)-6-isopropylbenzene-1,3-diol (0.13 g, 0.31 mmol) and DIPEA (0.1 mL, 0.57 mmol) in DMF (2 mL). After stirring at room temperature for 30 min, the reaction was diluted with $H_2O$ (10 mL), extracted with EtOAc (10 mL×3), and the combined organic phase was dried over $Na_2SO_4$ and concentrated. Column chromatography gave SDC-TRAP-0098 (0.13 g, 59%).

$^1$H NMR (400 MHz, Methanol-$d_4$) δ 8.52 (s, 1H), 7.52-7.44 (m, 2H), 7.29 (td, J=8.3, 2.0 Hz, 3H), 7.19-7.09 (m, 2H), 6.92 (s, 2H), 6.74 (s, 1H), 6.29 (s, 1H), 3.85 (s, 3H), 3.80 (s, 3H), 3.73 (s, 6H) 3.68 (s, 2H), 3.62 (s, 2H), 3.53 (s, 2H), 3.03 (p, J=6.9 Hz, 1H), 2.52 (t, J=4.7 Hz, 4H), 0.92 (d, J=6.9 Hz, 6H); ESMS calculated ($C_{42}H_{44}N_6O_{10}$): 792.3; found: 793.2 (M+H).

SDC-TRAP-0099

2-methoxy-5-(5-(3,4,5-trimethoxyphenyl)isoxazol-4-yl)phenyl-4-(4-(3-(2,4-dihydroxy-5-isopropylphenyl)-5-hydroxy-4H-1, 2,4-triazol-4-yl)phenyl)piperazine-1-carboxylate

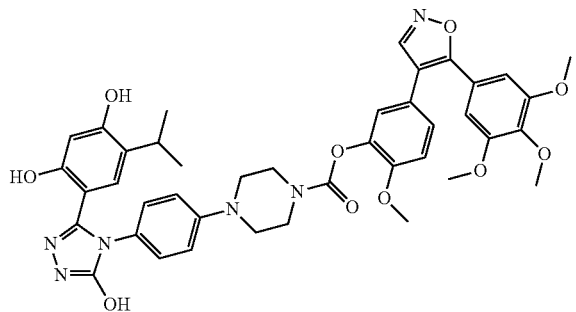 [SMILES: COc1ccc(-c2cnoc2-c2cc(OC)c(OC)c(OC)c2)cc1OC(=O)N1CCN(c2ccc(-n3c(O)nnc3-c3cc(C(C)C)c(O)cc3O)cc2)CC1]

$^1$H NMR (400 MHz, DMSO-$d_6$) δ 11.86 (s, 1H), 9.60 (s, 1H), 9.45 (s, 1H), 8.87 (s, 1H), 7.33 (dd, J=8.5, 2.2 Hz, 1H), 7.27 (d, J=2.2 Hz, 1H), 7.20 (d, J=8.6 Hz, 1H), 7.05 (d, J=9.0 Hz, 2H), 6.96 (d, J=9.0 Hz, 2H), 6.88 (s, 2H), 6.79 (s, 1H), 6.26 (s, 1H), 3.79 (s, 3H), 3.70 (d, J=1.1 Hz, 10H), 3.53 (s, 2H), 3.23-3.14 (m, 5H), 2.98 (p, J=6.8 Hz, 1H), 0.97 (d, J=6.8 Hz, 6H); ESMS calculated ($C_{41}H_{42}N_6O_{10}$): 778.3; found: 779.2 (M+H).

SDC-TRAP-0158

5-(2,4-dihydroxy-5-isopropylphenyl)-N-ethyl-4-(4-(4-((1-((2-methoxy-5-(5-(3,4,5-trimethoxyphenyl)isoxazol-4-yl)phenyl)amino)-1-oxo-3-phenylpropan-2-yl)carbamoyl)phenoxy)phenyl)-4H-1,2,4-triazole-3-carboxamide ESMS calculated ($C_{55}H_{53}N_7O_{11}$): 987.4; found: 988.3 (M+H).

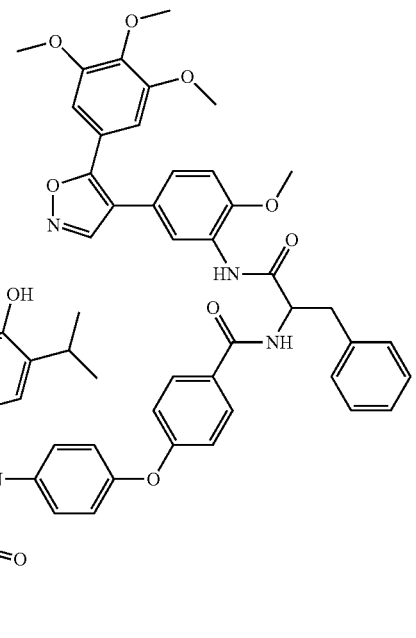

SDC-TRAP-0085

(Z)-2-methoxy-5-(3,4,5-trimethoxystyryl)phenyl 4-(4-(3-(2,4-dihydroxy-5-isopropylphenyl)-5-hydroxy-4H-1,2,4-triazol-4-yl)benzyl)piperazine-1-carboxylate

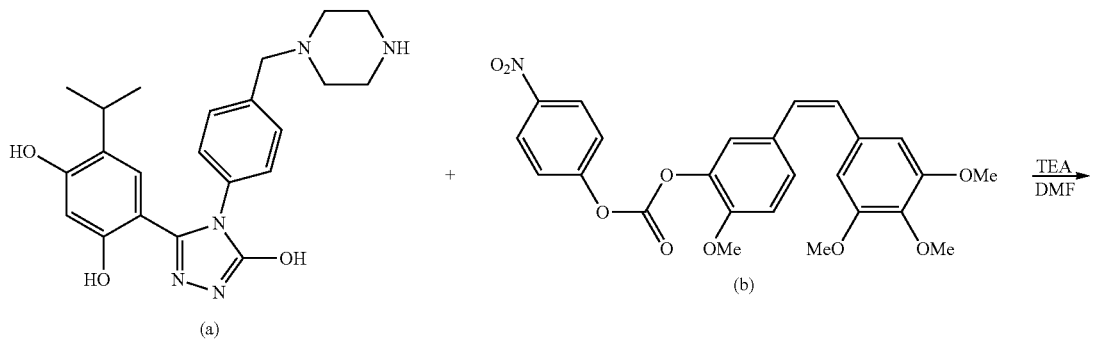

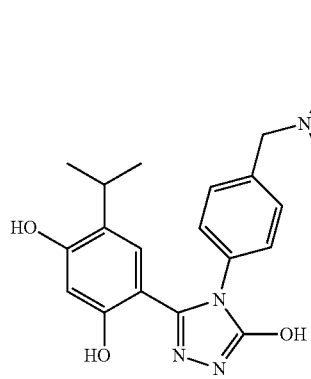

SDC-TRAP-0085

A mixture of 4-(5-hydroxy-4-(4-(piperazin-1-ylmethyl)phenyl)-4H-1,2,4-triazol-3-yl)-6-isopropylbenzene-1,3-diol (a, 0.1 mmol), (Z)-2-methoxy-5-(3,4,5-trimethoxystyryl)phenyl (4-nitrophenyl) carbonate (b, 0.1 mmol) and TEA (0.2 mmol) in DMF (2 mL) was stirred at room temperature for 2 days. The mixture was diluted with water (50 mL) and extracted with EtOAc. The organic layers were combined, concentrated and purified by column to give SDC-TRAP-0085 as a white solid (13 mg, 0.02 mmol).

$^1$H NMR (400 MHz, Chloroform-d) δ 10.78 (s, 1H), 9.76 (s, 1H), 7.52 (d, J=8.0 Hz, 2H), 7.32 (d, J=8.1 Hz, 2H), 7.15-7.04 (m, 2H), 6.83 (d, J=8.5 Hz, 1H), 6.56-6.38 (m, 6H), 6.35 (s, 1H), 3.82 (d, J=10.9 Hz, 6H), 3.71 (s, 9H), 3.57 (d, J=16.1 Hz, 4H), 2.53 (s, 4H), 0.70 (d, J=6.8 Hz, 6H). ppm; ESMS calculated for $C_{41}H_{45}N_5O_9$: 751.3; found: 752.2 (M+H$^+$).

SDC-TRAP-0025

1-(2-(5-(3-(2,4-dihydroxy-5-isopropylphenyl)-5-hydroxy-4H-1,2,4-triazol-4-yl)-1H-indol-1-yl)ethyl)-3-(5-fluoro-2-oxo-1,2-dihydropyrimidin-4-yl)urea

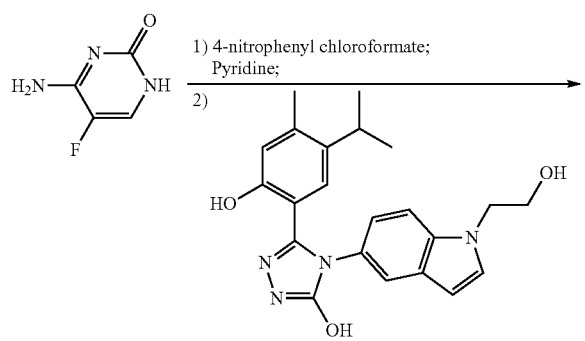

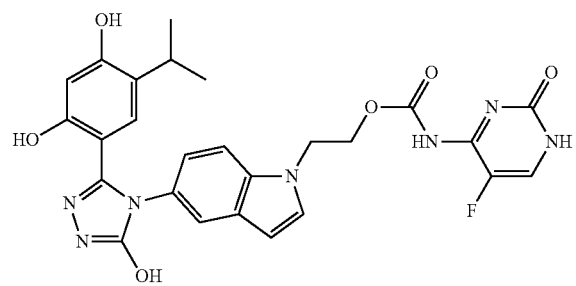

SDC-TRAP-0025

To a solution of 5-fluorocytosine (0.14 g, 1.1 mmol) in pyridine (4 mL) was added 4-nitrophenyl chloroformate (0.22 g, 1.1 mmol). The reaction was heated in a microwave at 90° C. for 30 min. To the resulting solution was added 4-(5-hydroxy-4-(1-(2-hydroxyethyl)-1H-indol-5-yl)-4H-1,2,4-triazol-3-yl)-6-isopropylbenzene-1,3-diol (0.15 g, 0.38 mmol). The reaction was heated in microwave at 100° C. for 1 hr. The solution was concentrated and column chromatography gave SDC-TRAP-0025 (0.07 g, 34%).

$^1$H NMR (400 MHz, DMSO-d$_6$) δ 11.86 (s, 1H), 9.52 (s, 1H), 9.46 (d, J=4.8 Hz, 1H), 8.10-7.82 (m, 2H), 7.59-7.39 (m, 3H), 6.95 (t, J=7.7 Hz, 1H), 6.73 (d, J=9.6 Hz, 1H), 6.44 (dd, J=16.8, 3.3 Hz, 1H), 6.22 (s, 1H), 4.31 (dt, J=12.6, 6.4 Hz, 2H), 3.57-3.48 (m, 2H), 2.90 (h, J=7.1 Hz, 1H), 0.84 (t, J=7.8 Hz, 6H); ESMS calculated ($C_{26}H_{25}FN_8O_5$): 548.2; found: 549.1 (M+H).

in vitro activity was determined for these compounds using the HER2 degradation assay set forth herein:

| STA# | HER2 degradation IC$_{50}$ (nM) |
|---|---|
| SDC-TRAP-0148 | 3037 |
| SDC-TRAP-0159 | >1000 |
| SDC-TRAP-0098 | 232 |
| SDC-TRAP-0099 | 677 |
| SDC-TRAP-0158 | >5000 |
| SDC-TRAP-0085 | 889 |
| SDC-TRAP-0025 | 403 |

Mouse Plasma Stability Data

| Compound ID | % Remaining (1 h) |
|---|---|
| SDC-TRAP-0098 | 96.0% |
| SDC-TRAP-0099 | 95.2% |
| SDC-TRAP-0158 | 92.7% |

Tissue Distribution Data for SDC-TRAP-0098

| Analyte | | Plasma Conc. (µM) | | | Tumor Conc. (nmol/g of tissue) | | | Tumor/Plasma Ratio | |
|---|---|---|---|---|---|---|---|---|---|
| Target Time (h) | .8 | SDC-TRAP-0052 | SDC-TRAP-0001 | SDC-TRAP-0098 | SDC-TRAP-0052 | SDC-TRAP-0001 | SDC-TRAP-0098 | SDC-TRAP-0052 | SDC-TRAP-0001 |
| 0.083 | 481 | 0.0833 | 0.700 | 5.02 | 0.0175 | 0.0360 | 0.01 | 0.21 | 0.05 |
| 1 | 7.48 | 0.437 | 0.250 | 4.62 | 0.111 | 0.161 | 0.62 | 0.25 | 0.65 |
| 6 | 0.387 | 0.131 | 0.0122 | 3.18 | 0.292 | 0.117 | 8.22 | 2.23 | 9.64 |
| 24 | 0.00306 | 0.0375 | BQL | 0.920 | 0.611 | 0.0614 | 300 | 16.3 | — |
| 48 | BQL | 0.0125 | BQL | 0.182 | 0.770 | 0.0211 | — | 61.8 | — |

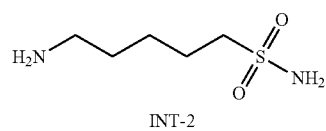

INT-2

Example 31: SDC-TRAP-0232

5-(2,4-dihydroxy-5-isopropylphenyl)-4-(4-(morpholinomethyl)phenyl)-N-(5-sulfamoylpentyl)-4H-1,2,4-triazole-3-carboxamide The synthesis of SDC-TRAP-0232 is outlined in the following scheme. The final amide coupling was performed using boric acid as the catalyst in reflux dioxane. The synthesis of INT-2 is described elsewhere in literature.

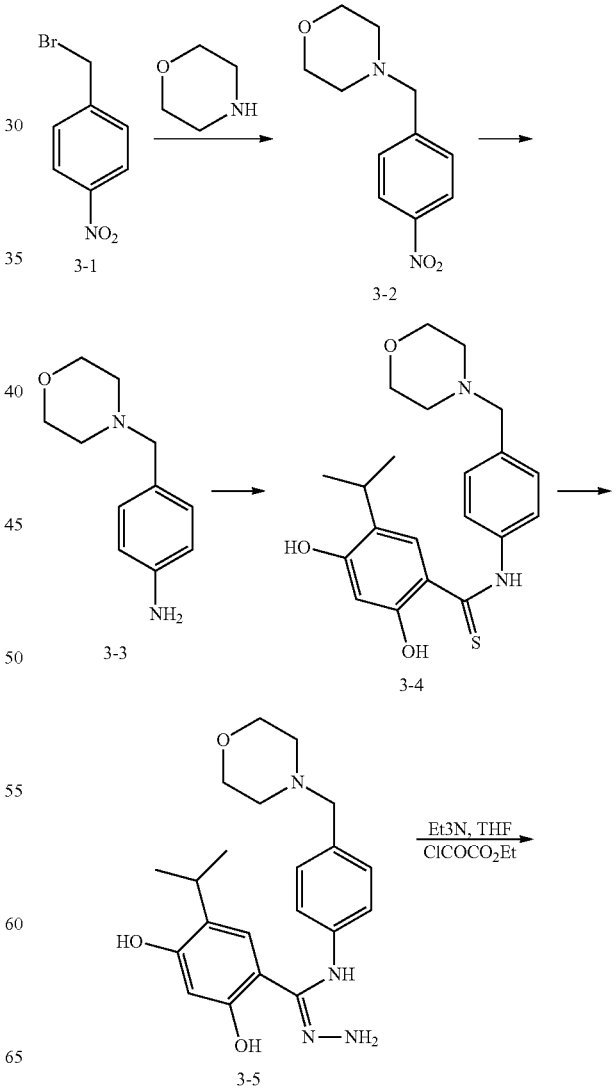

-continued

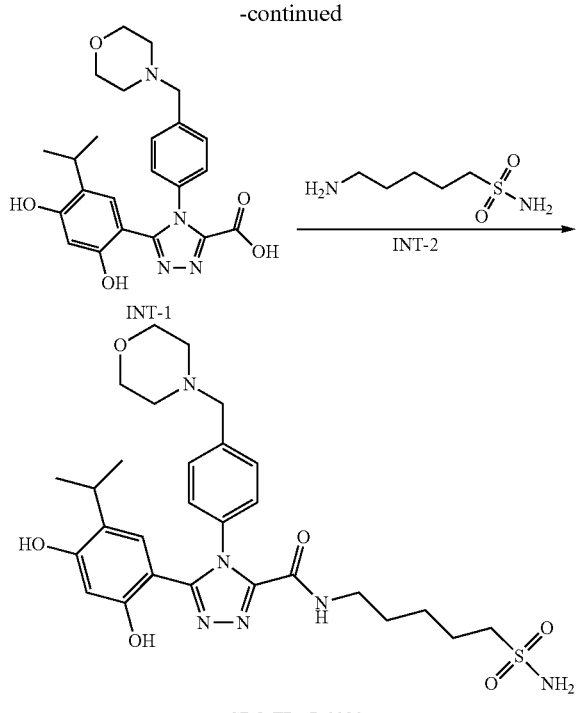

¹H NMR (400 MHz, DMSO-d₆) δ 8.93 (t, J=6 Hz, 1H), 7.39 (d, J=8 Hz, 2H), 7.30 (d, J=8 Hz, 2H), 6.71 (bs, 1H), 6.53 (s, 1H), 6.28 (s, 1H), 3.59 (bs, 4H), 3.50 (s, 2H), 3.31 (bs, 1H), 3.23-3.11 (m, 2H), 2.94-2.87 (m, 2H), 2.38 (bs, 4H), 1.67-1.61 (m, 2H), 1.47-1.36 (m, 2H), 1.36-1.30 (m, 2H), 0.78 (d, J=7.2 Hz, 6H). ESMS cacld (C28H38N6O6S): 586.26; found: 587.2 (M+H).

Example 32: SDC-TRAP-0233

SDC-TRAP-0233

N-(2-(5-(3-(2,4-dihydroxy-5-isopropylphenyl)-5-hydroxy-4H-1,2,4-triazol-4-yl)-1H-indol-1-yl)ethyl)-5-((3aS,4S,6aR)-2-oxohexahydro-1H-thieno[3,4-d]imidazol-4-yl)pentanamide SDC-TRAP-0233 was synthesized from the corresponding HSP90 inhibitor using standard amide coupling conditions.

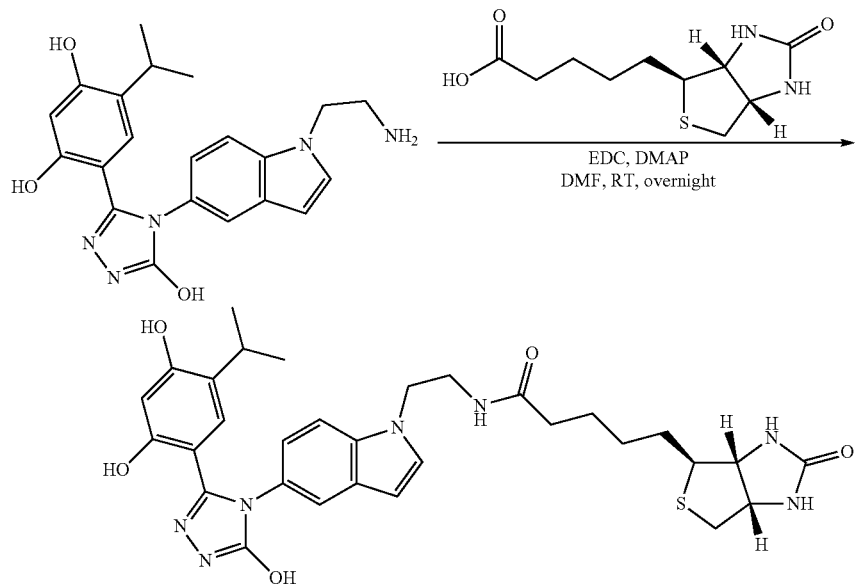

¹H NMR (400 MHz, DMSO-d₆) δ 11.87 (s, 1H), 9.54 (s, 1H), 9.46 (d, J=4.8 Hz, 1H), 7.94-7.93 (m, 1H), 7.47-7.36 (m, 3H), 6.95-6.92 (m, 1H), 6.77 (s, 1H), 6.44-6.37 (m, 3H), 6.22 (s, 1H), 4.32-4.10 (m, 4H), 3.37-3.35 (m, 2H), 3.10-3.06 (m, 1H), 2.95-2.88 (m, 1H), 2.84-2.79 (m, 1H), 2.58 (d, J=12.0 Hz, 1H), 2.02 (t, J=8.0 Hz, 2H), 1.60-1.26 (m, 6H), 0.86 (t, J=7.8 Hz, 6H).

ESMS cacld (C31H37N7O5S): 619.2; found: 620.2 (M+H).

Example 33: SDC-TRAP-234

SDC-TRAP-0234

N-(2-(5-(3-(2,4-dihydroxy-5-isopropylphenyl)-5-hydroxy-4H-1,2,4-triazol-4-yl)-1H-indol-1-yl)ethyl)-6-(5-((3aR,4R,6aS)-2-oxohexahydro-1H-thieno[3,4-d]imidazol-4-yl)pentanamido)hexanamide SDC-TRAP-0234 was synthesized starting from the corresponding HSP90 inhibitor with the coupling of a Boc protected aminohexanoic acid. Subsequent deprotection followed by coupling of biotin using standard coupling conditions afforded the desired product.

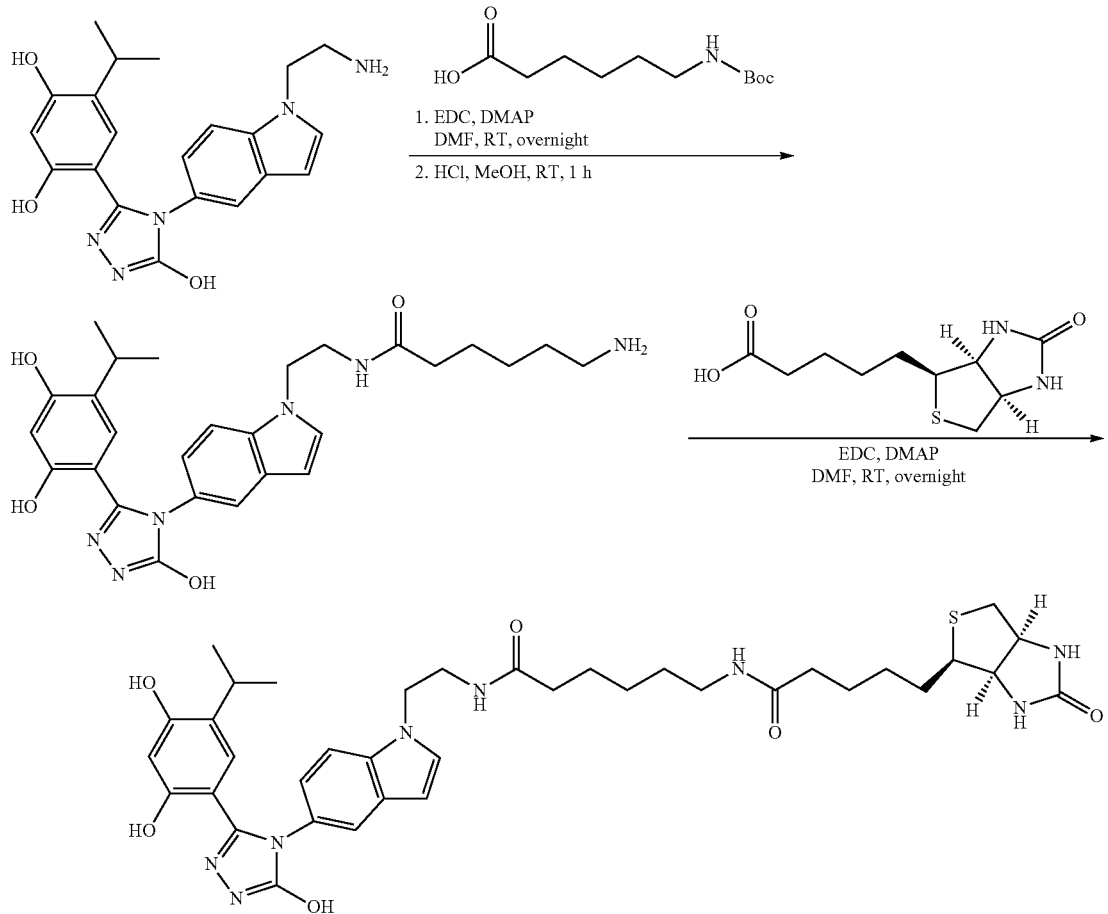

SDC-TRAP-0234

$^1$H NMR (400 MHz, DMSO-d$_6$) δ 11.86 (s, 1H), 9.55 (s, 1H), 9.46 (s, 1H), 7.93 (t, J=6.0 Hz, 1H), 7.74 (t, J=6.0 Hz, 1H), 7.46 (d, J=8.0 Hz, 1H), 7.41 (d, J=4.0 Hz, 1H), 7.35 (d, J=4.0 Hz, 1H), 6.94 (dd, J=8.0, 4.0 Hz, 1H), 6.76 (s, 1H), 6.43-6.41 (m, 2H), 6.36 (s, 1H), 6.22 (s, 1H), 4.31-4.10 (m, 4H), 3.09-2.79 (m, 8H), 2.05-2.01 (m, 4H), 1.61-1.12 (m, 12H), 0.86 (t, J=7.8 Hz, 6H). ESMS cacld (C37H48N8O6S): 732.34; found: 733.3 (M+H).

Example 34: Identification and Use of SDC-TRAP for Prevention and Treatment of Chronic Bronchitis and Asthma Chronic bronchitis is a chronic inflammation of the bronchi in the lungs. It is generally considered one of the two forms of chronic obstructive pulmonary disease (COPD), the other being emphysema. It is defined clinically as a persistent cough that produces sputum (phlegm) and mucus, for at least three months per year in two consecutive years.

Asthma is an inflammatory disorder that causes the airways of the lungs to swell and narrow, leading to wheezing, shortness of breath, chest tightness, and coughing. Asthma can be chronic or be triggered by environmental triggers including, but not limited to, animal hair or dander, dust, changes in weather, exercise, mold, and pollen.

Drugs used for the treatment of chronic bronchitis, COPD, and asthma include, but are not limited to, smooth muscarinic acetylcholine receptor inhibitors such as ipratropium bromide; anticholinergic bronchodilators such as tiotropium; long-acting β2-adrenergic receptor agonists such as salmeterol, formoterol, and albuterol; anti-inflammatory agents such as inhaled steroids, montelukast, a leukotriene receptor antagonist (LTRA), and roflumilast, a selective, long-acting inhibitor of the enzyme phosphodiesterase-4 (PDE-4); xanthines such as theophylline; and mucolytic agents such as bromhexine and acetylcysteine. In cases where chronic bronchitis is caused or exacerbated by bacterial infection, antibiotics can be used for treatment.

Many of the agents used for the treatment of chronic bronchitis, COPD, and asthma work through receptors that are present throughout the body, thereby potentially causing undesirable side effects. Although many of the drugs are available for administration by inhalation, which can increase delivery to the target site and reduce side effects, decreased lung function in the disease population may result in improper dosing and reduced compliance.

Roflumilast (3-(cyclopropylmethoxy)-N-(3,5-dichloropyridin-4-yl)-4-(difluoromethoxy)benzamide), a selective, long-acting inhibitor of the enzyme phosphodiesterase-4 (PDE-4), is formulated as a tablet for oral administration and is approved for use in the treatment of chronic bronchitis and COPD. Roflumilast can be used as a binding moiety in combination with one or more drugs to make an SDC-TRAP that can be used for the treatment of chronic bronchitis, COPD, or asthma, such as those listed above and throughout the application, to target other agents to the site of interest, i.e., the lungs, while permitting oral delivery.

A roflumilast-effector molecule SDC-TRAP can be formed, for example, using any known linker, such as those provided herein, with the desired effector molecule. The specific linker and conjugation method used will depend, for example, on the chemical nature of the effector molecule.

Assays to determine the cytotoxicity of the roflumilast SDC-TRAP molecule conjugate are performed using methods similar to those provided in Example 4. Cell viability assays are performed on non-transformed cells, preferably lung cells, to identify SDC-TRAPs with acceptable toxicities, preferably compounds with toxicity that is not greater than either of the parent compounds.

Roflumilast SDC-TRAP molecules are also tested to confirm that their efficacy is not inhibited by the formation of the complex. Assays to test PDE-4 activity are well known in the art and are commercially available (e.g., PerkinElmer LANCE® Ultra cAMP kit). The activity of the effector molecule is tested using appropriate methods.

Methods to assess pharmacokinetic and pharmacodynamic properties of an agent are well known in the art. Tissue distribution studies are performed to assess distribution of the conjugate as compared to distribution of each roflumilast and the effector molecule. An increase accumulation of the roflumilast SDC-TRAP molecules in the lung as compared to the unconjugated effector molecule is observed. Such assays are performed using orally delivered SDC-TRAPs of active agents that may typically be administered by inhalation. Roflumilast SDC-TRAP molecules are also identified for having longer serum stability.

Having identified roflumilast SDC-TRAP molecules with the desired activity, cytotoxicity, pharmacokinetic properties, and improved pulmonary delivery, the SDC-TRAPs are tested for their efficacy of an appropriate animal model of chronic bronchitis, COPD, and/or asthma. Animal models of chronic bronchitis, COPD, and asthma are well known in the art. The activity of the conjugate is compared to the activity of each roflumilast and the effector molecule alone. Roflumilast SDC-TRAP molecules having one or more improved properties as compared to either of the parent molecules are further characterized in other animal systems and humans.

The SDC-TRAPs are found to have one or more improved properties in the treatment of humans including, but not limited to, decreased toxicity, improved dosing schedule, or improved efficacy.

Example 35: Identification and Use of SDC-TRAP for Prevention and Treatment of Skin Cancers and Actinic Keratosis Skin cancers (neoplasms) are named after the type of skin cell from which they arise. Skin cancers include basal cell carcinoma, squamous cell carcinoma, malignant melanomas, and Bowen's disease. Actinic keratosis can be, but is not always, a precursor to squamous cell carcinoma.

Drugs used for the treatment of skin cancer are selected based on the type and severity of the skin cancer. Superficial, non-melanoma skin cancers can be treated with topical agents, either alone or in combination with surgery or other therapeutic interventions. Such agents include, but are not limited to, retinoids, 5-fluorouracil, diclofenac, ingenol mebutate, and imiquimod. Topical delivery permits administration of the chemotherapeutic agent directly to the site of the tumor or skin lesion. However, the delivery of active agents into the skin can be challenging. Moreover, many topical therapeutic agents can be irritating to the skin, resulting in scar formation, further inhibiting the delivery of the active agent to the site.

Imiquimod 3-(2-methylpropyl)-3,5,8-triazatricyclo[7.4.0.02,6]trideca-1(9),2(6),4,7,10,12-hexaen-7-amine) is a patient-applied cream used to treat certain diseases of the skin, including skin cancers (basal cell carcinoma, Bowen's disease, superficial squamous cell carcinoma, some superficial malignant melanomas, and actinic keratosis) as well as genital warts (condylomata *acuminata*). Imiquimod and its analogs activate the immune system by activating immune cells through the toll-like receptor 7 (TLR7), commonly involved in pathogen recognition. Imiquimod can be used in combination with one or more drugs used for the treatment of skin diseases to make an SDC-TRAP molecule.

An imiquimod SDC-TRAP molecule can be formed, for example, using any known linker, such as those provided herein, with the desired effector molecule. The specific linker and conjugation method used will depend, for example, on the chemical nature of the effector molecule.

Assays to determine the cytotoxicity of the imiquimod SDC-TRAP molecules are performed using methods similar to those provided in Example 4. Cell viability assays are performed on non-transformed cells, preferably skin cells, to identify SDC-TRAPs with acceptable toxicities, preferably compounds with toxicity that is not greater than either of the parent compounds. Cytotoxicity and skin irritation assays are also performed, for example, on pig skin, which is frequently used as a model for human skin in toxicity/irritation assays, using routine methods.

Imiquimod SDC-TRAP molecules are also tested to confirm that their efficacy is not inhibited by the formation of the conjugate. A number of skin cancer cell lines are well known in the art. Dose response curves are generated to demonstrate the efficacy of imiquimod SDC-TRAP molecules in killing cancer cells. Preferably, the imiquimod SDC-TRAP molecules are more effective at killing skin cancer cells than imiquimod or the effector molecule alone.

Methods to assess pharmacokinetic and pharmacodynamic properties of an agent are well known in the art. As noted above, pig skin is frequently used as a model for human skin, both in toxicity/irritation assays, but also in assaying uptake and delivery of agents into skin layers and cells. Topical formulations of imiquimod, the effector molecule, and imiquimod SDC-TRAP molecules are assayed for uptake, transport through the skin, and persistence in the skin using routine methods.

Having identified a imiquimod SDC-TRAP molecule with the desired activity, cytotoxicity, pharmacokinetic properties, and improved tissue delivery, the SDC-TRAPs are tested for their efficacy in an appropriate animal model of skin cancer. A animal models of skin cancer are well known in the art. For example, xenograph tumor models using squamous cell carcinoma, basal cell carcinoma, or melanoma cell lines are used with subcutaneously implanted tumors. Topical formulations of imiquimod, the effector molecule, and imiquimod SDC-TRAP molecules are applied. The activity of the conjugate is compared to the activity of each imiquimod and the effector molecule alone. Imiquimod SDC-TRAP molecules having one or more improved properties as compared to either of the parent molecules are further characterized in other animal systems and humans.

The SDC-TRAPs are found to have one or more improved properties in the treatment of humans including, but not limited to, decreased toxicity, improved dosing schedule, or alternate route of administration.

Example 36: Determining the Permeability of SDC-TRAP Molecules

In order to test the ability SDC-TRAP molecules of the invention to enter cells, an artificial membrane permeability assay ("PAMPA") was used. PAMPAs are useful tool for predicting in vivo drug permeability for drugs that enter cells by passive transport mechanisms. LC/MS was used in conjunction with PAMPA assays to determine the ability of the SDC-TRAP molecules of the invention to permeate cells.

Pre-coated PAMPA plates were warmed to room temperature for at least 30 minutes prior to adding assay components.

Stock solutions were prepared with the SDC-TRAP molecules to be tested. In order to make a working solution, either 50 µL of 100 µM Stock in DMSO+950 µL of PBS or 50 µL of 200 µM stock was added to 96 deep well plate, resulting in a 5 µM final concentration or a 10 µM final concentration, respectively. 300 µL of the working solution containing each compound to be tested was added to the appropriate well of a donor PAMPA plate. 200 µL of PBS was added into the corresponding wells of an acceptor PAMPA plates.

The acceptor plate was lowered onto the donor plate and allowed to incubate for five hours. After five hours, a 50 µL aliquot was removed from each well of each plate and added into a new 96 deep-well plate.

100 µL of methanol containing an internal standard was added to each aliquot and analyzed by LC/MS. The internal standard was 150 ng/ml SDC-TRAP-0002.

In order to calculate the permeability for each SDC-TRAP molecule and the control molecules, the following formula was used:

Permeability (in Unit of Cm/s):

$$P_e = \frac{-\ln[1 - C_A(t)/Cequilibrium]}{A*(1/V_D + 1/V_A)*t}$$

$$Cequilibrium = \frac{C_D(t)*V_D + C_A(t)*V_A}{V_D + V_A}$$

Mass Retention:

$$R = \frac{1 - [C_D(t)*V_D + C_A(t)*V_A]}{C_0*V_D}$$

$C_0$=initial compound concentration in donor well (mM)
$C_D(t)$=compound concentration in donor well at time t. (mM)
$C_A(t)$=compound concentration in acceptor well at time t. (mM)
$V_D$=donor well volume=0.3 mL
$V_A$=acceptor well volume=0.2 mL.
A=filter area=0.3 cm$^2$
t=incubation time=18000 s (5 h)

For the data presented in the table below, peak area was used in place of concentration in the formula above.

| SDC-TRAP-# | Permeability (cm/s) | ($10^{-6}$ cm/s) | Mass Retention (%) |
|---|---|---|---|
| SDC-TRAP-0018 | 2.68E−08 | 0.0268 | 14.7 |
| SDC-TRAP-0048 | 2.83E−08 | 0.0283 | 10.8 |
| SDC-TRAP-0049 | 1.24E−08 | 0.0124 | 14.1 |
| SDC-TRAP-0052 | 7.69E−09 | 0.00769 | 7.02 |
| SDC-TRAP-0062 | 2.50E−08 | 0.025 | 18.0 |
| SDC-TRAP-0193 | 8.59E−09 | 0.00859 | 10.2 |
| SDC-TRAP-0195 | 0.00E+00 | 0 | 27.1 |
| SDC-TRAP-0196 | 0.00E+00 | 0 | 22.3 |
| SDC-TRAP-0210 | 0.00E+00 | 0 | 34.8 |
| SDC-TRAP-0232 | 6.89E−09 | 0.00689 | 21.0 |
| SDC-TRAP-0233 | 2.10E−08 | 0.021 | 10.9 |
| SDC-TRAP-0234 | 1.23E−08 | 0.0123 | 9.56 |
| Doxorubicin | 3.30E−09 | 0.0033 | 21.0 |
| Docetaxel | 5.00E−08 | 0.05 | 17.6 |
| SN-38 | 6.43E−07 | 0.643 | 38.2 |
| Lenalidomide | 6.20E−08 | 0.062 | 26.0 |
| Furosemide | 1.47E−08 | 0.0147 | 7.53 |
| Caffeine | 1.17E−05 | 11.7 | 20.8 |

The same protocol was used to test the permeability of the SDC-TRAP molecules identified in the table below.

| SDC-TRAP-# | Permeability (cm/s) | ($10^{-6}$ cm/s) | Mass Retention (%) |
|---|---|---|---|
| SDC-TRAP-0029 | 6.46E−09 | 0.00646 | 84.0 |
| SDC-TRAP-0046 | 1.22E−08 | 0.0122 | 88.1 |
| SDC-TRAP-0063 | 0E+00 | 0 | 18.7 |
| SDC-TRAP-0064 | 0E+00 | 0 | 48.4 |
| SDC-TRAP-0154 | 0E+00 | 0 | 10.3 |
| SDC-TRAP-0200 | 0E+00 | 0 | 10.6 |
| SDC-TRAP-0205 | 0E+00 | 0 | 10.9 |
| SDC-TRAP-0208 | 0E+00 | 0 | 25.0 |
| SDC-TRAP-0210 | 8.99E−09 | 0.00899 | 72.2 |
| SN-38 | 1.87E−06 | 1.87 | 46.6 |
| Furosemide | 2.50E−08 | 0.025 | 2.63 |
| Caffeine | 1.43E−05 | 14.3 | −0.11 |

All publications, patent applications, patents, and other documents cited herein are incorporated by reference in their entirety. In case of conflict, the present specification, including definitions, will control.

The specification should be understood as disclosing and encompassing all possible permutations and combinations of the described aspects, embodiments, and examples unless the context indicates otherwise. One of ordinary skill in the art will appreciate that the invention can be practiced by other than the summarized and described aspect, embodiments, and examples, which are presented for purposes of illustration, and that the invention is limited only by the following claims.

We claim:
1. A binding moiety-drug conjugate (SDC-TRAP) comprising a binding moiety and an effector moiety, wherein the binding moiety is an Hsp90 binding moiety and comprises compounds of the following general formula V

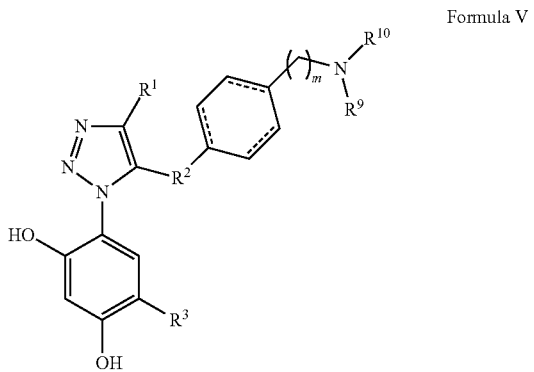

Formula V wherein:
$R^1$ is H, or $CONR^4R^5$;
$R^5$ is H, $(C_1-C_6)$-alkyl, or $(C_3-C_{10})$-cycloalkyl, each being optionally substituted once or more with OH, OMe, Cl, or F;
$R^4$ is H, $(C_1-C_4)$-alkyl, or $CH(R^{11})COR^{12}$; or
$R^4$ and $R^5$, taken together with the nitrogen atom to which they are attached, form a three- to seven-membered heterocycle optionally containing a further heteroatom selected from the group consisting of N, O and S; and wherein the heterocycle is optionally substituted once or more by OH, OMe, $(C_1-C_4)$-alkyl, optionally substituted phenyl, or benzyl;
$R^{11}$ is a side chain of a natural α-amino acid;
$R^{12}$ is OH, amino, alkylamino or dialkylamino;
$R^2$ is a bond, —NH(CO)—, —N($R^7$)— or —N($R^7$)CH$_2$—;
$R^7$ is H, $(C_1-C_4)$-alkyl or $CO_2R^8$;
$R^8$ is $(C_1-C_4)$-alkyl or benzyl;
the endocyclic symbols ===== are, for each single compound, all double bonds or all single bonds;
m is an integer comprised between 0 and 3;
$R^9$ and $R^{10}$ are, independently from each other, $(C_1-C_4)$-alkyl optionally substituted with OH, cycloalkyl, heterocycloalkyl, OMe, amino, $(C_1-C_6)$-alkylamino or $(C_1-C_{10})$-dialkylamino; heterocycloalkyl optionally substituted once or more by alkyl, amino, $(C_1-C_6)$-alkylamino or $(C_1-C_6)$-dialkylamino; cycloalkyl; or
$R^9$ and $R^{10}$, taken together with the nitrogen atom to which they are attached, form a heterocycle ring chosen from the group consisting of piperidyl, pyrrolidinyl, piperazinyl and morpholinyl, each of them being optionally substituted once or more by F, Cl, Br, OH, OMe, amino, $(C_1-C_6)$-alkylamino, $(C_1-C_6)$-dialkylamino, $(C_1-C_4)$-alkyl, hydroxyalkyl, optionally substituted phenyl, or benzyl; or an imidazole unsaturated heterocycle;
$R^3$ is Cl, Et or i-Pr;

their tautomers, their geometrical isomers, their optically active forms such as enantiomers, diastereomers and their racemate forms, as well as their pharmaceutically acceptable salts thereof.

2. The SDC-TRAP of claim 1, wherein the Hsp90 binding moiety is an Hsp90 ligand or a prodrug thereof.

3. The SDC-TRAP of claim 2 wherein the Hsp90 ligand is an Hsp90 inhibitor.

4. The SDC-TRAP of claim 1, wherein the effector moiety is a cytotoxic moiety.

5. The SDC-TRAP of claim 4, wherein the cytotoxic moiety is one or more selected from the group consisting of: SN-38, bendamustine, a VDA, doxorubicin, pemetrexed, vorinostat, lenalidomide, irinotecan, ganetespib, docetaxel, 17-AAG, 5-FU, abiraterone, crizotinib, KW-2189, BUMB2, DC1, CC-1065 and adozelesin, or (a) fragment(s) thereof.

6. The SDC-TRAP of claim 1, wherein the effector moiety is one or more selected from the group consisting of: docetaxel, paclitaxel, BEZ235, temsirolimus, PLX4032, cisplatin, AZD8055, crizotinib, topotecan and irinotecan.

7. The SDC-TRAP of claim 1, wherein the molecular weight of the SDC-TRAP is less than about 1600 Daltons, less than about 1200 Daltons, less than about 800 Daltons, less than about 600 Daltons, or less than about 400 Daltons.

8. The SDC-TRAP of claim 1, wherein the binding moiety and the effector moiety are covalently attached.

9. The SDC-TRAP of claim 8, wherein the binding moiety and the effector moiety are covalently attached by a linker.

10. The SDC-TRAP of claim 9, wherein the linker comprises a cleavable linker.

11. The SDC-TRAP of claim 10, wherein the cleavable linker comprises an enzymatically cleavable linker.

12. The SDC-TRAP of claim 9, wherein the linker is selected from the group consisting of disulfide, carbamate, amide, ester, and ether linkers.

13. The SDC-TRAP of claim 1, wherein the SDC-TRAP is able to enter a cell by passive diffusion or by active transport.

14. The SDC-TRAP of claim 1, wherein the binding moiety has a molecular weight of less than 800 Daltons.

15. The SDC-TRAP of claim 1, wherein the effector moiety has a molecular weight of less than 800 Daltons.

16. The SDC-TRAP of claim 1, wherein the binding moiety is selected from the group consisting of
4-isopropyl-6-[5-(4-(morpholin-4-ylmethyl-phenyl)-[1,2,3]-triazol-1-yl)]-benzene-1,3-diol;
4-{5-[4-(3-hydroxy-piperidin-1-ylmethyl)-phenyl]-[1,2,3]triazol-1-yl}-6-isopropyl-benzene-1,3-diol;
4-{5-[4-(4-benzyl-piperazin-1-ylmethyl)-phenyl]-[1,2,3]triazol-1-yl}-6-isopropyl-benzene-1,3-diol;
4-isopropyl-6-{5-[4-(4-phenyl-piperazin-1-ylmethyl)-phenyl]-[1,2,3]triazol-1-yl}-benzene-1,3-diol;
1-(2,4-dihydroxy-5-isopropyl-phenyl)-5-(4-morpholin-4-ylmethyl-phenyl)-1H-[1,2,3]triazole-4-carboxylic ethyl amide;
(R,S)-1-(2,4-dihydroxy-5-isopropyl-phenyl)-5-[4-(3-hydroxy-piperidin-1-ylmethyl)-phenyl]-1H-[1,2,3]triazole-4-carboxylic acid ethylamide;
1-(2,4-dihydroxy-5-isopropyl-phenyl)-5-(4-{[ethyl-(2-hydroxy-ethyl)-amino]-methyl}-phenyl)-1H-[1,2,3]triazole-4-carboxylic acid ethylamide;
1-(2,4-dihydroxy-5-isopropyl-phenyl)-5-{4-[2-(2-hydroxyethyl)-piperidin-1-ylmethyl]-phenyl})-1H-[1,2,3]triazole-4-carboxylic acid ethylamide;
1-(2,4-dihydroxy-5-isopropyl-phenyl)-5-(4-piperidin-1-ylmethyl-phenyl)-1H-[1,2,3]triazole-4-carboxylic acid ethylamide;

5-(4-diethylaminomethyl-phenyl)-1-(2,4-dihydroxy-5-isopropyl-phenyl)-1H-[1,2,3]triazole-4-carboxylic acid ethylamide;

1-(2,4-dihydroxy-5-isopropyl-phenyl)-5-[4-(4-methyl-piperazin-1-ylmethyl)-phenyl]-1H-[1,2,3]triazole-4-carboxylic acid ethylamide;

1-(2,4-dihydroxy-5-isopropylphenyl)-5-(4-piperazin-1-ylmethyl-phenyl)-1H-[1,2,3]triazole-4-carboxylic acid ethylamide;

1-(2,4-dihydroxy-5-isopropyl-phenyl)-5-[4-(4-dimethyl-amino-piperidin-1-ylmethyl)-phenyl]-1H-[1,2,3]triazole-4-carboxylic acid ethylamide;

1-(2,4-dihydroxy-5-isopropyl-phenyl)-5-{4-[(2-morpholin-4-yl-ethylamino)-methyl]-phenyl})-1H-[1,2,3]triazole-4-carboxylic acid ethylamide;

5-{4-[(cyclohexylmethyl-amino)methyl]-phenyl}-1-(2,4-dihydroxy-5-isopropyl-phenyl)-1H-1,2,3]triazole-4-carboxylic acid ethylamide;

5-(4-cyclohexylaminomethyl-phenyl)-1-(2,4-dihydroxy-5-isopropyl-phenyl)-1H-[1,2,3]triazole-4-carboxylic acid ethylamide;

5-{4-[(2-diethylaminoethylamino)-methyl]-phenyl}-1-(2,4-dihydroxy-5-isopropyl-phenyl)-1H-[1,2,3]triazole-4-carboxylic acid ethylamide;

5-{4-[(3-diethylamino-propylamino)-methyl]-phenyl}-1-(2,4-dihydroxy-5-isopropyl-phenyl)-1H-[1,2,3]triazole-4-carboxylic acid ethylamide;

1-(2,4-dihydroxy-5-isopropyl-phenyl)-5-{4-[(1-methyl-piperidin-4-ylamino)-methyl]-phenyl})-1H-[1,2,3]triazole-4-carboxylic acid ethylamide;

1-(2,4-dihydroxy-5-isopropyl-phenyl)-5-[4-((S)-3-dimethylamino-pyrrolidin-1-ylmethyl)-5 phenyl]-1H-[1,2,3]triazole-4-carboxylic acid ethylamide;

1-(2,4-dihydroxy-5-isopropyl-phenyl)-5-(4-pyrrolidin-1-ylmethyl-phenyl)-1H-[1,2,3] triazole-4-carboxylic acid ethylamide;

1-(2,4-dihydroxy-5-isopropyl-phenyl)-5-(4-imidazol-1-ylmethylphenyl)-1H-[1,2,3]triazole-4-carboxylic acid ethylamide;

4-isopropyl-6-[5-(4-morpholin-4-yl-phenylamino)-[1,2,3]triazol-1-yl]-benzene-1,3-diol;

(4-morpholin-4-yl-benzylamino)-[1,2,3]triazol-1-yl]-benzene-1,3-diol;

4-isopropyl-6-[5-1-(2,4-dihydroxy-5-isopropyl-phenyl)-5-(4-morpholin-4-yl-phenylamino)-1H-[1,2,3]triazole-4-carboxylic acid ethylamide;

1-(2,4-dihydroxy-5-isopropyl-phenyl)-5-(4-morpholin-4-yl-benzylamino)-1H-[1,2,3]triazole-4-carboxylic acid ethylamide;

1-(2,4-dihydroxy-5-isopropyl-phenyl)-5-(4-morpholin-4-ylmethyl-phenyl)-1H-[1,2,3]triazole-4-carboxylic acid hexylamide;

1-(2,4-dihydroxy-5-isopropyl-phenyl)-5-(4-morpholin-4-ylmethyl-phenyl)-1H-[1,2,3]triazole-4-carboxylic acid cyclopentylamide;

1-(2,4-dihydroxy-5-isopropyl-phenyl)-5-(4-morpholin-4-ylmethyl-phenyl)-1H-[1,2,3]triazole-4-carboxylic acid cyclohexylamide;

[1-(2,4-dihydroxy-5-isopropylphenyl)-5-(4-morpholin-4-ylmethyl-phenyl)-1H-[1,2,3] triazol-4-yl]-morpholin-4-yl-methanone;

(S)-2-{[1-(2,4-dihydroxy-5-isopropyl-phenyl)-5-(4-morpholin-4-ylmethylphenyl)-1H-[1,2,3]triazole-4-carbonyl]-amino}-3-methyl-butyric acid;

4-isopropyl-6-[5-(4-pyrrolidin-1-ylmethyl-phenyl)-[1,2,3]triazol-1-yl]-benzene-1,3-diol;

4-isopropyl-6-[5-(4-isoxazolidin-2-ylmethyl-phenyl)-[1,2,3]triazol-1-yl]-benzene-1,3-diol;

1-(2,4-dihydroxy-5-isopropyl-phenyl)-5-(4-isoxazolidin-2-ylmethyl-phenyl)-1H-[1,2,3]triazole-4-carboxylic acid ethylamide;

1-(2,4-dihydroxy-5-isopropyl-phenyl)-5-[4-(4-phenyl-piperazin-1-ylmethyl)-phenyl]-1H-[1,2,3]triazole-4-carboxylic acid ethylamide;

4-[5-(4-{[ethyl-(2-hydroxy-ethyl)-amino]-methyl}-phenyl)-[1,2,3]triazol-1-yl]-6-isopropyl-benzene-1,3-diol;

4-(5-{4-[2-(2-Hydroxy-ethyl)-piperidin-1-ylmethyl]-phenyl}-[1,2,3]triazol-1-yl)-6-isopropyl-benzene-1,3-diol;

4-isopropyl-6-[5-(4-piperidin-1-ylmethyl-phenyl)-[1,2,3]triazol-1-yl]-benzene-1,3-diol;

4-[5-(4-diethylaminomethyl-phenyl)-[1,2,3]triazol-1-yl]-6-isopropyl-benzene-1,3-diol;

N-[3-(2,4-dihydroxy-5-isopropyl-phenyl)-3H-[1,2,3]triazol-4-yl]-4-morpholin-4-yl-benzamide;

1-(2,4-dihydroxy-5-isopropyl-phenyl)-5-(4-morpholin-4-ylbenzoylamino)-1H-[1,2,3]triazole-4-carboxylic acid ethylamide;

N-[3-(2,4-dihydroxy-5-isopropyl-phenyl)-3H-[1,2,3]triazol-4-yl]-4-piperidin-1-yl-benzamide;

1-(2,4-dihydroxy-5-isopropyl-phenyl)-5-(4-piperidin-1-yl-benzoylamino)-1H-[1,2,3]triazole-4-carboxylic acid ethylamide;

N-[3-(2,4-dihydroxy-5-isopropyl-phenyl)-3H-[1,2,3]triazol-4-yl]-4-(3-hydroxy-piperidin-1-yl)-benzamide;

1-(2,4-dihydroxy-5-isopropyl-phenyl)-5-[4-(3-hydroxy-piperidin-1-yl)-benzoylamino]-1H-[1,2,3]triazole-4-carboxylic acid ethylamide;

N-[3-(2,4-dihydroxy-5-isopropyl-phenyl)-3H-[1,2,3]triazol-4-yl]-4-morpholin-4-ylmethyl-benzamide;

1-(2,4-dihydroxy-5-isopropyl-phenyl)-5-(4-morpholin-4-ylmethyl-benzoylamino)-1H-[1,2,3]triazole-4-carboxylic acid ethylamide;

4-morpholin-4-ylmethyl-cyclohexanecarboxylic acid [3-(2,4-dihydroxy-5-isopropyl-phenyl)-3H-[1,2,3]triazol-4-yl]-amide;

1-(2,4-dihydroxy-5-isopropyl-phenyl)-5-[(4-morpholin-4-ylmethyl-cyclohexanecarbonyl)-amino]-1H-[1,2,3]triazole-4-carboxylic acid ethylamide;

4-isopropyl-6-{5-[4-(4-methyl-piperazin-1-ylmethyl)-phenyl]-[1,2,3]triazol-1-yl}-benzene-1,3-diol;

4-isopropyl-6-[5-(4-morpholin-4-ylmethyl-phenyl)-[1,2,3]triazol-1-yl]-benzene-1,3-diol;

1-(2,4-dihydroxy-5-isopropyl-phenyl)-5-(4-morpholin-4-ylmethyl-phenyl)-1H-[1,2,3]triazole-4-carboxylic acid ethylamide;

5-[4-(4-benzyl-piperazin-1-ylmethyl)-phenyl]-1-(2,4-dihydroxy-5-isopropyl-phenyl)-1H-[1,2,3]triazole-4-carboxylic acid ethylamide;

N-[3-(2,4-dihydroxy-5-isopropyl-phenyl)-3H-[1,2,3]triazol-4-yl]-4-pyrrolidin-1-yl-benzamide;

1-(2,4-dihydroxy-5-isopropyl-phenyl)-5-(4-pyrrolidin-1-yl-benzoylamino)-1H-[1,2,3]triazole-4-carboxylic acid ethylamide; or 1-(2,4-dihydroxy-5-isopropylphenyl)-5-(4-morpholin-4-yl-methyl-phenyl)-1H-[1,2,3]triazole-4-carboxylic acid (2-chloro-ethyl)-amide;

their tautomers, their geometrical isomers, their optionally active forms such as enantiomers, diastereomers and their racemate forms, as well as their pharmaceutically acceptable salts thereof.

* * * * *